inventors: Jordi Frigola Mas, Girona (ES); Miguel A. Peinado, Barcelona (ES); Susan Joy Clark, Chatswood (AU)

United States Patent
Mas et al.

(10) Patent No.: US 9,157,122 B2
(45) Date of Patent: Oct. 13, 2015

(54) METHOD OF DIAGNOSING CANCER AND REAGENTS THEREFOR

(75) Inventors: Jordi Frigola Mas, Girona (ES); Miguel A. Peinado, Barcelona (ES); Susan Joy Clark, Chatswood (AU)

(73) Assignee: Garvan Institute of Medical Research, Darlinghurst (AU)

( * ) Notice: Subject to any disclaimer, the term of this patent is extended or adjusted under 35 U.S.C. 154(b) by 1475 days.

(21) Appl. No.: 11/667,628

(22) PCT Filed: Nov. 11, 2005

(86) PCT No.: PCT/AU2005/001726
§ 371 (c)(1),
(2), (4) Date: Dec. 13, 2007

(87) PCT Pub. No.: WO2006/050573
PCT Pub. Date: May 18, 2006

(65) Prior Publication Data
US 2009/0042184 A1 Feb. 12, 2009

(30) Foreign Application Priority Data

Nov. 11, 2004 (AU) ................................ 2004906486

(51) Int. Cl.
*C12Q 1/68* (2006.01)
(52) U.S. Cl.
CPC ........ *C12Q 1/6886* (2013.01); *C12Q 2523/125* (2013.01); *C12Q 2600/118* (2013.01); *C12Q 2600/136* (2013.01); *C12Q 2600/154* (2013.01); *C12Q 2600/156* (2013.01); *C12Q 2600/16* (2013.01)

(58) Field of Classification Search
None
See application file for complete search history.

(56) References Cited

PUBLICATIONS

Frigola et al. Methylome profiling of cancer cells by amplification of inter-methylated sites (AIMS). Nucleic Acids Research, 2002, vol. 30, No. 7 e28.
Georgescu M-M et al. Biological effects of c-Mer receptor tyrosine kinase in hematopoietic cells depend on the Grb2 binding site in the receptor and activation of NF-*kB*. Molecular and Cellular Biology, 1999, 19(2):1171-1181.
Weier H-UG et al. Assignment of protooncogene MERTK (a.k.a. c-mer) to human chromosome 2q14.1 by in situ hybridization. Cytogenet Cell Genet (1999) 84:91-92.
Yue C-M et al. Expression of ECRG4, a novel esophageal cancer-related gene, downregulated by CpG island hypermethylation in human esophageal cell carcinoma. World Journal of Gastroenterology, 2003, 9(6):1174-1178.
Pang RT-K et al. CpG methylation and transcription factor Sp1 and Sp3 regulate the expression of the human secretin receptor gene, Molecular Endocrinology, 2004, 18(2):471-483.
Yu J. et al. Methylation profiles of thirty four promoter-CpG islands and concordant methylation behaviours of sixteen genes that may contribute to carcinogenesis of astrocytoma. BMC Cancer, 2004, 4:65. retrieved from http://biomedcentral.com/content/pdf/1471-2407-4-65.pdf.

*Primary Examiner* — Karen Canella
(74) *Attorney, Agent, or Firm* — Carol L. Francis; Bozicevic, Field & Francis LLP

(57) ABSTRACT

The present invention provides methods for diagnosis and monitoring the efficacy of treatment of a cancer. More particularly, the methods of the invention comprise detecting an enhanced degree of chromatin modification within Chromosome 2 of the human genome from about map position 2q14.1 to about map position 2q14.3 in a sample derived from a subject. The methods include detecting an enhanced level of methylation, or detecting an enhanced level of modification of a histone positioned within the chromatin within the region of about 2q14.1 to 2q14.3 of Chromosome 2. The methods also include detecting a modulated level of expression of a gene within the region of about 2q14.1 to 2q14.3 of Chromosome 2. The gene may be selected from the group consisting of DEAD box polypeptide 18 (DDX18), translin (TSN), v-ral simian leukaemia viral oncogene homolog B (RALB), secretin recepto (SCTR), engrailed homolog 1 (EN1), macrophage receptor with collagenous structure (MARCO), protein tyrosine phosphatase non-receptor type 4 (PTPN4), insulin induced gene 2 (INSIG2), inhibin beta B (INHBB), GLI-Kruppel family member 2 (GLI2), FLJ10996, STEAP3, diazepam binding inhibitor (DBI), MGC10993, erythrocyte membrane protein band 4.1 like 5 (EPB41L5), FLJ14816, transcription factor CP2-like 1 (TFCP2L1).

12 Claims, 69 Drawing Sheets

| NAME | CpGi | Co-ord | Dis.(Kb) | HCT | SW | 9N | 9T | 165N | 165T |
|---|---|---|---|---|---|---|---|---|---|
| CpG29 | Yes | 119627212-119627460 | -58 | | | | | | |
| X | No | 119661213-119661555 | -20 | | | | | | |
| Z | No | 119686319-119686515 | 0 | | | | | | |
| CpG104 | Yes | 119687749-119688990 | 3 | | | | | | |
| CpG103 | Yes | 119694605-119696111 | 8 | | | | | | |
| CpG128 | Yes | 119697763-119699631 | 15 | | | | | | |
| CpG41 | Yes | 119702525-119703055 | 18 | | | | | | |
| CpG173 | Yes | 119708178-119710710 | 23 | | | | | | |
| CpG48 | Yes | 119711280-119711971 | 25 | | | | | | |

Figure 6

| SAMPLE | ENI | SCTR | INHBB | AGE | SEX | DUKE'S |
|---|---|---|---|---|---|---|
| 17 | ▓ | ▓ |  | 31 | W | C2 |
| 127 |  | ▓ |  | 31 | W | C2 |
| 143 | ▓ | ▓ | ▓ | 37 | W | C1 |
| 175 |  | ▓ |  | 46 | W | B2 |
| 19 |  | ▓ |  | 49 | W | B1 |
| 69 | ▓ | ▓ |  | 52 | M | B2 |
| 108 |  | ▓ |  | 62 | M | C2 |
| 122 | ▓ | ▓ | ▓ | 62 | M | C1 |
| 78 | ▓ | ▓ |  | 62 | M | B2 |
| 103 | ▓ | ▓ | ▓ | 66 | M | B2 |
| 9 | ▓ | ▓ |  | 67 | M | B2 |
| 21 | ▓ |  | ▓ | 68 | W | B2 |
| 144 |  | ▓ | ▓ | 72 | W | B2 |
| 72 | ▓ | ▓ | ▓ | 73 | M | C2 |
| 113 | ▓ | ▓ |  | 73 | W | B2 |
| 63 | ▓ | ▓ | ▓ | 74 | W | C2 |
| 223 | ▓ | ▓ | ▓ | 75 | M | B2 |
| 147 | ▓ | ▓ | ▓ | 76 | W | C2 |
| 165 | ▓ | ▓ | ▓ | 76 | M | C2 |
| 75 | ▓ | ▓ | ▓ | 77 | M | B2 |
| 102 | ▓ |  | ▓ | 77 | M | B2 |
| 151 | ▓ | ▓ | ▓ | 79 | M | B2 |
| 138 |  | ▓ |  | 80 | W | B2 |
| 171 | ▓ | ▓ | ▓ | 85 | M | C2 |
| 74 |  | ▓ |  | 87 | M | C2 |
| 90 |  |  |  | 88 | W | C2 |

| CELLS | EN1 | SCTR | INHBB |
|---|---|---|---|
| HCT116 | ■ | ■ | ■ |
| SW480 | ■ | | |
| LoVo | ■ | ■ | |
| KM12sm | ■ | ■ | ■ |
| CaCo2 | ■ | ■ | |
| DLD | ■ | ■ | |
| HT29 | ■ | | |
| KM12c | ■ | ■ | |
| LS174 | ■ | ■ | |
| LS411N | ■ | ■ | ■ |
| LISP1 | ■ | ■ | ■ |
| HCT15 | ■ | ■ | |

| Z Frag | DNA Source | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | Total |
|---|---|---|---|---|---|---|---|---|---|---|---|---|---|---|---|---|---|---|---|---|---|---|---|---|---|---|---|---|
| RH452 | T47D | Didn't sequence | | | | | | | | | | | | | | | | | | | | | | | | | | |
| RH453 | MDA MB 453 | + | + | + | + | + | + | + | + | + | + | + | + | + | + | + | + | + | + | + | + | + | + | + | + | + | + | 26 |
| RH454 | MDA MB 468 | - | - | - | - | - | - | - | - | - | - | - | - | - | - | - | - | - | B | B | B | B | B | B | B | B | B | 0 |
| RH455 | SKBR3 | - | - | - | - | - | - | - | - | - | - | - | - | - | - | - | - | - | B | B | B | B | B | B | B | B | B | 0 |
| RH456 | KPL1 | + | - | - | + | + | + | + | + | + | + | + | + | + | + | + | + | + | B | B | B | B | B | B | B | B | B | 17 |
| RH457 | MDA MB 231 | + | + | + | + | + | + | - | + | + | + | + | + | + | + | + | + | + | + | + | B | B | B | B | B | B | B | 20 |
| RH458 | DU4475 | + | + | + | + | + | + | + | + | + | + | + | + | + | B | B | B | + | B | B | B | B | B | B | B | B | B | 14 |
| RH459 | MCF-7 | + | + | + | + | + | + | + | + | + | + | + | + | + | + | + | + | + | + | + | + | + | + | B | B | B | B | 22 |
| RH460 | MDA MB 157 | + | + | + | + | + | + | + | + | + | + | + | + | + | + | + | + | + | + | + | + | + | + | + | + | B | B | 24 |
| RH461 | MCF-10A | + | + | + | - | + | + | - | + | + | - | + | + | + | + | + | + | + | + | + | + | + | + | + | + | + | B | 25 |
| RH462 | LNCaP | + | + | + | + | + | + | + | + | + | + | + | + | + | + | + | + | + | + | + | + | + | + | + | B | B | B | 23 |
| RH463 | DU145 | + | + | + | + | + | + | + | + | + | + | + | + | + | + | + | + | + | + | + | + | + | + | + | B | B | B | 23 |

| 128 Frag | DNA Source | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|---|
| RH464 | T47D | + | + | + | + | + | + | + | + | + | + | + | + | + | + | + | + | + | + | + | + | + | + | + | + | + | + | + | 27 |
| RH465 | MDA MB 453 | + | + | + | + | + | + | + | + | + | + | + | + | + | + | + | + | + | + | + | + | + | + | + | + | + | + | + | 27 |
| RH466 | MDA MB 468 | - | - | - | - | - | - | - | - | - | - | - | - | - | - | - | - | - | - | - | - | - | - | - | - | - | - | - | 0 |
| RH467 | SKBR3 | - | - | - | + | - | + | - | - | - | - | - | - | - | - | - | - | - | - | + | - | - | - | - | - | - | - | - | 4 |
| RH468 | KPL1 | + | + | + | + | + | + | + | + | + | + | + | + | + | + | + | + | + | + | + | + | + | + | + | + | + | + | + | 27 |
| RH469 | B16 | - | - | - | - | - | - | - | - | - | - | - | - | - | - | - | - | - | - | - | - | - | B | B | B | B | B | - | 0 |
| RH470 | MDA MB 231 | + | + | + | + | + | + | + | + | + | + | + | + | + | + | + | + | + | + | + | + | + | + | + | + | + | + | + | 27 |
| RH471 | DU4475 | - | - | - | - | - | - | - | - | - | - | - | - | - | - | - | - | - | - | - | - | - | - | - | - | - | + | - | 3 |
| RH472 | MCF-7 | + | + | + | + | + | + | + | + | + | + | + | + | + | + | + | + | + | + | + | + | + | + | + | + | + | + | + | 27 |
| RH473 | MDA MB 157 | - | - | - | - | - | - | - | - | - | - | - | - | - | - | - | - | - | - | - | - | - | - | - | - | - | - | - | 0 |
| RH474 | MCF-10A | + | + | + | + | + | + | + | + | + | + | + | + | - | + | + | + | + | + | + | + | + | + | + | + | + | + | + | 25 |
| RH475 | LNCaP | + | + | + | + | + | + | + | + | + | + | + | + | + | + | + | + | + | + | + | + | + | + | + | - | - | + | - | 21 |
| RH476 | DU145 | + | + | + | + | + | + | + | + | + | + | + | + | + | + | + | + | + | + | + | + | + | + | + | + | + | + | - | 26 |

Figure 19b

| 48 Frag | DNA Source | 1 | 2 | 3 | 4 | 5 | 6 | 7 | 8 | 9 | 10 | 11 | 12 | 13 | Total |
|---|---|---|---|---|---|---|---|---|---|---|---|---|---|---|---|
| RH477 | T47D | + | + | + | + | + | + | + | + | + | + | + | + | + | 13 |
| RH478 | MDA MB 453 | + | + | + | + | + | + | + | + | + | + | + | + | + | 13 |
| RH479 | MDA MB 468 | + | + | + | + | + | + | + | + | + | + | + | + | + | 13 |
| RH480 | SKBR3 | + | + | + | - | - | + | + | + | + | + | + | + | + | 11 |
| RH481 | KPL1 | + | + | + | + | + | + | + | + | + | + | + | + | + | 13 |
| RH482 | MDA MB 231 | + | + | + | + | + | + | + | + | + | + | + | + | + | 13 |
| RH483 | DU4475 | + | + | + | + | + | + | + | + | + | + | + | + | + | 13 |
| RH484 | MCF-7 | + | + | + | + | + | + | + | + | + | + | + | + | + | 13 |
| RH485 | MDA MB 157 | + | + | + | + | + | + | + | + | + | + | + | + | + | 13 |
| RH486 | MCF-10A | + | + | + | + | + | + | + | + | + | + | + | + | + | 13 |
| RH487 | LNCaP | + | + | + | + | + | + | + | + | + | + | + | + | + | 13 |

Figure 19c

| SCTR | DNA Source | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|---|
| RH620 | Bre 12 | - | - | - | - | - | - | - | - | - | - | - | - | - | - | - | - | - | - | - | - | - | - | - | - | - | - | - | 0 |
| RH621 | Bre 13 | - | - | - | - | - | - | - | - | - | - | - | - | - | - | - | - | - | - | - | - | - | - | - | - | - | - | - | 0 |
| RH674 | MDA MB 453 | + | + | + | + | + | + | + | + | + | + | + | + | + | + | + | + | + | + | + | + | + | + | + | + | + | + | ? | 26 |
| RH675 | DU145 | + | + | + | + | - | + | - | + | + | + | + | - | - | + | + | + | + | + | + | + | + | + | + | + | - | + | ? | 17 |
| RH676 | KPL1 | + | + | + | + | + | + | + | + | + | + | + | + | + | + | + | + | + | + | + | + | + | + | + | + | + | + | ? | 26 |
| RH677 | MDA MB 231 | High G Background | | | | | | | | | | | | | | | | | | | | | | | | | | | |
| RH678 | DU4475 | + | + | + | + | + | + | + | + | + | + | + | + | + | + | + | + | + | + | + | + | + | + | + | + | + | + | ? | 26 |
| RH679 | MCF-7 | + | + | + | + | + | + | + | + | + | + | + | + | + | + | + | + | + | + | + | + | + | + | + | + | + | + | ? | 26 |
| RH680 | MDA MB 157 | High G Background | | | | | | | | | | | | | | | | | | | | | | | | | | | |
| RH681 | MCF-10a | + | + | + | + | + | + | + | + | + | + | + | + | + | + | + | + | + | + | + | + | + | + | + | + | + | + | ? | 26 |
| RH622 | T47D | + | + | + | + | + | + | + | + | + | + | + | + | + | + | + | - | + | + | + | + | + | + | + | + | + | + | + | 27 |
| RH602 | LNCaP | ? | ? | ? | ? | - | - | + | - | + | + | + | + | + | + | + | - | + | + | + | + | + | + | + | + | + | + | ? | 20 |
| RH601 | SKBR3 | - | - | - | + | + | + | - | - | - | - | - | - | - | - | - | - | - | - | - | - | - | - | ? | ? | ? | ? | ? | 6 |
| RH600 | MDA MB 468 | + | + | + | + | + | + | + | + | + | + | + | + | + | + | + | - | + | + | + | + | + | + | ? | ? | ? | ? | ? | 22 |

Figure 19d

| Ovarian cell lines | EN1 | EN1 HL | INHBB | SCTR | SCTR HL |
|---|---|---|---|---|---|
| SW626 | M/M | M/M | U/U | M/M | M/M |
| OVCA420 | U/U | U/U | U/U | M/M | M/M |
| A2780 | U/U | U/U | U/U | M/PD | M/U |
| TOV21G | U/U | U/U | U/U | U/U | U/U |
| IGROV1 | M/M | M/M | M/M | U/U | U/U |
| SKOV3 | M/M | M/M | U/M | U/U | U/U |
| OV90 | M/M | M/M | U/M | M/U | M/M |
| TOV112D | U/U | M/U | U/U | U/U | U/U |
| HOSE6-3 | M/M | M/M | M/M | M/M | U/U |

Figure 20a

| Ovarian Tumours | EN1 HL | SCTR HL | Ovarian Tumours | EN1 HL | SCTR HL |
|---|---|---|---|---|---|
| 1 | U / U | M / U | 20 | M / M | U / U |
| 2 | U / U | U / U | 21 | M / M | U / U |
| 3 | M / M | M / M | 22 | M / M | M / U |
| 4 | U / U | U / U | 23 | M / M | M / U |
| 5 | M / U | M / U | 24 | -/- | M / M |
| 6 | M / M | U / U | 25 | M / U | U / U |
| 7 | M / U | U / U | 26 | M / M | U / U |
| 8 | M / M | U / U | 27 | U / U | U / U |
| 9 | M / U | M / U | 28 | U / U | M / U |
| 10 | U / U | U / U | 29 | M / U | U / U |
| 11 | U / U | U / U | 30 | M / M | U / U |
| 12 | M / U | M / U | 31 | M / M | M / M |
| 13 | U / U | U / U | 32 | M / M | U / U |
| 14 | U / U | U / U | 33 | M / M | U / U |
| 15 | M / M | U / U | 34 | U/- | U / U |
| 16 | U / U | U / U | 35 | M / M | U / U |
| 17 | M / M | U / U | 36 | M / M | U / U |
| 18 | U / U | M / U | 37 | U / U | U/- |
| 19 | U / U | U / U | | | |

Figure 20b

| Prostate | EN1 | EN1 HL | SCTR | SCTR HL |
|---|---|---|---|---|
| 1N | NA / NA | U/- | NA / NA | U/U |
| 1C | M/U | U/U | M/U | U/U |
| 2N | U/U | U/U | M/M | M/U |
| 2C | U/U | U/U | M/M | U/U |
| 3N | U/U | M/U | U/U | U/U |
| 3C | U/U | U/U | M/M | M/U |
| 4N | M/U | U/U | U/U | U/U |
| 4C | U/U | U/U | M/M | M/M |
| 5N | U/U | U/U | U/U | U/U |
| 5C | U/U | U/U | M/M | U/U |
| 6N | U/U | U/U | NA / NA | U/- |
| 6C | U/U | U/- | M/M | U/U |
| 7N | U/U | U/U | U/U | M/M |
| 7C | M/M | M/M | M/M | M/M |
| 8N | U/U | U/U | U/U | U/U |
| 8C | M/M | M/M | M/M | M/M |
| 9N | U/U | U/U | U/U | U/U |
| 9C | U/U | U/U | M/M | U/U |
| 10N | U/U | U/U | U/U | M/U |
| 10C | U/U | U/U | U/U | U/U |
| 11N | U/U | M/U | U/U | U/U |
| 11C | U/U | M/M | M/M | U/U |
| 12N | U/U | U/U | M/U | U/U |
| 12C | U/U | U/- | NA / NA | U/U |

EN-1 breast 12

| CpG Site | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|
| AM01 clone 4 | ■ | ■ | ■ | | ■ | | | ■ | ■ | | ■ | | | | | | | | | | | | | ■ | | | | 7 |
| AM02 clone 5 | ■ | ■ | | | ■ | | | ■ | ■ | | ■ | | | | | | | | | | | | | ■ | ■ | | | 7 |
| AM03 clone 6 | ■ | ■ | | | ■ | | | ■ | ■ | | ■ | | | | | | | | | | | | | ■ | | | | 7 |
| AM04 clone 7 | | | | ■ | ■ | | | | | | | | | | | | | | | | | | | | | | | 5 |
| AM05 clone 8 | ■ | ■ | | | | | | | | | | | | | | | | | ■ | | | | | | | | | 3 |
| AM06 clone 9 | | | | | | | | | | | | | | | | | | | | | | | | | | | | 1 |
| AM40 clone 3 | | ■ | | | | | | ■ | | | | | | | | | | | | | | | | | | | | 6 |
| AM41 clone 10 | | | | | | | | | | | | | | | | | | | | | | | | | | | ■ | 2 |
| AM42 clone 11 | | ■ | | | | | | | | | | | | | | | | | | | | | | | | | | 2 |
| AM42 clone 12 | ■ | ■ | | | ■ | | | | | | ■ | | | | | | | | | | | | | ■ | | | | 8 |
| Dir Seq AM132 PCR clean up | | | | | | | | | | | | | | | | | | | | | | | | | | | | 7 |

SCTR breast 12

| CpG Site | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|
| AM13 clone 26 | | | | | ■ | ■ | | | | | | | | | | | | | | | | | | | ■ | | | 6 |
| AM14 clone 27 | | | | | | | | | | | | | | | | | | | | | | | | | | | | 0 |
| AM15 clone 28 | | | | | | | | | | | | | | | | | | | | | | | | | | | | 0 |
| AM16 clone 29 | | | | | | | | | | | | | | | | | | | | | | | | | | | | 0 |
| AM17 clone 30 | | | | | | | | | | | | | | | | | | | | | | ■ | | | | | | 0 |
| AM18 clone 31 | | | | | | | | | | | | | | | | | | | | | | | | | | | | 0 |
| Dir Seq AM135 PCR clean up | | | | | | | | | | | | | | | | | | | | | | | | | | | | 1 |

INHBB breast 12

| CpG Site | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|
| AM25 clone 50 | | | | | | | | | | | | | | | | | | ■ | | | | | | | | | | 28 |
| AM26 clone 51 | | | | | | | | | | | | | | | | | | | | | | | | | | | | - |
| AM27 clone 52 | | | | | | | | | | | | | | | | | | | | | | | | | | | | - |
| AM28 clone 53 | | | | | | | | | | | | | | | | | | | | | | | | | | | | - |
| AM29 clone 54 | | | | | | | | | | | | | | | | | | | | | | | | | | | | - |
| AM30 clone 55 | | | | | | | | | | | | | | | | | | | | | | | | | | | | - |
| Dir Seq AM162 PCR clean up | | | | | | | | | | | | | | | | | | | | | | | | | | | | - |

| Breast Cell Lines | EN1 HL | SCTR HL |
|---|---|---|
| T47D | M/M | M/M |
| MDAMB453 | M/M | M/M |
| MDAMB468 | M/M | M/M |
| SKBR3 | M/M | M/M |
| LNCAP | U/U | M/M |
| DU145 | M/M | U/U |
| MDAMB231 | M/M | M/M |
| MCF-10A | U/U | U/U |
| MDAMB157 | U/U | M/U |
| MCF-7 | M/M | M/M |

Figure 22c

| Tumour | EN1 HL | SCTR HL | Tumour | EN1 | EN1 HL | SCTR | SCTR HL |
|---|---|---|---|---|---|---|---|
| 1 | U/M | U/M | 51 | | M/M | | U/U |
| 2 | U/M | U/U | 52 | | M/M | | U/U |
| 3 | M/M | M/M | 53 | | U/U | | M/M |
| 4 | M/M | U/M | 54 | | M/M | | M/M |
| 5 | M/- | U/- | 55 | | M/M | | M/M |
| 6 | M/- | U/U | 56 | | M/M | | M/M |
| 7 | U/U | U/U | 57 | | M/M | | M/M |
| 8 | U/M | U/U | 58 | | M/M | | U/U |
| 9 | M/M | U/U | 59 | | M/M | | U/U |
| 10 | M/M | M/M | 60 | | U/U | | U/U |
| 11 | U/M | U/M | 61 | | U/U | | U/U |
| 12 | M/M | M/M | 62 | | U/M | | U/M |
| 13 | M/M | M/M | 63 | NA | U/U | U | U/U |
| 14 | M/M | U/M | 64 | M | U/M | U | U/U |
| 15 | M/M | M/M | 65 | M | U/U | U | M/M |
| 16 | M/- | M/M | 66 | U | U/U | M | U/U |
| 17 | M/M | U/U | 67 | U | U/U | U | U/M |
| 18 | M/M | M/M | 68 | M | U/U | U | U/M |
| 19 | M/M | U/U | 69 | M | U/U | U | U/U |
| 20 | M/M | M/M | 70 | M | U/U | U | U/M |
| 21 | U/U | U/U | 71 | M | M/M | M | M/M |
| 22 | M/M | U/U | 72 | M | M/M | M | M/M |
| 23 | M/M | M/- | 73 | M | U/- | M | M/M |
| 24 | M/M | M/M | 74 | M | M/M | M | M/M |
| 25 | U/M | U/U | 75 | M | M/- | M | M/M |
| 26 | U/U | U/U | 76 | M | M/M | M | M/M |
| 27 | U/M | U/U | 77 | M | M/M | U | M/M |
| 28 | M/M | M/M | 78 | M | M/M | M | U/U |
| 29 | M/M | U/M | 79 | M | U/M | M | U/M |
| 30 | U/U | U/U | 80 | U | U/U | M | M/M |
| 31 | U/U | U/U | 81 | M | -/- | M | -/- |
| 32 | U/M | M/M | 82 | M | M/M | M | M/M |
| 33 | M/M | U/U | 83 | U | U/U | U | U/M |
| 34 | U/U | U/U | 84 | U | M/- | M | U/M |
| 35 | U/U | U/U | 85 | M | M/M | M | U/U |
| 36 | M/M | M/M | 86 | U | U/U | M | M/M |
| 37 | M/M | M/- | 87 | U | M/M | U | M/M |
| 38 | M/M | U/M | 88 | U | U/- | M | M/M |
| 39 | U/U | U/U | 89 | M | M/M | M | M/M |
| 40 | M/M | U/U | 90 | NA | U/- | NA | U/M |
| 41 | U/U | M/M | 91 | M/M | U/U | M/M | M/M |
| 42 | M/M | U/U | 92 | U/U | U/- | M/M | M/M |
| 43 | M/M | M/M | 93 | M/M | U/- | M/M | M/M |
| 44 | U/M | M/M | 94 | U/U | M/M | M/M | U/U |
| 45 | M/M | U/M | 95 | M/M | M/M | M/NA | U/U |
| 46 | U/U | U/U | 96 | U/U | M/M | M/M | M/M |
| 47 | U/M | M/M | 97 | M/M | M/- | M/M | M/M |
| 48 | M/M | U/U | 98 | M/M | M/M | M/M | M/M |
| 49 | M/M | U/M | 99 | U/M | M/M | M/M | M/M |
| 50 | M/M | M/M | 100 | M | M/M | M/M | M/M |

| EN-1 breast 13 | CpG Site | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|---|
| AM07 | clone 13 | . | . | . | . | . | . | . | . | . | . | . | . | . | . | . | . | . | . | . | . | . | . | . | . | . | . | . | 0 |
| AM08 | clone 14 | ■ | . | . | . | . | . | . | . | . | . | . | . | . | . | . | . | . | . | . | . | ■ | . | . | . | . | . | . | 3 |
| AM09 | clone 15 | . | . | . | . | ■ | . | . | . | . | . | . | . | . | . | . | . | . | . | . | . | . | . | . | . | . | . | . | 2 |
| AM10 | clone 16 | . | . | . | . | . | . | . | . | . | . | . | . | . | . | . | . | . | . | . | . | . | . | . | . | . | . | . | 1 |
| AM11 | clone 17 | ■ | ■ | . | . | . | . | . | . | . | . | . | . | . | . | . | . | . | . | . | . | . | . | . | . | . | . | . | 3 |
| AM12 | clone 18 | . | . | . | . | . | ■ | ■ | ■ | . | . | ■ | . | . | . | . | . | ■ | . | . | ■ | . | . | ■ | . | . | . | . | 5 |
| AM76 | clone 19 | . | . | . | . | . | . | . | . | . | . | . | . | . | . | . | . | . | . | . | . | . | . | . | . | . | . | . | 1 |
| AM77 | clone 20 | . | . | . | . | . | . | . | . | . | . | . | . | . | . | . | . | . | . | . | . | . | . | . | . | . | . | . | 1 |
| AM78 | clone 21 | . | . | . | ■ | ■ | . | . | . | . | . | . | . | . | . | . | . | . | . | . | . | ■ | . | . | . | . | . | . | 2 |
| AM79 | clone 22 | . | . | . | . | . | . | ■ | . | . | . | . | . | . | . | . | . | . | . | ■ | . | . | . | ■ | . | . | . | . | 3 |
| AM80 | clone 24 | . | . | ■ | ■ | ■ | . | . | . | . | . | . | . | . | . | . | . | . | . | . | . | . | . | . | . | . | . | . | 4 |
| Dir Seq AM161 | PCR clean up | . | . | . | . | . | . | . | . | . | . | . | . | . | . | . | . | . | . | . | . | . | . | . | . | . | . | . | |

| SCTR breast 13 | CpG Site | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|---|
| AM19 | clone 40 | . | . | . | . | . | . | . | . | . | . | . | . | . | . | . | . | . | . | . | . | . | ■ | ■ | . | . | . | . | 3 |
| AM20 | clone 41 | . | . | . | . | . | . | . | . | . | . | . | . | . | . | . | . | . | . | . | . | . | . | . | . | . | ■ | . | 0 |
| AM21 | clone 42 | . | . | ■ | . | . | . | . | . | . | . | . | . | . | . | . | . | . | . | . | ■ | ■ | ■ | . | . | . | . | . | 4 |
| AM23 | clone 44 | . | . | . | . | . | . | . | . | . | . | . | . | . | . | . | . | . | . | . | . | . | . | ■ | . | . | . | . | 2 |
| AM24 | clone 45 | . | . | . | . | . | . | . | . | . | . | . | . | . | . | . | . | . | . | . | . | . | . | . | . | . | . | . | 0 |
| Direct Sequencing | PCR clean up | . | . | . | . | . | . | . | . | . | . | . | . | . | . | . | . | . | . | . | . | . | . | . | . | . | . | . | 1 |

| INHBB breast 13 | CpG Site | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | Total |
|---|---|---|---|---|---|---|---|---|---|---|---|---|---|---|---|---|---|---|---|---|---|---|---|---|---|---|---|---|---|
| AM34 | clone 65 | . | . | . | . | . | . | . | . | . | . | . | . | . | . | . | . | . | . | . | . | . | . | . | . | . | . | . | 28 |
| AM35 | clone 66 | . | . | . | . | . | . | . | . | . | . | . | . | . | . | . | . | . | . | . | . | . | . | . | . | . | . | ■ | . |
| AM46 | clone 75 | . | . | . | . | . | . | . | . | . | . | . | . | . | . | . | . | . | . | . | . | . | . | . | . | . | . | . | . |
| AM47 | clone 76 | . | . | . | . | . | . | . | . | . | . | . | . | . | . | . | . | . | . | . | . | . | . | . | . | . | . | . | . |
| AM49 | clone 78 | . | . | . | . | . | . | . | . | . | . | . | . | . | . | . | . | . | . | . | . | . | . | . | . | . | . | . | . |
| Dir Seq AM139 | PCR clean up | . | . | . | . | . | . | . | . | . | . | . | . | . | . | . | . | . | . | . | . | . | . | . | . | . | . | . | . |

Figure 22f

| Pancreas Lines | EN1 | EN1 HL | INHBB | SCTR | SCTR HL |
|---|---|---|---|---|---|
| PANC-1 | M/M | U/U | U/U | U/U | U/U |
| ASPC-1 | M/M | M/M | U/U | M/M | M/M |
| BXPC-3 | U/U | U/U | M/M | U/U | M/- |
| MIAPACA-2 | M/M | M/M | M/M | U/U | M/M |
| CaPan-2 | M/M | M/M | U/U | M/M | U/U |
| HPAC | M/M | M/M | M/M | U/U | U/U |

Figure 23

METHOD OF DIAGNOSING CANCER AND REAGENTS THEREFOR

FIELD OF THE INVENTION

The present invention relates to the epigenetic state of a region of chromatin within the region of Chromosome 2 from about map position 2q14.1 to about 2q14.3 and its use to diagnose and/or monitor and/or prognose cancer

BACKGROUND OF THE INVENTION

1. General

This specification contains nucleotide and amino acid sequence information prepared using PatentIn Version 3.3, presented herein after the claims. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (e.g. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text; and
5. Perbal, B., A Practical Guide to Molecular Cloning (1984).

2. Description of the Related Art

Cancer is a major cause of morbidity throughout the world. For example, in 2001, the American Cancer Society estimated that 553,768 Americans died from a form of cancer. Cancer is responsible for 22.9 percent of all American deaths and is exceeded only by heart disease as a cause of mortality.

All studied forms of cancer share the characteristics abnormal cell division, growth, and differentiation. The initial clinical manifestations of cancers are generally heterogeneous, with over 70 types of cancer arising in each of a number of organs and tissues of the human body. Moreover, while some cancers may appear clinically similar they may actually represent different molecular diseases. This diversity in clinical and molecular characteristics make cancer difficult to diagnose. As a consequence, a variety of assays are required to detect even a small number of the known cancers.

Family history still remains the most reliable diagnostic procedure for identifying patients at risk of cancer.

Cancer surveillance has been effective for detecting some cancers in which risk can be identified, for example colorectal cancer in familial adenomatous polyposis coli and hereditary nonpolyposis colorectal cancer (Markey et al., *Curr. Gastroenterol. Rep.* 4: 404-413, 2002), but these syndromes cumulatively account for less than 1% of cancer patients (Samowitz et al., *Gastroenterology* 121: 830-838, 2001). Nevertheless, genetics is thought to contribute substantially to cancer risk, since the odds ratio for malignancy increases in patients with first degree relatives with cancer, e.g., 2 to 3-fold in colorectal cancer (Fuchs et al., *N. Engl. J. Med.* 331: 1669-1674, 1994). Therefore, there remains a need to develop genetic tests to identify these patients.

The detection of microsatellite instability as a diagnostic for cancer, requires the patient to have a detectable tumor beforehand and, as a consequence, is not an early test that can lead to early effective treatment. Microsatellite instability compares microsatellite marker length between the monoclonal tumor cell population and normal tissue derived from the same patient. As microsatellites are unstable in the population, an assay measuring such instability must include a control sample from the same subject. This leads to increased cost, as a number of samples must be assayed for each diagnosis performed.

Genetic changes that are associated with cancer include gene mutation in critical tumor-associated genes, as well as gene deletion or loss of heterozygosity (LOH) of larger regions harboring tumor suppressor genes. In addition to genetic changes it is clear that epigenetic changes are also a common hallmark of cancer DNA, with changes in both DNA methylations and histone modification of the CpG island regions spanning the promoters of tumor suppressor genes (Jones and Baylin, *Nat. Rev. Genet.* 3: 415-428, 2002). However, it is not clear as to the extent and nature of these epigenetic changes in cancer cells.

Changes in the state of methylation of DNA have been observed in cancer cells (Feinberg et al., Nature, 301: 89-92, 1983), including the loss of methylation at normally methylated sequences (hypomethylation) and the gain of methylated sequences at sites that are usually non-methylated (hypermethylation). For example, global hypomethylation has been reported in almost every human malignancy studied to date (Feinberg et al., supra and Bedford et al., *Cancer Res.*, 47: 5274-5276, 1987). More particularly, Gama-Sosa et al., (*Nucl. Acids Res.*, 11: 6883-6894) measured the levels 5-methylcytosine content by HPLC and showed a reduced level in cancer tissues compared to control tissues. However, the 5-methylcytosine content of a cell is not necessarily a measure of the level or extent of chromatin modification in these cells. Accordingly, the assay of Gama-Sosa et al., does not provide an accurate measurement of chromatin changes that are associated with cancer.

The major site for methylation in mammals is a cytosine located next to a guanine (5'-CpG-3'), including a so-called "CpG island". Generally, these targets of methylation are not distributed equally in the genome, but found in long GC-rich sequences present in satellite repeat sequences, middle repetitive rDNA sequences and centromeric repeat sequences. CpG islands are generally recognised as sequences of nucleic acid that comprise a GC content of over 50% (in contrast to a genome-wide average in humans of about 40%) and an observed over expected ration of CpG of 0.6 or greater (Gardiner-Garden and Frommer, *J. Mol. Biol.*, 196: 261 to 281, 1987; Takai and Jones, *Proc. Natl. Acad. Sci. USA*, 99: 3740-3745, 2002).

CpG islands can become de novo methylated in a cancer cell and this is associated with gene silencing. DNA hypermethylation of the CpG island region is also accompanied by local changes in histone modification, including de-acetylation and methylation of the lysine 9 residue of Histone H3 (K9-H3).

For example, CpG islands within the promoter regions of specific genes can be hypermethylated in some cancers, e.g., in the case of BRCA1 promoter hypermethylation in breast cancer (Dobrovic et al., *Cancer Res.*, 57: 3347-3350, 1997) and the VHL gene promoter hypermethylation in clear cell renal carcinomas (Herman et al., *Proc. Natl. Acad. Sci. USA*, 91: 9700-9704). However, the methylation of these genes is limited to discrete regions of these genes and shown to be useful only in relation to the detection of specific cancers (Plass, *Hum. Mol. Genet.*, 11: 2479-2488, 2002).

It is widely recognized that simple and rapid tests for the early detection of cancers, especially multiple cancer types, have considerable clinical potential. In view of the heterogeneity of cancers, it is difficult to produce a single diagnostic that is useful for different cancer types. Such tests have potential use for an initial diagnosis, as well as for determining prognostic outcomes e.g., for detecting tumor recurrence following surgical resection and/or chemotherapy. A molecular diagnostic approach that identifies patients with cancer or at risk of cancer, would offer a decisive advantage for intervention and treatment.

SUMMARY OF INVENTION

In work leading up to the present invention the inventors sought to identify changes in the human genome that occur in one or more cancers, to identify those regions of the genome in which changes are epigenetic and not necessarily limited to specific genes. Using samples from colon cancer subjects and cell models of prostate cancer and breast cancer as models of cancer generally, the inventors identified a short segment of chromosome 2 that is hypermethylated in tumors compared to healthy tissues or cells. This segment, designated the "Z fragment", showed increased levels of methylation in 63% of colorectal samples compared to normal matched controls. The Z fragment was mapped to an intergenic region of the human genome, located at map position 2q14.2.

Thus, in contrast to the prior art, hypermethylation of the Z fragment was not located in a specific gene, let alone in the nucleic acid forming the promoter region of a specific gene.

The inventors subsequently investigated changes in methylation of nucleic acid in the region flanking the Z fragment i.e., from about map position 2q14.1 to about 2q14.3, that contains a number of discrete CpG islands. The inventors showed that these CpG islands are extensively methylated in colorectal cancer tumor samples in addition to breast cancer and prostate cancer cell lines. For example, CpG islands associated with one or more of Engrailed-1 gene and/or secretin receptor gene and/or inhibin β-B gene was(were) methylated in 96% colorectal cancer samples tested and 96% of breast cancer samples tested. CpG islands associated with the Engrailed-1 gene and/or secretin receptor gene were methylated in 71% of ovarian cancer samples tested, 91% of prostate cancer samples tested and 78% of breast cancer samples tested. Accordingly, the modified methylation pattern in tumor samples was not limited to the Z fragment per se.

The inventors also showed that the degree of methylation of nucleic acid within the region of Chromosome 2 from about map position 2q14.1 to about 2q14.3 was predictive of the probability of survival of a subject suffering from cancer. For example, hypermethylation of a GpG island associated with the SCTR gene is predictive of an increased probability of survival in colorectal cancer subjects.

The inventors additionally demonstrated that the expression of several genes in the vicinity of the hypermethylated region of Chromosome 2 was reduced, indicating epigenetic effects in this region of the genome. In particular, the inventors showed reduced expression of genes in the region extending from about map position 2q14.1 to about map position 2q14.3 in tumor cell lines and colorectal cancer samples. This suppression of gene expression in tumor cells is irrespective of the methylation status of the promoter region of the gene(s) in this region.

Extending the studies further, the inventors showed that histones associated with the hypermethylated DNA were also modified (e.g., methylated and/or de-acetylated). The inventors showed histone modifications along a region of Chromosome 2 from about map position 2q14.1 to about map position 2q14.3 in tumor cell lines and colorectal cancer samples.

As methylation of gene promoters (or regions thereof) and histones is associated with gene silencing, the inventors determined the effect of a methylation inhibitor and/or a histone deacetylase inhibitor on expression of genes within this region of the genome. Both of these compounds were effective in enhancing gene expression levels from their repressed levels in cancer cells.

In particular, using a global methylation approach, AIMS (Amplification of Inter-Methylated Sites; Frigola et al., *Nucleic Acids Res.* 30: e28, 2002) and chromatin immunoprecipitation (Strizaker et al., *Cancer Res.*, 64: 3871-3877, 2004), the inventors have shown that epigenetic changes in cancer are not restricted to individual discrete CpG islands associated genes, but encompass multiple neighbouring CpG islands and genes. They demonstrate co-ordinate gene suppression across an entire 4 Mb cytogenetic band on human Chromosome 2q14.2 in colorectal cancer cells, and this suppression is relieved by "epigenetic therapy" using demethylation and de-acetylation treatment. The inventors demonstrate for the first time that epigenetic silencing in cancer can encompass large chromosomal regions, with equivalent implications in global gene silencing as that exhibited by gross genetic changes. The data provided suggest that aberrant DNA and histone methylation of large chromosomal regions are under co-ordinate control leading to concomitant epigenetic silencing of multiple linked genes in cancer cells.

These findings provide the basis for a novel method and reagents for diagnosing and/or prognosing cancer. Preferably, the method is for the early diagnosis of cancer or a predisposition therefor. For example, the present invention provides a method for diagnosing cancer or a predisposition therefor comprising identifying and/or detecting in a sample from the subject epigenetic modification, including DNA methylation and histone H3 lysine 9 (K-9) methylation relative to a non-cancerous sample within Chromosome 2 of the human genome from about map position 2q14.1 to about map position 2q14.3 and/or modified expression relative to a non-cancerous sample of a gene or nucleic acid positioned within Chromosome 2 from about map position 2q14.1 to about map position 2q14.3, wherein said e of the gene or nucleic acid is associated with said modified chromatin, and wherein said epigenetic modification and/or said modified expression is indicative of cancer or a predisposition therefor.

In one embodiment, the present invention provides a method for diagnosing a cancer or a predisposition therefor in a subject comprising identifying and/or detecting in a sample from the subject:
(i) modified chromatin relative to a non-cancerous sample said modified chromatin being positioned within Chromosome 2 of the human genome from about map position 2q14.1 to about map position 2q14.3; and/or
(ii) modified expression relative to a non-cancerous sample of a gene or nucleic acid positioned within Chromosome 2 from about map position 2q14.1 to about map position 2q14.3, wherein said modified expression of the gene or nucleic acid is associated with said modified chromatin;
wherein said modified chromatin and/or said modified expression is indicative of a cancer or a predisposition therefor in the subject.

Preferably, the present invention provides a method for diagnosing a cancer in a subject or a predisposition therefor comprising:
(i) providing or obtaining a biological sample comprising nucleic acid and/or protein from the subject; and
(ii) identifying or detecting using a detecting means modified chromatin relative to a non-cancerous sample within chromosome 2 of the human genome from about map position 2q14.1 to about map position 2q14.3 and/or modified expression relative to a non-cancerous sample of a gene or nucleic acid positioned within chromosome 2 from about map position 2q14.1 to about map position 2q14.3 wherein said modified expression of the gene or nucleic acid is associated with said modified chromatin,
wherein said modified chromatin and/or said modified expression is indicative of cancer or a predisposition therefor.

As used herein, the term "diagnosis", and variants thereof, such as, but not limited to "diagnose" or "diagnosing" shall include, but not be limited to, a primary diagnosis of a clinical state or any primary diagnosis of a clinical state. A diagnostic assay described herein is also useful for assessing the remission of a patient, or monitoring disease recurrence, or tumor recurrence, such as following surgery, radiation therapy, adjuvant therapy or chemotherapy, or determining the appearance of metastases of a primary tumor. All such uses of the assays described herein are encompassed by the present invention.

As used herein, the term "cancer" shall be taken to include a disease that is characterized by uncontrolled growth of cells within a subject. The term "cancer" shall not be limited to cancer of a specific tissue or cell type.

Those skilled in the art will be aware that as a carcinoma progresses, metastases occur in organs and tissues outside the site of the primary tumor. For example, in the case of many cancers, metastases commonly appear in a tissue selected from the group consisting of lymph nodes, lung, breast, liver, kidney and/or bone. Accordingly, the term "cancer" as used herein shall be taken to include a metastasis of a cancer in addition to a primary tumor.

Preferably, a cancer diagnosed using the method of the present invention comprises a cell characterized in having uncontrolled cell growth and having modified chromatin within chromosome 2 of the human genome from about map position 2q14.1 to about map position 2q14.3 and/or modified expression relative to a non-cancerous cell of a gene positioned within chromosome 2 from about map position 2q14.1 to about map position 2q14.3 compared to a non-cancerous cell.

In a preferred embodiment, the cancer is selected from the group consisting of a colon cancer, a prostate cancer, a breast cancer, an ovarian cancer or a pancreatic cancer. For example, the cancer is a colon cancer, a prostate cancer or a breast cancer. For example, the cancer is a colon cancer. Alternatively, the cancer is a prostate cancer. Alternatively, the cancer is a breast cancer.

As used herein, the term "chromatin" shall be taken to mean nucleic acid including a complex of nucleic acid (e.g., genomic DNA) and protein (e.g., one or more histones) such as a nucleosome. As will be understood by the skilled artisan, nucleic acid and protein e.g., histones, are generally packaged to form nucleosomes that form in the interphase nucleus of a cell It will be apparent from the disclosure herein that the state of chromatin can be determined for nucleic acid bound to protein, e.g., histone or in its naked form.

As used herein, the term "modified chromatin" shall be taken to mean a change in the relative amount of euchromatin and heterochromatin in a biological sample (e.g., a cell or a cell extract) from a subject produced by any means including reduced expression of a gene, hypermethylation or deacetylation of nucleic acid and/or histone. In the present context, modified chromatin is generally determined with reference to a baseline such as a non-cancerous sample, including a non-cancerous matched sample from a subject known to have a tumor.

As used herein, the term "unmodified chromatin" shall be taken to mean, for example, the that a gene is expressed at a level similar to or the same as a non-cancerous cell; and/or that the level of methylation of a nucleic acid is similar or the same as a non-cancerous cell; and/or that the level of acetylation/methylation of a histone that is the same or similar to a non-cancerous cell.

As will be apparent to the skilled person from the foregoing, "less-modified" chromatin will be altered to a smaller degree and/or only be altered in some aspects compared to modified chromatin. E.g., less modified chromatin may comprise nucleic acid that is hypermethylated, yet associated histones are not modified. Alternatively, or in addition, less modified chromatin comprises, for example, nucleic acid that is methylated to a degree less than that observed in modified chromatin.

The modified chromatin may include coding or non-coding nucleic acid. Non-coding nucleic acid is understood in the art to include an intron, a 5'-untranslated region, a 3' untranslated region, a promoter region of a genomic gene, or an intergenic region.

"Heterochromatin" is a region of chromatin that is highly condensed and associated with relatively low gene expression, i.e. substantially or completely inactive with respect to transcription. Without being bound by theory or mode of action, regions of DNA and some proteins (e.g., histones) in heterochromatin are often methylated and/or acetylated and these changes are thought to be associated with transcriptional inactivation and/or the condensation of the chromatin.

"Euchromatin" is a region of chromatin other than heterochromatin. Often euchromatin is poorly condensed and does not stain or stains poorly with compounds that bind to DNA. Euchromatin is associated with transcriptional activity in the genome. Furthermore, proteins associated with euchromatin may be modified, e.g., histones may be acetylated.

As used herein, the term "non-cancerous sample" shall be taken to include any sample from or including a normal or healthy cell or tissue, or a data set produced using information from a normal or healthy cell or tissue. For example, the non-cancerous sample selected from the group consisting of:
(i) a sample comprising a non-cancerous cell;
(ii) a sample from a normal tissue;
(iii) a sample from a healthy tissue;
(iv) an extract of any one of (i) to (iii);
(v) a data set comprising measurements of modified chromatin and/or gene expression for a healthy individual or a population of healthy individuals;
(vi) a data set comprising measurements of modified chromatin and/or gene expression for a normal individual or a population of normal individuals; and
(vii) a data set comprising measurements of the modified chromatin and/or gene expression from the subject being tested wherein the measurements are determined in a matched sample having normal cells. Preferably, the non-cancerous sample is (i) or (ii) or (v) or (vii).

As will be apparent to the skilled artisan from the preceding discussion, the modified chromatin region comprises a nucleic acid comprising at least a nucleotide sequence at least about 80% identical to the nucleotide sequence of the human Z fragment set forth in SEQ ID NO: 8.

The present inventors have also identified a number of genes within the region of chromatin modified in cancer. These genes within the diagnostic region of modified chromatin to which this invention relates comprise, for example, nucleic acid encoding one or more polypeptides selected from the group consisting of RALBB (SEQ ID NO: 35), DDX18 (SEQ ID NO: 37), secretin receptor (SCTR, SEQ ID NO: 39), engrailed-1 (SEQ ID NO: 41), Translin (SEQ ID NO: 43), macrophage receptor (MARCO, SEQ ID NO: 49), PTPN (SEQ ID NO: 51), insulin induced gene 2 (INSIG2, SEQ ID NO: 53), inhibin beta B (SEQ ID NO: 55), Gli2 (SEQ ID NO: 57), MGC13033 (SEQ ID NO: 59), TSAP6 (SEQ ID NO: 61), diazepam binding inhibitor (DBI, SEQ ID NO: 63), MGC10993 (SEQ ID NO: 65), EPB41L5 (SEQ ID NO: 67), FLJ14816 (SEQ ID NO: 69) and LBP9 (SEQ ID NO: 71).

Within the diagnostic region of modified chromatin, the present inventors have also identified a number of CpG islands that are hypermethylated in tumor samples relative to non-cancerous samples. The nucleotide sequences of these CpG islands are set forth herein as SEQ ID NOs: 1 to 33. The coordinates of CpG islands in the human genome as represented by the GenBank database of human genome sequences and Genome Browser (UCSC) locations as at July, 2003 are set forth in Table 1. The present invention clearly extends to using nucleic acid comprising one or more of said CpG islands to diagnose cancer in a subject.

TABLE 1

Sites of CpG islands methylated in cancer subjects.

| Identity | Mapped position on Chromosome 2 at July 2003 | Genbank Accession Number at July 2003 | Coordinates in Genbank record at July 2003 |
|---|---|---|---|
| DDX18 (CpG48) | chr2: 118667127-118667901 | AC009312 | 201413-202187 |
| INSIG2 (CpG 49) | chr2: 118940686-118941441 | AC009303 | 157655-158410 |
| CpG41.2 | chr2: 119038455-119039000 | AC093901 | 58772-59317 |
| CpG61 | chr2: 119076852-119077882 | AC093901 | 97169-98199 |
| CpG29 | chr2: 119626840-119628285 | AC018686 | 189282-190727 |
| 20Kb | chr2: 119661060-119661652 | AC012665 | 141-733 |
| Z(sma) | chr2: 119686319-119686515 | AC012665 | 25400-25596 |
| Z | chr2: 119686019-119687415 | AC012665 | 25100-26496 |
| CpG104 | chr2: 119688704-119689260 | AC012665 | 27785-28341 |
| CpG103 | chr2: 119694395-119696364 | AC012665 | 33476-35445 |
| CpG128 | chr2: 119697350-119701288 | AC012665 | 36431-40369 |
| CpG41 | chr2: 119702407-119703207 | AC012665 | 41488-42288 |
| CpG173 | chr2: 119709884-119710640 | AC012665 | 48965-49721 |
| CpG48 | chr2: 119711250-119712200 | AC012665 | 50331-51281 |
| CpG48rv | chr2: 119711663-119712200 | AC012665 | 51281-50744 |
| 5'-MARCO | chr2: 119794483-119795616 | AC013457 | 9525-10658 |
| CpG229 | chr2: 120009984-120010587 | AC016673 | 81784-82387 |
| TSAP6 (CpG 85) | chr2: 120076135-120077048 | AC016673 | 147935-148848 |
| DBI (CpG 85) | chr2: 120219365-120220719 | AC016736 | 107832-109186 |
| CpG85 | chr2: 120283727-120285081 | AC013275 | 24310-25664 |
| SCTR (CpG 67) | chr2: 120376560-120377666 | AC013275 | 117143-118249 |

TABLE 1-continued

Sites of CpG islands methylated in cancer subjects.

| Identity | Mapped position on Chromosome 2 at July 2003 | Genbank Accession Number at July 2003 | Coordinates in Genbank record at July 2003 |
| --- | --- | --- | --- |
| PTPN4 (CpG 86) | chr2: 120611869-120613338 | AC069154 | 162700-164169 |
| CpG102 | chr2: 120865458-120866450 | AC016691 | 56072-57064 |
| RALBB (CpG115) | chr2: 121104831-121106601 | AC012363 | 96835-98605 |
| INHBB(CpG285) | chr2: 121196743-121199830 | AC012363 | 188747-191799 |
| CpG26 | chr2: 121374777-121375541 | AC073257 | 61909-62673 |
| CpG206 | chr2: 121587789-121589963 | AC017033 | 3450-5624 |
| CpG22 | chr2: 121840762-121842394 | AC016764 | 74536-76168 |
| LBP9(CpG112) | chr2: 122137046-122138393 | AC079988 | 155212-156560 |
| CpG51 | chr2: 122382616-122383915 | AC012447 | 130012-131311 |
| CLASP1(CpG104) | chr2: 122501452-122502919 | AC018737 | 42832-44299 |
| CpG37 | chr2: 122589132-122589784 | AC018737 | 130512-131164 |
| TSN(CpG59) | chr2: 122607889-122608968 | AC018737 | 149269-150348 |

In this respect, the accession numbers and locations of the CpG islands described supra have been provided to describe the site of modified chromatin in cancer. These accession numbers and genome locations are those recorded by the Genome Browser at July 2003. The skilled artisan will be aware that the accession numbers and Chromosomal locations will vary depending on the database accessed. The skilled person will also be capable of determining the location and/or sequence of each CpG island using a different database (e.g., Unigene) based on the disclosure herein and/or the accession numbers and/or Chromosomal locations discussed supra.

In a preferred embodiment, the diagnostic region of modified chromatin comprises each of the CpG regions referred to in Table 1. Preferably, the region of chromatin extending from about map position 2q14.1 to about 2q14.3 comprises a nucleic acid comprising one or more nucleotide sequences referred to in Table 1 selected from the group consisting of CpG61, CpG29, 20 Kb, Z(sma), Z, CpG104, CpG103, CpG128, CpG41, CpG173, CpG48, CpG48rv, 5'-MARCO, CpG229, CpG67, INHBB(CpG285), CpG26, CpG206 and CpG22.

In another embodiment, the chromatin within Chromosome 2 of the human genome from about map position 2q14.1 to about map position 2q14.3 comprises one or more CpG islands comprising one or more nucleotide sequence(s) selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33. More preferably, the region of modified chromatin comprises a nucleic acid comprising one or more nucleotide sequences set forth in any one or more of SEQ ID NOs: 4 to 21. Even more preferably, the region of modified chromatin comprises a nucleic acid comprising one or more nucleotide sequences selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 25, SEQ ID NO: 28.

The present inventors have also shown that compounds useful for the treatment of a cancer also return the modified chromatin to a relatively normal or healthy state. For example, the present inventors have shown that treatment of a cancer cell with a histone de-acetylase inhibitor and/or a methylation inhibitor reduces the degree of modified chromatin in the region identified by the inventors. Accordingly, these findings also provide the basis of screening method for determining the efficacy of treatment of a subject for cancer. For example, in one embodiment, the present invention provides a method for monitoring the efficacy of treatment of a subject receiving treatment for a cancer, said method comprising identifying and/or detecting in a sample from the subject:

(i) unmodified chromatin or less-modified chromatin relative to a non-cancerous sample said unmodified chromatin or less-modified chromatin being positioned within Chromosome 2 of the human genome from about map position 2q14.1 to about map position 2q14.3; and/or (ii) unmodified expression relative to a non-cancerous sample of a gene or nucleic acid positioned within Chromosome 2 from about map position 2q14.1 to about map position 2q14.3, wherein said unmodified expression of the gene or nucleic acid is associated with said unmodified chromatin or less-modified chromatin;

wherein said unmodified chromatin or less-modified chromatin and/or said unmodified expression indicates that the treatment is effective.

In another embodiment, the present invention provides method for monitoring the efficacy of treatment of a subject receiving treatment for a cancer, said method comprising identifying and/or detecting in a sample from the subject:

(i) modified chromatin relative to a non-cancerous sample said modified chromatin being positioned within Chromosome 2 of the human genome from about map position 2q14.1 to about map position 2q14.3; and/or (ii) modified expression relative to a non-cancerous sample of a gene or nucleic acid positioned within Chromosome 2 from about map position 2q14.1 to about map position 2q14.3, wherein said modified expression of the gene or nucleic acid is associated with said modified chromatin wherein said modified chromatin and/or said modified expression indicates that the treatment is not effective.

The inventors also demonstrated that the degree of chromatin modification (e.g., nucleic acid methylation) within Chromosome 2 of the human genome from about map position 2q14.1 to about map position 2q14.3 is predictive of the probability of survival of a subject suffering from a cancer. Accordingly, another embodiment of the invention provides method for determining the likelihood of survival of a subject suffering from a cancer, said method comprising identifying and/or detecting in a sample from the subject
(i) modified chromatin relative to a non-cancerous sample said modified chromatin being positioned within Chromosome 2 of the human genome from about map position 2q14.1 to about map position 2q14.3; and/or
(ii) modified expression relative to a non-cancerous sample of a gene or nucleic acid positioned within Chromosome 2 from about map position 2q14.1 to about map position 2q14.3, wherein said modified expression of the gene or nucleic acid is associated with said modified chromatin;
wherein said modified chromatin and/or said modified expression indicates that the subject is likely to survive.

Preferably, the prognostic assay of the present invention permits determination of the likelihood that a subject being tested will survive to the short term (i.e., in the period up to about 1 year from primary diagnosis) or medium term (i.e., in the period up to about 1-3 years from primary diagnosis or longer). For example, the modified chromatin and/or said modified expression indicates that the subject is likely to survive for at least about 3 years or 4 years or 5 years. In this respect, the likelihood of survival is relative to a subject that has unmodified chromatin/less-modified chromatin and/or unmodified expression/less-modified expression.

Suitable nucleic regions of Chromosome 2 will be apparent to the skilled artisan from the description herein in respect of any embodiment of the present invention.

In one embodiment, modified chromatin is detected or identified by performing a process comprising determining the level of heterochromatin relative to euchromatin in the sample, wherein an enhanced level of heterochromatin relative to euchromatin is indicative of modified chromatin. Preferably, the method of the invention additionally comprises determining the level of heterochromatin relative to euchromatin in the non-cancerous sample.

As will be apparent to the skilled person, a method for detecting or identifying modified chromatin in a sample relative to a non-cancerous sample may comprise comparing (i) the level of heterochomatin relative to euchromatin the sample from the subject and (ii) the level of heterochromatin relative to euchromatin in the non-cancerous sample, wherein an enhanced level of heterochomatin relative to euchromatin in the sample from the subject compared to the non-cancerous sample is indicative of modified chromatin in the sample relative to the non-cancerous sample.

As will be apparent from the preceding discussion, detecting modified chromatin shall be taken to include detecting a marker of modified chromatin, such as, for example, detecting the level of methylation of nucleic acid and/or hypermethylation of nucleic acid in the chromatin, detecting the level of methylation and/or de-acetylation of one or more histones (e.g., histone H3) in the chromatin and/or detecting the level of expression of a gene or nucleic acid of one positioned within the chromatin. Suitable methods for the detection of such markers are known in the art and/or described herein.

For example, the method of the invention comprises:
(i) determining modified chromatin within Chromosome 2 of the human genome from about map position 2q14.1 to about map position 2q14.3 in a sample from said subject;
(ii) determining the chromatin modification within Chromosome 2 of the human genome from about map position 2q14.1 to about map position 2q14.3 in a non-cancerous sample; and
(iii) comparing the modified chromatin at (i) compared to (ii).

In one embodiment, modified chromatin or unmodified chromatin or less-modified chromatin is identified and/or detected by performing a process comprising identifying and/or detecting methylation of nucleic acid in the sample from the subject relative to a non-cancerous sample, wherein said nucleic acid is positioned within Chromosome 2 of the human genome from about map position 2q14.1 to about map position 2q14.3, and wherein enhanced methylation in the sample relative to the non-cancerous sample is indicative of modified chromatin and the same level or a reduced level of methylation in the sample from the subject relative to the non-cancerous sample is indicative of unmodified or less modified chromatin. For example, methylation of nucleic acid is determined by:
(i) identifying and/or detecting the level of methylation of a nucleic acid within Chromosome 2 of the human genome from about map position 2q14.1 to about map position 2q14.3 in the sample derived from the subject;
(ii) identifying and/or detecting the level of methylation of the nucleic acid within Chromosome 2 of the human genome from about map position 2q14.1 to about map position 2q14.3 in a non-cancerous sample; and
(ii) comparing the degree of methylation at (i) compared to (ii), Preferably, the modified methylation is identified and/or detected in one or more nucleic acid(s) comprising one or more nucleotide sequence(s) selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 25, SEQ ID NO: 28.

Alternatively, or in addition, the modified methylation is identified and/or detected in one or more nucleic acid(s) comprising one or more nucleotide sequence(s) referred to in Table 1. For example, a nucleic acid comprising a nucleotide sequence selected from the group consisting of CpG61, CpG29, 20 Kb, Z(sma), Z, CpG104, CpG103, CpG128, CpG41, CpG173, CpG48, CpG48rv, 5'-MARCO, CpG229, CpG67, INHBB(CpG285), CpG26, CpG206 and CpG22.

In this respect, the present inventors have clearly demonstrated the detection of a large proportion of cancer samples tested by detecting or identifying and/or detecting modified methylation of a plurality of CpG islands or nucleic acids disclosed herein. Accordingly, in one embodiment, the present invention comprises identifying and/or detecting modified methylation in a plurality of nucleic acids described herein. Nucleic acids that are methylated in cancer described herein in respect of any one or more embodiments of the invention are to be taken to apply mutatis mutandis to this embodiment of the invention.

Preferably, the modified methylation is identified and/or detected in a nucleic acid comprising a nucleotide sequence set forth in SEQ ID NO: 11 (or designated CpG128 in Table 1), a nucleic acid comprising a nucleotide sequence set forth in SEQ ID NO: 21 (or designated CpG67 in Table 1), and a nucleic acid comprising a nucleotide sequence set forth in SEQ ID NO: 25 (or designated INHBB(CpG285) in Table 1).

Even more preferably, the modified methylation is identified and/or detected in a nucleic acid comprising a nucleotide sequence set forth in SEQ ID NO: 11 (or designated CpG128 in Table 1) and a nucleic acid comprising a nucleotide sequence set forth in SEQ ID NO: 25 (or designated CpG67 in Table 1).

In one embodiment, the methylation of a nucleic acid is identified and/or detected by performing methylation-sensitive endonuclease digestion of DNA from the sample.

In another embodiment, the method for identifying and/or detecting the methylation of a nucleic acid comprises treating nucleic acid from the sample with an amount of a compound that selectively mutates non-methylated cytosine residues in nucleic acid under conditions sufficient to induce mutagenesis. For example, the compound is a metal salt of bisulphite, e.g., sodium bisulphite or potassium bisulphite.

The method of the invention may also comprise amplifying nucleic acid using primers that flank or are adjacent to a methylated cytosine residue or mutated residue at an equivalent position in non-methylated nucleic acid. For example, the primers flank or adjacent to a nucleic acid comprising one or more nucleotide sequences selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 25, SEQ ID NO: 28 or nucleic acid comprising one or more nucleotide sequences referred to in Table 1 selected from the group consisting of CpG61, CpG29, 20 Kb, Z(sma), Z, CpG104, CpG103, CpG128, CpG41, CpG173, CpG48, CpG48rv, 5'-MARCO, CpG229, CpG67, INHBB(CpG285), CpG26, CpG206 and CpG22. By way of exemplification only, a primer comprises a nucleotide sequence set forth in any one of SEQ ID NOs: 72 to 199.

As exemplified herein, the present inventors have also determined the nucleotide sequence of the amplified nucleic acid to thereby detect and/or identify modified methylated nucleic acid. Alternatively, or in addition, the inventors have also determined a temperature at which the amplified nucleic acid denatures, wherein said temperature is indicative of the methylation of the nucleic acid.

In another embodiment, the method for detecting and/or identifying methylation of a nucleic acid comprises detecting the amplified fragments with a nucleic acid probe capable of specifically hybridizing to the amplified fragment, for example, the nucleic acid probe is capable of selectively hybridizing to a nucleic acid comprising one or more methylated cytosine residues.

The present inventors have also used head-loop PCR to identify and/or detect modified methylation of one or a plurality of CpG sites in colorectal cancer, breast cancer or prostate cancer. Accordingly, the present invention additionally encompasses a method comprising:
(i) treating the nucleic acid with an amount of a compound that selectively mutates a non-methylated cytosine residue under conditions sufficient to induce mutagenesis thereby producing a mutated nucleic acid;
(ii) performing an amplification reaction with nucleic acid primers comprising a nucleotide sequence that is complementary to a sequence flanking or adjacent to a methylated cytosine residue or mutated residue at an equivalent position in non-methylated nucleic acid, wherein at least one of said probes or primers comprises a region that selectively hybridizes to an amplicon comprising a nucleotide sequence complementary to the mutated residue produced in the amplification reaction thereby forming a hairpin nucleic acid and preventing further amplification of said nucleic acid;
(iii) detecting the amplified nucleic acid.

In another embodiment of the invention, modified chromatin or unmodified chromatin or less-modified chromatin is identified and/or detected by performing a process comprising identifying and/or detecting a modified histone in the sample from the subject relative to the non-cancerous sample, wherein said modified histone is positioned within Chromosome 2 of the human genome from about map position 2q14.1 to about map position 2q14.3 and wherein an enhanced level of said modified histone in the sample relative to the non-cancerous sample is indicative of modified chromatin and the same or a reduced level of said modified histone in the sample from the subject relative to the non-cancerous tissue is indicative of unmodified or less-modified chromatin. For example, a histone modification selected from the group consisting of methylation of a histone, acetylation of a histone, de-acetylation of a histone, phosphorylation of a histone and mixtures thereof is determined. Preferably, the histone modification is methylation of a histone or de-acetylation of a histone. In a particularly preferred embodiment, the histone modification is methylation of a lysine residue in Histone H3.

In one embodiment, modified histone is identified and/or detected by performing a method comprising:
(i) identifying and/or detecting modified histone in chromatin within Chromosome 2 of the human genome from about map position 2q14.1 to about map position 2q14.3 in a sample from the subject;
(ii) identifying and/or detecting modified histone in chromatin within Chromosome 2 of the human genome from about map position 2q14.1 to about map position 2q14.3 in a non-cancerous sample; and
(iii) comparing the level of modified histone at (i) and (ii)

In this respect, the present inventors have identified and/or detected modified chromatin using chromatin immunoprecipitation (ChIP). Accordingly, one embodiment of the invention provides a method for determining modified chromatin in a sample, comprising:
(i) contacting a biological sample comprising chromatin within Chromosome 2 of the human genome from about map position 2q14.1 to about map position 2q14.3 with an antibody that selectively binds to a modified histone for a time and under conditions sufficient for an antibody-antigen complex to form; and
(ii) determining the amount of nucleic acid from within Chromosome 2 of the human genome from about map position 2q14.1 to about map position 2q14.3 bound to the antibody-antigen complex,
wherein the amount of said nucleic acid is indicative of the amount of modified histone in chromatin within chromosome 2 of the human genome from about map position 2q14.1 to about map position 2q14.3. For example, the amount of nucleic acid is determined using an amplification reaction, e.g., PCR. Preferably, said amplification reaction is performed using a probe or primer (e.g., comprising one or more nucleotide sequence selected from the group consisting of in SEQ ID NOs: 236-255) labeled with a detectable marker to facilitate determining the amount of said nucleic acid.

The present inventors have also demonstrated that modified expression of a gene or nucleic acid within Chromosome 2 from about map position 2q14.1 to about map position 2q14.3 of the human genome in a sample from a subject relative to a non-cancerous cell is indicative of an enhanced degree of chromatin modification. For example, modified expression is determined by performing a method comprising:
(i) determining the level of expression of a nucleic acid positioned within Chromosome 2 from about map position 2q14.1 to about map position 2q14.3 of the human genome in the sample derived from a subject;
(ii) determining the level of expression of a nucleic acid positioned within Chromosome 2 from about map position 2q14.1 to about map position 2q14.3 of the human genome in a suitable control sample,
wherein a reduced level of expression at (i) compared to (ii) is indicative of an enhanced degree of chromatin modification.

As exemplified herein, the present inventors have determined the level of mRNA encoded by a number of nucleic acid located within the diagnostic region of chromatin. Accordingly, in one embodiment, the method comprises determining the level of expression of a nucleic acid is selected from the group consisting of RALBB, DDX18, SCTR, EN1, TSN, MARCO, PTPN4, INSIG2, INHBB, Gli2, MGC13033, TSAP6, DBI, MGC10993, EPB41L5, FLJ14816, LBP9 and mixtures thereof.

In this respect, the level of expression of the nucleic acid is, preferably, determined by performing a process comprising hybridizing a nucleic acid probe or primer capable of specifically hybridizing to a transcript of a nucleic acid positioned within chromosome 2 from about map position 2q14.1 to about map position 2q14.3 to a nucleic acid in a biological sample derived from a subject and detecting the level of hybridization by a detection means. For example, the detection means is a hybridization reaction or an amplification reaction (e.g. PCR).

Suitable probes and/or primers will be apparent to the skilled artisan based on the description herein. For example, the probe or primer comprises a nucleotide sequence selected from the group consisting of SEQ ID NOs: 200-219. Preferably, such a probe or primer is labeled with a detectable marker (e.g., a fluorescent marker) to thereby facilitate determining the level of expression of a nucleic acid.

In another embodiment, the method of the invention comprises identifying and/or detecting the level of expression of gene or nucleic acid compared to a non-cancerous sample said nucleic acid or gene being positioned within Chromosome 2 of the human genome from about map position 2q14.1 to about map position 2q14.3, wherein a reduced level of expression indicates that the subject suffers from cancer or has a predisposition therefor or that the treatment is not effective or that the subject has a high probability of survival and wherein an enhanced level of expression indicates that the subject does not suffer from cancer or does not have a predisposition therefor or that the treatment is effective or that the subject has a low probability of survival.

In another embodiment, the level of expression of a nucleic acid is determined by determining the level of a polypeptide encoded by said nucleic acid. In accordance with this embodiment, the level of expression of the nucleic acid is determined by performing a process comprising:
(i) contacting a biological sample derived from a subject with an antibody capable of specifically binding to a protein encoded by a nucleic acid located within Chromosome 2 from about map position 2q14.1 to about map position 2q14.3 for a time and under conditions sufficient for an antibody/ligand complex to form; and
(ii) determining the amount of said complex,
wherein the amount of said complex is indicative of the level of expression of said nucleic acid.

Preferably, protein is selected from the group consisting of RALBB, DDX18, SCTR, EN1, TSN, MARCO, PTPN4, INSIG2, INHBB, Gli2, MGC13033, TSAP6, DBI, MGC10993, EPB41L5, FLJ14816 and LBP9.

The present invention also provides a process for diagnosing a cancer or a predisposition therefor or monitoring the efficacy of treatment or determining the likelihood of survival comprising recommending the method of the invention as described in any embodiment herein to a subject. Preferably, this process further comprises performing a method of the present invention as described in any one or more embodiments.

Accordingly, in one embodiment, the present invention provides a process of diagnosing a cancer or a predisposition therefor or monitoring the efficacy of treatment or determining the likelihood of survival, said process comprising:
(i) detecting a marker associated with a cancer in a subject; and
(ii) recommending or performing a method for diagnosing a cancer or a predisposition therefor or monitoring the efficacy of treatment or determining the likelihood of survival of the invention as described in any embodiment herein.

In another embodiment, the process comprises:
(i) performing a method for diagnosing a cancer or a predisposition therefor or monitoring the efficacy of treatment or determining the likelihood of survival of the invention as described in any embodiment herein; and
(ii) recommending or performing a method to detect one or more markers associated with a cancer in the subject.

Preferably, the method of the previous two embodiments comprises performing a method of the invention as described in any one or more embodiments herein and performing a method to detect one or more markers associated with a cancer in the subject.

The present invention also clearly contemplates a multi-analyte assay for diagnosing cancer. For example, such a multi-analyte assay comprises detecting a plurality of markers described herein. For example, the multi-analyte assay detects one or more markers described herein in any one or more embodiments of the present invention and detecting one or more additional markers of a cancer.

As the methods of the present invention are useful for determining whether or not a subject is likely to suffer from a cancer, these methods are also useful in methods of treatment of cancer. Accordingly, in one embodiment, the present invention provides a method of treatment comprising:
(i) performing a method described herein for diagnosing a cancer or a predisposition therefor; and
(ii) administering or recommending a therapeutic for the treatment or prophylaxis of cancer.

Preferably, the administration or recommendation of a therapeutic for the treatment of a cancer is based upon the diagnosis of a cancer.

As discussed supra, the present inventors have shown that compounds useful for the treatment of cancer reduce the degree of chromatin modification in the region of chromatin identified by the inventors. These findings also provide the basis for a screening method for identifying compounds useful for the treatment of cancer. Accordingly, in another embodiment, the presenter invention provides a method for determining a candidate compound for the treatment of a cancer comprising:
(i) administering a candidate compound to a cancer cell and determining the level of modified chromatin within Chromosome 2 from about map position 2q14.1 to about map position 2q14.3 in said cell;
(ii) determining the level of modified chromatin within Chromosome 2 from about map position 2q14.1 to about map position 2q14.3 in a non-cancerous cell; and
(iii) comparing the level of modified chromatin at (i) and (ii), wherein a similar level of modified chromatin at (i) relative to (ii) indicates that the compound is a candidate compound for the treatment of a cancer. Preferably, the cells at (i) and (ii) are derived from the same tissue type and, more preferably, the cells at (i) and (ii) are the same cell type.

The present invention also provides a method for determining a candidate compound for the treatment of a cancer comprising:

(i) administering a candidate compound to a cancer cell and determining the level of modified chromatin within Chromosome 2 from about map position 2q14.1 to about map position 2q14.3 in said cell;

(ii) determining the level of modified chromatin within Chromosome 2 from about map position 2q14.1 to about map position 2q14.3 in a cancer cell in the absence of the candidate compound; and (iii) comparing the level of modified chromatin at (i) and (ii), wherein a reduced level of modified chromatin at (i) relative to (ii) indicates that the compound is a candidate compound for the treatment of a cancer. Preferably, the cells at (i) and (ii) are of the same type.

The present inventors have also produced a number of probes and/or primers for determining the degree of chromatin modification in a sample and/or for diagnosing a cancer in said subject. Accordingly, the present invention additionally provides an isolated nucleic acid probe or primer that is capable of selectively hybridizing to a nucleic acid positioned within Chromosome 2 from about map position 2q14.1 to about map position 2q14.3 that is methylated in a cancer.

Also provided is an isolated nucleic acid probe or primer that is capable of selectively hybridizing to a nucleic acid positioned within Chromosome 2 from about map position 2q14.1 to about map position 2q14.3 that is bound by a modified histone in a cancer.

The present invention also provides an isolated nucleic acid probe or primer that is capable of selectively hybridizing to a nucleic acid positioned within Chromosome 2 from about map position 2q14.1 to about map position 2q14.3 that is expressed at a modified level in a cancer.

For example, the present invention provides an isolated nucleic acid probe or primer consisting of a nucleotide sequence selected from the group consisting of SEQ ID NOs: 72-219 or 224-259.

BRIEF DESCRIPTION OF THE DRAWINGS

FIG. 6 is a tabular representation showing a summary of the DNA methylation profile across the 83 kb region encompassing the Z fragment. The degree of methylation was determined by direct PCR sequencing in 2 colorectal cell lines (HCT116 and SW480) and 2 pairs of cancer (9T and 16T) and matched normal samples (9N and 165N). The name of the CpG islands are indicated (and correspond to those in FIG. 3), as are the co-ordinates from Genome Browser Human (July 2003) and the distance in kilobases (Kb) from the Z fragment. CpGi denotes presence or absence of a CpG island. A white square indicates about 0-25% methylation, a dotted pale grey square indicates about 25-50% methylation, a grey square indicates about 50-75% methylation and a black square indicates about 75-100% methylation.

FIG. 12a is a tabular representation showing DNA methylation of the following CpG sites: CpG128 (EN1 promoter), SCTR (SCTR) and INHBB (INHBB) in 26 colorectal samples. Methylation status was determined using direct PCR sequencing. Sample number, age, sex and Duke stage is also indicated. A methylated CpG island is indicated by a black square and an unmethylated CpG island is indicated by a white square.

FIG. 12b is a tabular representation showing DNA methylation of the following CpG sites: Z fragment, EN1, SCTR and INHBB in 50 colorectal samples. Methylation status was determined using heat-dissociation real-time PCR. A methylated CpG island is indicated by a black square and an unmethylated CpG island is indicated by a white square.

FIG. 13 is a tabular representation showing results of direct PCR bisulphite sequencing of the CpG islands, CpG128 (EN1 promoter), SCTR (SCTR) and INHBB (INHBB) in 13 colon cancer cell lines. A methylated CpG island is indicated by a black square and an unmethylated CpG island is indicated by a white square.

FIG. 19*a* is a graphical representation showing the methylation of CpG dinucleotides in breast cancer cell lines (T47D, MDA MB453, MDA MB 468, SKBR3, KPL1, MDA MB 231, DU4475, MCF-7, MDA MB 157 and MCF-10A) and prostate cancer cell lines (LNCaP and DU145). Each box in a row represents a distinct CpG dinucleotide. Each box in a column represents the result obtained from a distinct clone. The CpG island tested was the Z fragment as set forth in Table 1. Dark shading and/or the symbol "+" represents a methylated CpG dinucleotide. Light shading and/or the symbol "−" represents an unmethylated CpG dinucleotide. The symbol "B" represents a clone that was blocked and could not be scored by sequencing.

FIG. 19*b* is a graphical representation showing the methylation of CpG dinucleotides in breast cancer cell lines (T47D, MDA MB453, MDA MB 468, SKBR3, KPL1, MDA MB 231, DU4475, MCF-7, MDA MB 157 and MCF-10A) and prostate cancer cell lines (LNCaP and DU145). Each box in a row represents a distinct CpG dinucleotide. Each box in a column represents the result obtained from a distinct clone. The CpG island tested was CpG128 as set forth in Table 1. Dark shading and/or the symbol "+" represents a methylated CpG dinucleotide. Light shading and/or the symbol represents an umethylated CpG dinucleotide. The symbol "B" represents a clone that was blocked and could not be scored by sequencing.

FIG. 19*c* is a graphical representation showing the methylation of CpG dinucleotides in breast cancer cell lines (T47D, MDA MB453, MDA MB 468, SKBR3, KPL1, MDA MB 231, DU4475, MCF-7, MDA MB 157 and MCF-10A) and prostate cancer cell lines (LNCaP and DU145). Each box in a row represents a distinct CpG dinucleotide. Each box in a column represents the result obtained from a distinct clone. The CpG island tested was CpG48 as set forth in Table 1. Dark shading and/or the symbol "+" represents a methylated CpG dinucleotide. Light shading and/or the symbol represents an unmethylated CpG dinucleotide. The symbol "B" represents a clone that was blocked and could not be scored by sequencing.

FIG. 19*d* is a graphical representation showing the methylation of CpG dinucleotides in breast cancer cell lines (T47D, MDA MB453, MDA MB 468, SKBR3, KPL1, MDA MB 231, DU4475, MCF-7, MDA MB 157 and MCF-10A) and prostate cancer cell lines (LNCaP and DU145). Each box in a row represents a distinct CpG dinucleotide. Each box in a column represents the result obtained from a distinct clone. The CpG island tested was SCTR as set forth in Table 1. Dark shading and/or the symbol "+" represents a methylated CpG dinucleotide. Light shading and/or the symbol "−" represents an unmethylated CpG dinucleotide. The symbol "B" represents a clone that was blocked and could not be scored by sequencing.

FIG. 20*a* is a tabular representation showing the methylation status of three CpG islands in the ovarian cancer cell lines SW626, OVCA420, A2780, TOV21G, IGROV1, SKOV3, OV90, TOV112 and HOSE6-3, as indicated. The CpG islands tested were EN1, INHBB and SCTR, as indicated and correspond to the CpG islands described herein. Methylation status was determined using heat-dissociation real-time PCR (columns labeled with only the name of the CpG island) or headloop PCR (columns labeled with HL). Dark grey indicates methylation detected in duplicate assays (also indicated by the symbol "M/M"). Light grey indicates methylation detected in one of two assays (also indicated by the symbol "U/M"). White indicates no methylation across the CpG island (also indicated by the symbol "U/U").

FIG. 20b is a tabular representation showing the methylation status of two CpG islands in 27 ovarian cancer samples. The CpG islands tested were EN1 and SCTR, as indicated and correspond to the CpG islands described herein. Methylation status was determined using headloop PCR (columns labeled with HL). Dark grey indicates methylation detected in duplicate assays (also indicated by the symbol "M/M"). Light grey indicates methylation detected in one of two assays (also indicated by the symbol "U/M"). White indicates no methylation across the CpG island (also indicated by the symbol "U/U").

FIG. 22a is a tabular representation showing the methylation status of two CpG islands in 8 breast cancer cell lines (T47D, MDAMB453, MDAMB468, SKBR3, MDAMB231, MCF-10A, MDAMB157 and MCF-7) and two prostate cancer cell lines (LNCaP and DU145). The CpG islands tested were EN1 and SCTR, as indicated and correspond to the CpG islands described herein. Methylation status was determined using headloop PCR (columns labeled with HL). Dark grey indicates methylation detected in duplicate assays (also indicated by the symbol "M/M"). Light grey indicates methylation detected in one of two assays (also indicated by the symbol "U/M"). White indicates no methylation across the CpG island (also indicated by the symbol "U/U").

FIG. 22b is a tabular representation showing the methylation status of two CpG islands in 12 prostate cancer samples and matched control samples. The CpG islands tested were EN1 and SCTR, as indicated and correspond to the CpG islands described herein. Methylation status was determined using heat-dissociation real-time PCR (columns labeled with only the name of the CpG island) or headloop PCR (columns labeled with HL). Dark grey indicates methylation detected in duplicate assays (also indicated by the symbol "M/M"). Light grey indicates methylation detected in one of two assays (also indicated by the symbol "U/M"). White indicates no methylation across the CpG island (also indicated by the symbol "U/U").

FIG. 22c is a tabular representation showing the methylation of CpG dinucleotides in normal prostate epithelium for the CpG islands tested were EN1 and SCTR. Each box in a row represents a distinct CpG dinucleotide. Each box in a column represents the result obtained from a distinct clone. Dark shading and/or the symbol "+" represents a methylated CpG dinucleotide. Light shading and/or the symbol "−" represents an unmethylated CpG dinucleotide.

FIG. 22d is a tabular representation showing the methylation status of two CpG islands in 100 breast cancer samples. The CpG islands tested were EN1 and SCTR, as indicated and correspond to the CpG islands described herein. Methylation status was determined using heat-dissociation real-time PCR (columns labeled with only the name of the CpG island) or headloop PCR (columns labeled with HL). Dark grey indicates methylation detected in duplicate assays (also indicated by the symbol "M/M"). Light grey indicates methylation detected in one of two assays (also indicated by the symbol "U/M"). White indicates no methylation across the CpG island (also indicated by the symbol "U/U").

FIG. 22e is a tabular representation showing the methylation of CpG dinucleotides in normal breast tissue for the CpG islands tested were EN1 and SCTR. Each box in a row represents a distinct CpG dinucleotide. Each box in a column represents the result obtained from a distinct clone. Dark shading and/or the symbol "+" represents a methylated CpG dinucleotide. Light shading and/or the symbol "−" represents an unmethylated CpG dinucleotide.

FIG. 22f is a tabular representation showing the methylation of CpG dinucleotides in normal breast tissue for the CpG islands tested were EN1 and SCTR. Each box in a row represents a distinct CpG dinucleotide. Each box in a column represents the result obtained from a distinct clone. Dark shading and/or the symbol "+" represents a methylated CpG dinucleotide. Light shading and/or the symbol "−" represents an unmethylated CpG dinucleotide.

FIG. 23 is a tabular representation showing the methylation status of three CpG islands in 100 breast cancer samples. The CpG islands tested were EN1, INHBB and SCTR, as indicated and correspond to the CpG islands described herein. Methylation status was determined using heat-dissociation real-time PCR (columns labeled with only the name of the CpG island) or headloop PCR (columns labeled with HL). Dark grey indicates methylation detected in duplicate assays (also indicated by the symbol "M/M"). Light grey indicates methylation detected in one of two assays (also indicated by the symbol "U/M"). White indicates no methylation across the CpG island (also indicated by the symbol "U/U").

DETAILED DESCRIPTION OF THE PREFERRED EMBODIMENTS

Suitable Cancers

Figure 1:
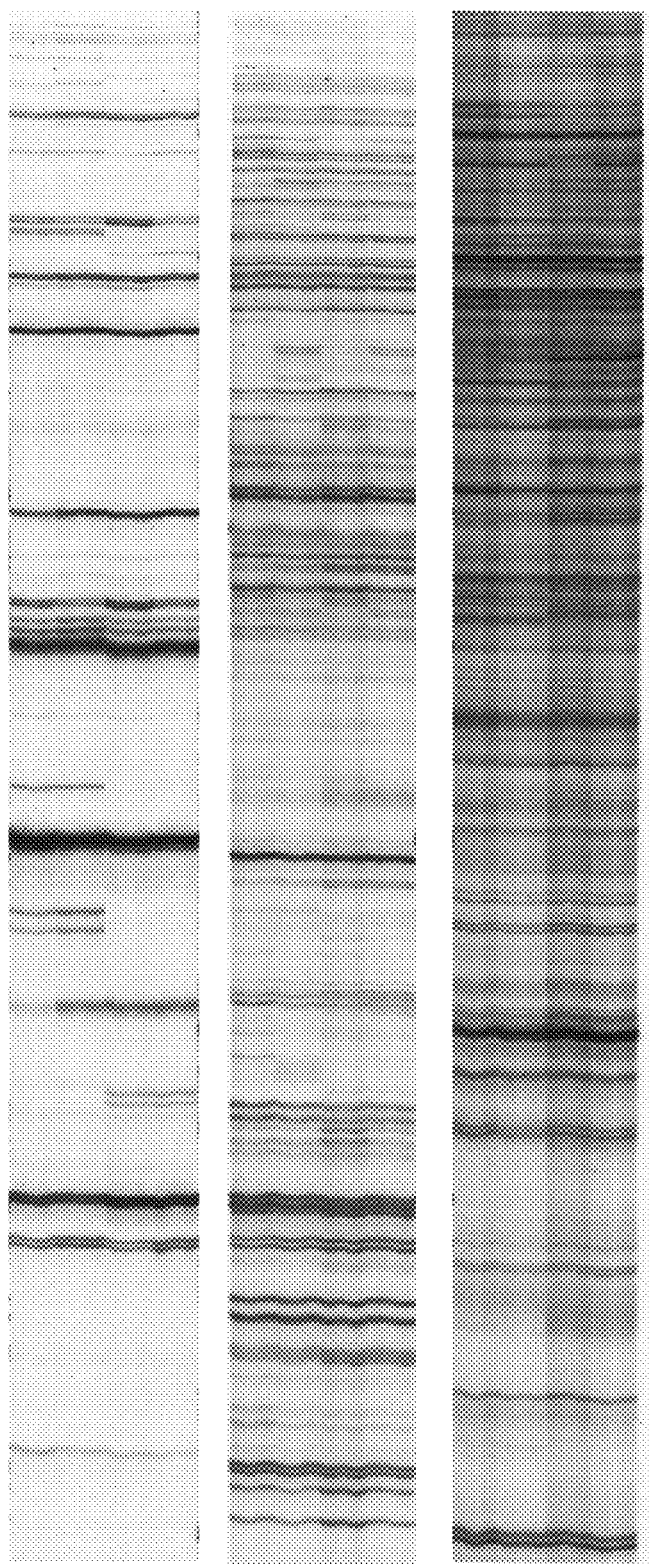
FIG. 1 is a copy of a photographic representation showing polyacrylamide gels on which nucleic acid isolated using the AIMS method has been electrophoresed. Lanes labeled "N" contain nucleic acid from normal non-cancerous samples and lanes labeled "T" contain nucleic acid from tumor samples.

The present invention encompasses the diagnosis of any cancer. For example, the present invention contemplates the diagnosis of a cancer selected from the group consisting of a breast cancer, a prostate cancer, a lung cancer, a cancer of the bronchus, a colon cancer, a rectal cancer, a cancer of the urinary bladder, a kidney cancer, a cancer of the renal pelvis, a pancreatic cancer, a head and/or neck cancer, a laryngeal cancer, a oropharyngeal cancer, a cancer of the tongue, an ovarian cancer, a thyroid cancer, a stomach cancer, a brain tumor, a cancer of the brain, a multiple myeloma, a cancer of the esophagus, a liver cancer, a cancer of the intrahepatic bile duct, a cervical cancer, a chronic lymphocytic leukemia, a soft tissue cancer, a heart cancer, a Hodgkin lymphoma, a non-Hodgkin lymphoma, a testicular cancer, a cancer of the small intestine, a cancer of the anus, a cancer of the anal canal, a cancer of the anorectum, a vulval cancer, a cancer of the gallbladder, a malignant mesothelioma, a bone cancer, a Ewing's sarcoma, an osteosarcoma, a rhabdomyosarcoma, a soft-tissue sarcoma, a cancer of the hypopharynx, a cancer of the eye, an orbital cancer, a cancer of the nasal cavity, a cancer of the middle ear, a cancer of the ureter, a gastrointestinal carinoid tumor, an adrenal cancer, a parathyroid cancer, a pituitary cancer, a gastric cancer, a hepatoma, an endometrial cancer, a uterine cancer, a gestational trophoblastic disease, a choriocarcinoma, a vaginal cancer, a fallopian tube cancer, an acute lymphocytic leukemia (ALL), an acute myelogenous leukemia (AML), a chronic lymphocytic leukemia (CLL), a chronic myelogenous leukemia (CML), a hairy cell leukemia, a myeloproliferative disorder, a mesothelioma, a non-small cell lunger cancer, a small-cell lung cancer, an AIDS related lymphoma, a cutaneous T-cell lymphoma, a mucosis fungoides, a Kaposi's sarcoma and a melanoma. As will be apparent to the skilled artisan several of the cancers listed supra encompass multiple forms of cancer. The present invention is not to be limited to any one specific form of a cancer.

Modified Chromatin on Chromosome 2

As discussed herein the present inventors have identified a region of chromatin on Chromosome 2 that is modified in cancerous cells compared to non-cancerous cells. This region of chromatin extends from about map position 2q14.1 to about 2q14.3. Preferably, the region of modified chromosome comprises or is contained within nucleic acid that extends from about nucleic acid within Chromosome 2 comprising the gene DDX18 to about nucleic acid within Chromosome 2 comprising the gene TSN.

As used herein, the term "DDX18" shall be taken to mean a nucleic acid, including any genomic gene, that is linked to or positioned at map position 2q14.1-2q14.2 of the human genome, or any mRNA transcript thereof, or any genomic gene or mRNA transcript from a human or non-human animal that comprises a nucleotide sequence having at least about 80% identity to the sequence of the protein coding region of a human DDX18 as set forth in SEQ ID NO: 36.

Preferably, the percentage identity to SEQ ID NO: 36 is at least about 85%, more preferably at least about 90%, even more preferably at least about 95% and still more preferably at least about 99%. In a particularly preferred embodiment, the DDX18 gene is a human DDX18 gene.

In determining whether or not two nucleotide sequences fall within a particular percentage identity limitation recited herein, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BEST-FIT program or other appropriate program of the Computer Genetics Group, Inc., University Research Park, Madison, Wis., United States of America (Devereaux et al, Nucl. Acids Res. 12, 387-395, 1984).

Alternatively, a suite of commonly used and freely available sequence comparison algorithms is provided by the National Center for Biotechnology Information (NCBI) Basic Local Alignment Search Tool (BLAST) (Altschul et al. *J. Mol. Biol.* 215: 403-410, 1990), which is available from several sources, including NCBI, Bethesda, Md. The BLAST software suite includes various sequence analysis programs including "blastn," that is used to align a known nucleotide sequence with other polynucleotide sequences from a variety of databases and "blastp" used to align a known amino acid sequence with one or more sequences from one or more databases. Also available is a tool called "BLAST 2 Sequences" that is used for direct pairwise comparison of two nucleotide sequences.

As used herein, the term "TSN" or "Translin" shall be taken to mean a nucleic acid, including any genomic gene, that is linked to or positioned at map position 2q14.2-2q14.3 of the human genome, or any mRNA transcript thereof, or any genomic gene or mRNA transcript from a human or non-human animal that comprises a nucleotide sequence having at least about 80% identity to the sequence of the protein coding region of a human TSN as set forth in SEQ ID NO: 42.

Preferably, the percentage identity to SEQ ID NO: 42 is at least about 85%, more preferably at least about 90%, even more preferably at least about 95% and still more preferably at least about 99%. In a particularly preferred embodiment, the TSN gene is a human TSN gene.

For the purposes of nomenclature the sequence of any gene set forth herein relates to the cDNA sequence or protein coding region of said gene. The person skilled in the art will be aware of the means to obtain the nucleotide sequence of the relevant genomic gene. For example, the sequence of the genomic genes on human Chromosome 2 are set forth in GenBank Accession Number NT086626, and obtainable from NCBI.

In another embodiment, the region of chromatin extending from about map position 2q14.1 to about 2q14.3 comprises one or more known or predicted genes or transcribed regions within Chromosome 2 between about map position 2q14.1 to about map position 2q14.3, wherein the gene is selected from the group consisting of RALB, DDX18, secretin receptor (SCTR), engrailed-1 (EN1), Translin (TSN), macrophage receptor (MARCO), PTPN, insulin induced gene 2 (INSIG2), inhibin beta B, Gli2, MGC13033, TSAP6, diazepam binding inhibitor (DBI), MGC10993, EPB41L5, FLJ14816 and LBP9.

In another embodiment, the region of chromatin extending from about map position 2q14.1 to about 2q14.3 comprises an intergenic region between any two of the previously described genes. Alternatively, the region comprises a plurality of genes and associated intergenic regions.

As used herein, the term "RALB" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human RALBB as set forth in SEQ ID NO: 34.

As used herein, the term "SCTR" or "secretin receptor" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human SCTR as set forth in SEQ ID NO: 38.

As used herein, the term "EN1" or "engrailed 1" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human EN1 as set forth in SEQ ID NO: 40.

As used herein, the term "MARCO" or "macrophage receptor" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human MARCO as set forth in SEQ ID NO: 48.

As used herein, the term "PTPN4" or "protein tyrosine phosphatase, non-receptor type 4" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human PTPN as set forth in SEQ ID NO: 50.

As used herein, the term "INSIG2" or "insulin induced gene 2" shall be taken to mean a nucleic acid, including any genomic gene, that is linked to or positioned at map position 2q14.1-2q14.2 of the human genome, or any mRNA transcript thereof, or any genomic gene or mRNA transcript from a human or non-human animal that comprises a nucleotide sequence having at least about 80% identity to the sequence of the protein coding region of a human INSIG2 as set forth in SEQ ID NO: 52.

As used herein, the term "INHBB" or "inhibin beta B" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human INHBB as set forth in SEQ ID NO: 54.

As used herein, the term "Gli2" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human Gli2 as set forth in SEQ ID NO: 56.

As used herein, the term "MGC13033" or "FLJ10996" shall be taken to mean a nucleic acid, including any genomic gene, that is linked to or positioned at map position 2q14.1-2q14.2 of the human genome, or any mRNA transcript thereof, or any genomic gene or mRNA transcript from a human or non-human animal that comprises a nucleotide sequence having at least about 80% identity to the sequence of the protein coding region of a human MGC13033 or FLJ10996 as set forth in SEQ ID NO: 58.

As used herein, the term "TSAP6" or "dudulin 2" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human TSAP as set forth in SEQ ID NO: 60.

As used herein, the term "DBI" or "diazepam binding inhibitor" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human DBI as set forth in SEQ ID NO: 62.

As used herein, the term "MGC10993" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human MGC10993 as set forth in SEQ ID NO: 64.

As used herein, the term "EPB41L5" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human EPB41L5 as set forth in SEQ ID NO: 66.

As used herein, the term "FLJ14816" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human FLJ14816 as set forth in SEQ ID NO: 68.

As used herein, the term "LBP9" shall be taken to mean a nucleic acid, including any genomic gene, that is linked to or positioned at map position 2q14.2 of the human genome, or any mRNA transcript thereof, or any genomic gene or mRNA transcript from a human or non-human animal that comprises a nucleotide sequence having at least about 80% identity to the sequence of the protein coding region of a human LBP9 as set forth in SEQ ID NO: 70.

As will be apparent from the foregoing, each of the genes referred to herein are to be taken to encompass expression products of said genes. However, in the context of determining nucleic acid within Chromosome 2 from about map position 2q14.1 to about map position 14.3 it will be apparent to the skilled artisan that the genomic gene is contemplated.

Preferably, the percentage identity to any of the previously described nucleotide sequences is at least about 85%, more preferably at least about 90%, even more preferably at least about 95% and still more preferably at least about 99%. In a particularly preferred embodiment, the RALB, DDX18, secretin receptor (SCTR), engrailed-1 (EN1), Translin (TSN), macrophage receptor (MARCO), PTPN, insulin induced gene 2 (INSIG2), inhibin beta B, Gli2, MGC13033, TSAP6, diazepam binding inhibitor (DBI), MGC10993, EPB41L5, FLJ14816 or LBP9 gene is a human RALB, DDX18, secretin receptor (SCTR), engrailed-1 (EN1), Translin (TSN), macrophage receptor (MARCO), PTPN, insulin induced gene 2 (INSIG2), inhibin beta B, Gli2, MGC13033, TSAP6, diazepam binding inhibitor (DBI), MGC10993, EPB41L5, FLJ14816 or LBP9 gene.

In a preferred embodiment, a region of chromatin extending from about map position 2q14.1 to about 2q14.3 comprises all of the RALB, DDX18, secretin receptor (SCTR), engrailed-1 (EN1), Translin (TSN), macrophage receptor (MARCO), PTPN, insulin induced gene 2 (INSIG2), inhibin beta B, Gli2, MGC13033, TSAP6, diazepam binding inhibitor (DBI), MGC10993, EPB41L5, FLJ14816 and LBP9 genes.

In another embodiment, the region of chromatin extending from about map position 2q14.1 to about 2q14.3 comprises one or more of the following nucleic acids:
(i) nucleic acid extending from DDX18 to INSIG2; or
(ii) nucleic acid extending from DDX18 to EN1; or
(iii) nucleic acid extending from DDX18 to MARCO; or
(iv) nucleic acid extending from DDX18 to TSAP6; or
(v) nucleic acid extending from DDX18 to LOC165257; or
(vi) nucleic acid extending from DDX18 to DBI; or
(vii) nucleic acid extending from DDX18 to SCTR; or (viii) nucleic acid extending from DDX18 to PTPN4; or
(ix) nucleic acid extending from DDX18 to EPB41L5; or
(x) nucleic acid extending from DDX18 to RALB; or
(xi) nucleic acid extending from DDX18 to INHBB; or
(xii) nucleic acid extending from DDX18 to GLI2; or
(xiii) nucleic acid extending from DDX18 to LBP9; or
(xiv) nucleic acid extending from DDX18 to CLASP1; or
(xv) nucleic acid extending from DDX18 to TSN; or
(xvi) nucleic acid extending from INSIG2 to EN1; or
(xvii) nucleic acid extending from INSIG2 to MARCO; or
(xviii) nucleic acid extending from INSIG2 to TSAP6; or
(xix) nucleic acid extending from INSIG2 to LOC165257; or
(xx) nucleic acid extending from INSIG2 to DBI; or
(xxi) nucleic acid extending from INSIG2 to SCTR; or
(xxii) nucleic acid extending from INSIG2 to PTPN4; or
(xxiii) nucleic acid extending from INSIG2 to EPB41L5; or
(xxiv) nucleic acid extending from INSIG2 to RALB; or
(xxv) nucleic acid extending from INSIG2 to INHBB; or
(xxvi) nucleic acid extending from INSIG2 to GLI2; or
(xxvii) nucleic acid extending from INSIG2 to LBP9; or
(xxviii) nucleic acid extending from INSIG2 to CLASP1; or
(xxix) nucleic acid extending from INSIG2 to TSN; or
(xxx) nucleic acid extending from EN1 to MARCO; or
(xxxi) nucleic acid extending from EN1 to TSAP6; or
(xxxii) nucleic acid extending from EN1 to LOC165257; or
(xxxiii) nucleic acid extending from EN1 to DBI; or
(xxxiv) nucleic acid extending from EN1 to SCTR; or
(xxxv) nucleic acid extending from EN1 to PTPN4; or
(xxxvi) nucleic acid extending from EN1 to EPB41L5; or
(xxxvii) nucleic acid extending from EN1 to RALB; or
(xxxix) nucleic acid extending from EN1 to INHBB; or
(xl) nucleic acid extending from EN1 to GLI2; or
(xli) nucleic acid extending from EN1 to LBP9; or
(xlii) nucleic acid extending from EN1 to CLASP1; or
(xliii) nucleic acid extending from EN1 to TSN; or
(xliv) nucleic acid extending from MARCO to TSAP6; or
(xlv) nucleic acid extending from MARCO to LOC165257; or
(xlvi) nucleic acid extending from MARCO to DBI; or
(xlvii) nucleic acid extending from MARCO to SCTR; or
(xlviii) nucleic acid extending from MARCO to PTPN4; or
(xlix) nucleic acid extending from MARCO to EPB41L5; or
(l) nucleic acid extending from MARCO to RALB; or
(li) nucleic acid extending from MARCO to INHBB; or
(lii) nucleic acid extending from MARCO to GLI2; or
(liii) nucleic acid extending from MARCO to LBP9; or
(liv) nucleic acid extending from MARCO to CLASP1; or
(lv) nucleic acid extending from MARCO to TSN; or
(lvi) nucleic acid extending from TSAP6 to LOC165257; or
(lvii) nucleic acid extending from TSAP6 to DBI; or
(lviii) nucleic acid extending from TSAP6 to SCTR; or
(lix) nucleic acid extending from TSAP6 to PTPN4; or
(lx) nucleic acid extending from TSAP6 to EPB41L5; or
(lxi) nucleic acid extending from TSAP6 to RALB; or
(lxii) nucleic acid extending from TSAP6 to INHBB; or
(lxii) nucleic acid extending from TSAP6 to GLI2; or
(lxiii) nucleic acid extending from TSAP6 to LBP9; or
(lxiii) nucleic acid extending from TSAP6 to CLASP1; or
(lxix) nucleic acid extending from TSAP6 to TSN; or
(lxx) nucleic acid extending from LOC16527 to DBI; or
(lxxi) nucleic acid extending from LOC16527 to SCTR; or
(lxxii) nucleic acid extending from LOC16527 to PTPN4; or
(lxxiii) nucleic acid extending from LOC16527 to EPB41L5; or
(lxxiv) nucleic acid extending from LOC16527 to RALB; or
(lxxv) nucleic acid extending from LOC16527 to INHBB; or
(lxxvi) nucleic acid extending from LOC16527 to GLI2; or
(lxxvii) nucleic acid extending from LOC16527 to LBP9; or
(lxxviii) nucleic acid extending from LOC16527 to CLASP1; or
(lxxix) nucleic acid extending from LOC16527 to TSN; or
(lxxx) nucleic acid extending from DBI to SCTR; or
(lxxxi) nucleic acid extending from DBI to PTPN4; or
(lxxxii) nucleic acid extending from DBI to EPB41L5; or
(lxxxiii) nucleic acid extending from DBI to RALB; or
(lxxxiv) nucleic acid extending from DBI to INHBB; or
(lxxxv) nucleic acid extending from DBI to GLI2; or
(lxxxvi) nucleic acid extending from DBI to LBP9; or
(lxxxvii) nucleic acid extending from DBI to CLASP1; or
(lxxxvii) nucleic acid extending from DBI to TSN; or
(lxxxix) nucleic acid extending from SCTR to PTPN4; or
(xc) nucleic acid extending from SCTR to EPB41L5; or
(xci) nucleic acid extending from SCTR to RALB; or
(xcii) nucleic acid extending from SCTR to INHBB; or
(xciii) nucleic acid extending from SCTR to GLI2; or
(xciv) nucleic acid extending from SCTR to LBP9; or
(xcv) nucleic acid extending from SCTR to CLASP1; or
(xcvi) nucleic acid extending from SCTR to TSN; or
(xcvii) nucleic acid extending from PTPN4 to EPB41L5; or
(xcviii) nucleic acid extending from PTPN4 to RALB; or
(xcix) nucleic acid extending from PTPN4 to INHBB; or
(c) nucleic acid extending from PTPN4 to GLI2; or
(ci) nucleic acid extending from PTPN4 to LBP9; or
(cii) nucleic acid extending from PTPN4 to CALSP1; or
(ciii) nucleic acid extending from PTPN4 to TSN; or
(civ) nucleic acid extending from EPB41L5 to RALB; or
(cv) nucleic acid extending from EPB41L5 to INHBB; or
(cvi) nucleic acid extending from EPB41L5 to GLI2; or
(cvii) nucleic acid extending from EPB41L5 to LBP9; or
(cviii) nucleic acid extending from EPB41L5 to CLASP1; or
(cix) nucleic acid extending from EPB41L5 to TSN; or
(cx) nucleic acid extending from RALB to INHBB; or
(cxi) nucleic acid extending from RALB to GLI2; or
(cxii) nucleic acid extending from RALB to LBP9; or
(cxiii) nucleic acid extending from RALB to CLASP1; or
(cxiv) nucleic acid extending from RALB to TSN; or
(cxv) nucleic acid extending from INHBB to GLI2; or
(cxvi) nucleic acid extending from INHBB to LBP9; or
(cxvii) nucleic acid extending from INHBB to CLASP1; or
(cxviii) nucleic acid extending from INHBB to TSN; or
(cxix) nucleic acid extending from GLI2 to LBP9; or
(cxx) nucleic acid extending from GLI2 to CLASP1; or
(cxxi) nucleic acid extending from GLI2 to TSN; or
(cxxii) nucleic acid extending from LBP9 to CLASP1; or
(cxxiii) nucleic acid extending from LBP9 to TSN; or
(cxxiv) nucleic acid extending from CLASP1 to TSN.

In another embodiment, the region of Chromosome 2 from about map position 2q14.1 to about map position 2q14.2 comprises one or more CpG rich regions or CpG islands. In a preferred embodiment, the region of chromatin extending from about map position 2q14.1 to about 2q14.3 comprises a nucleic acid comprising one or more nucleotide sequences set forth in any one or more of SEQ ID NOs: 1 to 33 or referred to in Table 1. In one embodiment, the region of chromatin extending from about map position 2q14.1 to about 2q14.3 comprises a nucleic acid comprising all of the nucleotide sequences set forth in any one of SEQ ID NOs: 1 to 33 and/or referred to in Table 1. Alternatively, the region of Chromosome 2 from about map position 2q14.1 to about map position 2q14.2 comprises a plurality of a nucleic acid comprising all of the nucleotide sequences set forth in any one of SEQ ID NOs: 1 to 33 and/or referred to in Table 1 and any intervening nucleic acid.

In a preferred embodiment, the region of chromatin extending from about map position 2q14.1 to about 2q14.3 comprises a nucleic acid comprising one or more nucleotide sequences set forth in any one or more of SEQ ID NOs: 2 to 25. Alternatively, the nucleotide sequence is designated as INSIG2, (CpG 49), CpG41.2, CpG61, CpG29, 20 Kb, Z(sma), Z, CpG104, CpG103, CpG128, CpG41, CpG173, CpG48, CpG48rv, 5'-MARCO, CpG229, TSAP6 (CpG 85), DBI (CpG 85), CpG85, SCTR (CpG 67), PTPN4 (CpG 86), CpG102, RALBB (CpG115) or INHBB(CpG285) in Table 1.

In an even more preferred embodiment, the region of chromatin extending from about map position 2q14.1 to about 2q14.3 comprises a nucleic acid comprising one or more nucleotide sequences set forth in any one or more of SEQ ID NOs: 4 to 21. Alternatively, the nucleotide sequence is designated as CpG61, CpG29, 20 Kb, Z(sma), Z, CpG104, CpG103, CpG128, CpG41, CpG173, CpG48, CpG48rv, 5'-MARCO, CpG229, TSAP6 (CpG 85), DBI (CpG 85), CpG85 or SCTR (CpG 67) in Table 1.

In an even more preferred embodiment, the region of chromatin extending from about map position 2q14.1 to about 2q14.3 comprises a nucleic acid comprising one or more nucleotide sequences set forth in any one or more of SEQ ID NOs: 6 to 17. Alternatively, the nucleotide sequence is designated as 20 Kb, Z(sma), Z, CpG104, CpG103, CpG128, CpG41, CpG173, CpG48, CpG48rv, 5'-MARCO and CpG229 in Table 1.

In another preferred embodiment, the region of chromatin extending from about map position 2q14.1 to about 2q14.3 comprises the Z fragment. As used herein the term "Z fragment" shall be taken to mean a nucleic acid that is linked to or positioned at map position 2q14.2-2q14.3 of the human genome having a nucleotide sequence at least about 80% identical to the nucleotide sequence of the human Z fragment set forth in SEQ ID NO: 8.

Preferably, the Z fragment comprises a plurality of CpG dinucleotides so as to enable methylation by a DNA methyl transferase enzyme.

Diagnostic Assay Formats

I. Detection of Methylation of Nucleic Acid

The present inventors have clearly demonstrated a number of changes to chromatin of Chromosome 2 that are enhanced in cancer cells compared to control non-cancerous cells. Accordingly, a method for detecting modified chromatin shall be taken to include detecting a marker of modified chromatin, such as, for example, detecting the level of methylation of nucleic acid and/or hypermethylation of nucleic acid in the chromatin, detecting the level of methylation and/or acetylation and/or de-acetylation of one or more histones (e.g., histone H3) in the chromatin. Suitable methods for the detection of such markers are known in the art and/or described herein.

In a preferred embodiment, the degree or level of methylation of nucleic acid or hypermethylation of nucleic acid is detected in a region of Chromosome 2 from about map position 2q14.1 to about map position 2q14.3 comprising one or more nucleotide sequences set forth in any one of SEQ ID NOs: 1 to 33 and/or referred to in Table 1 in diagnosing cancer in a subject. Alternatively, or in addition, the degree or level of methylation of nucleic acid or hypermethylation of nucleic acid is determined in a plurality of nucleic acids, each nucleic acid comprising one or more nucleotide sequences set forth in any one of SEQ ID NOs: 1 to 33 and/or referred to in Table 1.

The term "methylation of nucleic acid" shall be taken to mean the addition of a methyl group by the action of a DNA methyl transferase enzyme to a CpG island of nucleic acid, e.g., genomic DNA. As described herein, there are several methods known to those skilled in the art for determining the level or degree of methylation of nucleic acid.

By "enhanced" is meant that there are a significantly larger number of methylated CpG dinucleotides in the subject diagnosed than in a suitable control sample. The present invention is not to be limited by a precise number of methylated residues that are considered to be diagnostic of cancer in a subject, because some variation between patient samples will occur. The present invention is also not limited by positioning of the methylated residue.

The term "hypermethylated nucleic acid" and equivalents shall be taken to mean that a plurality of CpG dinucleotides in a specific or defined region of nucleic acid is methylated.

In a preferred embodiment, the degree of methylation is determined in a region of Chromosome 2 from about map position 2q14.1 to about map position 2q14.3 comprising any one or more combinations of nucleotide sequences described herein with reference to any embodiment of the invention. Preferably, the degree of methylation is determined in a region of Chromosome 2 comprising one or more nucleotide sequence(s) selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 21, SEQ ID NO: 25, SEQ ID NO: 28. Alternatively, or in addition, the method of the invention determines the degree of methylation at any one or more nucleic acids comprising one or more nucleotide sequences set forth in the previous sentence. For example, the degree of methylation is determined in a nucleic acid comprising a nucleotide sequence set forth in SEQ ID NO: 4; or a nucleic acid comprising a nucleotide sequence set forth in SEQ ID NO: 5; a nucleic acid comprising a nucleotide sequence set forth in SEQ ID NO: 6; or a nucleic acid comprising a nucleotide sequence set forth in SEQ ID NO: 7; or a nucleic acid comprising a nucleotide sequence set forth in SEQ ID NO: 8; or a nucleic acid comprising a nucleotide sequence set forth in SEQ ID NO: 9; or a nucleic acid comprising a nucleotide sequence set forth in SEQ ID NO: 10; or a nucleic acid comprising a nucleotide sequence set forth in SEQ ID NO: 11; or a nucleic acid comprising a nucleotide sequence set forth in SEQ ID NO: 12; or a nucleic acid comprising a nucleotide sequence set forth in SEQ ID NO: 13; or a nucleic acid comprising a nucleotide sequence set forth in SEQ ID NO: 14; or a nucleic acid comprising a nucleotide sequence set forth in SEQ ID NO: 15; or a nucleic acid comprising a nucleotide sequence set forth in SEQ ID NO: 16; or a nucleic acid comprising a nucleotide sequence set forth in SEQ ID NO: 17; or a nucleic acid comprising a nucleotide sequence set forth in SEQ ID NO: 21; or a nucleic acid comprising a nucleotide sequence set forth in SEQ ID NO: 25; or a nucleic acid comprising a nucleotide sequence set forth in SEQ ID NO: 28.

In a preferred embodiment, the degree of methylation is determined in a nucleic acid comprising a nucleotide sequence set forth in SEQ ID NO: 11 and a nucleic acid comprising a nucleotide sequence set forth in SEQ ID NO: 21 and nucleic acid comprising a nucleotide sequence set forth in SEQ ID NO: 25. Alternatively, the degree of methylation is determined in nucleic acid comprising a nucleotide sequence set forth in SEQ ID NO: 1; or the degree of methylation is determined in a nucleic acid comprising a nucleotide sequence set forth in SEQ ID NO: 21; or the degree of methylation is determined in a nucleic acid comprising a nucleotide sequence set forth in SEQ ID NO: 25.

Alternatively, the degree of methylation is determined in a region of Chromosome 2 comprising one or more nucleotide sequence(s) referred to in Table 1 selected from the group consisting of CpG61, CpG29, 20 Kb, Z(sma), Z, CpG104, CpG103, CpG128, CpG41, CpG173, CpG48, CpG48rv, 5'-MARCO, CpG229, CpG67, INHBB(CpG285), CpG26, CpG206 and CpG22. Alternatively, or in addition, the method of the invention determines the degree of methylation at any one or more nucleic acids comprising one or more nucleotide sequences set forth in the previous sentence. For example, the degree of methylation is determined in CpG61; or in CpG29; or in 20 Kb; or in Z(sma) or in Z; or in CpG104; or in CpG103 or in CpG128 or in CpG41; or in CpG173 or in CpG48 or in CpG48rv; or in 5'-MARCO; or in CpG229; or in CpG67; or in INHBB(CpG285); or in CpG26; or in CpG206; or in CpG22.

In a preferred embodiment, the degree of methylation is determined in a nucleic acid comprising the sequence of CpG128 referred to in Table 1; and in a nucleic acid comprising the sequence of CpG67 referred to in Table 1; a nucleic acid comprising the sequence of INHBB(CpG285) referred to in Table 1 a. Probe or Primer Design and/or Production

Several methods described herein for the diagnosis of a cancer use one or more probes and/or primers. Methods for designing probes and/or primers for use in, for example, PCR or hybridization are known in the art and described, for example, in Dieffenbach and Dveksler (Eds) (In: PCR Primer: A Laboratory Manual, Cold Spring Harbor Laboratories, NY, 1995). Furthermore, several software packages are publicly available that design optimal probes and/or primers for a variety of assays, e.g. Primer 3 available from the Center for Genome Research, Cambridge, Mass., USA.

Clearly, the potential use of the probe or primer should be considered during its design. For example, should the probe or primer be produced for use in, for example, a methylation specific PCR or ligase chain reaction (LCR) assay the nucleotide at the 3' end (or 5' end in the case of LCR) should correspond to a methylated nucleotide in a nucleic acid.

Probes and/or primers useful for detection of a marker associated with a cancer are assessed, for example, to determine those that do not form hairpins, self-prime or form primer dimers (e.g. with another probe or primer used in a detection assay).

Furthermore, a probe or primer (or the sequence thereof) is often assessed to determine the temperature at which it denatures from a target nucleic acid (i.e. the melting temperature of the probe or primer, or Tm). Methods for estimating Tm are known in the art and described, for example, in Santa Lucia, Proc. Natl. Acad. Sci. USA, 95: 1460-1465, 1995 or Bresslauer et al., Proc. Natl. Acad. Sci. USA, 83: 3746-3750, 1986.

Methods for producing/synthesizing a probe or primer of the present invention are known in the art. For example, oligonucleotide synthesis is described, in Gait (Ed) (In: Oligonucleotide Synthesis: A Practical Approach, IRL Press, Oxford, 1984). For example, a probe or primer may be obtained by biological synthesis (e.g. by digestion of a nucleic acid with a restriction endonuclease) or by chemical synthesis. For short sequences (up to about 100 nucleotides) chemical synthesis is preferable.

For longer sequences standard replication methods employed in molecular biology are useful, such as, for example, the use of M13 for single stranded DNA as described by Messing Methods Enzymol, 101, 20-78, 1983.

Other methods for oligonucleotide synthesis include, for example, phosphotriester and phosphodiester methods (Narang, et al. Meth. Enzymol 68: 90, 1979) and synthesis on a support (Beaucage, et al Tetrahedron Letters 22: 1859-1862, 1981) as well as phosphoramidate technique, Caruthers, M. H., et al., "Methods in Enzymology," Vol. 154, pp. 287-314 (1988), and others described in "Synthesis and Applications of DNA and RNA," S. A. Narang, editor, Academic Press, New York, 1987, and the references cited therein.

Probes comprising locked nucleic acid (LNA) are synthesized as described, for example, in Nielsen et al, J. Chem. Soc. Perkin Trans., 1: 3423, 1997; Singh and Wengel, Chem. Commun. 1247, 1998. While, probes comprising peptide-nucleic acid (PNA) are synthesized as described, for example, in Egholm et al., Am. Chem. Soc., 114: 1895, 1992; Egholm et al., Nature, 365: 566, 1993; and Orum et al., Nucl. Acids Res., 21: 5332, 1993.

b. Methylation-Sensitive Endonuclease Digestion of DNA

In one embodiment, the enhanced methylation in a subject sample is determined using a process comprising treating the nucleic acid with an amount of a methylation-sensitive restriction endonuclease enzyme under conditions sufficient for nucleic acid to be digested and then detecting the fragments produced. Exemplary methylation-sensitive endonucleases include, for example, HpaI or HpaII.

Preferably, assays include internal controls that are digested with a methylation-insensitive enzyme having the same specificity as the methylation-sensitive enzyme employed. For example, the methylation-insensitive enzyme MspI is an isoschizomer of the methylation-sensitive enzyme HpaII.

Hybridization Assay Formats

In one embodiment, the digestion of nucleic acid is detected by selective hybridization of a probe or primer to the undigested nucleic acid. Alternatively, the probe selectively hybridizes to both digested and undigested nucleic acid but facilitates differentiation between both forms, e.g., by electrophoresis. Suitable detection methods for achieving selective hybridization to a hybridization probe include, for example, Southern or other nucleic acid hybridization (Kawai et al., Mol. Cell. Biol. 14, 7421-7427, 1994; Gonzalgo et al., Cancer Res. 57, 594-599, 1997).

The term "selectively hybridizable" means that the probe is used under conditions where a target nucleic acid, e.g., a nucleic acid comprising or contained within one or more nucleotide sequences set forth in SEQ ID NOs: 1 to 33 or referred to in Table 1, hybridizes to the probe to produce a signal that is significantly above background (i.e., a high signal-to-noise ratio). The intensity of hybridization is measured, for example, by radiolabeling the probe, e.g. by incorporating $[\alpha\text{-}^{35}S]$ and/or $[\alpha\text{-}^{32}P]$dNTPs, $[\gamma\text{-}^{32}P]$ATP, biotin, a dye ligand (e.g., FAM or TAMRA), a fluorophore, or other suitable ligand into the probe prior to use and then detecting the ligand following hybridization.

Suitable hybridization conditions are determined based on the melting temperature (Tm) of a nucleic acid duplex comprising the probe, e.g., as described supra.

The skilled artisan will be aware that optimum hybridization reaction conditions should be determined empirically for each probe, although some generalities can be applied. Preferably, hybridizations employing short oligonucleotide probes are performed at low to medium stringency.

For the purposes of defining the level of stringency to be used in these diagnostic assays, a low stringency is defined herein as being a hybridization and/or a wash carried out in about 6×SSC buffer and/or about 0.1% (w/v) SDS at about 28° C. to about 40° C., or equivalent conditions. A moderate stringency is defined herein as being a hybridization and/or washing carried out in about 2×SSC buffer and/or about 0.1% (w/v) SDS at a temperature in the range of about 45° C. to about 65° C., or equivalent conditions.

In the case of a GC rich probe or primer or a longer probe or primer a high stringency hybridization and/or wash is preferred. A high stringency is defined herein as being a hybridization and/or wash carried out in about 0.1×SSC buffer and/or about 0.1% (w/v) SDS, or lower salt concentration, and/or at a temperature of at least 65° C., or equivalent conditions. Reference herein to a particular level of stringency encompasses equivalent conditions using wash/hybridization solutions other than SSC known to those skilled in the art.

Generally, the stringency is increased by reducing the concentration of SSC buffer, and/or increasing the concentration of SDS and/or increasing the temperature of the hybridization and/or wash. Those skilled in the art will be aware that the conditions for hybridization and/or wash may vary depending upon the nature of the hybridization matrix used to support the sample DNA, and/or the type of hybridization probe used and/or constituents of any buffer used in a hybridization. For example, formamide reduces the melting temperature of a probe or primer in a hybridization or an amplification reaction.

Conditions for specifically hybridizing nucleic acid, and conditions for washing to remove non-specific hybridizing nucleic acid, are understood by those skilled in the art. For the purposes of further clarification only, reference to the parameters affecting hybridization between nucleic acid molecules is found in Ausubel et al. (Current Protocols in Molecular Biology, Wiley Interscience, ISBN 047150338, 1992), which is herein incorporated by reference.

For detecting fragments produced by endonuclease digestion using a hybridization assay format, any suitable hybridization probe derived from a nucleic acid comprising or contained within a nucleotide sequence set forth in any one or more of SEQ ID NOs: 1 to 33 or referred to in Table 1 can be used in accordance with standard procedures. This is because the detection involves hybridization to all fragments produced, as opposed to a selective hybridization, and then comparing the fragments produced in the test sample to those fragments produced for a suitable control sample.

Preferred hybridization probes will comprise at least about 18 contiguous nucleotides in length from any one of SEQ ID NOs: 1 to 33 or Table 1, more preferably at least about 50 contiguous nucleotides from any one of SEQ ID NOs: 1 to 33 or Table 1, preferably incorporating one or more CpG dinucleotides that are hypermethylated in cancer. Alternatively, the probe or primer is adjacent to the site of cleavage of a methylation sensitive endonuclease thereby enabling detection of cleaved nucleic acid. Preferred probes will hybridize to a nucleic acid comprising a nucleotide sequence set forth in any one or more of SEQ ID NOs: 1 to 33 or referred to in Table 1 or a sequence that is complementary thereto, or a portion thereof including one or more CpG dinucleotides that are hypermethylated in cancer.

As will be known to the skilled artisan, longer probes are preferred, because these generally produce higher signal-to-noise ratio than shorter probes and/or permit higher stringency hybridization and wash conditions to be employed. Accordingly, it is preferably to use hybridization probes that comprise at least about 100 contiguous nucleotides from any one of SEQ ID NOs: 1 to 33 or referred to in Table 1 and even more preferably at least about 200 contiguous nucleotide residues. As will be apparent to the skilled artisan the entire of the sequence of the probe need not necessarily be set forth in any one of SEQ ID NOs: 1 to 33 or referred to in Table 1, rather a portion of the sequence of the probe is preferably, set forth in any one of SEQ ID NOs: 1 to 33 or referred to in Table 1. In this respect, it is preferred that the portion of the probe or primer comprising a nucleotide sequence set forth in any one of SEQ ID NOs: 1 to 33 or referred to in Table 1 is sufficient to permit detection of a nucleic acid, and preferably, differentiation between a methylated and a non-methylated nucleic acid.

In accordance with the present embodiment, a difference in the fragments produced for the test sample and a negative control sample is indicative of the subject having cancer. Similarly, in cases where the control sample comprises data from a tumor, cancer tissue or a cancerous cell or pre-cancerous cell, similarity, albeit not necessarily absolute identity, between the test sample and the control sample is indicative of a positive diagnosis (i.e. cancer).

Amplification Assay Formats

In an alternative embodiment, the fragments produced by the restriction enzyme are detected using an amplification system, such as, for example, polymerase chain reaction (PCR), rolling circle amplification (RCA), inverse polymerase chain reaction (iPCR), in situ PCR (Singer-Sam et al., Nucl. Acids Res. 18, 687, 1990), strand displacement amplification (SDA) or cycling probe technology.

Methods of PCR are known in the art and described, for example, by McPherson et al., PCR: A Practical Approach. (series eds, D. Rickwood and B. D. Hames), IRL Press Limited, Oxford. pp 1-253, 1991 and by Dieffenbach (ed) and Dveksler (ed) (In: PCR Primer: A Laboratory Manual, Cold Spring Harbour Laboratories, NY, 1995), the contents of which are each incorporated in their entirety by way of reference. Generally, for PCR two non-complementary nucleic acid primer molecules comprising at least about 18 nucleotides in length, and more preferably at least 20-30 nucleotides in length are hybridized to different strands of a nucleic acid template molecule at their respective annealing sites, and specific nucleic acid molecule copies of the template that intervene the annealing sites are amplified enzymatically. Amplification products may be detected, for example, using electrophoresis and detection with a detectable marker that binds nucleic acids. Alternatively, one or more of the oligonucleotides are labeled with a detectable marker (e.g. a fluorophore) and the amplification product detected using, for example, a lightcycler (Perkin Elmer, Wellesley, Mass., USA).

Strand displacement amplification (SDA) utilizes oligonucleotide primers, a DNA polymerase and a restriction endonuclease to amplify a target sequence. The oligonucleotides are hybridized to a target nucleic acid and the polymerase is used to produce a copy of the region intervening the primer annealing sites. The duplexes of copied nucleic acid and target nucleic acid are then nicked with an endonuclease that specifically recognizes a sequence at the beginning of the copied nucleic acid. The DNA polymerase recognizes the nicked DNA and produces another copy of the target region at the same time displacing the previously generated nucleic acid. The advantage of SDA is that it occurs in an isothermal format, thereby facilitating high-throughput automated analysis.

Cycling Probe Technology uses a chimeric synthetic primer that comprises DNA-RNA-DNA that is capable of hybridizing to a target sequence. Upon hybridization to a target sequence the RNA-DNA duplex formed is a target for RNaseH thereby cleaving the primer. The cleaved primer is then detected, for example, using mass spectrometry or electrophoresis.

Preferred amplification primers will comprise at least about 18 contiguous nucleotides in length from any one of SEQ ID NOs: 1 to 33 or referred to in Table 1, preferably, flanking or adjacent to or comprising a methylation-sensitive endonuclease recognition site.

For primers that flank or are adjacent to a methylation-sensitive endonuclease recognition site, it is preferred that such primers flank only those sites that are hypermethylated in cancer to ensure that a diagnostic amplification product is produced. In this regard, an amplification product will only be produced when the restriction site is not cleaved, i.e., when it is methylated. Accordingly, detection of an amplification product indicates that the CpG dinucleotide/s of interest is/are methylated.

As will be known to the skilled artisan, the precise length of the amplified product will vary depending upon the distance between the primers.

Clearly this form of analysis may be used to determine the methylation status of a plurality of CpG dinucleotides provided that each dinucleotide is within a methylation sensitive restriction endonuclease site.

In these methods, one or more of the primers may be labeled with a detectable marker to facilitate rapid detection of amplified nucleic acid, for example, a fluorescent label (e.g. Cy5 or Cy3) or a radioisotope (e.g. $^{32}$P).

The amplified nucleic acids are generally analyzed using, for example, non-denaturing agarose gel electrophoresis, non-denaturing polyacrylamide gel electrophoresis, mass spectrometry, liquid chromatography (e.g. HPLC or dHPLC), or capillary electrophoresis. (e.g. MALDI-TOF). High throughput detection methods, such as, for example, matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or DNA chip technology (e.g., WO98/49557; WO 96/17958; Fodor et al., *Science* 767-773, 1991; U.S. Pat. No. 5,143,854; and U.S. Pat. No. 5,837,832, the contents of which are all incorporated herein by reference), are especially preferred for all assay formats described herein.

Alternatively, amplification of a nucleic acid may be continuously monitored using a melting curve analysis method as described herein and/or in, for example, U.S. Pat. No. 6,174,670, which is incorporated herein by reference.

Alternatively, or in addition, the nucleotide sequence of the amplified DNA is determined according to standard procedures.

c. Other Assay Formats

In an alternative embodiment of the present invention, the enhanced methylation in a subject sample is determined by performing a process comprising treating the nucleic acid with an amount of DNaseI under conditions sufficient for nucleic acid to be digested and then detecting the fragments produced.

This assay format is predicated on the understanding that methylated DNA, e.g., hyper methylated DNA, has a more tightly-closed conformation than non-hyper methylated DNA and, as a consequence, is less susceptible to endonuclease digestion by DNase I.

In accordance with this embodiment, DNA fragments of different lengths are produced by DNase I digestion of methylated compared to non-methylated DNA. Such different DNA fragments are detected, for example, using an assay described supra.

Alternatively, the DNA fragments are detected using PCR-SSCP essentially as described, for example, in Gregory and Feil *Nucleic Acids Res.*, 27, e32i-e32iv, 1999. In adapting PCR-SSCP to the present invention, amplification primers flanking or comprising one or more CpG dinucleotides in a nucleic acid comprising a nucleotide sequence set forth in any one of SEQ ID NOs: 1 to 33 or Table 1 that are resistant to DNase I digestion in a cancer sample but not resistant to DNase I digestion in a healthy/normal control or healthy/normal test sample are used to amplify the DNase I-generated fragments. In this case, the production of a specific nucleic acid fragment using DNase I is diagnostic of cancer, because the DNA is not efficiently degraded. In contrast, template DNA from a healthy/normal subject sample is degraded by the action of DNase I and, as a consequence, amplification fails to produce a discrete amplification product. Alternative methods to PCR-SSCP, such as for example, PCR-dHPLC are also known in the art and contemplated by the present invention.

d. Selective Mutagenesis of Non-Methylated DNA

In an alternative embodiment of the present invention, the enhanced methylation in a subject sample is determined using a process comprising treating the nucleic acid with an amount of a compound that selectively mutates a non-methylated cytosine residue within a CpG dinucleotide under conditions sufficient to induce mutagenesis.

Preferred compounds mutate cytosine to uracil or thymidine, such as, for example, a metal salt of bisulfite, e.g., sodium bisulfite or potassium bisulfite (Frommer et al., *Proc. Natl. Acad. Sci. USA* 89, 1827-1831, 1992). Bisulfite treatment of DNA is known to distinguish methylated from non-methylated cytosine residues, by mutating cytosine residues that are not protected by methylation, including cytosine residues that are not within a CpG dinucleotide or that are positioned within a CpG dinucleotide that is not subject to methylation.

c(i) Sequence Based Detection

In one embodiment, the presence of one or more mutated nucleotides or the number of mutated sequences is determined by sequencing mutated DNA. One form of analysis comprises amplifying mutated nucleic acid using an amplification reaction described herein, for example, PCR. The amplified product is then directly sequenced or cloned and the cloned product sequenced. Methods for sequencing DNA are known in the art and include for example, the dideoxy chain termination method or the Maxam-Gilbert method (see Sambrook et al., Molecular Cloning, A Laboratory Manual (2nd Ed., CSHP, New York 1989) or Zyskind et al., Recombinant DNA Laboratory Manual, (Acad. Press, 1988)).

As the treatment of nucleic acid with a compound, such as, for example, bisulfite results in non-methylated cytosines being mutated to uracil or thymidine, analysis of the sequence determines the presence or absence of a methylated nucleotide. For example, by comparing the sequence obtained using a control sample or a sample that has not been treated with bisulfite, or the known nucleotide sequence of the region of interest with a treated sample facilitates the detection of differences in the nucleotide sequence. Any thymine residue detected at the site of a cytosine in the treated sample compared to a control or untreated sample may be considered to be caused by mutation as a result of bisulfite treatment. Suitable methods for the detection of methylation using sequencing of bisulfite treated nucleic acid are described, for example, in Frommer et al., *Proc. Natl. Acad. Sci. USA* 89: 1827-1831, 1992 or Clark et al., *Nucl. Acids Res.* 22: 2990-2997, 1994.

Preferred primers for amplification and/or sequencing comprise at least about 18 contiguous nucleotides in length from any one of SEQ ID NOs: 1 to 33 or Table 1, preferably encompassing one or more CpG dinucleotides that is/are hypermethylated in nucleic acid in a cancer cell.

For example, for any detection format described herein, e.g., bisulfite sequencing, that comprises an amplification step, the primers used may be a combination selected from the group consisting of:

(i) a primer comprising the sequence set forth in SEQ ID NO: 72 and a primer comprising a sequence that is the complement of SEQ ID NO: 73;
(ii) a primer comprising the sequence set forth in SEQ ID NO: 74 and a primer comprising the sequence set forth in SEQ ID NO: 75;
(iii) a primer comprising the sequence set forth in SEQ ID NO: 76 and a primer comprising a sequence that is the complement of SEQ ID NO: 77;
(iv) a primer comprising the sequence set forth in SEQ ID NO: 78 and a primer comprising a sequence that is the complement of SEQ ID NO: 79;
(v) a primer comprising the sequence set forth in SEQ ID NO: 80 and a primer comprising the sequence set forth in SEQ ID NO: 81;
(vi) a primer comprising the sequence set forth in SEQ ID NO: 82 and a primer comprising the sequence set forth in SEQ ID NO: 83;
(vii) a primer comprising the sequence set forth in SEQ ID NO: 84 and a primer comprising a sequence that is the complement of SEQ ID NO: 85;
(viii) a primer comprising the sequence set forth in SEQ ID NO: 86 and a primer comprising the sequence set forth in SEQ ID NO: 87;
(ix) a primer comprising the sequence set forth in SEQ ID NO: 88 and a primer comprising the sequence set forth in SEQ ID NO: 89;
(x) a primer comprising the sequence set forth in SEQ ID NO: 90 and a primer comprising a sequence that is the complement of SEQ ID NO: 91;
(xi) a primer comprising the sequence set forth in SEQ ID NO: 92 and a primer comprising the sequence set forth in SEQ ID NO: 93;
(xii) a primer comprising the sequence set forth in SEQ ID NO: 94 and a primer comprising the sequence set forth in SEQ ID NO: 95;
(xiii) a primer comprising the sequence set forth in SEQ ID NO: 96 and a primer comprising the sequence set forth in SEQ ID NO: 97;
(xiv) a primer comprising the sequence set forth in SEQ ID NO: 98 and a primer comprising the sequence set forth in SEQ ID NO: 99;
(xv) a primer comprising the sequence set forth in SEQ ID NO: 100 and a primer comprising the sequence set forth in SEQ ID NO: 101;
(xvi) a primer comprising the sequence set forth in SEQ ID NO: 102 and a primer comprising the sequence set forth in SEQ ID NO: 103;
(xvii) a primer comprising the sequence set forth in SEQ ID NO: 104 and a primer comprising the sequence set forth in SEQ ID NO: 105;
(xviii) a primer comprising the sequence set forth in SEQ ID NO: 106 and a primer comprising the sequence set forth in SEQ ID NO: 107;
(xix) a primer comprising the sequence set forth in SEQ ID NO: 108 and a primer comprising the sequence set forth in SEQ ID NO: 109;
(xx) a primer comprising the sequence set forth in SEQ ID NO: 110 and a primer comprising the sequence set forth in SEQ ID NO: 111;
(xxi) a primer comprising the sequence set forth in SEQ ID NO: 112 and a primer comprising the sequence set forth in SEQ ID NO: 113;
(xxii) a primer comprising the sequence set forth in SEQ ID NO: 114 and a primer comprising the sequence set forth in SEQ ID NO: 115;
(xxiii) a primer comprising the sequence set forth in SEQ ID NO: 116 and a primer comprising the sequence set forth in SEQ ID NO: 117;
(xxiv) a primer comprising the sequence set forth in SEQ ID NO: 118 and a primer comprising the sequence set forth in SEQ ID NO: 119;
(xxv) a primer comprising the sequence set forth in SEQ ID NO: 120 and a primer comprising the sequence set forth in SEQ ID NO: 121;
(xxvi) a primer comprising the sequence set forth in SEQ ID NO: 122 and a primer comprising the sequence set forth in SEQ ID NO: 123;
(xxvii) a primer comprising the sequence set forth in SEQ ID NO: 124 and a primer comprising the sequence set forth in SEQ ID NO: 125;
(xxviii) a primer comprising the sequence set forth in SEQ ID NO: 126 and a primer comprising the sequence set forth in SEQ ID NO: 127;
(xxix) a primer comprising the sequence set forth in SEQ ID NO: 128 and a primer comprising the sequence set forth in SEQ ID NO: 129;
(xxx) a primer comprising the sequence set forth in SEQ ID NO: 130 and a primer comprising the sequence set forth in SEQ ID NO: 131;
(xxxi) a primer comprising the sequence set forth in SEQ ID NO: 132 and a primer comprising the sequence set forth in SEQ ID NO: 133;
(xxxii) a primer comprising the sequence set forth in SEQ ID NO: 134 and a primer comprising the sequence set forth in SEQ ID NO: 135;
(xxxiii) a primer comprising the sequence set forth in SEQ ID NO: 136 and a primer comprising the sequence set forth in SEQ ID NO: 137;
(xxxiv) a primer comprising the sequence set forth in SEQ ID NO: 138 and a primer comprising the sequence set forth in SEQ ID NO: 139;
(xxxv) a primer comprising the sequence set forth in SEQ ID NO: 140 and a primer comprising the sequence set forth in SEQ ID NO: 141;
(xxxvi) a primer comprising the sequence set forth in SEQ ID NO: 142 and a primer comprising the sequence set forth in SEQ ID NO: 143;
(xxvii) a primer comprising the sequence set forth in SEQ ID NO: 144 and a primer comprising the sequence set forth in SEQ ID NO: 145;
(xxxviii) a primer comprising the sequence set forth in SEQ ID NO: 146 and a primer comprising the sequence set forth in SEQ ID NO: 147;
(xxxix) a primer comprising the sequence set forth in SEQ ID NO: 148 and a primer comprising the sequence set forth in SEQ ID NO: 149;
(xl) a primer comprising the sequence set forth in SEQ ID NO: 150 and a primer comprising the sequence set forth in SEQ ID NO: 151;
(xli) a primer comprising the sequence set forth in SEQ ID NO: 152 and a primer comprising the sequence set forth in SEQ ID NO: 153;
(xlii) a primer comprising the sequence set forth in SEQ ID NO: 154 and a primer comprising the sequence set forth in SEQ ID NO: 155;
(xliii) a primer comprising the sequence set forth in SEQ ID NO: 156 and a primer comprising the sequence set forth in SEQ ID NO: 157;

(xliv) a primer comprising the sequence set forth in SEQ ID NO: 158 and a primer comprising the sequence set forth in SEQ ID NO: 159;
(xlv) a primer comprising the sequence set forth in SEQ ID NO: 160 and a primer comprising the sequence set forth in SEQ ID NO: 161;
(xlvi) a primer comprising the sequence set forth in SEQ ID NO: 162 and a primer comprising the sequence set forth in SEQ ID NO: 163;
(xlvii) a primer comprising the sequence set forth in SEQ ID NO: 164 and a primer comprising the sequence set forth in SEQ ID NO: 165;
(xlviii) a primer comprising the sequence set forth in SEQ ID NO: 166 and a primer comprising the sequence set forth in SEQ ID NO: 167;
(xlix) a primer comprising the sequence set forth in SEQ ID NO: 168 and a primer comprising the sequence set forth in SEQ ID NO: 169;
(l) a primer comprising the sequence set forth in SEQ ID NO: 170 and a primer comprising the sequence set forth in SEQ ID NO: 171;
(li) a primer comprising the sequence set forth in SEQ ID NO: 172 and a primer comprising the sequence set forth in SEQ ID NO: 173;
(lii) a primer comprising the sequence set forth in SEQ ID NO: 174 and a primer comprising the sequence set forth in SEQ ID NO: 175;
(liii) a primer comprising the sequence set forth in SEQ ID NO: 176 and a primer comprising the sequence set forth in SEQ ID NO: 177;
(liv) a primer comprising the sequence set forth in SEQ ID NO: 178 and a primer comprising the sequence set forth in SEQ ID NO: 179;
(lv) a primer comprising the sequence set forth in SEQ ID NO: 180 and a primer comprising the sequence set forth in SEQ ID NO: 181;
(lvi) a primer comprising the sequence set forth in SEQ ID NO: 182 and a primer comprising the sequence set forth in SEQ ID NO: 183;
(lvii) a primer comprising the sequence set forth in SEQ ID NO: 184 and a primer comprising the sequence set forth in SEQ ID NO: 185;
(lviii) a primer comprising the sequence set forth in SEQ ID NO: 186 and a primer comprising the sequence set forth in SEQ ID NO: 187;
(lix) a primer comprising the sequence set forth in SEQ ID NO: 188 and a primer comprising the sequence set forth in SEQ ID NO: 189;
(lx) a primer comprising the sequence set forth in SEQ ID NO: 190 and a primer comprising the sequence set forth in SEQ ID NO: 191;
(lxi) a primer comprising the sequence set forth in SEQ ID NO: 192 and a primer comprising the sequence set forth in SEQ ID NO: 193;
(lxii) a primer comprising the sequence set forth in SEQ ID NO: 194 and a primer comprising the sequence set forth in SEQ ID NO: 195;
(lxiii) a primer comprising the sequence set forth in SEQ ID NO: 196 and a primer comprising the sequence set forth in SEQ ID NO: 197; and
(lxiv) a primer comprising the sequence set forth in SEQ ID NO: 198 and a primer comprising the sequence set forth in SEQ ID NO: 199.

It is to be understood that the detection step or amplification step of an assay format described herein clearly encompass the use of multiple rounds of amplifications and/or combinations of amplification, for example nested PCR, and classical nucleic acid hybridization steps, in any order. For example, as exemplified herein, nucleic acid linked to Chromosome 2 is amplified using a combination of primers set forth in the following groups of primers (primer groups are listed supra):

(i) Group (i) and Group (ii);
(ii) Group (iii) and Group (iv);
(iii) Group (v) and Group (vi);
(iv) Group (vii) and Group (viii);
(v) Group (ix) and Group (x);
(vi) Group (xi) and Group (xii);
(vii) Group (xiii) and Group (xiv);
(viii) Group (xv) and Group (xvi);
(ix) Group (xvii) and Group (xviii);
(x) Group (xix) and Group (xx);
(xi) Group (xxi) and Group (xxii);
(xii) Group (xxiii) and Group (xxiv);
(xiii) Group (xxv) and Group (xxvi);
(xiv) Group (xxvii) and Group (xxviii);
(xv) Group (xxix) and Group (xxx);
(xvi) Group (xxxi) and Group (xxxii);
(xvii) Group (xxxiii) and Group (xxxiv);
(xviii) Group (xxxv) and Group (xxxvi);
(xix) Group (xxxvii) and Group (xxxviii);
(xx) Group (xxxix) and Group (xl);
(xxi) Group (xli) and Group (xlii);
(xxii) Group (xliii) and Group (xliv);
(xxiii) Group (xlv) and Group (xlvi);
(xxiv) Group (xlvii) and Group (xlviii);
(xxv) Group (xlix) and Group (l);
(xxvi) Group (li) and Group (lii);
(xxvii) Group (liii) and Group (liv);
(xxviii) Group (lv) and Group (lvi);
(xxix) Group (lvii) and Group (lviii);
(xxx) Group (lix) and Group (lx);
(xxxi) Group (lxi) and Group (lxii);
(xxxii) Group (lxiii and Group (lxiv);
(xxxiii) Group (lxv) and Group (lxvi);
(xxxiv) Group (lxvii) and Group (lxviii);
(xxxv) Group (lxix) and Group (lxx);
(xxxvi) Group (lxxi) and Group (lxxii); and
(xxxvii) Group (lxxiii) and Group (lxxiv);

The performance of each and every of the above-mentioned second series of amplification reactions simultaneously or contemporaneously is also encompassed by the present invention.

Other primer combinations are also not to be excluded when using multiple amplifications to detect nucleic acid, the only requirement being that the primers are selected such that they comprise nucleotide sequences that occur within SEQ ID NOs: 1 to 33 and/or Table 1 at a position between the two amplification primer sequences used for the first series of amplifications. The skilled artisan will readily be capable of determining the nucleotide sequence of suitable amplification primers to perform this embodiment based upon the disclosure in any one or more of SEQ ID NOs: 1 to 33 and/or Table 1.

Furthermore, any of the primers described herein, e.g., those set forth in any one of SEQ ID NOs: 72 to 199 are useful for sequencing an amplified PCR product. Preferably, the primer used to sequence a nucleic acid was used in the amplification of the nucleic acid and/or hybridizes to the amplified nucleic acid.

In another embodiment, the presence of a mutated or non-mutated nucleotide in a bisulfite treated sample is detected using pyrosequencing, such as, for example, as described in Uhlmann et al., *Electrophoresis*, 23: 4072-4079, 2002. Essentially this method is a form of real-time sequencing that uses a primer that hybridizes to a site adjacent or close to the site of a cytosine that is methylated in a cancer cell. Following hybridization of the primer and template in the presence of a DNA polymerase each of four modified deoxynucleotide triphosphates are added separately according to a predetermined dispensation order. Only an added nucleotide that is complementary to the bisulfite treated sample is incorporated and inorganic pyrophosphate (PPi) is liberated. The PPi then drives a reaction resulting in production of detectable levels of light. Such a method allows determination of the identity of a specific nucleotide adjacent to the site of hybridization of the primer.

Methods of solid phase pyrosequencing are known in the art and reviewed in, for example, Landegren et al., *Genome Res.*, 8(8): 769-776, 1998. Such methods enable the high-throughput detection of methylation of a number of CpG dinucleotides.

A related method for determining the sequence of a bisulfite treated nucleotide is methylation-sensitive single nucleotide primer extension (Me-SnuPE) or SNaPmeth. Suitable methods are described, for example, in Gonzalgo and Jones *Nucl. Acids Res.*, 25: 2529-2531 or Uhlmann et al., *Electrophoresis*, 23: 4072-4079, 2002. An oligonucleotide is used that hybridizes to the region of a nucleic acid adjacent to the site of a cytosine that is methylated in a cancer cell. This oligonucleotide is then used in a primer extension protocol with a polymerase and a free nucleotide diphosphate or dideoxynucleotide triphosphate that corresponds to either or any of the possible bases that occur at this site following bisulfite treatment (i.e., thymine or cytosine). Preferably, the nucleotide-diphosphate is labeled with a detectable marker (e.g. a fluorophore). Following primer extension, unbound labeled nucleotide diphosphates are removed, e.g. using size exclusion chromatography or electrophoresis, or hydrolyzed, using for example, alkaline phosphatase, and the incorporation of the labeled nucleotide to the oligonucleotide is detected, indicating the base that is present at the site.

Clearly other high throughput sequencing methods are encompassed by the present invention. Such methods include, for example, solid phase minisequencing (as described, for example, in Syvämen et al, *Genomics*, 13: 1008-1017, 1992), or minisequencing with FRET (as described, for example, in Chen and Kwok, *Nucleic Acids Res.* 25: 347-353, 1997).

c(ii) Restriction Endonuclease-Based Assay Format

In one embodiment, the presence of a non-mutated sequence is detected using combined bisulfite restriction analysis (COBRA) essentially as described in Xiong and Laird, *Nucl. Acids Res.*, 25: 2532-2534, 2001. This method exploits the differences in restriction enzyme recognition sites between methylated and unmethylated nucleic acid after treatment with a compound that selectively mutates a non-methylated cytosine residue, e.g., bisulfite.

Following bisulfite treatment a region of interest comprising one or more CpG dinucleotides that are methylated in a cancer cell and are included in a restriction endonuclease recognition sequence is amplified using an amplification reaction described herein, e.g., PCR. The amplified product is then contacted with the restriction enzyme that cleaves at the site of the CpG dinucleotide for a time and under conditions sufficient for cleavage to occur. A restriction site may be selected to indicate the presence or absence of methylation. For example, the restriction endonuclease TaqI cleaves the sequence TCGA, following bisulfite treatment of a non-methylated nucleic acid the sequence will be TTGA and, as a consequence, will not be cleaved. The digested and/or non-digested nucleic acid is then detected using a detection means known in the art, such as, for example, electrophoresis and/or mass spectrometry. The cleavage or non-cleavage of the nucleic acid is indicative of cancer in a subject.

Clearly, this method may be employed in either a positive read-out or negative read-out system for the diagnosis of a cancer.

(c)(iii) Positive Read-Out Assay Format

In one embodiment, the assay format of the invention comprises a positive read-out system in which DNA from a cancer sample that has been treated, for example, with bisulfite is detected as a positive signal. Preferably, the non-hypermethylated DNA from a healthy or normal control subject is not detected or only weakly detected.

In a preferred embodiment, the enhanced methylation in a subject sample is determined using a process comprising:
(i) treating the nucleic acid with an amount of a compound that selectively mutates a non-methylated cytosine residue under conditions sufficient to induce mutagenesis thereby producing a mutated nucleic acid;
(ii) hybridizing a nucleic acid to a probe or primer comprising a nucleotide sequence that is complementary to a sequence comprising a methylated cytosine residue under conditions such that selective hybridization to the non-mutated nucleic acid occurs; and
(iii) detecting the selective hybridization.

In this context, the term "selective hybridization" means that hybridization of a probe or primer to the non-mutated nucleic acid occurs at a higher frequency or rate, or has a higher maximum reaction velocity, than hybridization of the same probe or primer to the corresponding mutated sequence. Preferably, the probe or primer does not hybridize to the non-methylated sequence carrying the mutation(s) under the reaction conditions used.

For positive read-out assay formats that detect DNA from a cancer subject sample as a positive signal following treatment with bisulfite, it is preferred to use probes and/or primers derived from nucleic acid comprising a nucleotide sequence set forth in any one of SEQ ID NOs: 1 to 33 or referred to in Table 1, in which cytosine residues are retained as cytosine other than those cytosine residues within a CpG dinucleotide that in not methylated in a cancer subject sample.

Hybridization-Based Assay Format

In one embodiment, the hybridization is detected using Southern, dot blot, slot blot or other nucleic acid hybridization means (Kawai et al., *Mol. Cell. Biol.* 14, 7421-7427, 1994; Gonzalgo et al., *Cancer Res.* 57, 594-599, 1997). Subject to appropriate probe selection, such assay formats are generally described herein above and apply mutatis mutandis to the presently described selective mutagenesis approach.

Preferably, a ligase chain reaction format is employed to distinguish between a mutated and non-mutated nucleic acid. Ligase chain reaction (described in EP 320,308 and U.S. Pat. No. 4,883,750) uses at least two oligonucleotide probes that anneal to a target nucleic acid in such a way that they are juxtaposed on the target nucleic acid (i.e., a nucleic acid comprising one or more sequences set forth in SEQ ID NOs: 1 to 33). In a ligase chain reaction assay, the target nucleic acid is hybridized to a first probe that is complementary to a diagnostic portion of the target sequence (the diagnostic probe) e.g., a nucleic acid comprising one or more methylated CpG dinucleotide(s), and with a second probe that is complementary to a nucleotide sequence contiguous with the diagnostic portion (the contiguous probe), under conditions wherein the diagnostic probe remains bound substantially only to the target nucleic acid. The diagnostic and contiguous probes can be of different lengths and/or have different melting temperatures such that the stringency of the hybridization can be adjusted to permit their selective hybridization to the target, wherein the probe having the higher melting temperature is hybridized at higher stringency and, following washing to remove unbound and/or non-selectively bound probe, the other probe having the lower melting temperature is hybridized at lower stringency. The diagnostic probe and contiguous probe are then covalently ligated such as, for example, using T4 DNA ligase, to thereby produce a larger target probe that is complementary to the target sequence, and the probes that are not ligated are removed by modifying the hybridization stringency. In this respect, probes that have not been ligated will selectively hybridize under lower stringency hybridization conditions than probes that have been ligated. Accordingly, the stringency of the hybridization can be increased to a stringency that is at least as high as the stringency used to hybridize the longer probe, and preferably at a higher stringency due to the increased length contributed by the shorter probe following ligation.

It is preferred to melt the target-probe duplex, elute the dissociated probe and confirm that is has been ligated, e.g., by determining its length using electrophoresis, mass spectrometry, nucleotide sequence analysis, gel filtration, or other means known to the skilled artisan.

In another preferred mode, one or both of the probes is labeled such that the presence or absence of the target sequence can be tested by melting the target-probe duplex, eluting the dissociated probe, and testing for the label(s). Where both probes are labeled, different ligands are used to permit distinction between the ligated and unligated probes, in which case the presence of both labels in the same eluate fraction confirms the ligation event.

If the target nucleic acid is bound to a solid matrix e.g., in a Southern hybridization, slot blot, dot blot, or microchip assay format, the presence of both the diagnostic and contiguous probes can be determined directly.

Probes suitable for such an assay format are readily derived from the description herein.

In accordance with this embodiment, the diagnostic probe and preferably also the contiguous probe should be selected such that they selectively hybridize to wild type sequences comprising one or more nucleotide sequences set forth in SEQ ID NOs: 1 to 33 and/or table 1 that are methylated in samples from subjects having cancer and thereby protected from mutation. By "selectively hybridize" in this context is meant that the probe(s) anneal at a significantly higher frequency under the conditions employed to a mutated target sequence of a hypermethylated CpG dinucleotide derived from a cancer sample compared to a mutated target sequence of a nucleic acid derived from a healthy or normal control sample, thereby producing a high signal-to-noise ratio in the assay. Preferably, the probe(s) have 3'-terminal and/or 5'-terminal sequences that comprise a CpG dinucleotide that is hypermethylated in cancer compared to a healthy or normal control sample, such that the diagnostic probe and contiguous probe are capable of being ligated only when the cytosine of the CpG dinucleotide has not been mutated to thymidine e.g., in the case of a methylated cytosine residue.

Alternatively, the diagnostic probe hybridizes to a site comprising a plurality of CpG dinucleotides that are methylated in a cancer sample and not in a normal or control sample. Accordingly, under stringent conditions, the probe is incapable of hybridizing to the test nucleic acid.

Methylation specific microarrays (MSO) are also useful for differentiating between a mutated and non-mutated sequence. A suitable method is described, for example, in Adorján et al, *Nucl. Acids Res.*, 30: e21, 2002. MSO uses nucleic acid that has been treated with a compound that selectively mutates a non-methylated cytosine residue (e.g., bisulfite) as template for an amplification reaction that amplifies both mutant and non-mutated nucleic acid. The amplification is performed with at least one primer that comprises a detectable label, such as, for example, a fluorophore, e.g., Cy3 or Cy5.

To produce a microarray for detection of mutated nucleic acid oligonucleotides are spotted onto, for example, a glass slide, preferably, with a degree of redundancy (for example, as described in Golub et al, *Science,* 286: 531-537, 1999). Preferably, for each CpG dinucleotide analyzed two different oligonucleotides are used. Each oligonucleotide comprises a sequence $N_{2-16}CGN_{2-16}$ or $N_{2-16}TGN_{2-16}$ (wherein N is a number of nucleotides adjacent or juxtaposed to the CpG dinucleotide of interest) reflecting the methylated or non-methylated status of the CpG dinucleotides.

The labeled amplification products are then hybridized to the oligonucleotides on the microarray under conditions that enable detection of single nucleotide differences. Following washing to remove unbound amplification product, hybridization is detected using, for example, a microarray scanner. Not only does this method allow for determination of the methylation status of a large number of CpG dinucleotides, it is also semi-quantitative, enabling determination of the degree of methylation at each CpG dinucleotide analyzed. As there may be some degree of heterogeneity of methylation in a single sample, such quantification may assist in the diagnosis of cancer.

Amplification-Based Assay Format

In an alternative embodiment, the hybridization is detected using an amplification system. In methylation-specific PCR formats (MSP; Herman et al. *Proc. Natl. Acad. Sci. USA* 93: 9821-9826, 1992), the hybridization is detection using a process comprising amplifying the bisulfite-treated DNA. In positive read-out formats, methylation of cytosine residues within the CpG dinucleotides of sequences set forth in SEQ ID NOs: 1 to 33 or Table 1 of a cancer sample is enhanced and, as a consequence, protected from mutation. Accordingly, by using one or more probe or primer that anneals specifically to the unmutated sequence under moderate and/or high stringency conditions an amplification product is only produced using a sample comprising a methylated nucleotide.

Any amplification assay format described herein can be used, such as, for example, polymerase chain reaction (PCR), rolling circle amplification (RCA), inverse polymerase chain reaction (iPCR), in situ PCR (Singer-Sam et al., Nucl. Acids Res. 18, 687, 1990), strand displacement amplification, or cycling probe technology.

PCR techniques have been developed for detection of gene mutations (Kuppuswamy et al., *Proc. Natl. Acad. Sci. USA* 88:1143-1147, 1991) and quantitation of allelic-specific expression (Szabo and Mann, *Genes Dev.* 9: 3097-3108, 1995; and Singer-Sam et al., *PCR Methods Appl.* 1: 160-163, 1992). Such techniques use internal primers, which anneal to a PCR-generated template and terminate immediately 5' of the single nucleotide to be assayed. Such as format is readily combined with ligase chain reaction as described herein above.

The use of a real-time quantitative assay format is particularly preferred.

Subject to the selection of appropriate primers, such assay formats are generally described herein above and apply mutatis mutandis to the presently described selective mutagenesis approach.

Methylation-specific melting-curve analysis (essentially as described in Worm et al., *Clin. Chem.*, 47: 1183-1189, 2001) and exemplified herein is also contemplated by the present invention. This process exploits the difference in melting temperature in amplification products produced using bisulfite treated methylated or unmethylated nucleic acid. In essence, non-discriminatory amplification of a bisulfite treated sample is performed in the presence of a fluorescent dye that specifically binds to double stranded DNA (e.g., SYBR Green I). By increasing the temperature of the amplification product while monitoring fluorescence the melting properties and thus the sequence of the amplification product is determined. A decrease in the fluorescence reflects melting of at least a domain in the amplification product. The temperature at which the fluorescence decreases is indicative of the nucleotide sequence of the amplified nucleic acid, thereby permitting the nucleotide at the site of one or more CpG dinucleotides to be determined. As the sequence of the nucleic acids amplified using the present invention The present invention also encompasses the use of real-time quantitative forms of PCR, such as, for example, Taq-Man (Holland et al., Proc. Natl. Acad. Sci. USA, 88, 7276-7280, 1991; Lee et al., Nucleic Acid Res. 21, 3761-3766, 1993) to perform this embodiment. For example, the Meth-ylLight method of Eads et al., Nucl. Acids Res. 28: E32, 2000 uses a modified TaqMan assay to detect methylation of a CpG dinucleotide. Essentially, this method comprises treating a nucleic acid sample with bisulfite and amplifying nucleic acid comprising one or more CpG dinucleotides that are methylated in a cancer cell and not in a control sample using an amplification reaction, e.g., PCR. The amplification reaction is performed in the presence of three oligonucleotides, a forward and reverse primer that flank the region of interest and a probe that hybridizes between the two primers to the site of the one or more methylated CpG dinucleotides. The probe is dual labeled with a 5' fluorescent reporter and a 3' quencher (or vice versa). When the probe is intact, the quencher dye absorbs the fluorescence of the reporter due to their proximity. Following annealing of to the PCR product the probe is cleaved by 5' to 3' exonuclease activity of, for example, Taq DNA polymerase. This cleavage releases the reporter from the quencher thereby resulting in an increased fluorescence signal that can be used to estimate the initial template methylation level. By using a probe or primer that selectively hybridizes to unmutated nucleic acid (i.e. methylated nucleic acid) the level of methylation is determined, e.g., using a standard curve.

Alternatively, rather than using a labeled probe that requires cleavage, a probe, such as, for example, a Molecular Beacon™ is used (see, for example, Mhlang and Malmberg, *Methods* 25: 463-471, 2001). Molecular beacons are single stranded nucleic acid molecules with a stem-and-loop structure. The loop structure is complementary to the region surrounding the one or more CpG dinucleotides that are methylated in a cancer sample and not in a control sample. The stem structure is formed by annealing two "arms" complementary to each other, which are on either side of the probe (loop). A fluorescent moiety is bound to one arm and a quenching moiety that suppresses any detectable fluorescence when the molecular beacon is not bound to a target sequence is bound to the other arm. Upon binding of the loop region to its target nucleic acid the arms are separated and fluorescence is detectable. However, even a single base mismatch significantly alters the level of fluorescence detected in a sample. Accordingly, the presence or absence of a particular base is determined by the level of fluorescence detected. Such an assay facilitates detection of one or more unmutated sites (i.e. methylated nucleotides) in a nucleic acid.

Fluorescently labeled locked nucleic acid (LNA) molecules or fluorescently labeled protein-nucleic acid (PNA) molecules are useful for the detection of nucleotide differences (e.g., as described in Simeonov and Nikiforov, *Nucleic Acids Research*, 30(17): 1-5, 2002). LNA and PNA molecules bind, with high affinity, to nucleic acid, in particular, DNA. Fluorophores (in particular, rhodomine or hexachlorofluorescein) conjugated to the LNA or PNA probe fluoresce at a significantly greater level upon hybridization of the probe to target nucleic acid. However, the level of increase of fluorescence is not enhanced to the same level when even a single nucleotide mismatch occurs. Accordingly, the degree of fluorescence detected in a sample is indicative of the presence of a mismatch between the LNA or PNA probe and the target nucleic acid, such as, in the presence of a mutated cytosine in a methylated CpG dinucleotide. Preferably, fluorescently labeled LNA or PNA technology is used to detect at least a single base change in a nucleic acid that has been previously amplified using, for example, an amplification method known in the art and/or described herein.

As will be apparent to the skilled artisan, LNA or PNA detection technology is amenable to a high-throughput detection of one or more markers by immobilizing an LNA or PNA probe to a solid support, as described in Orum et al., *Clin. Chem.* 45: 1898-1905, 1999.

Alternatively, a real-time assay, such as, for example, the so-called HeavyMethyl assay (Cottrell et al., *Nucl. Acids Res.* 32: e10, 2003) is used to determine the presence or level of methylation of nucleic acid in a test sample. Essentially, this method uses one or more non-extendible nucleic acid (e.g., oligonucleotide) blockers that bind to bisulfite-treated nucleic acid in a methylation specific manner (i.e., the blocker/s bind specifically to unmutated DNA under moderate to high stringency conditions). An amplification reaction is performed using one or more primers that may optionally be methylation specific but that flank the one or more blockers. In the presence of unmethylated nucleic acid (i.e., non-mutated DNA) the blocker/s bind and no PCR product is produced. Using a TaqMan assay essentially as described supra the level of methylation of nucleic acid in a sample is determined.

As exemplified herein, another amplification based assay useful for the detection of a methylated nucleic acid following treatment with a compound that selectively mutates a non-methylated cytosine residue makes use of head loop PCR technology (e.g., as described in published PCT Application No. PCT/AU03/00244; WO 03/072810). This form of amplification uses a probe or primer that comprises a region that binds to a nucleic acid and is capable of amplifying nucleic acid in an amplification reaction whether the nucleic acid is methylated or not. The primer additionally comprises a region that is complementary to a portion of the amplified nucleic acid enabling this region of the primer to hybridize to the amplified nucleic acid incorporating the primer thereby forming a hairpin. The now 3' terminal nucleotide/s of the annealed region (i.e. the most 5' nucleotide/s of the primer) hybridize to the site of one or more mutated cytosine residues (i.e., unmethylated in nucleic acid from a cancer subject). Accordingly, this facilitates self priming of amplification products from unmethylated nucleic acid, the thus formed hairpin structure blocking further amplification of this nucleic acid. In contrast, the complementary region may or may not by capable of hybridizing to an amplification product from methylated (mutated) nucleic acid, but is unable to "self prime" thereby enabling further amplification of this nucleic acid (e.g., by the inability of the now 3' nucleotide to hybridize to the amplification product). This method may be performed using a melting curve analysis method to determine the amount of methylated nucleic acid in a biological sample from a subject.

Other amplification based methods for detecting methylated nucleic acid following treatment with a compound that selectively mutates a non-methylated cytosine residue include, for example, methylation-specific single stranded conformation analysis (MS-SSCA) (Bianco et al., *Hum. Mutat.*, 14: 289-293, 1999), methylation-specific denaturing gradient gel electrophoresis (MS-DGGE) (Abrams and Stanton, *Methods Enzymol.*, 212: 71-74, 1992) and methylation-specific denaturing high-performance liquid chromatography (MS-DHPLC) (Deng et al, *Chin. J. Cancer Res.*, 12: 171-191, 2000). Each of these methods use different techniques for detecting nucleic acid differences in an amplification product based on differences in nucleotide sequence and/or secondary structure. Such methods are clearly contemplated by the present invention.

As with other amplification-based assay formats, the amplification product is analyzed using a range of procedures, including gel electrophoresis, gel filtration, mass spectrometry, and in the case of labeled primers, by identifying the label in the amplification product. In an alternative embodiment, restriction enzyme digestion of PCR products amplified from bisulfite-converted DNA is performed essentially as described by Sadri and Hornsby, *Nucl. Acids Res.* 24, 5058-5059, 1996; and Xiong and Laird, *Nucl. Acids Res.* 25, 2532-2534, 1997), to analyze the product formed.

High throughput detection methods, such as, for example, matrix-assisted laser desorption/ionization time of flight (MALDI-TOF), electrospray ionization (ESI), Mass spectrometry (including tandem mass spectrometry, e.g. LC MS/MS), biosensor technology, evanescent fiber-optics technology or DNA chip technology, can also be employed.

As with the other assay formats described herein that utilize hybridization and/or amplification detection systems, combinations of such processes as described herein above are particularly contemplated by the selective mutagenesis-based assay formats of the present invention. In a preferred embodiment, the enhanced methylation is detected by performing a process comprising:

(i) treating the nucleic acid with an amount of a compound that selectively mutates a non-methylated cytosine residue within a CpG dinucleotide under conditions sufficient to induce mutagenesis thereby producing a mutated nucleic acid;

(ii) hybridizing the nucleic acid to two non-overlapping and non-complementary primers each of which comprises a nucleotide sequence that is complementary to a sequence in the DNA comprising a methylated cytosine residue under conditions such that hybridization to the non-mutated nucleic acid occurs;

(iii) amplifying nucleic acid intervening the hybridized primers thereby producing a DNA fragment consisting of a sequence that comprises a primer sequence;

(iv) hybridizing the amplified DNA fragment to a probe comprising a nucleotide sequence that corresponds or is complementary to a sequence comprising a methylated cytosine residue under conditions such that hybridization to the non-mutated nucleic acid occurs; and (v) detecting the hybridization.

(c)(ii) Negative Read-Out Assays

In an alternative embodiment, the assay format comprises a negative read-out system in which reduced methylation of DNA from a healthy/normal control sample is detected as a positive signal and preferably, methylated DNA from a cancer sample is not detected or is only weakly detected.

In a preferred embodiment, the reduced methylation is determined using a process comprising:

(i) treating the nucleic acid with an amount of a compound that selectively mutates a non-methylated cytosine residue within a CpG island under conditions sufficient to induce mutagenesis thereby producing a mutated nucleic acid;

(ii) hybridizing the nucleic acid to a probe or primer comprising a nucleotide sequence that is complementary to a sequence comprising the mutated cytosine residue under conditions such that selective hybridization to the mutated nucleic acid occurs; and (iii) detecting the selective hybridization.

In this context, the term "selective hybridization" means that hybridization of a probe or primer to the mutated nucleic acid occurs at a higher frequency or rate, or has a higher maximum reaction velocity, than hybridization of the same probe or primer to the corresponding non-mutated sequence. Preferably, the probe or primer does not hybridize to the methylated sequence (or non-mutated sequence) under the reaction conditions used.

For negative read-out assay formats that detect DNA from a healthy/normal control subject sample as a positive signal following treatment with bisulfite, it is preferred to use probes and/or primers derived from any one of SEQ ID NOs: 1 to 33 or Table 1, in which cytosine residues within a CpG dinucleotide have been mutated to thymidine other than those cytosine residues within a CpG dinucleotide that appears to be methylated in a healthy/normal control subject.

Hybridization-Based Assay Format

In one embodiment the hybridization is detected using Southern, dot blot, slot blot or other nucleic acid hybridization means (Kawai et al., *Mol. Cell. Biol.* 14, 7421-7427, 1994; Gonzalgo et al., *Cancer Res.* 57, 594-599, 1997). Subject to appropriate probe selection, such assay formats are generally described herein above and apply mutatis mutandis to the presently described selective mutagenesis approach.

Preferably, a ligase chain reaction format is employed to distinguish between a non-mutated and mutated nucleic acid comprising a sequence included in a sequence set forth in any one or more of SEQ ID NOs: 1 to 33 or Table 1. In this respect, the assay requirements and conditions are as described herein above for positive read-out assays and apply mutatis mutandis to the present format. However the selection of probes will differ. For negative read-out assays, one or more probes are selected that selectively hybridize to the mutated sequence rather than the non-mutated sequence.

Preferably, the ligase chain reaction probe(s) have 3'-terminal and/or 5'-terminal sequences that comprise a CpG dinucleotide that is not methylated in a healthy control sample, but is hypermethylated in cancer, such that the diagnostic probe and contiguous probe are capable of being ligated only when the cytosine of the CpG dinucleotide is mutated to thymidine e.g., in the case of a non-methylated cytosine residue.

As will be apparent to the skilled artisan the MSO method described supra is amenable to either or both positive and/or negative readout assays. This is because the assay described detects both mutated and non-mutated sequences thereby facilitating determining the level of methylation. However, an assay detecting only methylated or non-methylated sequences is contemplated by the invention.

Amplification-Based Assay Format

In an alternative embodiment, the hybridization is detected using an amplification system using any amplification assay format as described herein above for positive read-out assay albeit using primers (and probes where applicable) selectively hybridize to a mutated nucleic acid.

In negative read-out formats, mutation of non-methylated cytosine residues within the CpG dinucleotides from about map position 2q14.1 to about map position 2q14.3 of a healthy/normal subject is enhanced relative to the cancer sample.

In adapting the HeavyMethyl assay described supra to a negative read-out format, the blockers that bind to bisulfite-treated nucleic acid in a methylation specific manner bind specifically to mutated DNA under moderate to high stringency conditions. An amplification reaction is performed using one or more primers that may optionally be methylation specific (i.e. only bind to mutated nucleic acid) but that flank the one or more blockers. In the presence of methylated nucleic acid (i.e., mutated DNA) the blocker/s bind and no PCR product is produced.

In a particularly preferred embodiment, the reduced methylation in the normal/healthy control subject is detected by performing a process comprising:
(i) treating the nucleic acid with an amount of a compound that selectively mutates non-methylated cytosine residues under conditions sufficient to induce mutagenesis thereby producing a mutated nucleic acid;
(ii) hybridizing the nucleic acid to two non-overlapping and non-complementary primers each of which comprises a nucleotide sequence that is complementary to a sequence in the DNA comprising a mutated cytosine residue under conditions such that hybridization to the mutated nucleic acid occurs;
(iii) amplifying nucleic acid intervening the hybridized primers thereby producing a DNA fragment consisting of a sequence that comprises a primer sequence;
(iv) hybridizing the amplified DNA fragment to a probe comprising a nucleotide sequence that corresponds or is complementary to a sequence comprising a mutated cytosine residue under conditions such that hybridization to the mutated nucleic acid occurs; and
(v) detecting the hybridization.

As will be apparent to the skilled artisan a negative read-out assay preferable includes a suitable control sample to ensure that the negative result is caused by methylated nucleic acid rather than a reaction failing.

II. Detection of Modified Histone

As used herein the term "histone modification" shall be taken to mean a post-translational modification of a histone protein, such as, for example, a histone H3 (SEQ ID NO: 220), histone H4 (SEQ ID NO: 221) histone H2A (SEQ ID NO: 222) or histone H2B (SEQ ID NO: 223). A post-translational modification includes, for example, methylation of a histone and/or acetylation of a histone and/or de-acetylation of a histone and/or phosphorylation of a histone. For example, a histone is subject to a post-translational modification selected from the group consisting of acetylation of a lysine residue, acetylation of an arginine residue, methylation of a lysine residue, methylation of an arginine residue, phosphorylation of a serine residue, phosphorylation of a threonine residue, ubiquitylation of a lysine residue, sumoylation of a lysine residue and ribosylation.

The following post translational modifications are known to occur in human Histone H3 (SEQ ID NO: 220) (positions are with reference to the sequence set forth in SEQ ID NO: 220), methylation at arginine 2, phosphorylation at threonine 2, methylation at lysine 4, methylation of lysine 9, acetylation of lysine 9, phosphorylation at serine 10, phosphorylation at threonine 11, methylation at lysine 14, acetylation at lysine 14, methylation at arginine 17, acetylation at lysine 18, methylation at lysine 23, acetylation at lysine 23, methylation at arginine 26, methylation at lysine 27, acetylation at lysine 27, phosphorylation at serine 28, phosphorylation at serine 32, methylation at lysine 36, methylation at lysine 37, methylation at lysine 79, acetylation at lysine 115, phosphorylation at threonine 118, acetylation at position 122 or methylation at arginine 128.

The following post translational modifications are known to occur in human Histone H4 (SEQ ID NO: 221) (positions are with reference to the sequence set forth in SEQ ID NO: 221), phosphorylation at serine 1, methylation at arginine 3, acetylation at lysine 5, acetylation at lysine 8, methylation at lysine 12, acetylation at lysine 12, acetylation at lysine 16, methylation at lysine 20, acetylation at lysine 20, phosphorylation at serine 47, methylation at lysine 59, acetylation at lysine 77, methylation at lysine 79, acetylation at lysine 79 or methylation at arginine 92.

The following post translational modifications are known to occur in human Histone H2A (SEQ ID NO: 222) (positions are with reference to the sequence set forth in SEQ ID NO: 222), phosphorylation at serine 1, acetylation at lysine 5, acetylation at lysine 9, acetylation at lysine 13, acetylation at lysine 15, acetylation at lysine 36, methylation at lysine 95, methylation at lysine 99, acetylation at lysine 119 or ubiquitylation at lysine 119.

The following post translational modifications are known to occur in human Histone H2B (SEQ ID NO: 223) (positions are with reference to the sequence set forth in SEQ ID NO: 223), methylation at lysine 5, acetylation at lysine 5, acetylation at lysine 12, phosphorylation at serine 14, acetylation at lysine 15, acetylation at lysine 20, methylation at lysine 23, acetylation at lysine 24, phosphorylation at serine 32, phosphorylation at serine 36, methylation at lysine 43, acetylation at lysine 85, methylation at arginine 99, acetylation at lysine 108, acetylation at lysine 116, acetylation at lysine 120 or ubiquitylation at lysine 120.

The association of several of these post-translational modifications with the level of expression of a gene with which the histone is associated is known in the art and described, for example, in Peterson and Laniel, *Current Biology*, 14: R550.

The present invention clearly encompasses the detection of any one or more of the post-translational modifications listed supra or any other post-translational modification of a histone for the diagnosis of a cancer. The detection of, for example, acetylation also encompasses the detection of de-acetylation.

Histone Immunoprecipitation

Methods for determining the post-translational modification of a histone in chromatin linked to from about map position 2q14.1 to about map position 2q14.3 of the human genome will be apparent to the skilled artisan and include, for example, chromatin immunoprecipitation (ChIP) and a detection method (e.g., essentially as described in Kondo et al., *Mo. Cell Biol.*, 23: 206-215, 2003).

The process of ChIP generally comprises, for example, treating a sample comprising chromatin to crosslink the histones to DNA (e.g., by treating with formaldehyde). The sample is then lysed, if necessary, and nucleic acid sheared, e.g., by sonication or passing through a fine gauge needle. The sample is then contacted with an antibody that specifically binds to a modified histone for a time and under conditions sufficient for an antibody-antigen complex to form and the antibody isolated. The crosslinks are then reversed, e.g., by heating a sample to approximately 65° C. for a time and under conditions to reverse the crosslinking (e.g., for at least 6 hours). Nucleic acid that was bound to the modified histone is then detected using a detection means known in the art and/or described herein, e.g., PCR.

ChIP uses an antibody that selectively binds to a histone that is post-translationally modified at one or more positions. In this context, the term "selectively binds to" means that the antibody binds to or forms an antibody-antigen complex with a post-translationally modified histone at a higher frequency or rate that binding of the same antibody to the corresponding unmodified histone. Preferably, the antibody does not bind to the unmodified histone under the reaction conditions used at a readily detectable level.

As used herein the term "antibody" refers to intact monoclonal or polyclonal antibodies, immunoglobulin (IgA, IgD, IgG, IgM, IgE) fractions, humanized antibodies, or recombinant single chain antibodies, as well as fragments thereof, such as, for example Fab, F(ab)$_2$, and Fv fragments.

Antibodies referred to herein are obtained from a commercial source, or alternatively, produced by conventional means. For example, antibodies to a number of post-translationally modified histones including, for example, acetyl-histone H2A (lys5), acetyl-histone H2B(lys12 or lys20) acetyl-histone H3 (various sites), acetyl-histone H3(lys18 or lys 23 or lys9), acetyl-histone H4 (lys12 or lys 8) are available from, for example Cell Signalling Technology or Abcam Ltd. (Cambridge, UK).

High titer antibodies are preferred, as these are more useful commercially in kits for analytical, diagnostic and/or therapeutic applications. By "high titer" is meant a titer of at least about $1:10^3$ or $1:10^4$ or $1:10^5$. Methods of determining the titer of an antibody will be apparent to the skilled artisan. For example, the titer of an antibody in purified antiserum may be determined using an ELISA assay to determine the amount of IgG in a sample. Typically an anti-IgG antibody or Protein G is used in such an assay. The amount detected in a sample is compared to a control sample of a known amount of purified and/or recombinant IgG. Alternatively, a kit for determining antibody may be used, e.g. the Easy TITER kit from Pierce (Rockford, Ill., USA).

Alternatively, an antibody is prepared suing a standard method in the art. Antibodies may be prepared by any of a variety of techniques known to those of ordinary skill in the art, and described, for example in, Harlow and Lane (In: Antibodies: A Laboratory Manual, Cold Spring Harbor Laboratory, 1988). In one such technique, an immunogen comprising the antigenic polypeptide (e.g., a post-translationally modified histone or fragment thereof) is initially injected into any one of a wide variety of animals (e.g., mice, rats, rabbits, sheep, humans, dogs, pigs, chickens and goats). The immunogen is derived from a natural source, produced by recombinant expression means, or artificially generated, such as by chemical synthesis (e.g., BOC chemistry or FMOC chemistry). In this step, the polypeptides or fragments thereof of described herein may serve as the immunogen.

Optionally, a peptide, polypeptide or protein is joined to a carrier protein, such as bovine serum albumin or keyhole limpet hemocyanin. The immunogen and the optional carrier for the protein is injected into the animal host, preferably according to a predetermined schedule incorporating one or more booster immunizations, and blood collected from said the animals periodically. Optionally, the immunogen may be injected in the presence of an adjuvant, such as, for example Freund's complete or incomplete adjuvant, lysolecithin and dinitrophenol to enhance the immune response to the immunogen. Monoclonal or polyclonal antibodies specific for the polypeptide may then be purified from the blood isolated from an animal by, for example, affinity chromatography using the polypeptide coupled to a suitable solid support.

Preferably, the antibody is purified using a modified histone. Following purification, the antibody is, for example, passed over an affinity purification column comprising an unmodified form of the histone and the unbound antibody/ies collected. Accordingly only those antibodies capable of selectively binding the modified histone are purified.

Monoclonal antibodies specific for the antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described supra. The spleen cells are immortalized by, for example, fusion with a myeloma cell fusion partner, preferably one that is syngenic with the immunized animal. A variety of fusion techniques may be employed, for example, the spleen cells and myeloma cells may be combined with a nonionic detergent or electrofused and then grown in a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and growth media in which the cells have been grown is tested for the presence of binding activity against the polypeptide (immunogen). Hybridomas having high reactivity and specificity are preferred.

Monoclonal antibodies are isolated from the supernatants of growing hybridoma colonies using methods such as, for example, affinity purification as described supra. In addition, various techniques may be employed to enhance the yield, such as injection of the hybridoma cell line into the peritoneal cavity of a suitable vertebrate host, such as a mouse. Monoclonal antibodies are then harvested from the ascites fluid or the blood of such an animal subject. Contaminants are removed from the antibodies by conventional techniques, such as chromatography, gel filtration, precipitation, and/or extraction. A protein the expression of which is reduced (or a fragment thereof) may be used to produce a suitable monoclonal antibody.

It is preferable that an immunogen used in the production of an antibody is one that is sufficiently antigenic to stimulate the production of antibodies that will bind to the immunogen and is preferably, a high titer antibody. In one embodiment, an immunogen may be an entire protein.

Alternatively, or in addition, an antibody raised against a peptide immunogen will recognize the full-length protein from which the immunogen was derived when the protein is denatured. By "denatured" is meant that conformational epitopes of the protein are disrupted under conditions that retain linear B cell epitopes of the protein. As will be known to a skilled artisan linear epitopes and conformational epitopes may overlap.

Alternatively, a monoclonal antibody capable of binding to a polypeptide of interest or a fragment thereof is produced using a method such as, for example, a human B-cell hybridoma technique (Kozbar et al., *Immunol. Today* 4:72, 1983), a EBV-hybridoma technique to produce human monoclonal antibodies (Cole et al. *Monoclonal Antibodies in Cancer Therapy,* 1985 Allen R. Bliss, Inc., pages 77-96), or screening of combinatorial antibody libraries (Huse et al., *Science* 246: 1275, 1989).

Such an antibody is then particularly useful in determining the level of expression of a protein to diagnose a cancer.

Following obtaining or producing one or more antibodies that selectively bind to one or more modified histones, said modified histone/s are isolated from a biological sample by a process comprising contacting the antibody with the biological sample for a time and under conditions sufficient for an antibody-antigen interaction to occur and isolating the antibody. As will be apparent to the skilled artisan, the antibody may be immobilized on a solid support to facilitate isolation of the antibody. Suitable solid supports include, for example, agarose, Sepharose, polycarbonate, polystyrene or glass.

Nucleic Acid Detection

Following isolation of nucleic acid that was bound to the isolated histone the presence or absence of nucleic acid within chromosome 2 of the human genome from about map position 2q14.1 to about map position 2q14.3 is determined. Methods for determining the presence or absence of a nucleic acid will be apparent to the skilled artisan and include for example, an amplification reaction.

For example, a PCR reaction is performed with a set of primers that specifically amplify nucleic acid within chromosome 2 of the human genome from about map position 2q14.1 to about map position 2q14.3. Detection of an amplification product indicates that the chromatin within chromosome 2 of the human genome from about map position 2q14.1 to about map position 2q14.3 is modified and that the subject from whom the sample used in the assay was isolated has cancer.

Clearly, any amplification reaction capable of detecting a specific nucleic acid is contemplated by the present invention. For example, the present embodiment of the invention contemplates the use of an amplification reaction selected from the group consisting of rolling circle amplification (RCA), inverse polymerase chain reaction (iPCR), in situ PCR (Singer-Sam et al., *Nucl. Acids Res.* 18, 687, 1990), strand displacement amplification, or cycling probe technology for the diagnosis of cancer.

Suitable combinations of primers will be apparent to the skilled artisan based on the disclosure herein in respect of any of the embodiments of the invention.

In a preferred embodiment, the detection of nucleic acid bound to a modified histone uses a primer combination selected from the group consisting of:

(i) a primer comprising the sequence set forth in SEQ ID NO: 235 and a primer comprising the sequence set forth in SEQ ID NO: 236;

(ii) a primer comprising the sequence set forth in SEQ ID NO: 237 and a primer comprising the sequence set forth in SEQ ID NO: 238;

(iii) a primer comprising the sequence set forth in SEQ ID NO: 239 and a primer comprising the sequence set forth in SEQ ID NO: 240;

(iv) a primer comprising the sequence set forth in SEQ ID NO: 241 and a primer comprising the sequence set forth in SEQ ID NO: 242;

(v) a primer comprising the sequence set forth in SEQ ID NO: 243 and a primer comprising the sequence set forth in SEQ ID NO: 244;

(vi) a primer comprising the sequence set forth in SEQ ID NO: 245 and a primer comprising the sequence set forth in SEQ ID NO: 246;

(vii) a primer comprising the sequence set forth in SEQ ID NO: 247 and a primer comprising the sequence set forth in SEQ ID NO: 248;

(viii) a primer comprising the sequence set forth in SEQ ID NO: 249 and a primer comprising the sequence set forth in SEQ ID NO: 250;

(ix) a primer comprising the sequence set forth in SEQ ID NO: 251 and a primer comprising the sequence set forth in SEQ ID NO: 252;

(x) a primer comprising the sequence set forth in SEQ ID NO: 253 and a primer comprising the sequence set forth in SEQ ID NO: 254; and (xi) a primer comprising the sequence set forth in SEQ ID NO: 255 and a primer comprising the sequence set forth in SEQ ID NO: 256;

Other primer combinations are also not to be excluded when using multiple amplifications to detect nucleic acid, the only requirement being that the primers are selected such that they comprise nucleotide sequences that occur within SEQ ID NOs: 1 to 33 and/or Table 1 at a position between the two amplification primer sequences used for the first series of amplifications. The skilled artisan will readily be capable of determining the nucleotide sequence of suitable amplification primers to perform this embodiment based upon the disclosure in any one or more of SEQ ID NOs: 1 to 33 and/or Table 1 and, as a consequence, the present invention is not to be limited by the precise sequence of amplification primers used.

Alternatively, the presence of a nucleic acid within chromosome 2 of the human genome from about map position 2q14.1 to about map position 2q14.3 is determined using, for example, a hybridization technique, such as, for example, a Southern Blot or a slot blot.

In one embodiment, the presence of a nucleic acid within chromosome 2 of the human genome from about map position 2q14.1 to about map position 2q14.3 is determined using, for example, a microarray, essentially as described in, Kondo et al., *Proc. Natl. Acad. Sci. USA,* 101: 7398-7403, 2004 or Chua et al., *The Plant Journal,* 37: 789-800, 2004. In accordance with this embodiment, chromatin is immunoprecipitated with an antibody that selectively binds to a modified histone and the isolated nucleic acid isolated. The isolated nucleic acid is then labeled with a detectable marker, such as, for example, a fluorophore, e.g., using ligation-mediated PCR or any other suitable method. Nucleic acid is then hybridized to a suitable microarray (as available from, for example, Affymetrix) and the identity of hybridized nucleic acid determined. Alternatively, a microarray comprising probes specific to chromosome 2 of the human genome from about map position 2q14.1 to about map position 2q14.3 is used to determine the presence of nucleic acid that is diagnostic of cancer.

For example, the microarray comprises one or more oligonucleotides comprising a nucleotide sequence set forth in any one of SEQ ID NOs: 235 to 256 to determine the presence of nucleic acid bound to a modified histone.

In accordance with this embodiment, a method for determining the presence of a modified histone in chromatin within chromosome 2 of the human genome from about map position 2q14.1 to about map position 2q14.3 comprises:

(i) contacting a biological sample comprising chromatin with an antibody that selectively binds to a modified histone for a time and under conditions sufficient for an antibody-antigen complex to form;

(ii) isolating the antibody; and (iii) isolating or identifying nucleic acid bound to a histone isolated with the antibody and detecting nucleic acid within chromosome 2 of the human genome from about map position 2q14.1 to about map position 2q14.3, wherein detection of said nucleic acid indicates the presence of a modified histone in chromatin within chromosome 2 of the human genome from about map position 2q14.1 to about map position 2q14.3 and that a subject has cancer.

III Detection of Reduced Gene Expression

The present inventors have clearly demonstrated that the expression of any of a number of genes within chromosome 2 from about map position 2q14.1 to about map position 2q14.3 is reduced in cancer subjects and in cancer cell lines.

Nucleic Acid Detection

In one embodiment, the level of gene expression is determined by detecting the level of mRNA transcribed from a gene within chromosome 2 from about map position 2q14.1 to about map position 2q14.3 or cDNA produced therefrom.

In one embodiment, the mRNA is detected by hybridizing a nucleic acid probe or primer capable of specifically hybridizing to a transcript of a gene within chromosome 2 from about map position 2q14.1 to about map position 2q14.3 to a nucleic acid in a biological sample derived from a subject and detecting the hybridization by a detection means, wherein hybridization of the probe or primer indicates that the subject being tested suffers from cancer. Preferably, the detection means is an amplification reaction, or a nucleic acid hybridization reaction, such as, for example, as described herein.

In this context, the term "selective hybridization" means that hybridization of a probe or primer to the transcript of a gene within chromosome 2 from about map position 2q14.1 to about map position 2q14.3 occurs at a higher frequency or rate, or has a higher maximum reaction velocity, than hybridization of the same probe or primer to any other nucleic acid. Preferably, the probe or primer does not hybridize to another nucleic acid at a detectable level under the reaction conditions used.

A preferred transcript for performance of the method of the invention is selected from the group consisting of RALBB (SEQ ID NO: 34), DDX18 (SEQ ID NO: 36), SCTR (SEQ ID NO: 38), EN1 (SEQ ID NO: 40), TSN (SEQ ID NO: 42), MARCO (SEQ ID NO: 48), PTPN4 (SEQ ID NO: 50), INSIG2 (SEQ ID NO: 52), INHBB (SEQ ID NO: 54), Gli2 (SEQ ID NO: 56), MGC13033 (SEQ ID NO: 58), TSAP6 (SEQ ID NO: 60), DBI (SEQ ID NO: 62), MGC10993 (SEQ ID NO: 64), EPB41L5 (SEQ ID NO: 66), FLJ14816 (SEQ ID NO: 68) and LBP9 (SEQ ID NO: 70).

In one embodiment, the method of the invention comprises detecting a RALBB transcript. In another embodiment, the method of the invention comprises detecting a DDX18 transcript. In a further embodiment, the method of the invention comprises detecting a SCTR transcript. In a still further embodiment, the method of the invention comprises detecting an EN1 transcript. In another embodiment, the method of the invention comprises detecting a TSN transcript. In yet another embodiment, the method of the invention comprises detecting a MARCO transcript. Alternatively, the method of the invention comprises detecting a PTPN4 transcript. In another alternative embodiment, the method comprises detecting an INSIG2 transcript. In another embodiment, the method of the invention comprises detecting an INHBB transcript. In another embodiment, the method of the invention comprises detecting a Gli2 transcript. In another embodiment, the method of the invention comprises detecting a MGC13033 transcript. In another embodiment, the method of the invention comprises detecting a TSAP6 transcript. In another embodiment, the method of the invention comprises detecting a DBI transcript. In another embodiment, the method of the invention comprises detecting a MGC10993 transcript. In another embodiment, the method of the invention comprises detecting an EPB41L5 transcript. In another embodiment, the method of the invention comprises detecting a FLJ14816 transcript. In another embodiment, the method of the invention comprises detecting a LBP9 transcript.

As transcripts of a gene within chromosome 2 from about map position 2q14.1 to about map position 2q14.3 are detected using mRNA or cDNA derived therefrom, assays that detect changes in mRNA are preferred (e.g. Northern hybridization, RT-PCR, NASBA, TMA or ligase chain reaction).

Northern blotting is described in, for example, Ausubel et al (In: Current Protocols in Molecular Biology. Wiley Interscience, ISBN 047 150338, 1987) and Sambrook et al (In: Molecular Cloning: Molecular Cloning: A Laboratory Manual, Cold Spring Harbor Laboratories, New York, Third Edition 2001). Essentially this method comprises immobilizing nucleic acid (RNA) on a solid support, such as, for example, a membrane. A probe or primer that is labeled with a detectable marker (such as, for example, a fluorescent label (e.g., Texas Red or FITC), an enzymatic label (e.g., horseradish peroxidase or alkaline phosphatase or a radioactive label (e.g., $^{32}P$ or $^{125}I$) is then brought into direct contact with the membrane for a time and under conditions sufficient for hybridization to occur (preferably, under moderate and more preferably high stringency conditions). Following washing to remove any non-specifically bound probe, the detectable marker is detected. Methods for detection will vary with the detectable marker used, but include, for example, densitometry a radioactive or fluorescent label or a calorimetric assay for an enzymatic label. A suitable method of detection will be apparent to the skilled artisan.

Methods of RT-PCR are known in the art and described, for example, in Dieffenbach (ed) and Dveksler (ed) (In: PCR Primer: A Laboratory Manual, Cold Spring Harbour Laboratories, NY, 1995). Essentially, this method comprises performing a PCR reaction using cDNA produced by reverse transcribing mRNA from a cell using a reverse transcriptase. Methods of PCR described supra are to be taken to apply mutatis mutandis to this embodiment of the invention.

Similarly LCR may be performed using cDNA. Preferably, one or more of the probes or primers used in the reaction specifically hybridize to the transcript of interest. Method of LCR are described supra and are to be taken to apply mutatis mutandis to this embodiment of the invention.

Methods of TMA or self-sustained sequence replication (3SR) use two or more oligonucleotides that flank a target sequence, a RNA polymerase, RNase H and a reverse transcriptase. One oligonucleotide (that also comprises a RNA polymerase binding site) hybridizes to an RNA molecule that comprises the target sequence and the reverse transcriptase produces cDNA copy of this region. RNase H is used to digest the RNA in the RNA-DNA complex, and the second oligonucleotide used to produce a copy of the cDNA. The RNA polymerase is then used to produce a RNA copy of the cDNA, and the process repeated.

NASBA systems relies on the simultaneous activity of three enzymes (a reverse transcriptase, RNase H and RNA polymerase) to selectively amplify target mRNA sequences. The mRNA template is transcribed to cDNA by reverse transcription using an oligonucleotide that hybridizes to the target sequence and comprises a RNA polymerase binding site at its 5' end. The template RNA is digested with RNase H and double stranded DNA is synthesized. The RNA polymerase then produces multiple RNA copies of the cDNA and the process is repeated.

Q-beta replicase mediated amplification is a RNA amplification method, similar to TMA or NASBA, however, this method utilizes a RNA-dependent RNA polymerase derived from bacteriophage Q-beta that can synthesize up to one billion strands of RNA product from a single template.

Accordingly, this method rapidly amplifies the number of product produced from a single template.

SDA assays described supra are also useful for determining the level of expression of a gene and are taken to apply mutatis mutandis to this embodiment of the invention.

The present invention clearly contemplates the use of a microarray to determine the level of expression of one or more genes within chromosome 2 from about map position 2q14.1 to about map position 2q14.3. Such a method enables the detection of a number of different transcripts, thereby providing a multi-analyte test and improving the sensitivity and/or accuracy of the diagnostic assay of the invention.

Clearly, the hybridization to and/or amplification of a marker associated with a cancer using any of these methods is detectable using, for example, electrophoresis and/or mass spectrometry. In this regard, one or more of the probes/primers and/or one or more of the nucleotides used in an amplification reactions may be labeled with a detectable marker to facilitate rapid detection of a marker, for example, a fluorescent label (e.g. Cy5 or Cy3) or a radioisotope (e.g. $^{32}$P).

Alternatively, amplification of a nucleic acid may be continuously monitored using a melting curve analysis method, such as that described in, for example, U.S. Pat. No. 6,174,670.

Alternatively, the level of a transcript is normalized against the level of a known transcript that is not modulated in cancer to facilitate comparison of the level of the transcript in a control sample. Suitable known transcripts are known in the art and include, for example, actin, glyceraldehyde 3-phosphate dehydrogenase (GAPDH), P2 microglobulin, hydroxymethylbilane synthase, hypoxanthine phosphoribosyl-transferase 1 (HPRT), ribosomal protein L13c, succinate dehydrogenase complex subunit A and TATA box binding protein (TBP).

The skilled artisan will readily be capable of determining the nucleotide sequence of suitable amplification primers to perform this embodiment based upon the disclosure herein of a transcript selected from the group consisting of RALBB (SEQ ID NO: 34), DDX18 (SEQ ID NO: 36), SCTR (SEQ ID NO: 38), EN1 (SEQ ID NO: 40), TSN (SEQ ID NO: 42), MARCO (SEQ ID NO: 48), PTPN4 (SEQ ID NO: 50), INSIG2 (SEQ ID NO: 52), INHBB (SEQ ID NO: 54), Gli2 (SEQ ID NO: 56), MGC13033 (SEQ ID NO: 58), TSAP6 (SEQ ID NO: 60), DBI (SEQ ID NO: 62), MGC10993 (SEQ ID NO: 64), EPB41L5 (SEQ ID NO: 66), FLJ14816 (SEQ ID NO: 68) and LBP9 (SEQ ID NO: 70). As a consequence, the present invention is not to be limited by the precise sequence of amplification primers used.

Methods for designing and producing suitable primers are described supra and are to be taken to apply mutatis mutandis to the present embodiment.

Suitable primer combinations of primers for the detection of the level of expression of a gene within chromosome 2 from about map position 2q14.1 to about map position 2q14.3 include, for example, (i) a primer comprising the sequence set forth in SEQ ID NO: 199 and a primer comprising a sequence that is the complement of SEQ ID NO: 200 to determine the level of expression of DDX18;

(ii) a primer comprising the sequence set forth in SEQ ID NO: 201 and a primer comprising a sequence that is the complement of SEQ ID NO: 202 to determine the level of expression of INSIG2;

(iii) a primer comprising the sequence set forth in SEQ ID NO: 203 and a primer comprising a sequence that is the complement of SEQ ID NO: 204 to determine the level of expression of EN1;

(iv) a primer comprising the sequence set forth in SEQ ID NO: 205 and a primer comprising a sequence that is the complement of SEQ ID NO: 206 to determine the level of expression of MARCO;

(v) a primer comprising the sequence set forth in SEQ ID NO: 207 and a primer comprising a sequence that is the complement of SEQ ID NO: 208 to determine the level of expression SCTR;

(vi) a primer comprising the sequence set forth in SEQ ID NO: 209 and a primer comprising a sequence that is the complement of SEQ ID NO: 210 to determine the level of expression of PTPN4;

(vii) a primer comprising the sequence set forth in SEQ ID NO: 211 and a primer comprising a sequence that is the complement of SEQ ID NO: 212 to determine the level of expression of RALB;

(viii) a primer comprising the sequence set forth in SEQ ID NO: 213 and a primer comprising a sequence that is the complement of SEQ ID NO: 214 to determine the level of expression of INHBB;

(ix) a primer comprising the sequence set forth in SEQ ID NO: 215 and a primer comprising a sequence that is the complement of SEQ ID NO: 216 to determine the level of expression of Gli2; and (x) a primer comprising the sequence set forth in SEQ ID NO: 217 and a primer comprising a sequence that is the complement of SEQ ID NO: 218 to determine the level of expression of TSN.

Polypeptide Detection

In an alternative embodiment, the level of gene expression is determined by detecting the level of a protein encoded by a gene within chromosome 2 from about map position 2q14.1 to about map position 2q14.3.

Preferably, the protein is selected from the group consisting of RALBB (SEQ ID NO: 35), DDX18 (SEQ ID NO: 37), SCTR (SEQ ID NO: 39), EN1 (SEQ ID NO: 41), TSN (SEQ ID NO: 43), MARCO (SEQ ID NO: 45), PTPN4 (SEQ ID NO: 57), INSIG2 (SEQ ID NO: 53), INHBB (SEQ ID NO: 55), Gli2 (SEQ ID NO: 57), MGC13033 (SEQ ID NO: 59), TSAP6 (SEQ ID NO: 61), DBI (SEQ ID NO: 63), MGC10993 (SEQ ID NO: 65), EPB41L5 (SEQ ID NO: 67), FLJ14816 (SEQ ID NO: 69) and LBP9 (SEQ ID NO: 71). In this respect, the present invention is not necessarily limited to the detection of a protein comprising the specific amino acid sequence recited herein. Rather, the present invention encompasses the detection of variant sequences (e.g., having at least about 80% or 90% or 95% or 98% amino acid sequence identity) or the detection of an immunogenic fragment or epitope of said protein.

In one embodiment, the method of the invention comprises detecting a RALBB polypeptide. In another embodiment, the method of the invention comprises detecting a DDX18 polypeptide. In a further embodiment, the method of the invention comprises detecting a SCTR polypeptide. In a still further embodiment, the method of the invention comprises detecting an EN1 polypeptide. In another embodiment, the method of the invention comprises detecting a TSN polypeptide. In yet another embodiment, the method of the invention comprises detecting a MARCO polypeptide. Alternatively, the method of the invention comprises detecting a PTPN4 polypeptide. In another alternative embodiment, the method comprises detecting an INSIG2 polypeptide. In another embodiment, the method of the invention comprises detecting an INHBB polypeptide. In another embodiment, the method of the invention comprises detecting a Gli2 polypeptide. In another embodiment, the method of the invention comprises detecting a MGC13033 polypeptide. In another embodiment, the method of the invention comprises detecting a TSAP6 polypeptide. In another embodiment, the method of the invention comprises detecting a DBI polypeptide. In another embodiment, the method of the invention comprises detecting a MGC10993 polypeptide. In another embodiment, the method of the invention comprises detecting an EPB41L5 polypeptide. In another embodiment, the method of the invention comprises detecting a FLJ14816 polypeptide. In another embodiment, the method of the invention comprises detecting a LBP9 polypeptide.

A suitable antibody will be apparent to the skilled artisan or produced by conventional means, such as, for example, as described supra. For example, a monoclonal antibody to MARCO is available from Cell Sciences; a polyclonal anti-EN1 antibody is commercially available from Sigma-Aldrich; an inhibin beta b monoclonal antibody is available from Serotec; an anti-Gli2 antibody is available from abcam; a monoclonal antibody to PTPN4 is available from Purely Proteins Ltd and an anti-Gli2 antibody is available from Research Genetics.

The amount, level or presence of a polypeptide is determined using any of a variety of techniques known to the skilled artisan such as, for example, a technique selected from the group consisting of, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In one embodiment the assay used to determine the amount or level of a protein is a semi-quantitative assay. In another embodiment the assay used to determine the amount or level of a protein in a quantitative assay. As will be apparent from the preceding description, such an assay may require the use of a suitable control, e.g. from a normal individual or matched normal control.

Standard solid-phase ELISA or FLISA formats are particularly useful in determining the concentration of a protein from a variety of samples.

In one form such an assay involves immobilizing a biological sample onto a solid matrix, such as, for example a polystyrene or polycarbonate microwell or dipstick, a membrane, or a glass support (e.g. a glass slide).

An antibody that specifically binds to a protein described supra is brought into direct contact with the immobilized biological sample, and forms a direct bond with any of its target protein present in said sample. This antibody is generally labeled with a detectable reporter molecule, such as for example, a fluorescent label (e.g. FITC or Texas Red) or a fluorescent semiconductor nanocrystal (as described in U.S. Pat. No. 6,306,610) in the case of a FLISA or an enzyme (e.g. horseradish peroxidase (HRP), alkaline phosphatase (AP) or β-galactosidase) in the case of an ELISA, or alternatively a second labeled antibody can be used that binds to the first antibody. Following washing to remove any unbound antibody the label is detected either directly, in the case of a fluorescent label, or through the addition of a substrate, such as for example hydrogen peroxide, TMB, or toluidine, or 5-bromo-4-chloro-3-indol-beta-D-galaotopyranoside (x-gal) in the case of an enzymatic label.

Such ELISA or FLISA based systems are particularly suitable for quantification of the amount of a protein in a sample. For example, the detection system is calibrated against known amounts of a protein standard to which the antibody binds, such as for example, an isolated and/or recombinant form of the relevant protein or immunogenic fragment thereof or epitope thereof.

In another form, an ELISA comprises immobilizing an antibody or ligand that specifically binds a protein described supra on a solid matrix, such as, for example, a membrane, a polystyrene or polycarbonate microwell, a polystyrene or polycarbonate dipstick or a glass support. A sample is then brought into physical relation with said antibody, and the polypeptide is bound or 'captured'. The bound protein is then detected using a labeled antibody. For example, a labeled antibody that binds to an epitope that is distinct from the first (capture) antibody is used to detect the captured protein. Alternatively, a third labeled antibody can be used that binds the second (detecting) antibody.

It will be apparent to the skilled person that the assay formats described herein are amenable to high throughput formats, such as, for example automation of screening processes, or a microarray format as described in Mendoza et al., *Biotechniques* 27(4): 778-788, 1999. Furthermore, variations of the above-described assay will be apparent to those skilled in the art, such as, for example, a competitive ELISA.

Alternatively, the presence or amount of a protein selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9 is detected using a radioimmunoassay (RIA). The basic principle of the assay is the use of a radiolabeled antibody or antigen to detect antibody-antigen interactions. An antibody or ligand that specifically binds to a protein described supra is bound to a solid support and a sample brought into direct contact with said antibody. To detect the level of bound antigen, an isolated and/or recombinant form of the antigen is radiolabeled and brought into contact with the same antibody. Following washing, the level of bound radioactivity is detected. As any antigen in the biological sample inhibits binding of the radiolabeled antigen the level of radioactivity detected is inversely proportional to the level of antigen in the sample. Such an assay may be quantitated by using a standard curve using increasing known concentrations of the isolated antigen.

As will be apparent to the skilled artisan, such an assay may be modified to use any reporter molecule, such as, for example, an enzyme or a fluorescent molecule, in place of a radioactive label.

In another embodiment, Western blotting is used to determine the level of a protein described supra in a sample. In such an assay protein from a sample is separated using sodium doedecyl sulphate polyacrylamide gel electrophoresis (SDS-PAGE) using techniques known in the art and described in, for example, Scopes (In: Protein Purification: Principles and Practice, Third Edition, Springer Verlag, 1994). Separated proteins are then transferred to a solid support, such as, for example, a membrane (e.g., a PVDF membrane), using methods known in the art, for example, electrotransfer. This membrane is then blocked and probed with a labeled antibody or ligand that specifically binds to a protein described supra. Alternatively, a labeled secondary, or even tertiary, antibody or ligand is used to detect the binding of a specific primary antibody. The level of label is then determined using an assay appropriate for the label used. An appropriate assay will be apparent to the skilled artisan.

For example, the level or presence a polypeptide described supra is determined using methods known in the art, such as, for example, densitometry. In one embodiment, the intensity of a protein band or spot is normalized against the total amount of protein loaded on a SDS-PAGE gel using methods known in the art. Alternatively, the level of a protein selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9 detected is normalized against the level of a control/reference protein. Such control proteins are known in the art, and include, for example, actin, glyceraldehyde 3-phosphate dehydrogenase (GAPDH), β2 microglobulin, hydroxy-methylbilane synthase, hypoxanthine phosphoribosyl-transferase 1 (HPRT), ribosomal protein L13c, succinate dehydrogenase complex subunit A and TATA box binding protein (TBP).

In an alternative embodiment, a protein selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9 is detected within a cell (e.g., a cancer cell), using a method known in the art, such as, for example, immunohistochemistry or immunofluorescence.

For example, a cell or tissue section that is to be analyzed to determine the level of a protein described supra is fixed to stabilize and protect both the cell and the proteins contained within the cell. Preferably, the method of fixation does not disrupt or destroy the antigenicity of the protein. Methods of fixing a cell are known in the art and include for example, treatment with paraformaldehyde, treatment with alcohol, treatment with acetone, treatment with methanol, treatment with Bouin's fixative and treatment with glutaraldehyde. Following fixation a cell is incubated with a ligand or antibody capable of binding to the protein. The ligand or antibody is, for example, labeled with a detectable marker, such as, for example, a fluorescent label (e.g. FITC or Texas Red), a fluorescent semiconductor nanocrystal (as described in U.S. Pat. No. 6,306,610) or an enzyme (e.g. horseradish peroxidase (HRP)), alkaline phosphatase (AP) or β-galactosidase. Alternatively, a second labeled antibody that binds to the first antibody is used to detect the first antibody. Following washing to remove any unbound antibody, the level of the protein bound to said labeled antibody is detected using the relevant detection means. Means for detecting a fluorescent label will vary depending upon the type of label used and will be apparent to the skilled artisan.

Methods using immunofluorescence are preferable, as they are quantitative or at least semi-quantitative. Methods of quantitating the degree of fluorescence of a stained cell are known in the art and described, for example, in Immunohistochemistry (Cuello, 1984 John Wiley and Sons, ASIN 0471900524).

The detection of the level of a protein selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9 using a method such as, for example, mass spectrometry, matrix-assisted laser desorption/ionization time of flight (MALDI-TOF), electrospray ionisation (ESI), protein chip, biosensor technology, or fluorescence resonance energy transfer, is clearly contemplated in the present invention.

Biosensor devices generally employ an electrode surface in combination with current or impedance measuring elements to be integrated into a device in combination with the assay substrate (such as that described in U.S. Pat. No. 5,567,301). An antibody/ligand that specifically binds to a protein of interest is preferably incorporated onto the surface of a biosensor device and a biological sample contacted to said device. A change in the detected current or impedance by the biosensor device indicates protein binding to said antibody. Some forms of biosensors known in the art also rely on surface plasmon resonance to detect protein interactions, whereby a change in the surface plasmon resonance surface of reflection is indicative of a protein binding to a ligand or antibody (U.S. Pat. Nos. 5,485,277 and 5,492,840).

Biosensors are of particular use in high throughput analysis due to the ease of adapting such systems to micro- or nano-scales. Furthermore, such systems are conveniently adapted to incorporate several detection reagents, allowing for multiplexing of diagnostic reagents in a single biosensor unit. This permits the simultaneous detection of several proteins or peptides in a small amount of body fluid.

Evanescent biosensors are also preferred as they do not require the pretreatment of a biological sample prior to detection of a protein of interest. An evanescent biosensor generally relies upon light of a predetermined wavelength interacting with a fluorescent molecule, such as for example, a fluorescent antibody attached near the probe's surface, to emit fluorescence at a different wavelength upon binding of the target polypeptide to the antibody or ligand.

Micro- or nano-cantilever biosensors are also preferred as they do not require the use of a detectable label. A cantilever biosensor utilizes a ligand and/or antibody capable of specifically detecting the analyte of interest that is bound to the surface of a deflectable arm of a micro- or nano-cantilever. Upon binding of the analyte of interest (e.g. one or more proteins selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9) the deflectable arm of the cantilever is deflected in a vertical direction (i.e. upwards or downwards). The change in the deflection of the deflectable arm is then detected by any of a variety of methods, such as, for example, atomic force microscopy, a change in oscillation of the deflectable arm or a change in pizoresistivity. Exemplary micro-cantilever sensors are described in USSN 20030010097.

Alternatively, a biosensor that utilizes a lipid membrane is used. Such a biosensor uses a lipid membrane that incorporates a lipid bilayer that comprises an ion channel or ionophore, wherein the lipid bilayer is tethered to a metal electrode (such biosensors are described in AU 623,747, U.S. Pat. No. 5,234,566 and USSN 20030143726). One form of such a biosensor involves two receptors or antibodies that bind to each other being incorporated into a lipid bilayer. One of these receptors/antibodies is bound to an ion channel or ionophore that spans the outer half of the membrane, and this membrane/antibody is also capable of binding to the analyte of interest. The second receptor/antibody is tethered to a membrane molecule (i.e. not the ionophore or ion channel). When the receptors/antibodies are not bound to each other, the ion channel aligns with another half membrane spanning ionophore (i.e. an ionophore that spans the inner half of the membrane) thereby facilitating detectable ion transmission across the membrane. However, when the two receptors/antibodies bind each other, the outer membrane ionophore is displaced thereby disrupting membrane conductivity. The analyte of interest competes with the second receptor/antibody for the binding site on the first receptor/antibody. The presence of the analyte breaks the bond between the two receptors/antibodies and allows the half membrane ionophores to align and provide an ion conductive path.

To produce protein chips, the proteins, peptides, polypeptides, antibodies or ligands that are able to bind specific antibodies or proteins of interest are bound to a solid support such as for example glass, polycarbonate, polytetrafluoroethylene, polystyrene, silicon oxide, metal or silicon nitride. This immobilization is either direct (e.g. by covalent linkage, such as, for example, Schiff's base formation, disulfide linkage, or amide or urea bond formation) or indirect. Methods of generating a protein chip are known in the art and are described in for example U.S. Patent Application No. 20020136821, 20020192654, 20020102617 and U.S. Pat. No. 6,391,625. To bind a protein to a solid support it is often necessary to treat the solid support so as to create chemically reactive groups on the surface, such as, for example, with an aldehyde-containing silane reagent. Alternatively, an antibody or ligand may be captured on a microfabricated polyacrylamide gel pad and accelerated into the gel using microelectrophoresis as described in, Arenkov et al. *Anal. Biochem.* 278:123-131, 2000.

A protein chip may comprise only one protein, ligand or antibody, and be used to screen one or more patient samples for the presence of one or a plurality of polypeptides of interest. Such a chip may also be used to simultaneously screen an array of patient samples for a polypeptide of interest.

Preferably, a protein sample to be analyzed using a protein chip is attached to a reporter molecule, such as, for example, a fluorescent molecule, a radioactive molecule, an enzyme, or an antibody that is detectable using methods known in the art. Accordingly, by contacting a protein chip with a labeled sample and subsequent washing to remove any unbound proteins the presence of a bound protein is detected using methods known in the art, such as, for example, using a DNA microarray reader.

Alternatively, biomolecular interaction analysis-mass spectrometry (BIA-MS) is used to rapidly detect and characterize a protein present in complex biological samples at the low- to sub-fmole level (Nelson et al. *Electrophoresis* 21: 1155-1163, 2000). One technique useful in the analysis of a protein chip is surface enhanced laser desorption/ionization-time of flight-mass spectrometry (SELDI-TOF-MS) technology to characterize a protein bound to the protein chip. Alternatively, the protein chip is analyzed using ESI as described in U.S. Patent Application 20020139751.

IV Multiplex Assay Formats

The present invention particularly contemplates multiplex or multianalyte format assays to improve the accuracy or specificity of a diagnosis of cancer. Such assays may also improve the population coverage by an assay.

A preferred multiplex assay comprises, for example, detecting hypermethylation of one or more CpG dinucleotides in a plurality of nucleic acids within Chromosome 2 from about map position 2q14.1 to about map position 2q14.3 each nucleic acid comprising a nucleotide sequence set forth in any of SEQ ID NOs: 1 to 33 or Table 1. Clearly, this form of assay indicates the presence or absence of hypermethylation of CpG islands in a test sample.

In a preferred embodiment, the multiplex assay detects hypermethylation of one or more CpG dinucleotides in a plurality of nucleic acids within Chromosome 2 from about map position 2q14.1 to about map position 2q14.3 each nucleic acid comprising a nucleotide sequence set forth in any of SEQ ID NOs: 2 to 25. Alternatively, the nucleotide sequence is designated as INSIG2, (CpG 49), CpG41.2, CpG61, CpG29, 20 Kb, Z(sma), Z, CpG104, CpG103, CpG128, CpG41, CpG173, CpG48, CpG48rv, 5'-MARCO, CpG229, TSAP6 (CpG 85), DBI (CpG 85), CpG85, SCTR (CpG 67), PTPN4 (CpG 86), CpG102, RALBB (CpG115) or INHBB(CpG285) in Table 1.

In an even more preferred embodiment, the multiplex assay detects hypermethylation of one or more CpG dinucleotides in a plurality of nucleic acids within Chromosome 2 from about map position 2q14.1 to about map position 2q14.3 each nucleic acid comprising a nucleotide sequence set forth in any of SEQ ID NOs: 4 to 21. Alternatively, the nucleotide sequence is designated as CpG61, CpG29, 20 Kb, Z(sma), Z, CpG104, CpG103, CpG128, CpG41, CpG173, CpG48, CpG48rv, 5'-MARCO, CpG229, TSAP6 (CpG 85), DBI (CpG 85), CpG85 or SCTR (CpG 67) in Table 1.

As exemplified herein, the present inventors have detected methylation in a CpG island comprising a nucleotide sequence set forth in SEQ ID NO: 11, and a CpG island comprising a nucleotide sequence set forth in SEQ ID NO: 21 and CpG island comprising a nucleotide sequence set forth in SEQ ID NO: 25. Using such a multianalyte method, the inventors detected approximately 96% of colorectal cancer subjects tested. Accordingly, in a preferred embodiment, the method of the invention determines the level of methylation of one or more CpG dinucleotides in a nucleic acid comprising a nucleotide sequence set forth in SEQ ID NO: 11, and in a nucleic acid comprising a nucleotide sequence set forth in SEQ ID NO: 21 and in a nucleic acid comprising a nucleotide sequence set forth in SEQ ID NO: 25. In another embodiment, the method of the invention comprises determining the degree of methylation of a nucleic acid comprising a nucleotide sequence set forth in SEQ ID NO: 11, and in a nucleic acid comprising a nucleotide sequence set forth in SEQ ID NO: 21 and in a nucleic acid comprising a nucleotide sequence set forth in SEQ ID NO: 25.

In a further embodiment, the method of the invention comprises determining the degree of methylation of a nucleic acid comprising a nucleotide sequence set forth in SEQ ID NO: 11 and in a nucleic acid comprising a nucleotide sequence set forth in SEQ ID NO: 21.

In a further embodiment, the method of the invention comprises determining the degree of methylation of a nucleic acid comprising a nucleotide sequence set forth in SEQ ID NO: 11 and in a nucleic acid comprising a nucleotide sequence set forth in SEQ ID NO: 25.

In a further embodiment, the method of the invention comprises determining the degree of methylation of a nucleic acid comprising a nucleotide sequence set forth in SEQ ID NO: 21 and in a nucleic acid comprising a nucleotide sequence set forth in SEQ ID NO: 25.

Clearly, the multiplex assay of the invention is not to be limited to the detection of methylation at a single CpG dinucleotide within a region of interest. Rather the invention contemplates detection of methylation at a sufficient number of CpG dinucleotides in each nucleic acid to provide a diagnosis. For example, the invention contemplates detection of methylation at 1 or 2 or 3 or 4 or 5 or 7 or 9 or 10 or 15 or 20 or 25 or 30 CpG dinucleotides in each nucleic acid.

As will be apparent from the foregoing description a methylation specific microarray is particularly amenable to such high density analysis. Previously, up to 232 CpG dinucleotides have been analyzed using such a microarray (Adorján et al, *Nucl. Acids Res.* 30: e21, 2002).

The present invention also contemplates determining histone modification at one or more sites within Chromosome 2 from about map position 2q14.1 to about map position 2q14.3. For example, ChIP is performed to determine whether or not histones associated with a plurality of genes selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9 are modified. The invention is not to be limited to the detection of histone modification associated with a gene, as histone associated with intergenic regions also occurs.

In another embodiment, the method of the invention determines the level of expression of a plurality of genes selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9 to diagnose cancer. The level of mRNA or protein may be detected. Alternatively, the level of mRNA transcribed from one or more genes and the level of one or more proteins expressed by the same or different genes is determined.

Each of the previously described detection techniques need necessarily be used independently of one another to diagnose cancer. Accordingly, a single sample may be analyzed to determine the level of methylation of one or more CpG dinucleotides in one or more of nucleic acids within Chromosome 2 from about map position 2q14.1 to about map position 2q14.3 each nucleic acid comprising a nucleotide sequence set forth in any of SEQ ID NOs: 1 to 33 or Table 1 and the level of expression of one or more genes selected from the group consisting of RALB, DDX18, SCTR, EN1, TSN, MARCO, PTPN4, INSIG2, INHBB, Gli2, MGC13033, TSAP6, DBI, MGC10993, EPB41L5, FLJ14816 and LBP9 is also determined. In accordance with this embodiment, enhanced methylation and reduced gene expression is indicative of cancer.

Based on the teachings provided herein, a variety of combinations of assays will be apparent to the skilled artisan.

The present invention also contemplates the use of a known diagnostic assay in combination with an assay described herein. For example, the level of serum PSA may be determined in combination with an assay described herein to diagnose cancer. Alternatively, a mutation in a BRCA gene and an assay described herein may be used to diagnose breast cancer.

Biological Samples

A biological sample useful for the method of the present invention is preferably from a tissue suspected of comprising a cancer or cancer cell. More preferably, the cell is from a region of a tissue thought to comprise a cancer or cancer cell. Clearly this does not exclude cells that have originated in a particular tissue but are isolated from a remote source, for example, a body fluid or a stool sample in the case of a colon cancer or urine in the case of a urogenital cancer.

In one embodiment, the sample comprises a body fluid or a derivative of a body fluid or a body secretion. For example, the body fluid is selected from the group consisting of whole blood, urine, saliva, breast milk, pleural fluid, sweat, tears and mixtures thereof. An example of a derivative of a body fluid is selected from the group consisting of plasma, serum or buffy coat fraction. For example, a body secretion comprises stool.

Preferably, the biological sample comprises a nucleated cell or an extract thereof. More preferably, the biological sample comprises a cancer cell or an extract thereof.

In another embodiment, the biological sample comprises nucleic acid and/or protein from a cancer cell. The nucleic acid and/or protein may be separate need not be isolated with a cell, but rather may be from, for example, a lysed cell.

In the present context, the term "cancer cell" includes any biological specimen or sample comprising a cancer cell irrespective of its degree of isolation or purity, such as, for example, tissues, organs, cell lines, bodily fluids, or histology specimens that comprise a cell in the early stages of transformation or having been transformed.

As the present invention is particularly useful for the early detection of cancer in the medium to long term, the definition of "cancer cell" is not to be limited by the stage of a cancer in the subject from which said cancer cell is derived (i.e. whether or not the patient is in remission or undergoing disease recurrence or whether or not the cancer is a primary tumor or the consequence of metastases). Nor is the term "cancer cell" to be limited by the stage of the cell cycle of said cancer cell.

In a preferred embodiment, the biological sample comprises a cell or a plurality of cells derived from a tissue selected from the group consisting of a colorectum, a prostate, a breast, a pancreas and an ovary. Preferably, the biological sample comprises a cell or a plurality of cells derived from a tissue selected from the group consisting of a colorectum, a prostate and a breast. Preferably, the biological sample comprises a cell or a plurality of cells derived from a colorectum. Preferably, the biological sample comprises a cell or a plurality of cells derived from a prostate. Preferably, the biological sample comprises a cell or a plurality of cells derived from a breast.

Preferably, the biological sample has been isolated previously from the subject. In accordance with this embodiment, the diagnostic method of the invention is performed ex vivo. In such cases, the sample may be processed or partially processed into a nucleic acid sample that is substantially free of contaminating protein. All such embodiments are encompassed by the present invention.

Methods for isolating a biological sample from a subject are known in the art and include, for example, surgery, biopsy, collection of a body fluid, for example, by paracentesis or thoracentesis or collection of, for example, blood or a fraction thereof. All such methods for isolating a biological sample shall be considered to be within the scope of providing or obtaining a biological sample.

For example, a cell or plurality of cells derived from a colorectum is collected or isolated using a method, such as, for example, a colonoscopy and/or collected from a stool sample. In the case of a sample from a prostate, the sample is collected, for example, by surgery (e.g., a radical prostatectomy) or a biopsy. In the case of a breast cancer, a sample is collected, for example, using a fine needle aspiration biopsy, a core needle biopsy, or a surgical biopsy.

The biological sample need not necessarily comprise a cell, but may merely comprise a cell extract. Preferably, the cell extract comprises the analyte/s required for analysis, e.g., genomic DNA and/or mRNA and/or protein. In this regard, providing or obtaining a biological sample shall be considered to encompass producing a cell extract.

It will be apparent from the preceding description that the diagnostic method provided by the present invention involves a degree of quantification to determine elevated or enhanced methylation of nucleic acid in tissue that is suspected of comprising a cancer cell or metastases thereof, or enhanced histone modification in tissue that is suspected of comprising a cancer cell or metastases thereof, or reduced gene expression in tissue that is suspected of comprising a cancer cell or metastases thereof. Such quantification is readily provided by the inclusion of appropriate control samples in the assays as described below.

As will be apparent to the skilled artisan, when internal controls are not included in each assay conducted, the control may be derived from an established data set.

Data pertaining to the control subjects are selected from the group consisting of:

1. a data set comprising measurements of the degree of methylation, histone modification and/or gene expression for a typical population of subjects known to have a particular form of cancer that is currently being tested or a typical population of subjects known to have cancer generally;
2. a data set comprising measurements of the degree of methylation, histone modification and/or gene expression for the subject being tested wherein said measurements have been made previously, such as, for example, when the subject was known to healthy or, in the case of a subject having cancer, when the subject was diagnosed or at an earlier stage in disease progression;

3. a data set comprising measurements of the degree of methylation, histone modification and/or gene expression for a healthy individual or a population of healthy individuals;
4. a data set comprising measurements of the degree of methylation, histone modification and/or gene expression for a normal individual or a population of normal individuals; and
5. a data set comprising measurements of the degree of methylation, histone modification and/or gene expression from the subject being tested wherein the measurements are determined in a matched sample.

Those skilled in the art are readily capable of determining the baseline for comparison in any diagnostic assay of the present invention without undue experimentation, based upon the teaching provided herein.

In the present context, the term "typical population" with respect to subjects known to have cancer shall be taken to refer to a population or sample of subjects diagnosed with a specific form of cancer that is representative of the spectrum of subjects suffering from that cancer. Alternatively, a panel of subjects suffering from a variety of cancers (e.g., of the same tissue or cancer generally) that is representative of the spectrum of subjects suffering from cancer is used. This is not to be taken as requiring a strict normal distribution of morphological or clinicopathopathological parameters in the population, since some variation in such a distribution is permissible. Preferably, a "typical population" will exhibit a spectrum of cancers at different stages of disease progression and with tumors at different stages and having different morphologies or degrees of differentiation. It is particularly preferred that a "typical population" exhibits the expression characteristics of a cohort of subjects or non-cancerous cell lines as described herein.

In the present context, the term "healthy individual" shall be taken to mean an individual who is known not to suffer from cancer, such knowledge being derived from clinical data on the individual. It is preferred that the healthy individual is asymptomatic with respect to the any symptoms associated with cancer.

The term "normal individual" shall be taken to mean an individual having a normal level of methylation, histone modification and/or gene expression as described herein in a particular sample derived from said individual.

As will be known to those skilled in the art, data obtained from a sufficiently large sample of the population will normalize, allowing the generation of a data set for determining the average level of a particular parameter. Accordingly, the level of methylation, histone modification and/or gene expression as described herein can be determined for any population of individuals, and for any sample derived from said individual, for subsequent comparison to levels determined for a sample being assayed. Where such normalized data sets are relied upon, internal controls are preferably included in each assay conducted to control for variation.

The term "matched sample" shall be taken to mean that a control sample is derived from the same subject as the test sample is derived, at approximately the same point in time. Preferably, the control sample shows little or no morphological and/or pathological indications of cancer. Matched samples are not applicable to blood-based or serum-based assays. Accordingly, it is preferable that the matched sample is from a region of the same tissue as the test sample, however does not appear to comprise a cancer cell. Preferably, the matched sample does not include malignant cells or exhibit any symptom of the disease. Preferably, the sample comprises less than about 20% malignant cells, more preferably less than about 10% malignant cells, even more preferably less than about 5% malignant cells and most preferably less than about 1% malignant cells. Morphological and pathological indications of malignant cells are known in the art and/or described herein.

Probes/Primers

The present invention additionally provides an isolated nucleic acid probe or primer that is capable of selectively hybridizing to a region of Chromosome 2 from about map position 2q14.1 to about map position 2q14.3.

In those cases where the probe are not already available, they must be synthesized. Apparatus for such synthesis is presently available commercially, such as the Applied Biosystems 380A DNA synthesizer and techniques for synthesis of various nucleic acids are available in the literature.

For example, a nucleotide comprising deoxynucleotides (e.g., a DNA based oligonucleotide) is produced using standard solid-phase phosphoramidite chemistry. Essentially, this method uses protected nucleoside phosphoramidites to produce a short oligonucleotide (i.e., up to about 80 nucleotides). Typically, an initial 5'-protected nucleoside is attached to a polymer resin by its 3'-hydroxy group. The 5' hydroxyl group is then de-protected and the subsequent nucleoside-3'-phosphoramidite in the sequence is coupled to the de-protected group. An internucleotide bond is then formed by oxidizing the linked nucleosides to form a phosphotriester. By repeating the steps of de-protection, coupling and oxidation an oligonucleotide of desired length and sequence is obtained. Suitable methods of oligonucleotide synthesis are described, for example, in Caruthers, M. H., et al., "Methods in Enzymology," Vol. 154, pp. 287-314 (1988).

In one embodiment, the probes are prepared for ligation, e.g., if ligase is to be used, the probe which will have its 5' end adjacent the 3' end of the other probe when hybridized to the sample nucleic acid is phosphorylated in order to later be able to form a phosphodiester bond between the two probes. One of the probes is then labeled. This labeling can be done as part of the phosphorylation process above using radioactive phosphorus, or can be accomplished as a separate operation by covalently attaching chromophores, fluorescent moieties, enzymes, antigens, chemiluminescent moieties, groups with specific binding activity, or electrochemically detectable moieties, etc. such as, for example, using T4 polynucleotide kinase.

For the detection of methylated nucleic acid a preferred probe or primer comprises a nucleotide sequence set forth in any one of SEQ ID NOs: 72 to 199. For determining the level of expression of a gene within Chromosome 2 from about map position 2q14.1 to about map position 2q14.3 a preferred probe or primer comprises a nucleotide sequence set forth in any one of SEQ ID NOs: 200 to 219. For determining nucleic acid bound to a modified histone in chromatin within Chromosome 2 from about map position 2q14.1 to about map position 2q14.3 a preferred probe or primer comprises a nucleotide sequence set forth in any one of SEQ ID NOs: 236 to 256. For pyrosequencing a nucleic acid within Chromosome 2 from about map position 2q14.1 to about map position 2q14.3 a preferred probe or primer comprises a nucleotide sequence set forth in any one of SEQ ID NOs: 224-235.

Other preferred probes or primers are selected from the group consisting of:

(i) a probe having of at least 18 nucleotides in length and comprising a sequence set forth in any one of SEQ ID NOs: 1 to 33 or Table 1;

(ii) a probe of at least 18 nucleotides in length and comprising a sequence set forth in any one of SEQ ID NOs: 1 to 33 or Table 1 wherein the 5' or 3' terminal nucleotide of the probe is methylated in a cancer;

(iii) a probe of at least about 18 nucleotides in length and comprising a sequence set forth in a nucleotide sequence selected from the group consisting of SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68 and SEQ ID NO: 70; and (iv) a probe comprising a nucleotide sequence complementary to any one of (i) to (iii).

IV Therapeutic Compounds

The present inventors have demonstrated that the modified chromatin within Chromosome 2 from about map position 2q14.1 to about map position 2q14.3 is returned to its normal state following treatment with one or more therapeutic compounds. Furthermore, the expression of several genes in this region are returned to normal levels following treatment with a therapeutic compound.

Accordingly, the present invention additionally provides a method for determining a candidate compound for the treatment of a cancer.

The present invention clearly encompasses the use of any in silico analytical method and/or industrial process for carrying the screening methods described herein into a pilot scale production or industrial scale production of an inhibitory compound identified in such screens. This invention also provides for the provision of information for any such production. Accordingly, a further aspect of the present invention provides a process for identifying or determining a compound or modulator supra, said method comprising:

(i) performing a method as described herein to thereby identify or determine a compound for the treatment of a cancer;

(ii) optionally, determining the structure of the compound; and (iii) providing the compound or the name or structure of the compound such as, for example, in a paper form, machine-readable form, or computer-readable form.

Naturally, for compounds that are known albeit not previously tested for their function using a screen provided by the present invention, determination of the structure of the compound is implicit in step (i) supra. This is because the skilled artisan will be aware of the name and/or structure of the compound at the time of performing the screen.

As used herein, the term "providing the compound" shall be taken to include any chemical or recombinant synthetic means for producing said compound or alternatively, the provision of a compound that has been previously synthesized by any person or means.

In a preferred embodiment, the compound or the name or structure of the compound is provided with an indication as to its use e.g., as determined by a screen described herein.

A further aspect of the present invention provides a process for producing a compound supra, said method comprising:

(i) performing a method as described herein to thereby identify or determine a compound for the treatment of a cancer;

(ii) optionally, determining the structure of the compound;

(iii) optionally, providing the name or structure of the compound such as, for example, in a paper form, machine-readable form, or computer-readable form; and (iv) providing the compound.

In a preferred embodiment, the synthesized compound or the name or structure of the compound is provided with an indication as to its use e.g., as determined by a screen described herein.

A further aspect of the present invention provides a method for manufacturing a compound for the treatment of a cancer comprising:

(i) determining a candidate compound for the treatment of a cancer; and (ii) using the compound in the manufacture of a therapeutic or prophylactic for the treatment of a cancer.

In one embodiment, the method comprises the additional step of isolating the candidate compound. Alternatively, a compound is identified and is produced for use in the manufacture of a compound for the treatment of a cancer.

Formulation of a pharmaceutical compound will vary according to the route of administration selected (e.g., solution, emulsion, capsule). An appropriate composition comprising the identified modulator to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

As will be apparent to a skilled artisan, a compound that is active in vivo is particular preferred. A compound that is active in a human subject is even more preferred. Accordingly, when manufacturing a compound that is for the treatment of a cancer it is preferable to ensure that any components added to the compound do not inhibit or modify the activity of said compound.

The present invention is further described in the following non-limiting examples.

EXAMPLE 1

Identification of a Hypermethylated Region of Chromosome 2 in Colon Cancer

Samples used in the identification of hypermethylated DNA in colon cancer were derived from 112 colorectal carcinomas with paired non-adjacent areas of normal colonic mucosa. Samples were collected as and frozen within 2 hours of removal and stored at −80° C. until analysis. All samples were obtained from the Hospital de la Santa Creu u Sant Pau (Barcelona, Spain).

Figure 2:
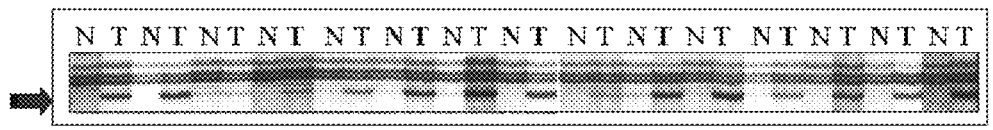
FIG. 2 is a copy of a photographic representation showing gels on which nucleic acid isolated using the AIMS method has been electrophoresed. Lanes labeled "N" contain nucleic acid from normal non-cancerous samples and lanes labeled "T" contain nucleic acid from tumor samples. The Z fragment discussed herein is indicated by the arrow.

Using the global methylation approach, amplification of inter-methylated sites (AIMS) assay (essentially as described in Frigole et al., *Nucleic Acids Res.* 30: e28, 2002) the inventors identified a SmaI fragment, designated the Z fragment, that was differentially methylated in 71 out of 112 (63%) of colorectal/normal tumor matched pairs. An example of a gel showing an AIMS assay identifying the Z band is shown in FIGS. 1 and 2.

Figure 3:
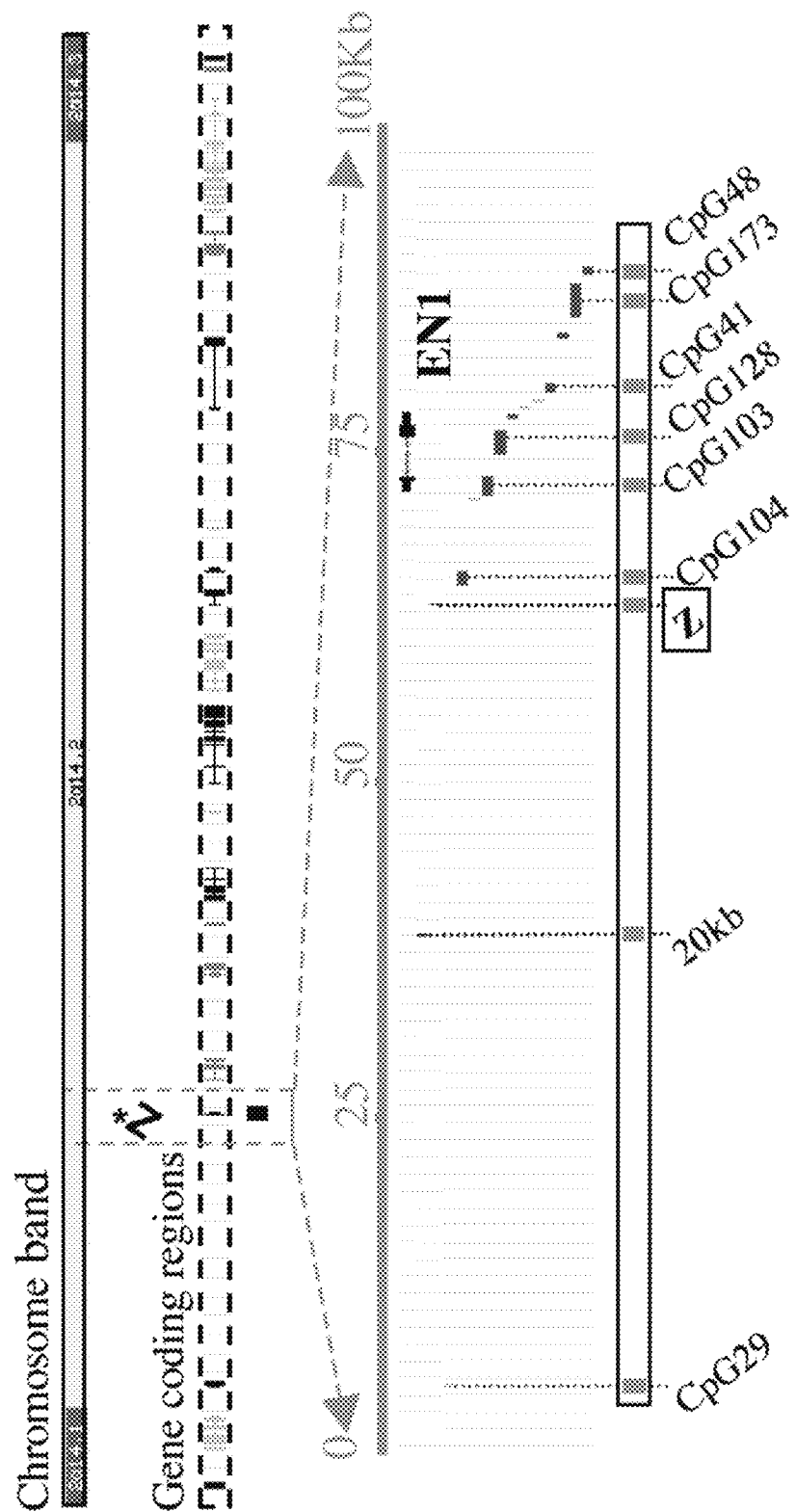
FIG. 3 is a diagrammatic representation showing the chromosomal location on 2q14.2 of the differentially methylated Z fragment sequence (*), in the context of the location of the genes and CpG islands identified via Genome Browser (July 2003). An expanded view of the region encompassing the Z fragment shows it is positioned 1.2 kb upstream from a 25 Kb region that contains 11 discrete CpG islands, as indicated by green filled squares and one defined gene Engrailed-1 (EN1). Dark lines represent CpG islands greater than 300 bp in length and light lines CpG islands less than 300 bp. The CpG number indicates the number of CpG sites per island.

The Z fragment was isolated from an acrylamide gel, sequenced and mapped to human Chromosome 2 map position 2q14.2 (FIG. 3) using in silico methods. The Z fragment is not associated with any known or predicted genes, with the closest gene being Engrailed 1 (EN1).

Using the Genome Browser (July 2003) the Z fragment was found to be approximately 1.2 kb downstream of a CpG rich region spanning 25 kilobases (kb). This region contains a number of genes, many of which contain CpG islands either within the gene or within the promoter region of the gene. The methylation status of these CpG islands was then determined using direct bisulfite sequencing and clonal analysis.

EXAMPLE 2

DNA Hypermethylation of CpG Islands Neighbouring Engrailed-1

2.1 Methods
Bisulfite Treatment

DNA was extracted from the HCT116/SW480 cells using the Puregene extraction kit (Gentra Systems) and Trizol reagent (Invitrogen) from colorectal cancer or normal matched samples according to the manufacturer's protocol. The bisulfite reaction was carried out using 2 μg of restricted DNA for 16 h at 55° C. under conditions essentially as previously described (Clark et al., *Nuc. Acids Res.*, 22: 2990-2997, 1994). After neutralization, the bisulphite treated DNA was ethanol precipitated, dried, resuspended in 50 μl of $H_2O$ and stored at −20° C. Approximately 2 μl of DNA was used for each of the nested PCR amplifications. The primers used for the amplifications are set forth in SEQ ID NOs: 71 to SEQ ID NO: 198. The combinations used are described herein. At least three independent PCR reactions were performed to ensure a representative methylation profile.

Direct PCR Sequence Analysis

Pooled PCR fragments were purified using the Wizard PCR purification system and then directly sequenced using the reverse primer of the PCR amplification in the Dye Terminator sequencing kit with AmpliTaq DNA polymerase and the automated 3730 DNA analyzer with KB™ basecaller in Sequence analysis v5.1 (Applied Biosystems). The degree of methylation at each CpG site from the direct sequencing profile was estimated by measuring the relative peak height of the cytosine versus thymine profile. The degree of methylation was then expressed as either 0%, 25%, 50%, 75% or 100%. The average of overall methylation across any particular PCR amplified CpG island was obtained by dividing the total summation of the degree of methylation at each CpG site across the CpG island, by the total number of CpG sites in that island. Using this calculation the CpG island region was classified as extensively methylated (75-100%), methylated (50-75%), moderately methylated (25-50%) and low to unmethylated (0-25%).

Real-Time PCR Melting Temperature Dissociation

2×SYBR Green 1 Master mix (P/N 4309155) was added to the PCR following completion of initial thermal cycling. The reactions were cycled at 95° C. for 15 secs, 60° C. for 20 secs, with the temperature increasing gradually from 60° C. to 90° C. and the melting dissociation trace was analyzed on the ABI Prism 7700HT Sequence Detection System. CpGenome Universal Methylated Control DNA (Chemicon International, Inc.) was used as a positive control to amplify fully methylated DNA for the dissociation curve. Human genomic DNA (Roche) was used as a positive control to amplify fully unmethylated DNA for the dissociation curve.

PCR and Clonal Analysis

Pooled PCR fragments, directly purified using the Wizard PCR DNA purification system were cloned into the pGEM®-T-Easy Vector (Promega) using the Rapid Ligation Buffer System (Promega). Approximately 12 individual clones were sequenced from the pooled PCR reactions using the Dye Terminator cycle sequencing kit with AmpliTaq DNA polymerase, FS (Applied Biosystems) and the automated 373A NA Sequencer (Applied Biosystems). Bisulfite sequencing of individual clones validated the semi-quantitative methylation levels obtained from direct PCR sequencing analysis. Average methylation from individual clones was calculated as a percentage of the number of methylated CpG sites over the number of total CpG sites sequenced.

2.2 Results

Figure 4:
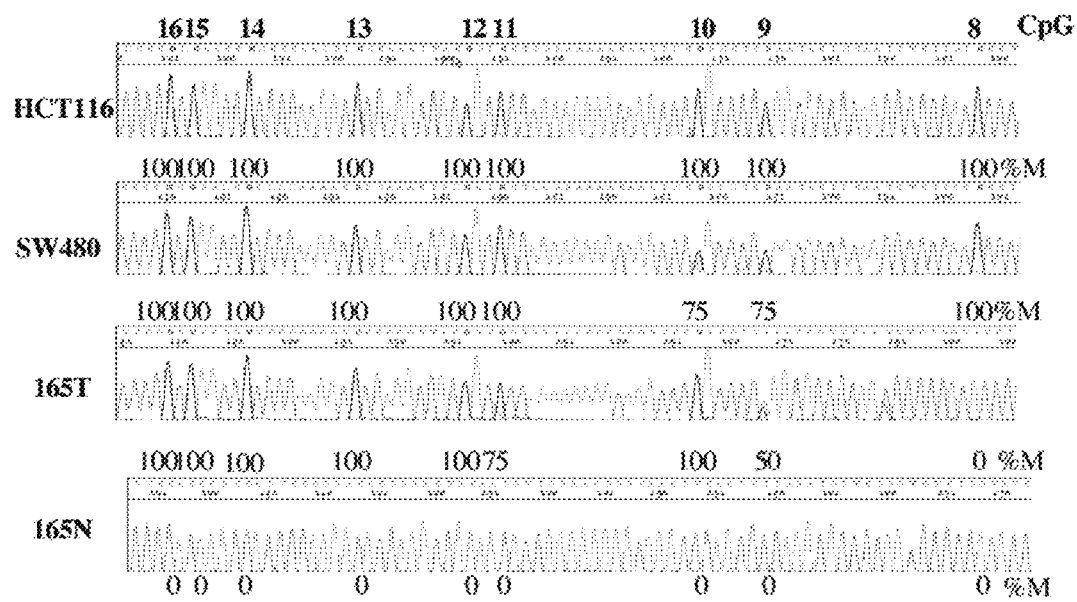
FIG. 4 is a graphical representation showing results of direct bisulphite sequencing electrophoretograms of EN1 promoter (CpG 128) in two colon cancer cell lines HCT116 and SW480 and a matched normal and tumour pair (165T and 165N) (as indicated at the left-hand side of the figure). The CpG sites are numbered relative to the start of the PCR fragment. The percent methylation at each CpG site, as determined by the relative C to T peak heights is indicated below the sequence profile.

To determine whether or not the 25 Kb cluster of CpG islands discussed in Examples 1 were differentially methylated in cancer, direct bisulfite sequencing and PCR melting dissociation temperature were used. Direct bisulfite PCR sequencing facilitates semi-quantitation of the methylation of each CpG site, across the fragment. For example, methylation was scored as 0%, 25%, 50%, 75% or 100%, depending on the cytosine to thymine ratio. An example of the direct sequencing results is shown in FIG. 4.

Figure 5A:
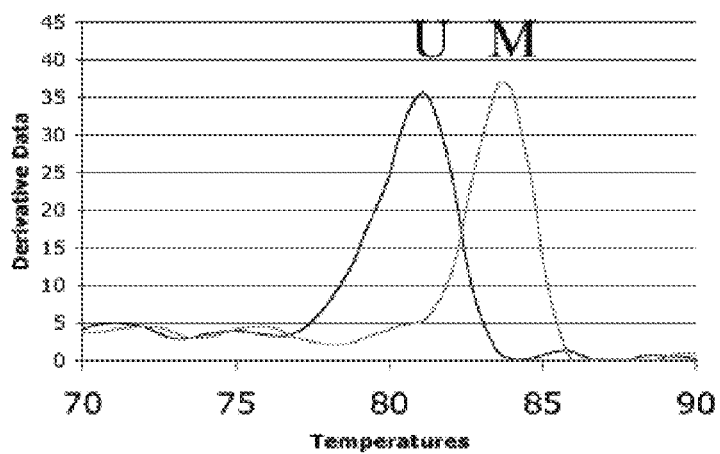
FIG. 5a is a graphical representation showing results of real-time PCR dissociation melting temperature analysis. The temperature at which the PCR product dissociates is indicative of unmethylated (U) DNA, methylated (M) DNA or a mixture of both methylated and unmethylated DNA. In the example shown, (U) indicates the melt curve of unmethylated control DNA; (M) indicates the melt temperature of methylated control DNA.
Figure 5B:
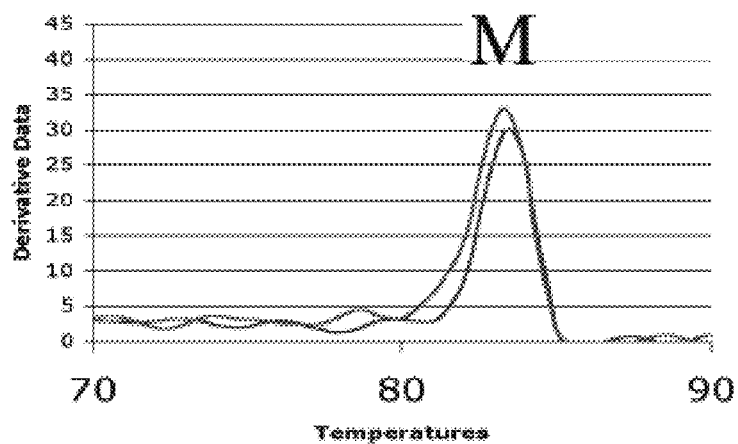
FIG. 5b is a graphical representation showing results of a real-time PCR dissociation melting temperature assay in which nucleic acid comprising a CpG island is amplified using PCR following bisulfite treatment and the melting temperature of the PCR product is determined. The temperature at which the PCR product dissociates is indicative of unmethylated (U) DNA, methylated (M) DNA or a mixture of both methylated and unmethylated DNA. The graph shown indicates the melt curve of the EN1 promoter from HCT116 and SW480 bisulphite treated DNA. In the sample shown, the majority of the DNA was amplified from methylated (M) DNA thereby causing dissociation at a single temperature.
Figure 5C:
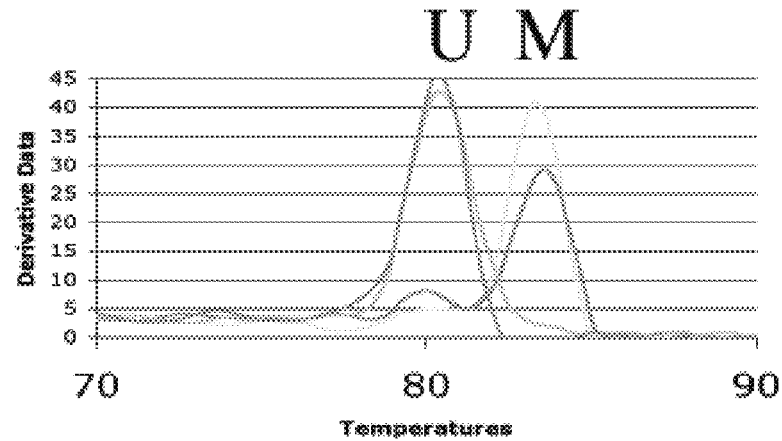
FIG. 5c is a graphical representation showing results of real-time PCR dissociation melting temperature assay in which nucleic acid comprising a CpG island is amplified using PCR following bisulfite treatment and the melting temperature of the PCR product is determined. The temperature at which the PCR product dissociates is indicative of unmethylated (U) DNA, methylated (M) DNA or a mixture of both methylated and unmethylated DNA. The graph shown indicates the melt curve of the EN1 promoter from bisulfite treated DNA from matched tumour and normal pairs (9N/9T and 165N/165T). In the sample shown, there is a mixture of methylated (M) and unmethylated (U) DNA thereby causing dissociation at different temperatures.

PCR melting dissociation temperature allowed the overall methylation status of each PCR fragment to be assessed, by comparing the difference in melting temperature between the methylated and unmethylated DNA. For example, the CpG island (CpG 128) EN1 promoter, that was amplified from fully methylated bisulfite-treated DNA dissociates at 83.6° C., whereas the PCR fragment amplified from bisulfite treated unmethylated DNA, dissociates at 81° C. (FIG. 5). Using the difference in the dissociation temperatures for EN1 CpG 128, it is clear that the tumor DNA from the cell lines HCT116, SW480 and from 9T and 165T is methylated whereas the normal DNA, 9N and 165N is unmethylated (FIG. 5).

A summary of the methylation status of the Z fragment and 6 of the 11 CpG islands (CpG104, CpG103, CpG128, CpG41, CpG173, CpG48) from two colorectal cell lines HCT116 and SW480 and from 2 tumour/normal matched pairs (9N/T and 165N/T), is shown in FIG. 6. The Z fragment and all the neighbouring CpG islands, across the 25 Kb region, including the EN1 promoter (CpG128), were found to be unmethylated in the normal colorectal tissue (9N & 165N), but were extensively methylated in the two colorectal cancer cell lines and in the 2 cancer DNA samples 9T & 165T.

Figure 7:
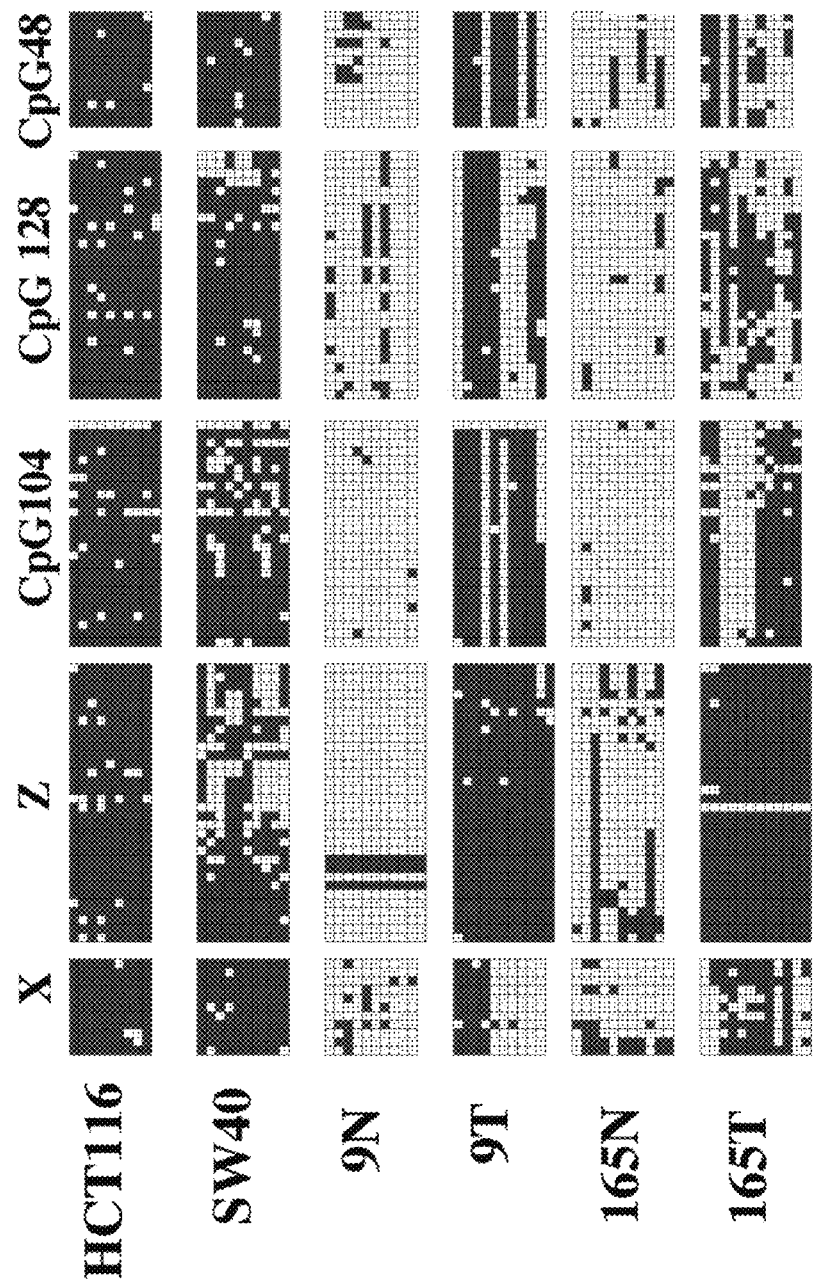
FIG. 7 is a graphical representation showing results of genomic bisulphite sequencing of individual clones across the 83 kb region encompassing the Z fragment. Selected PCR fragments were sequenced from 2 colorectal cell lines (HCT116 and SW480) and 2 pairs of cancer (9T and 16T) and matched normal samples (9N and 165N). Each square denotes a CpG site. Black squares indicate a methylated CpG site, and white squares indicate an unmethylated CpG site.

To determine the degree of methylation heterogeneity and to obtain a more detailed methylation profile of individual molecules, clonal sequencing analysis of a subset of the CpG islands was performed (FIG. 7). The clonal sequencing supported the overall direct bisulfite PCR semiquantitative sequencing analysis.

To determine whether or not the differential methylation also extended upstream of the Z fragment, direct bisulphite PCR sequencing, PCR melting temperature dissociation and methylation clonal sequencing analysis was performed. This analysis was performed using a CpG depleted region, 20 kb upstream from the Z fragment, termed (X) or (20 Kb) (bp=182, GC %=63 CpG o/e=0.6), as well as the next closest upstream CpG island (CpG29) that was located 58 kb upstream of the Z fragment, shown in FIG. 3. The CpG sites in the CpG depleted DNA (X) and the CpG sites in the CpG island CpG29, were found to be extensively methylated in HCT116 and in the 2 cancer DNA samples relative to methylation in the matched normal samples (FIG. 6). CpG29 however, was partially methylated in the cancer cell line SW480, whereas the CpG depleted DNA (X), located 20 kb region upstream from the Z fragment, was hypermethylated in both cell lines. These results demonstrate contiguous hypermethylation of neighbouring CpG islands, in the cancer cells, across a region that spans 83 Kb from CpG29 to CpG48. In addition, our results showed that differential hypermethylation also occurs in non CpG island regions and CpG depleted regions (Z fragment and a region 20 kb upstream from the Z fragment), indicating that hypermethylation is not just restricted to CpG island regions in cancer cells but can encompass CpG sites in the intervening genomic regions that are also unmethylated in normal cells.

EXAMPLE 3

DNA Methylation Across Chromosome 2q14.2 in Cancer

Figure 8A:
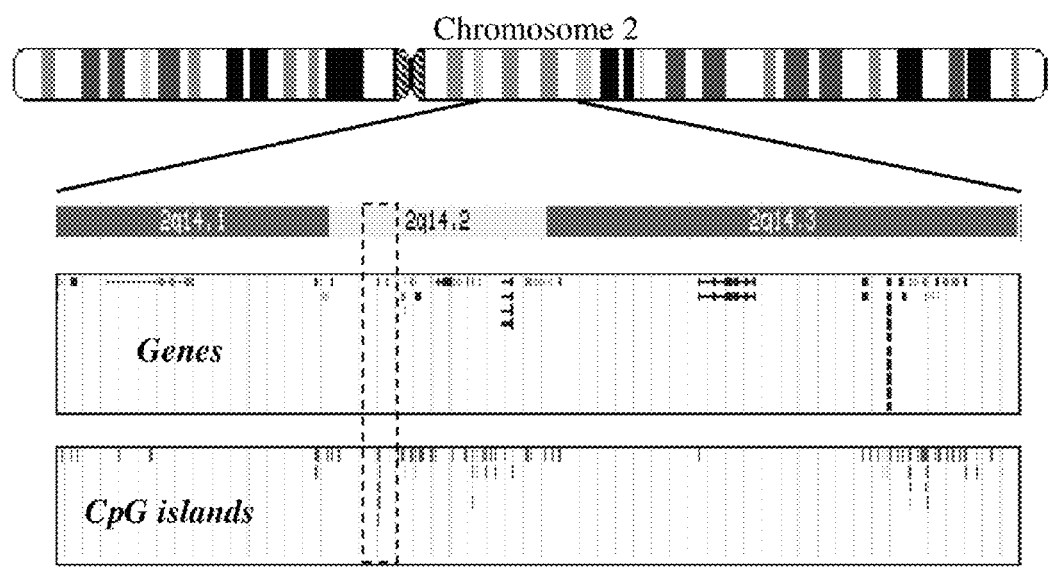
FIG. 8a is a graphical representation showing the chromosomal location of 2q14.2 on chromosome 2. The location of genes and CpG islands within Chromosome position 2q14.2 are indicated in the panels (identified using Genome Browser, July 2003). The dotted lines indicate the region spanning the Z fragment that was analysed as shown in FIGS. 3-7.
Figure 8B:
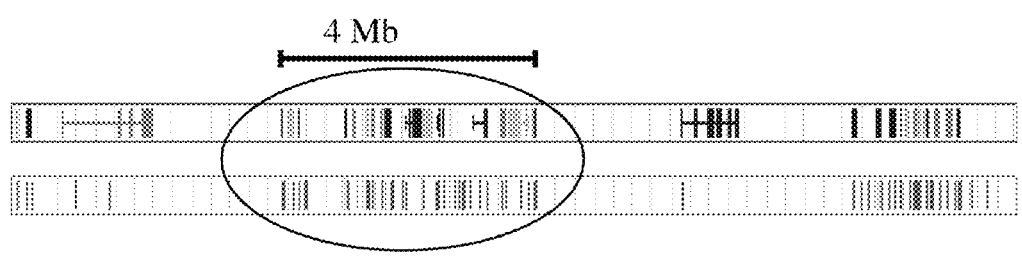
FIG. 8b is a graphical representation showing the location of genes (top panel) and CpG islands (bottom panel) within Chromosome position 2q14.2 (identified using Genome Browser, July 2003). The circle indicates the region spanning the Z fragment that was analysed as shown in FIGS. 3-7.

The analysis of the methylation status of DNA on either side of the 83 Kb methylated region described in Example 2 was then extended to determine the length of the differentially methylated region and to define the boundaries of the CpG island hypermethylation across the Chromosome 2q14.2 cytogenetic band. As shown in FIGS. 8a and 8b, Chromosome 2q14.2 is a 4 Mb region that is both gene rich and rich in CpG islands.

Figure 8C:
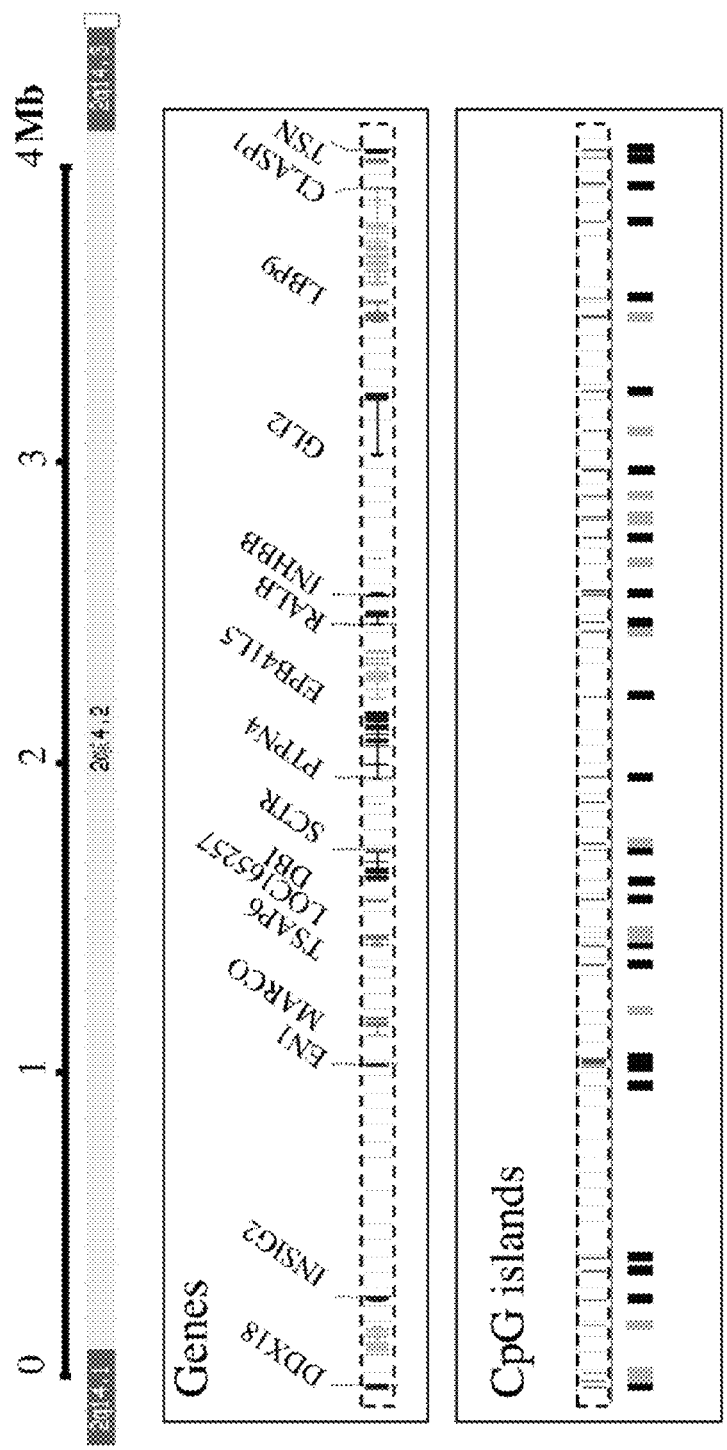
FIG. 8c is a graphical representation showing a detailed analysis of the location of the defined genes and associated CpG islands across the 4 Mb region of Chromosome 2 shown in FIGS. 8a and 8b. In the upper panel the 10 defined genes are indicated in dark letters and the grey letters represent the provisional genes, based on data in the SWISS-PROT database. The lower panel shows the location of the CpG islands, the islands that have been bisulfite sequenced (n=31) in this study are indicated in black and the CpG islands not analyzed in grey (n=15).

FIG. 8c shows the locations of defined and predicted genes and associated CpG islands localized to Chromosome 2q14.2. Ten defined genes reside in 2q14.2; of these eight have CpG island associated promoters, one (GLI2) has a 3' CpG island and MARCO has no associated CpG island.

Figure 9A:
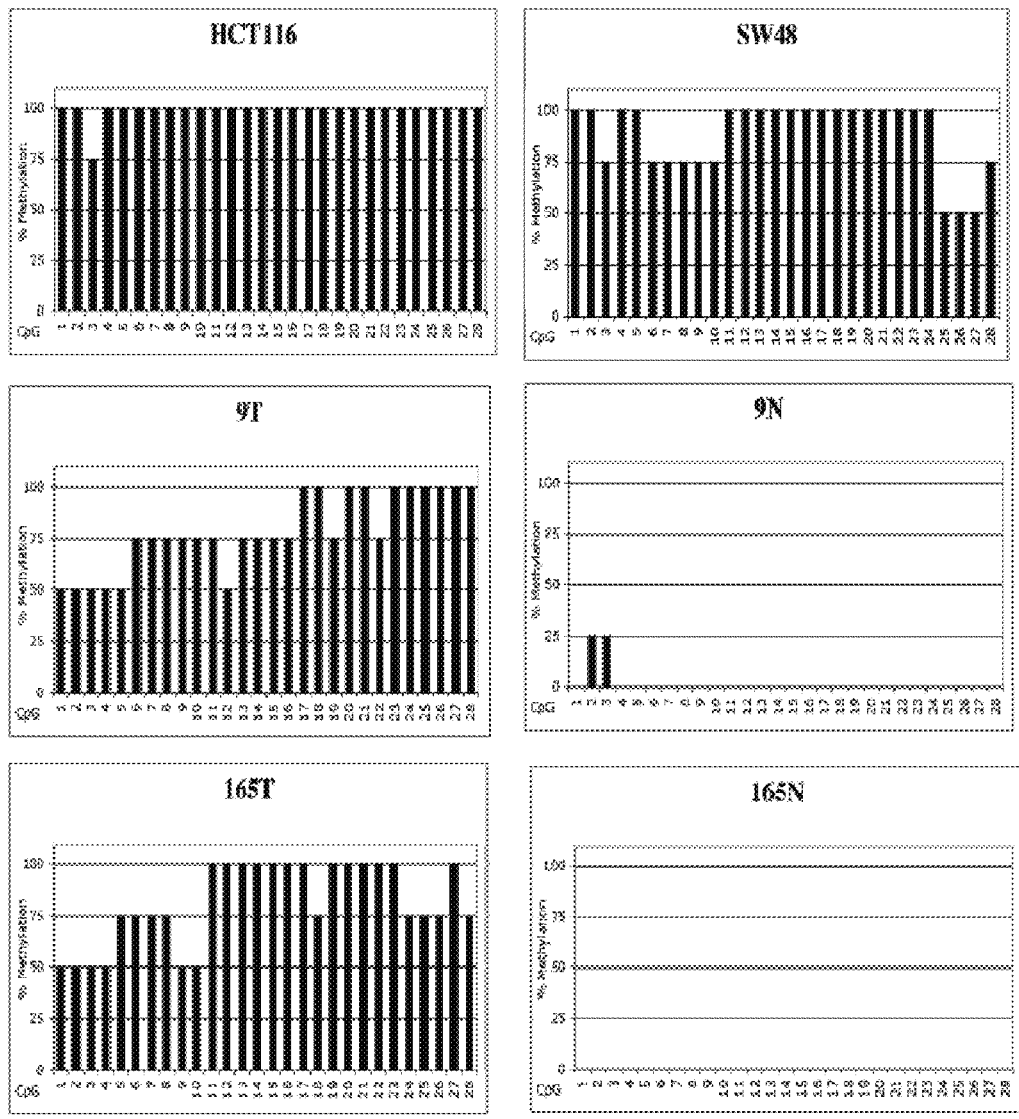
FIG. 9a is a graphical representation showing a summary of results of genomic bisulphite direct sequencing of the CpG island associated with the EN1 gene using DNA from the colorectal cell line HCT116 and SW480 and in the cancer and matched normal (165N and 165T and 9N and 9T) samples. The CpG sites are numbered; the % methylation at each CpG sites is plotted on each graph.
Figure 9B:
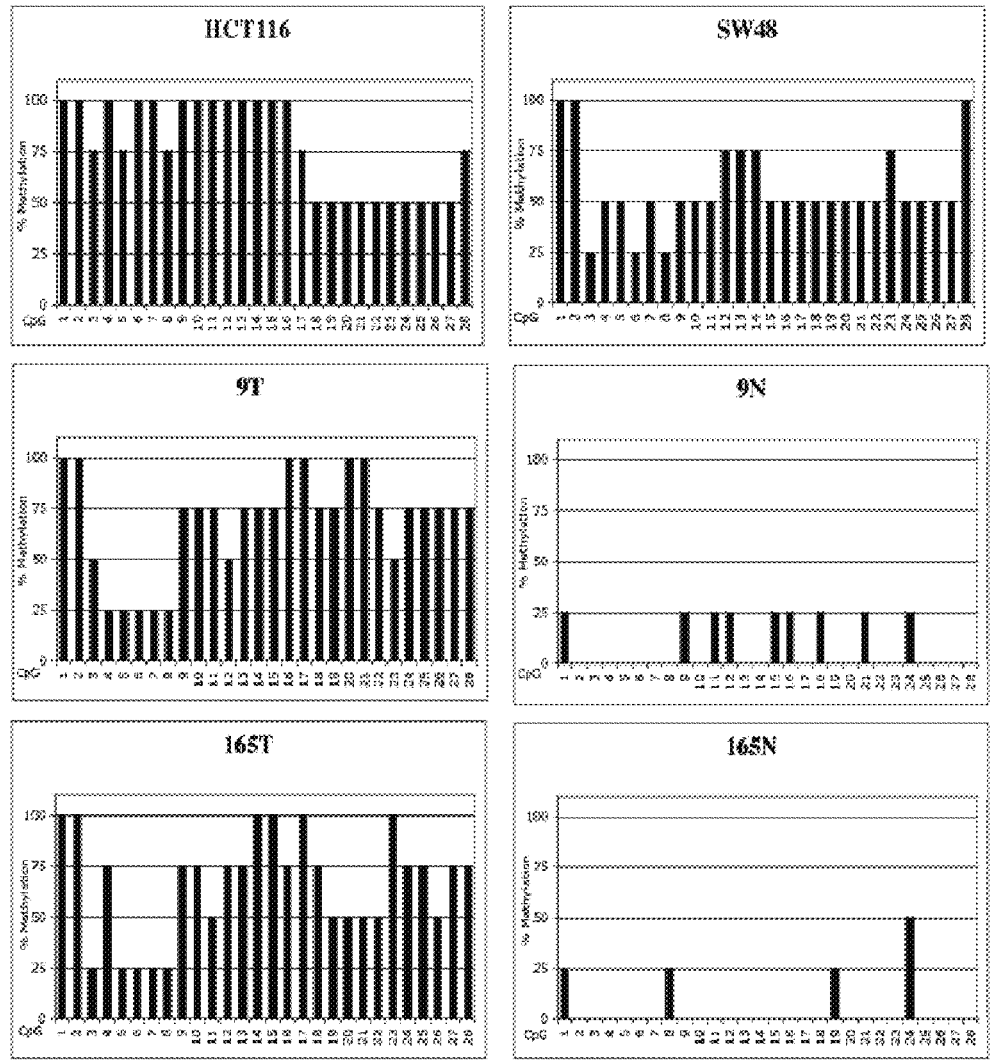
FIG. 9b is a graphical representation showing a summary of results of genomic bisulphite direct sequencing of the CpG island associated with the INHBB gene using DNA from the colorectal cell line HCT116 and SW480 and in the cancer and matched normal (165N and 165T and 9N and 9T) samples. The CpG sites are numbered; the % methylation at each CpG sites is plotted on each graph.
Figure 9C:
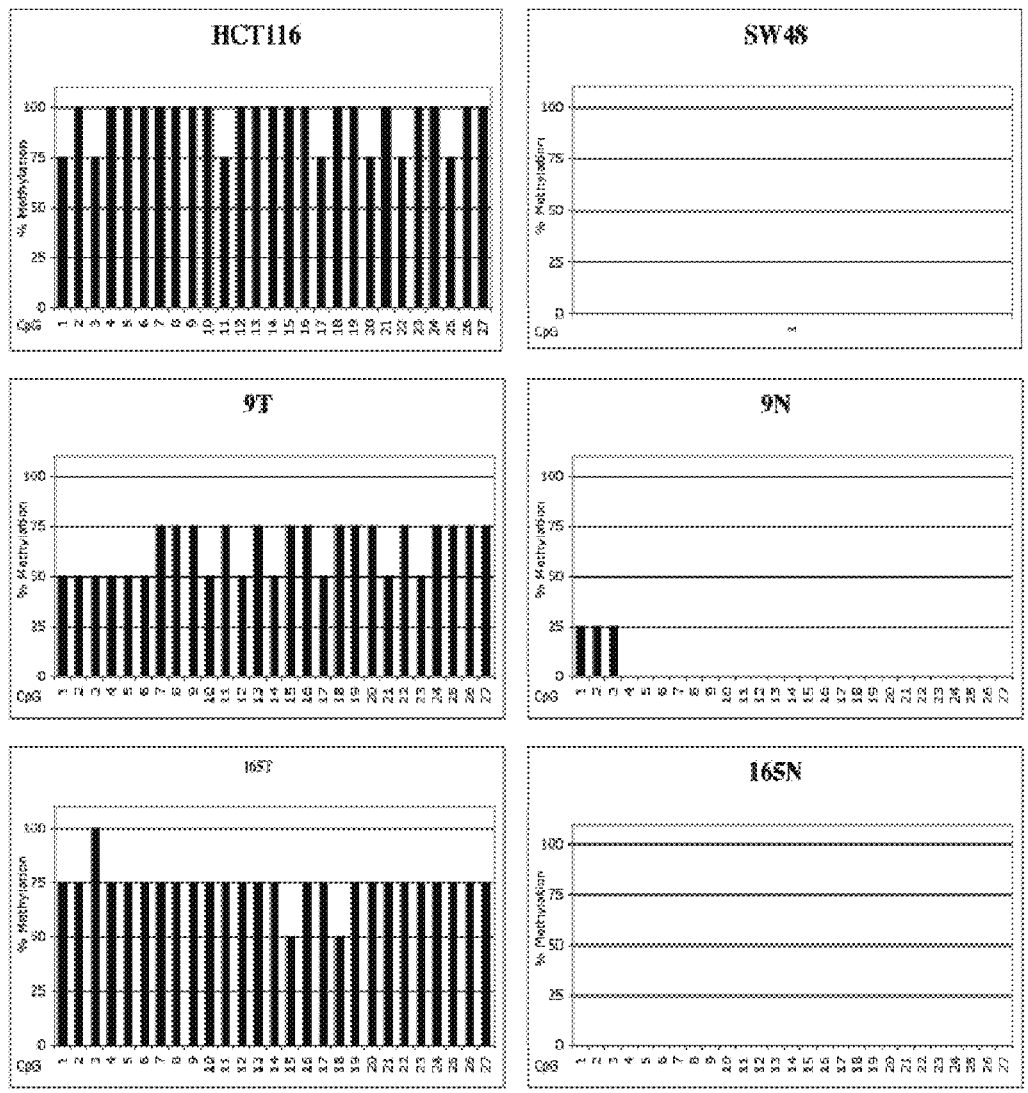
FIG. 9c is a graphical representation showing a summary of results of genomic bisulphite direct sequencing of the CpG island associated with the SCTR gene using DNA from the colorectal cell line HCT116 and SW480 and in the cancer and matched normal (165N and 165T and 9N and 9T) samples. The CpG sites are numbered; the % methylation at each CpG sites is plotted on each graph.

To determine the methylation status of Chromosome 2q14.2 direct bisulfite PCR sequencing and clonal analysis were used to analyze CpG islands associated with known genes (eight in total), in addition to a number of intervening CpG islands. Many of these intervening CpG islands are associated with predicted genes. Exemplary results from the analysis of methylation of CpG islands associated with the EN1 gene, INHBB gene and SCTR gene in colorectal cancer cell lines and in matched tumor and control samples are shown in FIGS. 9a-c. These graphs indicate the percentage methylation at each CpG site in each CpG island.

Figure 10A:
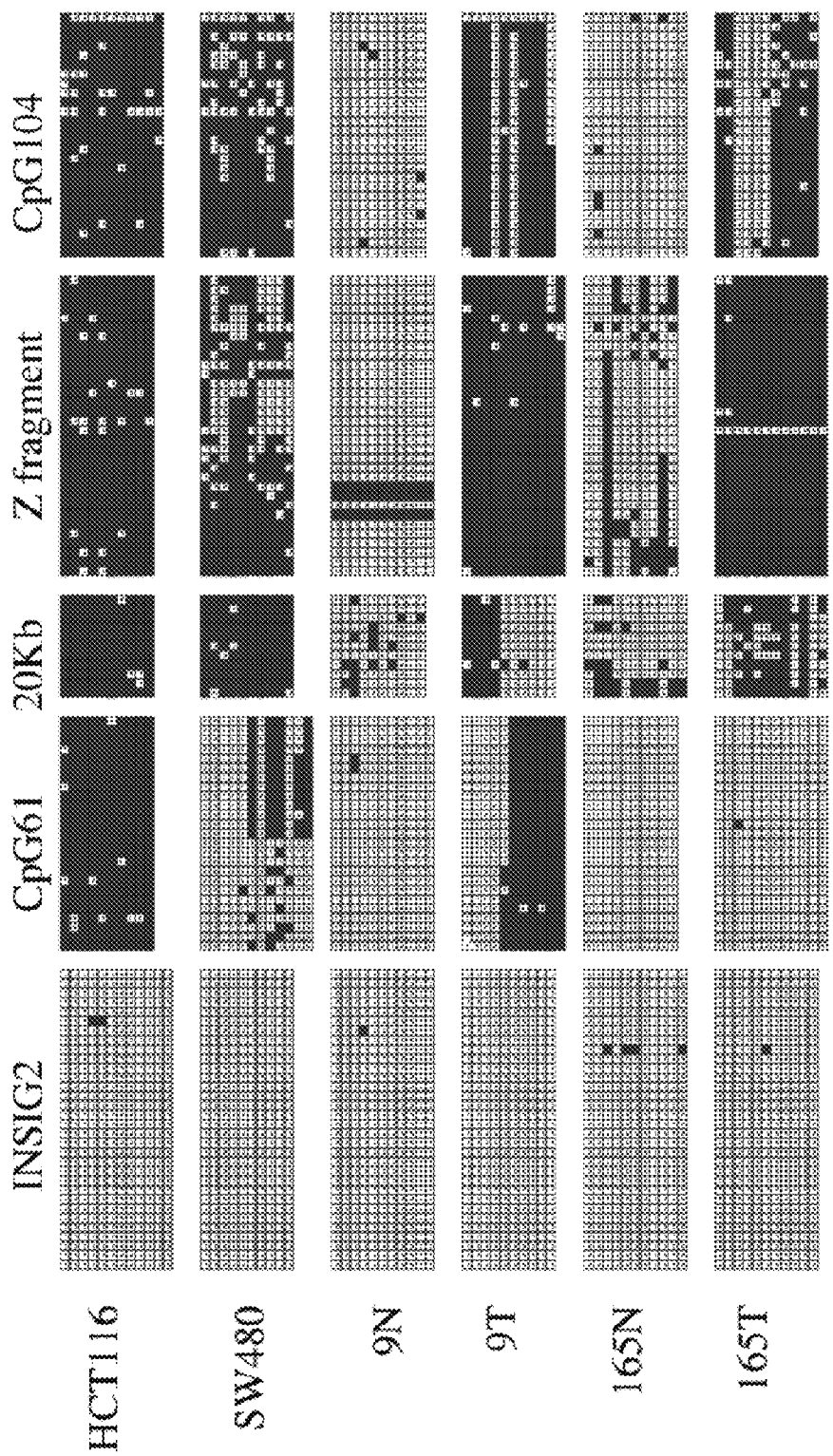
FIG. 10a is a graphical representation showing genomic bisulphite sequencing of individual clones of the CpG sites INSIG2, CpG61, 20 Kb, Z fragment and CpG104 linked to Chromosome position 2q14.2 (as indicated). For each CpG island 10-12 clones derived from a pool of 3 independent PCRs were sequenced. DNA was analysed from two colorectal cell lines (HCT116 and SW480) and two pairs of cancer and matched normal samples (9N and 9T, 165N and 165T) as indicated. White squares indicate an unmethylated CpG site; black squares denote a methylated CpG site.
Figure 10B:
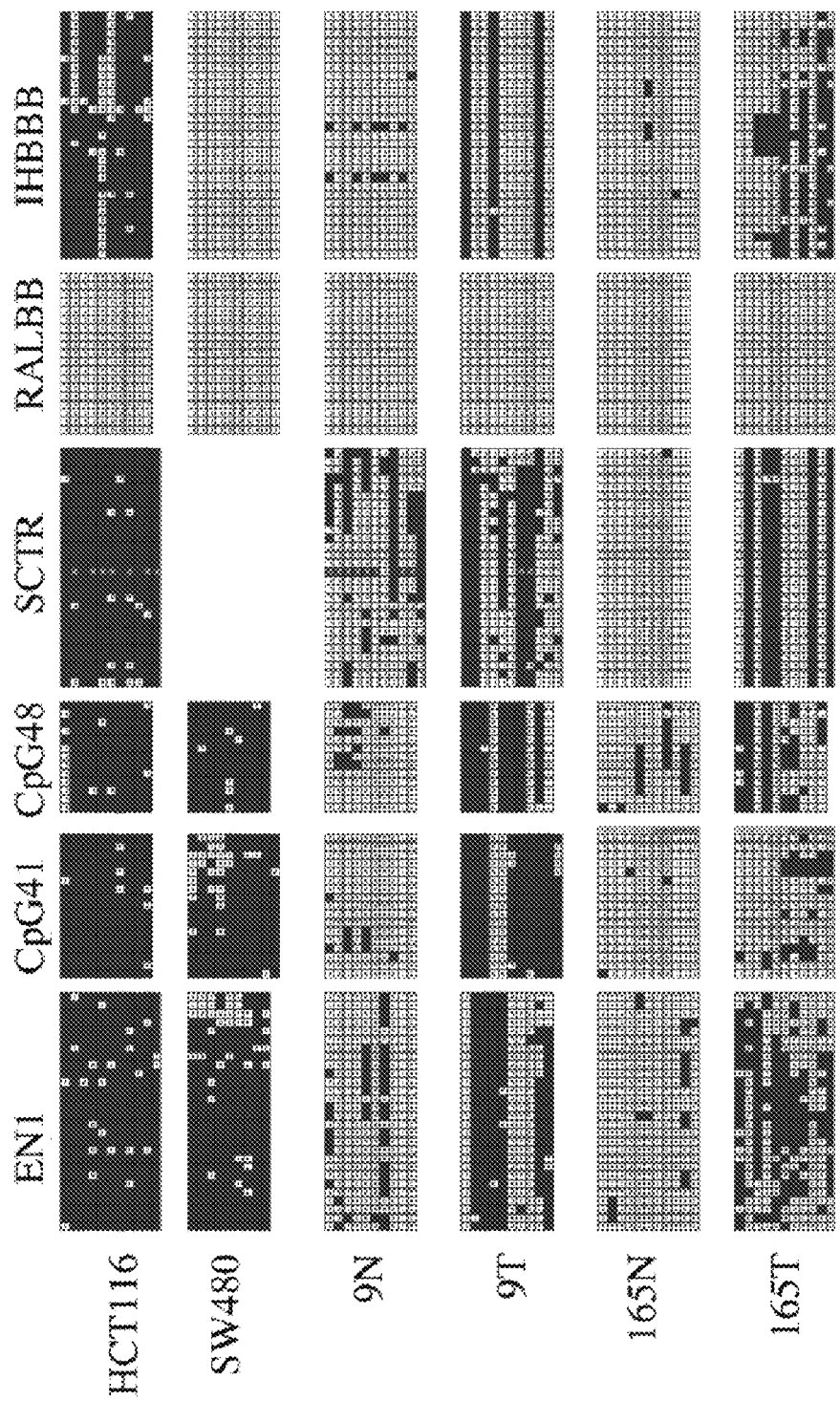
FIG. 10b is a graphical representation showing genomic bisulphite sequencing of individual clones of the CpG sites EN1, CpG41, CpG48, SCTR, RALBB and INHBB linked to Chromosome position 2q14.2 (as indicated). For each CpG island 10-12 clones derived from a pool of 3 independent PCRs were sequenced. DNA was analysed from two colorectal cell lines (HCT116 and SW480) and two pairs of cancer and matched normal samples (9N and 9T, 165N and 165T) as indicated. White squares indicate an unmethylated CpG site; black squares denote a methylated CpG site.

FIGS. 10a and 10b show the results of clonal sequencing of 10-12 clones from a pool of 3 different PCR reactions. Results are shown for colorectal cancer cell lines and in matched tumor and control samples.

Figure 11:
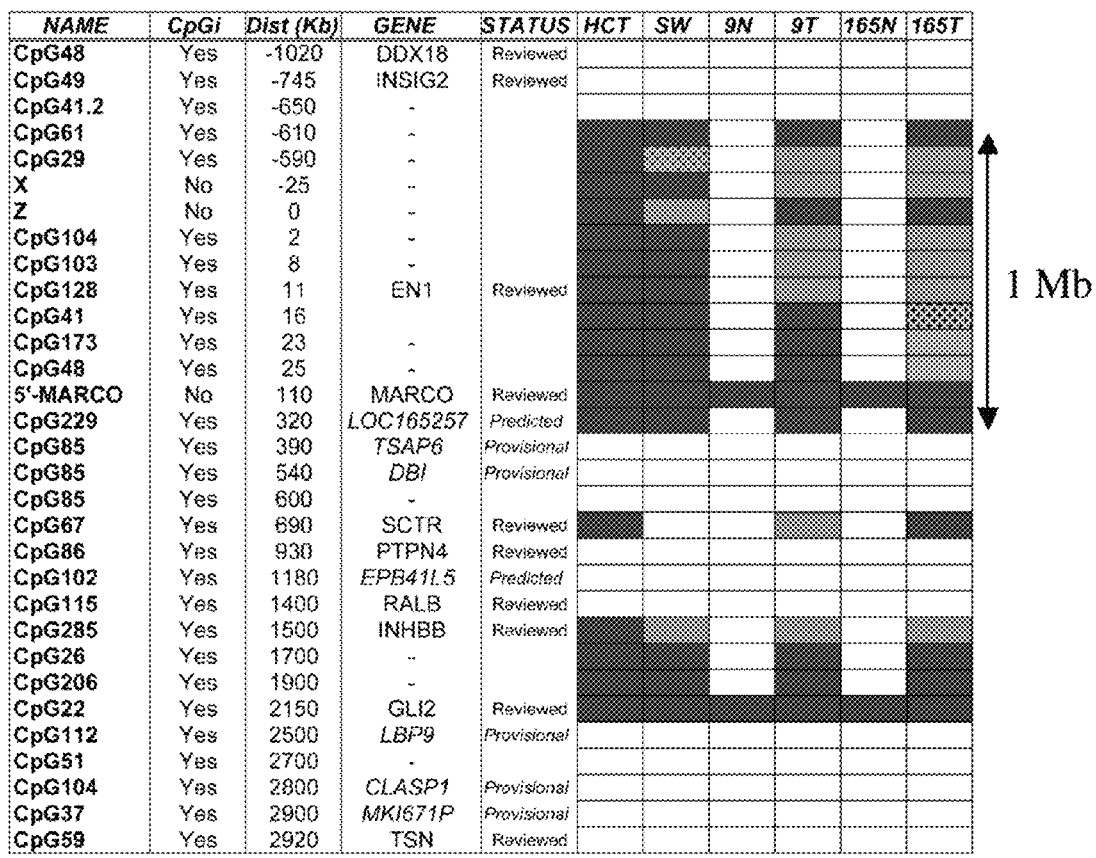
FIG. 11 is a tabular representation showing a summary of the DNA methylation profile across the 4 Mb region of chromosome 2q14.2. Direct PCR sequencing methylation analysis of the CpG islands and CpG depleted regions in two colorectal cell lines (HCT116 and SW480) and two pairs of cancer and matched normal samples (9N/9T, 165N/165T). CpGi denotes presence or absence of a CpG island. The distance in kilobases (Kb) from the Z fragment is also indicated. The names and status of the defined and provisional and predicted genes are also indicated. Average overall methylation of the CpG island is indicated as follows: a white square, about 0-25% methylation; a dotted pale grey square, about 25-50% methylation; a grey square, about 50-75% methylation; and a black square, about 75-100% methylation.

The results shown in FIGS. 9 and 10 are summarized in FIG. 11. FIG. 11 shows the DNA methylation profile for all CpG island and non island regions sequenced across the 4 Mb region on 2q14.2, from both the colorectal cancer cell lines and from the cancer versus matched normal samples. DNA from cancer cells was found to be contiguously hypermethylated across the 2q14.2 Chromosome regions. For example, DNA from the cancer cells was contiguous hypermethylated in a region that spanned nearly 1 Mb, from CpG island (CpG61) 610 kb upstream of the Z fragment to CpG island (CpG 229), 325 kb downstream of the Z fragment. The hypermethylated 1 Mb region contained 15 CpG islands but only two islands, CpG128 and CpG229, were associated with either a known gene (EN1) or a predicted gene (LOC165257 encoding a C1q-domain containing protein). Two further regions of extensive hypermethylation, in the colorectal cancer cells, were also identified along the 14.2q cytogenetic band from chromosome 2 (FIG. 11). The first region of hypermethylation was located 690 Kb downstream of the Z fragment, and included the CpG island (CpG67) spanning the promoter of the SCTR gene (coding for the secretin receptor). The second hypermethylated region was located 1.5-2.15 Mb downstream of the Z fragment, spans 650 kb in length and encompasses four CpG islands; (CpG285) spans the promoter of the INHBB gene (inhibin beta B); CpG 26 and CpG206 were not associated with gene promoter regions and CpG22 was located at the 3' end of the GLI2 gene (encoding a $C_2H_2$-type zinc finger protein). Each of the three hypermethylated regions, within the cytogenetic band 14.2q on chromosome 2, was flanked by unmethylated CpG islands. Three unmethylated CpG islands are located upstream of the 1 Mb hypermethylated region, overlapping the junction to the 14.1 band, and include the CpG islands associated with the genes INSIG2 (encoding insulin induced protein 2) and DDX18 (encoding DEAD box polypeptide 18). Similarly, the CpG islands that are located at the 14.3q band junction, remain unmethylated in the colorectal cancer cells and these islands are associated with two genes CLASP (encoding the CLIP-associating protein) and TSN (translin). Two sets of CpG island clusters between the three methylated regions, also remain unmethylated in both cancer cell lines and cancer tissue samples and normal colorectal DNA. The first set of these islands is associated with the genes TSAP6 (coding for hypothetical protein Dudulin2) and DBI (encoding Diazepam Binding Inhibitor) and the second set is associated with the PTPN4 gene (encoding Protein tyrosine phosphatase, non-receptor type 4) and RALB (encoding a v-ral simian leukemia viral oncogene homolog B; ras related; GTP binding protein) (FIG. 11).

EXAMPLE 4

DNA Methylation in Colorectal Tumors

To determine whether or not hypermethylation of Chromosome 2q14.2 is common to colorectal cancer, the methylation status of promoter CpG islands associated with the genes EN1 (CpG128), SCTR(CpG67) and INHBB (CpG285) was determined using genomic DNA isolated from 26 colorectal cancers. As shown in FIG. 12a, EN1 was found to be hypermethylated in $18/26$ (70%) of samples, SCTR was hypermethylated in $23/26$ (88%) of samples and INHBB was hypermethylated in $15/26$ (58%) of samples. Furthermore, $25/26$ (96%) of samples displayed aberrant methylation of at least one of the CpG islands tested.

As shown in FIG. 12a, the extent of hypermethylation was independent of sex, age or Dukes stage, indicating that these changes are an early even in colorectal cancer.

Figure 12B:
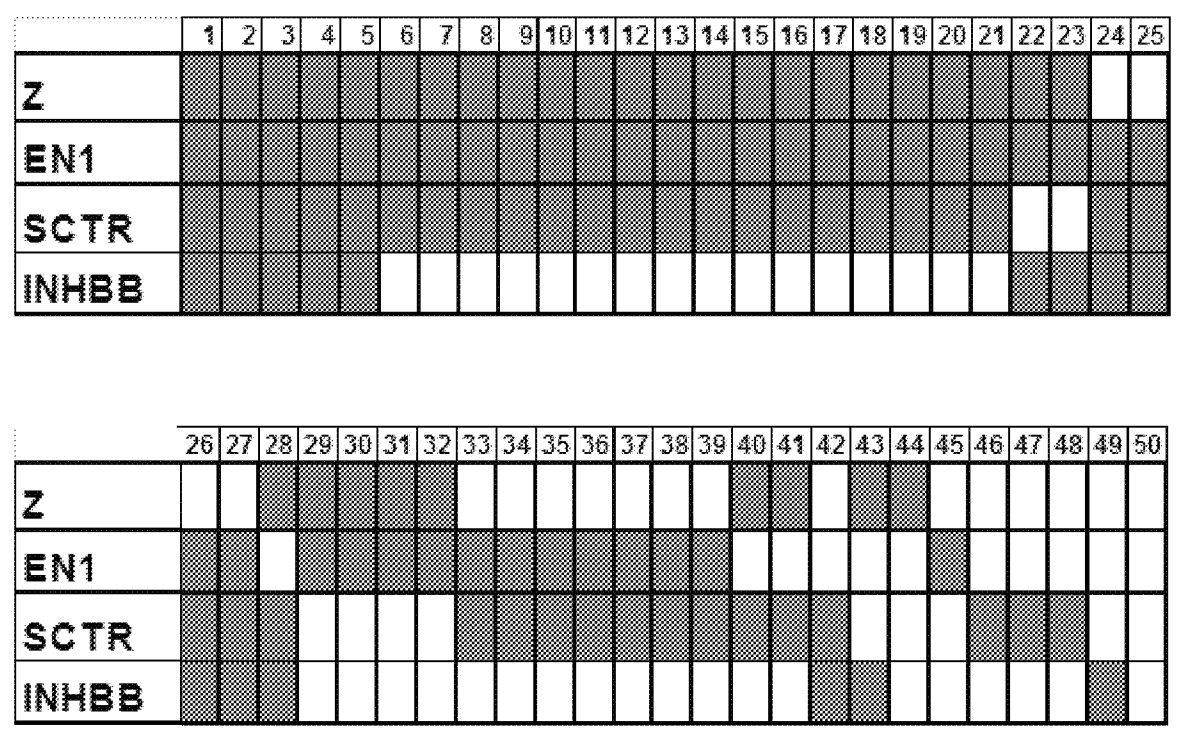

Extending these studies, using heat-dissociation real-time PCR analysis the degree of methylation of the Z fragment, a CpG island associated with EN1, a CpG island associated with SCTR and a CpG island associated with INHBB was determined in 100 colorectal cancer samples. As shown in FIG. 12b, the Z fragment was methylated in 68% of samples, EN1 was methylated in 78% of colorectal cancer, SCTR was methylated in 78% of colorectal cancers and INHBB was methylated in 30% of colorectal cancers.

When the methylation status detected for CpG islands associated with EN1, SCTR and INHBB was combined, 96% of colorectal samples were shown to have increased methylation at one or more of these sites. These results indicate that the detection of the methylation status of one or more CpG islands within Chromosome 2 (between about map position 2q14.1 and about map position 2q14.3) is useful for detecting a considerable proportion of colorectal cancers.

FIG. 13 shows the methylation status of the EN1 (CpG128), SCTR(CpG67) and INHBB (CpG285) CpG islands in 12 colorectal cell lines. Hypermethylation of at least one of the CpG islands was observed in each of the cell lines tested.

EXAMPLE 5

Gene Expression is Suppressed in the Hypermethylated Region 5.1 Methods
RNA Extraction and Quantitative Real-Time RT-PCR RNA was extracted using Trizol reagent (Invitrogen) according to the manufacturer's protocol. cDNA was reverse transcribed from 2 μg of total RNA using SuperScript™ III RNase H⁻ Reverse Transcriptase (Invitrogen Life technologies), according to the manufacturer's instructions. The reaction was primed with 200 ng of random hexamers (Roche).

The reverse transcription reaction was then diluted 1:20 with sterile $H_2O$ before addition to a PCR reaction. Expression levels of each of the genes DDX18, INSIG2, EN1, MARCO, SCTR, PTPN4, RALBB, GLI2 and TSN was quantitated using a flourogenic real-time detection method using the ABI Prism 7000 Sequence Detection System. 5 μl of the reverse transcription reaction was used in the quantitative real-time PCR reaction using 2×SYBR Green 1 Master Mix (P/N 4309155) with 50 ng of each primer. The primers used for amplification comprise a sequence set forth in any one of SEQ ID Nos 119 to 218. Primers were used in a combination described herein.

To control for the amount and integrity of the RNA, the Human 18S ribosomal RNA (rRNA) kit (P/N 4308329) (Applied Biosystems), containing the rRNA forward and reverse primers and rRNA VIC™ probe, was used. 5 μl of the reverse transcription was used in a 20 μl reaction in TaqMan Universal PCR Master Mix (P/N 4304437) with 1 μl of the 20× Human 18S rRNA mix. The reactions were performed in triplicate and the standard deviation was calculated using the Comparative method (ABI PRISM 7700 Sequence Detection system User Bulletin #2, 1997 P/N 4303859). The cycle number corresponding to where the measured fluorescence crosses a threshold is directly proportional to the amount of starting material. The mean expression levels are represented as the ratio between each gene and 18S rRNA expression.

5.2 Results

Figure 14:
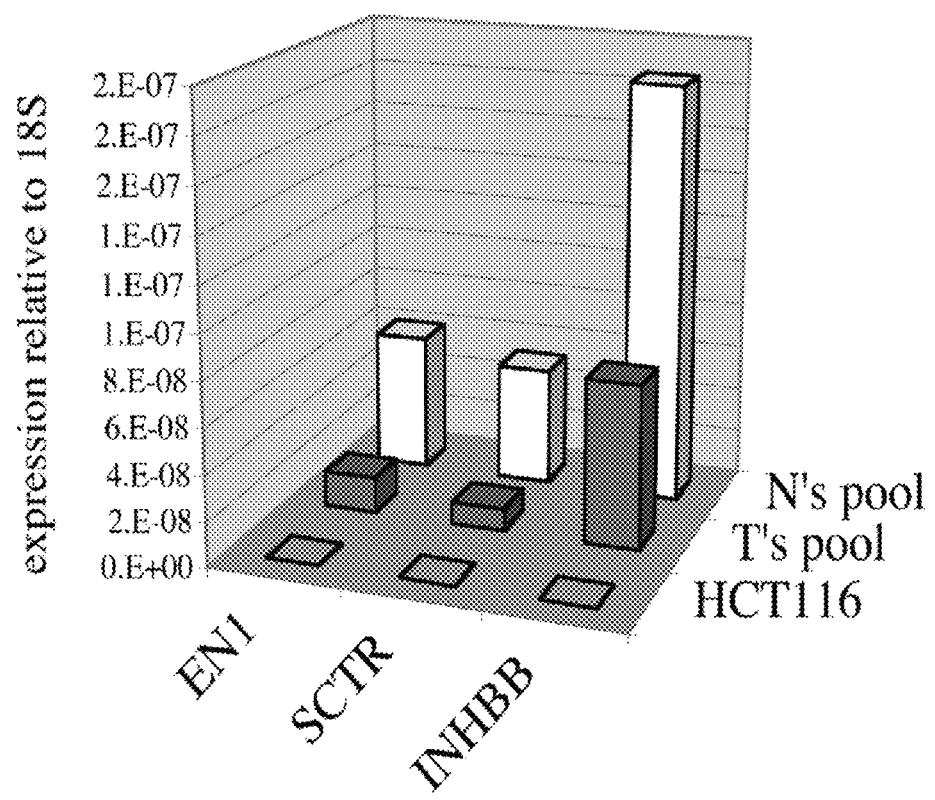
FIG. 14 is a graphical representation showing mRNA expression levels of EN1, SCTR and INHBB as determined by RT-PCR from HCT116 cells and compared to the expression levels of RNA isolated from pooled (10) colorectal tumour tissue samples and the corresponding pooled (10) normal tissue samples. The level of expression by RT-PCR was normalised with 18s expression.
Figure 15:
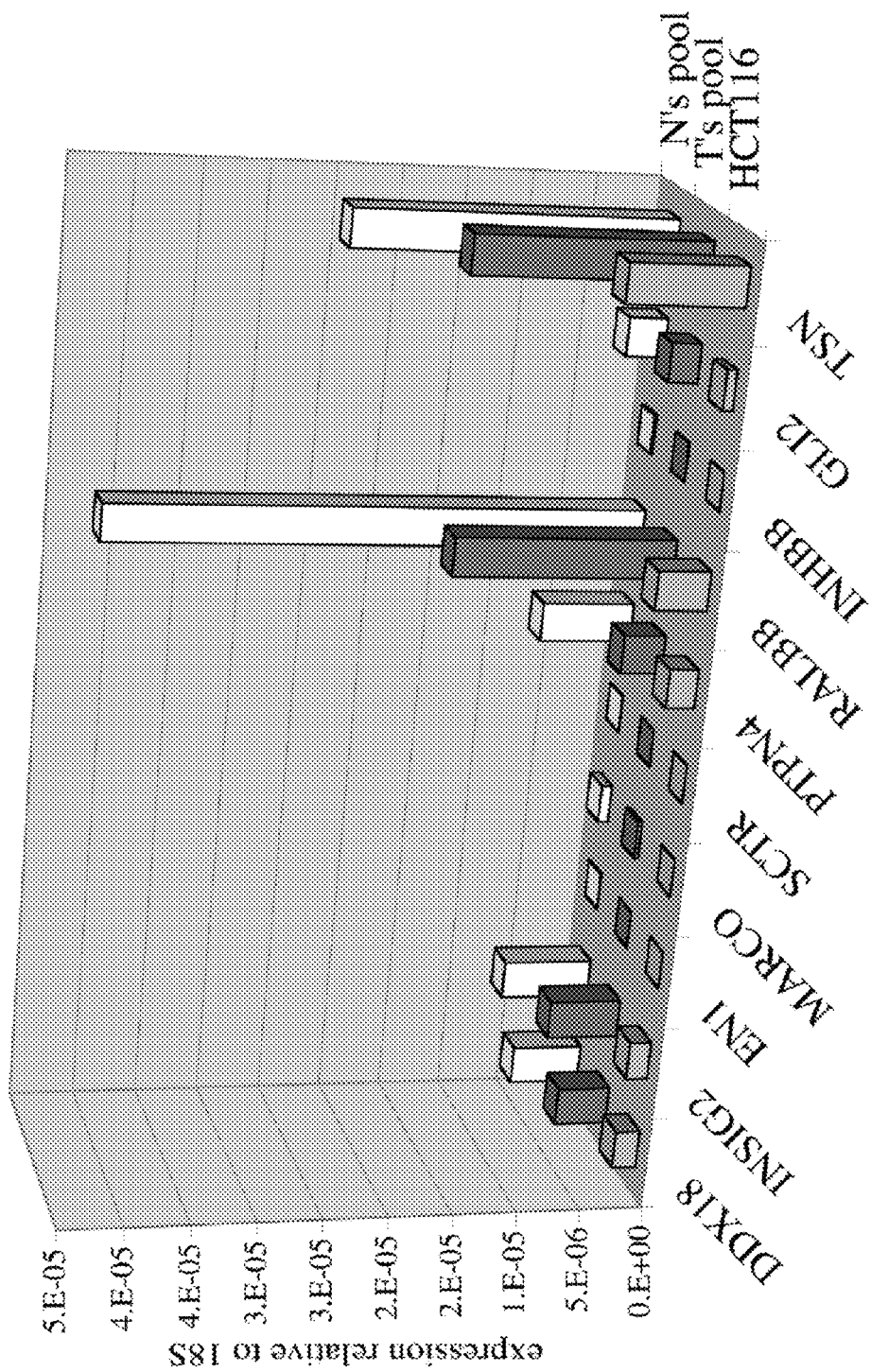
FIG. 15 is a graphical representation showing the level of mRNA expression of all the known genes (DDX18, INSIG2, EN1, MARCO, SCTR, PTPN4, RALBB, INHBB, GLI2 and TSN, as indicated) in the 2q14.2 cytogenic band as determined by RTPCR. Expression levels were determined HCT116 cells, pooled tumour and pooled matched normal samples as indicated.

A number of known genes are located on Chromosome 2 between about map position 2q14.1 and 2q14.2 (i.e., the region encompassing the hypermethylated region described supra). This region includes the genes DDX18, INSIG2, EN1, MARCO, PTPN4, RALBB, GLI2 and TSN. To determine whether or not the hypermethylation of the CpG islands in the hypermethylated region correlated with suppression of gene expression in the cancer cells, the mRNA expression levels of EN1, SCTR and INHBB was determined in cancer and control samples by real-time RT-PCR. Expression levels were determined using samples from HCT116 cells and compared to the expression levels from 10 colorectal tumor tissue samples (pooled) versus the expression from 10 matched normal tissues (pooled). cDNA was prepared from RNA isolated from each individual sample, the cDNA was pooled and amplified in triplicate using real-time PCR and the expression levels for each gene was measured relative to expression of 18sRNA. Pooled cDNA samples were used to determine gene suppression and to avoid variations that may occur in individual samples due to varying purity of the tissue samples. As shown in FIG. 14, expression of EN1, SCTR and INHBB was completely inactivated in HCT116 cells. Moreover, the level of expression of these three genes was significantly reduced in the pooled primary cancer samples relative to the level of expression in the matched normal samples The level of mRNA expression of all the known genes in the 14.2 cytogenetic band by real-time RT-PCR from HCT116 cells to the expression levels measured from the pool of 10 colorectal tumor versus pool of 10 matched normal samples (FIG. 15). This assay was performed to determine if the high degree of methylation observed in the three separate regions across 2q14.2 influenced the expression of the neighbouring unmethylated CpG island associated genes in the colorectal cancer cells.

Results indicate that regardless of the DNA methylation status of the associated CpG islands, all the genes were suppressed in the HCT116 cell lines relative to expression in the normal colorectal cells. Additionally, the expression levels measured from the pooled tumor tissue samples was significantly reduced relative to the expression from the pooled matched normal samples.

The normal level of individual gene expression was observed to vary gene by gene across the 14.2q region. The genes that were associated with CpG islands that remained unmethylated in the cancer cells (DDX18, INSIG, PTPN4, RALBB, TSN) expressed at a higher level in the normal colorectal cells. In contrast, CpG island-associated genes (EN1, SCTR, and INHBB) that were hypermethylated in cancer cells displayed minimal (basal) expression in normal cells. Moreover, genes that do not have 5'CpG island promoters (GLI2 and MARCO), but were methylated in both cancer and normal cells show reduced basal levels of expression in cancer versus normal cells. These data show that there is an overall suppression of gene expression across the 14.2q band on chromosome 2 in colorectal cancer even in genes that remain unmethylated in the cancer cells.

EXAMPLE 6

Chromatin Remodeling Across the Chromosome 2q14.2 Cytogenetic Band is Associated with Reduced Gene Expression 6.1 Methods
Cells and Culture Conditions The colon cancer cell line HCT116 was cultured in D-MEM/F12 (Gibco/BRL) medium supplemented with MEM sodium pyruvate and L-Glutamine and 10% fetal calf serum at 37° C. with 10% $CO_2$. Cells were split 1:8 every 3-4 days.

5-Aza-2'-deoxycytidine and TSA Treatment of Cells

Cells were split 12 h to 24 h prior to treatment. 5-Aza-2'-deoxycytidine (5-aza-dC)(Sigma) was prepared as a 1 mg/ml stock in sterile water, filter-sterilized and frozen as aliquots. 100 mm tissue culture dishes were seeded with $0.5 \times 10^6$ cells and following 24 h incubation the cells were treated with 0.5 μm 5-aza-dC. The cells were treated for 24 hours after which the medium was replaced with fresh medium and the cells cultured for a further 48 h before harvesting.

Cells were treated with trichostatin A (TSA) (Sigma) at 25, 50 and 100 nM for 24 h. Alternatively, an identical volume of ethanol was used as a control.

For co-treatment of cells with 5-aza-dC and TSA, 5-aza-dC was added initially for 24 h, after which it was removed and TSA was added for a further 24 h. The concentrations and the treatment conditions used were chosen based on preliminary studies showing optimal reactivation of gene expression.

Expression levels of the genes DDX18, INSIG2, EN1, MARCO, PTPN4, RALBB, GLI2 and TSN was determined essentially as described above.

6.2 Results

To address whether or not the suppression observed in the umethylated CpG island associated genes was correlated with the flanking CpG island methylation and/or associated chromatin modification in the colorectal cancer cells HCT116 cells were treated with the demethylating agent 5-Aza-2'-deoxycytidine (5Aza-C) and/or with an inhibitor of histone deacetylase trichostatin A (TSA) (Results are shown in FIG. 16). As a control for effective treatment conditions the expression of the p21 gene was determined. p21 is an example of a gene in HCT116 that is silent. However, treatment with 5AzaC or TSA results in the activation of p21 expression. Under the treatment conditions used, p21 expression was activated more than 3 fold using TSA treatment and more than 2 fold with 5AzaC treatment alone and in combination with TSA (FIG. 16a).

Figure 16A:
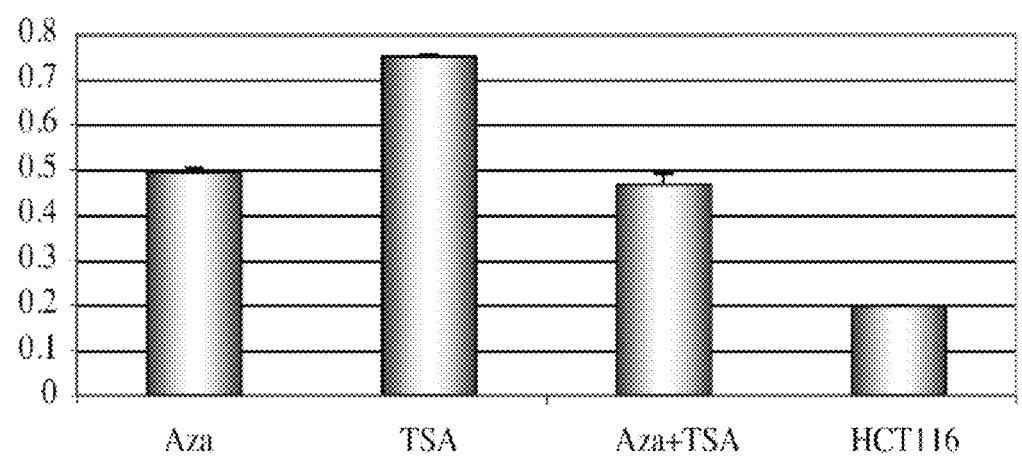
FIG. 16a is a graphical representation showing the effect of 5-Aza-2' deoxycytidine (Aza) and TSA on the expression of a control gene, p21. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16B:
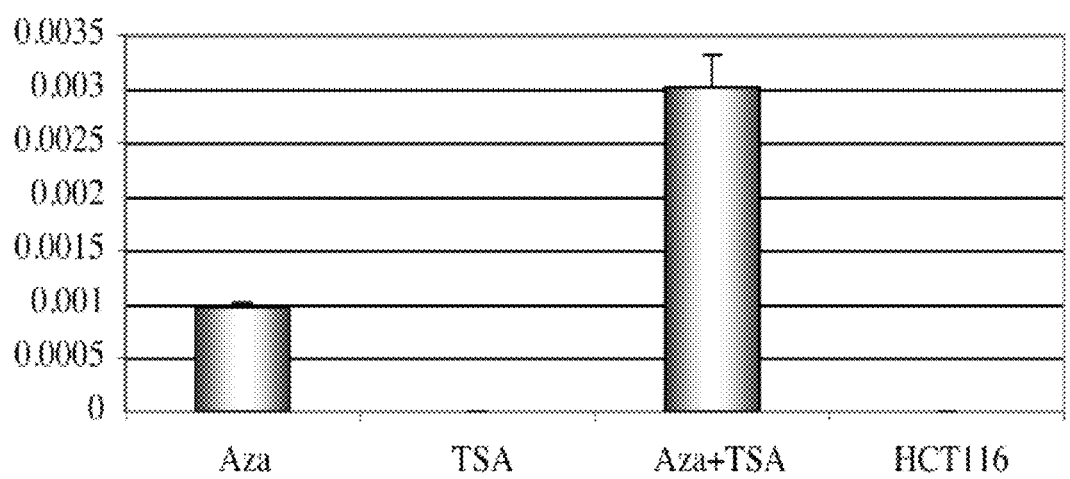
FIG. 16b is a graphical representation showing the effect of 5-Aza-2' deoxycytidine (Aza) and TSA on the expression of EN1. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16C:
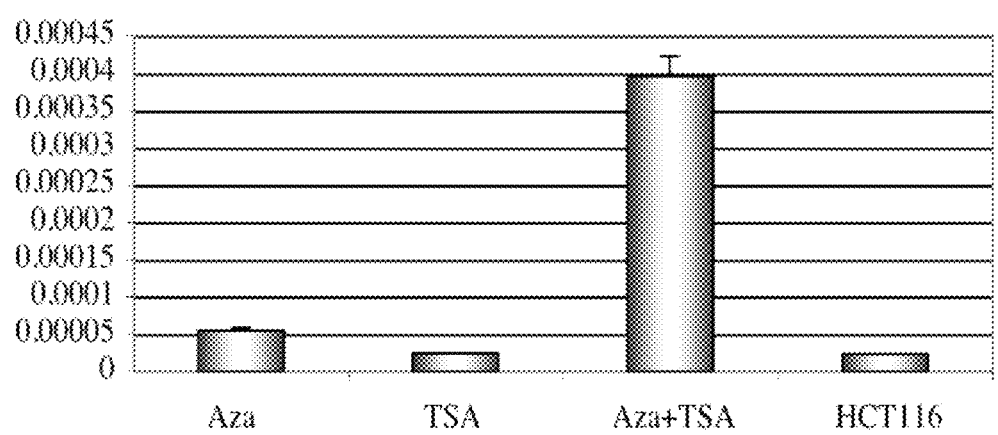
FIG. 16c is a graphical representation showing the effect of 5-Aza-2' deoxycytidine (Aza) and TSA on the expression of SCTR. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16D:
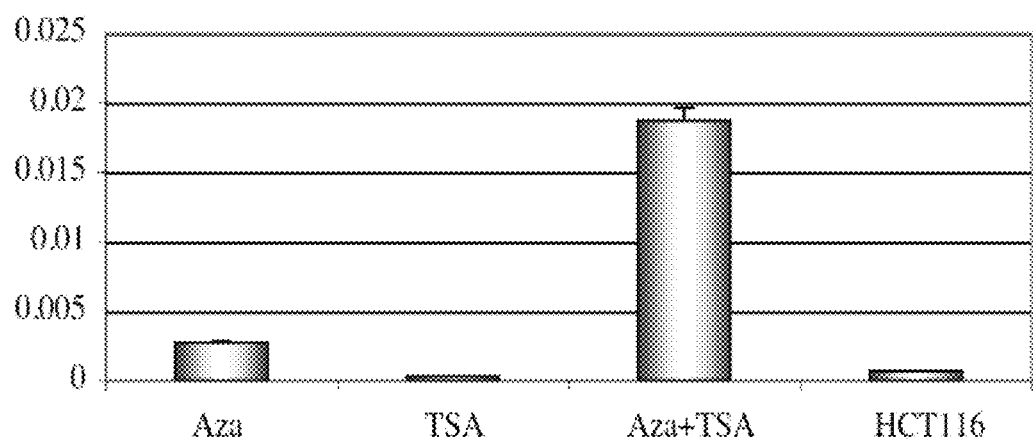
FIG. 16d is a graphical representation showing the effect of 5-Aza-2' deoxycytidine (Aza) and TSA on the expression of INHBB. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16E:
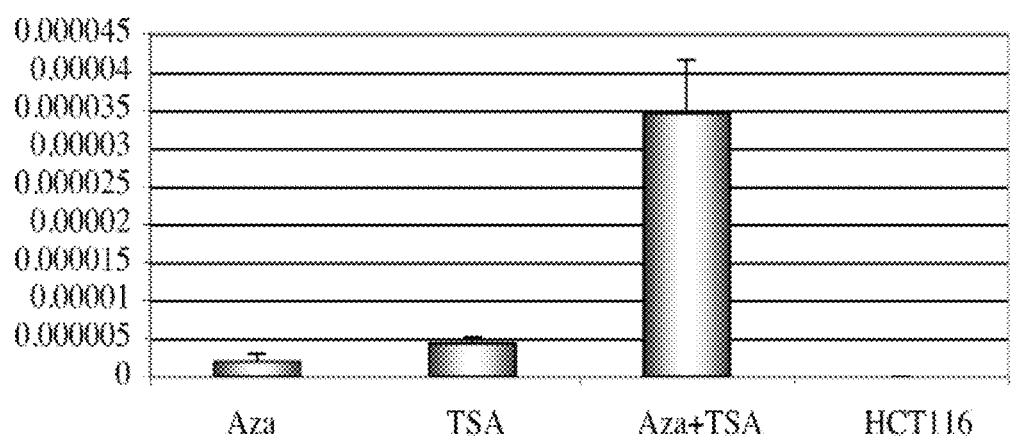
FIG. 16e is a graphical representation showing the effect of 5-Aza-2' deoxycytidine (Aza) and TSA on the expression of MARCO. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16F:
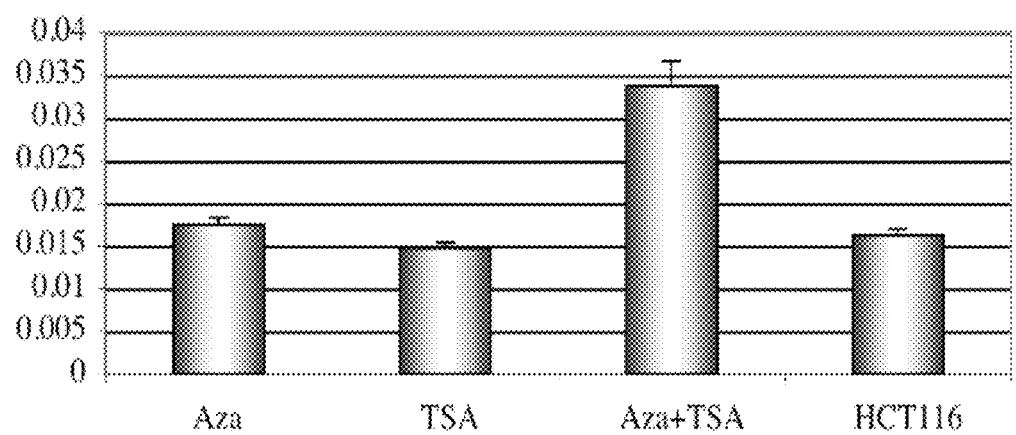
FIG. 16f is a graphical representation showing the effect of 5-Aza-2' deoxycytidine (Aza) and TSA on the expression of GLI2. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16G:
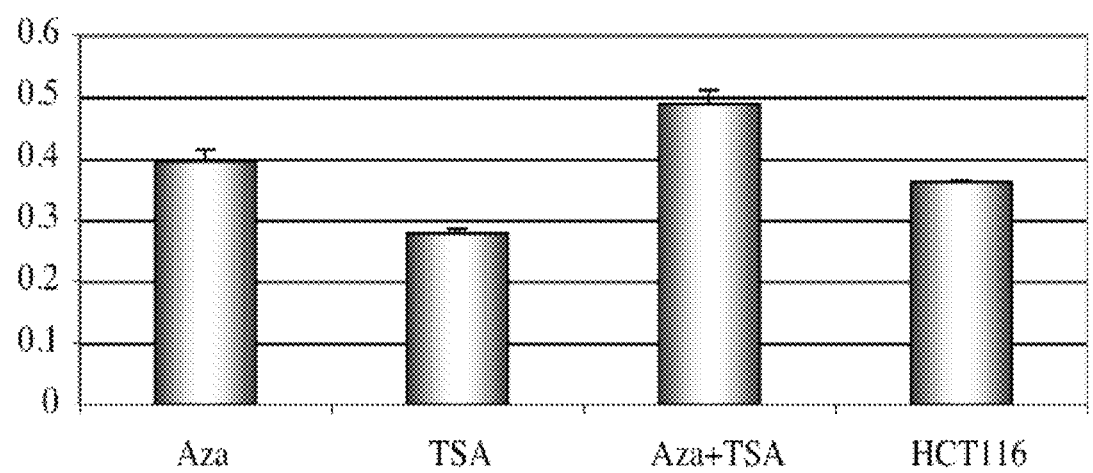
FIG. 16g is a graphical representation showing the effect of 5-Aza-2' deoxycytidine (Aza) and TSA on the expression of DDX18. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16H:
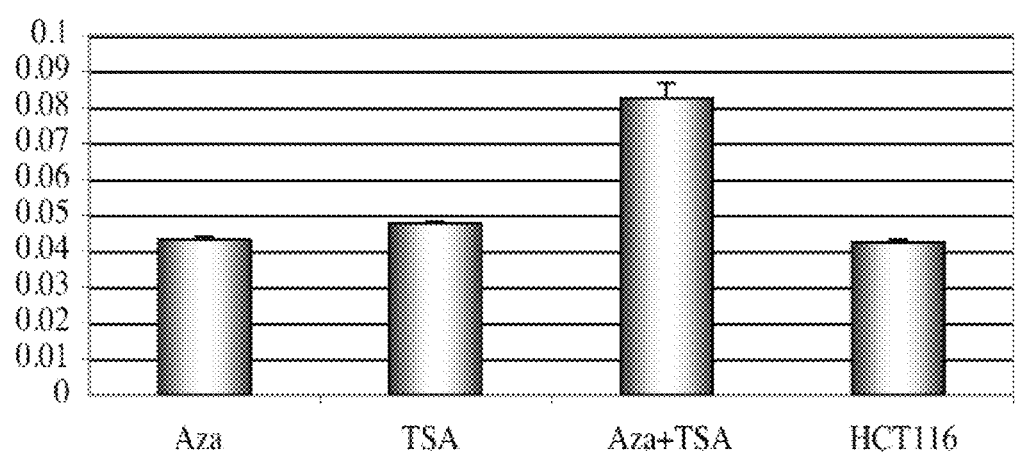
FIG. 16h is a graphical representation showing the effect of 5-Aza-2' deoxycytidine (Aza) and TSA on the expression of INSIG2. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16I:
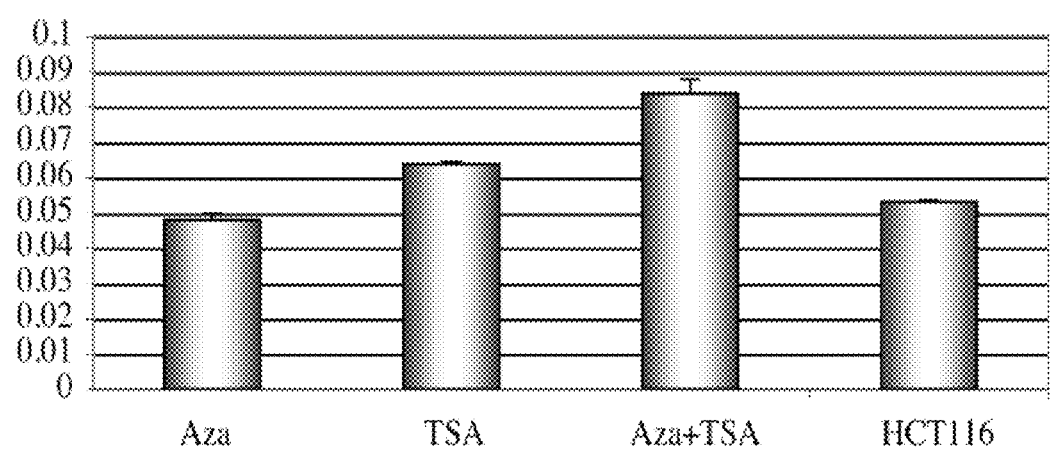
FIG. 16i is a graphical representation showing the effect of 5-Aza-2' deoxycytidine (Aza) and TSA on the expression of PTPN. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16J:
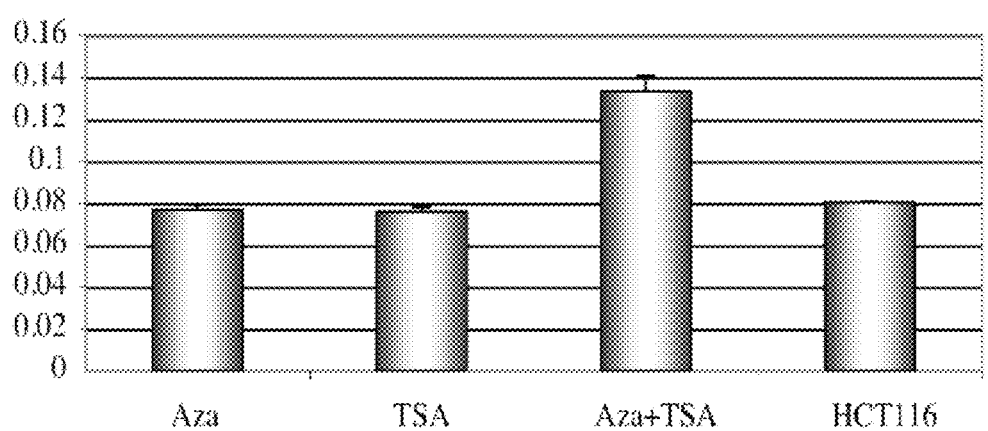
FIG. 16j is a graphical representation showing the effect of 5-Aza-2' deoxycytidine (Aza) and TSA on the expression of RALBB. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.
Figure 16K:
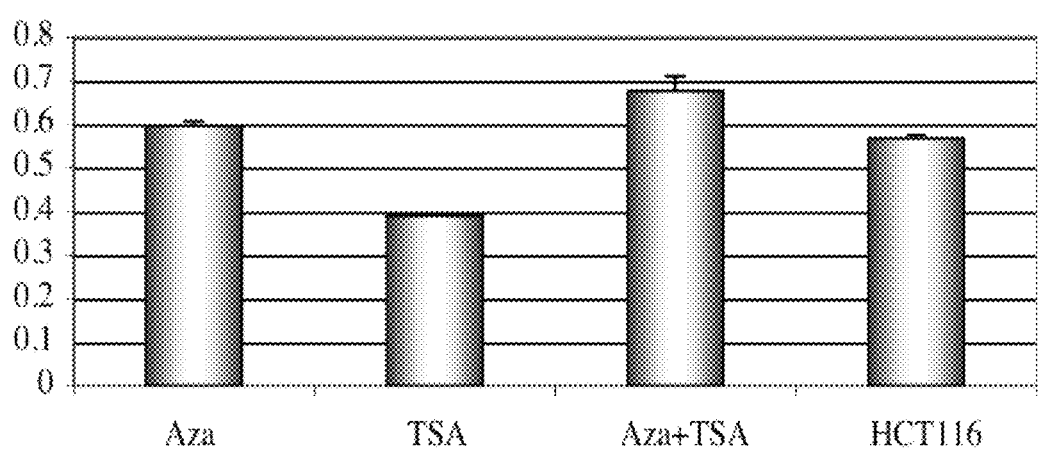
FIG. 16k is a graphical representation showing the effect of 5-Aza-2' deoxycytidine (Aza) and TSA on the expression of TSN. RNA was isolated from untreated HCT116 cells, and HCT116 cells treated with 5-Aza-2' deoxycytidine (Aza), TSA or a combination of TSA and 5-Aza-2' deoxycytidine (Aza/TSA). RNA was reverse transcribed and expression was quantitated by real-time PCR and normalised using 18s RNA expression.

Treatment of HCT116 cells with 5AzaC or TSA alone resulted in small increases of expression of genes linked to Chromosome position 2q14.2 that are hypermethylated in HCT116 (i.e., EN1, SCTR and INHBB). However, treatment with a combination of 5Aza and TSA resulted in substantial reactivation of all these genes (FIG. 16b, c and d). Likewise, MARCO and GLI2 which both do not have CpG island associated promoters but are either methylated in the promoter region or in the 3' downstream associated island, showed an increase in expression with a combination treatment of 5AzaC and TSA (FIGS. 16e and f).

CpG island-associated genes that are unmethylated and transcriptionally repressed in the HCT116, also showed some reactivation after treatment with 5Aza or TSA alone. However, all genes showed considerably increased expression levels after treatment with a combination of 5AzaC and TSA (FIG. 16g-k). Interestingly the greatest activation was observed for the unmethylated genes (INSIG2, PTPN4 and RALBB) that were closest to the methylated CpG rich regions. Without being bound by theory or mode of action, these results indicate that gene suppression of the unmethylated genes linked to Chromosome position 2q14.2, is influenced by the neighbouring DNA methylation. Furthermore, chromatin state of the hypermethylated CpG islands may be associated with modified histones.

EXAMPLE 5

Enhanced Gene Expression is Associated with Increased Histone Remodeling 5.1 ChIP Analysis.

ChIP assays were carried out according to the manufacturer (Upstate Biotechnology) and described in Stirzaker et al., Cancer Res 64: 3871-3877, 2004. Briefly, ~1×10$^6$ HCT116 cells, in a 10 cm dish, were fixed by adding formaldehyde at a final concentration of 1% and incubating for 10 minutes at 37° C. The cells were washed twice with ice cold PBS containing protease inhibitors (1 mM phenylmethylsulfonyl fluoride (PMSF), 1 µg/ml aprotinin and 1 µg/ml pepstatin A), harvested and treated with SDS lysis buffer for 10 min on ice. The resulting lysates were sonicated to shear the DNA to fragment lengths of 200 to 500 basepairs. The complexes were immunoprecipitated with an antibody specific for dimethyl-histone H3(lys9), Upstate Biotechnology (#07-212) or acetylated histone. 10 µl of antibody were used for each immunoprecipitation according to the manufacturer. No antibody controls were also included for each ChIP assay and no precipitation was observed. The antibody/protein complexes were collected by salmon sperm DNA/protein A agarose slurry and washed several times following the manufacturer's instructions. The immune complexes were eluted with 1% SDS and 0.1 M NaHCO3 and the crosslinks were reversed by incubation at 65° C. for 4 hours in the presence of 200 mM NaCl. The samples were treated with proteinase K for 1 hour and the DNA was purified by phenol/chloroform extraction, ethanol precipitation and resuspended in 30 µl H2O.

The amount of target that was immunoprecipitated, was measured by Real-Time PCR using the ABI Prism 7900HT Sequence Detection System. Amplification primers are set forth SEQ ID NOs: 235 to 256. PCR reactions were set up according to the SDS compendium (ver 2.1) for the 7900HT Applied Biosystems Sequence Detector as described previously (Stirzaker, supra). Either immunoprecipitated DNA, no-antibody control or input chromatin were used in each PCR and the PCRs were set up in triplicate. Standard deviation was calculated using the Comparative method (ABI PRISM 7700 Sequence Detection System User Bulletin #2, 1997 (P/N 4303859). For each sample an average CT value was obtained for immunoprecipitated material and for the input chromatin. The difference in CT values (delta CT) reflects the difference in the amount of material that was immunoprecipitated relative to the amount of input (ABI PRISM 7700 Sequence Detection system User Bulletin #2, 1997 (P/N 4303859).

5.2 Results

To determine if chromatin modification was associated with the suppression of all the genes across the entire band in cancer, regardless of the DNA methylation status, ChIP (chromatin immunoprecipitation) analysis and real-time PCR was performed. This analysis quantitates, for example, the level of methylated K9-H3 in the HCT116 cells or the level of se-acetylation of histones in cells, before and after treatment with 5AzaC and TSA (FIG. 17). p21 was also used as a control gene for the ChIP assays, because it's promoter is unmethylated and is suppressed in HCT116 cells, but activated substantially after TSA treatment.

Figure 17A:
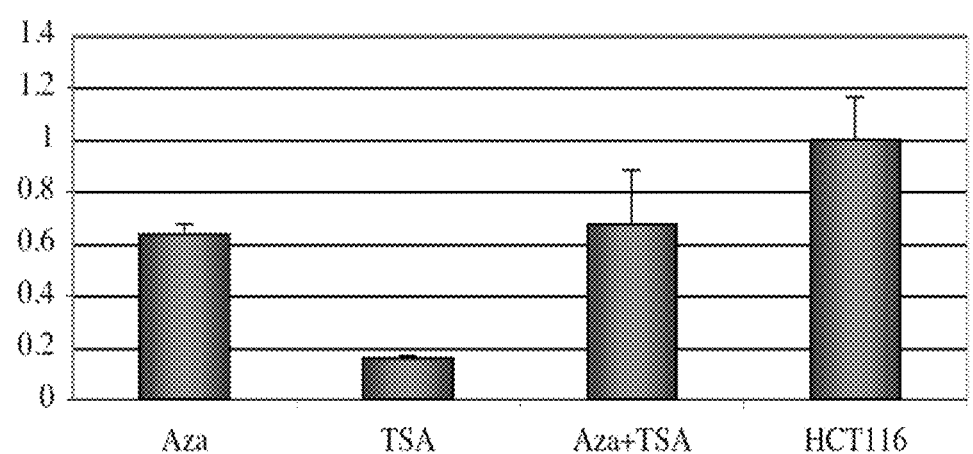
FIG. 17a is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for a control gene, p21.
Figure 17B:
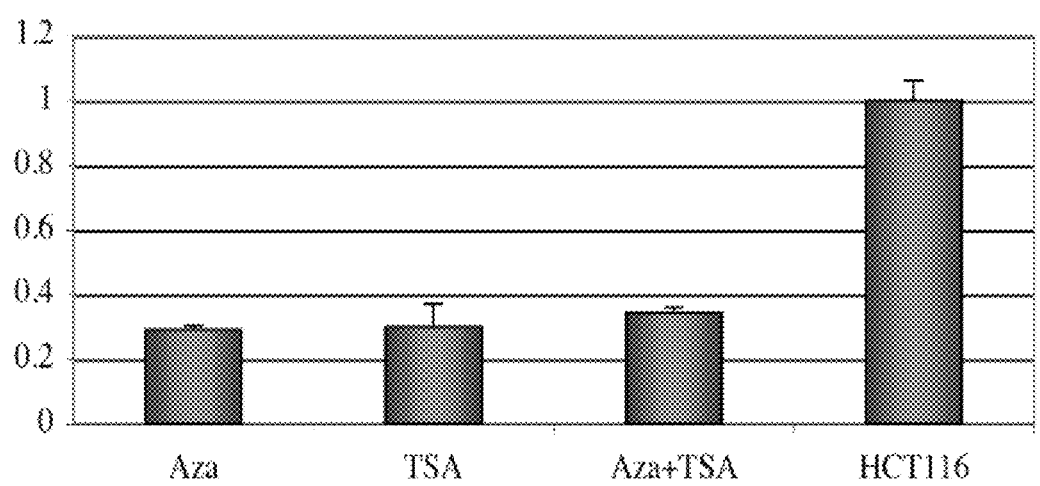
FIG. 17b is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for EN1.
Figure 17C:
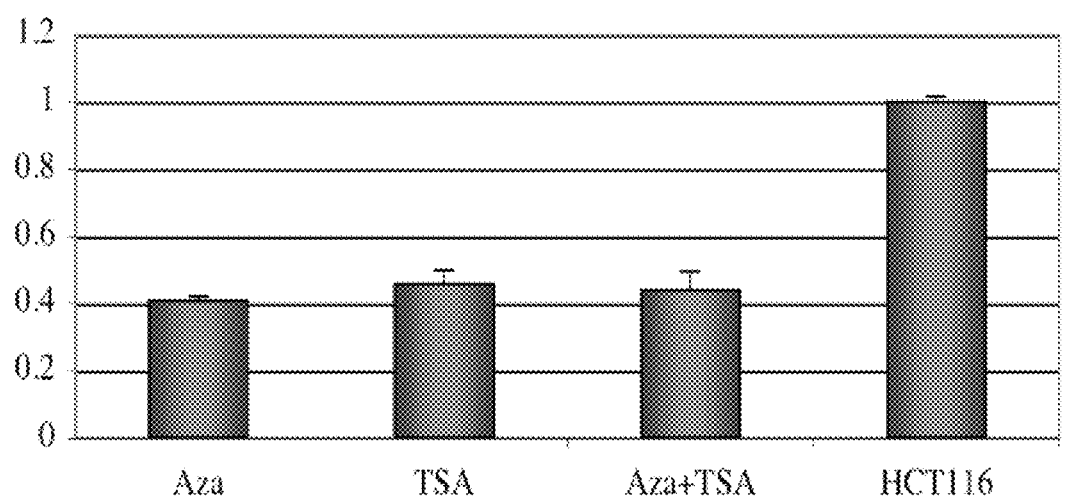
FIG. 17c is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for SCTR.
Figure 17D:
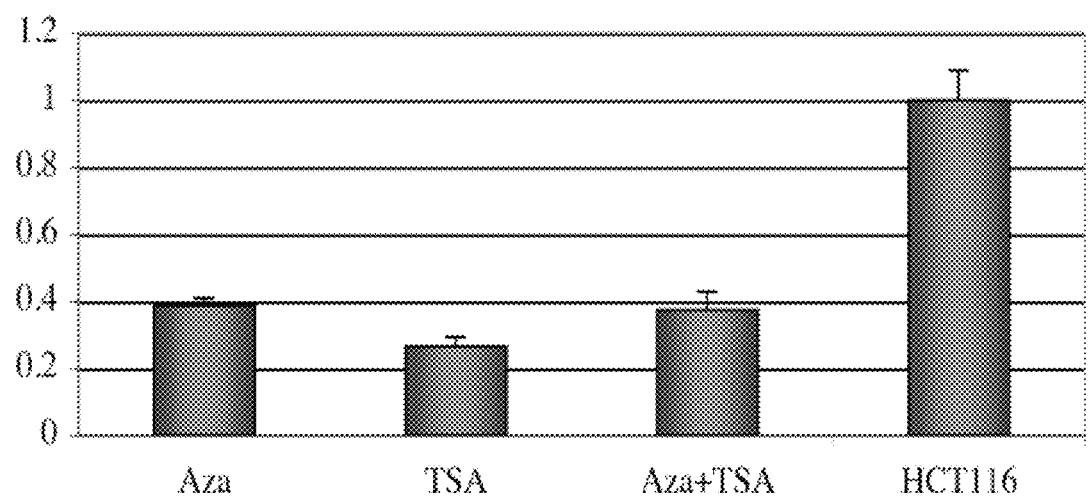
FIG. 17d is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for INHBB.

Following TSA treatment, there was substantial demethylation of the H3-K9 histones that are associated with the p21 CpG island promoter region (FIG. 17a). Demethylation of the H3-K9 histones also occurred after 5AzaC and a combination of TSA and 5AzaC treatments and the level of histone demethylation inversely correlated with the level of p21 gene expression.

Figure 17E:
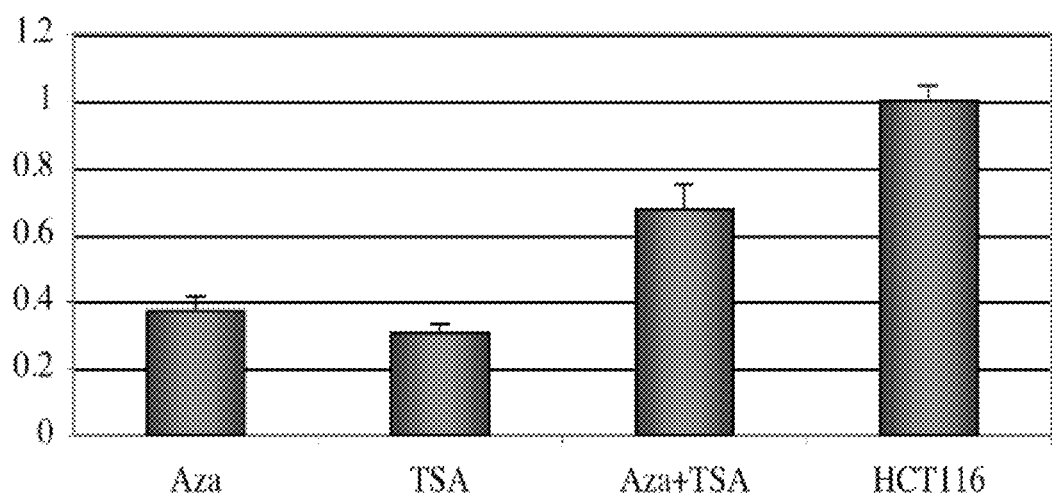
FIG. 17e is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for MARCO.
Figure 17F:
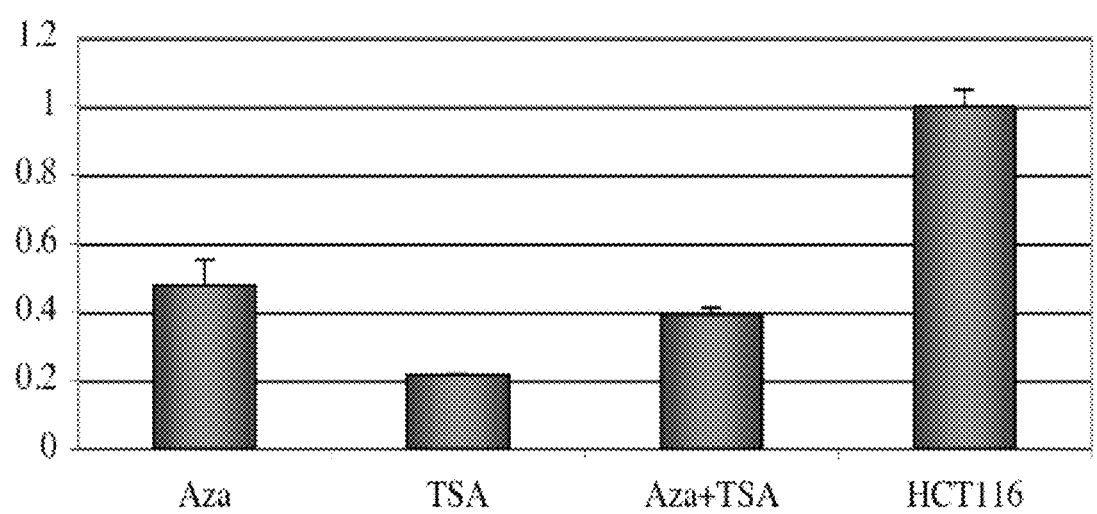
FIG. 17f is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for GLI2.
Figure 17G:
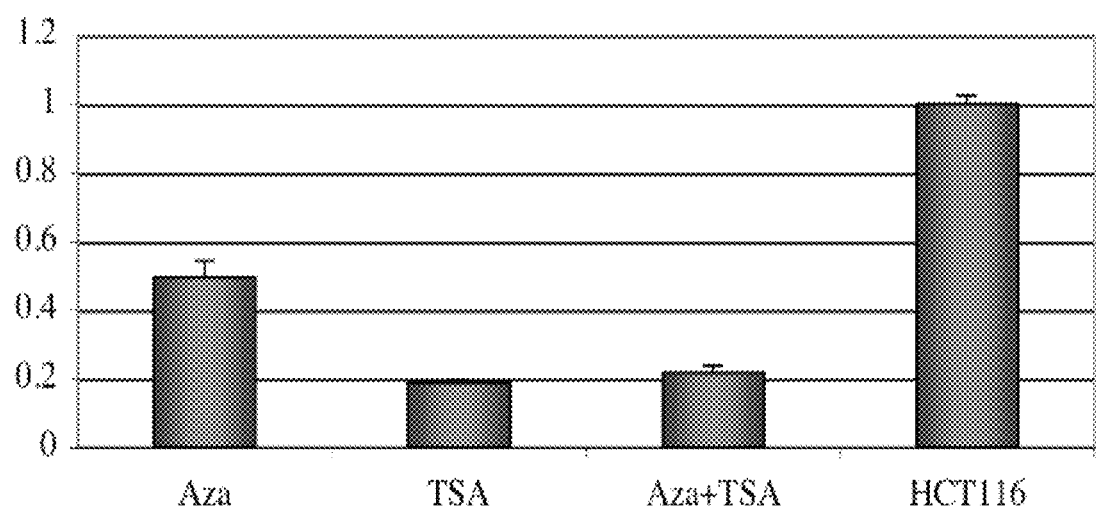
FIG. 17g is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for DDX18.
Figure 17H:
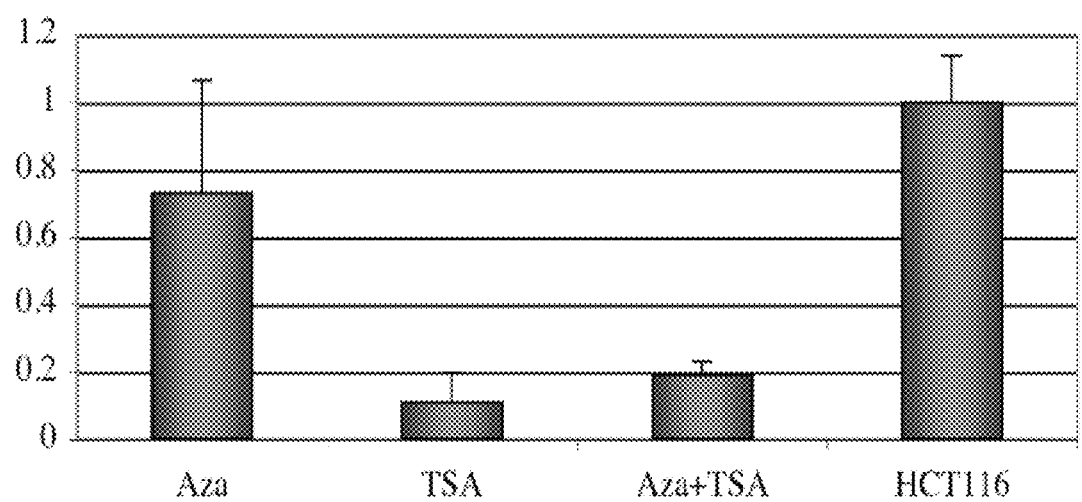
FIG. 17h is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for INSIG2.
Figure 17I:
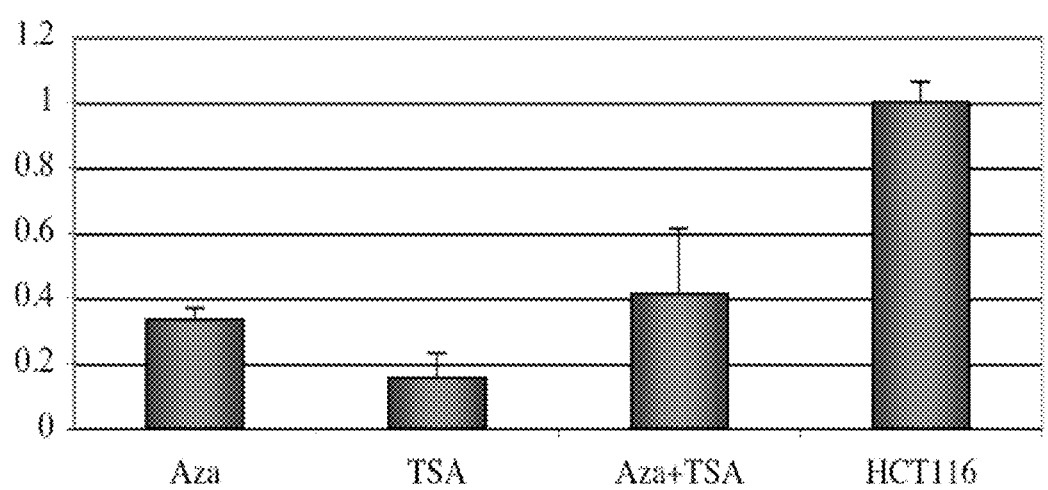
FIG. 17i is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for PTPN.
Figure 17J:
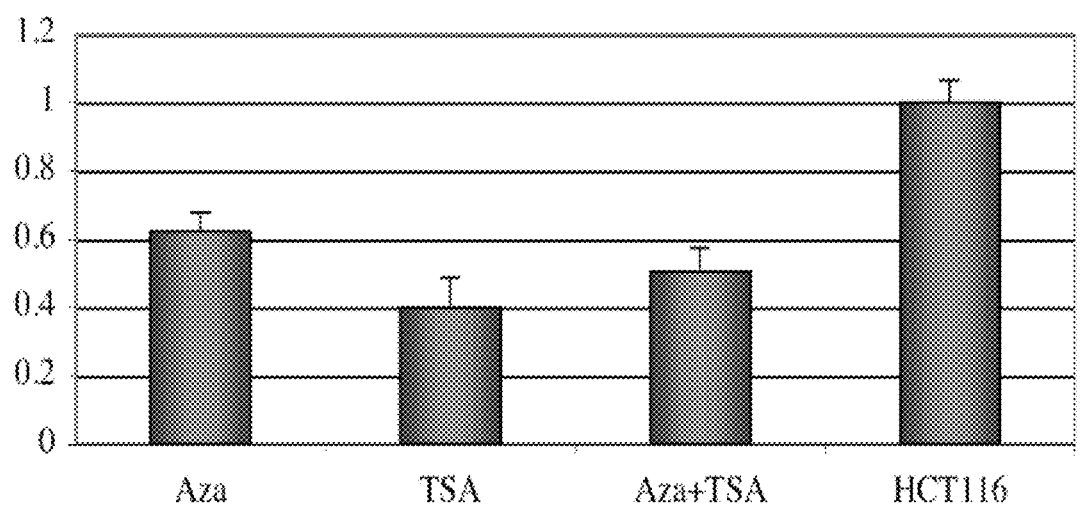
FIG. 17j is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for RALBB.
Figure 17K:
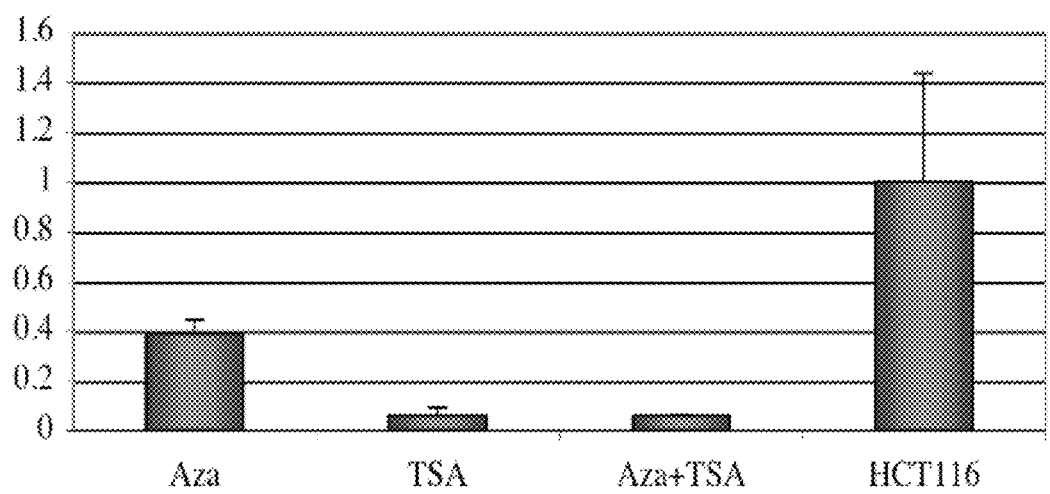
FIG. 17k is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-dimethylated lys 9 Histone 3 antibody. The amount of target that was immunoprecipitated was quantified by Real-Time PCR, and the amount of immunoprecipitated target DNA is calculated as a ratio of immunoprecipitated DNA to the total amount of input DNA used for the immunoprecipitation. All the results in the graph are expressed relative to HCT116 untreated cells. The relative binding of dimethylated H3-K9 is shown for TSN.
Figure 18A:
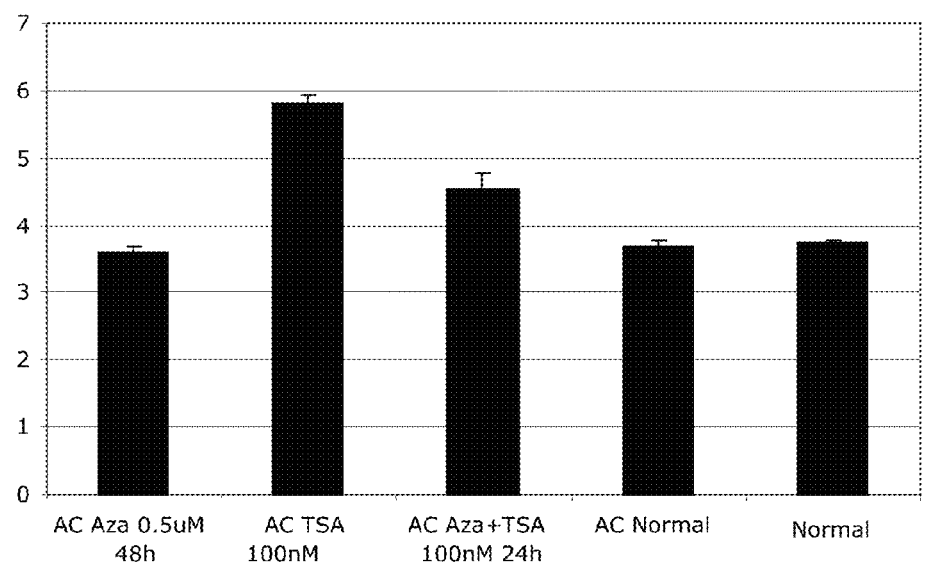
FIG. 18a is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for the control gene p21.
Figure 18B:
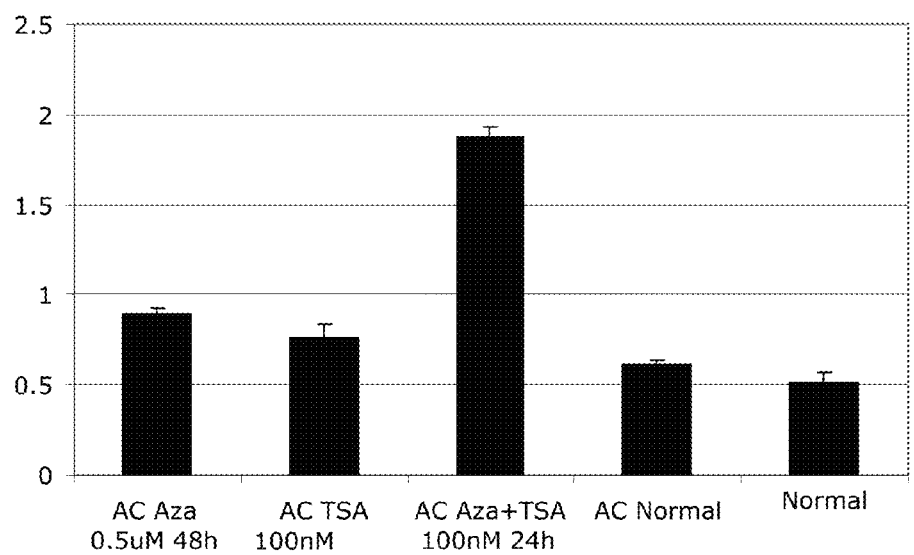
FIG. 18b is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for EN1.
Figure 18C:
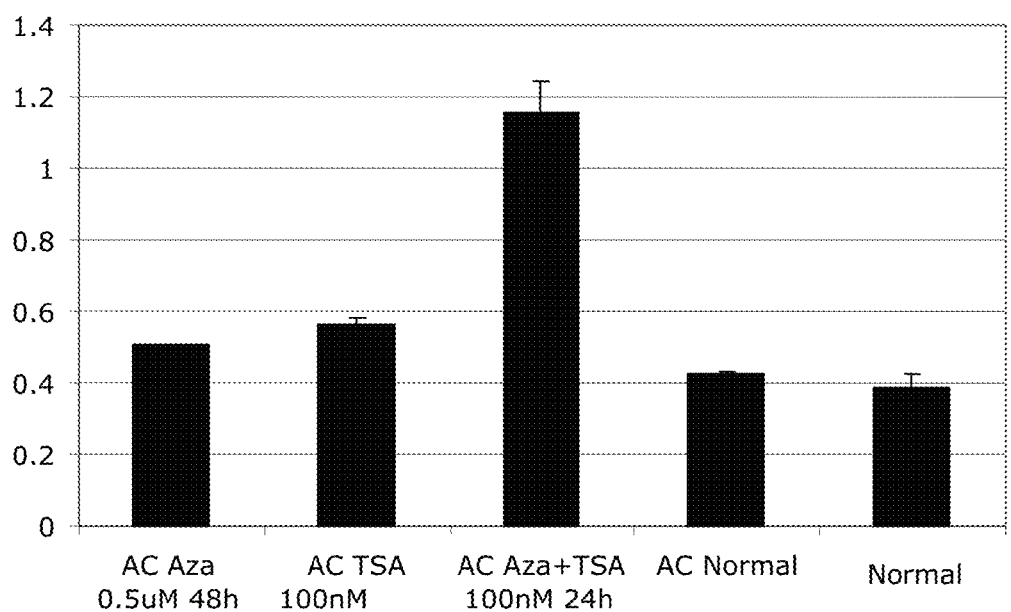
FIG. 18c is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for SCTR.
Figure 18D:
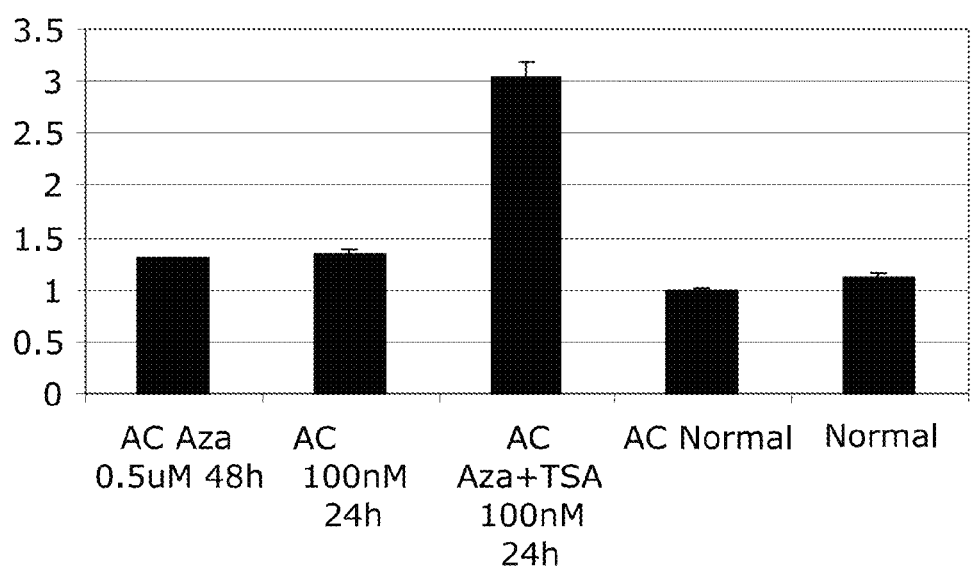
FIG. 18d is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for INHBB.
Figure 18E:
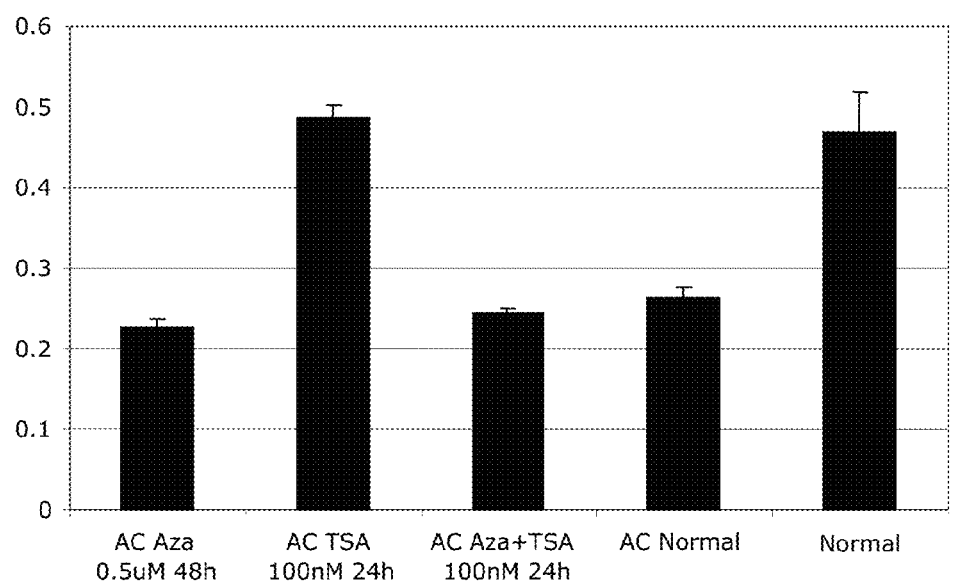
FIG. 18e is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for MARCO.
Figure 18F:
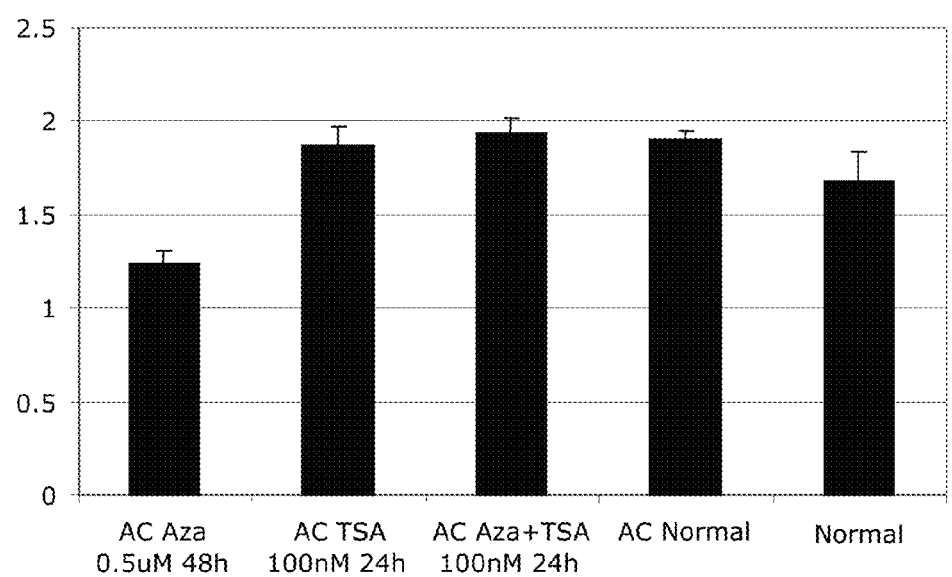
FIG. 18f is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for GLI2.
Figure 18G:
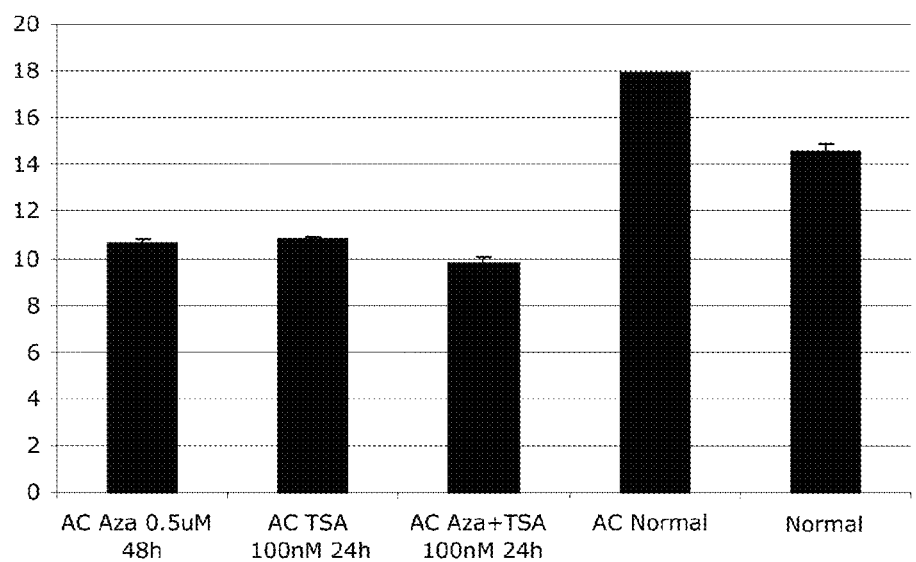
FIG. 18*g* is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for DDX18.
Figure 18H:
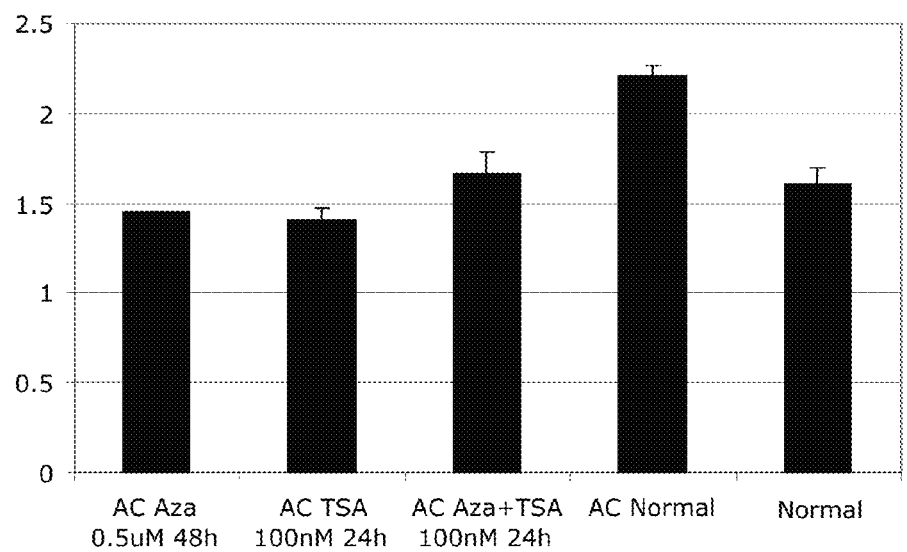
FIG. 18*h* is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for INSIG2.
Figure 18I:
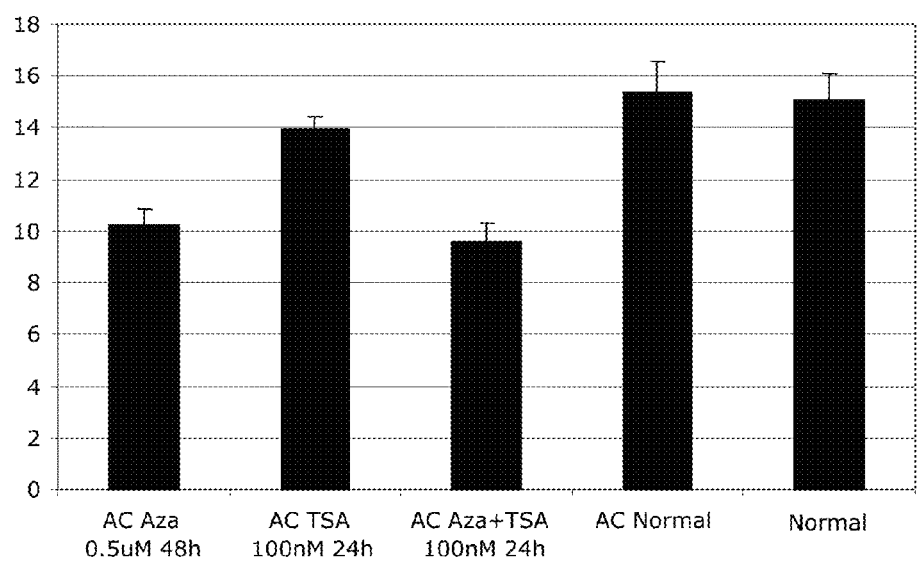
FIG. 18*i* is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for PTPN.
Figure 18J:
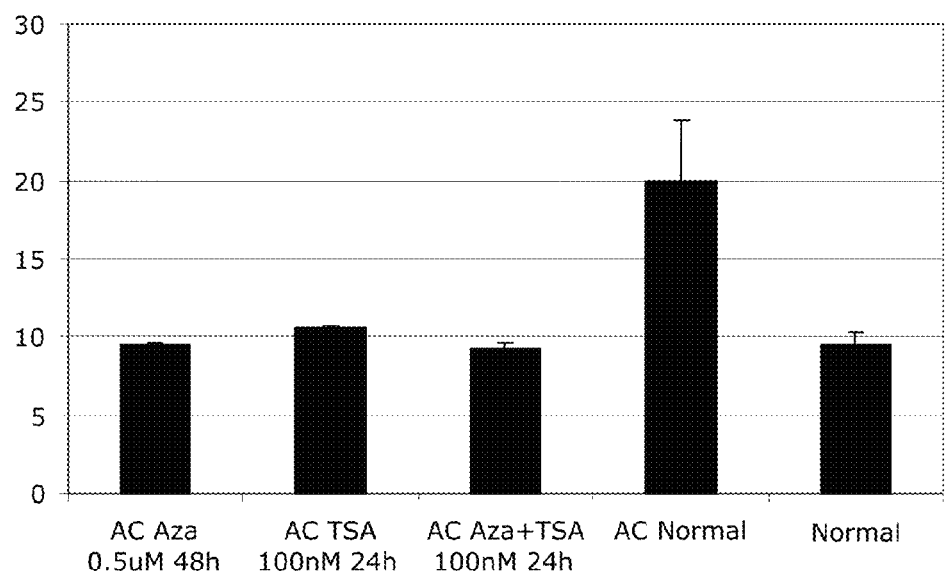
FIG. 18*j* is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for RALBB.
Figure 18K:
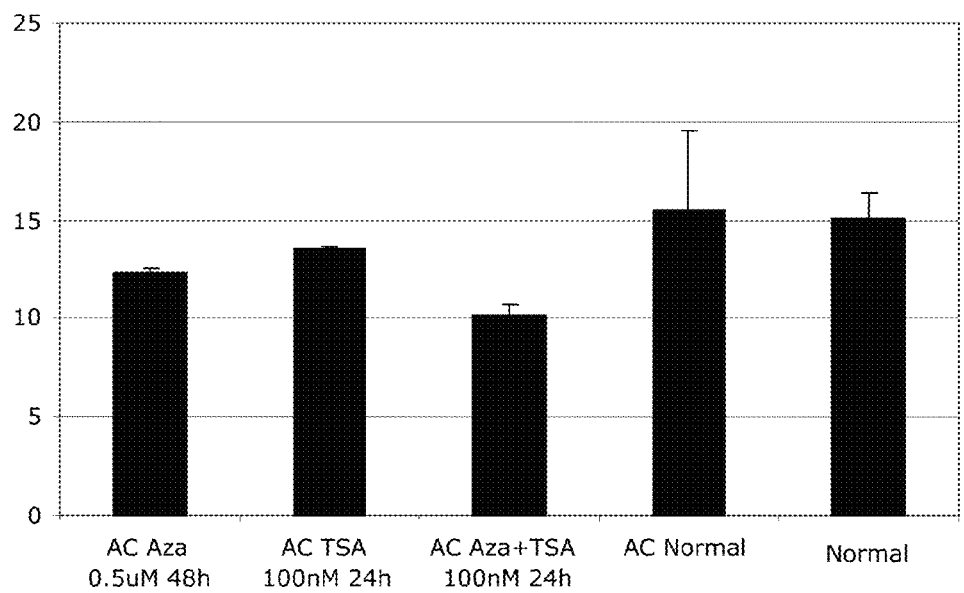
FIG. 18*k* is a graphical representation showing results of a chromatin immunoprecipitation (ChIP) assay. Chromatin from HCT116 cells that were either untreated, or treated with Aza-2' deoxycytidine (Aza), TSA or a combination of TSA and 5-Aza-2' deoxycytidine (Aza/TSA) was immunoprecipitated with an anti-acetylated histone antibody. The amount of target that was immunoprecipitated was quantified by real-Time PCR, and the amount of immunoprecipitated target DNA was calculated as a ratio of immunoprecipitated DNA to the total amount of input DNA used for the immunoprecipitation. All the results in the graph are expressed relative to HCT116 untreated cells. The relative binding is shown for TSN.

The binding of methylated H3-K9 histones to the genes in the three DNA methylated regions across 2q14.2. Methylated K9-H3 histones were bound to the promoter region of each of the DNA methylated CpG island associated genes (EN1, SCTR and INHBB) (FIGS. 17b, c and d) and methylated 3'CpG island (GLI2) the methylated non-CpG island genes (MARCO) (FIGS. 17e and f). Moreover, binding was reduced by treatment with 5Aza and TSA alone or in combination. These data indicate that there is a correlation between demethylation of the DNA and demethylation of the associated H3-K9 histones and this epigenetic change correlated with elevated gene transcription (as shown in FIG. 16b-f.

The binding of methylated H3-K9 histones on the unmethylated gene regions was also determined. Similar to the unmethylated control p21, after TSA treatment of the HCT 116 colon cancer cells, there was substantial demethylation of the H3-K9 histones associated with all the unmethylated genes (DDX18, INSIG2, PTPN, RALBB) that are suppressed across 2q14.2 relative to untreated cells (FIG. 17g-k). Furthermore, treatment with 5AzaC alone, or in combination with TSA, resulted in demethylation of the histones at H3-K9. These results indicate that the DNA linked to Chromosome position 2q14.2 in the cancer cells is associated with dimethylation of the H3-K9 residue of the associated chromatin, regardless of the DNA methylation status of individual genes. Without being bound by theory or mode of action, these results indicate that long-range genomic gene suppression across the 4 Mb DNA region, encompassing the entire 14.2q band on chromosome 2, appears to be associated with methylation of the histones regardless of the DNA methylation status.

Increased H3-K9 acetylation was observed following treatment with TSA and/or a combination of TSA/5AzaC for genes that were hypermethylated in HCT116 cells (see FIG. 18).

EXAMPLE 6

Hypermethylation of a Region of Chromosome 2 in Breast Cancer and Prostate Cancer Cell Lines Using the methods essentially as described in Example 2 the methylation of a number of CpG rich regions within Chromosome 2 (between about map position 2q14.1 and about map position 2q14.3) was determined in a number of cell models of prostate cancer and breast cancer. In particular, the cell models assessed were the breast cancer cell lines T47D, MDA MB453, MDA MB 468, SKBR3, KPL1, MDA MB 231, DU4475, MCF-7, MDA MB 157 and MCF-10A and the prostate cancer cell lines LNCaP and DU145. As shown in FIG. 19, the majority of these cell lines showed hypermethylation in a number of CpG rich regions. A summary of some of these data are set forth in Table 4.

TABLE 4

Methylation of several CpG islands in breast and prostate cancer cell lines

| CELL LINE | CpG 128 | SCTR |
|---|---|---|
| Breast | | |
| T47D | + | + |
| MDA MB 453 | + | + |
| MDA MB 468 | | + |
| SKBR3 | | |
| KPL1 | + | + |
| MDA MB 231 | + | ? |
| DU4475 | | + |
| MCF-7 | + | + |
| MDA MB 157 | | ? |
| MCF-10A | + | + |
| Prostate | | |
| LNCaP | + | + |
| DU145 | + | + |

EXAMPLE 7

Pyrosequencing of the Z Fragment in Nucleic Acid from Cancer Subjects

Genomic DNA is isolated from the patient and cell line samples described in Examples 1 and 6 using standard methods known in the art.

Sodium bisulfite conversion of while genomic DNA is performed essentially as described in Olek et al., Nucl. Acids Res., 24:5064-5066, 1996, with slight modifications according to Eads et al., Nucl. Acids Res. 28: e32, 2000. Briefly, 250 ng of genomic DNA is denatured at 95° C. for 10 min, followed by incubation in 0.3M NaOH solution at 42° C. for 15 min. DNA and 10 µl of 4% low melt agarose (Seaplaque; FMC Bioproducts, Rockland, Me., USA) are mixed, and a single bead with a volume of 20 µl is formed in prechilled mineral oil. Bisulfite conversion is performed with a 5M sodium bisulfite solution at 50° C. for 14 hours, under exclusion of light. TE-buffer (pH 8) is then used for washing the bead several times. Desulfonation is performed with 0.2M NaOH for 15 minutes and repeated. The final wash is neutralized with 1M HCl followed by washing with TE. To amplify by PCR, the agarose beads are diluted with $H_2O$.

Bisulfite converted genomic DNA is then amplified using PCR with primers comprising the sequence set forth in SEQ ID NOs: 91 and 92. One primer was biotinylated in one reaction, and the other in another reaction. Following amplification unincorporated primers and dNTPs are separated from the amplification product using the PCR purification kit of Qiagen.

Single stranded PCR products are required for pyrosequencing. The biotinylated fragments are immobilized on streptavidin-coated Dynabeads M-280 Streptavidin (Dynal AS, Oslo, Norway), according to the protocol of the SNP reagent kit (Pyrosequencing, Uppsala, Sweden). Following incubation for 15 min at 65° C., the reactions are transferred to a PSQ-96 well reaction plate (Pyrosequencing) and denatured with 0.5M NaOH for 10 min. Single stranded PCR fragments are captured with a magnet, transferred to a PSQ 96-well plate and washed once with annealing buffer (Pyrosequencing). Following another transfer, the single stranded PCR fragments produced using a primer comprising the sequence set forth in SEQ ID NO: 91 are hybridized with a primer comprising one of the sequences set forth in SEQ ID NOs: 223 to 228. Single stranded PCR fragments produced using a primer comprising the sequence set forth in SEQ ID NO: 92 are hybridized with a primer comprising one of the sequences set forth in SEQ ID NOs: 223 to 234. Hybridization is performed with 10 pmol of primer in annealing buffer (Pyrosequencing) at 80° C. for 2 min then room temperature. The sequencing reaction is performed at 25° C. in a column of 40 µl of annealing buffer on the automated PSQ 96 System from Pyrosequencing. Enzyme and substrate from the SNP reagent kit are each dissolved in water. Each of the deoxynucleotides and the enzyme and substrate are then loaded into the sequencing cartridge. The order of the nucleotide dispensation is defined as C then T then G then A. Peak heights identified using the Pryoprogram are used to calculate the level of several CpG dinucleotides in the Z fragment in cancer subjects (e.g., % C=peak height C/(peak height C+peak height T)×100).

Using this method the level of methylation of several CpG dinucleotides is determined in cancer and control samples and used to diagnose cancerous samples.

EXAMPLE 8

Microarray Based Detection of Methylation

Bisulfite Treatment and PCR Amplification

Genomic DNA is isolated from the patient and cell line samples described in Examples 1 and 6 using standard methods known in the art.

Bisulfite treatment of genomic DNA is performed essentially as described in Example 7. Genomic DNA is digested with MssI (MBI Fermentas, St Leon-Rot, Germany) prior to modification by bisulfite. The previously studied CpG rich regions of Chromosome 2 are amplified using PCR essentially as describe in Example 2, however the primers used in the nested step include a Cy5 label at the 5', or non-extending, end to facilitate detection.

Microarray Production

Oligonucleotides with a C6-amino modification at the 5'-end are spotted with 4-fold redundancy on activated glass slides (Golub et al., *Science*, 286: 531-537, 1999). For each analyzed CpG position two oligonucleotides, $N_{2-16}CGN_{2-16}$ and $N_{2-16}TGN_{2-16}$, reflecting the methylated and non-methylated status of the CpG dinucleotides, are spotted and immobilized on the glass array. The CpG dinucleotides used are selected from the regions CpG61, 20 Kb, Z fragment, CpG 104, CpG128, CpG 128, CpG48 and SCTR as described in Table 1 (SEQ ID NOs: 4, 6, 8, 9, 11, 12, 14 and 21, respectively). Oligonucleotides are designed such that they matched only the bisulfite-modified DNA fragments to exclude signals arising from incomplete bisulfite conversion. The oligonucleotide microarrays are hybridized with a combination of up to 56 Cy5-labelled PCR fragments essentially as described in Chen et al., *Nucleic Acids Res.*, 27, 389-395, 1999.

Hybridization conditions are selected to allow detection of the single nucleotide differences between the TG and CG variants. Log ratios for the two signals are calculated based on comparison of intensity of the fluorescent signals. Sensitivity for detection of methylation changes is determined using artificially up- and down-methylated DNA fragments mixed at different ratios. For each of these mixtures, a series of experiments is conducted to define the range of CG:TG ratios that corresponds to varying degrees of methylation at each of the CpG sites tested. These data determine the degree of methylation change detectable by the assay. Accordingly, by using log ratio of the CG and TG the differential methylation between samples is determined.

Subsequently, the fluorescent images of the hybridized slides are obtained using a GenePix 4000 microarray scanner (Axon Instruments). Hybridization experiments are repeated at least three times for each sample.

This method is then used to determine the degree of methylation at each site in the previously described samples.

Statistical Methods

For class prediction a support vector machine (SVM) on a set of selected CpG sites is used. First the CpG sites are ranked for a given separation task by the significance of the difference between the two class means. The significance of each CpG is estimated by a two sample t-test (Mendenhall, W. and Sincich, T. (1995) *Statistics for Engineering and the Sciences*. Prentice-Hall, N.J.). Then a SVM is trained on the most significant CpG positions, where the optimal number of CpG sites depends on the complexity of the separation task. Generalisation performance is estimated by averaging over 50 cross-validation runs on randomly permutated samples partitioned into eight groups, i.e., selection of the most significant CpG sites and training of the SVM are performed on training sets of seven groups and the eighth group is used as an independent test set. The significance value for the class prediction represents the probability that the SVM classifies the same data points at least as well as observed if the tissue classes are assigned randomly. The significance value is estimated by sampling the distribution of cross-validation errors over 50 random shuffles of the labels, keeping the initial class priors. A Gaussian distribution is fitted to these 50 error estimates and used to calculate the probability of random generation of separations at least as good as the observed one.

A number of colon cancer samples and matched control samples are used as a training group to determine the most informative CpG methylation sites for the diagnosis of cancer. These sites are then used to classify each of the colon cancer cell lines. Using this technique the minimum number of informative CpG dinucleotide methylation sites required to diagnose colon cancer is determined.

Expanding the study, the results determined using colon cancer samples are used to classify the prostate and breast cancer cell lines according to methylation patterns. Using these data the minimum number of informative CpG dinucleotide methylation sites required to diagnose a variety of cancers is determined.

EXAMPLE 9

Methylation of a Region of Chromosome 2 in Ovarian Cancer 9.1 Samples

The degree of methylation of CpG islands associated with EN1, INHBB and SCTR was determined using head-loop PCR and/or heat-dissociation real-time PCR analysis in a number of ovarian cancer samples. In particular, nucleic acid was isolated from the ovarian cancer cell lines SW626, OVCA420, A2780, TOV21G, IGROV1, SKOV3, OV90, TOV112 and HOSE6-3. Nucleic acid was also isolated from 37 ovarian tumors.

All nuclei acids samples were isolated and treated with bisulfate as described herein, for example, in Example 2.

9.1 Analysis of Methylation of Nucleic Acid

Melting curve analysis and sequencing analysis of methylated nucleic acid was performed essentially as described in Example 2. In this respect heat dissociation PCR was performed using primers comprising the nucleotide sequence set forth in SEQ ID NOs: 260, 261, 264, 265, 268, 269. Reactions were cycled under the following conditions: 95° C. for 4 mins, [95° C. for 45 sec, 50° C. for 1.5 min, 72° C. for 2 mins] for 5 cycles and [95° C. for 1.5 mins, 52° C. for 1.5 mins, 72° C. for 4 mins] for 20 cycles and 72° C. for 4 mins. Reactions were then performed with the primers comprising nucleotide sequences set forth in SEQ ID NOs: 262, 263, 266, 267, 270, 271 as follows 95° C. for 4 mins, [95° C. for 45 sec, 52° C. for 1.5 min, 72° C. for 2 min] for 20 cycles and [95° C. for 45 sec, 54° C. for 1.5 min, 72° C. for 1.5 min] for 23 cycles and [95° C. for 15 sec, 60° C. for 15 sec and 95° C. for 15 sec].

Headloop PCR reactions were performed essentially as described in Rand et al., *Nucleic Acids Research* 33:e127, 2005. Generally Headloop PCR is used to amplify two sequences that are closely related (e.g., that differ only at specific residues). The reverse primer used to amplify nucleic acid matches both sequences exactly, as does a regio of a forward primer used to initially amplify nucleic acid. The forward primer additionally comprises a 5' extension that is complementary to a region within one of the sequences to be amplified (e.g., a sequence comprising mutations caused by bisulfite treatment). When a copy of the product of first round synthesis produced using the forward primer is produced, the 5' extension is incorporated into the second strand product. After denaturation the incorporated 3' tail extension is able to loop back and anneal to its complementary region, and be extended to form a hairpin structure. Since intramolecular annealing is known to be very rapid, the extension re-anneals to its complementary region after denaturation and no longer provides a template for further amplification. However, in the case of a sequence that does not comprise the mutated sites (e.g., that is complementary to a methylated nucleic acid), mismatch(es) to the equivalent region limit self-priming to form a hairpin and the DNA is able to undergo further amplification with the forward and reverse primers. If the forward primer is chosen as the base for a Headloop primer, the sequence of the 5' extension on the primer is the reverse complement of the target top strand sequence. If the Headloop primer is based on the reverse primer the extension will comprise the sequence of the target region as directly read from the top strand.

Headloop primers were designed that hybridize to regions of the CpG islands associated with EN1 and SCTR described herein. A headloop extension is added to one primer for each amplification reaction. These headloop extension is designed such that after the incorporation of the primer into the PCR product the extension loops back, anneals to the target region of nucleic acid complementary to unmethylated nucleic acid, priming to form an extended hairpin molecule. The target region includes a number of CpG sites that are methylated in cancer, defining the 3' priming base for headloop extension to form a hairpin structure. Accordingly, methylated nucleic acid is preferentially amplified using these primers.

Headloop primers comprise the nucleotide sequences set forth in SEQ ID NOs: 272-275. PCR reactions were cycled as follows, 95° C. for 2 min, [95° C. for 15 sec, 60° C. for 1 min] for 60 cycles and denatured by cycling at 95° C. for 15 sec, 60° C. for 15 sec, 95° C. for 15 sec.

9.2 Results

As shown in FIG. 20a, heat dissociation real-time PCR and headloop PCR generally detected methylated DNA in similar samples. These results indicate that either or both techniques are useful for the analysis of the methylation status of DNA.

Furthermore, as shown in FIG. 20a, at least one of the CpG islands analyzed are methylated in approximately 88% of ovarian cancer cell lines tested. For example, EN1 is methylated in 56% (heat dissociation real-time PCR) or 67% (headloop PCR) of samples tested, INHBB is methylated in 44% (heat dissociation real-time PCR) of samples tested and SCTR is methylated in 56% (heat dissociation real-time PCR) or 44% (headloop PCR) of samples tested. These results indicate that a considerable proportion of ovarian cancer cell lines methylate at least one, and in some cases several of the sites tested.

Extending these studies, the methylation status of CpG dinucleotides in CpG islands associated with EN1 and SCTR was analyzed in 37 ovarian cancer tumors using headloop PCR. As shown in FIG. 20b approximately 59% of tumors tested methylated CpG dinucleotides in a CpG island associated with EN1. Approximately 30% of tumors tested methylated CpG dinucleotides in a CpG island associated with SCTR. However, approximately 70% of ovarian tumors tested methylated CpG dinucleotides in at least one of the sites tested.

EXAMPLE 10

Headloop PCR Analysis of Methylation of a Region of Chromosome 2 in Prostate Cancer and Breast Cancer Headloop PCR analysis and heat-dissociation real-time PCR analysis were performed essentially as described hereinabove.

Figure 21:
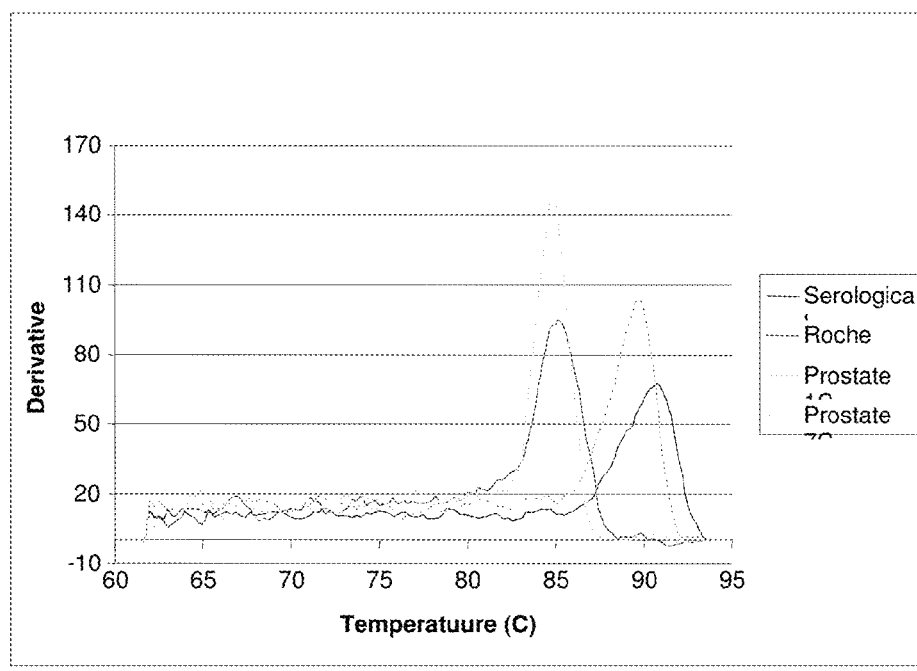
FIG. 21 is a graphical representation showing results of a headloop PCR analysis of the CpG island associated with the CpG island associated with En1 using control nucleic acid (labeled as Serological and Roche) or from prostate cancer samples (labeled Prostate 1 and Prostate 7). The symbol "U" indicates unmethylated DNA and the symbol "M" indicated methylated DNA.

Headloop PCR analysis was used to determine the methylation of CpG islands associated with EN1 and SCTR in the breast cancer cell lines T47D, MDAMB453, MDAMB468, SKBR3, MDAMB231, MCF-10A, MDAMB157 and MCF-7 and in the prostate cancer cell lines LNCaP and DU145. Results of this analysis are shown in FIG. 21. As shown in FIG. 22a CpG dinucleotides in a Cpg island associated with EN1 were methylated in approximately 70% of cell lines tested. CpG dinucleotides in a Cpg island associated with SCTR were methylated in approximately 80% of cell lines tested. Furthermore, approximately 91% of cell lines tested methylated at least one of the CpG sites tested.

These studies were then extended to analyze the methylation status of 12 prostate cancer samples and matched controls. In this case, headloop PCR analysis was used to determine the methylation of CpG islands associated with EN1 and SCTR. Heat-dissociation real-time PCR analysis was used to analyze the methylation status of CpG islands associated with EN1 and SCTR. As shown in FIG. 22b, 17% (detected using heat-dissociation real-time PCR analysis) or 25% (detected using headloop PCR) of samples methylated CpG dinucleotides in a CpG island associated with EN1. 50% (detected using heat-dissociation real-time PCR analysis) or 33% (detected using headloop PCR) of samples methylated CpG dinucleotides in a CpG island associated with SCTR. 91% of samples methylated at least one of the CpG islands tested to date.

To determine the level of methylation of the region of within Chromosome 2 between about map position 2q14.1 and about map position 2q14.3 in normal prostate tissue, control samples were treated with bisulfite, amplified using PCR, cloned and sequenced, essentially as described hereinabove. As shown in FIG. 22c, the majority of sites sequenced in the CpG islands EN-1 and SCTR are not methylated in normal prostate epithelium.

Furthermore, the methylation status of these nucleic acids was determined in 100 breast tumors. As shown in FIG. 22d, 66% (detected using heat-dissociation real-time PCR analysis) or 40% (detected using headloop PCR) of samples methylated CpG dinucleotides in a CpG island associated with EN1. 71% (detected using heat-dissociation real-time PCR analysis) or 63% (detected using headloop PCR) of samples methylated CpG dinucleotides in a CpG island associated with SCTR. Considering both of these sites, 78% of samples methylated at least one of the CpG islands tested to date.

To determine the level of methylation of the region of within Chromosome 2 between about map position 2q14.1 and about map position 2q14.3 in normal breast tissue, control samples were treated with bisulfite, amplified using PCR, cloned and sequenced, essentially as described hereinabove.

Figure 22E:
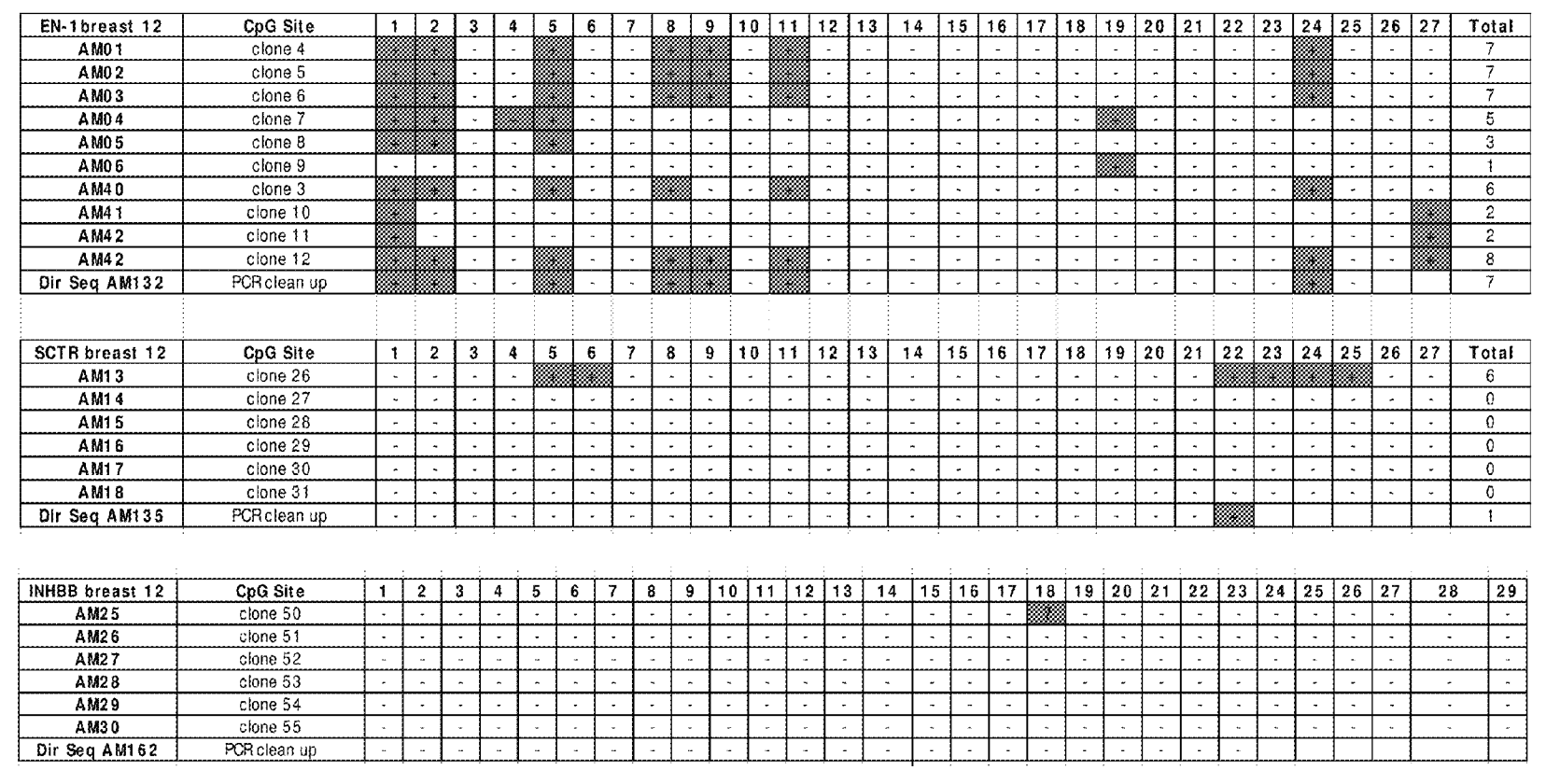

As shown in FIGS. 22e and f, the majority of sites sequenced in the CpG islands EN-1 and SCTR were not methylated in normal breast samples.

EXAMPLE 11

Methylation of a Region of Chromosome 2 in Pancreatic Cancer Cells

Headloop PCR analysis and heat-dissociation real-time PCR analysis were performed essentially as described hereinabove.

Headloop PCR analysis and heat-dissociation real-time PCR analysis were used to determine the methylation of CpG islands associated with EN1, INHBB and SCTR in the pancreatic cancer cell lines PANC-1, ASPC-1, BXPC-3, MIA-PACA-2, CaPan-2 and HPAC. As shown in FIG. 23, CpG dinucleotides in a Cpg island associated with EN1 were methylated in approximately 83% of cell lines tested using heat-dissociation real-time PCR analysis and 67% of cell lines tested using headloop PCR. CpG dinucleotides in a CpG island associated with INHBB were methylated in approximately 50% of cell lines tested using heat-dissociation real-time PCR analysis. CpG dinucleotides in a Cpg island associated with SCTR were methylated in approximately 33% of cell lines tested using heat-dissociation real-time PCR analysis and 50% of cell lines tested using headloop PCR. Clearly, these results demonstrate that pancreatic cancer cell lines methylate nucleic acid within Chromosome 2 (between about map position 2q14.1 and about map position 2q14.3).

Furthermore, approximately 100% of cell lines tested methylated at least one of the CpG sites tested.

EXAMPLE 12

Figure 24:
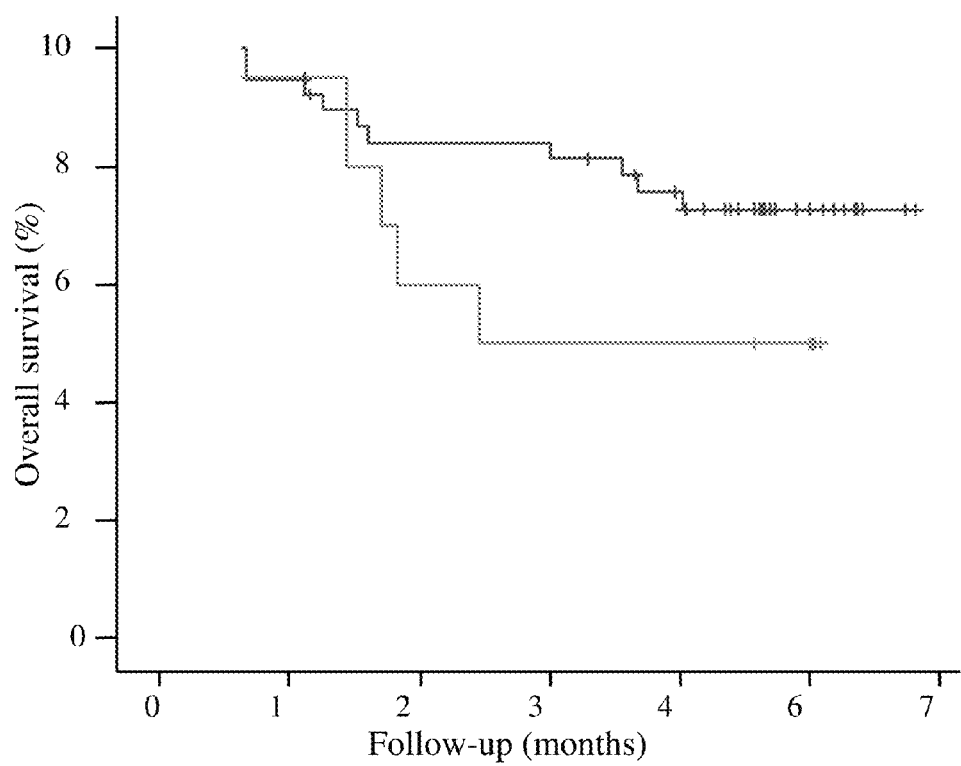
FIG. 24 is a graphical representation showing Kaplan-Meier survival curves for subjects suffering from colorectal cancer. The dark line indicates the survival of subjects suffering from colorectal cancer in which the CpG island associated with SCTR is methylated. The light line indicates the survival of subjects suffering from colorectal cancer in which the CpG island associated with SCTR is not methylated.

Methylation of a CpG Island Associated with SCTR is Indicative of the Likelihood of Survival Using patient survival data for subjects suffering from colorectal cancer the relationship between methylation of a CpG island and likelihood of survival was determined. In particular, Kaplan-Meier survival curves were produced showing patient survival relative to the methylation status of the CpG island associated with SCTR. As shown in FIG. 24 subjects having the CpG island methylated had an increased likelihood of survival compared to subjects that did not methylate the CpG island. Accordingly, these results indicate that the methylation status of nucleic acids within Chromosome 2 (between about map position 2q14.1 and about map position 2q14.3) is indicative of the likelihood of survival of a subject suffering from a cancer.

We claim:

1. A process for diagnosing a cancer, determining a prognosis for a subject suffering from a cancer or determining the efficacy of treatment of a cancer comprising:
   (i) identifying and/or detecting enhanced methylation of a nucleic acid positioned within Chromosome 2 from about map position 2q14.1 to about map position 2q14.3 in a sample from a subject by performing a method comprising:
      (a) treating the sample with an amount of a compound that selectively mutates a non-methylated cytosine residue under conditions sufficient to induce mutagenesis thereby producing a mutated nucleic acid;
      (b) performing an amplification reaction with nucleic acid primers comprising a nucleotide sequence that is complementary to a sequence flanking or adjacent to a methylated cytosine residue or mutated residue at an equivalent position in non-methylated nucleic acid, wherein said methylated cytosine residue or said mutated residue is within a nucleic acid comprising a nucleotide sequence selected from the group consisting of SEQ ID NO: 11, SEQ ID NO: 21 and SEQ ID NO: 25; and
      (c) identifying and/or detecting the temperature at which the amplified nucleic acid produced at (b) denatures, wherein the temperature at which the nucleic acid denatures is indicative of the presence of a methylated cytosine residue or a mutated residue and the level of methylation of said nucleic acid; and
   (ii) comparing the level of methylation of the nucleic acid at (i) to the degree of methylation in a non-cancerous cell, wherein an enhanced level methylation in the nucleic acid at (i) compared to the level of methylation in the non-cancerous cell is indicative of enhanced methylation in the sample from the subject and cancer or a predisposition therefor.

2. A process for diagnosing a cancer, determining a prognosis for a subject suffering from a cancer or determining the efficacy of treatment of a cancer comprising:
   (i) identifying and/or detecting enhanced methylation of a nucleic acid positioned within Chromosome 2 from about map position 2q14.1 to about map position 2q14.3 in a sample from a subject by performing a method comprising:
      (a) treating said sample with an amount of a compound that selectively mutates a non-methylated cytosine residue under conditions sufficient to induce mutagenesis thereby producing a mutated nucleic acid;
      (b) performing an amplification reaction with nucleic acid primers comprising a nucleotide sequence that is complementary to a sequence flanking or adjacent to a methylated cytosine residue or mutated residue at an equivalent position in non-methylated nucleic acid, wherein at least one of said probes or primers comprises a region that selectively hybridizes to an amplicon comprising a nucleotide sequence complementary to the mutated residue produced in the amplification reaction thereby forming a hairpin nucleic acid and preventing further amplification of said nucleic acid, and wherein said methylated cytosine residue or said mutated residue is within a nucleic acid comprising a nucleotide sequence set forth in SEQ ID NO: 11 or SEQ ID NO: 21; and
      (c) identifying and/or detecting the amplified nucleic acid, wherein the detection of said amplified nucleic acid is indicative of the presence of a methylated cytosine residue or a mutated residue and the level of methylation of said nucleic acid; and
   (ii) comparing the level of methylation of the nucleic acid at (i) to the level of methylation in a non-cancerous sample, wherein an enhanced level of methylation in the nucleic acid at (i) compared to the level of methylation in the non-cancerous sample is indicative of enhanced methylation in the sample from the subject and cancer or a predisposition therefor.

3. The method according to claim 1 or claim 2 wherein the cancer is selected from the group consisting of prostate cancer, breast cancer, colorectal cancer, pancreatic cancer, ovarian cancer and combinations thereof.

4. The method according to claim 1 or claim 2 wherein the sample comprises a body fluid or a derivative of a body fluid or a body secretion.

5. The method according to claim 4 wherein the body fluid is selected from the group consisting of whole blood, urine, saliva, breast milk, pleural fluid, sweat, tears and mixtures thereof.

6. A process for diagnosing a cancer, determining a prognosis for a subject suffering from a cancer or determining the efficacy of treatment of a cancer comprising:
   (i) identifying and/or detecting enhanced methylation of a nucleic acid positioned within Chromosome 2 from about map position 2q14.1 to about map position 2q14.3 in a sample from a subject by performing a method comprising:
      (a) treating the sample with an amount of a compound that selectively mutates a non-methylated cytosine residue under conditions sufficient to induce mutagenesis thereby producing a mutated nucleic acid;
      (b) performing an amplification reaction with nucleic acid primers comprising a nucleotide sequence that is complementary to a sequence flanking or adjacent to a methylated cytosine residue or mutated residue at an equivalent position in non-methylated nucleic acid, wherein said methylated cytosine residue or said mutated residue is within a nucleic acid comprising a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33; and
      (c) identifying and/or detecting the temperature at which the amplified nucleic acid produced at (b) denatures, wherein the temperature at which the nucleic acid denatures is indicative of the presence of a methylated cytosine residue or a mutated residue and the level of methylation of said nucleic acid; and
   (ii) comparing the level of methylation of the nucleic acid at (i) to the degree of methylation in a non-cancerous cell, wherein an enhanced level methylation in the nucleic acid at (i) compared to the level of methylation in the non-cancerous cell is indicative of enhanced methylation in the sample from the subject and cancer or a predisposition therefor.

7. A process for diagnosing a cancer, determining a prognosis for a subject suffering from a cancer or determining the efficacy of treatment of a cancer comprising:
   (i) identifying and/or detecting enhanced methylation of a nucleic acid positioned within Chromosome 2 from about map position 2q14.1 to about map position 2q14.3 in a sample from a subject by performing a method comprising:
      (a) treating said sample with an amount of a compound that selectively mutates a non-methylated cytosine residue under conditions sufficient to induce mutagenesis thereby producing a mutated nucleic acid;
      (b) performing an amplification reaction with nucleic acid primers comprising a nucleotide sequence that is complementary to a sequence flanking or adjacent to a methylated cytosine residue or mutated residue at an equivalent position in non-methylated nucleic acid, wherein at least one of said probes or primers comprises a region that selectively hybridizes to an amplicon comprising a nucleotide sequence complementary to the mutated residue produced in the amplification reaction thereby forming a hairpin nucleic acid and preventing further amplification of said nucleic acid, and wherein said methylated cytosine residue or said mutated residue is within a nucleic acid comprising a nucleotide sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33; and
      (c) identifying and/or detecting the amplified nucleic acid, wherein the detection of said amplified nucleic acid is indicative of the presence of a methylated cytosine residue or a mutated residue and the level of methylation of said nucleic acid; and
   (ii) comparing the level of methylation of the nucleic acid at (i) to the level of methylation in a non-cancerous sample, wherein an enhanced level of methylation in the nucleic acid at (i) compared to the level of methylation in the non-cancerous sample is indicative of enhanced methylation in the sample from the subject and cancer or a predisposition therefor.

8. A process for diagnosing a cancer, determining a prognosis for a subject suffering from a cancer or determining the efficacy of treatment of a cancer comprising:
   (i) identifying and/or detecting enhanced methylation of a nucleic acid positioned within Chromosome 2 from about map position 2q14.1 to about map position 2q14.3 in a sample from a subject by performing a method comprising:
      (a) treating the sample with an amount of a compound that selectively mutates a non-methylated cytosine residue under conditions sufficient to induce mutagenesis thereby producing a mutated nucleic acid;
      (b) performing an assay to determine a level of methylation of said nucleic acid, said assay comprising detecting one or more methylated cytosine residues within the nucleic acid and/or detecting one or more mutated residues at equivalent positions within the nucleic acid which is/are non-methylated, wherein the nucleic acid comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33;

(ii) comparing the level of methylation of the nucleic acid at (i) to the level of methylation of the nucleic acid in a non-cancerous cell, wherein an enhanced level methylation in the nucleic acid at (i) compared to the level of methylation in the nucleic acid in the non-cancerous cell is indicative of enhanced methylation in the sample from the subject and cancer or a predisposition therefor.

9. The method according to any one of claims 1, 2 or 6 to 8, wherein the compound that selectively mutates a non-methylated cytosine residue is a metal salt of bisulphite.

10. The method according to any one of claims 6 to 8, wherein the cancer is selected from the group consisting of prostate cancer, breast cancer, colorectal cancer, pancreatic cancer, ovarian cancer and combinations thereof.

11. The method according to any one of claims 6 to 8, wherein the sample comprises a body fluid or a derivative of a body fluid or a body secretion.

12. The method according to claim 11, wherein the body fluid is selected from the group consisting of whole blood, urine, saliva, breast milk, pleural fluid, sweat, tears and mixtures thereof.

* * * * *

SEQUENCE LISTING

```
<160> NUMBER OF SEQ ID NOS: 275

<210> SEQ ID NO 1
<211> LENGTH: 778
<212> TYPE: DNA
<213> ORGANISM: Homo sapiens

<400> SEQUENCE: 1
ttctgcaccc acagaggata ggaacataaa aatgcggact ccctaaggcc tccttcccct      60
ccacgttctt tcttcagtct tcctctaggg ggagctcaag ttagctttag cacagtgtga     120
agccagtgca gcgtctcgct tccacttctc caggggggcgc tgcaaagatt ttggtcgcca     180
aagatatcac ggtgcgcgcg tctggaagca tttccgctct ggagcatttt cgttccgccg     240
ggtgccagcg ttcctgtgac gcgtttcctg ttggccgagc tgcgcacgtg cggccggaag     300
ggaagtaacg tcagcctgag aactgagtag ctgtactgtg tggcgcctta ttctaggcac     360
ttgttgggca gaatgtcaca cctgccgatg aaactcctgc gtaagaagat cgagaagcgg     420
aacctcaaat tgcggcagcg gaacctaaag tttcagggtg agatgcgttg actcgcggtg     480
gctcagaaga cccacgcgcg agccctggcg cgttcgggcg gccggggggcc cagctgctct     540 gtgtgacgga ggcagcttcc cctgcagcgt gtgtgattgg ggagagtgaa aaggcagctt     600
ccactcggga cccgcgctgc tgcccactcg tcgcgtggct ccagcgctgc tcctgaccttt    660 tctgagcaat cagtgtcttc ttacaacgtt agagcgggag gactccccgt tcacttctag     720
gcttacgact aaccctgcct tttgcatttc caccttagct tttggttccc tcaccacc        778

<210> SEQ ID NO 2
<211> LENGTH: 760
<212> TYPE: DNA
<213> ORGANISM: Homo sapiens

<400> SEQUENCE: 2
ctcgaggaac gattttgaat gaaaagcaca taaagtgctg tagcatggag acgagagaca      60
```

| | |
|---|---|
| aataactatg cccttctccc aaaataagtt atgacttact aggggaggaa aaggagcaaa | 120 |
| gagtataaag cccggtcctc tgcgggaagt acccggaggc ctgccccgga acgcgctcct | 180 |
| ttcggctacg agatgagggg cacgcagacg gacgcgcccc tcggtgagtg tgcgtgtatc | 240 |
| agtgcatgat tcctttactc cgcccacagg gtctgggcat ccgtcattac ctacggctgc | 300 |
| ctggtcagca acaacagca gatccgacaa ccgccagtca cctcgacggt ccacgcccac | 360 |
| cgctagcctc cagtttcccg cagaccgaaa gcccttttgc cccggctcgc aggtccacgt | 420 |
| cttattgaca gcaggaaccg gaagctcttc tgccccgatc gcctgcgcgc ggcctcgttg | 480 |
| gccgcacagg cgcagtggag ctcgggcgga gttgtgggag tggaggagga agaggcggta | 540 |
| gggggtacgg gggctggtcc cagaagatgg cggaggcggg ggtgagttgg gggtctcccg | 600 |
| gcgaagcgcg ggtgacgtgg tgctgaggaa agcggcctga ggaggagggt ggcccttggg | 660 |
| aagaagaact acttgtgttt ttgcagcctg ggaaccctgg tggcaggtgc ggggagccag | 720 |
| gaccactgat gggcctgcag ggcaaggggc tccgcttacc | 760 |

<210> SEQ ID NO 3
<211> LENGTH: 545
<212> TYPE: DNA
<213> ORGANISM: Homo sapiens

<400> SEQUENCE: 3

| | |
|---|---|
| agggggaggt gactcacagc gggcagtggc agtgggagct gcagtgctga ggatctgggt | 60 |
| ggggtataag gagcgattgt aaggcagaaa caccaaggag ttatatccct gatgtattgg | 120 |
| caggaagggc tagagaaaga aacaaaaaca aagacttcct tggccctgcg cctgtccagg | 180 |
| ctctgctaag agccacgttc cctgcataca gacgtcggcg ggcctttctg ggtgacagtg | 240 |
| ctgagccgcg gctgcagtgt caccaagcgg cacctcggcc ccggccccgc ccgcgccagc | 300 |
| tgggacagtc tggagacctt cttttcatgc cgtcaagtct cattttgcca aggatttatt | 360 |
| tttcttcggg gagagaggga gagcgggggc aaaggatgtt ctcttaaagt atccagcgat | 420 |
| cagagccgct gaagcctcca accagaaact caaacttccc tggattgact tttccccctt | 480 |
| tgttcacatc atctcacaaa tatttggctt tccccggcca cgtctgttct atttctgctc | 540 |
| cggag | 545 |

<210> SEQ ID NO 4
<211> LENGTH: 696
<212> TYPE: DNA
<213> ORGANISM: Homo sapiens

<400> SEQUENCE: 4

| | |
|---|---|
| ggggcctcgc aacggctcgg gtttagtgtg atctggggag gctgcagccc agttccggct | 60 |
| accgtgggcg cctgagcaga gccggggcga gttgtaaacc tcagagaaag gcacttgtcc | 120 |
| ccagcaaaac gcttggagag gaccgtgcac gctgtgctgc ccccgccccg agacgcgccg | 180 |
| ggccgccggg tcaccggttt tccgaaaggg acccggcaga gacaaagtgc cttcgccgct | 240 |
| gcgataggtt ggttttactt tgcaataaac agcccctaat gggaccgggc gccgggcgga | 300 |
| gagctcggcc cggggcgcgg cctttgccgc ctggctctgc gggccgcccc gccgggcgcc | 360 |
| aggttttggg gggtggcccg gccccgcgtc cgccactgca ggccgctctc ctccttcccg | 420 |
| cgcacacagc ggagaaaaaa ggacgcaaac agcatttac acttttccca ctttagcggg | 480 |
| aatcggagga gccgggcgag aaagcccgaa aaggaggcg gttatttacg accgcgggt | 540 |
| tggagtctgg caccagatgg tgggggtctg tcaggcccgg ccgccccgcc cagcgcccg | 600 |

```
caaacagcgc cggttggca gcgtcgcctg agcagccccc atcttcgctt ccagcccctc    660
ccgtatattt tctcccgtcc aagtcgatca aagacg                             696

<210> SEQ ID NO 5
<211> LENGTH: 259
<212> TYPE: DNA
<213> ORGANISM: Homo sapiens

<400> SEQUENCE: 5
ccagccactc gactttgcgg aggggctga aagcctcagt agcggacccg gccgggaaag     60
gcggagccga cagctgtcgc ggggcgggc ttccagggcc gggaggtgga aggcggagag    120
cggcgagggc tccggctccg acccagccg agcgcgcagc gtgaagcgga aacgccggg    180 ttagcgccag gctgaatcct cgctctgact cctattgcgg tgggatgtgg tctctgagtc   240
tccgtttacc gattttacg                                                259

<210> SEQ ID NO 6
<211> LENGTH: 333
<212> TYPE: DNA
<213> ORGANISM: Homo sapiens

<400> SEQUENCE: 6
ctcagcttgg acctagatcc tgtttcgatt tcttctctca tcgtgccagg ggcgatgagg    60
ttcagttgtg cttctggaag gatccagggt tgagggttct ccaatcgcag caaagggccc   120
gggctgggtg ttgccgagcg gtcctcggct ccccggtgga ccatgcccct ccagaggtct   180
ggcccagcgt cgctctgctc tgcaaaaaag tggctctccg ctgatctcga atgcaccagc   240
gagcctccag attctgggtg aagccgattt tggaaatcca tatgccgccc tagcaaacac   300
atcaggattg aggttaccgc ataagagcag cct                                333

<210> SEQ ID NO 7
<211> LENGTH: 196
<212> TYPE: DNA
<213> ORGANISM: Homo sapiens

<400> SEQUENCE: 7
cccgggctgt gtttgccatt cgcgggaata aatgaagcat cggtaatctc cataaaagag    60 cttttcacgct tcattctctg aaactaagtt gaggcttaga cggaaaggag aaaagagact  120
tttaatttaa agtaatgatc atcaacactc aggtgctaga gggtctctgg ggaaaggggg   180
tccctacccc acccgg                                                   196

<210> SEQ ID NO 8
<211> LENGTH: 199
<212> TYPE: DNA
<213> ORGANISM: Homo sapiens

<400> SEQUENCE: 8
ttcccgggct gtgtttgcca ttcgcgggaa taaatgaagc atcggtaatc tccataaaag    60
agctttcacg cttcattctc tgaaactaag ttgaggctta gacggaaagg agaaaagaga   120
cttttaattt aaagtaatga tcatcaacac tcaggtgcta gagggtctct ggggaaaggg   180
ggtccctacc ccacccggg                                                199

<210> SEQ ID NO 9
<211> LENGTH: 1242
<212> TYPE: DNA
```

<213> ORGANISM: Homo sapiens

<400> SEQUENCE: 9

| | | | | | |
|---|---|---|---|---|---|
| gcgagcaggt | cctccccagc | ccgcaccgag | aaggcaggcg | cccgggccct | ctgactccag | 60 |
| tggctcagag | ccggctcagg | actggcaggg | cgaggagccg | gcgggccgag | ccagcgaggg | 120 |
| tttgggctgc | ccgcggtgtg | tgtgcaagag | cgcgcgcctc | gtgtaaccat | tcaggaccag | 180 |
| ttgaagcaac | acaaataaag | tcaggtctct | tcagccttgc | tgtccacccc | tccccctctt | 240 |
| cctggtttga | ccctggcctg | gccgctctga | ggcccagttt | gcgcagccga | cattgcgtgg | 300 |
| ctactctcat | taccagggga | agggcgctcc | ccttttccct | ggtaatactc | cgggagcccc | 360 |
| tactcggaag | cccaagagtc | aaagggatac | aggggtgact | ggagagcagc | ggggacagc | 420 |
| gtggcctcac | ccaaggtcag | cgctggtccc | cacgtgtcgg | ccgggggagg | ggaggggagc | 480 |
| ggacagtcgg | agcgttcgga | tgtccagttg | agccgcggcg | cggggcagcc | ggggcgcaa | 540 |
| agttggaggc | agggctgggc | gacgaggaga | gaggagggc | cggagccga | agggacgccc | 600 |
| gggtgcaccc | cgctgcagag | gccgagtccg | agcggccgga | gaaggctggt | cgcagaaggg | 660 |
| cggcctccgg | tgcaaaaaac | ggaaaccttg | gagcagagga | tgaggaggaa | tacggaggcg | 720 |
| gggagcccac | agaaaaagat | gttgaggaaa | gaagaggaga | ccccggccta | aacaaatcga | 780 |
| aactgtgcaa | tgaacgtggc | ccgggagaac | cggggtgag | gggcgatggc | tggagctgcg | 840 |
| gcccaagcac | agctttcaga | cgcttgcccg | gaccctggcg | cggggaggcg | gccgggactg | 900 |
| cctttctgcg | cgcgtccctg | gagagcgggt | gggcaggacc | tgcgcccgc | ggtgggcaag | 960 |
| aagatttggg | gtttcgcagt | tcctgggtc | ggggcgggg | gtgaagtgcc | ctcagagacc | 1020 |
| tcggcggagc | cccagttgcg | ctcccatctc | cagcccccac | tggagagagg | gggtccaggg | 1080 |
| ccgtacccctc | ctgcggcctg | ggctgcgctg | accggaagtg | cctgtaagaa | gcgccctccg | 1140 |
| cggaccgtgc | cgggcgcggg | cagctccagc | cgggttggag | caaggccaag | acgcccggat | 1200 |
| ggggcgggcc | gtttcggcgg | acccagtctg | gacgcaggtg | cg | | 1242 |

<210> SEQ ID NO 10
<211> LENGTH: 1508
<212> TYPE: DNA
<213> ORGANISM: Homo sapiens

<400> SEQUENCE: 10

| | | | | | |
|---|---|---|---|---|---|
| cggtgcgggg | agctgccccg | cagcccaggc | agcgtttccg | aagccaggac | tgtggttgtc | 60 |
| ggcctttgag | ttccttgaa | cgcaatcgga | gaccaggcgt | gtcccgccag | acccttcaga | 120 |
| cccaggctaa | acccaaatct | gggtcgcgct | tccccttcgc | cctgcattcg | ttgtgcggtg | 180 |
| atcgcaaggc | ccggccggct | ccccgcccgg | cgtgcgcagg | ggcgctgggg | cgctgtgtgc | 240 |
| ccggacccac | gtccttcccg | agcccgcaaa | caggagagcc | gccagcgctc | gtgagcacag | 300 |
| tgtacacttt | atttcagact | acaggtttct | gaacataata | aaatctttgg | cttgtagcgg | 360 |
| cggttcagtc | tcgcagtctg | tggggtcgta | tttctcaaca | agtctccgga | aaacgaaagg | 420 |
| ggggcagaac | agacagaccg | acagaaggga | cccgggaggt | gggggagaag | aggtgggcag | 480 |
| acacgaaagg | aaacacactc | tcgcacacaa | agaaaagtcc | cagagaaacc | agggccggcg | 540 |
| atgcgggtcg | ggaggcaccg | gagaagcaat | gacattcaaa | tgaaaaaggc | aacgaaaacg | 600 |
| aaactgggcg | ggggcagcga | ggcggtgggg | gagggggataa | aataattata | ataattataa | 660 |
| taattataac | aataataata | aaggagatta | ataaaaatgt | ccagcaaata | gagatcgcta | 720 |
| cacgtatgtg | ttttccttac | ctgaaattaa | atatatacaa | ggtcgtaagc | ggtttggcta | 780 |

```
gatagagctt taaggagttc gcagtttcgt cccttatact gggaatagag aatggatctt     840 attttcgat agcacctgtc cgagtctttc tcccttttca aaaatgctgc gtttcaacgt      900
cattgtccat tctgaggctc tcttctgtc tctctcgctc ttttccctgc gctccctccc     960
tccttggagc agatgctttc tccccagcg aggggccggg agacgacggc ggcggtgccg     1020 ggaggggggcg cgggcgcggc cccggcctgt ggcggctact cgctctcgtc tttgtcctgg   1080
accgtggtgg tggagtggtt gtacagtccc tgggccatga ggtgcagcgc caggccgttc   1140
ttgatgcctg tggctttctt gatcttggcg cgcttgttct ggaaccagat cttgatctgg   1200
gactcgttga ggctgagttc ctgggccagg gtctgccgcc gctgctccgt gatgtagcgg   1260
tttgcctgga actccgcctt gagtctctgc agctgctcgg ccgtgaacgc ggtccgcggc   1320
cgcttgtcct ccttctcgtt cttcttcttc ttcagcttcc tggtgcgcgg acctgcagcg   1380
gcggagaggg ccggggtggg gtggggtgg ggaccgaggg cagaagggag ggggagagg     1440 gcaaaggaag ccgtgagaat agcattgccg agctgggccg cgagcccgc gcttccgggg    1500 cgatctcg                                                            1508

<210> SEQ ID NO 11
<211> LENGTH: 1880
<212> TYPE: DNA
<213> ORGANISM: Homo sapiens

<400> SEQUENCE: 11
atcgttccta gtctcccggc cagcccgagc cgtgcagcct gacagctcaa tcactctatc     60
catcaggcga gtcaatcaaa gcagcttttc ggaggttcag ggagcccgac gtgtcaataa    120
cggggctcga gatggcggga gctgatagtg cgcatcgatc cgcgcccggc cggcagctgt    180
ggggcggcga gagaccagcc agaggaaagc ggcgcgtggc tacgttgttc ccggcccct    240 gccggaccgg gtgtctggag tgctgatctt gggccaaagc ttctgccgct ctcccagaca    300
ctgcgggccg gggcgtcagg caggccttgg ccttctctcc cggagcccag ctcaggtctc    360
ctcctcgggt tcgccaagcg cgaggggcac acggaaaagt ggtggaagga aagccgagaa    420
aaacaggcct acggatgcca gaagtctgct ggatgtgcgg gtgaaaaaag gaaagcgccg    480
cgcggggagg atgcgggaac cgttccgcgg agaagctacg gaggaaactg gctctcatgc    540
ccttggacac gcttcctggc ctgagcctga cctgttttct ctcctctccc actgttttc     600 agctccagaa aaccaggggc tgccagcacc cacctttttg gcaactgcct ttccctggtt    660
tctacccacc cgggtcagac tcttttcgct acccagccgg gggagaggga cggctttcag    720
acgctttcct ccctgtcttc ctgtgtttcc catgtttatc aatgtaaacg gtctctccgc    780
agaaaatatc gagatggtgt ttgtgtctgt aaggacacac agtgaatata atttttctga    840
acaaggcctt ctctggtcaa atctggcctt cggacgatca ggctggtggg atttcagaca    900
cacatcacta ggcccacctt cctgccttat ctaaacaccc tggaaagaaa atcactgact    960
atgtactttt cctaagaata taaagataa gagacaaaga aggccccagg gattcagagt    1020
tcaaaatcaa agaatcgaga cccgagcctc ctgtgccacg agctgtagct tctcgggtgg   1080
tggccgcaga ggccaggatc gcatagctgg atgaacattc ggttgtgact ggaactgggg   1140
tgaggaagca ggcgtgagag actggagtac ccgaggccgg gtttgctctc cctagcgccg   1200
cagcttggcg ttctggggcg gtccgcgggg ccagaaggca tggcgcagcc cggagttggg   1260
tactcaccgg aggatggacg atccgaataa cgtgtgcagt acaccaggc gggccatacg     1320
```

```
agaggctgct gcgagtcagt tttgaccacg ggcccgccgt tggctgagcc cataagtagg    1380
atagccgggt tgccgtgctc cgggtatttg gtgccctgcg ctccggggct ccccgcgccg    1440
cctccactgc cgccgccacc ggtgtccgag ggcttggctg ctgcggccgc cgccgccgcc    1500
gccactgccg ccgcggccgc cgccgccgcc gcagccgggt tcccagcttt agacgcgccc    1560
gcgccggcgg cggctggctg ggagccgtcg ggtgggccac agttcgcgtc cggggcgcac    1620
aggagcgagg cagcgcctgg cgcccgggtg cccaacgggt ggacagggtc tctacctgcg    1680
gcagtctggc ctctgtcacg ctcgacccgg cctcctcctc ctgcgcctcc tctggccgcc    1740
gcagccacca gaagctgcgg tggcggctgc tcctttttgc agccgaagtc cggcctcagg    1800
atgttgtcga tgaaaaagtt ggtggtgcgg tgcagctggg ccgctggctg cggctggtga    1860
gcaggcgccg cgagatgctg                                                1880

<210> SEQ ID NO 12
<211> LENGTH: 532
<212> TYPE: DNA
<213> ORGANISM: Homo sapiens

<400> SEQUENCE: 12
cgtagctttt gtgcgccgcg gtccctttca gcgcggtaaa tagggtctcg acgccttatc      60
tcgcctgcag gagacgcctc gagaagggct gcggaagata atttataggt tttaattact     120
cttcattccg cctgatcagc ttggcgttca tcacaggcct gtgaataaaa ccctggtcaa     180
aagctctgtc acatcgcgct ggcaagacgc ttaatcaaag tgagcggccc cgcgcgccgc     240
gcggcccggc tcctccacgt aatttccagc cagctgataa agccagctga ataatacggc     300 ggcccttttgg agacaccatt tacagaaatg acttattga cggcttaacg tcggtaattc     360
attttacctt tcatgtagtg gagcccggat ttgttacagt aatgggatga taaatgcacc     420
cgcggcccac gagctcgagc tggattaggc ggcactctgc gcgctggctc gtcccccac      480 ctccccgagg cccggcctgg gccggacgct cggtaccccg cgccgctctg cg             532

<210> SEQ ID NO 13
<211> LENGTH: 2533
<212> TYPE: DNA
<213> ORGANISM: Homo sapiens

<400> SEQUENCE: 13
gaggaggctg cagggacgcg catggaagag ccggtgcgtg ggagggtttg cgggggggac      60
atcgcgcccc ctaggggtga ccccagtggg tcccgtgtgc tctccgcgga gccggcggag     120
ccttgtcctc tgcacccggc gcgcagcggc cccttaaaca gtggaaccgt gaggccgctc     180
taagccgaag ggctggaatc tgggtttctc gggttttatt ttagaccatt cggcaccaag     240
cccgagctcc cccgccgcac cgcttccagt cccctttctt tccatagagc gacccgaagc     300
cggcggtggc gcaggagcc gagtctgatg agctcgcggg cggctgaagg ccggcttccc     360
tgtggggaac gcgccacctg tcggcgccag tgagaactgc gtctgtgtgg cgccctcggg    420
gtattcgggg ctgcggggag atgtgtgcct gaagccctgc gcttgcggtg gggacgtccg    480 gcctcttttcc tggcaattga cccctgaggc gggagagaca acggaattcc cacaaaggga    540
tccttctcgg gatctcccca cctcaagaca gctaaagctg gaggaaaagc cctccggggg    600 ggtgggggt gcgggtttgc cctgcgattc cgaaagcaga aaatacccga gccacacagg     660
gacgggcgcc gcgttggtag tcggggctac gttcctactc cctctacctc cccgcgcgctg    720 tgtgaccctg ggcggaaccc cgctgctctc tgggcctcag tgttcttatt cgtaaactga    780
```

-continued

```
gggcgttgga tgagattggt cctctcccaa ctctgacctt gaaactgata ctgaatctga      840
gcagcgtctg tagacacctg tgccttgcct tctatttcta gccttgaata aatcctggac      900
ttttatgtgc catttatatc ctaatctcat atatatttaa tgtataactg ctgccattat      960
tgttttctca attgtctagg ttttcatttg gatggggtta ggatggtcca aattatcccg     1020
ataagtgccc attaacttaa acctttttaa aaaatgaaac cagtaaaact tcattcactt     1080
tgcagtgtgg acactgctgg agagcaccca tgtcgtgggt ccagcgagga cacaaggagg     1140
ggcttagaga catgcgggag gcttagatga aagacagca  cccgggcagc ggtcagtgtt     1200
agagagagga cccgtaagaa gggccgaggc tagagggaga gcgaagactg agccaacgac     1260
gcacctgagc cctggggtgg gggtggagac gtggctccta acccaaatct ccctgccagg     1320
cagtgtccga cgagcatcga cggcaggcgt cgagaccagt gcagggtagc tcagacctca     1380
agccacgctt gaccttccca tgaaatgaat aaaactcgaa agccagggaa aggggacagt     1440
actttgatcc ggagatcgct tataacctct gcttggagtt ccgagttcgt gcggctcaag     1500
ggaggctaca gtccagcaag ctctgggctc caagcgtggg gacggcagcc cccaagcttg     1560
gcgcacccct cgggaagccc cggaacggtc ctcgccagac atagccggct gtcctggtcc     1620
ttagcttcag gctggcggcg caaggccaga gcggctgcct tctaggcacc tgggtggagg     1680
tctcgcatag cattccctga gaagcgaaac tgcccttggg gccgcagcga gcctgccaca     1740
tcgaactgga gaccctctgc tttcgggata gatgggacgt ttctgctctg tccttcttgg     1800
agtcccggaa tcgttctggg gccgcgtgct gcctggaggc ggtgaatttc agggtcttga     1860
gaagccgcgc acacacggga ttctgggcga gcgtcccgtc tcttaattcc tattaagaga     1920
cgggaaaatc gagggactgg aagtcccatc attgtcgcgt gagcagcctc ctgaacacca     1980
agcgagacct gagggttccg ctggggcctc gccctgacac ccgggccctc cgtgtggtcg     2040
agagtttgcg cccgctcccg ctagggcagc gaggtcccac ttgcggccgg ctggggcatg     2100
gtggcaccgg ttgtctactc cccacttgtg acaccgacag cttccaactc ctcagaccca     2160
ccccgtggaa ttctggactt tgtgagggcc gccggggtcc tggccctggg gtcagctgcc     2220
atctgactaa gccaggacgg cggagctcca ggccttgctc cagcactgcc ggtgcgtcgg     2280
ggcccgcgga gagcccaggg cgggagctgt gggctgagcc gggtggccgc gtggacacag     2340
atgcccggcc ggactgagcg gcagccaaga ctctccgtcc atcccgccgc tggactcgac     2400
tctcccagac ccgccacgga acccagattt gagcacgcaa gataaagacg ccagaggcga     2460
gtgcgcggcg gagaactggc cgcgacacgg gaagcttctg gggcgcagaa cgctggctcc     2520
gactcgcgcg gcg                                                        2533
```

<210> SEQ ID NO 14
<211> LENGTH: 692
<212> TYPE: DNA
<213> ORGANISM: Homo sapiens

<400> SEQUENCE: 14

```
gcgaggtctc agcgctccca ggcgctccag tggggccgcg ttccccgcca gggtgggtca       60
ggggaatact ctgcctgcgc cctctccgag ggtccgcgca gagcgagcgc ctctttaggt      120
ggggcctctg gctccgaccc ctgctcccaa cagggatctt cgtttgcatc acccagagga      180
gctggccaga gagccgcgcc ggaggccgca tctccccttg ttggtattgt tgtcggcttg      240 cttcttctg gcttcccagc tcagtgaccc cggaaagggt cgagcatccg actccggcat       300
```

```
gctggttggc tgccccggga ggcggaggta gggggccaga aatgctgacc tgggcaggcc        360
cccagccctg agctcctggg gtggacatct cagggtcccg ggcctccaag ctcatggccg        420
gtctccgcgg cggcggggtg acccaccaag ggcaagactt tttcagactt gcctatggtc        480
accaggcaat gactccgact ggtacgtgag ggagctcggg tcccaccttg aggacaaggc        540
ccagccttcc ccggagccgc acctcaactg tcagggtgca agtggtggtg atccgggagc        600
agtcgaggcc cgtgacaaaa ccaggatgac ccagcgtttt ctaaccgcgc tgaggcagtc        660
gcctctccgg gtcgctccac tcccggactc cg                                     692

<210> SEQ ID NO 15
<211> LENGTH: 249
<212> TYPE: DNA
<213> ORGANISM: Homo sapiens

<400> SEQUENCE: 15
cggagtccgg gagtggagcg acccggagag gcgactgcct cagcgcggtt agaaaacgct         60
gggtcatcct ggttttgtca cgggcctcga ctgctcccgg atcaccacca cttgcaccct        120
gacagttgag gtgcggctcc ggggaaggct gggccttgtc ctcaaggtgg acccgagct         180 ccctcacgta ccagtcggag tcattgcctg gtgaccatag gcaagtctga aaagtcttg         240 cccttggtg                                                               249

<210> SEQ ID NO 16
<211> LENGTH: 1134
<212> TYPE: DNA
<213> ORGANISM: Homo sapiens

<400> SEQUENCE: 16
actcattgtt agaacaagtg aacttgcatt tctaacaagt tctcaggtga tactaatact         60
gctggtccat ggaccacact ttgagcagca aggatgaact ctaaaggttg aggcaggtca        120
gagaagggag atttcactgt gggctggaga ggtcctggga cagagagctg agtctgggcc        180
catggcaggg cttggttggc cctctctgga gccatccagc ttttgggtct cagggacctg        240
ggagtgacgg gtgcattcag aggcccgtaa cttgtgtccc aaagcctcct cgatccccct        300
taacaagcag cagcactgtg tgggagatcc acatgtgaat agcccgtgtt tgagaaatgt        360
ccaatcctga tcatgtcagg aaacatcctg caaattctga aatcagagcc aaagggaagt        420
gctgcgaggt ttacaaccag ctgcagtggt tcgatgggaa ggatctttct ccaagtggtt        480
cctcttgagg ggagcatttc tgctggctcc aggactttgg ccatctataa agcttggcaa        540
tgagaaataa gaaaattctc aaggaggacg agctcttgag tgagacccaa caagctgctt        600
ttcaccaaat tgcaatggag cctttcgaaa tcaatggtaa agtacgattc cccaataatg        660
gaaatgacca gaaatgtagt ctttctgcta gcgagatacg aaaatagaca agtcaataga        720
aagtctaggt ttggcttatt gctgcatttt gcacgtaatc atcactaata ctgtctggag        780
tgcttcaatt tggaatttct ggaatgctaa taatagatgc tgtatttta gcatatagtc        840 aggttttctt tagcttcact attgttttaa tcatatttaa atatttccc ttgaaaaaat         900 gccaatgctt attaaatgtc cccttttttt aatgaatgtc ttattctgac acacaggttg        960
ggtgatacaa tgaaaacgca aaacagggc actgaaaggg gaccacaaaa ctgaagccaa       1020
gcatgacagt tttcaaaaca cagcttcttt aaaattcttt aagggatttt ctgttataac       1080
tgatgtgctg gtcaggaaac atattctgta tttcatgttg actgaaatat gttc             1134
```

<210> SEQ ID NO 17
<211> LENGTH: 2536
<212> TYPE: DNA
<213> ORGANISM: Homo sapiens

<400> SEQUENCE: 17

| | | | | | |
|---|---|---|---|---|---|
| gccgcctcaa | gggctcgggc | gtcccttcct | cccttgccgg | gatggggatg | gagaccagga | 60 |
| gcacagccct | gagcgtggtg | ggtcgcagac | gcactgaggc | caggagcggg | gcagggagga | 120 |
| cgcagggatt | tgtcttttcc | aaaggagatg | tcaggaagtg | ttatgaatcg | agagtggcct | 180 |
| tgccaagga | gccgcgcccg | ggcggagacc | gggcggcctg | cagccacccc | gcctcgcacc | 240 |
| ccccgcgccc | ctaatccggg | tacagaagaa | agcccgagaa | cgtgctgtac | ttgttattat | 300 |
| tgcctccgtg | agccttcccg | ccatccagct | tcacatacac | ttcgtcccct | gaatccaagt | 360 |
| gcagcaccac | gctgttactg | gcgtagtcgt | agttctggtc | ggcgtcctgt | gcaatggcgc | 420 |
| tggcccggac | ctggggacaa | gcggtgggag | caggtgagcc | ggggcaccte | ttcccgcgcc | 480 |
| tttgctcagc | ccacaccagg | cgcgccactc | acgggcctcc | cgcctgctgc | ttcagggtcc | 540 |
| acactcccac | cccagctcca | tgttctctct | ccaacttagt | caactccttc | caggtccccc | 600 |
| ctcctcctcg | cgccgacgag | tctgggaaat | agggagaggg | gaagcttcat | gaacactgac | 660 |
| ccagagtgga | agggtgggag | ccaggggcca | gggccaagag | gaaaggaggc | tgcagggcaa | 720 |
| gggggcgacc | tggagagaac | taagaactg | aggtttccga | gaagcccacg | gagaggcagg | 780 |
| cagggacgca | agtggccaag | gagtgtagtt | taggtatggg | ggtctctggg | ctctcaaggc | 840 |
| ccaacatttg | gctctacgtc | ccggtgagcg | cggcctcggc | gcatcgggaa | gcggagatac | 900 |
| tgtggcaccg | aggcgcgttc | attcccgggg | ctcgcagggt | agcccgcggg | tggagagaaa | 960 |
| ggaggctggt | tcctgggag | gttcaggcg | cgggcgaggg | tttacggggg | ccggtgagtg | 1020 |
| tagggtcac | tgacctgccc | gttcttgcag | aggtccgccc | acatgctggt | gccgtcgccg | 1080 |
| ccgcgcatga | ggatgtggta | ggtgaagaag | tagatgccgc | gtacctggca | gctgaacttg | 1140 |
| cccgtggtgg | ggtcatagtg | attgccgagg | ttggtgacca | cgtcatcgaa | cttcagcacc | 1200 |
| tcatagcctt | cgtgggggct | cttgagaccc | acatagaagg | cgatcttggg | gccgctgaag | 1260 |
| gtggcgctca | gcgcactggt | cacttcaccc | tcggaatcgc | cacctacccc | ggccccgccg | 1320 |
| cccaccaccc | cgacgccgct | ggccgtgccc | gccgtcagtt | gcagccctgg | cagcccgggc | 1380 |
| cgccccgagt | cgcccttctc | tcccggaggg | ccccctgggtc | caggcgggcc | cggctctcca | 1440 |
| gggggccccc | gcggccctgg | cttgcccggt | cgccccgggt | cgcccttggg | tccctggatg | 1500 |
| aaaggaggag | gagggttggc | gctgaggtcc | tgcatgactt | ccaggcggc | ggtgctgggt | 1560 |
| ccgggtggct | gcgcctttgc | acccgggggc | tccccgccgg | gcgcggcagt | gtaagggtcg | 1620 |
| cagatcatgc | ggcaggtgcc | catcatctca | tagtgcgcgg | cgcctcgggg | cgccgcctgc | 1680 |
| agcagcagcg | gcacggcgat | gagcagcccg | agcgccatgg | ccaagagtac | gccgacggcc | 1740 |
| gccaggcagg | cacgccgccg | ccgctgccac | agcgggagg | cgaccgccac | cagctcctcc | 1800 |
| ttgccgcccg | gggaggtaat | ggtggggcgg | cgcggcggc | cccgctcccc | gcgctcgggg | 1860 |
| accggctccg | cgggtcctgg | ccgcgccccc | gacgtggcga | ccccagccc | cggctaccca | 1920 |
| actacttcag | cgagaggcgc | cgggacctct | gagcctgggc | ccaccgcgct | ggggctggtc | 1980 |
| gggagagccg | cggacgcccg | cgcgcatgac | gtggggcaca | caagacgaat | ccggcgcccc | 2040 |
| gagggtccgg | cgccggccag | ggagtgcttg | cgctggccgg | ggagtctgct | tgcggcgtcc | 2100 |
| ggcgctggct | ccgcggcgct | gcctcccgcc | aggctccgct | ccgctgggtt | tagtgggggct | 2160 |

| | |
|---|---|
| cctagcgcag tgagggcgcc ccggctccgc ggcgcgctct gctgtgctct ctcgctgttc | 2220 |
| gctggctccc gcgcgagggg gggacccgc taccctgacg taaggagtcc ggggctgagc | 2280 |
| ggcggaggcg gcgaagcagc gcgcgctgcc atcactcggg agacggagcc ctcatgtcat | 2340 |
| cagcctccta tctggcggcg tcctcggcag aaggcggtgaa ggcgcggttc ccctggcgg | 2400 |
| ctcccaggag ccacaagtgg gcgcagcggg cgcggtccca agccggggca catcggacac | 2460 |
| acccacccgc ggccacactc acgcgccccc caccgataac acacacagac acccacgcac | 2520 |
| gcagtggcgg ggcacg | 2536 |

<210> SEQ ID NO 18
<211> LENGTH: 739
<212> TYPE: DNA
<213> ORGANISM: Homo sapiens

<400> SEQUENCE: 18

| | |
|---|---|
| cggtgccctc cgtggccggg ttaagaggag gtcccggagt tctgctcact tcagccgtgt | 60 |
| gccgggcact gcaaatcagg aagtgttggc gccggctggc gacctcccgc ctggggccag | 120 |
| gggaggaggg tggttggacg ctgccaccgc tgccggggct gtgcagggct gggcggggag | 180 |
| cgaggacccg gcggctcctg attgcggccc cggggggaggt ggccgagccg gataagctgc | 240 |
| ggcgggctgg agggcggcca cctcccctgc aggtccggcc ctcccgggcg ggtggggcgc | 300 |
| gggggaggag gagcctcggg ccgagccacc gccttcgccg cggaccttca gctgccgcgg | 360 |
| tcgctccgag cggcgggccg cagaggtgag tgtaccctcc cccggtctcc gcggggctgc | 420 |
| gtgctgcgcc cggtccccga gacgcccgcc cggttgcacc ctgcgccgtc gctgcgcgga | 480 |
| cctcgggtgc cgccacacgt ctggaggcga cttctgtccc ctgggaccga gccacgtgcg | 540 |
| cccggcggca gagaaaccgg gttccggggc ccccaccccg tgtgccttcc ttccctaggc | 600 |
| gtggaagccg cttgcgccgc gcaggttagg cagggccggc ggcgacagtg gcggggagca | 660 |
| ggctccggag ccccgggtgc agatgtgggc gcccctccgg atgacccgg ctgagtccac | 720 |
| aggtcccgtg tgccccacg | 739 |

<210> SEQ ID NO 19
<211> LENGTH: 5533
<212> TYPE: DNA
<213> ORGANISM: Homo sapiens

<400> SEQUENCE: 19

| | |
|---|---|
| cgcctcctcc gctgtctccc tggagttctt gcaagtcggc caggatgtct caggtacagc | 60 |
| gcgtgcacag ccaggctgcg aaggtgcagc gggcgggagg cccgttgggg gctcagccgg | 120 |
| ctgccagaag ctctcgggct cttttccttcc gtgcccctca cttgctcatg ggcccatgcc | 180 |
| tagccctgat tcgttggaca gagccttgtg agcgggattt tccgtttggg gatttctaaa | 240 |
| tctgctgccc accccgcaac tgccggaaag ttgcccatgg ggtggacttc gctgtgtagc | 300 |
| gggagagggg tgggagtcga gggtgcttga tggagagatg ggggaagggg ttgcacggat | 360 |
| tggaggagcg aggagactca gtccccatcc cgaagcacag gcaggacgt cgcggcggag | 420 |
| tggggaagcg aggagtccgt ggccgagagc ttggaggtca ggggaagtac ggggccggct | 480 |
| gctcagagtg cgggacgagg agaatcgcgg cccggggaga ggtgacccag gggcccctcc | 540 |
| cttctctcca gtgtagaccc ttgtctgaga ccgagctatg tggggcgacc tctggctcct | 600 |
| cccgcctgcc tctgccaatc cgggcactgg gacagaggtc ggtgttgaac gcgcgggccc | 660 |
| caggggggagg gaggggacca acgggctccg gcgctgacac cgcggcactc atgccctgtc | 720 |

```
cccctttcagc tgtttccagc atactgtgcc ccgtctgtcc tcaggccagg gcttcgctgc    780
agccccggcc actccctagt gcctggcccg gtggtggcca ggcagttggc cgcgctgctt    840
ctcccgcaga ggggaccccc actggggcg aaggcttggc ctgccctctt cactgctgta    900
tttccagacc tgatgcctgc gtttgtgaga gctctggata tatggttttc gattgaatga    960
gtgaactgga ggggcttccc cttcttgtgt tgctgaatct ttctagctgc cctgttgggg   1020
cagggagggg cagacacact tcaggggctg cattgcccga agggtgccac ctttcccacc   1080
tctccatccc cgtaactggg ctgtcatcag gccacagtag gattcttacc ctctcccacc   1140
cagaggaggc cctcaatcct ctcctctccc ttccatttag gctgagtttg agaaagctgc   1200
agaggaggtt aggcacctta agaccaagcc atcggatgag gagatgctgt tcatctatgg   1260
ccactacaaa caagcaactg tgggcgacat aaatacaggt atgcagagcg ggggttggaa   1320
gggcatctgc tcatcaaagc aggctcagca gctcagactg gaagtccctg ggaacttcac   1380
tctcaaactg cctgaggccc tactcttcag gtggggtatg gtgatggttc ctgaggtgga   1440
aaagaccatg ttccggattc tcagtgtctc cagtagtaac agaattcaaa tcctggtttt   1500
agaaggtctt tactggttat caccagcagc tactctctac tagggaagaa gcaaaggctg   1560
cagcttggaa aagacttgct gaaggctctc agctcagtag tatcattgtt gagccgttca   1620
gcttctgccc tagatgggca ggatcaaagt tggagcactt tttggagcac ttgacagcct   1680
ggccaagcct gatgtcagga gcagagaagc acctggtttc ttgggctagg tcagagcatt   1740
tcgctaacaa gtctgtgcct tcctgatgat aacttttttcc ctgcccagaa atcttggtgc   1800 agatttttgag gctgtgcttt ggactgtcat gttctgtaat aacatctttc ctgccttggg   1860
caggtttcat tctgtcccta agtccctgaa acatgggtgg atactgaggc aacagcgcag   1920
tgcattctgt gcaaggactc agggttatca tggcagcaca aagggaggt ctcccctgcc    1980 cctgctgagg aagaaggcga gcatggtccc tatttccgca gtagctgggg tggaagatgg   2040
agcaggtggg ctggctgcca accagctgga agcaggaaat agtacccaga tgacagatc    2100 acaggcagta ccatatcaaa ccctgggggtt cacatggagc acttagttga agaaggtctt   2160
atggcgaagg tgagttttac agtgagttcg taaactctgt ccttccaggg aggggaagga   2220
aaggtgaagt ggggaggcc agaggtgcca agatgctttt ctgacaaaca gtattttcac    2280
agagactggc ctgtgcccgt actagagtta ccgattttca catgagtcta gatagactgg   2340
cataggaatc tatcacttac tgatcaaaga ggtgtcatcg gctctctcta gggctgtact   2400
atacagccct attacacgat tataaaacat gatagtccaa acacgatagt ttagtataat   2460
agccagtagc cacatatgac tatataaatt ttaactgagg ctgggcgcta tggctcatgc   2520
ctgtaatccc agcactttgg gaggccgaag caagcgaatc atgaggtcag gagtttgaga   2580
ccaacctggc taacgtagtg aaaccccatc tctactaaaa atacaaaaat tagctgggca   2640
tggtggcata tgcctgtagt cccagctact gggaggctg aggcaggaga tcgcttgaa    2700 cctgggaggt agaggttgtg gtgagccgag gtcgcaccac tgcactccag cctgggcaac   2760
agaacgagac tctgtctcta aaaaaaaaaa ttttaactga aaatagttaa ataaaatcaa   2820
gtttagtctt cattcacagg aaccacattt cagatgccca gtagtcattt caggtacttg   2880
gtgtggcaag tggctcctga attggacatt gcaaatatac atgtacattt ccatttccac   2940
cgcttggaga gagctgtcga ggagtgctat tctaggatcc tgatgatgac cacaagggca   3000
gtttgtttca gctgtcccctg ggaacacttc cctgaaagcg ctcagggaca ttttctcagg   3060
```

```
cacagtgctc caggctacgg actctgattg ttccctgtgg ctttggggct gggcatcgta    3120
gtgaaatagg acaacaggga gatggtgagt gtgtttccca actgcagatg acaacaggtc    3180
tataagcata aagtcatcat ataacttaaa gaaaccttac cctcggtgaa atctcccaca    3240
gatcagcaag aaatagacta acaattcggt agaaaaatgg ggctaggata taaacagttc    3300
ataggaaagg acacctgata tcattaatga ttagggagag aaattgggta gctaacagca    3360
ggggtgagag agaaacttta tagtattttc ctctgtagct tttgaatttt aagacatatg    3420
aatggatttt ttttttaatt gtaattaaag tataattttt ttaaaagaga aattttggag    3480
tcatttaact tgtaagacaa aggctatctt gtaataagaa tactgttctt cctatttgct    3540
ctagatttta agtttggatt ggcatacatt ggttttctta gggcagaacc cactctacta    3600
gacctattta accccatgac agagcctaga aggaacaggt gtaatagaag atggcattta    3660
tggcaagaag gttgatcaag ttctccatta gaatttgaac cagatctaat gccttttctt    3720
cccttgttta agaacggccc gggatgttgg acttcacggg caaggccaag tgggatgcct    3780
ggaatgagct gaaaggtaat tgttctaatc aatttctctc atttgtgaaa cccagtagtg    3840
aaagagtctt cattatgaag tgtaagggaa gaggagagaa acaaagtca atggggcacg    3900 tgtgggaaac cagcctgacc tgtgccgaaa tgggaaaaaa ccgggccacc tacttttct    3960 cctaacacca tttatgcctt ttctaaaagc accatctctg agcaggagca tcatctagag    4020 aggagggggct gggaaccagg ccactgaaaa atagtttggg aaatgatgta gttggcgtag    4080
gctttggatg tgttcagaat aaggggtggt ttcctgtctg caactccctc tcccctacaa    4140
ggccaggcgg tgaccccta accccagtgg ccctccccag ttccttccta gccagaagga    4200
tacataaaag aagggaatga gctaatgcat ggcctgccgc tggcatcgta ggctcagtga    4260
atggagccat tatatgctaa gcaccagcag ccaagaagta tccaagctcg tacttaatca    4320
cgtgccacct gcagcagcaa gacccaagag ttggcaccaa agctcctggc agcattagtg    4380
ttcctgctgg ctagttttctg aataagccct ctgtccttct gcgaatgaga aacccttgaa    4440
ttcagaaagg gccacaatac aataaacaca ctcctaggat ctgcaagtaa ctgggaaggg    4500
aatgcccatc tgcctgccca ttttcatggg acatttccat accatcctca ggccccatgt    4560
actctccagt gcttcagaac aagctctgag ttccaaaggg tctctatcct tcaccataga    4620
atccaggaaa ctgggtgtca ctgtctctga gggatacatt cagtgtcctt tctactgcag    4680
caagaagaca aagatttgtc tcattcccct ccaagaagca gccacttttg gtcagagttc    4740
ctgaaacttt tctcatagcc tctctctggg gagaagaggg tgcctggctt tgcttttca    4800 ctgccagctt aacagctctg gaagatagga gcccaaaaca gagacactga aaaggccaaa    4860
gccaatatca gccacgagag ttagcaggac cagtaaagtc accacgatga cagtttccta    4920
cctgtctgga gggtggcacc tctctcccaa ggctcacaat ggccattccc ccaggacagg    4980
tgggggacgc aggtgtccag cagatgggcg acagatcttg gccagcccca ccaggctttc    5040
tgagcacagt tgcttatgga gcattcactt cgggccaggt tctgtggata ctgtctcctg    5100
taattagtag aatctcaact ttattaagtg agaaactgag cctaggagag ttacagcaga    5160
gctgcctggg gctctggagg ctgcttgttt cctaccatgc tacctccctg acacataatc    5220
ctgtcgattc cttacaggga cttccaagga agatgccatg aaagcttaca tcaacaaagt    5280
agaagagcta aagaaaaaat acgggatatg agagactgga tttggttact gtgccatgtg    5340
tttatcctaa actgagacaa tgccttgttt ttttctaata ccgtggatgg tgggaattcg    5400
ggaaaataac cagttaaacc agctactcaa ggctgctcac catacggctc taacagatta    5460
```

```
ggggctaaaa cgattactga ctttccttga gtagttttta tctgaaatca attaaaagtg   5520
tatttgttac ttt                                                       5533
```

<210> SEQ ID NO 20
<211> LENGTH: 1355
<212> TYPE: DNA
<213> ORGANISM: Homo sapiens

<400> SEQUENCE: 20

```
gggcgcgctt gtaatcccag ctactcggga ggctgaggca ggagaatcgc ttgaacgggt     60
ttgaacccag gaggcgaagg ttgcagtgag ccgtgatcgc gtcattgcac tccagcctgg    120
gccacaagcg ctagacaacg tccagaaaaa aaaaagaga cctcagtt cccatcgagg      180 tggagaaaaa ataaccacat ttgtttggca tatttgcatt tttaatagtc cctgaggagt    240
tcaggaggaa acagggtttt acatcccctt ttagggacgc aagtaggatt gccccaaaaa    300
gttccactcc gttcacactc agcgagggcc cggcaagagc cccacctttc acattcatta    360
tttcccttac taaccgaggc tccgagacgc taaacaagca gcccaaggtc acaccgcaga    420
gtgagggcag cagagcctct cgcctgcct cctcccttcg gacccgccg cgttcccaga      480 ggctggactc agcaagctgg aacaggaatc gaaccctcag gccctcgtcg ccgtcccagc    540
cctcgaggaa tctgcgcccc aggcgaagct gtcctcggag gttcgggagc gtcggagtga    600
cttcccgatc ctttcccctg gacccgagg gatccctccc cccaagtgcc gggtcctccc    660
cgcggctccc caggggctcc tccggccgcc ctcgctgact cagcgtaatc cgagccgcgg    720
agggcggcgg ggttggcgga gcccgccgg ggttaatcgc cgagctttga acgccccctc    780
ccgccccgcc cgcctccagc agccgccccg ccctgcgga gaagtccgg gctggcgccg     840 gcggccacag cggagcagct ggagcgatcg aggctgcagc gcggccgccg ggcgcagcat    900
gactgccgtc ggcgtgcagg tagccggcgc ctggcgggc gctgaccgg ggtgctgccc      960 cgccgtggga ggttgggggt gggaggacgg agggaggggc gtacccaccg cgagcgccgg   1020
cgtcgggctg ggggtgcgag cgcccccgt gccgcccc tgttgcaaac ctgggtccgg      1080
aggaggctgg gcggggagca acctcgggggg gcctgcctgc ctcacatagc tgctcccgag   1140
gcgcggactc cggctgcttc tgctcgcggc cttgcaagca cccgaggctc ccaaacttca   1200 tttgaaaga ttttcttct cttggtgtc accagtgact tactggtcag tttaccataa     1260
gggtccccct ttgtgagaaa tgaggcgcgt ctggggtgga gggacagaat cgacttgcaa   1320
agtgaggctt atgtaacaga ggatgcgtct cttgg                              1355
```

<210> SEQ ID NO 21
<211> LENGTH: 1107
<212> TYPE: DNA
<213> ORGANISM: Homo sapiens

<400> SEQUENCE: 21

```
cactgccacg ggcggctcca gaatttccgt gtaggagagt ttcagaagcc agaccagagg     60 aagggggtcgg tggtgggcac agggattcat cttagagccg ccttcgtctg gcgcgcacga   120
tgtttttctt tgggaaaggg tccctccgga gaagagctgg gagagattaa tgttgggagg   180
attgggaggg aagagtccct attcctcatg ggaagatctg ctagtccctc tccacctgca   240
tcctgcccga ggccggagaa agggcgagac tgtcgctccc tcgggtcccc agcctgcaga   300
agggcgcagt actcaccgag tgcgcggcgc aggcgagcag caccggcagt agtagctgct   360
```

```
gcagcggcgg cgacaggtgg ggacgcatgg tgcccgcacg ttccccgagg gcgccccgac      420
gtccgcctgc ccgtgccctc tgcccgctcg ggagctcagc gccccgcgca gggtcccggg      480
ctccggccgg ccgctgcgcc ccgaggagcc atggctgagc cacccgacct gcggcgggcc      540
ccgggactgc tcctcctcgg accaggtggc cgcgcgcgct aagccgcccg ccccattgat      600
caggacgcgg ctttgccggc gcgcctcctc cacccggcag ggactggcgc ggggtcggcg      660
cggaggctgg caggggagga ggcagaggga gggcgcgggg accggagtc ggctcccgca       720 ggctgggccc aagctggagg aggccaggag agggcacgct ggcttagcct tctacgcggc      780
aatcccgccc aaccccgggt ccggaaagag cactgtctct ggagtccacg acagaaagc      840 gcaagctcgc tgggggccgg tgggcaactt aggtcacctt tgtaagcctc ggctttctca     900
tccctaacaa cacgtctgat aatacccact ctcggactga agttgtcac acagtcgagg      960 cccattgcat ctattccccc cgatagctac cttgcacttt atttccgatt ttttcattat     1020
tgaagtcatt agcgctaatt ccatgaagtt tcactcccat gaactcctcc tttgatgatg    1080
accaaggagg atctgtggta cactcag                                          1107

<210> SEQ ID NO 22
<211> LENGTH: 1470
<212> TYPE: DNA
<213> ORGANISM: Homo sapiens

<400> SEQUENCE: 22
cgccagtagg caactgtggt attaccaata agtttgtatc accaataaaa tattataatg      60
cacctggcta aaaaccctgg cgtgataaca ccaaattcat gttattagaa ggaattaaat     120
tttaaaaagc acaccgttcc aggcacacag aaggagcccc cgaacgtttg ttttataaac    180
gcaggttggt tgctgaggct ttgttttgga gcctacgttt aggagaggaa atgattcaaa     240
actgcccccc aaaacctata tcctccagga gcactgaggt tggggcgacc tgctgccaac    300
tggtctggtt ttccctttta acacacgctt cttgcccact atccggtccc tgcggtcagt    360
gggtgcagca ggggtcgcag tccaaacaac caatcgcgac gcggctgcgg ggcggggcc     420 acagcgctcc gcctcccccc tccaatccgc cctcccaatc ctcctaggcc gctctctctc    480
gcacctgcgt gtccctctgc gctccgactg gtgcgacttc tccctgcgct agcgaggcag    540
ggttttggcc tcgcctctcg cgagatcgcc tcctgttgct gccgccgccg ctcctggcca    600
ctgactggcg gcgcctgcgc agccgccatg ttcggttgct atgctgcggc ctaggagagg    660
gggtgtgctt gagggaggag gaagagatag aggaggagga gggggaggaa gaggaggtgg    720
agaaggaggg gggtgactga gctcctcttg cactctcaca cacaaacgct gcccaggatt    780
acccgccagc tcacgccgcg cagtgcgctt ttccgctcct cgcgcccac caccaacatt     840 gttctctcag gactcctggg tcccaggggc cggaattggg cctgagcggg agaggaaaga    900
gacttggctt tggccgcggg gtcggaggat tggggcagg ccccctcccc cacgcacttt      960
tgggggtgtg gattatctca tccctgcagg gaggtaggag aggtcgccgg ctgcccgcct    1020
ccctgccacc tccccagcgg cgccggcccg cggctgccca gcagcatgag gtggtgctgg    1080
cggctccggg tcgtggcgcg accgctgcgg cggcggctgc tcgggggcg ctgaggtagc     1140 ccccggagc ggcacggagg acgcgcttct cctctgcgcg ccggggcctc gaggcttttt    1200
ttctccagcc gagaggacgc ggctgtgata tacgaaggta agaggttctc cggtccccgc   1260
cggcctctcg gccctgcacg ttgaacggga ggctcttacc tgcatgtgtg gctcctggga    1320
ggtgagccag gtggggcaag ccggaggtac gaggatgatt tgaaaggaag gaaaaaagga    1380
```

```
caaaaacaaa caaacaaaca aacaaaaaaa cgctttcttt cctttcttcc tgggacctct    1440
gcttttgcgg gggttatagt tggaatctct                                    1470

<210> SEQ ID NO 23
<211> LENGTH: 754
<212> TYPE: DNA
<213> ORGANISM: Homo sapiens

<400> SEQUENCE: 23
cggacgggcg cctcctccgc gggcggaggg ccgcagcggg aactgggttt cggcagcgcc     60
cctttaaacc agccgcggac gcccggctgc tggcgctagt tccagcccgg ccgggcccgg    120
cctcgccggt ttctctccag tcgccgcgcc ggccaatttc cggggcggtg tcatcgcccg    180
tttaagagcg gagcgctccg ccctgggggc ggagctggga gggagcttta aggggtggac    240
gggcgggagg tcggggtcct ccggggatta gagccggtgg gctcgttgtg ggcgccattt    300
ctcggcgtct accgaggagc cgccccttc tcagccttgc tcggctcttc cccgctctgg    360
tcgccggggc tgcgccgtcc ccagctcagg taagcgcgag gcccggcggc ggcgccgcag    420
tacagtccgc tgcgctccta gccgagtgga cccttcctcg cccgcgcctg cggtagcggc    480
cttgtccccg gggaggcggg cggggccgc acccagaccc tagggcggcc ggcccctctc    540
tcgtcgggcc ggcagggcat taatcccgcc ggagggaggg gcggcggcgg ccaatgaggc    600
agggccgccg agtttcggtc gataccgcgc gacgggccgg ggcggagggc ccggggcagc    660
cgggttaatg tttgccgagc ggacgcgctc cccgagccgc gggtacccct cgctggtccg    720
ctgggctgcc gtccagcggg agagacaaaa gtcg                               754

<210> SEQ ID NO 24
<211> LENGTH: 1831
<212> TYPE: DNA
<213> ORGANISM: Homo sapiens

<400> SEQUENCE: 24
gcagacgttt aaactgtcag ttgcgatggc ttgtgactct catgaggtct gcgtaggggt     60
cagcacggtc acaaaacctg tggaggagga ggtggttagg aaggaaaatc caccgagatg    120
aagctgtact ggatacaaaa tcacacgttc ctgggctttg cagggagct tgcccactgc    180 acttcctgcc tcgaggctat ggctggggtg ggattctggc ccttgtaggc ggcctgggtc    240
cagtctccgc catgcactca ctaactccat tactgctaat gggatgtcat cagcgaagcg    300
agtggtggcg gcaggtggag tcccgcccca agacccccgg gcggcatccc catcgccgcg    360
ctccagcact cttcgccacc tcgtaatttt cttctgtttc tgtatgatca ggtctgtcct    420
tcgcttttgc tttccattac ttcgtcctag ccctggcctg aatcccacaa ctggcgcccc    480
accttgtgca cccgcacccg ccctcaatac cggcgggcag ctcctccact gccgcagggt    540
taccagctgc gtgtccgagg ggcagagaga gaaacagagg gggacgggc aggcgcgctg    600 ggcccgcccc ccgtgcctg gggcagcttc tcattggtga aacctcctcc ccggccgccc    660
gctgcttgga aaatcagcct cggattggct gacagccccc cgacgggcgt ggcttccgag    720
gagagggcaa gaacggaagc gagggcgcgc tctcgagagg aggggttgcc taggcgacgc    780
cggaggcgcg ctcgggggt gggaaagcga gcccggcagc tcaatgacaa atcggtggag    840
gacgctgggg gtccgccccc ggagggggc ggggcgcgtt taagagctgc gggcggggtg    900
cggacggcgg aggcggcggg actggtccct ggtaagggcg cggcgcccgc gggcccccgg    960
```

```
cggggtgggg cgcgggctgg ggagtggggt acgccgcacg cccgcagcct cttgctccct   1020
ccgtgccggg ctgtggccgg gcggcggcag gacatgtcgc gccccgaggc cggcggaggg   1080
cgacgccccg gcagcggccc cgctccgctc cgggaggact ccctggggga gtctcggctt   1140
cctgggctgc ctgggctga ggaagtgggg gcggcctccg cctctccctt gtagccgcgg   1200
ttccttccct atcccgcaga tggctctgct tccacttcct gccgcgggcc tcccgctcgg   1260
gaccgtccac ttcctcagtc ctccggccgc ggcttgggca gggtcagggc tgggaagtgt   1320
tgcaaaaact taactgccct cggaacttgc acgcgccgtg aactgggcgg tgttcctaaa   1380
gggcttcggt ttgctggttt tgttttggtc ctgtcttgca aatgagcata aagttgtttc   1440
tccccccagcc tcctcccctt tcctttctga taggggccag cggcgaaggg gcttctaagg   1500
ggaagcgcct ggactgggca tcgccgtccc ggttcttgcc gcctgtggga gtgtgaggtt   1560
aaccgtgctc ggtgcagggt tgcggggcgc ggagcttgct gcgtccacac tgcttgtgtg   1620
agcagtgtcc tctctgtgct catttccaac gagaaacgtt ggaactttgg tgttcttatc   1680
aggtgagtct tcgggagaga agtgcttgtg cctggcggac tgaatgaatt ggccgtggaa   1740
gagacttggc tgattgctca tctgggttac ctgtgactca tcttcagccc ttgtagaaca   1800
gtgcactttc tgctctgtcc tggtttccta a                                  1831

<210> SEQ ID NO 25
<211> LENGTH: 3053
<212> TYPE: DNA
<213> ORGANISM: Homo sapiens

<400> SEQUENCE: 25
gaagaggtag gcgataggaa aggtgaggac tctatccaag gtcactcctg caaagctggc     60
agtggctgag cccgagtgga acccgggtct gagtgaagcc aaagtttgtc tgctggcgaa    120
agtgggaatt ccctgggggt gggggtgggg gtggggtact gtagaccctg ccagcccctc    180
aagcccctgag gctcagtggc ctccgggccg cgcgcctggg atcccgcaca atcgggcgt    240
tcctcctggc ccagcagacg cagccgctgg ccaggcctcc agtggctact gccttcccgc    300
cctccagctc gcagggtcca cgcctcggcc agtgcgacgg cggccgggg agctgggtga     360
gggcactgca gccccagagc ggcagccgcc ggcggagcct gcctctggca tcccaggccg    420
cgccgcaccc cgctcgcctc gccaggctcg gccgcgaggg agcgccccgg gagggccggg    480
ggcggccacg gcggcgggag tcgcctctgc tggttgggga gggcggcagc tgggacagag    540
gcagggcctg cgcggcggcg gggaggcggg agtgggccgg gaggagcgcc tgggtccagc    600
gcctggaacc cgtcggtgcc gccggccgcc cagctgggca agggtccggg gcgcccacgt    660
ggtgggaaag tttcgaggta gcaaaagtag cccggcattg cggggggtgg gaggggagag    720
gaggggaggg gagagggccg gctcgcccct ccttctcggg aaggcagaaa ggaaaaaagc    780
ggtgggaagc aggggtgagc gcggggagcg ggcagcccca acctgaacag attccgcttt    840
ctcctcctcc cccacccccg ggaagctcga gcggggaggt acggaccgtc tcctctcgca    900
cgggcaggac gacaccctcc ctccccccct tttttctgcc aacgtctatc tcaacgcgcg    960
cgcacatacg gagattgtgc ggcttttttc cccttgggga gaaaaaacgg ggagagtaaa   1020
agaagagaga ccaaagagaa gaactcctcc tcggcgagct ccgcactccg tgccgcggcc   1080
cggcgcgggg acgccgccgc cgccgcccgg ctctctcccg gccctgcggc gggtgccagt   1140
acgagcgcga gcgagggcac tgcacccggg gacgctgcga gacttttcgg cgctcgagcc   1200
gacctcgccg ccgccgcggc aggcagaaga gacaggagcg agaagggccc tgcctccccc   1260
```

```
tcgccttcct cgcccggcgc cccgcgcccg gccgggccgc gcaggcaggc ggagggaagg    1320
agggaggctg cgaggaggcg ggcggagcag aggccccggc gaagcgcgct gcggccgccc    1380
gcccgtggat gcggcgccca gggatcctgg agacaacttt gccgtgtgac gcgccgggag    1440
gactgcaggg cccgcggccg agggctcggc gccgcctgtg agcgggcccg cgcggccggc    1500
tctcccgggc accaagcttg ctccgcgcca ctgcccgccg gccgcggcg aggacgacct    1560 gcccgtctcc gccgccggcg gcccttcctg gcgcgaggca gtgagggcga ggcgctcagg    1620
tgcgagcgcg ggccccgcc gcagcgcccg ccgcagcgcc gcgccaagcc gcgcccggct    1680
ccgctccggg gggctccagc gccttcgctt ccgtctcagc caagttgcgt ggacccgctc    1740
tttcgccacc ttccccagcc gccggccgaa ccgccgctcc cactgacgct gctttcgctt    1800
cacccgaacc ggggctgcgg ggccccgac gcggaaagga tggggagaag gctgcagatg    1860
ccgaggcgcc ccgagacgcc cgtgcggcag tgacccgcga cctccgcccc gccggcgcg    1920 cccctcgggc ccccggggcc ctcggcgccc cttccctgcc gcgcgggaac ccccgaggcc    1980
cggccggccc cctccccctg cgagccggcg gcagccctcc cggcggggcgg gcgggcggag    2040 gcccgggcgg gcgcgggcgc gggcggggc ggggcggggc ggcgcgcccg gagcccggag    2100
cccggccctg cgctcggctc gactcggctc gcctcgcggc gggcgccctc gtcgccagcg    2160
gcgcaccatg gacgggctgc ccggtcgggc gctgggggcc gcctgccttc tgctgctggc    2220
ggccggctgg ctggggcctg aggcctgggg ctcacccacg ccccgccga cgcctgccgc    2280 gccgccgcca ccccgccac ccggatcccc gggtggctcg caggacacct gtacgtcgtg    2340
cggcggcttc cggcggccag aggagctcgg ccgagtggac ggcgacttcc tggaggcggt    2400
gaagcggcac atcttgagcc gcctgcagat gcggggccgg cccaacatca cgcacgccgt    2460
gcctaaggcc gccatggtca cggccctgcg caagctgcac gcgggcaagg tgcgcgagga    2520
cggccgcgtg gagatcccgc acctcgacgc cacgcagcc ccgggcgccg acggccagga    2580
gcgcgtttcc gaaatcatca gcttcgccga gacaggtggg tccggccctc cggctgtctg    2640
ccgcggtccc cgctcgctcc cgctctccct ctccttgcta gctccggctg ccaccgccgc    2700
caccgcagcc cgcgcgccct ggggcagcct ggactcccgg cagagctcct tcggccgtgg    2760
ccctgcgcgc tccgcccggg ttgcagtcct cttccccag gccgcagacc cttgcctgct    2820
gcctcaaccc cccgccgccg atcgcctggc cctccacccc tgctctccgg aatcgggccc    2880
cagcgcctct gggcgcgcgt cccctcccg gcagatgcgc gcggccctgg ctctgcgggc    2940
acttgcttgg tgattgctta atgttttgt ttcccacgat cggagtgtag gcttagcagt    3000
gtggatggag atgtgtgtgc ttgttgatat acgtgggccg gaggagagag aga           3053
```

<210> SEQ ID NO 26
<211> LENGTH: 340
<212> TYPE: DNA
<213> ORGANISM: Homo sapiens

<400> SEQUENCE: 26

```
ggcgttattt accgcagctc tgcacgtgag gcgcagcgga agcgcatggg agtcgcggag      60
agcgtctttt ggacagctta tctcttggca agattaagcc ggctctccgg ctctccacag     120
aggggcccgt attgcaggcc tgcggggagg gctgggcccg ccgagtttgc accttttttac    180 ccggcatctg tccctgggat caggagagcc gggaggctgg attagatggg tcagcgccct    240
gattgacagt gacacttcct cccgtgcccc cgcctgcccc ccggcctctc ccgctgttcc    300
```

| | |
|---|---|
| tctcctgcct cacccgggcc ccatcctgtt cccgagagcg | 340 |

<210> SEQ ID NO 27
<211> LENGTH: 2375
<212> TYPE: DNA
<213> ORGANISM: Homo sapiens

<400> SEQUENCE: 27

| | |
|---|---|
| tttctcgcca gcgtgtgctc agatggcgac gagggctagc ggcggcgggg gacgcctcag | 60 |
| gaccccggc acctgcgctc gctgcccgcg ggaagagggt ccgcgtggac ccagcccccg | 120 |
| cgtcccttct ctggcgtccc cggcttccgc gcgggcgtcc agagaagcgg gcgccctggg | 180 |
| aacagcgacc caggcatctc cccgaggagg gaagtgggag gtggggaggg cgggggggatt | 240 |
| tcagagattg aaaacagagc agcccttgcc cctcagctcc ggagctcatc tgacttgagt | 300 |
| tagcgacacc cccaaccccc cccccacac ctagtcgtct aaaaaaagtg tcggagattg | 360 |
| gcgcgtcctt tggttccttt ctcgaacttt ccttgtaggt gcgttttctt tccttggtgc | 420 |
| tgggtgggga gagtccctgt gctccccctt tcccctcccc ccgccccggc ggcgttcggg | 480 |
| tcccctgcg tccccggca gggagcgggc gggctggctg gcgggttctt ggggcccggg | 540 |
| tgtgcccgca ccgtgcgcgc gggggcgctg cgcagtccgg cggcgctgat ggattgcaga | 600 |
| agtgccggcg cttgccagcc gaggcagcac ggctccgcgg acttttttc aaactcccat | 660 |
| caatgagact tcgaggagga gcgggcggcg gcggcggctg cgactgcgaa cgcggaggaa | 720 |
| ggccaggagc cgcaggagga gccggaggaa agagcttggg ccgcgcggcg cgccgcagcc | 780 |
| tcggggagcc gcctgctcgc cggcggtagg ggctgcgcgg cgcccgcccg cctctcggtc | 840 |
| ccctctcttg cctggcccgc cccgccccgg ctggctggag ccccggcaca aggcagccag | 900 |
| ccgagggtcg ccgcgccagc caaggtggga tggggccca cagccaccgc ccggcgcccg | 960 |
| agaggccacc tgcgtgctag aggcaaactt ttgtctctct cggtaaagtt gcattggcct | 1020 |
| tcttttgctt gcttttcgtg acgaagcgcc tcccacctcg gccaagcgcg ggccgactgg | 1080 |
| gatgctgcgc cgtctcgggg ggtccctcgg ccgggtaccg gcgcctaggc cttgggatcg | 1140 |
| gggccctggg cttcggggga ctagaggcta gtaggcgcga ccccgcctgg ggctctggac | 1200 |
| gagcagggcg gggacgtaag gagagtcctg gggcttggag ctcgtggcca gaggtcgatg | 1260 |
| ttgcaccctc tccctacctg ggggagagca ccactcttct cggggtgcac agcgagccgg | 1320 |
| cctccgcgcg ccggcggggg tctgtttttt caggggggtgg agggtgggat cggaggctgg | 1380 |
| gatgctccga agctgccgta ggtgggcatg ggagcgtgtc tgcggcgta ctgagcgcgg | 1440 |
| aggggctgca gccagccact tgagaacttc gaactccact tctccgcgct gcgcgtcccg | 1500 |
| gagccctgcc tttctttctt ccttcctcaa tccttcctcc ccctcgcccg gcccggccgc | 1560 |
| cccctccccc tctgctgggc tctcctcctc ggcccccccct ctttgcctct cttctcctcc | 1620 |
| tctcctgccc tcggccctga gatccgcttg acttcccaaa gggatccgca cgtaatcctt | 1680 |
| tgccgggtcc tccggttccc ccttccacct cactttcatc cctgcccccc tactcatcgt | 1740 |
| ctctccccac ccccgacaat ctctcaacaa gtatatttgc tgaggaattt gaaaaatcca | 1800 |
| ctactgcaac ttgatctgta tgtgatggat ggggagaggc gcggagagag ttgggcgcca | 1860 |
| atcctattaa gggtttagag aggggagtct ttccccgga cggggcgggg gcggggagct | 1920 |
| gggagggagc gtgtgcttgc gtgtgtgagt gtgagcgcgc ccgccgcgct ggagagctgg | 1980 |
| gagtccaccc agctcggcgc cttttcagcc cggcggtaac tgctgtcatt tcctaggaaa | 2040 |
| cccgactttt accgcgcggg gagctgggga tggagcccgt gcgcctcacc ctgggtgatc | 2100 |

```
ggtcgctgag gctctcgggg acctcgagcc ccccgagggg tgcctctttc cactaccttc    2160
tcttttgtgt aattgttctg tggctcctag agttgatccc agctgaaaaa gtagacctgt    2220
ccctactgtc tggtcccgcg ccctgggagt cttgtaggcg tccctctgtc ccccagcccg    2280
ggcatcccgc tcggtgcgcg acctctggca cgggctttgc agctcggtgg ccgcagcggt    2340
gtcccgggcc ccctctccgc cgctcttgcc gggcg                                2375
```

<210> SEQ ID NO 28
<211> LENGTH: 1634
<212> TYPE: DNA
<213> ORGANISM: Homo sapiens

<400> SEQUENCE: 28

```
atcctgtctc taaaaagaga aagagagaaa gaaagcatgc atctcctgag tgcgctgtgt      60
tgcaagccct cttctcgggc tccaggccca gtgcgatgac tgagcacggt caaagcaagc     120
agccacccac ccttgtcccg gtgctgaccc ctctgctctc ccgcaggctc catcctggaa     180
aacttcagtg gcagtggggg cggcgggccc gcggggctgc tgccgaaccc gcggctgtcg     240
gagctgtccg cgagcgaggt gaccatgctg agccagctgc aggagcgccg cgacagctcc     300
accagcacgg tcagctcggc ctacaccgtg agccgccgct cctccggcat ctcccctac     360 ttctccagcc gccgctccag cgaggcctcg ccctgggcg ccggccgccc gcacaacgcg     420
agctccgctg actcctacga ccccatctcc acggacgcgt cgcggcgctc gagcgaggcc     480
agccagtgca gcggcggctc cgggctgctc aacctcacgc cggcgcagca gtacagcctg     540
cgggccaagt acgcggcagc cactggcggc ccccgccca ctccgctgcc gggcctggag     600
cgcatgagcc tgcggaccag gctgcgctg ctggacgcgc ccgagcgcac gctgcccgcc     660
ggctgcccac gcccactggg gccgcggcgt ggcagcgacg ggccgaccta tggccacggc     720 cacgcgggg ctgcgcccgc cttcccccac gaggctccag gcggcggagc caggcgggcc     780
agcgaccctg tgcggcggcc cgatgccctg tccctgccgc gggtgcagcg cttccacagc     840
acccacaacg tgaaccccgg cccgctgccg ccctgtgccg acaggcgagg cctccgcctg     900
cagagccacc cgagcaccga cggcggcctg gcccgcggcg cctactcgcc ccggccgcct     960
agcatcagcg agaacgtggc gatggaggcc gtggcggcag gagtggacgg cgcggggccc    1020
gaggccgacc tggggctgcc ggaggacgac ctggtgcttc cagacgacgt ggtgcagtac    1080
atcaaggcgc acgccagtgg cgctctggac gagggcaccg ggcaggtgta tcccacggaa    1140
agcactggct tctctgacaa ccccagacta cccagcccgg ggctgcacgg ccagcgcagg    1200
atggtggctg cggactccaa cgtgggcccc tccgcccta tgctgggagg atgccagtta    1260
ggctttgggg cgcctccag cctgaacaaa aataacatgc ctgtgcagtg gaatgaggtg    1320
agctccggca ccgtagacgc cctggccagc caggtgaagc ctccacccctt tcctcagggc    1380 aacctggcgg tggtgcagca gaagcctgcc tttggccagt acccgggcta cagtccgcaa    1440
ggcctacagg ctagccctgg gggcctggac agcacgcagc cacacctgca gccccgcagc    1500
ggagccccct cccagggcat ccccagggta aactacatgc agcagctgcg acagccagtg    1560
gcaggcagcc agtgtcctgg catgactacc actatgagcc cccatgcctg ctatggccaa    1620 gtccacccccc agct                                                      1634
```

<210> SEQ ID NO 29
<211> LENGTH: 1349
<212> TYPE: DNA

<213> ORGANISM: Homo sapiens

<400> SEQUENCE: 29

```
cagaacaggg aaaaacaatc ctccgggagc gagagcacac ggggtcctac tgctaagagg      60
ggcctgtggg gaactgtgca aaacacgcag gacttacttt cccctctgaa gggcactact     120
caaatccctc cagcagaaga aagatttcca tcaagggcaa taaccacgcg ggcctcgggc     180
gaacacgcgc aagaccatcg cgggaagtgg ggcggcctgc cctccgagc ccgccgcccg     240
cccctcgtcc aaggaagggc actgcagagg cgcgaggct gggagagggg ccccggcgga     300
gacgggcaaa gagcagggga cgaacttccc cgggccgggc accaggctgc tggcaggaag     360
tttcctctgc ttctccgata cgcggggag aggagggccg caggggcgg acgggccagg       420
ggaggcggcg ggccggcagg tgcgcgccct gcaccctctc tgccgcctgg gaggagccct     480
cgcagacata gggctctgcg cgctcgcctc cccagcgggc ccccaactcc gcacgtcggg     540
tcccgccggc gtccatctgt cagtccctag gcgggacgct gggcgggtct ctcagtcccc     600
agagggcgga cagcggggag gccagggccc agcaggggcg ccccctctcc gccctggac      660
gtccaacggc gcccgccccg ccggcccggc ccgagacccg cggggaccgc gcgcggccct     720
taccgcaggt agctgccgga gttgtgctgg ttgtagtgct cgggctgcgt gtgccagaag     780
agcatggctg gaactcccag cgcgccgacc ggggcgcggc agcaagcgca gacgcggggc     840
gcgccgaggt cccagcggcg gcttcgcgct ccgaacccgc ggtgccggcc ggctcggcgc     900
atttatcggc ggcccagggg cgggacagcg gtgagacccg ccccccagga agcgcggccc     960
ggagggcggc tccccgcggc agccgcacct ggctgactcc cgcgcgtgcc tttccggcga    1020
gcgagcgcgc ctccggggcg gccagaccag agggctctag ggccggccgg gtgctctccc    1080
caaactccga tgtggggctc aggtgaccct tgccgccccc aacccgctcc acacggcccc    1140
tctggcctct gctccccact ctacgcccag ggccggtctc cagagcggct ccgagatttc    1200
cagcctaggc cctctctgtc gcctttcctc gctcttgttt tttcatagca cttcagacgc    1260
tctgaaatca tggggttttt tttgttggtt ttttttttttt ttgagacggg gtctcgctct    1320
gccacccagg ctggagtgca gtggcgcga                                      1349
```

<210> SEQ ID NO 30
<211> LENGTH: 711
<212> TYPE: DNA
<213> ORGANISM: Homo sapiens

<400> SEQUENCE: 30

```
ggggcggccg acccaggctg cgagtgctta gggggctgc ggggaggc ggggactggc        60
tgtttgggag gagcggaagg gagggagagg gggctgagg ggaggcaggg tggctgccgg     120
gagggtttgg gagccgggga ggccgaggga aggctggggg tctgaagggg ccgggtccgc    180
tccacaagtg ccgcagctca cctgtgccga tctgcgcctt gaaccgatcc tgcagccggg    240
tcaccagggc ggacaggatg tccatgccca gcagaaccac ctgcagcggg aaacaccggg    300
agcctgttag cagccggcct gcggggcagc gctcccgccc accgctccg ggaggccta     360
gacatttccg gcccagacgc agtccgagag tccagacgca tgccgactgg aggaccaaag    420
agattagcac gaagaaggat gatcttccac aaaaagagct atgtacagct ataatggaaa    480
atactcggtg aggagaaacg aaataaaagg caatacagcg tagccaaacc cgggttagct    540
gcgggtggag ttcaagagcg cgccgcggtc ccgcccccgc cagccccgcc ccggcgagaa    600
aagcgtatgc aaattttcga gcggccgacg cgcggtcttc tgggtaaaac cgagccgccg    660
```

```
cttttgcgac ccttcgggag cctcagaaaa caaagaattg gggtgtcgtc g            711
```

<210> SEQ ID NO 31
<211> LENGTH: 1468
<212> TYPE: DNA
<213> ORGANISM: Homo sapiens

<400> SEQUENCE: 31

```
gcttaactca gcacttgttc gctttcccag cttcagaaag aagctcttcg aaggccccgg    60
gaaccaaggg gaccttgtgc atcccatcaa gccggccgct ccgctcggcg ccgctcgcgc   120
agcttttgtc tggcccggtt gggagcccag gacgggagcc cgggccgccc gcctcccggc   180
accccttctc tctggatctt tcttcacacc catcactcgc caatgactag ttgttgtggg   240
tttctctccc tcgcccccctc ccttcctttc aaacgcgccc cgggctcgct ggcttctccc   300
acccggcagg ggagactcgg gttaggaagg gggcccgggt ggggtctgga aaagggaaac   360
agagaggggc acacaaagcc cgactgaccc cagggccgat cccctccctc tgcaaagcag   420
cctgggctca gcgacctact ggttggataa acaaccctcg catcccgctc ctcgccaggc   480
tcccacctca gggccgcccc atccccccaa agtgcaccca agagccgatg acagcgctgg   540
acatcgcccc cacccagacc cggcgcccgc cactgcgcgg gaggggccag ggccgcgaga   600
gggctcgggt ctgaccctcc gcccctgac cgggtactta cagccctgtt tttcgttact    660
gttgccgctg cggaccagag agccgccgcc ttctcctcca ccccaatgag gttaagcgct   720
tggtgcgggg attaaaaaaa aaaaaaaga aaaaaaaaa aaagaccgag agagcgagag   780
agacgccgag ggcgcctgcg cagtgcggtc accctttttc ttcttaccgc caccaacccg   840
ggtacaccat agagagcgta aaccgagacc agagaggcgg ctgcctctct atggtaacgc   900
cccgcgcagg cgctggcctg gccgtgttag gcttcgctgg cgtaaagtcc ccgggagctt   960
tgcccctcac ggagaacgtt agttgaccct gatggggacc cgtagggtaa aggttttgtt  1020
tttgttttt tttacggaaa aggttgtggt taggccccctt ggaaagttgc gacaaaactc  1080
gagttagaca aggaaggtcg gaactaagtg gccacagcaa caatgcacca gcaagcaggg  1140
agcgtgatag gaagagctaa agaggaatcg ggaaaccctg ggtaaaagtc gtccaagtgg  1200
aacttccttt ggtcgggggt ctgatactcg aaggaaacgg tctttcactt ctgggttagg  1260
gcgtccgccc agagggcgac tgcaatgaag gaaattgtgc cctgcgactt cccgtaacag  1320
agctgtgtgt ccacgctccc ttttccgagc aggcgcggac gcttgtgccg gaagtaaact  1380
tgttaacggt tctttgcctt tggggaggg gagacagccc agagaaggct ttggagaccc   1440
ttgagtcggc cagcgagcag ggtttctt                                     1468
```

<210> SEQ ID NO 32
<211> LENGTH: 385
<212> TYPE: DNA
<213> ORGANISM: Homo sapiens

<400> SEQUENCE: 32

```
gaacagcgta aacccctttcg tctcggaaac cgtggcctgc aagcttaaga ggtcggtccc    60
tgattcggtc gaatccactt gggagaccct ggaggtaatg aaggcgagca cgaaggcaag   120
gggcgcccgg gccggaaacc gtgcaacccc agatacccctc tagacccggt ccatcgcccc   180
cgctcgcagc ctgggccagg gtgcctgctc acctgggtta tgcgcttgcg aacctgcgcc   240
acctcctttt gaaactcgac atcttcctgc ggattaagcg acaggattgg cccagccggg   300
```

```
ccagaaaaag tcgccatgcc aaaagccgcc gacgctaacc acgcggcgct cccggaaacg      360
tcgggctccc agctcccccg aggcg                                            385

<210> SEQ ID NO 33
<211> LENGTH: 11584
<212> TYPE: DNA
<213> ORGANISM: Homo sapiens

<400> SEQUENCE: 33
ggccgttgcg attgattgcg ctggttgcct gcggcgtcca cttccttggc cgcccttgct       60
acactggctg attgttgtgc agccggcgcc atgtctgtga gcgagatctt cgtggagctg      120
cagggctttt tggctgccga gcaggacatc cgagaggcga gcccctcccc ttccccattc      180
cctttgcctt tccatgccta gttgggccac ttcgcccggc cctcctctgt cgctcagtct      240
cgggcggtgg ggacgcctcc gagggtgggt tgcttcccct ctagctttag gttaggcact      300
ccccgccccc gcccaaaatt ttgctgctct gtcctgattc cccgtgttcg agtctcagct      360
tctcagcatc acttgcctcg tttgtgtcag ttttccttcc tttcagcact tgtttatatc      420
gaaggctcga ttagcacctg gtcttcagcg aatgagcgtt tcgtgtattt ttgttggtgt      480
cttaaaagca catgtgatct gcttaaaact ctcctgtgat ttcctatgcc acacaggata      540
aaaaatcaga ctctactgtg gctcacatgg tttctcttca atctcgttta tgctctctgt      600 cttttgtgtat gatgttcact ttacctcttc tagtgcccca aatagcttcc tgcctgtttg      660
cttttcctgg aatttgcttc tttcccgttc ttttcctgat tgtctcgtat ttatctcatt      720
ggcgtcacag tctaagcgat ctatttcctg ttatgttttc tagtagcaca ttaacttttt      780
ttaatgtgtg taatattgat tattttaaaa aaatcttctc cctcattgta tgttaaaccg      840
ccagagggaa gggattgtgt gcttggttcc ccggtattta cacagtgcct cgcacataag      900
tatgctcagt gaatatttta aaaatgaatt agaggcgggg agcggcgcct catgcctgta      960
attccagcat tttgggaggc cgaggcggcc agatcacctg aggtaaggag tttgagacca     1020
gcctggccaa catggggaaa ccctgtctct actaaaaata taaaagaaca ttaactgggc     1080
atggttgcgc acacctgtaa tcccagctac tcgggaggct gaagcaggag aatggcgtga     1140
acccgggagg cggaggttgc ggtgagctga gatcgcgcca ctgcactcca gcctgggtga     1200
cagagcgaga ctccgtctca aaaaaaaaa aaaaagaaa aagaattag aaatacccga       1260 ctcttgtgtt gcatttaact cttcattttg caagttgcgt tcacacacgt catccattat     1320
aatgtcccaa ttgaatactt gggtttaatg ggtggctatt attctttaaa gggtatctga     1380
ggaatctaag gcttttttagt gacttttga agtcttacag aggaaataag tggaaaagtc     1440
aggattcaaa cttggttatg atagatcaca taagctatct aatgtgtttt gtgtgagtgt     1500
atgacaatga ttctgttgag tatctgattt ttattttaa ttctctctag gaaatcagaa     1560
aagttgtaca gagtttagaa caaacagctc gagagatttt aactctactg caagggtcc     1620 atcagggtgc tgggtttcag gacagtaagt tctttgtttt gtatccaatt atcagtctct     1680
tatttagagg gagagtttct atccagaaga cattttataa tgaaaaatgg ctatcatgct     1740
ttatggtgag taaaaattga agaagtaggt gatttgataa ttttggttga tttttcttcc     1800
acttccacac agtatggttt aaacagagat gttttctatt gcgagggcat tctactgatg     1860
ataattacaa ttgcttaacc catttcctgt ttagaaaaaa aaagtgcagc tctctgccag     1920
cacagtattc tcagggtaag cgggaaaagg gtttattatt attttttaa tttttttttt     1980 ttctgagacg gagtttcact cttgttgccc aggctggagt gcagtggtgc catctcagct     2040
```

```
cactgcaacc tccgcctcct gggttcaagc aattctcctg cctcagcctc ctgagtagct    2100
ggtgttacag gtgcccgcca tcacgcccag ctactttttt ttttttttggt attttattta    2160 gagatggggt ttcactttgt tggccaggct ggtcttgcac tcctgacctc agatgatccg    2220
cctggctggg cctctcaaag tgctgggatt acaggcgtga gccactgcac ctggcccaag    2280
ggtttgtaac tcttttgtgt tatctagtga cttttatttg gcccttgtg tgtgtgtgtg      2340 tgtatgtgtg tatgtgtgta tatgcacctg tgtgtatttg aatccagcct ttcagtgatt    2400
gaataccttt taatatgaga ttaacagtat aaaatgttct caaattaatg tgtttataat    2460
cagcctcttg aatgaaaata aaatatgtca agtttagaca tggaaccttc attgtaaggt    2520
attgccagca cagctaaagg agctgaagta tattttcaga tacaagaatg atataataat    2580
gcatttacac gtgccagagg caagtgattt ttcttaatga tacggagttg gtcatcctga    2640
ttgtgaatac ttggtaaagg cttttttctg ccaaatatgg gaggaagaag caatccaatt    2700
ttaggcatcc tctgaggagt gaacaggaat agcagctggt gtgcatctcc ttaaggatga    2760
cgttatttat gacaaccaaa ccaattacca gtgtgtctcc taatatattc ccttttagca    2820
agttgtttat ttttcagtat agctaattag tagggaaact ggggatgata ttttgaaagc    2880
caggttgaaa agcacagatg tgtacgttag ttgtgaggtt ttttttgttga ttaatttcca    2940 gatagattac ttagattatt aagcaagaac tgtatttgaa atttggttaa gttttttcatt    3000 tggttatctt ttgtgactag ttccaaagag gtgtttgaaa gctcgagaac attttggtac    3060
agtaaaaaca catctaacat ctttgaagac caaatttcct gctgaacagt attacaggtt    3120
tgtaagaaaa atagcattat tttataatgt taagtaaaaa aaaggagaaa aattatgtgt    3180
accaaatgat tgcttacaac taggcaaaca tcctgtgtag aagtaacaaa agagaaaaa    3240 accgaactaa taatggtcat gacaaaaatt ggtgatttta ttttttttctt cttttactg    3300 tctaaatctt aaggaacatg tattacttt gcagtgaaaa agcaattaaa agaaaatgt    3360 ggtatgaggg tcaaaagtga gaatatcttt ttgctatatt caagtttctt gtgaaattgg    3420
atgaactata gttagtgaaa taatgagatt aggtggcagt atatatatgg agtcgagttt    3480
tactttgaag cttgaatttc actgccaagt gatgtaatta gctaatatt tatgccatgt      3540 tttcttatta aaatcaacac tgttgatttt aagatacacc attatttat gtaccagtag      3600 ggaaggaaaa ttttgccagt cataaatgtg aaacatgggc caggcgtggt ggctcacacc    3660
tgtaatccta gcactttggg aggcctaggt gggcagatca cctgaggtca ggagtttgag    3720
acagcctggc tagcatggcg aaaccccgtc tctactaaaa atacgaaaat tagccaggtg    3780
tggtggctta tccctgtaac cccagccact tcagaggctg aggcaggaga tcgcttgaa    3840 ccaggcaggc ggaggttgca gtgagccaag attgtgccat tgcactccag cctgggcaac    3900
agagtgagac tccatctaaa aaaaaaaaac aacttgtgaa acatggattg tgaaatgtct    3960
cctggtttca taggtgttaa actgggaaaa actgcacctg aatcaaaagt ttctacttat    4020
tttaattttc ttactgaaaa agatgttctt ttaagacgta tatatcagca gtaaataggt    4080
tgagtatttt caggggggtgg gtagtataac cttatgagaa tattcttta agggagaggt    4140 tgacaaacca ctagtggctg ctgcctctgg gagctaagaa ttgcttttgt ttttttcaaga    4200 gttgttaaaa aaaagaaaat cccagataag aatatgtaac agtgaaagcg tcccacaaag    4260
cctaaaatat ttactacttg gcccctttaca gaaaacattt gctgatcctt gctgtaaggc    4320
aggggttccc aaccccccagg ccatggactg gtactggtct gtggcctgtt aggaactggg    4380
```

```
atgcacagaa ggaggtgagc ggtaggtgag cgagtgaagc ttcatctgta tttacagccg   4440
cttcccatca cttgcagtac tgcctgagct ccacctcctg tcagattggt ggcagcattc   4500
gattctcata gtagtgcgaa ccctattgtg gactgtgcat gcgagggatc taggttgcat   4560
gctccttatg agaatctaat acctgatgat ctgaagtgga acagtttcat cctgaaacca   4620 tccgccccc ttctgtggaa aaattgtctt ccatgaaacc agtccctggt gttgaaaagg    4680
tcagggactg ctgttgtaat agctgaagca cagagagagg taggacagta gaacaggtgg   4740
ggtctttaga gaccatcttc tctggaggtc acacacaggc tgccctctgg ctggatttgg    4800
ccttcagaag ggtttgtgtg acctgcatta tgttgagacc tttttttttga atgtattgcc    4860 acatttgaga atcaggaggc attgcataaa tatccacagg ttgtaaaatt tcctttttttc   4920 aggcttctag ctcagtattc tattttaagt gcatttgttt agtgattgca atggtaatt    4980 ttgtgaatca gaattttctt ggtattctgc actcaaatca aaatggagga atacgttgag   5040
gatgatacat aactgcagtt gtcttcaatc atcagttaca aattttatt ttttcagag      5100 cagtatcact gttcttactg attaaattta gaaggcacaa ttgctcttgt catctgtaat     5160
cttcagtttt ctttttttctg tcttttttttt ttttttttttg agacggagtg tcgctctgtc    5220
gttcagggtg gagtgcagtg gtgtgatctt gcgcactgca acctctgcct cccaggttca     5280
agcagttctc ctgcctcagc ctcccgagta gctgggacta gggcgcctg ccaccacgcc      5340 tggctaattt ttgtattttt agtagagagg gggttttgcc atgttggcca ggctggtctt    5400
gaactcctta cctcagattg atcaacctgc ctctgcttct caaagtgctg ggattacagg   5460
cgtgagccat cgcacccggc gtaaattttc atactcatca aaattagacc atatttgtca   5520
ctgattaaac ttaattgtta taaattcgaa cttgtaaaat taatgctaaa tgtcatattt   5580
ctctttatat attgggggtt tgtgtaagat tttatttgaa aaatgatcgc atttctaaac   5640
cgtttgaaca tggctgtatt aaacccatct ttctgaaggt ccctaacctt ggaggctaaa   5700
tgtgcttatt ttcatgcaga tttcatgagc actggaggtt tgtgttgcag cgcttggtct   5760
tcttggcagc atttgttgtg tatttggaaa cagaaacact agtgactcga gaagcagtta   5820
cagaaattct tggcagtaag tgtctttatt agtgggatct gcagaatcag gcatggttgc   5880 ttacttttttg gtggaaaggg tggttgtact tgtttatta aaacaaacaa gaattaacta   5940
aaaaccactt atagttgtag cttggtatct gaggatgatg cttccagagc tcttccaata   6000
cccaaatctg aggatgttca agtcccttat ataactggtg tagtatttgc atataaccta   6060
tacacattct cccacatact ttaaatcatc tctagatttc ttaaaatatc taatacagta   6120
taagtgctat gtaaatatt ttttttttttt gagacagagt ctctgtcgcc caggctggag   6180
tgcagtggtg caatctccgc tcactgcaac ctccacctcc caggttcaag tgattctcct   6240
gcctcagcct cccgagtagc tgggattaca ggtgcctgcc actatgccca gctaattttt   6300
tgtatttttt tttttttttcc gaatggagt tttgctcttg ttgcccaggc tgtagtgcaa   6360
tgacgcaatc tcagctcacc acaacctcca cctcctgggt tcaagcattt ctcctacctc   6420
agcctcctga gtagctggaa ttacaggcat gcaccaccac acccggctaa ttttgtattt   6480
ttagtagaga tgaggtttct ccatgttggt cgggctagtc ttgaactcct gacctcaggt   6540
gatccgcctg cctcagcctc ccaaagtgct gggattacag gcgtgagtga ccgcactcag   6600 ccaattttt gtattttttt agtagaaaca gggtttcacc atgttggcca ggctggtctt   6660
gaactcctga cctcgtgatt tgcccgcctt ggcctcccaa agtgctggga ttacaggcat   6720
gagccaccac gcctggcctt ttcccaaata ttttctatcc atagttggtt agcgcagagg   6780
```

```
gccgactcta cctggaaatg taaaagctaa aaataacaat ggcaaacaca tttgcacttg    6840
ctttagtttt taaaattgaa tttttaaaaa tttcaagcct acagaaaaat tgaaagaata    6900
gtacaatgaa tacctgttta catgccactt agatttacca cttgttaaca ttttgctaca    6960
tctgcttaat cttctcattt tgtgtgtgtc tttgtcagcc atttgaaagt tgcaaatatc    7020
gtaactcctt tctgaaatgc tttatcatgt gctttctaac aagaagtata ttctgtgaca    7080
caactagata ctgtttttga tagtattttt gagggaagac tgaattgaat tttgcttaag    7140
aactcaaaaa atccatagtg aggtctagtt gccaaggttg tgaatatatt aaaaagccag    7200 ttttttaaaag attcatcctt tcttcactta ctttgggaga aattatgtgt atatttttat    7260
attctgaggc ttaacttgca ttcacagcat gactttattt tcatgtgttt tttagttgag    7320
ccagatcggg agaaaggatt tcatctggat gtagaagatt atctctcagg agttctaatt    7380
cttgccagtg aactggtaag ctcagtaact tgctggttgc tttttttgatc tttctgcttc    7440 actgtcagtt tttttttttt tttttttttt tgagacagag tcccgctctg tcgcctaggc    7500
tggagtgcag tggcgcaatc tcggctcact gcaagctccg cctcccgagt tcatgccatt    7560
ctcctgcctc agcctcctga gtagctggga ctacaggcgc ccgccaccac acccggctaa    7620 ttttttttttg tattttagt agagacgggg tttcaccgtg ttagccagga tggtctcgat    7680
ctcctgacct cgtgatccgc ccaccttggc ctcccagagt gctgggatta taggcgtgag    7740
ccactgtgcc tggcccactg tctgttttta aaatgggtac caaaattcag aacgtcttaa    7800
ttcttttcta agccatctct cggtcaccag gtagtcactg actggcactg tatgtgttac    7860
aatttactag gcatcagaga aaagccagat caaatgatga gtgcatactt actgagttaa    7920 gaattttttaa ccgatgataa gacctcttcc ttttagggta gtggcaaaac atttattcct    7980
ggtaactgtt aatccatgta attgttttgg acactcattt gtctatataa ctaagttatt    8040
cttatccttt attcctttaa ccactatcta gggaaattgc cctgtaaaag tctaaagaaa    8100
aaaaaagctg tcagtagcaa aattgagtag ttgtgataga gactgtgcca gtctgcagag    8160
gtgaaaatat ttactatctg gctcgttaag aaaaagtttg cttgtccttg ctccagagga    8220
aagcagtcca gggctggtct gatgattcct tgatctttgg ccctaggttc ttctagcttc    8280
agcttctttc ttatgttcca gaactgttgc tctagtcaca tcttcactct agccagcagt    8340
aggaggaaat agggaaaatg gtatgccctc ccgctttaag gacatttctt tgaagttgta    8400
cacacaactt ctgttaacat tctggtgcct tgcctgcagg gaggcagaaa tggagtctat    8460
tggagtgggt atgtgtgcat tgaaaacctg aggaagatgg tgagaatgga tgatggggtc    8520
cacttgtagg ctgtaccact tgtctggctt gttggagaca cctgaccagt aaacaggaag    8580
catcttgtta gtattagtta agtgtaaggt gtctttagga ccatacatgt tggggccggg    8640
cacagtcgct tacgcttgta atgctggcag ttttggagac caaggtggga ggatcccttg    8700
aggccaggag ttccacacca gcctaagcaa caaagcaaga ccccttctct atattaaaaa    8760
caaacaaaca aacaaaaaac ccgtatgttg acagtgcact aaaggggtaa gcctggaaaa    8820
gtggagagga ttttacagaa aggggaatct ttttattat tttaatatat ttttttaaagc    8880 cagtcaaatg gagcagtagg gggttgtata ctgacaccga gaaggggagt cttgggttgg    8940
gtcttgaaat caatgttagt tctccttcaa gacagggtta cactaacata attttagatt    9000
cttatcccaa gtctgcctta cttgattcta ggtgactgga gttgcagctt agtaggtggg    9060
ctctagaaat gtgatcattt ggccaaggtt ggaagaggta gtggagctgc tgtgattatt    9120
```

```
ttgtcgtttc tttcttcgat atgatagcag atgagctgta agatgcttg tgtaatgtaa      9180 cactttatta tgcaatagcc agtttaagaa attagagaaa ttttagatgt tagtaatgtt      9240
aaattttact tggcagaact ggtctcattt tcagtgggat tcttttcaga gaagctcctg      9300
tcttgtctgt acttgtgtgt accctgagat agaagatcag cgtggctgtc taggcttgcg      9360
gttcttctgg ttgtgattca gaggaagatg cgctgagaag gagccatgtt gtaacaagcc      9420 cctgtttttct ctttcctggt acagtcgagg ctgtctgtca acagcgtgac tgctggagac     9480
tactcccgac ccctccacat ctccaccttc atcaatgagc tggattccgg ttttcgcctt      9540
ctcaacctga aaatgactc cctgaggaag cgctacgacg gattgaaata tgacgtgaag        9600
aaagtagagg aagtggtcta tgatctctcc atccggggct ttaataagga gacggcagca      9660
gcttgtgttg aaaaatagga ggctctcctt gctcctggcc ttgctgacct cagcggttgc      9720
caggaagggg tgagcacaga gtgcctctta cggtagttag gatgctcagt tgctaaacac      9780
tgcgctttat ttcttaacc agttgtggtg tgagtatcag aattgaaaca cttttttggg        9840
ggtaaaaaat atagccttta catggacaga atttttttttg ttgtttcagt gaatatgcct     9900
gtaattcagt gtatttcagt tccgtcagaa agtgtaaatg ttagtttctt ggtaaagtcc      9960
ttttcttgct taccttgact gttgatgtac tgattgagaa gttcattgtc tcgtttgtga     10020
ttcttccaga tgtgatgctt gatattttct atatgcgagt tagccatcca cacccaggca     10080
tagcctggat acagtataaa aatagataat taaaaagatg gttgccaagc aaggaaaact     10140
tattttatat tttcccttcc ttattttaag cattgtgagt aaatcagatg ttgaattctt     10200
ttgccaaggg aattatagct gcaggttctc tctcactgcc atcaaactgt aaaagattaa     10260
actgcgaagt caagctcaac agattatttt ggaaagtttt tgtattaagg gatttagtaa     10320
catcattttg ttttccacca ggcagggagt agggcttagt gttttaaaac acctctgctt     10380
tctgatgttg ccttaatatt ctgctattgc agcaattaaa aattgtcttc atgtacattt     10440
ggaactaaca cgtgatgtga tatattccta aactatgaaa ccttttttcct agtagtcagc    10500 tagatcattt gttctgggag tataaagcca cccacgtaag ttaataagca aaatcctgac     10560
tattatgttg ttagagaaaa atgctttgct ttgtctggaa gaaagataaa atagtgaatt     10620
ataaataagt caggccgggc gtggtggctc acacctgtaa tcccagcaca ctgggaggcc     10680
gaggcagggg gactgcttga gctcaggagt tcgagaccag cctgggcaac aaagtgagac     10740
tccatctcta tataaaaaca aaaccacga aagcacacac aaaataaatc agtgggattt      10800
ggtaatgtgt tttagagtaa gaaatttcag gttgttggtg actatcccaa cagtcatgtt     10860
ttaaatgtac agtttggggc aagtcatgta aatactgttg gtggtcttcc ccacacgccc     10920
caattttcag gtagtactaa gagtatgtgc caggaaactc ttgctattga attgagatga     10980
ttaaaatggt gacttaatcc gtagttattt tgcacccact gaaaggaaag tgctttccag     11040
aataatatga agtatctaaa agtgtcacct tttcttgcct gatcaacaat tgggcttcc      11100 tgtttgtaca aggggccatt tggcatacct ttcacagctt ttatcaggcc aagttaaagg     11160
ctgactacat ttttttcatca tgaggaaagc agttgaaatg aggcatgagt tactgtgcat    11220
tgggatttta gaacaatttt cttgtgacag ctcttttttgt gaagttaggt tcttaaaagt    11280
gcccatgatg gtcacttaaa atgtgcagta atagcactgc caggatcaag catgaaaggc     11340
ttttaaatta gatcatccca cagacaatac gtttgataat agttttttct tttaacctct     11400
ttaagtattg attctgcttg agaatattga agtacttgcc agaagttgtg gatttcagtt     11460
ttaacaaatg ctattaaagt ggagaagcac actctggtct tggaattcca tttgaggatt     11520
```

-continued

```
tagaagtgtc atgtttataa ctattcagtt gtgtttgttg ctggcttgtt gtaaagcaat    11580
aaaa                                                                  11584

<210> SEQ ID NO 34
<211> LENGTH: 621
<212> TYPE: DNA
<213> ORGANISM: Homo sapiens
<220> FEATURE:
<221> NAME/KEY: CDS
<222> LOCATION: (1)..(621)

<400> SEQUENCE: 34 atg gct gcc aac aag agt aag ggc cag agc tcc ttg gcc ctc cac aag      48
Met Ala Ala Asn Lys Ser Lys Gly Gln Ser Ser Leu Ala Leu His Lys
1               5                   10                  15 gtg atc atg gtt ggc agc gga ggc gtt ggc aag tca gcc ctg acg ctt      96
Val Ile Met Val Gly Ser Gly Gly Val Gly Lys Ser Ala Leu Thr Leu
                20                  25                  30 cag ttc atg tat gac gag ttt gta gaa gac tat gaa cct acc aaa gct     144
Gln Phe Met Tyr Asp Glu Phe Val Glu Asp Tyr Glu Pro Thr Lys Ala
            35                  40                  45 gac agt tat aga aag aaa gtg gtt ctt gat ggg gaa gaa gtt cag ata     192
Asp Ser Tyr Arg Lys Lys Val Val Leu Asp Gly Glu Glu Val Gln Ile
        50                  55                  60 gat att ctg gac acc gct ggg caa gag gac tac gca gcc att cga gat     240
Asp Ile Leu Asp Thr Ala Gly Gln Glu Asp Tyr Ala Ala Ile Arg Asp
65                  70                  75                  80 aac tac ttt cgg agt ggg gaa ggg ttt ctt ctt gtg ttc tca atc aca     288
Asn Tyr Phe Arg Ser Gly Glu Gly Phe Leu Leu Val Phe Ser Ile Thr
                85                  90                  95 gaa cat gaa tcc ttt aca gca act gcc gaa ttc agg gaa cag att ctc     336
Glu His Glu Ser Phe Thr Ala Thr Ala Glu Phe Arg Glu Gln Ile Leu
                100                 105                 110 cgt gtg aag gct gaa gaa gat aaa att cca ctg ctc gtc gtg gga aac     384
Arg Val Lys Ala Glu Glu Asp Lys Ile Pro Leu Leu Val Val Gly Asn
            115                 120                 125 aag tct gac cta gag gag cgg agg cag gtg cct gtg gag gag gcc agg     432
Lys Ser Asp Leu Glu Glu Arg Arg Gln Val Pro Val Glu Glu Ala Arg
        130                 135                 140 agt aaa gcc gaa gag tgg ggc gtg cag tac gtg gag acg tca gcg aag     480
Ser Lys Ala Glu Glu Trp Gly Val Gln Tyr Val Glu Thr Ser Ala Lys
145                 150                 155                 160 acc cgg gcc aac gtg gac aag gtg ttc ttt gac cta atg aga gaa atc     528
Thr Arg Ala Asn Val Asp Lys Val Phe Phe Asp Leu Met Arg Glu Ile
                165                 170                 175 aga aca aag aag atg tca gaa aac aaa gac aag aat ggc aag aaa agc     576
Arg Thr Lys Lys Met Ser Glu Asn Lys Asp Lys Asn Gly Lys Lys Ser
                180                 185                 190 agc aag aac aag aaa agt ttt aaa gaa aga tgt tgc tta cta tga         621
Ser Lys Asn Lys Lys Ser Phe Lys Glu Arg Cys Cys Leu Leu
            195                 200                 205

<210> SEQ ID NO 35
<211> LENGTH: 206
<212> TYPE: DNA
<213> ORGANISM: Homo sapiens

<400> SEQUENCE: 35

Met Ala Ala Asn Lys Ser Lys Gly Gln Ser Ser Leu Ala Leu His Lys
1               5                   10                  15
```

```
Val Ile Met Val Gly Ser Gly Val Gly Lys Ser Ala Leu Thr Leu
            20                  25                  30

Gln Phe Met Tyr Asp Glu Phe Val Glu Asp Tyr Glu Pro Thr Lys Ala
        35                  40                  45

Asp Ser Tyr Arg Lys Lys Val Val Leu Asp Gly Glu Glu Val Gln Ile
50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Leu Val Phe Ser Ile Thr
                85                  90                  95

Glu His Glu Ser Phe Thr Ala Thr Ala Glu Phe Arg Glu Gln Ile Leu
            100                 105                 110

Arg Val Lys Ala Glu Glu Asp Lys Ile Pro Leu Leu Val Val Gly Asn
        115                 120                 125

Lys Ser Asp Leu Glu Glu Arg Arg Gln Val Pro Val Glu Glu Ala Arg
130                 135                 140

Ser Lys Ala Glu Glu Trp Gly Val Gln Tyr Val Glu Thr Ser Ala Lys
145                 150                 155                 160

Thr Arg Ala Asn Val Asp Lys Val Phe Phe Asp Leu Met Arg Glu Ile
                165                 170                 175

Arg Thr Lys Lys Met Ser Glu Asn Lys Asp Lys Asn Gly Lys Lys Ser
            180                 185                 190

Ser Lys Asn Lys Lys Ser Phe Lys Glu Arg Cys Cys Leu Leu
        195                 200                 205

<210> SEQ ID NO 36
<211> LENGTH: 3790
<212> TYPE: DNA
<213> ORGANISM: Homo sapiens
<220> FEATURE:
<221> NAME/KEY: CDS
<222> LOCATION: (100)..(2112)

<400> SEQUENCE: 36
gccgagctgc gcacgtgcgg ccggaaggga agtaacgtca gcctgagaac tgagtagctg      60
tactgtgtgg cgccttattc taggcacttg ttgggcaga atg tca cac ctg ccg        114
                                            Met Ser His Leu Pro
                                              1               5 atg aaa ctc ctg cgt aag aag atc gag aag cgg aac ctc aaa ttg cgg       162
Met Lys Leu Leu Arg Lys Lys Ile Glu Lys Arg Asn Leu Lys Leu Arg
            10                  15                  20 cag cgg aac cta aag ttt cag ggg gcc tca aat ctg acc cta tcg gaa       210
Gln Arg Asn Leu Lys Phe Gln Gly Ala Ser Asn Leu Thr Leu Ser Glu
        25                  30                  35 act caa aat gga gat gta tct gaa gaa aca atg gga agt aga aag gtt       258
Thr Gln Asn Gly Asp Val Ser Glu Glu Thr Met Gly Ser Arg Lys Val
40                  45                  50 aaa aaa tca aaa caa aag ccc atg aat gtg ggc tta tca gaa act caa       306
Lys Lys Ser Lys Gln Lys Pro Met Asn Val Gly Leu Ser Glu Thr Gln
                55                  60                  65 aat gga ggc atg tct caa gaa gca gtg gga aat ata aaa gtt aca aag       354
Asn Gly Gly Met Ser Gln Glu Ala Val Gly Asn Ile Lys Val Thr Lys
70                  75                  80                  85 tct ccc cag aaa tcc act gta tta acc aat gga gaa gca gca atg cag       402
Ser Pro Gln Lys Ser Thr Val Leu Thr Asn Gly Glu Ala Ala Met Gln
                90                  95                 100 tct tcc aat tca gaa tca aaa aag aaa aag aaa aag aga aaa atg          450
Ser Ser Asn Ser Glu Ser Lys Lys Lys Lys Lys Lys Arg Lys Met
```

```
              105                 110                 115
gtg aat gat gct gag cct gat acg aaa aaa gca aaa act gaa aac aaa       498
Val Asn Asp Ala Glu Pro Asp Thr Lys Lys Ala Lys Thr Glu Asn Lys
        120                 125                 130 ggg aaa tct gaa gaa gaa agt gcc gag act act aaa gaa aca gaa aat       546
Gly Lys Ser Glu Glu Glu Ser Ala Glu Thr Thr Lys Glu Thr Glu Asn
135                 140                 145 aat gtg gag aag cca gat aat gat gaa gat gag agt gag gtg ccc agt       594
Asn Val Glu Lys Pro Asp Asn Asp Glu Asp Glu Ser Glu Val Pro Ser
150                 155                 160                 165 ctg ccc ctg gga ctg aca gga gct ttt gag gat act tcg ttt gct tct       642
Leu Pro Leu Gly Leu Thr Gly Ala Phe Glu Asp Thr Ser Phe Ala Ser
                170                 175                 180 cta tgt aat ctt gtc aat gaa aac act ctg aag gca ata aaa gaa atg       690
Leu Cys Asn Leu Val Asn Glu Asn Thr Leu Lys Ala Ile Lys Glu Met
            185                 190                 195 ggt ttt aca aac atg act gaa att cag cat aaa agt atc aga cca ctt       738
Gly Phe Thr Asn Met Thr Glu Ile Gln His Lys Ser Ile Arg Pro Leu
        200                 205                 210 ctg gaa ggc agg gat ctt cta gca gct gca aaa aca ggc agt ggt aaa       786
Leu Glu Gly Arg Asp Leu Leu Ala Ala Ala Lys Thr Gly Ser Gly Lys
215                 220                 225 acc ctg gct ttt ctc atc cct gca gtt gaa ctc att gtt aag tta agg       834
Thr Leu Ala Phe Leu Ile Pro Ala Val Glu Leu Ile Val Lys Leu Arg
230                 235                 240                 245 ttc atg ccc agg aat gga aca gga gtc ctt att ctc tca cct act aga       882
Phe Met Pro Arg Asn Gly Thr Gly Val Leu Ile Leu Ser Pro Thr Arg
                250                 255                 260 gaa cta gcc atg caa acc ttt ggt gtt ctt aag gag ctg atg act cac       930
Glu Leu Ala Met Gln Thr Phe Gly Val Leu Lys Glu Leu Met Thr His
            265                 270                 275 cac gtg cat acc tat ggc ttg ata atg ggt ggc agt aac aga tct gct       978
His Val His Thr Tyr Gly Leu Ile Met Gly Gly Ser Asn Arg Ser Ala
        280                 285                 290 gaa gca cag aaa ctt ggt aat ggg atc aac atc att gtg gcc aca cca      1026
Glu Ala Gln Lys Leu Gly Asn Gly Ile Asn Ile Ile Val Ala Thr Pro
295                 300                 305 ggc cgt ctg ctg gac cat atg cag aat acc cca gga ttt atg tat aaa      1074
Gly Arg Leu Leu Asp His Met Gln Asn Thr Pro Gly Phe Met Tyr Lys
310                 315                 320                 325 aac ctg cag tgt ctg gtt att gat gaa gct gat cgt atc ttg gat gtg      1122
Asn Leu Gln Cys Leu Val Ile Asp Glu Ala Asp Arg Ile Leu Asp Val
                330                 335                 340 ggg ttt gaa gag gaa tta aag caa att att aaa ctt ttg cca aca cgt      1170
Gly Phe Glu Glu Glu Leu Lys Gln Ile Ile Lys Leu Leu Pro Thr Arg
            345                 350                 355 aga cag act atg ctc ttt tct gcc acc caa act cga aaa gtt gaa gac      1218
Arg Gln Thr Met Leu Phe Ser Ala Thr Gln Thr Arg Lys Val Glu Asp
        360                 365                 370 ctg gca agg att tct ctg aaa aag gag cca ttg tat gtt ggc gtt gat      1266
Leu Ala Arg Ile Ser Leu Lys Lys Glu Pro Leu Tyr Val Gly Val Asp
375                 380                 385 gat gat aaa gcg aat gca aca gtg gat ggt ctt gaa cag gga tat gtt      1314
Asp Asp Lys Ala Asn Ala Thr Val Asp Gly Leu Glu Gln Gly Tyr Val
390                 395                 400                 405 gtt tgt cct tct gaa aag aga ttc ctt ctc ctc ttt aca ttc ctt aag      1362
Val Cys Pro Ser Glu Lys Arg Phe Leu Leu Leu Phe Thr Phe Leu Lys
                410                 415                 420 aag aac cga aag aag aag ctt atg gtc ttc ttt tca tct tgt atg tct      1410
```

```
              Lys Asn Arg Lys Lys Lys Leu Met Val Phe Phe Ser Cys Met Ser
                          425                 430                 435 gtg aaa tac cac tat gag ttg ctg aac tac att gat ttg ccc gtc ttg         1458
Val Lys Tyr His Tyr Glu Leu Leu Asn Tyr Ile Asp Leu Pro Val Leu
        440                 445                 450 gcc att cat gga aag caa aag caa aat aag cgt aca acc aca ttc ttc         1506
Ala Ile His Gly Lys Gln Lys Gln Asn Lys Arg Thr Thr Thr Phe Phe
455                 460                 465 cag ttc tgc aat gca gat tcg gga aca cta ttg tgt acg gat gtg gca         1554
Gln Phe Cys Asn Ala Asp Ser Gly Thr Leu Leu Cys Thr Asp Val Ala
470                 475                 480                 485 gcg aga gga cta gac att cct gaa gtc gac tgg att gtt cag tat gac         1602
Ala Arg Gly Leu Asp Ile Pro Glu Val Asp Trp Ile Val Gln Tyr Asp
                490                 495                 500 cct ccg gat gac cct aag gaa tat att cat cgt gtg ggt aga aca gcc         1650
Pro Pro Asp Asp Pro Lys Glu Tyr Ile His Arg Val Gly Arg Thr Ala
            505                 510                 515 aga ggc cta aat ggg aga ggg cat gcc ttg ctc att ttg cgc cca gaa         1698
Arg Gly Leu Asn Gly Arg Gly His Ala Leu Leu Ile Leu Arg Pro Glu
        520                 525                 530 gaa ttg ggt ttt ctt cgc tac ttg aaa caa tcc aag gtt cca tta agt         1746
Glu Leu Gly Phe Leu Arg Tyr Leu Lys Gln Ser Lys Val Pro Leu Ser
535                 540                 545 gaa ttt gac ttt tcc tgg tct aaa att tct gac att cag tct cag ctt         1794
Glu Phe Asp Phe Ser Trp Ser Lys Ile Ser Asp Ile Gln Ser Gln Leu
550                 555                 560                 565 gag aaa ttg att gaa aag aat tac ttt ctt cat aag tca gcc cag gaa         1842
Glu Lys Leu Ile Glu Lys Asn Tyr Phe Leu His Lys Ser Ala Gln Glu
                570                 575                 580 gca tat aag tca tac ata cga gcc tat gat tcc cat tct ctg aaa cag         1890
Ala Tyr Lys Ser Tyr Ile Arg Ala Tyr Asp Ser His Ser Leu Lys Gln
            585                 590                 595 atc ttt aat gtt aat aac cta aat ttg cct cag gtt gct ctg tca ttt         1938
Ile Phe Asn Val Asn Asn Leu Asn Leu Pro Gln Val Ala Leu Ser Phe
        600                 605                 610 ggt ttc aag gtg cct ccc ttc gtt gat ctg aac gtc aac agt aat gaa         1986
Gly Phe Lys Val Pro Pro Phe Val Asp Leu Asn Val Asn Ser Asn Glu
615                 620                 625 ggc aag cag aaa aag cga gga ggt ggt gga ttt ggc tac cag aaa             2034
Gly Lys Gln Lys Lys Arg Gly Gly Gly Gly Phe Gly Tyr Gln Lys
630                 635                 640                 645 acc aag aaa gtt gag aaa tcc aaa atc ttt aaa cac att agc aag aaa         2082
Thr Lys Lys Val Glu Lys Ser Lys Ile Phe Lys His Ile Ser Lys Lys
                650                 655                 660 tca tct gac agc agg cag ttc tct cac tga acacatgcct tcctttcatc          2132
Ser Ser Asp Ser Arg Gln Phe Ser His
            665                 670 ttgaataact tgtcctaaa atgaattttt ttccccttg atttaacagg attttgtag          2192 actttagaat ttggacttac ctaacaagag tataaattga cttgggttgc aagcactgag       2252
cactgttact tctatcacgt ctctctttta tttctgggat ataaaacagg ctttaagttt       2312
cttggttgcc caagggcaga gcaaggaata tctggtgttt cttgtgatga taatatttta      2372
attttaaata tccctccctc atacaagtgt atgttaccat tttaatataa ttcttttgt       2432 acctttcctt cttgttttgc gaagattttt gtggcatgga ttgctgtgct cactgctgta      2492
aaaggtgacc tagtgtactg ggcagctggt ggcggtgcag aaaagagtct caggttattt     2552
tttgttttta gttattctt ggaccttgac agtatctaat gactcctcct gaaaatgctg      2612
```

```
cagtataaaa gagcaaagag ctttgggaaa tacctaagaa gcaccttaag attagggtgg    2672
cattgctttt atagattctt gattttaaag caacaggcct ttctcaggtg ttgcattttt    2732
tggagcaaaa actatgggtt gtaatttgaa taaagtgtca ctaagcagtt ataacgtttg    2792
atggctgggg ggtaggaaga ggatggaatt gagatgtttg agcctcattt acatcaatag    2852
aggtgtaatg tactgcattt cttcatttgg taacataaca aagactttca tacaaagaac    2912
gatgatgctc ctcattaaga tttgtttaat tcaaggtggt ttggatttgg taagcctttg    2972
cactctgtag agtacttaga agacaagggc aacttacttg gagttagagc caagctgtca    3032
gacggtgccc agcacacatt aatgttagct tctttctgag aaaaaaatac ctcttccagg    3092
ccctgaaaca aaaaatacat ttgctgtgaa gattgaaaat gaacaaagtt agaaaaaaaa    3152
acagcaaaat cagtgattta gtcagatgag ttttcgttg taggagcact tgatttctag    3212
tgtgttttgt acagtatata actacaagat agtacatttt gtagcagttc aaagccaaag    3272
ttgctagcat cattttgctg ttgtgccagt taatcatagg atcccattaa ataagtgtgc    3332
taacatcgaa tatagagaaa actggtaaag aacattccag taggaaaaga aaagaacaat    3392
cttccatttc tgggcttggc caccatcacc ctggtcggac ctgtcctgga cttccaacct    3452
tgactgctga gctcctggct tagcttcttg ggttcctaat tcctggtgtt taataattct    3512
ctccacgatc atgttttct gatttttttt ttcagaaata atgttttta aaagacaaaa    3572 acaagggaa gaatatttaa ttactgagca gaagtaaata ctgttggcat tttgtacata    3632
atctaatttt tatatgcatg ttcatgcttt ttaatttttt tatcaaaaat taagtcatct    3692
acctactact tgtaaccagc ttgtttcata acatgttatt ttcctgtgtc attaaataat    3752
tacttcaatg ttgaaaaaaa aaaaaaaaa aaaaaaaa                              3790

<210> SEQ ID NO 37
<211> LENGTH: 670
<212> TYPE: DNA
<213> ORGANISM: Homo sapiens

<400> SEQUENCE: 37

Met Ser His Leu Pro Met Lys Leu Leu Arg Lys Lys Ile Glu Lys Arg
1               5                   10                  15

Asn Leu Lys Leu Arg Gln Arg Asn Leu Lys Phe Gln Gly Ala Ser Asn
                20                  25                  30

Leu Thr Leu Ser Glu Thr Gln Asn Gly Asp Val Ser Glu Thr Met
            35                  40                  45

Gly Ser Arg Lys Val Lys Ser Lys Gln Lys Pro Met Asn Val Gly
        50                  55                  60

Leu Ser Glu Thr Gln Asn Gly Gly Met Ser Gln Glu Ala Val Gly Asn
65                  70                  75                  80

Ile Lys Val Thr Lys Ser Pro Gln Lys Ser Thr Val Leu Thr Asn Gly
                85                  90                  95

Glu Ala Ala Met Gln Ser Ser Asn Ser Glu Ser Lys Lys Lys Lys
            100                 105                 110

Lys Lys Arg Lys Met Val Asn Asp Ala Glu Pro Asp Thr Lys Lys Ala
        115                 120                 125

Lys Thr Glu Asn Lys Gly Lys Ser Glu Glu Glu Ser Ala Glu Thr Thr
    130                 135                 140

Lys Glu Thr Glu Asn Asn Val Glu Lys Pro Asp Asn Asp Glu Asp Glu
145                 150                 155                 160

Ser Glu Val Pro Ser Leu Pro Leu Gly Leu Thr Gly Ala Phe Glu Asp
```

```
                    165                 170                 175
Thr Ser Phe Ala Ser Leu Cys Asn Leu Val Asn Glu Asn Thr Leu Lys
                180                 185                 190

Ala Ile Lys Glu Met Gly Phe Thr Asn Met Thr Glu Ile Gln His Lys
                195                 200                 205

Ser Ile Arg Pro Leu Leu Glu Gly Arg Asp Leu Leu Ala Ala Ala Lys
            210                 215                 220

Thr Gly Ser Gly Lys Thr Leu Ala Phe Leu Ile Pro Ala Val Glu Leu
225                 230                 235                 240

Ile Val Lys Leu Arg Phe Met Pro Arg Asn Gly Thr Gly Val Leu Ile
                245                 250                 255

Leu Ser Pro Thr Arg Glu Leu Ala Met Gln Thr Phe Gly Val Leu Lys
            260                 265                 270

Glu Leu Met Thr His His Val His Thr Tyr Gly Leu Ile Met Gly Gly
            275                 280                 285

Ser Asn Arg Ser Ala Glu Ala Gln Lys Leu Gly Asn Gly Ile Asn Ile
        290                 295                 300

Ile Val Ala Thr Pro Gly Arg Leu Leu Asp His Met Gln Asn Thr Pro
305                 310                 315                 320

Gly Phe Met Tyr Lys Asn Leu Gln Cys Leu Val Ile Asp Glu Ala Asp
            325                 330                 335

Arg Ile Leu Asp Val Gly Phe Glu Glu Glu Leu Lys Gln Ile Ile Lys
            340                 345                 350

Leu Leu Pro Thr Arg Arg Gln Thr Met Leu Phe Ser Ala Thr Gln Thr
        355                 360                 365

Arg Lys Val Glu Asp Leu Ala Arg Ile Ser Leu Lys Lys Glu Pro Leu
        370                 375                 380

Tyr Val Gly Val Asp Asp Asp Lys Ala Asn Ala Thr Val Asp Gly Leu
385                 390                 395                 400

Glu Gln Gly Tyr Val Val Cys Pro Ser Glu Lys Arg Phe Leu Leu Leu
                405                 410                 415

Phe Thr Phe Leu Lys Lys Asn Arg Lys Lys Lys Leu Met Val Phe Phe
            420                 425                 430

Ser Ser Cys Met Ser Val Lys Tyr His Tyr Glu Leu Leu Asn Tyr Ile
        435                 440                 445

Asp Leu Pro Val Leu Ala Ile His Gly Lys Gln Lys Gln Asn Lys Arg
        450                 455                 460

Thr Thr Thr Phe Phe Gln Phe Cys Asn Ala Asp Ser Gly Thr Leu Leu
465                 470                 475                 480

Cys Thr Asp Val Ala Ala Arg Gly Leu Asp Ile Pro Glu Val Asp Trp
                485                 490                 495

Ile Val Gln Tyr Asp Pro Pro Asp Asp Pro Lys Glu Tyr Ile His Arg
            500                 505                 510

Val Gly Arg Thr Ala Arg Gly Leu Asn Gly Arg Gly His Ala Leu Leu
            515                 520                 525

Ile Leu Arg Pro Glu Glu Leu Gly Phe Leu Arg Tyr Leu Lys Gln Ser
        530                 535                 540

Lys Val Pro Leu Ser Glu Phe Asp Phe Ser Trp Ser Lys Ile Ser Asp
545                 550                 555                 560

Ile Gln Ser Gln Leu Glu Lys Leu Ile Glu Lys Asn Tyr Phe Leu His
            565                 570                 575

Lys Ser Ala Gln Glu Ala Tyr Lys Ser Tyr Ile Arg Ala Tyr Asp Ser
        580                 585                 590
```

His Ser Leu Lys Gln Ile Phe Asn Val Asn Leu Asn Leu Pro Gln
    595                 600                 605

Val Ala Leu Ser Phe Gly Phe Lys Val Pro Pro Phe Val Asp Leu Asn
610                 615                 620

Val Asn Ser Asn Glu Gly Lys Gln Lys Arg Gly Gly Gly Gly
625                 630                 635                 640

Phe Gly Tyr Gln Lys Thr Lys Lys Val Glu Lys Ser Lys Ile Phe Lys
                645                 650                 655

His Ile Ser Lys Lys Ser Ser Asp Ser Arg Gln Phe Ser His
            660                 665                 670

<210> SEQ ID NO 38
<211> LENGTH: 1703
<212> TYPE: DNA
<213> ORGANISM: Homo sapiens
<220> FEATURE:
<221> NAME/KEY: CDS
<222> LOCATION: (109)..(1431)

<400> SEQUENCE: 38

```
acgaggccgg ccggagcccg ggaccctgcg cggggcgctg agctcccgag cgggcagagg      60
gcacgggcag gcggacgtcg gggcgccctc ggggaacgtg cgggcacc atg cgt ccc     117
                                                   Met Arg Pro
                                                     1
```

| cac ctg tcg ccg ccg ctg cag cag cta cta ctg ccg gtg ctg ctc gcc | 165 |
|---|---|
| His Leu Ser Pro Pro Leu Gln Gln Leu Leu Leu Pro Val Leu Leu Ala | |
| 5                10                  15 | |

| tgc gcc gcg cac tcg act gga gcc ctt ccc cga cta tgt gac gtg cta | 213 |
|---|---|
| Cys Ala Ala His Ser Thr Gly Ala Leu Pro Arg Leu Cys Asp Val Leu | |
| 20                  25                  30                  35 | |

| caa gtg ctg tgg gaa gag caa gac cag tgc ctg cag gaa ctc tcc aga | 261 |
|---|---|
| Gln Val Leu Trp Glu Glu Gln Asp Gln Cys Leu Gln Glu Leu Ser Arg | |
|                 40                  45                  50 | |

| gag cag aca gga gac ctg ggc acg gag cag cca gtg cca ggt tgt gag | 309 |
|---|---|
| Glu Gln Thr Gly Asp Leu Gly Thr Glu Gln Pro Val Pro Gly Cys Glu | |
|         55                  60                  65 | |

| ggg atg tgg gac aac ata agc tgc tgg ccc tct tct gtg ccg ggc cgg | 357 |
|---|---|
| Gly Met Trp Asp Asn Ile Ser Cys Trp Pro Ser Ser Val Pro Gly Arg | |
|     70                  75                  80 | |

| atg gtg gag gtg gaa tgc ccg aga ttc ctc cgg atg ctc acc agc aga | 405 |
|---|---|
| Met Val Glu Val Glu Cys Pro Arg Phe Leu Arg Met Leu Thr Ser Arg | |
| 85                  90                  95 | |

| aat ggt tcc ttg ttc cga aac tgc aca cag gat ggc tgg tca gaa acc | 453 |
|---|---|
| Asn Gly Ser Leu Phe Arg Asn Cys Thr Gln Asp Gly Trp Ser Glu Thr | |
| 100                 105                 110                 115 | |

| ttc ccc agg cct aat ctg gcc tgt ggc gtt aat gtg aac gac tct tcc | 501 |
|---|---|
| Phe Pro Arg Pro Asn Leu Ala Cys Gly Val Asn Val Asn Asp Ser Ser | |
|                 120                 125                 130 | |

| aac gag aag cgg cac tcc tac ctg ctg aag ctg aaa gtc atg tac acc | 549 |
|---|---|
| Asn Glu Lys Arg His Ser Tyr Leu Leu Lys Leu Lys Val Met Tyr Thr | |
|         135                 140                 145 | |

| gtg ggc tac agc tcc tcc ctg gtc atg ctc ctg gtc gcc ctt ggc atc | 597 |
|---|---|
| Val Gly Tyr Ser Ser Ser Leu Val Met Leu Leu Val Ala Leu Gly Ile | |
|     150                 155                 160 | |

| ctc tgt gct ttc cgg agg ctc cac tgc act cgc aac tac atc cac atg | 645 |
|---|---|
| Leu Cys Ala Phe Arg Arg Leu His Cys Thr Arg Asn Tyr Ile His Met | |
| 165                 170                 175 | |

| cac ctg ttc gtg tcc ttc atc ctt cgt gcc ctg tcc aac ttc atc aag | 693 |
|---|---|
| His Leu Phe Val Ser Phe Ile Leu Arg Ala Leu Ser Asn Phe Ile Lys | |

```
                180                 185                 190                 195
gac gcc gtg ctc ttc tcc tca gat gat gtc acc tac tgc gat ccg cac       741
Asp Ala Val Leu Phe Ser Ser Asp Asp Val Thr Tyr Cys Asp Pro His
            200                 205                 210 agg gcg ggc tgc aag ctg gtc atg gtg ctg ttc cag tac tgc atc atg       789
Arg Ala Gly Cys Lys Leu Val Met Val Leu Phe Gln Tyr Cys Ile Met
        215                 220                 225 gcc aac tac tcc tgg ctg ctg gtg gaa ggc ctc tac ctt cac aca ctc       837
Ala Asn Tyr Ser Trp Leu Leu Val Glu Gly Leu Tyr Leu His Thr Leu
                230                 235                 240 ctc gcc atc tcc ttc ttc tct gaa aga aag tac ctc cag gga ttt gtg       885
Leu Ala Ile Ser Phe Phe Ser Glu Arg Lys Tyr Leu Gln Gly Phe Val
            245                 250                 255 gca ttc gga tgg ggt tct cca gcc att ttt gtt gct ttg tgg gct att       933
Ala Phe Gly Trp Gly Ser Pro Ala Ile Phe Val Ala Leu Trp Ala Ile
260                 265                 270                 275 gcc aga cac ttt ctg gaa gat gtt ggg tgc tgg gac atc aat gcc aac       981
Ala Arg His Phe Leu Glu Asp Val Gly Cys Trp Asp Ile Asn Ala Asn
                280                 285                 290 gca tcc atc tgg tgg atc att cgt ggt cct gtg atc ctc tcc atc ctg      1029
Ala Ser Ile Trp Trp Ile Ile Arg Gly Pro Val Ile Leu Ser Ile Leu
            295                 300                 305 att aat ttc atc ctt ttc ata aac att cta aga atc ctg atg aga aaa      1077
Ile Asn Phe Ile Leu Phe Ile Asn Ile Leu Arg Ile Leu Met Arg Lys
        310                 315                 320 ctt aga acc caa gaa aca aga gga aat gaa gtc agc cat tat aag cgc      1125
Leu Arg Thr Gln Glu Thr Arg Gly Asn Glu Val Ser His Tyr Lys Arg
325                 330                 335 ctg gcc agg tcc act ctc ctg ctg atc ccc ctc ttt ggc atc cac tac      1173
Leu Ala Arg Ser Thr Leu Leu Leu Ile Pro Leu Phe Gly Ile His Tyr
340                 345                 350                 355 atc gtc ttc gcc ttc tcc cca gag gac gct atg gag atc cag ctg ttt      1221
Ile Val Phe Ala Phe Ser Pro Glu Asp Ala Met Glu Ile Gln Leu Phe
                360                 365                 370 ttt gaa cta gcc ctt ggc tca ttc cag gga ctg gtg gtg gcc gtc ctc      1269
Phe Glu Leu Ala Leu Gly Ser Phe Gln Gly Leu Val Val Ala Val Leu
            375                 380                 385 tac tgc ttc ctc aat ggg gag gtg cag ctg gag gtt cag aag aag tgg      1317
Tyr Cys Phe Leu Asn Gly Glu Val Gln Leu Glu Val Gln Lys Lys Trp
        390                 395                 400 cag caa tgg cac ctc cgt gag ttc cca ctg cac ccc gtg gcc tcc ttc      1365
Gln Gln Trp His Leu Arg Glu Phe Pro Leu His Pro Val Ala Ser Phe
405                 410                 415 agc aac agc acc aag gcc agc cac ttg gag cag agc cag ggc acc tgc      1413
Ser Asn Ser Thr Lys Ala Ser His Leu Glu Gln Ser Gln Gly Thr Cys
420                 425                 430                 435 agg acc agc atc atc tga gaggctggag cagggtcacc cacggacaga             1461
Arg Thr Ser Ile Ile
                440 gaccaagaga ggtcctgcga aggctgggca ctgctgtggg acagccagtc ttcccagcag    1521 acaccctgtg tcctccttca gctgaagatg cccctcccca ggccttggac tcttccgaag    1581 ggatgtgagg cactgtgggg caggacaagg gcctgggatt tggttcgttt gctcttctgg    1641 gaagagaagt tcaggggtcc cagaaaggga cagggaaata aatggtgcct gggatgagat    1701 tc                                                                   1703

<210> SEQ ID NO 39
<211> LENGTH: 440
```

<212> TYPE: DNA
<213> ORGANISM: Homo sapiens

<400> SEQUENCE: 39

```
Met Arg Pro His Leu Ser Pro Pro Leu Gln Gln Leu Leu Leu Pro Val
1               5                   10                  15

Leu Leu Ala Cys Ala Ala His Ser Thr Gly Ala Leu Pro Arg Leu Cys
            20                  25                  30

Asp Val Leu Gln Val Leu Trp Glu Gln Asp Gln Cys Leu Gln Glu
        35                  40                  45

Leu Ser Arg Glu Gln Thr Gly Asp Leu Gly Thr Glu Gln Pro Val Pro
        50                  55                  60

Gly Cys Glu Gly Met Trp Asp Asn Ile Ser Cys Trp Pro Ser Ser Val
65                  70                  75                  80

Pro Gly Arg Met Val Glu Val Glu Cys Pro Arg Phe Leu Arg Met Leu
                85                  90                  95

Thr Ser Arg Asn Gly Ser Leu Phe Arg Asn Cys Thr Gln Asp Gly Trp
            100                 105                 110

Ser Glu Thr Phe Pro Arg Pro Asn Leu Ala Cys Gly Val Asn Val Asn
            115                 120                 125

Asp Ser Ser Asn Glu Lys Arg His Ser Tyr Leu Leu Lys Leu Lys Val
130                 135                 140

Met Tyr Thr Val Gly Tyr Ser Ser Ser Leu Val Met Leu Leu Val Ala
145                 150                 155                 160

Leu Gly Ile Leu Cys Ala Phe Arg Arg Leu His Cys Thr Arg Asn Tyr
                165                 170                 175

Ile His Met His Leu Phe Val Ser Phe Ile Leu Arg Ala Leu Ser Asn
            180                 185                 190

Phe Ile Lys Asp Ala Val Leu Phe Ser Ser Asp Asp Val Thr Tyr Cys
            195                 200                 205

Asp Pro His Arg Ala Gly Cys Lys Leu Val Met Val Leu Phe Gln Tyr
            210                 215                 220

Cys Ile Met Ala Asn Tyr Ser Trp Leu Leu Val Glu Gly Leu Tyr Leu
225                 230                 235                 240

His Thr Leu Leu Ala Ile Ser Phe Phe Ser Glu Arg Lys Tyr Leu Gln
                245                 250                 255

Gly Phe Val Ala Phe Gly Trp Gly Ser Pro Ala Ile Phe Val Ala Leu
            260                 265                 270

Trp Ala Ile Ala Arg His Phe Leu Glu Asp Val Gly Cys Trp Asp Ile
            275                 280                 285

Asn Ala Asn Ala Ser Ile Trp Trp Ile Ile Arg Gly Pro Val Ile Leu
            290                 295                 300

Ser Ile Leu Ile Asn Phe Ile Leu Phe Ile Asn Ile Leu Arg Ile Leu
305                 310                 315                 320

Met Arg Lys Leu Arg Thr Gln Glu Thr Arg Gly Asn Glu Val Ser His
                325                 330                 335

Tyr Lys Arg Leu Ala Arg Ser Thr Leu Leu Leu Ile Pro Leu Phe Gly
            340                 345                 350

Ile His Tyr Ile Val Phe Ala Phe Ser Pro Glu Asp Ala Met Glu Ile
            355                 360                 365

Gln Leu Phe Phe Glu Leu Ala Leu Gly Ser Phe Gln Gly Leu Val Val
            370                 375                 380

Ala Val Leu Tyr Cys Phe Leu Asn Gly Glu Val Gln Leu Glu Val Gln
385                 390                 395                 400
```

```
Lys Lys Trp Gln Gln Trp His Leu Arg Glu Phe Pro Leu His Pro Val
            405                 410                 415

Ala Ser Phe Ser Asn Ser Thr Lys Ala Ser His Leu Glu Gln Ser Gln
            420                 425                 430

Gly Thr Cys Arg Thr Ser Ile Ile
            435                 440

<210> SEQ ID NO 40
<211> LENGTH: 2943
<212> TYPE: DNA
<213> ORGANISM: Homo sapiens
<220> FEATURE:
<221> NAME/KEY: CDS
<222> LOCATION: (1016)..(2194)

<400> SEQUENCE: 40
gagctcacag acccataatc ctgcatttct ctaacaagtt gtttatggag ttgcttctcc      60
atttgcctac atcccaaaat tcacccctcc cggtttcttc tgccccctcc tgagtcccgg     120
cctgaaggag ggggagggac gcgggtgcgg cgcgggtggg ggagggcgga cccgacgcac     180
agggccagcg ccgaggcgcc ccctctccgc cagcggttga cgcccccgga ttatttatcc     240
gcaaagtccc gcgcgcgccc attgggccga ggcccgagtg tcagcgcgag tcccggctcg     300
ccattggctc cgcacacgtg cggccctgac tcacgtgctt ccggtttgaa ggcaaaaagt     360
gtgcctgggt gatttttttt ttaagcgaga gagtttgtgc aaagatccga gctgtcagag     420
atttgaaaaa aaaaaaaaaa acaaaaaaaa aaaaaccagc ccggcgctgg cggagacgcg     480
ctctccctgc aaaaaaagca aggcgattaa aggcgctgc cagcctcacg ctctgggcac      540
agctgagcgt gacactcggg gaagtcaaac ccctcactac tgcctaggaa gatggctaga     600
ctttaaatac tatttttttc cctttaagaa aaaaattatt ggagcttttt ttcttgcttt     660 cttttttcctt ttctttttct tttttttcctt catttttttg gccgtggctt actcccatt     720 taaatcaaat cattgaatct ggttgcagaa agaaaaaaga aatagccaag tgtctccata     780
tctggatgtc tacaaattag agagggagag acagcgagat ctatctgcta gataagaacg     840
agcgatccag gccagacgcc tgagcttttt tcctgcaccc gccccgtgcc ttcgctgagg     900
cttcgcctgc ctccttcctc cgcgcacccc cacgggccgc tggcaaagtg gggtggggag     960
cgaggcggtg ggggcggggg ccggcgcggc ggccggggcg gcggggcggc cgagc atg    1018
                                                              Met
                                                                1 gaa gaa cag cag ccg gaa cct aaa agt cag cgc gac tcg gcc ctc ggc    1066
Glu Glu Gln Gln Pro Glu Pro Lys Ser Gln Arg Asp Ser Ala Leu Gly
       5                   10                  15 ggc gcg gcg gcg gcg act ccg ggc ggc ctc agc ctg agc ctc agt ccg    1114
Gly Ala Ala Ala Ala Thr Pro Gly Gly Leu Ser Leu Ser Leu Ser Pro
    20                  25                  30 ggc gcc agc ggc agc agc ggc agc ggc agc gat gga gac agc gtg ccg    1162
Gly Ala Ser Gly Ser Ser Gly Ser Gly Ser Asp Gly Asp Ser Val Pro
35                  40                  45 gtg tcc ccg cag cct gcg ccc ccc tcg ccg ccc gcg gcg cct tgc ctg    1210
Val Ser Pro Gln Pro Ala Pro Pro Ser Pro Pro Ala Ala Pro Cys Leu
50                  55                  60                  65 ccg ccc ctg gcc cac cac ccg cac ctc ccc cca cac ccc ccg ccc cg    1258
Pro Pro Leu Ala His His Pro His Leu Pro Pro His Pro Pro Pro Pro
                70                  75                  80 ccg cct cag cat ctc gcg gcg cct gct cac cag ccg cag cca gcg gcc    1306
Pro Pro Gln His Leu Ala Ala Pro Ala His Gln Pro Gln Pro Ala Ala
```

```
                          85                  90                  95
cag ctg cac cgc acc acc aac ttt ttc atc gac aac atc ctg agg ccg    1354
Gln Leu His Arg Thr Thr Asn Phe Phe Ile Asp Asn Ile Leu Arg Pro
            100                 105                 110 gac ttc ggc tgc aaa aag gag cag ccg cca ccg cag ctt ctg gtg gct    1402
Asp Phe Gly Cys Lys Lys Glu Gln Pro Pro Pro Gln Leu Leu Val Ala
    115                 120                 125 gcg gcg gcc aga gga ggc gca gga gga gga ggc cgg gtc gag cgt gac    1450
Ala Ala Ala Arg Gly Gly Ala Gly Gly Gly Gly Arg Val Glu Arg Asp
130                 135                 140                 145 aga ggc cag act gcc gca ggt aga gac cct gtc cac ccg ttg ggc acc    1498
Arg Gly Gln Thr Ala Ala Gly Arg Asp Pro Val His Pro Leu Gly Thr
                150                 155                 160 cgg gcg cca ggc gct gcc tcg ctc ctg tgc gcc ccg gac gcg aac tgt    1546
Arg Ala Pro Gly Ala Ala Ser Leu Leu Cys Ala Pro Asp Ala Asn Cys
            165                 170                 175 ggc cca ccc gac ggc tcc cag cca gcc gcc gcc ggc gcg ggc gcg tct    1594
Gly Pro Pro Asp Gly Ser Gln Pro Ala Ala Ala Gly Ala Gly Ala Ser
        180                 185                 190 aaa gct ggg aac ccg gct gcg gcg gcg gcg gcc gcg gcg gca gtg         1642
Lys Ala Gly Asn Pro Ala Ala Ala Ala Ala Ala Ala Ala Ala Val
195                 200                 205 gcg gcg gcg gcg gcg gcc gca gca gcc aag ccc tcg gac acc ggt ggc    1690
Ala Ala Ala Ala Ala Ala Ala Ala Ala Lys Pro Ser Asp Thr Gly Gly
210                 215                 220                 225 ggc ggc agt gga ggc ggc gcg ggg agc ccc gga gcg cag ggc acc aaa    1738
Gly Gly Ser Gly Gly Gly Ala Gly Ser Pro Gly Ala Gln Gly Thr Lys
                230                 235                 240 tac ccg gag cac ggc aac ccg gct atc cta ctt atg ggc tca gcc aac    1786
Tyr Pro Glu His Gly Asn Pro Ala Ile Leu Leu Met Gly Ser Ala Asn
            245                 250                 255 ggc ggg ccc gtg gtc aaa act gac tcg cag cag cct ctc gta tgg ccc    1834
Gly Gly Pro Val Val Lys Thr Asp Ser Gln Gln Pro Leu Val Trp Pro
        260                 265                 270 gcc tgg gtg tac tgc aca cgt tat tcg gat cgt cca tcc tcc ggt ccg    1882
Ala Trp Val Tyr Cys Thr Arg Tyr Ser Asp Arg Pro Ser Ser Gly Pro
275                 280                 285 cgc acc agg aag ctg aag aag aag aag aac gag aag gag gac aag cgg    1930
Arg Thr Arg Lys Leu Lys Lys Lys Lys Asn Glu Lys Glu Asp Lys Arg
290                 295                 300                 305 ccg cgg acc gcg ttc acg gcc gag cag ctg cag aga ctc aag gcg gag    1978
Pro Arg Thr Ala Phe Thr Ala Glu Gln Leu Gln Arg Leu Lys Ala Glu
                310                 315                 320 ttc cag gca aac cgc tac atc acg gag cag cgg cgg cag acc ctg gcc    2026
Phe Gln Ala Asn Arg Tyr Ile Thr Glu Gln Arg Arg Gln Thr Leu Ala
            325                 330                 335 cag gaa ctc agc ctc aac gag tcc cag atc aag atc tgg ttc cag aac    2074
Gln Glu Leu Ser Leu Asn Glu Ser Gln Ile Lys Ile Trp Phe Gln Asn
        340                 345                 350 aag cgc gcc aag atc aag aaa gcc aca ggc atc aag aac ggc ctg gcg    2122
Lys Arg Ala Lys Ile Lys Lys Ala Thr Gly Ile Lys Asn Gly Leu Ala
355                 360                 365 ctg cac ctc atg gcc cag gga ctg tac aac cac tcc acc acc acg gtc    2170
Leu His Leu Met Ala Gln Gly Leu Tyr Asn His Ser Thr Thr Thr Val
370                 375                 380                 385 cag gac aaa gac gag agc gag tag ccgccacagg ccggggccgc gcccgcgccc   2224
Gln Asp Lys Asp Glu Ser Glu
                390 cctcccggca ccgccgccgt cgtctcccgg cccctcgctg ggggagaaag catctgctcc  2284
```

-continued

```
aaggagggag ggagcgcagg gaaaagagcg agagagacag aaagagagcc tcagaatgga    2344
caatgacgtt gaaacgcagc attttttgaaa agggagaaag actcggacag gtgctatcga  2404
aaaataagat ccattctcta ttcccagtat aagggacgaa actgcgaact ccttaaagct   2464
ctatctagcc aaaccgctta cgaccttgta tatatttaat ttcaggtaag gaaaacacat   2524
acgtgtagcg atctctattt gctggacatt tttattaatc tcctttatta ttattgttat   2584
aattattata attattataa ttattttatg gccctccccc accgcctcgc tgccccgcc    2644 cagtttcgtt ttcgttgcct ttttcatttg aatgtcattg cttctccggt gcctcccgac   2704
ccgcatcgcc ggccctggtt tctctgggac ttttctttgt gtgcgagagt gtgtttcctt   2764
tcgtgtctgc ccacctcttc tcccccacct cccgggtccc ttctgtcggt ctgtctgttc   2824
tgccccccct tcgttttccg gagacttgtt gagaaatacg accccacaga ctgcgagact   2884
gaaccgccgc tacaagccaa agattttatt atgttcagaa acctgtagtc tgaaataaa    2943
```

<210> SEQ ID NO 41
<211> LENGTH: 392
<212> TYPE: DNA
<213> ORGANISM: Homo sapiens

<400> SEQUENCE: 41

```
Met Glu Glu Gln Gln Pro Glu Pro Lys Ser Gln Arg Asp Ser Ala Leu
 1               5                  10                  15

Gly Gly Ala Ala Ala Thr Pro Gly Gly Leu Ser Leu Ser Leu Ser
             20                  25                  30

Pro Gly Ala Ser Gly Ser Ser Gly Ser Gly Ser Asp Gly Asp Ser Val
         35                  40                  45

Pro Val Ser Pro Gln Pro Ala Pro Pro Ser Pro Pro Ala Ala Pro Cys
     50                  55                  60

Leu Pro Pro Leu Ala His His Pro His Leu Pro His Pro Pro Pro
 65                  70                  75                  80

Pro Pro Pro Gln His Leu Ala Ala Pro Ala His Gln Pro Gln Pro Ala
                 85                  90                  95

Ala Gln Leu His Arg Thr Thr Asn Phe Phe Ile Asp Asn Ile Leu Arg
            100                 105                 110

Pro Asp Phe Gly Cys Lys Lys Glu Gln Pro Pro Gln Leu Leu Val
        115                 120                 125

Ala Ala Ala Ala Arg Gly Gly Ala Gly Gly Gly Arg Val Glu Arg
    130                 135                 140

Asp Arg Gly Gln Thr Ala Ala Gly Arg Asp Pro Val His Pro Leu Gly
145                 150                 155                 160

Thr Arg Ala Pro Gly Ala Ala Ser Leu Leu Cys Ala Pro Asp Ala Asn
                165                 170                 175

Cys Gly Pro Pro Asp Gly Ser Gln Pro Ala Ala Gly Ala Gly Ala
            180                 185                 190

Ser Lys Ala Gly Asn Pro Ala Ala Ala Ala Ala Ala Ala Ala
        195                 200                 205

Val Ala Ala Ala Ala Ala Ala Ala Ala Lys Pro Ser Asp Thr Gly
    210                 215                 220

Gly Gly Gly Ser Gly Gly Gly Ala Gly Ser Pro Gly Ala Gln Gly Thr
225                 230                 235                 240

Lys Tyr Pro Glu His Gly Asn Pro Ala Ile Leu Leu Met Gly Ser Ala
                245                 250                 255
```

```
Asn Gly Gly Pro Val Val Lys Thr Asp Ser Gln Gln Pro Leu Val Trp
            260                 265                 270

Pro Ala Trp Val Tyr Cys Thr Arg Tyr Ser Asp Arg Pro Ser Ser Gly
        275                 280                 285

Pro Arg Thr Arg Lys Leu Lys Lys Lys Asn Glu Lys Glu Asp Lys
    290                 295                 300

Arg Pro Arg Thr Ala Phe Thr Ala Glu Gln Leu Gln Arg Leu Lys Ala
305                 310                 315                 320

Glu Phe Gln Ala Asn Arg Tyr Ile Thr Glu Gln Arg Arg Gln Thr Leu
                325                 330                 335

Ala Gln Glu Leu Ser Leu Asn Glu Ser Gln Ile Lys Ile Trp Phe Gln
            340                 345                 350

Asn Lys Arg Ala Lys Ile Lys Lys Ala Thr Gly Ile Lys Asn Gly Leu
        355                 360                 365

Ala Leu His Leu Met Ala Gln Gly Leu Tyr Asn His Ser Thr Thr Thr
    370                 375                 380

Val Gln Asp Lys Asp Glu Ser Glu
385                 390

<210> SEQ ID NO 42
<211> LENGTH: 3408
<212> TYPE: DNA
<213> ORGANISM: Homo sapiens
<220> FEATURE:
<221> NAME/KEY: CDS
<222> LOCATION: (236)..(922)

<400> SEQUENCE: 42
cctttggacg cgcgcctcgg ttccgaacgc agcggacggc gcctcaggca gcgcggcgga      60
cagcccgtcc tccggcgcgc cgcgagcctc ggaggaccct agcgacggtc gtggcgtaag     120
accgggggga cgcggcggta gcggcggccg ttgcgattga ttgcgctggt tgcctgcggc     180
gtccacttcc ttggccgccc ttgctacact ggctgattgt tgtgcagccg cgcgcc atg    238
                                                              Met
                                                                1 tct gtg agc gag atc ttc gtg gag ctg cag ggc ttt ttg gct gcc gag      286
Ser Val Ser Glu Ile Phe Val Glu Leu Gln Gly Phe Leu Ala Ala Glu
      5                  10                  15 cag gac atc cga gag gaa atc aga aaa gtt gta cag agt tta gaa caa      334
Gln Asp Ile Arg Glu Glu Ile Arg Lys Val Val Gln Ser Leu Glu Gln
 20                  25                  30 aca gct cga gag att tta act cta ctg caa ggg gtc cat cag ggt gct      382
Thr Ala Arg Glu Ile Leu Thr Leu Leu Gln Gly Val His Gln Gly Ala
 35                  40                  45 ggg ttt cag gac att cca aag agg tgt ttg aaa gct cga gaa cat ttt      430
Gly Phe Gln Asp Ile Pro Lys Arg Cys Leu Lys Ala Arg Glu His Phe
 50                  55                  60                  65 ggt aca gta aaa aca cat cta aca tct ttg aag acc aaa ttt cct gct      478
Gly Thr Val Lys Thr His Leu Thr Ser Leu Lys Thr Lys Phe Pro Ala
             70                  75                  80 gaa cag tat tac aga ttt cat gag cac tgg agg ttt gtg ttg cag cgc      526
Glu Gln Tyr Tyr Arg Phe His Glu His Trp Arg Phe Val Leu Gln Arg
         85                  90                  95 ttg gtc ttc ttg gca gca ttt gtt gtg tat ttg gaa aca gaa aca cta      574
Leu Val Phe Leu Ala Ala Phe Val Val Tyr Leu Glu Thr Glu Thr Leu
    100                 105                 110 gtg act cga gaa gca gtt aca gaa att ctt ggc att gag cca gat cgg      622
Val Thr Arg Glu Ala Val Thr Glu Ile Leu Gly Ile Glu Pro Asp Arg
115                 120                 125
```

```
gag aaa gga ttt cat ctg gat gta gaa gat tat ctc tca gga gtt cta      670
Glu Lys Gly Phe His Leu Asp Val Glu Asp Tyr Leu Ser Gly Val Leu
130                 135                 140                 145 att ctt gcc agt gaa ctg tcg agg ctg tct gtc aac agc gtg act gct      718
Ile Leu Ala Ser Glu Leu Ser Arg Leu Ser Val Asn Ser Val Thr Ala
            150                 155                 160 gga gac tac tcc cga ccc ctc cac atc tcc acc ttc atc aat gag ctg      766
Gly Asp Tyr Ser Arg Pro Leu His Ile Ser Thr Phe Ile Asn Glu Leu
        165                 170                 175 gat tcc ggt ttt cgc ctt ctc aac ctg aaa aat gac tcc ctg agg aag      814
Asp Ser Gly Phe Arg Leu Leu Asn Leu Lys Asn Asp Ser Leu Arg Lys
    180                 185                 190 cgc tac gac gga ttg aaa tat gac gtg aag aaa gta gag gaa gtg gtc      862
Arg Tyr Asp Gly Leu Lys Tyr Asp Val Lys Lys Val Glu Glu Val Val
195                 200                 205 tat gat ctc tcc atc cgg ggc ttt aat aag gag acg gca gca gct tgt      910
Tyr Asp Leu Ser Ile Arg Gly Phe Asn Lys Glu Thr Ala Ala Ala Cys
210                 215                 220                 225 gtt gaa aaa tag gaggctctcc ttgctcctgg ccttgctgac ctcagcggtt          962
Val Glu Lys gccaggaagg ggtgagcaca gagtgcctct tacggtagtt aggatgctca gttgctaaac   1022
actgcgcttt attttcttaa ccagttgtgg tgtgagtatc agaattgaaa cacttttttg   1082
ggggtaaaaa atatagcctt tacatggaca gaattttttt tgttgtttca gtgaatatgc   1142
ctgtaattca gtgtatttca gttccgtcag aaagtgtaaa tgttagtttc ttggtaaagt   1202
ccttttcttg cttaccttga ctgttgatgt actgattgag aagttcattg tctcgtttgt   1262
gattcttcca gatgtgatgc ttgatatttt ctatatgcga gttagccatc cacacccagg   1322
catagcctgg atacagtata aaatagata attaaaaaga tggttgccaa gcaaggaaaa    1382
cttattttat attttcccctt ccttatttta agcattgtga gtaaatcaga tgttgaattc   1442
ttttgccaag ggaattatag ctgcaggttc tctctcactg ccatcaaact gtaaaagatt   1502
aaactgcgaa gtcaagctca acagattatt ttggaaagtt tttgtattaa gggatttagt   1562
aacatcattt tgttttccac caggcaggga gtagggctta gtgttttaaa acacctctgc   1622
tttctgatgt tgccttaata ttctgctatt gcagcaatta aaaattgtct tcatgtacat   1682
ttggaactaa cacgtgatgt gatatattcc taaactatga aaccttttttc ctagtagtca   1742
gctagatcat ttgttctggg agtataaagc cacccacgta agttaataag caaaatcctg   1802
actattatgt tgttagagaa aaatgctttg ctttgtctgg aagaaagata aaatagtgaa    1862
ttataaataa gtcaggccgg gcgtggtggc tcacacctgt aatcccagca cactgggagg   1922
ccgaggcagg gggactgctt gagctcagga gttcgagacc agcctgggca acaaagtgag   1982
actccatctc tatataaaaa caaaaccac gaaagcacac acaaaataaa tcagtgggat    2042
ttggtaatgt gttttagagt aagaaatttc aggttgttgg tgactatccc aacagtcatg   2102
ttttaaatgt acagtttggg gcaagtcatg taaatactgt tggtggtctt ccccacacgc   2162
cccaattttc aggtagtact aagagtatgt gccaggaaac tcttgctatt gaattgagat   2222
gattaaaatg gtgacttaat ccgtagttat tttgcaccca ctgaaaggaa agtgcttttcc   2282
agaataatat gaagtatcta aaagtgtcac cttttcttgc ctgatcaaca atttgggctt   2342
cctgtttgta caaggggcca tttggcatac cttcacagc ttttatcagg ccaagttaaa    2402
ggctgactac atttttcat catgaggaaa gcagttgaaa tgaggcatga gttactgtgc    2462
attgggattt tagaacaatt tcttgtgac agctctttt gtgaagttag gttcttaaaa     2522
```

| | | | | |
|---|---|---|---|---|
| gtgcccatga tggtcactta aaatgtgcag taatagcact gccaggatca agcatgaaag | 2582 |
| gcttttaaat tagatcatcc cacagacaat acgtttgata atagttttt cttttaacct | 2642 |
| ctttaagtat tgattctgct tgagaatatt gaagtacttg ccagaagttg tggatttcag | 2702 |
| ttttaacaaa tgctattaaa gtggagaagc acactctggt cttggaattc catttgagga | 2762 |
| tttagaagtg tcatgtttat aactattcag ttgtgtttgt tgctggcttg ttgtaaagca | 2822 |
| ataaatttt tttggtcttt ttgtaagtga gtgtgctgct gtaagaaatc tcccatgtgc | 2882 |
| ataacaaatt ctgaatattt tttgaggcta agaagaccg gggtgacaag cagatactgc | 2942 |
| tgtgtaatgg ttacactaac caaaagacac cagccactca gagttctata ctgtaaagcg | 3002 |
| cagataacat ttgtgtgtta taccttgatt ggggaattaa aagtcattta actgaagatg | 3062 |
| ttgagaaacc tgggctctgg ttttagtata ccggaattac tttttccaa ttttagaaaa | 3122 |
| tcaagcaggt tagagaaaat agagatgaat taggggacac tgtcttatgg attcatttat | 3182 |
| aagaagagaa ccagccatat acacttgggg agatttgcca catcttaaac ttgaataata | 3242 |
| gtatgagtaa tgcttaaggg agtttaatag agaaggaaag ctttggcagt gttttgagaa | 3302 |
| cttaagtggc taaagagatg agacaaacat gcaggtcgct actggcatag tttcataatt | 3362 |
| gtgtactcgg aaattaaagt ttgcttgttt cttggtctgg attaaa | 3408 |

<210> SEQ ID NO 43
<211> LENGTH: 228
<212> TYPE: DNA
<213> ORGANISM: Homo sapiens

<400> SEQUENCE: 43

```
Met Ser Val Ser Glu Ile Phe Val Glu Leu Gln Gly Phe Leu Ala Ala
1               5                   10                  15

Glu Gln Asp Ile Arg Glu Ile Arg Lys Val Val Gln Ser Leu Glu
            20                  25                  30

Gln Thr Ala Arg Glu Ile Leu Thr Leu Leu Gln Gly Val His Gln Gly
        35                  40                  45

Ala Gly Phe Gln Asp Ile Pro Lys Arg Cys Leu Lys Ala Arg Glu His
    50                  55                  60

Phe Gly Thr Val Lys Thr His Leu Thr Ser Leu Lys Thr Lys Phe Pro
65                  70                  75                  80

Ala Glu Gln Tyr Tyr Arg Phe His Glu His Trp Arg Phe Val Leu Gln
                85                  90                  95

Arg Leu Val Phe Leu Ala Ala Phe Val Val Tyr Leu Glu Thr Glu Thr
            100                 105                 110

Leu Val Thr Arg Glu Ala Val Thr Glu Ile Leu Gly Ile Glu Pro Asp
        115                 120                 125

Arg Glu Lys Gly Phe His Leu Asp Val Glu Asp Tyr Leu Ser Gly Val
    130                 135                 140

Leu Ile Leu Ala Ser Glu Leu Ser Arg Leu Ser Val Asn Ser Val Thr
145                 150                 155                 160

Ala Gly Asp Tyr Ser Arg Pro Leu His Ile Ser Thr Phe Ile Asn Glu
                165                 170                 175

Leu Asp Ser Gly Phe Arg Leu Leu Asn Leu Lys Asn Asp Ser Leu Arg
            180                 185                 190

Lys Arg Tyr Asp Gly Leu Lys Tyr Asp Val Lys Lys Val Glu Glu Val
        195                 200                 205

Val Tyr Asp Leu Ser Ile Arg Gly Phe Asn Lys Glu Thr Ala Ala Ala
```

```
                210                 215                 220
Cys Val Glu Lys
225

<210> SEQ ID NO 44
<211> LENGTH: 987
<212> TYPE: DNA
<213> ORGANISM: Homo sapiens
<220> FEATURE:
<221> NAME/KEY: CDS
<222> LOCATION: (41)..(511)

<400> SEQUENCE: 44
cggagagggg gagaacagac aacgggcggc ggggagcagc atg gag ccg gcg gcg         55
                                            Met Glu Pro Ala Ala
                                            1               5 ggg agc agc atg gag cct tcg gct gac tgg ctg gcc acg gcc gcg gcc        103
Gly Ser Ser Met Glu Pro Ser Ala Asp Trp Leu Ala Thr Ala Ala Ala
            10                  15                  20 cgg ggt cgg gta gag gag gtg cgg gcg ctg ctg gag gcg ggg gcg ctg        151
Arg Gly Arg Val Glu Glu Val Arg Ala Leu Leu Glu Ala Gly Ala Leu
        25                  30                  35 ccc aac gca ccg aat agt tac ggt cgg agg ccg atc cag gtc atg atg        199
Pro Asn Ala Pro Asn Ser Tyr Gly Arg Arg Pro Ile Gln Val Met Met
    40                  45                  50 atg ggc agc gcc cga gtg gcg gag ctg ctg ctc cac ggc gcg gag           247
Met Gly Ser Ala Arg Val Ala Glu Leu Leu Leu Leu His Gly Ala Glu
55                  60                  65 ccc aac tgc gcc gac ccc gcc act ctc acc cga ccc gtg cac gac gct        295
Pro Asn Cys Ala Asp Pro Ala Thr Leu Thr Arg Pro Val His Asp Ala
70                  75                  80                  85 gcc cgg gag ggc ttc ctg gac acg ctg gtg gtg ctg cac cgg gcc ggg        343
Ala Arg Glu Gly Phe Leu Asp Thr Leu Val Val Leu His Arg Ala Gly
                90                  95                  100 gcg cgg ctg gac gtg cgc gat gcc tgg ggc cgt ctg ccc gtg gac ctg        391
Ala Arg Leu Asp Val Arg Asp Ala Trp Gly Arg Leu Pro Val Asp Leu
            105                 110                 115 gct gag gag ctg ggc cat cgc gat gtc gca cgg tac ctg cgc gcg gct        439
Ala Glu Glu Leu Gly His Arg Asp Val Ala Arg Tyr Leu Arg Ala Ala
        120                 125                 130 gcg ggg ggc acc aga ggc agt aac cat gcc cgc ata gat gcc gcg gaa        487
Ala Gly Gly Thr Arg Gly Ser Asn His Ala Arg Ile Asp Ala Ala Glu
    135                 140                 145 ggt ccc tca gac atc ccc gat tga aagaaccaga gaggctctga gaaacctcgg       541
Gly Pro Ser Asp Ile Pro Asp
150                 155 gaaacttaga tcatcagtca ccgaaggtcc tacagggcca caactgcccc cgccacaacc      601 cacccccgctt tcgtagtttt catttagaaa atagagcttt taaaaatgtc ctgccttta     661 acgtagatat aagccttccc ccactaccgt aaatgtccat ttatatcatt ttttatatat     721
tcttataaaa atgtaaaaaa gaaaacacc gcttctgcct tttcactgtg ttggagtttt      781
ctggagtgag cactcacgcc ctaagcgcac attcatgtgg gcatttcttg cgagcctcgc      841
agcctccgga agctgtcgac ttcatgacaa gcattttgtg aactagggaa gctcagggggg     901 gttactggct tctcttgagt cacactgcta gcaaatggca gaaccaaagc tcaaataaaa      961
ataaaataat tttcattcat tcactc                                          987

<210> SEQ ID NO 45
<211> LENGTH: 156
```

```
<212> TYPE: DNA
<213> ORGANISM: Homo sapiens

<400> SEQUENCE: 45

Met Glu Pro Ala Ala Gly Ser Ser Met Glu Pro Ser Ala Asp Trp Leu
1               5                   10                  15

Ala Thr Ala Ala Ala Arg Gly Arg Val Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
        50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
        130                 135                 140

Ile Asp Ala Ala Glu Gly Pro Ser Asp Ile Pro Asp
145                 150                 155

<210> SEQ ID NO 46
<211> LENGTH: 495
<212> TYPE: DNA
<213> ORGANISM: Homo sapiens
<220> FEATURE:
<221> NAME/KEY: CDS
<222> LOCATION: (1)..(495)

<400> SEQUENCE: 46 atg tca gaa ccg gct ggg gat gtc cgt cag aac cca tgc ggc agc aag      48
Met Ser Glu Pro Ala Gly Asp Val Arg Gln Asn Pro Cys Gly Ser Lys
1               5                   10                  15 gcc tgc cgc cgc ctc ttc ggc cca gtg gac agc gag cag ctg agc cgc      96
Ala Cys Arg Arg Leu Phe Gly Pro Val Asp Ser Glu Gln Leu Ser Arg
            20                  25                  30 gac tgt gat gcg cta atg gcg ggc tgc atc cag gag gcc cgt gag cga     144
Asp Cys Asp Ala Leu Met Ala Gly Cys Ile Gln Glu Ala Arg Glu Arg
        35                  40                  45 tgg aac ttc gac ttt gtc acc gag aca cca ctg gag ggt gac ttc gcc     192
Trp Asn Phe Asp Phe Val Thr Glu Thr Pro Leu Glu Gly Asp Phe Ala
    50                  55                  60 tgg gag cgt gtg cgg ggc ctt ggc ctg ccc aag ctc tac ctt ccc acg     240
Trp Glu Arg Val Arg Gly Leu Gly Leu Pro Lys Leu Tyr Leu Pro Thr
65                  70                  75                  80 ggg ccc cgg cga ggc cgg gat gag ttg gga gga ggc agg cgg cct ggc     288
Gly Pro Arg Arg Gly Arg Asp Glu Leu Gly Gly Gly Arg Arg Pro Gly
                85                  90                  95 acc tca cct gct ctg ctg cag ggg aca gca gag gaa gac cat gtg gac     336
Thr Ser Pro Ala Leu Leu Gln Gly Thr Ala Glu Glu Asp His Val Asp
            100                 105                 110 ctg tca ctg tct tgt acc ctt gtg cct cgc tca ggg gag cag gct gaa     384
Leu Ser Leu Ser Cys Thr Leu Val Pro Arg Ser Gly Glu Gln Ala Glu
        115                 120                 125 ggg tcc cca ggt gga cct gga gac tct cag ggt cga aaa cgg cgg cag     432
```

```
Gly Ser Pro Gly Gly Pro Gly Asp Ser Gln Gly Arg Lys Arg Gln
            130                 135                 140 acc agc atg aca gat ttc tac cac tcc aaa cgc cgg ctg atc ttc tcc    480
Thr Ser Met Thr Asp Phe Tyr His Ser Lys Arg Arg Leu Ile Phe Ser
145                 150                 155                 160 aag agg aag ccc tag                                                495
Lys Arg Lys Pro <210> SEQ ID NO 47
<211> LENGTH: 164
<212> TYPE: DNA
<213> ORGANISM: Homo sapiens

<400> SEQUENCE: 47

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Gln
    130                 135                 140

Thr Ser Met Thr Asp Phe Tyr His Ser Lys Arg Arg Leu Ile Phe Ser
145                 150                 155                 160

Lys Arg Lys Pro

<210> SEQ ID NO 48
<211> LENGTH: 1712
<212> TYPE: DNA
<213> ORGANISM: Homo sapiens
<220> FEATURE:
<221> NAME/KEY: CDS
<222> LOCATION: (1)..(1563)

<400> SEQUENCE: 48 atg aga aat aag aaa att ctc aag gag gac gag ctc ttg agt gag acc    48
Met Arg Asn Lys Lys Ile Leu Lys Glu Asp Glu Leu Leu Ser Glu Thr
1               5                   10                  15 caa caa gct gct ttt cac caa att gca atg gag cct ttc gaa atc aat    96
Gln Gln Ala Ala Phe His Gln Ile Ala Met Glu Pro Phe Glu Ile Asn
            20                  25                  30 gtt cca aag ccc aag agg aga aat ggg gtg aac ttc tcc cta gct gtg    144
Val Pro Lys Pro Lys Arg Arg Asn Gly Val Asn Phe Ser Leu Ala Val
        35                  40                  45 gtg gtc atc tac ctg atc ctc ctc acc gct ggc gct ggg ctg ctg gtg    192
Val Val Ile Tyr Leu Ile Leu Leu Thr Ala Gly Ala Gly Leu Leu Val
    50                  55                  60 gtc caa gtt ctg aat ctg cag gcg cgg ctc cgg gtc ctg gag atg tat    240
Val Gln Val Leu Asn Leu Gln Ala Arg Leu Arg Val Leu Glu Met Tyr
```

-continued

```
             65                  70                  75                  80 ttc ctc aat gac act ctg gcg gct gag gac agc ccg tcc ttc tcc ttg        288
Phe Leu Asn Asp Thr Leu Ala Ala Glu Asp Ser Pro Ser Phe Ser Leu
                    85                  90                  95 ctg cag tca gca cac cct gga gaa cac ctg gct cag ggt gca tcg agg        336
Leu Gln Ser Ala His Pro Gly Glu His Leu Ala Gln Gly Ala Ser Arg
            100                 105                 110 ctg caa gtc ctg cag gcc caa ctc acc tgg gtc cgc gtc agc cat gag        384
Leu Gln Val Leu Gln Ala Gln Leu Thr Trp Val Arg Val Ser His Glu
        115                 120                 125 cac ttg ctg cag cgg gta gac aac ttc act cag aac cca ggg atg ttc        432
His Leu Leu Gln Arg Val Asp Asn Phe Thr Gln Asn Pro Gly Met Phe
    130                 135                 140 aga atc aaa ggt gaa caa ggc gcc cca ggt ctt caa ggt cac aag ggg        480
Arg Ile Lys Gly Glu Gln Gly Ala Pro Gly Leu Gln Gly His Lys Gly
145                 150                 155                 160 gcc atg ggc atg cct ggt gcc cct ggc ccg ccg gga cca cct gct gag        528
Ala Met Gly Met Pro Gly Ala Pro Gly Pro Pro Gly Pro Pro Ala Glu
                    165                 170                 175 aag gga gcc aag ggg gct atg gga cga gat gga gca aca ggc ccc tcg        576
Lys Gly Ala Lys Gly Ala Met Gly Arg Asp Gly Ala Thr Gly Pro Ser
            180                 185                 190 gga ccc caa ggc cca ccg gga gtc aag gga gag gcg ggc ctc caa gga        624
Gly Pro Gln Gly Pro Pro Gly Val Lys Gly Glu Ala Gly Leu Gln Gly
        195                 200                 205 ccc cag ggt gct cca ggg aag caa gga gcc act ggc acc cca gga ccc        672
Pro Gln Gly Ala Pro Gly Lys Gln Gly Ala Thr Gly Thr Pro Gly Pro
    210                 215                 220 caa gga gag aag ggc agc aaa ggc gat ggg ggt ctc att ggc cca aaa        720
Gln Gly Glu Lys Gly Ser Lys Gly Asp Gly Gly Leu Ile Gly Pro Lys
225                 230                 235                 240 ggg gaa act gga act aag gga gag aaa gga gac ctg ggt ctc cca gga        768
Gly Glu Thr Gly Thr Lys Gly Glu Lys Gly Asp Leu Gly Leu Pro Gly
                    245                 250                 255 agc aaa ggg gac agg ggc atg aaa gga gat gca ggg gtc atg ggg cct        816
Ser Lys Gly Asp Arg Gly Met Lys Gly Asp Ala Gly Val Met Gly Pro
            260                 265                 270 cct gga gcc cag ggg agt aaa ggt gac ttc ggg agg cca ggc cca cca        864
Pro Gly Ala Gln Gly Ser Lys Gly Asp Phe Gly Arg Pro Gly Pro Pro
        275                 280                 285 ggt ttg gct ggt ttt cct gga gct aaa gga gat caa gga caa cct gga        912
Gly Leu Ala Gly Phe Pro Gly Ala Lys Gly Asp Gln Gly Gln Pro Gly
    290                 295                 300 ctg cag ggt gtt ccg ggc cct cct ggt gca gtg gga cac cca ggt gcc        960
Leu Gln Gly Val Pro Gly Pro Pro Gly Ala Val Gly His Pro Gly Ala
305                 310                 315                 320 aag ggt gag cct ggc agt gct ggc tcc cct ggg cga gca gga ctt cca       1008
Lys Gly Glu Pro Gly Ser Ala Gly Ser Pro Gly Arg Ala Gly Leu Pro
                    325                 330                 335 ggg agc ccc ggg agt cca gga gcc aca ggc ctg aaa gga agc aaa ggg       1056
Gly Ser Pro Gly Ser Pro Gly Ala Thr Gly Leu Lys Gly Ser Lys Gly
            340                 345                 350 gac aca gga ctt caa gga cag caa gga aga aaa gga gaa tca gga gtt       1104
Asp Thr Gly Leu Gln Gly Gln Gln Gly Arg Lys Gly Glu Ser Gly Val
        355                 360                 365 cca ggc cct gca ggt gtg aag gga gaa cag ggg agc cca ggg ctg gca       1152
Pro Gly Pro Ala Gly Val Lys Gly Glu Gln Gly Ser Pro Gly Leu Ala
    370                 375                 380 ggt ccc aag gga gcc cct gga caa gct ggc cag aag gga gac cag gga       1200
Gly Pro Lys Gly Ala Pro Gly Gln Ala Gly Gln Lys Gly Asp Gln Gly
```

```
               Gly Pro Lys Gly Ala Pro Gly Gln Ala Gly Gln Lys Gly Asp Gln Gly
               385                 390                 395                 400 gtg aaa gga tct tct ggg gag caa gga gta aag gga gaa aaa ggt gaa        1248
Val Lys Gly Ser Ser Gly Glu Gln Gly Val Lys Gly Glu Lys Gly Glu
            405                 410                 415 aga ggt gaa aac tca gtg tcc gtc agg att gtc ggc agt agt aac cga        1296
Arg Gly Glu Asn Ser Val Ser Val Arg Ile Val Gly Ser Ser Asn Arg
        420                 425                 430 ggc cgg gct gaa gtt tac tac agt ggt acc tgg ggg aca att tgc gat        1344
Gly Arg Ala Glu Val Tyr Tyr Ser Gly Thr Trp Gly Thr Ile Cys Asp
    435                 440                 445 gac gag tgg caa aat tct gat gcc att gtc ttc tgc cgc atg ctg ggt        1392
Asp Glu Trp Gln Asn Ser Asp Ala Ile Val Phe Cys Arg Met Leu Gly
450                 455                 460 tac tcc aaa gga agg gcc ctg tac aaa gtg gga gct ggc act ggg cag        1440
Tyr Ser Lys Gly Arg Ala Leu Tyr Lys Val Gly Ala Gly Thr Gly Gln
465                 470                 475                 480 atc tgg ctg gat aat gtt cag tgt cgg ggc acg gag agt acc ctg tgg        1488
Ile Trp Leu Asp Asn Val Gln Cys Arg Gly Thr Glu Ser Thr Leu Trp
                485                 490                 495 agc tgc acc aag aat agc tgg ggc cat cat gac tgc agc cac gag gag        1536
Ser Cys Thr Lys Asn Ser Trp Gly His His Asp Cys Ser His Glu Glu
            500                 505                 510 gac gca ggc gtg gag tgc agc gtc tga cccggaaacc ctttcacttc              1583
Asp Ala Gly Val Glu Cys Ser Val
        515                 520 tctgctcccg aggtgtcctc gggctcatat gtgggaaggc agaggatctc tgaggagttc      1643
cctggggaca actgagcagc ctctggagag gggccattaa taaagctcaa catcaaaaaa      1703
accggaatt                                                              1712

<210> SEQ ID NO 49
<211> LENGTH: 520
<212> TYPE: DNA
<213> ORGANISM: Homo sapiens

<400> SEQUENCE: 49

Met Arg Asn Lys Lys Ile Leu Lys Glu Asp Glu Leu Leu Ser Glu Thr
1               5                   10                  15

Gln Gln Ala Ala Phe His Gln Ile Ala Met Glu Pro Phe Glu Ile Asn
            20                  25                  30

Val Pro Lys Pro Lys Arg Arg Asn Gly Val Asn Phe Ser Leu Ala Val
        35                  40                  45

Val Val Ile Tyr Leu Ile Leu Leu Thr Ala Gly Ala Gly Leu Leu Val
    50                  55                  60

Val Gln Val Leu Asn Leu Gln Ala Arg Leu Arg Val Leu Glu Met Tyr
65                  70                  75                  80

Phe Leu Asn Asp Thr Leu Ala Ala Glu Asp Ser Pro Ser Phe Ser Leu
                85                  90                  95

Leu Gln Ser Ala His Pro Gly Glu His Leu Ala Gln Gly Ala Ser Arg
            100                 105                 110

Leu Gln Val Leu Gln Ala Gln Leu Thr Trp Val Arg Val Ser His Glu
        115                 120                 125

His Leu Leu Gln Arg Val Asp Asn Phe Thr Gln Asn Pro Gly Met Phe
    130                 135                 140

Arg Ile Lys Gly Glu Gln Gly Ala Pro Gly Leu Gln Gly His Lys Gly
145                 150                 155                 160
```

```
Ala Met Gly Met Pro Gly Ala Pro Gly Pro Gly Pro Pro Gly Pro Ala Glu
            165                 170                 175
Lys Gly Ala Lys Gly Ala Met Gly Arg Asp Gly Ala Thr Gly Pro Ser
        180                 185                 190
Gly Pro Gln Gly Pro Pro Gly Val Lys Gly Glu Ala Gly Leu Gln Gly
    195                 200                 205
Pro Gln Gly Ala Pro Gly Lys Gln Gly Ala Thr Gly Thr Pro Gly Pro
210                 215                 220
Gln Gly Glu Lys Gly Ser Lys Gly Asp Gly Leu Ile Gly Pro Lys
225                 230                 235                 240
Gly Glu Thr Gly Thr Lys Gly Glu Lys Gly Asp Leu Gly Leu Pro Gly
                245                 250                 255
Ser Lys Gly Asp Arg Gly Met Lys Gly Asp Ala Gly Val Met Gly Pro
            260                 265                 270
Pro Gly Ala Gln Gly Ser Lys Gly Asp Phe Gly Arg Pro Gly Pro Pro
        275                 280                 285
Gly Leu Ala Gly Phe Pro Gly Ala Lys Gly Asp Gln Gly Gln Pro Gly
    290                 295                 300
Leu Gln Gly Val Pro Gly Pro Pro Gly Ala Val Gly His Pro Gly Ala
305                 310                 315                 320
Lys Gly Glu Pro Gly Ser Ala Gly Ser Pro Gly Arg Ala Gly Leu Pro
                325                 330                 335
Gly Ser Pro Gly Ser Pro Gly Ala Thr Gly Leu Lys Gly Ser Lys Gly
            340                 345                 350
Asp Thr Gly Leu Gln Gly Gln Gly Arg Lys Gly Glu Ser Gly Val
        355                 360                 365
Pro Gly Pro Ala Gly Val Lys Gly Glu Gln Gly Ser Pro Gly Leu Ala
    370                 375                 380
Gly Pro Lys Gly Ala Pro Gly Gln Ala Gly Gln Lys Gly Asp Gln Gly
385                 390                 395                 400
Val Lys Gly Ser Ser Gly Glu Gln Gly Val Lys Gly Glu Lys Gly Glu
                405                 410                 415
Arg Gly Glu Asn Ser Val Ser Val Arg Ile Val Gly Ser Ser Asn Arg
            420                 425                 430
Gly Arg Ala Glu Val Tyr Tyr Ser Gly Thr Trp Gly Thr Ile Cys Asp
        435                 440                 445
Asp Glu Trp Gln Asn Ser Asp Ala Ile Val Phe Cys Arg Met Leu Gly
    450                 455                 460
Tyr Ser Lys Gly Arg Ala Leu Tyr Lys Val Gly Ala Gly Thr Gly Gln
465                 470                 475                 480
Ile Trp Leu Asp Asn Val Gln Cys Arg Gly Thr Glu Ser Thr Leu Trp
                485                 490                 495
Ser Cys Thr Lys Asn Ser Trp Gly His His Asp Cys Ser His Glu Glu
            500                 505                 510
Asp Ala Gly Val Glu Cys Ser Val
        515                 520

<210> SEQ ID NO 50
<211> LENGTH: 3963
<212> TYPE: DNA
<213> ORGANISM: Homo sapiens
<220> FEATURE:
<221> NAME/KEY: CDS
<222> LOCATION: (772)..(3552)

<400> SEQUENCE: 50
```

-continued

```
cctgcgtgtc cctctgcgct ccgactggtg cgacttctcc ctgcgctagc gaggcagggt      60
tttggcctcg cctctcgcga gatcgcctcc tgttgctgcc gccgccgctc ctggccactg     120
actggcggcg cctgcgcagc cgccatgttc ggttgctatg ctgcggccta ggagaggggg     180
tgtgcttgag ggaggaggaa gagatagagg aggaggaggg ggaggaagag gaggtggaga     240 aggaggggg tgactgagct cctcttgcac tctcacacac aaacgctgcc caggattacc      300
cgccagctca cgccgcgcag tgcgcttttc cgctcctcgc gccccaccac caacattgtt     360
ctctcaggac tcctgggtcc caggggtcgg aattgggcct gagcgggaga ggaaagagac     420
ttggctttgg ccgcggggtc ggaggattgg ggccaggccc cctcccccac gcacttttgg     480
gggtgtggat tatctcatcc ctgcaggag gtaggagagg tcgccggctg cccgcctccc      540
tgccacctcc ccagcggcgc cggcccgcgc ctgcccagca gcatgaggtg tgctggcgg      600 ctccgggtcg tggcgcgacc gctgcggcgg cggctgctcg gggggcgctg aggtagcccc     660
ccggagcggc acgaggacg cgcttctcct ctgcgcgccg gggcctcgag gcttttttc      720 tccagccgag aggacgcggc tgtgatatac gaagactttg tgtggacagt a atg acc     777
                                                         Met Thr
                                                           1
```

| | | | | | | | | | | | | | | | | |
|---|---|---|---|---|---|---|---|---|---|---|---|---|---|---|---|---|
| tca | cgt | ttc | cga | ttg | cct | gct | ggc | aga | acc | tac | aat | gta | cga | gca | tca | 825 |
| Ser | Arg | Phe | Arg | Leu | Pro | Ala | Gly | Arg | Thr | Tyr | Asn | Val | Arg | Ala | Ser | |
| | | 5 | | | | | 10 | | | | | 15 | | | | |

```
gag ttg gcc cga gac aga cag cat act gaa gtg gtt tgc aac atc ctt     873
Glu Leu Ala Arg Asp Arg Gln His Thr Glu Val Val Cys Asn Ile Leu
     20              25                  30 ctt ctg gat aac act gta caa gct ttc aaa gtc aat aaa cat gat cag     921
Leu Leu Asp Asn Thr Val Gln Ala Phe Lys Val Asn Lys His Asp Gln
35              40                  45                  50 ggg caa gtc ttg ttg gat gtc gtc ttc aag cat cta gat ttg act gag     969
Gly Gln Val Leu Leu Asp Val Val Phe Lys His Leu Asp Leu Thr Glu
             55                  60                  65 cag gac tat ttt ggt tta cag ttg gct gat gat tcc aca gat aac cca    1017
Gln Asp Tyr Phe Gly Leu Gln Leu Ala Asp Asp Ser Thr Asp Asn Pro
         70                  75                  80 agg tgg ctg gat cca aac aaa cca ata agg aag cag cta aag aga gga    1065
Arg Trp Leu Asp Pro Asn Lys Pro Ile Arg Lys Gln Leu Lys Arg Gly
     85                  90                  95 tct cct tac agt ttg aac ttt aga gtc aaa ttt ttt gta agt gac ccc    1113
Ser Pro Tyr Ser Leu Asn Phe Arg Val Lys Phe Phe Val Ser Asp Pro
100                 105                 110 aac aag tta caa gaa gaa tat aca agg tac cag tat ttt ttg caa att    1161
Asn Lys Leu Gln Glu Glu Tyr Thr Arg Tyr Gln Tyr Phe Leu Gln Ile
115                 120                 125                 130 aaa caa gac att ctt act gga aga tta ccc tgt cct tct aat act gct    1209
Lys Gln Asp Ile Leu Thr Gly Arg Leu Pro Cys Pro Ser Asn Thr Ala
                135                 140                 145 gcc ctt tta gct tca ttt gct gtt cag tct gaa ctt gga gac tac gat    1257
Ala Leu Leu Ala Ser Phe Ala Val Gln Ser Glu Leu Gly Asp Tyr Asp
             150                 155                 160 cag tca gag aac ttg tca ggc tac ctc tca gat tat tct ttc att cct    1305
Gln Ser Glu Asn Leu Ser Gly Tyr Leu Ser Asp Tyr Ser Phe Ile Pro
         165                 170                 175 aat caa cct caa gat ttt gaa aaa gaa att gca aaa tta cat cag caa    1353
Asn Gln Pro Gln Asp Phe Glu Lys Glu Ile Ala Lys Leu His Gln Gln
     180                 185                 190 cac ata ggc tta tct cct gca gaa gca gaa ttt aat tac cta aac aca    1401
His Ile Gly Leu Ser Pro Ala Glu Ala Glu Phe Asn Tyr Leu Asn Thr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 195 |     |     |     |     | 200 |     |     |     |     | 205 |     |     |     |     | 210 |      |

```
gca cgt acc tta gaa ctc tat gga gtt gaa ttc cac tat gca agg gat    1449
Ala Arg Thr Leu Glu Leu Tyr Gly Val Glu Phe His Tyr Ala Arg Asp
            215                 220                 225 cag agt aac aat gaa att atg att gga gtg atg tca gga gga att ctg    1497
Gln Ser Asn Asn Glu Ile Met Ile Gly Val Met Ser Gly Gly Ile Leu
        230                 235                 240 att tat aag aac agg gta cga atg aat acc ttt cca tgg ttg aag att    1545
Ile Tyr Lys Asn Arg Val Arg Met Asn Thr Phe Pro Trp Leu Lys Ile
    245                 250                 255 gta aaa att tct ttt aag tgc aaa cag ttt ttt att caa ctt aga aaa    1593
Val Lys Ile Ser Phe Lys Cys Lys Gln Phe Phe Ile Gln Leu Arg Lys
260                 265                 270 gaa ttg cat gaa tct aga gaa aca tta ttg gga ttt aat atg gtg aat    1641
Glu Leu His Glu Ser Arg Glu Thr Leu Leu Gly Phe Asn Met Val Asn
275                 280                 285                 290 tac aga gca tgt aaa aat ttg tgg aaa gca tgt gta gaa cat cac aca    1689
Tyr Arg Ala Cys Lys Asn Leu Trp Lys Ala Cys Val Glu His His Thr
                295                 300                 305 ttc ttc cgt ttg gac aga cca ctt cca cct caa aag aat ttt ttt gca    1737
Phe Phe Arg Leu Asp Arg Pro Leu Pro Pro Gln Lys Asn Phe Phe Ala
            310                 315                 320 cat tat ttt aca tta ggt tca aaa ttc cgg tac tgt ggg aga act gaa    1785
His Tyr Phe Thr Leu Gly Ser Lys Phe Arg Tyr Cys Gly Arg Thr Glu
        325                 330                 335 gtc caa tca gtt cag tat ggc aaa gaa aag gca aat aaa gac agg gta    1833
Val Gln Ser Val Gln Tyr Gly Lys Glu Lys Ala Asn Lys Asp Arg Val
    340                 345                 350 ttt gca aga tcc cca agt aag ccc ttg gca cgg aaa tta atg gat tgg    1881
Phe Ala Arg Ser Pro Ser Lys Pro Leu Ala Arg Lys Leu Met Asp Trp
355                 360                 365                 370 gaa gta gta agc aga aat tca ata tct gat gac agg tta gaa aca caa    1929
Glu Val Val Ser Arg Asn Ser Ile Ser Asp Asp Arg Leu Glu Thr Gln
                375                 380                 385 agt ctt cca tca cga tct cca ccg gga act cct aat cat cga aat tct    1977
Ser Leu Pro Ser Arg Ser Pro Pro Gly Thr Pro Asn His Arg Asn Ser
            390                 395                 400 aca ttc acg cag gaa gga acc cgg tta cga cca tct tca gtt ggt cat    2025
Thr Phe Thr Gln Glu Gly Thr Arg Leu Arg Pro Ser Ser Val Gly His
        405                 410                 415 ttg gta gac cat atg gtt cat act tcc cca agc gaa gtg ttt gta aat    2073
Leu Val Asp His Met Val His Thr Ser Pro Ser Glu Val Phe Val Asn
    420                 425                 430 cag aga tct ccg tca tca aca caa gct aat agc att gtt ctg gaa tca    2121
Gln Arg Ser Pro Ser Ser Thr Gln Ala Asn Ser Ile Val Leu Glu Ser
435                 440                 445                 450 tca cca tca caa gag acc cct gga gat ggg aag cct cca gct tta cca    2169
Ser Pro Ser Gln Glu Thr Pro Gly Asp Gly Lys Pro Pro Ala Leu Pro
                455                 460                 465 ccc aaa cag tca aag aaa aac agt tgg aac caa att cat tat tca cat    2217
Pro Lys Gln Ser Lys Lys Asn Ser Trp Asn Gln Ile His Tyr Ser His
            470                 475                 480 tcg caa caa gat cta gaa agt cat att aat gaa aca ttt gat att cca    2265
Ser Gln Gln Asp Leu Glu Ser His Ile Asn Glu Thr Phe Asp Ile Pro
        485                 490                 495 tct tct cct gaa aaa ccc act cct aat ggt ggt att cca cat gat aat    2313
Ser Ser Pro Glu Lys Pro Thr Pro Asn Gly Gly Ile Pro His Asp Asn
    500                 505                 510 ctt gtc cta atc aga atg aaa cct gat gaa aat ggg agg ttt gga ttc    2361
```

| | | | | | | | | | | | | | | |
|---|---|---|---|---|---|---|---|---|---|---|---|---|---|---|
| Leu | Val | Leu | Ile | Arg | Met | Lys | Pro | Asp | Glu | Asn | Gly | Arg | Phe | Gly | Phe |
| 515 | | | | | 520 | | | | | 525 | | | | | 530 |

| aat | gta | aag | gga | gga | tat | gat | cag | aag | atg | cct | gtg | att | gtg | tct | cga | 2409 |
|---|---|---|---|---|---|---|---|---|---|---|---|---|---|---|---|---|
| Asn | Val | Lys | Gly | Gly | Tyr | Asp | Gln | Lys | Met | Pro | Val | Ile | Val | Ser | Arg | |
| | | | 535 | | | | | 540 | | | | | 545 | | | |

| gta | gca | cca | gga | aca | cct | gct | gac | ctc | tgt | gtc | cct | aga | ctg | aat | gaa | 2457 |
|---|---|---|---|---|---|---|---|---|---|---|---|---|---|---|---|---|
| Val | Ala | Pro | Gly | Thr | Pro | Ala | Asp | Leu | Cys | Val | Pro | Arg | Leu | Asn | Glu | |
| | | | 550 | | | | | 555 | | | | | 560 | | | |

| ggg | gac | caa | gtt | gta | ctg | atc | aat | ggt | cgg | gac | att | gca | gaa | cac | act | 2505 |
|---|---|---|---|---|---|---|---|---|---|---|---|---|---|---|---|---|
| Gly | Asp | Gln | Val | Val | Leu | Ile | Asn | Gly | Arg | Asp | Ile | Ala | Glu | His | Thr | |
| | | 565 | | | | | 570 | | | | | 575 | | | | |

| cat | gat | cag | gtt | gtg | ctg | ttt | att | aaa | gct | agt | tgt | gag | aga | cat | tct | 2553 |
|---|---|---|---|---|---|---|---|---|---|---|---|---|---|---|---|---|
| His | Asp | Gln | Val | Val | Leu | Phe | Ile | Lys | Ala | Ser | Cys | Glu | Arg | His | Ser | |
| | 580 | | | | | 585 | | | | | 590 | | | | | |

| ggg | gaa | ctc | atg | ctt | cta | gtt | cga | cct | aat | gct | gta | tat | gat | gta | gtg | 2601 |
|---|---|---|---|---|---|---|---|---|---|---|---|---|---|---|---|---|
| Gly | Glu | Leu | Met | Leu | Leu | Val | Arg | Pro | Asn | Ala | Val | Tyr | Asp | Val | Val | |
| 595 | | | | | 600 | | | | | 605 | | | | | 610 | |

| gaa | gaa | aag | cta | gaa | aat | gag | cca | gat | ttc | cag | tat | att | cct | gag | aaa | 2649 |
|---|---|---|---|---|---|---|---|---|---|---|---|---|---|---|---|---|
| Glu | Glu | Lys | Leu | Glu | Asn | Glu | Pro | Asp | Phe | Gln | Tyr | Ile | Pro | Glu | Lys | |
| | | | | 615 | | | | | 620 | | | | | 625 | | |

| gcc | cca | cta | gat | agt | gtg | cat | cag | gat | gac | cat | tcc | ctg | cgg | gag | tca | 2697 |
|---|---|---|---|---|---|---|---|---|---|---|---|---|---|---|---|---|
| Ala | Pro | Leu | Asp | Ser | Val | His | Gln | Asp | Asp | His | Ser | Leu | Arg | Glu | Ser | |
| | | | 630 | | | | | 635 | | | | | 640 | | | |

| atg | atc | cag | cta | gct | gag | ggg | ctt | atc | act | gga | aca | gtc | ctg | aca | cag | 2745 |
|---|---|---|---|---|---|---|---|---|---|---|---|---|---|---|---|---|
| Met | Ile | Gln | Leu | Ala | Glu | Gly | Leu | Ile | Thr | Gly | Thr | Val | Leu | Thr | Gln | |
| | | 645 | | | | | 650 | | | | | 655 | | | | |

| ttt | gat | caa | ctg | tat | cgg | aaa | aaa | cct | gga | atg | aca | atg | tcc | tgt | gcc | 2793 |
|---|---|---|---|---|---|---|---|---|---|---|---|---|---|---|---|---|
| Phe | Asp | Gln | Leu | Tyr | Arg | Lys | Lys | Pro | Gly | Met | Thr | Met | Ser | Cys | Ala | |
| 660 | | | | | 665 | | | | | 670 | | | | | | |

| aaa | tta | cct | cag | aat | att | tcc | aaa | aat | aga | tac | aga | gat | att | tcg | cct | 2841 |
|---|---|---|---|---|---|---|---|---|---|---|---|---|---|---|---|---|
| Lys | Leu | Pro | Gln | Asn | Ile | Ser | Lys | Asn | Arg | Tyr | Arg | Asp | Ile | Ser | Pro | |
| 675 | | | | 680 | | | | | 685 | | | | | 690 | | |

| tat | gat | gcc | aca | cgg | gtc | att | tta | aaa | ggt | aat | gaa | gac | tac | atc | aat | 2889 |
|---|---|---|---|---|---|---|---|---|---|---|---|---|---|---|---|---|
| Tyr | Asp | Ala | Thr | Arg | Val | Ile | Leu | Lys | Gly | Asn | Glu | Asp | Tyr | Ile | Asn | |
| | | | 695 | | | | | 700 | | | | | 705 | | | |

| gcg | aac | tat | ata | aat | atg | gaa | att | cct | tct | tcc | agc | att | ata | aat | cag | 2937 |
|---|---|---|---|---|---|---|---|---|---|---|---|---|---|---|---|---|
| Ala | Asn | Tyr | Ile | Asn | Met | Glu | Ile | Pro | Ser | Ser | Ser | Ile | Ile | Asn | Gln | |
| | | | 710 | | | | | 715 | | | | | 720 | | | |

| tac | att | gct | tgt | caa | ggg | cca | tta | cca | cac | act | tgt | aca | gat | ttt | tgg | 2985 |
|---|---|---|---|---|---|---|---|---|---|---|---|---|---|---|---|---|
| Tyr | Ile | Ala | Cys | Gln | Gly | Pro | Leu | Pro | His | Thr | Cys | Thr | Asp | Phe | Trp | |
| | | 725 | | | | | 730 | | | | | 735 | | | | |

| cag | atg | act | tgg | gaa | caa | ggc | tcc | tct | atg | gtt | gta | atg | ttg | acc | aca | 3033 |
|---|---|---|---|---|---|---|---|---|---|---|---|---|---|---|---|---|
| Gln | Met | Thr | Trp | Glu | Gln | Gly | Ser | Ser | Met | Val | Val | Met | Leu | Thr | Thr | |
| | 740 | | | | | 745 | | | | | 750 | | | | | |

| caa | gtt | gaa | cgt | ggc | aga | gtt | aaa | tgt | cac | caa | tat | tgg | cca | gaa | ccc | 3081 |
|---|---|---|---|---|---|---|---|---|---|---|---|---|---|---|---|---|
| Gln | Val | Glu | Arg | Gly | Arg | Val | Lys | Cys | His | Gln | Tyr | Trp | Pro | Glu | Pro | |
| 755 | | | | | 760 | | | | | 765 | | | | | 770 | |

| aca | ggc | agt | tca | tct | tat | gga | tgc | tac | caa | gtt | acc | tgc | cac | tct | gaa | 3129 |
|---|---|---|---|---|---|---|---|---|---|---|---|---|---|---|---|---|
| Thr | Gly | Ser | Ser | Ser | Tyr | Gly | Cys | Tyr | Gln | Val | Thr | Cys | His | Ser | Glu | |
| | | | 775 | | | | | 780 | | | | | 785 | | | |

| gaa | gga | aac | act | gcc | tat | atc | ttc | agg | aag | atg | acc | cta | ttt | aac | caa | 3177 |
|---|---|---|---|---|---|---|---|---|---|---|---|---|---|---|---|---|
| Glu | Gly | Asn | Thr | Ala | Tyr | Ile | Phe | Arg | Lys | Met | Thr | Leu | Phe | Asn | Gln | |
| | | | 790 | | | | | 795 | | | | | 800 | | | |

| gag | aaa | aat | gaa | agt | cgt | cca | ctc | act | cag | atc | cag | tac | ata | gcc | tgg | 3225 |
|---|---|---|---|---|---|---|---|---|---|---|---|---|---|---|---|---|
| Glu | Lys | Asn | Glu | Ser | Arg | Pro | Leu | Thr | Gln | Ile | Gln | Tyr | Ile | Ala | Trp | |
| | | 805 | | | | | 810 | | | | | 815 | | | | |

| cct | gac | cat | gga | gtc | cct | gat | gat | tcg | agt | gac | ttt | cta | gat | ttt | gtt | 3273 |
|---|---|---|---|---|---|---|---|---|---|---|---|---|---|---|---|---|
| Pro | Asp | His | Gly | Val | Pro | Asp | Asp | Ser | Ser | Asp | Phe | Leu | Asp | Phe | Val | |
| | 820 | | | | | 825 | | | | | 830 | | | | | |

```
tgt cat gta cga aac aag agg gct ggc aag gaa gaa ccc gtt gtt gtc    3321
Cys His Val Arg Asn Lys Arg Ala Gly Lys Glu Glu Pro Val Val Val
835                 840                 845                 850 cat tgc agt gct gga atc gga aga act ggg gtt ctt att act atg gaa    3369
His Cys Ser Ala Gly Ile Gly Arg Thr Gly Val Leu Ile Thr Met Glu
            855                 860                 865 aca gcc atg tgt ctc att gaa tgc aat cag cca gtt tat cca cta gat    3417
Thr Ala Met Cys Leu Ile Glu Cys Asn Gln Pro Val Tyr Pro Leu Asp
                870                 875                 880 att gta aga aca atg aga gat cag cga gcc atg atg atc caa aca cct    3465
Ile Val Arg Thr Met Arg Asp Gln Arg Ala Met Met Ile Gln Thr Pro
        885                 890                 895 agt caa tac aga ttt gta tgt gaa gct att ttg aaa gtt tat gaa gaa    3513
Ser Gln Tyr Arg Phe Val Cys Glu Ala Ile Leu Lys Val Tyr Glu Glu
    900                 905                 910 ggc ttt gtt aaa ccc tta aca aca tca aca aat aaa taa gaaagcaaaa    3562
Gly Phe Val Lys Pro Leu Thr Thr Ser Thr Asn Lys
915                 920                 925 agatctggga tatgtgttgg aaaactgctt tcccttatgt tcactgtgcc ataatgctgc    3622
tcgcaggaaa tggcatttta caaaaaaaaa atgaagaact caaaaaaact ttgaaaactt    3682
cagcactgtt gcactttatg ttttaaaaaa tgtcactctt tcaaaatcta taactcatgt    3742
atttgaagac tgtttcatgc tttgctccga acaaatagta aataactgag tatgttcagg    3802
gtaatttatg aaattttgtg gtggtgccat gcaatcccct tttggtagaa ttgccacaaa    3862
caaggctcaa aattctcatc atctctgtta tacacctgta tcatgaaagc aaaaagaagt    3922
aaacatcagg agtcagctct gaaaaaaaaa aaaaaaaaa a                        3963

<210> SEQ ID NO 51
<211> LENGTH: 926
<212> TYPE: DNA
<213> ORGANISM: Homo sapiens

<400> SEQUENCE: 51

Met Thr Ser Arg Phe Arg Leu Pro Ala Gly Arg Thr Tyr Asn Val Arg
1               5                   10                  15

Ala Ser Glu Leu Ala Arg Asp Arg Gln His Thr Glu Val Val Cys Asn
            20                  25                  30

Ile Leu Leu Leu Asp Asn Thr Val Gln Ala Phe Lys Val Asn Lys His
        35                  40                  45

Asp Gln Gly Gln Val Leu Leu Asp Val Val Phe Lys His Leu Asp Leu
    50                  55                  60

Thr Glu Gln Asp Tyr Phe Gly Leu Gln Leu Ala Asp Asp Ser Thr Asp
65                  70                  75                  80

Asn Pro Arg Trp Leu Asp Pro Asn Lys Pro Ile Arg Lys Gln Leu Lys
                85                  90                  95

Arg Gly Ser Pro Tyr Ser Leu Asn Phe Arg Val Lys Phe Phe Val Ser
            100                 105                 110

Asp Pro Asn Lys Leu Gln Glu Glu Tyr Thr Arg Tyr Gln Tyr Phe Leu
        115                 120                 125

Gln Ile Lys Gln Asp Ile Leu Thr Gly Arg Leu Pro Cys Pro Ser Asn
    130                 135                 140

Thr Ala Ala Leu Leu Ala Ser Phe Ala Val Gln Ser Glu Leu Gly Asp
145                 150                 155                 160

Tyr Asp Gln Ser Glu Asn Leu Ser Gly Tyr Leu Ser Asp Tyr Ser Phe
                165                 170                 175
```

```
Ile Pro Asn Gln Pro Gln Asp Phe Glu Lys Glu Ile Ala Lys Leu His
            180                 185                 190

Gln Gln His Ile Gly Leu Ser Pro Ala Glu Ala Glu Phe Asn Tyr Leu
        195                 200                 205

Asn Thr Ala Arg Thr Leu Glu Leu Tyr Gly Val Glu Phe His Tyr Ala
        210                 215                 220

Arg Asp Gln Ser Asn Asn Glu Ile Met Ile Gly Val Met Ser Gly Gly
225                 230                 235                 240

Ile Leu Ile Tyr Lys Asn Arg Val Arg Met Asn Thr Phe Pro Trp Leu
                245                 250                 255

Lys Ile Val Lys Ile Ser Phe Lys Cys Lys Gln Phe Phe Ile Gln Leu
        260                 265                 270

Arg Lys Glu Leu His Glu Ser Arg Glu Thr Leu Leu Gly Phe Asn Met
        275                 280                 285

Val Asn Tyr Arg Ala Cys Lys Asn Leu Trp Lys Ala Cys Val Glu His
        290                 295                 300

His Thr Phe Phe Arg Leu Asp Arg Pro Leu Pro Pro Gln Lys Asn Phe
305                 310                 315                 320

Phe Ala His Tyr Phe Thr Leu Gly Ser Lys Phe Arg Tyr Cys Gly Arg
                325                 330                 335

Thr Glu Val Gln Ser Val Gln Tyr Gly Lys Glu Lys Ala Asn Lys Asp
        340                 345                 350

Arg Val Phe Ala Arg Ser Pro Ser Lys Pro Leu Ala Arg Lys Leu Met
        355                 360                 365

Asp Trp Glu Val Val Ser Arg Asn Ser Ile Ser Asp Asp Arg Leu Glu
        370                 375                 380

Thr Gln Ser Leu Pro Ser Arg Ser Pro Pro Gly Thr Pro Asn His Arg
385                 390                 395                 400

Asn Ser Thr Phe Thr Gln Glu Gly Thr Arg Leu Arg Pro Ser Ser Val
                405                 410                 415

Gly His Leu Val Asp His Met Val His Thr Ser Pro Ser Glu Val Phe
        420                 425                 430

Val Asn Gln Arg Ser Pro Ser Ser Thr Gln Ala Asn Ser Ile Val Leu
        435                 440                 445

Glu Ser Ser Pro Ser Gln Glu Thr Pro Gly Asp Gly Lys Pro Pro Ala
450                 455                 460

Leu Pro Pro Lys Gln Ser Lys Lys Asn Ser Trp Asn Gln Ile His Tyr
465                 470                 475                 480

Ser His Ser Gln Gln Asp Leu Glu Ser His Ile Asn Glu Thr Phe Asp
                485                 490                 495

Ile Pro Ser Ser Pro Glu Lys Pro Thr Pro Asn Gly Gly Ile Pro His
        500                 505                 510

Asp Asn Leu Val Leu Ile Arg Met Lys Pro Asp Glu Asn Gly Arg Phe
        515                 520                 525

Gly Phe Asn Val Lys Gly Gly Tyr Asp Gln Lys Met Pro Val Ile Val
        530                 535                 540

Ser Arg Val Ala Pro Gly Thr Pro Ala Asp Leu Cys Val Pro Arg Leu
545                 550                 555                 560

Asn Glu Gly Asp Gln Val Leu Ile Asn Gly Arg Asp Ile Ala Glu
                565                 570                 575

His Thr His Asp Gln Val Val Leu Phe Ile Lys Ala Ser Cys Glu Arg
                580                 585                 590

His Ser Gly Glu Leu Met Leu Leu Val Arg Pro Asn Ala Val Tyr Asp
```

```
                595                 600                 605
Val Val Glu Glu Lys Leu Glu Asn Glu Pro Asp Phe Gln Tyr Ile Pro
610                 615                 620

Glu Lys Ala Pro Leu Asp Ser Val His Gln Asp His Ser Leu Arg
625                 630                 635                 640

Glu Ser Met Ile Gln Leu Ala Glu Gly Leu Ile Thr Gly Thr Val Leu
                645                 650                 655

Thr Gln Phe Asp Gln Leu Tyr Arg Lys Lys Pro Gly Met Thr Met Ser
                660                 665                 670

Cys Ala Lys Leu Pro Gln Asn Ile Ser Lys Asn Arg Tyr Arg Asp Ile
                675                 680                 685

Ser Pro Tyr Asp Ala Thr Arg Val Ile Leu Lys Gly Asn Glu Asp Tyr
690                 695                 700

Ile Asn Ala Asn Tyr Ile Asn Met Glu Ile Pro Ser Ser Ser Ile Ile
705                 710                 715                 720

Asn Gln Tyr Ile Ala Cys Gln Gly Pro Leu Pro His Thr Cys Thr Asp
                725                 730                 735

Phe Trp Gln Met Thr Trp Glu Gln Gly Ser Ser Met Val Val Met Leu
                740                 745                 750

Thr Thr Gln Val Glu Arg Gly Arg Val Lys Cys His Gln Tyr Trp Pro
                755                 760                 765

Glu Pro Thr Gly Ser Ser Tyr Gly Cys Tyr Gln Val Thr Cys His
770                 775                 780

Ser Glu Glu Gly Asn Thr Ala Tyr Ile Phe Arg Lys Met Thr Leu Phe
785                 790                 795                 800

Asn Gln Glu Lys Asn Glu Ser Arg Pro Leu Thr Gln Ile Gln Tyr Ile
                805                 810                 815

Ala Trp Pro Asp His Gly Val Pro Asp Ser Ser Asp Phe Leu Asp
                820                 825                 830

Phe Val Cys His Val Arg Asn Lys Arg Ala Gly Lys Glu Glu Pro Val
                835                 840                 845

Val Val His Cys Ser Ala Gly Ile Gly Arg Thr Gly Val Leu Ile Thr
                850                 855                 860

Met Glu Thr Ala Met Cys Leu Ile Glu Cys Asn Gln Pro Val Tyr Pro
865                 870                 875                 880

Leu Asp Ile Val Arg Thr Met Arg Asp Gln Arg Ala Met Met Ile Gln
                885                 890                 895

Thr Pro Ser Gln Tyr Arg Phe Val Cys Glu Ala Ile Leu Lys Val Tyr
                900                 905                 910

Glu Glu Gly Phe Val Lys Pro Leu Thr Thr Ser Thr Asn Lys
                915                 920                 925

<210> SEQ ID NO 52
<211> LENGTH: 2592
<212> TYPE: DNA
<213> ORGANISM: Homo sapiens
<220> FEATURE:
<221> NAME/KEY: CDS
<222> LOCATION: (207)..(884)

<400> SEQUENCE: 52
gtgggagtgg aggaggaaga ggcggtaggg ggtacggggg ctggtcccag aagatggcgg     60
aggcggggga tttctggtag gtcctacttt aggacaagat gtggtaccgt tgaagcgtca    120
gtctttgatt cacagacagt tgagcttttc agctgggaag cctttccatt ttttttttt    180
```

```
taacggcttt ctgaacctat gaaacc atg gca gaa gga gag aca gag tca cct       233
                             Met Ala Glu Gly Glu Thr Glu Ser Pro
                             1               5 ggg ccc aaa aag tgt ggc cca tat att tca tct gtc act agc cag agt        281
Gly Pro Lys Lys Cys Gly Pro Tyr Ile Ser Ser Val Thr Ser Gln Ser
10              15                  20                  25 gtg aac ttg atg att cga gga gta gtg cta ttt ttt att gga gta ttt        329
Val Asn Leu Met Ile Arg Gly Val Val Leu Phe Phe Ile Gly Val Phe
                30                  35                  40 ctt gca tta gtg tta aat tta ctt cag att cag aga aat gtg acg ctc        377
Leu Ala Leu Val Leu Asn Leu Leu Gln Ile Gln Arg Asn Val Thr Leu
                45                  50                  55 ttt cca cct gat gtg att gca agc atc ttt tct tct gca tgg tgg gta        425
Phe Pro Pro Asp Val Ile Ala Ser Ile Phe Ser Ser Ala Trp Trp Val
            60                  65                  70 ccc cca tgc tgt ggc acg gct tca gct gtg att ggg tta tta tac ccc        473
Pro Pro Cys Cys Gly Thr Ala Ser Ala Val Ile Gly Leu Leu Tyr Pro
75              80                  85 tgc att gac aga cat cta gga gaa cca cat aaa ttt aaa aga gag tgg        521
Cys Ile Asp Arg His Leu Gly Glu Pro His Lys Phe Lys Arg Glu Trp
90              95                  100                 105 tcc agt gta atg cgg tgt gta gca gtc ttt gtt ggt ata aat cat gcc        569
Ser Ser Val Met Arg Cys Val Ala Val Phe Val Gly Ile Asn His Ala
                110                 115                 120 agt gct aaa gtg gat ttc gat aac aac ata cag ttg tct ctc aca ctg        617
Ser Ala Lys Val Asp Phe Asp Asn Asn Ile Gln Leu Ser Leu Thr Leu
                125                 130                 135 gct gca cta tcc att gga ctg tgg tgg act ttt gat aga tct aga agt        665
Ala Ala Leu Ser Ile Gly Leu Trp Trp Thr Phe Asp Arg Ser Arg Ser
                140                 145                 150 ggt ttt ggc ctt gga gta gga att gcc ttc ttg gca act gtg gtc act        713
Gly Phe Gly Leu Gly Val Gly Ile Ala Phe Leu Ala Thr Val Val Thr
155                 160                 165 caa ctg cta gta tat aat ggt gtt tac caa tat aca tct cca gat ttc        761
Gln Leu Leu Val Tyr Asn Gly Val Tyr Gln Tyr Thr Ser Pro Asp Phe
170                 175                 180                 185 ctc tat gtt cgt tct tgg tta cca tgt ata ttt ttt gct gga ggc ata        809
Leu Tyr Val Arg Ser Trp Leu Pro Cys Ile Phe Phe Ala Gly Gly Ile
                190                 195                 200 aca atg gga aac att ggt cga caa ctg gca atg tac gaa tgt aaa gtt        857
Thr Met Gly Asn Ile Gly Arg Gln Leu Ala Met Tyr Glu Cys Lys Val
                205                 210                 215 atc gca gaa aaa tct cat cag gaa tga agaaggcaaa aaatatcttt              904
Ile Ala Glu Lys Ser His Gln Glu
            220                 225 tgtacagaaa agcaagatga aaaggatgtg aaatggtaga tataccaaca aaacttcaga      964
ctgtaaaatt gccaggatgc agttttcccc ttgattggcg tgtgtgtata tatggataaa     1024
tatatatata cacacacaca tattactgca atctgtgatt gcttcatctg taaatcagtt     1084
gtaaaccttt acatatttga cttaaataac tgtaagatat atatgtacta cattaaaaag     1144
tgttgattaa tagatgaaat ttttaaatta attttttaaa acatgccata cattgtatca     1204
caatgttaat gtgccaagat attgttcctg tcatgcagag tataagaatg ctttgaacaa     1264
tttgtagact tagtgaaata aaataagagg aaagccaaaa acaaacaaac aaaaagcata     1324
tggggagctg gtattttctc tttagcttac tgttgtgcct ttttattttt ctaatcacag     1384
cagtatgagt tatgagtgcc ctaatttgtg gttagtttct aatttaatgt tgtttcatag     1444
agtttggagt gttttgatac agggtgaaaa tgaacttctg gtttcaaacc tgcgttactg     1504
```

-continued

```
gagacagccc aaagagtaat tttctgtttt gacaggtttt actggaagta tatgtgatga    1564
gcagaagagg ttatcagcat taaattgttt tggttctaaa tttggaacag tatatataat    1624
taaaagtaag gaacattaga ggatttaatt agaataaata catgttttgg aaatacagtg    1684
acctcttgca gtgtcacaaa agtgcaaagt gatattagct gtcatctgca atacagaatc    1744
tcattgcttt tgcacatgga gcatatagga aactccaaac agatcacaat gaggtttcta    1804
aatctgttgg gttctgtctt ctattgggtt ctgtgaagca aaccactgta gctttagctg    1864
ggttcagtca tatgactcgt tggtggaatg cctaggtttt tcatcttaca tgcagtcttg    1924
ggggtggatg aatacataat ttcttatgta ttcgtgtatc cattagtgaa tagttcaagt    1984
ctgtttaaga gtgtattgag atggcattct ctgcatgtta aagatcttaa tggcaaccag    2044
cacctcttaa gtatggttta aacatattct tagctaattt tttccattag ttttgaaat     2104 tggtggcagt tgtctgatcc acaagggcaa gatcttctga gtactctggg gtgtgagtat    2164
gtgtgcacac gtgtgtgttg gagtgagtga gagaatgtgt ctgtgcatgt ggccatgctt    2224
tcctagaatg tcaagtagat atttttacac tttgagtttt aaagcaatta ctatcagact    2284
gagatcttgt atgccaaact ttaatctgct tttatgtttt caggctgaag gtgtgaaaat    2344
cctaagagga tttcatattg aatatgtgta cacaatctta actatcgtgg tggaaaacat    2404
actactataa tttattatta tatcttccag ataatgttat tcatttagaa caaataaggt    2464 atattttta gaatcaactt tgtaagcact ataaaatctt taataagtta taaggtctat    2524
gatgtgttta ctttaaaaat tgctgttaaa agcaacacgt attaaatatg taattatcaa    2584
aaaaaaaa                                                             2592
```

<210> SEQ ID NO 53
<211> LENGTH: 225
<212> TYPE: DNA
<213> ORGANISM: Homo sapiens

<400> SEQUENCE: 53

```
Met Ala Glu Gly Glu Thr Glu Ser Pro Gly Pro Lys Lys Cys Gly Pro
1               5                   10                  15

Tyr Ile Ser Ser Val Thr Ser Gln Ser Val Asn Leu Met Ile Arg Gly
            20                  25                  30

Val Val Leu Phe Phe Ile Gly Val Phe Leu Ala Leu Val Leu Asn Leu
        35                  40                  45

Leu Gln Ile Gln Arg Asn Val Thr Leu Phe Pro Pro Asp Val Ile Ala
    50                  55                  60

Ser Ile Phe Ser Ser Ala Trp Trp Val Pro Pro Cys Cys Gly Thr Ala
65                  70                  75                  80

Ser Ala Val Ile Gly Leu Leu Tyr Pro Cys Ile Asp Arg His Leu Gly
                85                  90                  95

Glu Pro His Lys Phe Lys Arg Glu Trp Ser Ser Val Met Arg Cys Val
            100                 105                 110

Ala Val Phe Val Gly Ile Asn His Ala Ser Ala Lys Val Asp Phe Asp
        115                 120                 125

Asn Asn Ile Gln Leu Ser Leu Thr Leu Ala Ala Leu Ser Ile Gly Leu
    130                 135                 140

Trp Trp Thr Phe Asp Arg Ser Arg Ser Gly Phe Gly Leu Gly Val Gly
145                 150                 155                 160

Ile Ala Phe Leu Ala Thr Val Val Thr Gln Leu Leu Val Tyr Asn Gly
                165                 170                 175
```

```
Val Tyr Gln Tyr Thr Ser Pro Asp Phe Leu Tyr Val Arg Ser Trp Leu
            180                 185                 190

Pro Cys Ile Phe Phe Ala Gly Gly Ile Thr Met Gly Asn Ile Gly Arg
            195                 200                 205

Gln Leu Ala Met Tyr Glu Cys Lys Val Ile Ala Glu Lys Ser His Gln
            210                 215                 220

Glu
225

<210> SEQ ID NO 54
<211> LENGTH: 3516
<212> TYPE: DNA
<213> ORGANISM: Homo sapiens
<220> FEATURE:
<221> NAME/KEY: CDS
<222> LOCATION: (767)..(1990)

<400> SEQUENCE: 54
```

| | | | | | |
|---|---|---|---|---|---|
| ggatcctgga gacaactttg ccgtgtgacg cgccggagg actgcagggc ccgcggccga | | | | | 60 |
| gggctcggcg ccgcctgtga gcgggcccgc gcggccggct ctcccgggca ccaagcttgc | | | | | 120 |
| tccgcgccac tgcccgccgg cccgcggcga ggacgacctg cccgtctccg ccgcggcgg | | | | | 180 |
| cccttcctgg cgcgaggcag tgagggcgag gcgctcaggt gcgagcgcgg ggccccgccg | | | | | 240 |
| cagcgcccgc cgcagcgccg cgccaagccg cgcccggctc cgctccgggg gctccagcg | | | | | 300 |
| ccttcgcttc cgtctcagcc aagttgcgtg acccgctct ttcgccacct tccccagccg | | | | | 360 |
| ccggccgaac cgccgctccc actgacgctg cttcgcttc acccgaaccg gggctgcggg | | | | | 420 |
| gcccccgacg cggaaaggat ggggagaagg ctgcagatgc cgaggcgccc cgagacgccc | | | | | 480 |
| gtgcggcagt gacccgcgac ctccgccccg cccggcgcgc cctcgggcc ccgggggccc | | | | | 540 |
| tcggcgcccc ttccctgccg cgcgggaacc cccgaggccc ggccggcccc ctccccctgc | | | | | 600 |
| gagccggcgg cagccctccc ggcgggcggg cgggcggagg cccgggcggg cgcgggcgcg | | | | | 660 |
| ggcgggggcg gggcggggcg gcgcgcccgg agcccggagc ccggccctgc gctcggctcg | | | | | 720 |
| actcggctcg cctcgcggcg ggcgccctcg tcgccagcgg cgcacc atg gac ggg | | | | | 775 |
| | | | | Met Asp Gly | |
| | | | | 1 | |

```
ctg ccc ggt cgg gcg ctg ggg gcc gcc tgc ctt ctg ctg ctg gcg gcc       823
Leu Pro Gly Arg Ala Leu Gly Ala Ala Cys Leu Leu Leu Leu Ala Ala
    5                  10                  15 ggc tgg ctg ggg cct gag gcc tgg ggc tca ccc acg ccc ccg ccg acg       871
Gly Trp Leu Gly Pro Glu Ala Trp Gly Ser Pro Thr Pro Pro Pro Thr
 20                  25                  30                  35 cct gcc gcg ccg ccg cca ccc ccg cca ccc gga gcc ccg ggt ggc tcg       919
Pro Ala Ala Pro Pro Pro Pro Pro Pro Gly Ala Pro Gly Gly Ser
                 40                  45                  50 cag gac acc tgt acg tcg tgc ggc ggc ttc cgg cgg cca gag gag ctc       967
Gln Asp Thr Cys Thr Ser Cys Gly Gly Phe Arg Arg Pro Glu Glu Leu
                 55                  60                  65 ggc cga gtg gac ggc gac ttc ctg gag gcg gtg aag cgg cac atc ttg      1015
Gly Arg Val Asp Gly Asp Phe Leu Glu Ala Val Lys Arg His Ile Leu
        70                  75                  80 agc cgc ctg cag atg cgg ggc cgg ccc aac atc acg cac gcc gtg cct      1063
Ser Arg Leu Gln Met Arg Gly Arg Pro Asn Ile Thr His Ala Val Pro
     85                  90                  95 aag gcc gcc atg gtc acg gcc ctg cgc aag ctg cac gcg ggc aag gtg      1111
Lys Ala Ala Met Val Thr Ala Leu Arg Lys Leu His Ala Gly Lys Val
100                 105                 110                 115
```

```
cgc gag gac ggc cgc gtg gag atc ccg cac ctc gac ggc cac gcc agc    1159
Arg Glu Asp Gly Arg Val Glu Ile Pro His Leu Asp Gly His Ala Ser
            120                 125                 130 ccg ggc gcc gac ggc cag gag cgc gtt tcc gaa atc atc agc ttc gcc    1207
Pro Gly Ala Asp Gly Gln Glu Arg Val Ser Glu Ile Ile Ser Phe Ala
        135                 140                 145 gag aca gat ggc ctc gcc tcc tcc cgg gtc cgc cta tac ttc ttc atc    1255
Glu Thr Asp Gly Leu Ala Ser Ser Arg Val Arg Leu Tyr Phe Phe Ile
    150                 155                 160 tcc aac gaa ggc aac cag aac ctg ttt gtg gtc cag gcc agc ctg tgg    1303
Ser Asn Glu Gly Asn Gln Asn Leu Phe Val Val Gln Ala Ser Leu Trp
165                 170                 175 ctt tac ctg aaa ctc ctg ccc tac gtc ctg gag aag ggc agc cgg cgg    1351
Leu Tyr Leu Lys Leu Leu Pro Tyr Val Leu Glu Lys Gly Ser Arg Arg
180                 185                 190                 195 aag gtg cgg gtc aaa gtg tac ttc cag gag cag ggc cac ggt gac agg    1399
Lys Val Arg Val Lys Val Tyr Phe Gln Glu Gln Gly His Gly Asp Arg
            200                 205                 210 tgg aac atg gtg gag aag agg gtg gac ctc aag cgc agc ggc tgg cat    1447
Trp Asn Met Val Glu Lys Arg Val Asp Leu Lys Arg Ser Gly Trp His
        215                 220                 225 acc ttc cca ctc acg gag gcc atc cag gcc ttg ttt gag cgg ggc gag    1495
Thr Phe Pro Leu Thr Glu Ala Ile Gln Ala Leu Phe Glu Arg Gly Glu
    230                 235                 240 cgg cga ctc aac cta gac gtg cag tgt gac agc tgc cag gag ctg gcc    1543
Arg Arg Leu Asn Leu Asp Val Gln Cys Asp Ser Cys Gln Glu Leu Ala
245                 250                 255 gtg gtg ccg gtg ttc gtg gac cca ggc gaa gag tcg cac cga ccc ttt    1591
Val Val Pro Val Phe Val Asp Pro Gly Glu Glu Ser His Arg Pro Phe
260                 265                 270                 275 gtg gtg gtg cag gct cgg ctg ggc gac agc agg cac cgc att cgc aag    1639
Val Val Val Gln Ala Arg Leu Gly Asp Ser Arg His Arg Ile Arg Lys
            280                 285                 290 cga ggc ctg gag tgc gat ggc cgg acc aac ctc tgt tgc agg caa cag    1687
Arg Gly Leu Glu Cys Asp Gly Arg Thr Asn Leu Cys Cys Arg Gln Gln
        295                 300                 305 ttc ttc att gac ttc cgc ctc atc ggc tgg aac gac tgg atc ata gca    1735
Phe Phe Ile Asp Phe Arg Leu Ile Gly Trp Asn Asp Trp Ile Ile Ala
    310                 315                 320 ccc acc ggc tac tac ggc aac tac tgt gag ggc agc tgc cca gcc tac    1783
Pro Thr Gly Tyr Tyr Gly Asn Tyr Cys Glu Gly Ser Cys Pro Ala Tyr
325                 330                 335 ctg gca ggg gtc ccc ggc tct gcc tcc tcc ttc cac acg gct gtg gtg    1831
Leu Ala Gly Val Pro Gly Ser Ala Ser Ser Phe His Thr Ala Val Val
340                 345                 350                 355 aac cag tac cgc atg cgg ggt ctg aac ccc ggc acg gtg aac tcc tgc    1879
Asn Gln Tyr Arg Met Arg Gly Leu Asn Pro Gly Thr Val Asn Ser Cys
            360                 365                 370 tgc att ccc acc aag ctg agc acc atg tcc atg ctg tac ttc gat gat    1927
Cys Ile Pro Thr Lys Leu Ser Thr Met Ser Met Leu Tyr Phe Asp Asp
        375                 380                 385 gag tac aac atc gtc aag cgg gac gtg ccc aac atg att gtg gag gag    1975
Glu Tyr Asn Ile Val Lys Arg Asp Val Pro Asn Met Ile Val Glu Glu
    390                 395                 400 tgc ggc tgc gcc tga cagtgcaagg caggggcacg gtggtgggc acggagggca     2030
Cys Gly Cys Ala
405 gtcccgggtg ggcttcttcc agccccccgc gggaacgggg tacacggtgg gctgagtaca   2090
```

```
gtcattctgt tgggctgtgg agatagtgcc agggtgcggc ctgagatatt tttctacagc    2150
ttcatagagc aaccagtcaa aaccagagcg agaaccctca actgacatga aatactttaa    2210
aatgcacacg tagccacgca cagccagacg catcctgcca cccacacagc agcctccagg    2270
ataccagcaa atggatgcgg tgacaaatgg cagcttagct acaaatgcct gtcagtcgga    2330
gagaatgggg tgagcagcca ccattccacc agctggcccg gccacgtctc gaagttgcgc    2390
cttcccgagc acacataaaa gcacaaagac agagacgcag agagagagag agagccacgg    2450
agaggaaaag cagatgcagg ggtggggagc gcagctcggc ggaggctgcg tgtgccccgt    2510
ggcttttacc aggcctgctc tgcctggctc gatgtctgct tcttcccagc ctgggatcct    2570
tcgtgcttca aggcctgggg agcctgtcct tccatgccct tgtcgaggga aagagaccca    2630
gaaaggacac aacccgtcag agacctggga gcagggcaa tgaccgtttg actgtttgtg    2690
gcttgggcct ctgacatgac ttatgtgtgt gtgtgttttt ggggtgggga gggagggaga    2750
gaagaggggg ctaaatttga tgctttaact gatctccaac agttgacagg tcatccttgc    2810
cagttgtata actgaaaaag gacttttcta ccaggtatga ccttttaagt gaaaatctga    2870
attgttctaa atgaaagaa aaaagttgc aatctgtgcc cttcattggg gacattcctc    2930
taggactggt ttggggacgg gtgggaatga cccctaggca agggggatgag accgcaggag    2990 gaaatggcgg ggaggtggca ttcttgaact gctgaggatg gggggtgtcc cctcagcgga    3050
ggccaaggga ggggagcagc ctagttggtc ttggagagat ggggaaggct ttcagctgat    3110
ttgcagaagt tgcccatgtg ggcccaacca tcagggctgg ccgtggacgt ggcccctgcc    3170
cactcacctg cccgcctgcc cgcccgcccg catagcactt gcagacctgc ctgaacgcac    3230
atgacatagc acttgccgat ctgcgtgtgc ccagaagtgg cccttggccg agcgccgaac    3290
tcgctcgccc tctagatgtc caagtgccac gtgaactatg caatttaaag ggttgaccca    3350
cactagacga aactggactc gtacgactct tttatatttt tttatacttg aaatgaaatc    3410
ctttgcttct tttttaagcg aatgattgct tttaatgttt gcactgattt agttgcatga    3470
ttagtcagaa actgccattt gaaaaaaaag ttattttat agcagc                   3516
```

<210> SEQ ID NO 55
<211> LENGTH: 407
<212> TYPE: DNA
<213> ORGANISM: Homo sapiens

<400> SEQUENCE: 55

```
Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Pro Pro Pro Pro Pro Gly Ala Pro
        35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125
```

```
His Ala Ser Pro Gly Ala Asp Gly Gln Glu Arg Val Ser Glu Ile Ile
        130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Gln Ala
                165                 170                 175

Ser Leu Trp Leu Tyr Leu Lys Leu Leu Pro Tyr Val Leu Glu Lys Gly
                180                 185                 190

Ser Arg Arg Lys Val Arg Val Lys Val Tyr Phe Gln Glu Gln Gly His
            195                 200                 205

Gly Asp Arg Trp Asn Met Val Glu Lys Arg Val Asp Leu Lys Arg Ser
        210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
                245                 250                 255

Glu Leu Ala Val Val Pro Val Phe Val Asp Pro Gly Glu Glu Ser His
                260                 265                 270

Arg Pro Phe Val Val Val Gln Ala Arg Leu Gly Asp Ser Arg His Arg
            275                 280                 285

Ile Arg Lys Arg Gly Leu Glu Cys Asp Gly Arg Thr Asn Leu Cys Cys
        290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
                340                 345                 350

Ala Val Val Asn Gln Tyr Arg Met Arg Gly Leu Asn Pro Gly Thr Val
            355                 360                 365

Asn Ser Cys Cys Ile Pro Thr Lys Leu Ser Thr Met Ser Met Leu Tyr
        370                 375                 380

Phe Asp Asp Glu Tyr Asn Ile Val Lys Arg Asp Val Pro Asn Met Ile
385                 390                 395                 400

Val Glu Glu Cys Gly Cys Ala
                405

<210> SEQ ID NO 56
<211> LENGTH: 4960
<212> TYPE: DNA
<213> ORGANISM: Homo sapiens
<220> FEATURE:
<221> NAME/KEY: CDS
<222> LOCATION: (572)..(4348)

<400> SEQUENCE: 56
gcgcccgccg ccttacctga ggccgccatc cacgccggtt gagtcgcgtt ctgccgcctc     60
ccgcctgtgg tgcctcctga actgcgtccg ccgtctagtg aagttcgtgg actcctacaa    120
taatgctata aatgcataga agaaaagaca caggactgtg aaagaaagtg atgatgcgat    180
gtctaaaacg ttcaaggcac cgcatctgtg atcaagaata catgtgctgc tttaccgaca    240
catcaaagag caaggattgc cacccaggac gatgagcggc tgagatggag acgtctgcct    300
cagccactgc ctccgagaag caagaagcca aaagtgggat cctggaggcc gctggcttcc    360
ccgacccggg taaaaaggcc tctcctttgg tggtggctgc agcggcagca gcagcggtag    420
```

-continued

```
ctgcccaagg agcccagcct tcaccttccc ccaccccatc aaccccgtgg cctaccagca    480
gattctgagc cagcagaggg gtctggggtc agcctttgga cacacaccac ccctgatcca    540
gccctcaccc accttcctgg cccagcagcc c atg gcc ctc acc tcc atc aat      592
                                   Met Ala Leu Thr Ser Ile Asn
                                     1               5 gcc acg ccc acc cag ctc agc agc agc agc aac tgt ctg agt gac acc      640
Ala Thr Pro Thr Gln Leu Ser Ser Ser Ser Asn Cys Leu Ser Asp Thr
            10                  15                  20 aac cag aac aag cag agc agt gag tcg gcc gtc agc agc acc gtc aac      688
Asn Gln Asn Lys Gln Ser Ser Glu Ser Ala Val Ser Ser Thr Val Asn
 25                  30                  35 cct gtc gcc att cac aag cgc agc aag gtc aag acc gag cct gag ggc      736
Pro Val Ala Ile His Lys Arg Ser Lys Val Lys Thr Glu Pro Glu Gly
 40                  45                  50                  55 ctg cgg ccg gcc tcc cct ctg gcg ctg acg cag ggc cag gtg ctg gac      784
Leu Arg Pro Ala Ser Pro Leu Ala Leu Thr Gln Gly Gln Val Leu Asp
                 60                  65                  70 acg gct cat gtg ggt gtg ccc ttc ccc tct ccc cag gag cag ctg gct      832
Thr Ala His Val Gly Val Pro Phe Pro Ser Pro Gln Glu Gln Leu Ala
             75                  80                  85 gac ctc aag gaa gat ctg gac agg gat gac tgt aag cag gag gct gag      880
Asp Leu Lys Glu Asp Leu Asp Arg Asp Asp Cys Lys Gln Glu Ala Glu
         90                  95                 100 gtg gtc atc tat gag acc aac tgc cac tgg gaa gac tgc acc aag gag      928
Val Val Ile Tyr Glu Thr Asn Cys His Trp Glu Asp Cys Thr Lys Glu
        105                 110                 115 tac gac acc cag gag cag ctg gtg cat cac atc aac aac gag cac atc      976
Tyr Asp Thr Gln Glu Gln Leu Val His His Ile Asn Asn Glu His Ile
120                 125                 130                 135 cac ggg gag aag aag gag ttt gtg tgc cgc tgg cag gcc tgc acg cgg     1024
His Gly Glu Lys Lys Glu Phe Val Cys Arg Trp Gln Ala Cys Thr Arg
                140                 145                 150 gag cag aag ccc ttc aag gcg cag tac atg ctg gtg gtg cac atg cgg     1072
Glu Gln Lys Pro Phe Lys Ala Gln Tyr Met Leu Val Val His Met Arg
            155                 160                 165 cga cac acg ggc gag aag ccc cac aag tgc acg ttc gag ggc tgc tcg     1120
Arg His Thr Gly Glu Lys Pro His Lys Cys Thr Phe Glu Gly Cys Ser
        170                 175                 180 aag gcc tac tcc cgc ctg gag aac ctg aag aca cac ctg cgg tcc cac     1168
Lys Ala Tyr Ser Arg Leu Glu Asn Leu Lys Thr His Leu Arg Ser His
185                 190                 195 acc ggg gag aag cca tat gtg tgt gag cac gag ggc tgc aac aaa gcc     1216
Thr Gly Glu Lys Pro Tyr Val Cys Glu His Glu Gly Cys Asn Lys Ala
200                 205                 210                 215 ttc tcc aac gcc tcg gac cgc gcc aag cac cag aat cgc acc cac tcc     1264
Phe Ser Asn Ala Ser Asp Arg Ala Lys His Gln Asn Arg Thr His Ser
                220                 225                 230 aac gag aaa ccc tac atc tgc aag atc cca ggc tgc acc aag aga tac     1312
Asn Glu Lys Pro Tyr Ile Cys Lys Ile Pro Gly Cys Thr Lys Arg Tyr
            235                 240                 245 aca gac ccc agc tct ctc cgg aag cat gtg aaa acg gtc cac ggc cca     1360
Thr Asp Pro Ser Ser Leu Arg Lys His Val Lys Thr Val His Gly Pro
        250                 255                 260 gat gcc cac gtc acc aag aag cag cgc aat gac gtg cac ctc cgc aca     1408
Asp Ala His Val Thr Lys Lys Gln Arg Asn Asp Val His Leu Arg Thr
265                 270                 275 ccg ctg ctc aaa gag aat ggg gac agt gag gcc ggc acg gag cct ggc     1456
Pro Leu Leu Lys Glu Asn Gly Asp Ser Glu Ala Gly Thr Glu Pro Gly
```

-continued

```
                280                 285                 290                 295
ggc cca gag agc acc gag gcc agc agc acc agc cag gcc gtg gag gac          1504
Gly Pro Glu Ser Thr Glu Ala Ser Ser Thr Ser Gln Ala Val Glu Asp
                    300                 305                 310 tgc ctg cac gtc aga gcc atc aag acc gag agc tcc ggg ctg tgt cag          1552
Cys Leu His Val Arg Ala Ile Lys Thr Glu Ser Ser Gly Leu Cys Gln
            315                 320                 325 tcc agc ccc ggg gcc cag tcg tcc tgc agc agc gag ccc tct cct ctg          1600
Ser Ser Pro Gly Ala Gln Ser Ser Cys Ser Ser Glu Pro Ser Pro Leu
                330                 335                 340 ggc agt gcc ccc aac aat gac agt ggc gtg gag atg ccg ggg acg ggg          1648
Gly Ser Ala Pro Asn Asn Asp Ser Gly Val Glu Met Pro Gly Thr Gly
            345                 350                 355 ccc ggg agc ctg gga gac ctg acg gca ctg gat gac aca ccc cca ggg          1696
Pro Gly Ser Leu Gly Asp Leu Thr Ala Leu Asp Asp Thr Pro Pro Gly
360                 365                 370                 375 gcc gac acc tca gcc ctg gct gcc ccc tcc gct ggt ggc ctc cag ctg          1744
Ala Asp Thr Ser Ala Leu Ala Ala Pro Ser Ala Gly Gly Leu Gln Leu
                380                 385                 390 cgc aaa cac atg acc acc atg cac cgg ttc gag cag ctc aag aag gag          1792
Arg Lys His Met Thr Thr Met His Arg Phe Glu Gln Leu Lys Lys Glu
            395                 400                 405 aag ctc aag tca ctc aag gat tcc tgc tca tgg gcc ggg ccg act cca          1840
Lys Leu Lys Ser Leu Lys Asp Ser Cys Ser Trp Ala Gly Pro Thr Pro
                410                 415                 420 cac acg cgg aac acc aag ctg cct ccc ctc ccg gga agt ggc tcc atc          1888
His Thr Arg Asn Thr Lys Leu Pro Pro Leu Pro Gly Ser Gly Ser Ile
            425                 430                 435 ctg gaa aac ttc agt ggc agt ggg ggc ggc ggg ccc gcg ggg ctg ctg          1936
Leu Glu Asn Phe Ser Gly Ser Gly Gly Gly Gly Pro Ala Gly Leu Leu
440                 445                 450                 455 ccg aac ccg cgg ctg tcg gag ctg tcc gcg agc gag gtg acc atg ctg          1984
Pro Asn Pro Arg Leu Ser Glu Leu Ser Ala Ser Glu Val Thr Met Leu
                460                 465                 470 agc cag ctg cag gag cgc cgc gac agc tcc acc agc acg gtc agc tcg          2032
Ser Gln Leu Gln Glu Arg Arg Asp Ser Ser Thr Ser Thr Val Ser Ser
            475                 480                 485 gcc tac acc gtg agc cgc cgc tcc tcc ggc atc tcc ccc tac ttc tcc          2080
Ala Tyr Thr Val Ser Arg Arg Ser Ser Gly Ile Ser Pro Tyr Phe Ser
                490                 495                 500 agc cgc cgc tcc agc gag gcc tcg ccc ctg ggc gcc ggc cgc ccg cac          2128
Ser Arg Arg Ser Ser Glu Ala Ser Pro Leu Gly Ala Gly Arg Pro His
            505                 510                 515 aac gcg agc tcc gct gac tcc tac gac ccc atc tcc acg gac gcg tcg          2176
Asn Ala Ser Ser Ala Asp Ser Tyr Asp Pro Ile Ser Thr Asp Ala Ser
520                 525                 530                 535 cgg cgc tcg agc gag gcc agc cag tgc agc ggc tcc ggg ctg ctc          2224
Arg Arg Ser Ser Glu Ala Ser Gln Cys Ser Gly Ser Gly Leu Leu
                540                 545                 550 aac ctc acg ccg gcg cag cag tac agc ctg cgg gcc aag tac gcg gca          2272
Asn Leu Thr Pro Ala Gln Gln Tyr Ser Leu Arg Ala Lys Tyr Ala Ala
            555                 560                 565 gcc act ggc ggc ccc ccg ccc act ccg ctg ccg ggc ctg gag cgc atg          2320
Ala Thr Gly Gly Pro Pro Pro Thr Pro Leu Pro Gly Leu Glu Arg Met
                570                 575                 580 agc ctg cgg acc agg ctg gcg ctg ctg gac gcg gcc gag ggc acg ctg          2368
Ser Leu Arg Thr Arg Leu Ala Leu Leu Asp Ala Ala Glu Gly Thr Leu
            585                 590                 595 ccc gcc ggc tgc cca cgc cca ctg ggg ccg cgg cgt ggc agc gac ggg          2416
```

```
                Pro Ala Gly Cys Pro Arg Pro Leu Gly Pro Arg Arg Gly Ser Asp Gly
                600                 605                 610                 615 ccg acc tat ggc cac ggc cac gcg ggg gct gcg ccc gcc ttc ccc cac                    2464
Pro Thr Tyr Gly His Gly His Ala Gly Ala Ala Pro Ala Phe Pro His
                620                 625                 630 gag gct cca ggc ggc gga acc agg cgg gcc agc gac cct gtg cgg cgg                    2512
Glu Ala Pro Gly Gly Gly Thr Arg Arg Ala Ser Asp Pro Val Arg Arg
                635                 640                 645 ccc gat gcc ctg tcc ctg ccg cgg gtg cag cgc ttc cac agc acc cac                    2560
Pro Asp Ala Leu Ser Leu Pro Arg Val Gln Arg Phe His Ser Thr His
                650                 655                 660 aac gtg aac ccc ggc ccg ctg ccg ccc tgt gcc gac agg cga ggc ctc                    2608
Asn Val Asn Pro Gly Pro Leu Pro Pro Cys Ala Asp Arg Arg Gly Leu
                665                 670                 675 cgc ctg cag agc cac ccg agc acc gac ggc ggc ctg gcc cgc ggc gcc                    2656
Arg Leu Gln Ser His Pro Ser Thr Asp Gly Gly Leu Ala Arg Gly Ala
680                 685                 690                 695 tac tcg ccc cgg ccg cct agc atc agc gag aac gtg gcg atg gag gcc                    2704
Tyr Ser Pro Arg Pro Pro Ser Ile Ser Glu Asn Val Ala Met Glu Ala
                700                 705                 710 gtg gcg gca gga gtg gac ggc gcg ggg ccc gag gcc gac ctg ggg ctg                    2752
Val Ala Ala Gly Val Asp Gly Ala Gly Pro Glu Ala Asp Leu Gly Leu
                715                 720                 725 ccg gag gac gac ctg gtg ctt cca gac gac gtg gtg cag tac atc aag                    2800
Pro Glu Asp Asp Leu Val Leu Pro Asp Asp Val Val Gln Tyr Ile Lys
                730                 735                 740 gcg cac gcc agt ggc gct ctg gac gag ggc acc ggg cag gtg tat ccc                    2848
Ala His Ala Ser Gly Ala Leu Asp Glu Gly Thr Gly Gln Val Tyr Pro
745                 750                 755 acg gaa agc act ggc ttc tct gac aac ccc aga cta ccc agc ccg ggg                    2896
Thr Glu Ser Thr Gly Phe Ser Asp Asn Pro Arg Leu Pro Ser Pro Gly
760                 765                 770                 775 ctg cac ggc cag cgc agg atg gtg gct gcg gac tcc aac gtg ggc ccc                    2944
Leu His Gly Gln Arg Arg Met Val Ala Ala Asp Ser Asn Val Gly Pro
                780                 785                 790 tcc gcc cct atg ctg gga gga tgc cag tta ggc ttt ggg gcg ccc tcc                    2992
Ser Ala Pro Met Leu Gly Gly Cys Gln Leu Gly Phe Gly Ala Pro Ser
                795                 800                 805 agc ctg aac aaa aat aac atg cct gtg cag tgg aat gag gtg agc tcc                    3040
Ser Leu Asn Lys Asn Asn Met Pro Val Gln Trp Asn Glu Val Ser Ser
                810                 815                 820 ggc acc gta gac tcc ctg gcc agc cag gtg aag cct cca ccc ttt cct                    3088
Gly Thr Val Asp Ser Leu Ala Ser Gln Val Lys Pro Pro Pro Phe Pro
825                 830                 835 cag ggc aac ctg gcg gtg gtg cag cag aag cct gcc ttt ggc cag tac                    3136
Gln Gly Asn Leu Ala Val Val Gln Gln Lys Pro Ala Phe Gly Gln Tyr
840                 845                 850                 855 ccg ggc tac agt ccg caa ggc cta cag gct agc cct ggg ggc ctg gac                    3184
Pro Gly Tyr Ser Pro Gln Gly Leu Gln Ala Ser Pro Gly Gly Leu Asp
                860                 865                 870 agc acg cag cca cac ctg cag ccc cgc agc gga gcc ccc tcc cag ggc                    3232
Ser Thr Gln Pro His Leu Gln Pro Arg Ser Gly Ala Pro Ser Gln Gly
                875                 880                 885 atc ccc agg gta aac tac atg cag cag ctg cga cag cca gtg gca ggc                    3280
Ile Pro Arg Val Asn Tyr Met Gln Gln Leu Arg Gln Pro Val Ala Gly
                890                 895                 900 agc cag tgt cct ggc atg act acc act atg agc ccc cat gcc tgc tat                    3328
Ser Gln Cys Pro Gly Met Thr Thr Thr Met Ser Pro His Ala Cys Tyr
905                 910                 915
```

```
ggc caa gtc cac ccc cag ctg agc ccc agc acc atc agt ggg gcc ctc     3376
Gly Gln Val His Pro Gln Leu Ser Pro Ser Thr Ile Ser Gly Ala Leu
920             925                 930                 935 aac cag ttc ccc caa tcc tgc agc aac atg cca gcc aag cca ggg cat     3424
Asn Gln Phe Pro Gln Ser Cys Ser Asn Met Pro Ala Lys Pro Gly His
            940                 945                 950 ctg ggg cac cct cag cag aca gaa gtg gca cct gac ccc acc acg atg     3472
Leu Gly His Pro Gln Gln Thr Glu Val Ala Pro Asp Pro Thr Thr Met
        955                 960                 965 ggc aat cgc cac agg gaa ctt ggg gtc ccc aat tca gcc ctg gct gga     3520
Gly Asn Arg His Arg Glu Leu Gly Val Pro Asn Ser Ala Leu Ala Gly
    970                 975                 980 gtg ccg cca cct cac cca gtc cag agc tac cca cag cag agc cat cac     3568
Val Pro Pro Pro His Pro Val Gln Ser Tyr Pro Gln Gln Ser His His
985                 990                 995 ctg gca gcc tcc atg agc cag gag ggc tac cac cag gtc ccc agc        3613
Leu Ala Ala Ser Met Ser Gln Glu Gly Tyr His Gln Val Pro Ser
1000            1005                1010 ctt ctg cct gcc cgc cag cct ggc ttc atg gag ccc caa aca ggc        3658
Leu Leu Pro Ala Arg Gln Pro Gly Phe Met Glu Pro Gln Thr Gly
1015            1020                1025 ccg atg ggg gtg gct aca gca ggc ttt ggc cta gtg cag ccc cgg        3703
Pro Met Gly Val Ala Thr Ala Gly Phe Gly Leu Val Gln Pro Arg
1030            1035                1040 cct ccc ctc gag ccc agc ccc act ggc cgc cac cgt ggg gta cgt        3748
Pro Pro Leu Glu Pro Ser Pro Thr Gly Arg His Arg Gly Val Arg
1045            1050                1055 gct gtg cag cag cag ctg gcc tac gcc agg gcc aca ggc cat gcc        3793
Ala Val Gln Gln Gln Leu Ala Tyr Ala Arg Ala Thr Gly His Ala
1060            1065                1070 atg gct gcc atg ccg tcc agt cag gaa aca gca gag gct gtg ccc        3838
Met Ala Ala Met Pro Ser Ser Gln Glu Thr Ala Glu Ala Val Pro
1075            1080                1085 aag gga gcg atg ggc aac atg ggg tcg gtg cct ccc cag ccg cct        3883
Lys Gly Ala Met Gly Asn Met Gly Ser Val Pro Pro Gln Pro Pro
1090            1095                1100 ccg cag gac gca ggt ggg gcc ccg gac cac agc atg ctc tac tac        3928
Pro Gln Asp Ala Gly Gly Ala Pro Asp His Ser Met Leu Tyr Tyr
1105            1110                1115 tac ggc cag atc cac atg tac gaa cag gat gga ggc ctg gag aac        3973
Tyr Gly Gln Ile His Met Tyr Glu Gln Asp Gly Gly Leu Glu Asn
1120            1125                1130 ctc ggg agc tgc cag gtc atg cgg tcc cag cca cca cag cca cag        4018
Leu Gly Ser Cys Gln Val Met Arg Ser Gln Pro Pro Gln Pro Gln
1135            1140                1145 gcc tgt cag gac agc atc cag ccc cag ccc ttg ccc tca cca ggg        4063
Ala Cys Gln Asp Ser Ile Gln Pro Gln Pro Leu Pro Ser Pro Gly
1150            1155                1160 gtc aac cag gtg tcc agc act gtg gac tcc cag ctc ctg gag gcc        4108
Val Asn Gln Val Ser Ser Thr Val Asp Ser Gln Leu Leu Glu Ala
1165            1170                1175 ccc cag att gac ttc gat gcc atc atg gat gat ggc gat cac tcg        4153
Pro Gln Ile Asp Phe Asp Ala Ile Met Asp Asp Gly Asp His Ser
1180            1185                1190 agt ttg ttc tcg ggt gct ctg agc ccc agc ctc ctc cac agc ctc        4198
Ser Leu Phe Ser Gly Ala Leu Ser Pro Ser Leu Leu His Ser Leu
1195            1200                1205 tcc cag aac tcc tcc cgc ctc acc acc ccc cga aac tcc ttg acc        4243
Ser Gln Asn Ser Ser Arg Leu Thr Thr Pro Arg Asn Ser Leu Thr
1210            1215                1220
```

| | | |
|---|---|---|
| ctg ccc tcc atc ccc gca ggc atc agc aac atg gct gtc ggg gac<br>Leu Pro Ser Ile Pro Ala Gly Ile Ser Asn Met Ala Val Gly Asp<br>1225                    1230                    1235 | | 4288 |
| atg agc tcc atg ctc acc agc ctc gcc gag gag agc aag ttc ctg<br>Met Ser Ser Met Leu Thr Ser Leu Ala Glu Glu Ser Lys Phe Leu<br>1240                    1245                    1250 | | 4333 |
| aac atg atg acc tag aggcccgagc gcctggtgct gagtgcaccc ggaggggtca<br>Asn Met Met Thr<br>1255 | | 4388 |
| tcgctgccca gagcctgggg attccagctg tcttgtcttt ttccaaaaaa gtgttaaata | | 4448 |
| ggcttgaggg gttgttgcgc aatggccgct tcagatgaca gatgttgtaa gagaaggttt | | 4508 |
| atgggcatcc tctctggtct tttggattat tcctcagaac aatgaaaaaa gtctccatag | | 4568 |
| gacaggaagg aatgcaaaac tcatttacac agtgctttcc agcctttggt gcttacagga | | 4628 |
| ccgcgctgtt ccggcttctt cacggctgac attcggctaa cgagggatta ctttggccaa | | 4688 |
| aaccttcaa aggatatgca gaaagatggt agggagcatt tgggtttgaa tctgaatgct | | 4748 |
| atactggata ctctgctccg gaaagatgag cttttattc tactacttgg aaggaaaagg | | 4808 |
| aattcctcta tgaagcctaa ctcttgaggt ctctaacata ccttgtcata gaggaaaagc | | 4868 |
| acagattata cctggatgat tcaggagagt gtatatgaat gaataaggca tccaagtata | | 4928 |
| tatgaatgaa taaagtatgt aagtatcacc ag | | 4960 |

```
<210> SEQ ID NO 57
<211> LENGTH: 1258
<212> TYPE: DNA
<213> ORGANISM: Homo sapiens

<400> SEQUENCE: 57
```

Met Ala Leu Thr Ser Ile Asn Ala Thr Pro Thr Gln Leu Ser Ser
1               5                    10                  15

Ser Asn Cys Leu Ser Asp Thr Asn Gln Asn Lys Gln Ser Ser Glu Ser
          20                   25                  30

Ala Val Ser Ser Thr Val Asn Pro Val Ala Ile His Lys Arg Ser Lys
         35                   40                  45

Val Lys Thr Glu Pro Glu Gly Leu Arg Pro Ala Ser Pro Leu Ala Leu
 50                   55                  60

Thr Gln Gly Gln Val Leu Asp Thr Ala His Val Gly Val Pro Phe Pro
65               70                  75                  80

Ser Pro Gln Glu Gln Leu Ala Asp Leu Lys Glu Asp Leu Asp Arg Asp
         85                   90                  95

Asp Cys Lys Gln Glu Ala Glu Val Val Ile Tyr Glu Thr Asn Cys His
        100                 105               110

Trp Glu Asp Cys Thr Lys Glu Tyr Asp Thr Gln Glu Gln Leu Val His
        115                 120               125

His Ile Asn Asn Glu His Ile His Gly Glu Lys Lys Glu Phe Val Cys
     130                 135               140

Arg Trp Gln Ala Cys Thr Arg Glu Gln Lys Pro Phe Lys Ala Gln Tyr
145              150                  155               160

Met Leu Val Val His Met Arg Arg His Thr Gly Glu Lys Pro His Lys
        165                 170               175

Cys Thr Phe Glu Gly Cys Ser Lys Ala Tyr Ser Arg Leu Glu Asn Leu
        180                 185               190

Lys Thr His Leu Arg Ser His Thr Gly Glu Lys Pro Tyr Val Cys Glu
     195                 200               205

```
His Glu Gly Cys Asn Lys Ala Phe Ser Asn Ala Ser Asp Arg Ala Lys
    210                 215                 220

His Gln Asn Arg Thr His Ser Asn Glu Lys Pro Tyr Ile Cys Lys Ile
225                 230                 235                 240

Pro Gly Cys Thr Lys Arg Tyr Thr Asp Pro Ser Ser Leu Arg Lys His
                245                 250                 255

Val Lys Thr Val His Gly Pro Asp Ala His Val Thr Lys Lys Gln Arg
            260                 265                 270

Asn Asp Val His Leu Arg Thr Pro Leu Leu Lys Glu Asn Gly Asp Ser
        275                 280                 285

Glu Ala Gly Thr Glu Pro Gly Gly Pro Glu Ser Thr Glu Ala Ser Ser
    290                 295                 300

Thr Ser Gln Ala Val Glu Asp Cys Leu His Val Arg Ala Ile Lys Thr
305                 310                 315                 320

Glu Ser Ser Gly Leu Cys Gln Ser Ser Pro Gly Ala Gln Ser Ser Cys
                325                 330                 335

Ser Ser Glu Pro Ser Pro Leu Gly Ser Ala Pro Asn Asn Asp Ser Gly
            340                 345                 350

Val Glu Met Pro Gly Thr Gly Pro Gly Ser Leu Gly Asp Leu Thr Ala
        355                 360                 365

Leu Asp Asp Thr Pro Pro Gly Ala Asp Thr Ser Ala Leu Ala Ala Pro
    370                 375                 380

Ser Ala Gly Gly Leu Gln Leu Arg Lys His Met Thr Thr Met His Arg
385                 390                 395                 400

Phe Glu Gln Leu Lys Lys Glu Lys Leu Lys Ser Leu Lys Asp Ser Cys
                405                 410                 415

Ser Trp Ala Gly Pro Thr Pro His Thr Arg Asn Thr Lys Leu Pro Pro
            420                 425                 430

Leu Pro Gly Ser Gly Ser Ile Leu Glu Asn Phe Ser Gly Ser Gly Gly
    435                 440                 445

Gly Gly Pro Ala Gly Leu Leu Pro Asn Pro Arg Leu Ser Glu Leu Ser
    450                 455                 460

Ala Ser Glu Val Thr Met Leu Ser Gln Leu Gln Glu Arg Arg Asp Ser
465                 470                 475                 480

Ser Thr Ser Thr Val Ser Ser Ala Tyr Thr Val Ser Arg Arg Ser Ser
                485                 490                 495

Gly Ile Ser Pro Tyr Phe Ser Ser Arg Arg Ser Ser Glu Ala Ser Pro
            500                 505                 510

Leu Gly Ala Gly Arg Pro His Asn Ala Ser Ser Ala Asp Ser Tyr Asp
    515                 520                 525

Pro Ile Ser Thr Asp Ala Ser Arg Arg Ser Ser Glu Ala Ser Gln Cys
    530                 535                 540

Ser Gly Gly Ser Gly Leu Leu Asn Leu Thr Pro Ala Gln Gln Tyr Ser
545                 550                 555                 560

Leu Arg Ala Lys Tyr Ala Ala Ala Thr Gly Pro Pro Pro Thr Pro
                565                 570                 575

Leu Pro Gly Leu Glu Arg Met Ser Leu Arg Thr Arg Leu Ala Leu Leu
            580                 585                 590

Asp Ala Ala Glu Gly Thr Leu Pro Ala Gly Cys Pro Arg Pro Leu Gly
    595                 600                 605

Pro Arg Arg Gly Ser Asp Gly Pro Thr Tyr Gly His Gly His Ala Gly
    610                 615                 620
```

```
Ala Ala Pro Ala Phe Pro His Glu Ala Pro Gly Gly Thr Arg Arg
625                 630                 635                 640

Ala Ser Asp Pro Val Arg Arg Pro Asp Ala Leu Ser Leu Pro Arg Val
                645                 650                 655

Gln Arg Phe His Ser Thr His Asn Val Asn Pro Gly Pro Leu Pro Pro
            660                 665                 670

Cys Ala Asp Arg Arg Gly Leu Arg Leu Gln Ser His Pro Ser Thr Asp
        675                 680                 685

Gly Gly Leu Ala Arg Gly Ala Tyr Ser Pro Arg Pro Ser Ile Ser
    690                 695                 700

Glu Asn Val Ala Met Glu Ala Val Ala Ala Gly Val Asp Gly Ala Gly
705                 710                 715                 720

Pro Glu Ala Asp Leu Gly Leu Pro Glu Asp Leu Val Leu Pro Asp
                725                 730                 735

Asp Val Val Gln Tyr Ile Lys Ala His Ala Ser Gly Ala Leu Asp Glu
            740                 745                 750

Gly Thr Gly Gln Val Tyr Pro Thr Glu Ser Thr Gly Phe Ser Asp Asn
        755                 760                 765

Pro Arg Leu Pro Ser Pro Gly Leu His Gly Gln Arg Arg Met Val Ala
    770                 775                 780

Ala Asp Ser Asn Val Gly Pro Ser Ala Pro Met Leu Gly Gly Cys Gln
785                 790                 795                 800

Leu Gly Phe Gly Ala Pro Ser Ser Leu Asn Lys Asn Asn Met Pro Val
                805                 810                 815

Gln Trp Asn Glu Val Ser Ser Gly Thr Val Asp Ser Leu Ala Ser Gln
            820                 825                 830

Val Lys Pro Pro Pro Phe Pro Gln Gly Asn Leu Ala Val Gln Gln
        835                 840                 845

Lys Pro Ala Phe Gly Gln Tyr Pro Gly Tyr Ser Pro Gln Gly Leu Gln
    850                 855                 860

Ala Ser Pro Gly Gly Leu Asp Ser Thr Gln Pro His Leu Gln Pro Arg
865                 870                 875                 880

Ser Gly Ala Pro Ser Gln Gly Ile Pro Arg Val Asn Tyr Met Gln Gln
                885                 890                 895

Leu Arg Gln Pro Val Ala Gly Ser Gln Cys Pro Gly Met Thr Thr Thr
            900                 905                 910

Met Ser Pro His Ala Cys Tyr Gly Gln Val His Pro Gln Leu Ser Pro
        915                 920                 925

Ser Thr Ile Ser Gly Ala Leu Asn Gln Phe Pro Gln Ser Cys Ser Asn
    930                 935                 940

Met Pro Ala Lys Pro Gly His Leu Gly His Pro Gln Gln Thr Glu Val
945                 950                 955                 960

Ala Pro Asp Pro Thr Thr Met Gly Asn Arg His Arg Glu Leu Gly Val
                965                 970                 975

Pro Asn Ser Ala Leu Ala Gly Val Pro Pro His Pro Val Gln Ser
            980                 985                 990

Tyr Pro Gln Gln Ser His His Leu Ala Ala Ser Met Ser Gln Glu Gly
        995                 1000                1005

Tyr His Gln Val Pro Ser Leu Leu Pro Ala Arg Gln Pro Gly Phe
    1010                1015                1020

Met Glu Pro Gln Thr Gly Pro Met Gly Val Ala Thr Ala Gly Phe
    1025                1030                1035

Gly Leu Val Gln Pro Arg Pro Pro Leu Glu Pro Ser Pro Thr Gly
```

| | | | | | | | | | | | |
|---|---|---|---|---|---|---|---|---|---|---|---|
| | | 1040 | | | 1045 | | | 1050 | | | |
| Arg | His | Arg | Gly | Val | Arg | Ala | Val | Gln | Gln | Leu | Ala Tyr Ala |
| | | 1055 | | | 1060 | | | 1065 | | | |
| Arg | Ala | Thr | Gly | His | Ala | Met | Ala | Ala | Met | Pro | Ser Ser Gln Glu |
| | | 1070 | | | 1075 | | | 1080 | | | |
| Thr | Ala | Glu | Ala | Val | Pro | Lys | Gly | Ala | Met | Gly | Asn Met Gly Ser |
| | | 1085 | | | 1090 | | | 1095 | | | |
| Val | Pro | Pro | Gln | Pro | Pro | Pro | Gln | Asp | Ala | Gly | Ala Pro Asp |
| | | 1100 | | | 1105 | | | 1110 | | | |
| His | Ser | Met | Leu | Tyr | Tyr | Tyr | Gly | Gln | Ile | His | Met Tyr Glu Gln |
| | | 1115 | | | 1120 | | | 1125 | | | |
| Asp | Gly | Gly | Leu | Glu | Asn | Leu | Gly | Ser | Cys | Gln | Val Met Arg Ser |
| | | 1130 | | | 1135 | | | 1140 | | | |
| Gln | Pro | Pro | Gln | Pro | Gln | Ala | Cys | Gln | Asp | Ser | Ile Gln Pro Gln |
| | | 1145 | | | 1150 | | | 1155 | | | |
| Pro | Leu | Pro | Ser | Pro | Gly | Val | Asn | Gln | Val | Ser | Thr Val Asp |
| | | 1160 | | | 1165 | | | 1170 | | | |
| Ser | Gln | Leu | Leu | Glu | Ala | Pro | Gln | Ile | Asp | Phe | Asp Ala Ile Met |
| | | 1175 | | | 1180 | | | 1185 | | | |
| Asp | Asp | Gly | Asp | His | Ser | Ser | Leu | Phe | Ser | Gly | Ala Leu Ser Pro |
| | | 1190 | | | 1195 | | | 1200 | | | |
| Ser | Leu | Leu | His | Ser | Leu | Ser | Gln | Asn | Ser | Ser | Arg Leu Thr Thr |
| | | 1205 | | | 1210 | | | 1215 | | | |
| Pro | Arg | Asn | Ser | Leu | Thr | Leu | Pro | Ser | Ile | Pro | Ala Gly Ile Ser |
| | | 1220 | | | 1225 | | | 1230 | | | |
| Asn | Met | Ala | Val | Gly | Asp | Met | Ser | Ser | Met | Leu | Thr Ser Leu Ala |
| | | 1235 | | | 1240 | | | 1245 | | | |
| Glu | Glu | Ser | Lys | Phe | Leu | Asn | Met | Met | Thr | | |
| | | 1250 | | | 1255 | | | | | | |

```
<210> SEQ ID NO 58
<211> LENGTH: 2802
<212> TYPE: DNA
<213> ORGANISM: Homo sapiens
<220> FEATURE:
<221> NAME/KEY: CDS
<222> LOCATION: (310)..(2037)

<400> SEQUENCE: 58
agcggaggcg gcggcggcgg cggcggcggc agagggagtt ccgctttgc actccacccc      60 ggtagcagct ccgcgcagg gacagcttcc tccggacgct tggcgggctt cgctctcgcc    120
ttacgacagc ccgtcggat catgggtttg cccagggggc cggagggcca gggtctcccg    180
gaggtggaaa caagagaaga tgaagaacaa aatgtcaagt tgactgaaat tctggagctc    240
ttggttgcag ctgggcattt cagggcaaga attaaaggct tatcacccct tgacaaggta    300 gtaggagga  atg act tgg tgt atc act act tgc aac ttt gat gta gat gtt    351
           Met Thr Trp Cys Ile Thr Thr Cys Asn Phe Asp Val Asp Val
            1               5                  10 gat ttg ctc ttt caa gaa aac tct acg ata ggt caa aaa ata gct ctg      399
Asp Leu Leu Phe Gln Glu Asn Ser Thr Ile Gly Gln Lys Ile Ala Leu
15                  20                  25                  30 tca gaa aaa att gtc tcg gtc ctg cca agg atg aaa tgc cca cac cag      447
Ser Glu Lys Ile Val Ser Val Leu Pro Arg Met Lys Cys Pro His Gln
                35                  40                  45 ctg gag ccc cac cag atc cag ggg atg gat ttt att cac ata ttt cct      495
Leu Glu Pro His Gln Ile Gln Gly Met Asp Phe Ile His Ile Phe Pro
```

-continued

```
                         50                  55                  60
gtt gtt cag tgg ctg gtg aaa cga gct ata gaa aca aaa gaa gag atg        543
Val Val Gln Trp Leu Val Lys Arg Ala Ile Glu Thr Lys Glu Glu Met
             65                  70                  75 ggt gac tat atc cgc tcc tac tct gta tcc cag ttc cag aag act tac        591
Gly Asp Tyr Ile Arg Ser Tyr Ser Val Ser Gln Phe Gln Lys Thr Tyr
     80                  85                  90 agt ctc cct gag gat gat gac ttc ata aag aga aaa gaa aag gcc atc        639
Ser Leu Pro Glu Asp Asp Asp Phe Ile Lys Arg Lys Glu Lys Ala Ile
 95                 100                 105                 110 aag aca gtt gtg gac ctc tca gaa gtg tac aag ccc cgt cgg aaa tac        687
Lys Thr Val Val Asp Leu Ser Glu Val Tyr Lys Pro Arg Arg Lys Tyr
                115                 120                 125 aaa cgc cac cag gga gca gag gag cta ctt gat gaa gaa tct cga atc        735
Lys Arg His Gln Gly Ala Glu Glu Leu Leu Asp Glu Glu Ser Arg Ile
                130                 135                 140 cat gct aca ctt ttg gaa tat ggc agg aga tat gga ttt agc tgc cag        783
His Ala Thr Leu Leu Glu Tyr Gly Arg Arg Tyr Gly Phe Ser Cys Gln
            145                 150                 155 agc aaa atg gag aag gct gag gac aag aaa acg gca ctt cca gca ggg        831
Ser Lys Met Glu Lys Ala Glu Asp Lys Lys Thr Ala Leu Pro Ala Gly
        160                 165                 170 ctg tca gct aca gaa aaa gct gat gcc cac gag gaa gat gag ctt cga        879
Leu Ser Ala Thr Glu Lys Ala Asp Ala His Glu Glu Asp Glu Leu Arg
175                 180                 185                 190 gca gct gaa gag cag cgt att cag tcg ctg atg acc aag atg acc gct        927
Ala Ala Glu Glu Gln Arg Ile Gln Ser Leu Met Thr Lys Met Thr Ala
                195                 200                 205 atg gca aat gag gag agc cgt ctc acc gca agc tcc gtg ggc cag att        975
Met Ala Asn Glu Glu Ser Arg Leu Thr Ala Ser Ser Val Gly Gln Ile
                210                 215                 220 gtg gga ctc tgc tct gct gag atc aag cag att gtg tcc gag tat gca       1023
Val Gly Leu Cys Ser Ala Glu Ile Lys Gln Ile Val Ser Glu Tyr Ala
            225                 230                 235 gag aag cag tct gag cta tca gct gaa gaa agt cca gaa aaa tta gga       1071
Glu Lys Gln Ser Glu Leu Ser Ala Glu Glu Ser Pro Glu Lys Leu Gly
        240                 245                 250 acc tcc cag cta cat cgc cgg aaa gtc att tcc ttg aac aaa cag att       1119
Thr Ser Gln Leu His Arg Arg Lys Val Ile Ser Leu Asn Lys Gln Ile
255                 260                 265                 270 gcg caa aag acc aaa cat ctt gaa gag ctg cga gca agt cac acc agc       1167
Ala Gln Lys Thr Lys His Leu Glu Glu Leu Arg Ala Ser His Thr Ser
                275                 280                 285 cta caa gcc aga tat aat gaa gcc aag aaa acg ctg aca gag ctg aag       1215
Leu Gln Ala Arg Tyr Asn Glu Ala Lys Lys Thr Leu Thr Glu Leu Lys
            290                 295                 300 act tac agt gag aaa ctg gac aaa gag caa gca gcc ctc gag aag ata       1263
Thr Tyr Ser Glu Lys Leu Asp Lys Glu Gln Ala Ala Leu Glu Lys Ile
        305                 310                 315 gaa tcc aaa gct gat cca agt atc cta cag aac ctg aga gca ctt gta       1311
Glu Ser Lys Ala Asp Pro Ser Ile Leu Gln Asn Leu Arg Ala Leu Val
320                 325                 330 gcc atg aat gaa aat ctg aaa agt caa gaa cag gaa ttt aaa gca cat       1359
Ala Met Asn Glu Asn Leu Lys Ser Gln Glu Gln Glu Phe Lys Ala His
                335                 340                 345                 350 tgt cga gag gag atg aca cga cta cag caa gaa att gaa aac ctg aaa       1407
Cys Arg Glu Glu Met Thr Arg Leu Gln Gln Glu Ile Glu Asn Leu Lys
            355                 360                 365 gct gag aga gca cca cgt gga gat gaa aag acc ctc tcc agt gga gag       1455
```

```
Ala Glu Arg Ala Pro Arg Gly Asp Glu Lys Thr Leu Ser Ser Gly Glu
            370                 375                 380 ccg cct ggt acc ttg acc tct gca atg act cat gac gaa gac cta gac    1503
Pro Pro Gly Thr Leu Thr Ser Ala Met Thr His Asp Glu Asp Leu Asp
        385                 390                 395 aga cgg tat aat atg gag aaa gag aaa ctt tac aag ata cgt tta cta    1551
Arg Arg Tyr Asn Met Glu Lys Glu Lys Leu Tyr Lys Ile Arg Leu Leu
    400                 405                 410 cag gct cga aga aat cga gaa ata gca att ttg cac cgc aag att gat    1599
Gln Ala Arg Arg Asn Arg Glu Ile Ala Ile Leu His Arg Lys Ile Asp
415                 420                 425                 430 gaa gtc cct agc cgt gcc gag cta ata cag tat cag aag aga ttt att    1647
Glu Val Pro Ser Arg Ala Glu Leu Ile Gln Tyr Gln Lys Arg Phe Ile
                435                 440                 445 gaa ctc tac cgc cag att tca gca gtg cac aaa gaa acc aag cag ttc    1695
Glu Leu Tyr Arg Gln Ile Ser Ala Val His Lys Glu Thr Lys Gln Phe
        450                 455                 460 ttc act tta tat aat acc ctg gat gat aaa aag gtt tat ttg gaa aaa    1743
Phe Thr Leu Tyr Asn Thr Leu Asp Asp Lys Lys Val Tyr Leu Glu Lys
    465                 470                 475 gag att agt ctg ctg aac tca att cat gag aac ttc tca cag gcc atg    1791
Glu Ile Ser Leu Leu Asn Ser Ile His Glu Asn Phe Ser Gln Ala Met
480                 485                 490 gcc tcc cct gct gcc cgg gac cag ttt tta cgt cag atg gaa cag att    1839
Ala Ser Pro Ala Ala Arg Asp Gln Phe Leu Arg Gln Met Glu Gln Ile
495                 500                 505                 510 gtg gaa gga att aag caa agt aga atg aag atg gaa aag aaa aag caa    1887
Val Glu Gly Ile Lys Gln Ser Arg Met Lys Met Glu Lys Lys Lys Gln
                515                 520                 525 gag aac aaa atg aga aga gac cag ttg aac gac cag tac ttg gag ctg    1935
Glu Asn Lys Met Arg Arg Asp Gln Leu Asn Asp Gln Tyr Leu Glu Leu
        530                 535                 540 tta gaa aag cag agg cta tac ttt aag act gtg aaa gag ttc aag gag    1983
Leu Glu Lys Gln Arg Leu Tyr Phe Lys Thr Val Lys Glu Phe Lys Glu
    545                 550                 555 gag ggc cgc aag aac gag atg ctg ctg tcc aag gtg aaa gcg aag gcc    2031
Glu Gly Arg Lys Asn Glu Met Leu Leu Ser Lys Val Lys Ala Lys Ala
560                 565                 570 tcc tga acatccccag ccgtggctgt atgtcattga ttttactttt aagcaccgta     2087
Ser
575 tatcacctac aagatcatga aatggttctg aaagcgacag tagagagatg cagttgtgat   2147 gatttcaaca acctggatgt tttctttctc ctctttgctt ccattcatct ctgttggctg   2207 ctgttgatgg agtcagacag taaacacgtg gcttggataa cacccatcat cctatgaaga   2267 atataggag tacttgttct ctgttgattc aacttttatg tctccagtaa cattgcgctt    2327 atgaaggtac ctgtatttgt atggactctg aataagaag aattcatttg tttagcaagt    2387 attagttcag caaccactga gaataagca ctgaggaaga ttcagagacg tgtaaaacac    2447 agttcctact gcacaagtac ccagcaggtg gcccagggag gcagatacag cacacttgac   2507 cgcagaactg ggctatccaa gatgtttttc agtaaacaga aggcatttag ctgaaatgat   2567 cagcccatgt agtgttggtc acttgggcct ttcacctgcc atggtacctt tgttcccag    2627 ctcctccagg tgccagccag caggcttggt ggtgacagca actggaacga agttcagtg    2687 ttgtttaat tttatacgt tactcaagtt gatttctcag aaaattgaaa acagaccttg     2747 tgctgaggac acgtcaataa aaattatacc ttcccctaca aaaaaaaaaa aaaaa        2802
```

<210> SEQ ID NO 59
<211> LENGTH: 575
<212> TYPE: DNA
<213> ORGANISM: Homo sapiens

<400> SEQUENCE: 59

```
Met Thr Trp Cys Ile Thr Thr Cys Asn Phe Asp Val Asp Val Asp Leu
1               5                   10                  15
Leu Phe Gln Glu Asn Ser Thr Ile Gly Gln Lys Ile Ala Leu Ser Glu
            20                  25                  30
Lys Ile Val Ser Val Leu Pro Arg Met Lys Cys Pro His Gln Leu Glu
        35                  40                  45
Pro His Gln Ile Gln Gly Met Asp Phe Ile His Ile Phe Pro Val Val
    50                  55                  60
Gln Trp Leu Val Lys Arg Ala Ile Glu Thr Lys Glu Glu Met Gly Asp
65                  70                  75                  80
Tyr Ile Arg Ser Tyr Ser Val Ser Gln Phe Gln Lys Thr Tyr Ser Leu
                85                  90                  95
Pro Glu Asp Asp Phe Ile Lys Arg Lys Glu Lys Ala Ile Lys Thr
            100                 105                 110
Val Val Asp Leu Ser Glu Val Tyr Lys Pro Arg Arg Lys Tyr Lys Arg
        115                 120                 125
His Gln Gly Ala Glu Glu Leu Leu Asp Glu Ser Arg Ile His Ala
    130                 135                 140
Thr Leu Leu Glu Tyr Gly Arg Arg Tyr Gly Phe Ser Cys Gln Ser Lys
145                 150                 155                 160
Met Glu Lys Ala Glu Asp Lys Lys Thr Ala Leu Pro Ala Gly Leu Ser
                165                 170                 175
Ala Thr Glu Lys Ala Asp Ala His Glu Glu Asp Glu Leu Arg Ala Ala
            180                 185                 190
Glu Glu Gln Arg Ile Gln Ser Leu Met Thr Lys Met Thr Ala Met Ala
        195                 200                 205
Asn Glu Glu Ser Arg Leu Thr Ala Ser Ser Val Gly Gln Ile Val Gly
    210                 215                 220
Leu Cys Ser Ala Glu Ile Lys Gln Ile Val Ser Glu Tyr Ala Glu Lys
225                 230                 235                 240
Gln Ser Glu Leu Ser Ala Glu Ser Pro Glu Lys Leu Gly Thr Ser
                245                 250                 255
Gln Leu His Arg Arg Lys Val Ile Ser Leu Asn Lys Gln Ile Ala Gln
            260                 265                 270
Lys Thr Lys His Leu Glu Glu Leu Arg Ala Ser His Thr Ser Leu Gln
        275                 280                 285
Ala Arg Tyr Asn Glu Ala Lys Lys Thr Leu Thr Glu Leu Lys Thr Tyr
    290                 295                 300
Ser Glu Lys Leu Asp Lys Glu Gln Ala Ala Leu Glu Lys Ile Glu Ser
305                 310                 315                 320
Lys Ala Asp Pro Ser Ile Leu Gln Asn Leu Arg Ala Leu Val Ala Met
                325                 330                 335
Asn Glu Asn Leu Lys Ser Gln Glu Gln Glu Phe Lys Ala His Cys Arg
            340                 345                 350
Glu Glu Met Thr Arg Leu Gln Gln Gln Ile Glu Asn Leu Lys Ala Glu
        355                 360                 365
Arg Ala Pro Arg Gly Asp Glu Lys Thr Leu Ser Ser Gly Glu Pro Pro
    370                 375                 380
```

```
Gly Thr Leu Thr Ser Ala Met Thr His Asp Glu Asp Leu Asp Arg Arg
385                 390                 395                 400

Tyr Asn Met Glu Lys Glu Lys Leu Tyr Lys Ile Arg Leu Leu Gln Ala
                405                 410                 415

Arg Arg Asn Arg Glu Ile Ala Ile Leu His Arg Lys Ile Asp Glu Val
            420                 425                 430

Pro Ser Arg Ala Glu Leu Ile Gln Tyr Gln Lys Arg Phe Ile Glu Leu
        435                 440                 445

Tyr Arg Gln Ile Ser Ala Val His Lys Glu Thr Lys Gln Phe Phe Thr
    450                 455                 460

Leu Tyr Asn Thr Leu Asp Asp Lys Lys Val Tyr Leu Glu Lys Glu Ile
465                 470                 475                 480

Ser Leu Leu Asn Ser Ile His Glu Asn Phe Ser Gln Ala Met Ala Ser
                485                 490                 495

Pro Ala Ala Arg Asp Gln Phe Leu Arg Gln Met Glu Gln Ile Val Glu
            500                 505                 510

Gly Ile Lys Gln Ser Arg Met Lys Met Glu Lys Lys Gln Glu Asn
        515                 520                 525

Lys Met Arg Arg Asp Gln Leu Asn Asp Gln Tyr Leu Glu Leu Glu
    530                 535                 540

Lys Gln Arg Leu Tyr Phe Lys Thr Val Lys Glu Phe Lys Glu Glu Gly
545                 550                 555                 560

Arg Lys Asn Glu Met Leu Leu Ser Lys Val Lys Ala Lys Ala Ser
                565                 570                 575

<210> SEQ ID NO 60
<211> LENGTH: 3912
<212> TYPE: DNA
<213> ORGANISM: Homo sapiens
<220> FEATURE:
<221> NAME/KEY: CDS
<222> LOCATION: (135)..(1601)

<400> SEQUENCE: 60
accgccttcg ccgcggacct tcagctgccg cggtcgctcc gagcggcggg ccgcagaggt      60
tcaagcgatt ctcctgcttc agcctccgga gtagctggga ttacaggcac gtgccaacac     120
acccagccac caaa atg cca gaa gag atg gac aag cca ctg atc agc ctc       170
              Met Pro Glu Glu Met Asp Lys Pro Leu Ile Ser Leu
              1               5                   10 cac ctg gtg gac agc gat agt agc ctt gcc aag gtc ccc gat gag gcc       218
His Leu Val Asp Ser Asp Ser Ser Leu Ala Lys Val Pro Asp Glu Ala
    15                  20                  25 ccc aaa gtg ggc atc ctg ggt agc ggg gac ttt gcc cgc tcc ctg gcc       266
Pro Lys Val Gly Ile Leu Gly Ser Gly Asp Phe Ala Arg Ser Leu Ala
30              35                  40 aca cgc ctg gtg ggc tct ggc ttc aaa gtg gtg gtg ggg agc cgc aac       314
Thr Arg Leu Val Gly Ser Gly Phe Lys Val Val Val Gly Ser Arg Asn
45              50                  55                  60 ccc aaa cgc aca gcc agg ctg ttt ccc tca gcg gcc caa gtg act ttc       362
Pro Lys Arg Thr Ala Arg Leu Phe Pro Ser Ala Ala Gln Val Thr Phe
                65                  70                  75 caa gag gag gca gtg agc tcc ccg gag gtc atc ttt gtg gct gtg ttc       410
Gln Glu Glu Ala Val Ser Ser Pro Glu Val Ile Phe Val Ala Val Phe
            80                  85                  90 cgg gag cac tac tct tca ctg tgc agt ctc agt gac cag ctg gcg ggc       458
Arg Glu His Tyr Ser Ser Leu Cys Ser Leu Ser Asp Gln Leu Ala Gly
        95                  100                 105
```

```
aag atc ctg gtg gat gtg agc aac cct aca gag caa gag cac ctt cag      506
Lys Ile Leu Val Asp Val Ser Asn Pro Thr Glu Gln Glu His Leu Gln
    110             115                 120 cat cgt gag tcc aat gct gag tac ctg gcc tcc ctc ttc ccc act tgc      554
His Arg Glu Ser Asn Ala Glu Tyr Leu Ala Ser Leu Phe Pro Thr Cys
125             130                 135                 140 aca gtg gtc aag gcc ttc aat gtc atc tct gcc tgg acc ctg cag gct      602
Thr Val Val Lys Ala Phe Asn Val Ile Ser Ala Trp Thr Leu Gln Ala
                145                 150                 155 ggc cca agg gat ggt aac agg cag gtg ccc atc tgc ggt gac cag cca      650
Gly Pro Arg Asp Gly Asn Arg Gln Val Pro Ile Cys Gly Asp Gln Pro
            160                 165                 170 gaa gcc aag cgt gct gtc tcg gag atg gcg ctc gcc atg ggc ttc atg      698
Glu Ala Lys Arg Ala Val Ser Glu Met Ala Leu Ala Met Gly Phe Met
        175                 180                 185 ccc gtg gac atg gga tcc ctg gcg tca gcc tgg gag gtg gag gcc atg      746
Pro Val Asp Met Gly Ser Leu Ala Ser Ala Trp Glu Val Glu Ala Met
    190                 195                 200 ccc ctg cgc ctc ctc ccg gcc tgg aag gtg ccc acc ctg ctg gcc ctg      794
Pro Leu Arg Leu Leu Pro Ala Trp Lys Val Pro Thr Leu Leu Ala Leu
205             210                 215                 220 ggg ctc ttc gtc tgc ttc tat gcc tac aac ttc gtc cgg gac gtt ctg      842
Gly Leu Phe Val Cys Phe Tyr Ala Tyr Asn Phe Val Arg Asp Val Leu
                225                 230                 235 cag ccc tat gtg cag gaa agc cag aac aag ttc ttc aag ctg ccc gtg      890
Gln Pro Tyr Val Gln Glu Ser Gln Asn Lys Phe Phe Lys Leu Pro Val
            240                 245                 250 tcc gtg gtc aac acc aca ctg ccg tgc gtg gcc tac gtg ctg ctg tca      938
Ser Val Val Asn Thr Thr Leu Pro Cys Val Ala Tyr Val Leu Leu Ser
        255                 260                 265 ctc gtg tac ttg ccc ggc gtg ctg gcg gct gcc ctg cag ctg cgg cgc      986
Leu Val Tyr Leu Pro Gly Val Leu Ala Ala Ala Leu Gln Leu Arg Arg
    270                 275                 280 ggc acc aag tac cag cgc ttc ccc gac tgg ctg gac cac tgg cta cag     1034
Gly Thr Lys Tyr Gln Arg Phe Pro Asp Trp Leu Asp His Trp Leu Gln
285             290                 295                 300 cac cgc aag cag atc ggg ctg ctc agc ttc ttc tgc gcc gcc ctg cac     1082
His Arg Lys Gln Ile Gly Leu Leu Ser Phe Phe Cys Ala Ala Leu His
                305                 310                 315 gcc ctc tac agc ttc tgc ttg ccg ctg cgc cgc gcc cac cgc tac gac     1130
Ala Leu Tyr Ser Phe Cys Leu Pro Leu Arg Arg Ala His Arg Tyr Asp
            320                 325                 330 ctg gtc aac ctg gca gtc aag cag gtc ttg gcc aac aag agc cac ctc     1178
Leu Val Asn Leu Ala Val Lys Gln Val Leu Ala Asn Lys Ser His Leu
        335                 340                 345 tgg gtg gag gag gag gtc tgg cgg atg gag atc tac ctc tcc ctg gga     1226
Trp Val Glu Glu Glu Val Trp Arg Met Glu Ile Tyr Leu Ser Leu Gly
    350                 355                 360 gtg ctg gcc ctc ggc acg ttg tcc ctg ctg gcc gtg acc tca ctg ccg     1274
Val Leu Ala Leu Gly Thr Leu Ser Leu Leu Ala Val Thr Ser Leu Pro
365             370                 375                 380 tcc att gca aac tcg ctc aac tgg agg gag ttc agc ttc gtt cag tcc     1322
Ser Ile Ala Asn Ser Leu Asn Trp Arg Glu Phe Ser Phe Val Gln Ser
                385                 390                 395 tca ctg ggc ttt gtg gcc ctc gtg ctg agc aca ctg cac acg ctc acc     1370
Ser Leu Gly Phe Val Ala Leu Val Leu Ser Thr Leu His Thr Leu Thr
            400                 405                 410 tac ggc tgg acc cgc gcc ttc gag gag agc cgc tac aag ttc tac ctg     1418
Tyr Gly Trp Thr Arg Ala Phe Glu Glu Ser Arg Tyr Lys Phe Tyr Leu
```

```
           415                 420                 425
cct ccc acc ttc acg ctc acg ctg ctg gtg ccc tgc gtc gtc atc ctg      1466
Pro Pro Thr Phe Thr Leu Thr Leu Leu Val Pro Cys Val Val Ile Leu
        430                 435                 440 gcc aaa gcc ctg ttt ctc ctg ccc tgc atc agc cgc aga ctc gcc agg      1514
Ala Lys Ala Leu Phe Leu Leu Pro Cys Ile Ser Arg Arg Leu Ala Arg
445                 450                 455                 460 atc cgg aga ggc tgg gag agg gag agc acc atc aag ttc acg ctg ccc      1562
Ile Arg Arg Gly Trp Glu Arg Glu Ser Thr Ile Lys Phe Thr Leu Pro
                465                 470                 475 aca gac cac gcc ctg gcc gag aag acg agc cac gta tga ggtgcctgcc       1611
Thr Asp His Ala Leu Ala Glu Lys Thr Ser His Val
            480                 485 ctgggctctg gaccccgggc acacgaggga cggtgccctg agcccgttag gttttctttt    1671
cttggtggtg caaagtggta taactgtgtg caaataggag gtttgaggtc caaattcctg    1731
ggactcaaat gtatgcagta ctattcagaa tgatatacac acatatgtgt atatgtattt    1791
acatatattc cacatatata acaggatttg caattataca tagctagcta aaaagttggg    1851
tctctgagat ttcaacttgt agatttaaaa acaagtgccg tacgttaaga gaagagcaga    1911
tcatgctatt gtgacatttg cagagatata cacacacttt ttgtacagaa gaggcttgtg    1971
ctgtggtggg ttcgatttat ccctgcccac cccatcccca caacttccct tttgctactt    2031
ccccaaggct cttgcagagc tagggctctg aaggggaggg aaggcaacgg ctctgcccag    2091
agccatccct ggagcatgtg agcagcggct ggtctcttcc ctccacctgg ggcagcagca    2151
ggaggcctgg gggggaggaa aatcaggcag tcggcctgga gtctgtgcct ggtcctttgc    2211
ccggtggtgg gaggatggag ggattgggct gaagctgctc cacctcatcc ttgctgagtg    2271
ggggagacat tttccctgaa agtcagaagt caccatagag cctgcaaatg gatcctcctg    2331
tgagagtgac gtcacctcct ttccagagcc attagtgagc ctggcttggg aacaagtgta    2391
atttccttcc ctcctttaac ctggcgatga gcgtccttta aaccactgtg ccttctcacc    2451
ctttccatct tcagtttgaa cgactcccag gaaggcctag agcagaccct ttagaaatca    2511
gcccaagggg gagagcaaga gaaaacactc tagggagtaa agctccccgg gcgtcagagt    2571
tgagccctgc ctgggctgaa ggactgtctt cacgaagtca gtcctgagga aaaatattgg    2631
ggactccaaa tgtcctctgg cagaggaccc agaaaaccac actggctcca acttcctcct    2691
catgggcat tacacttcaa aacagtgggg agcaactttt ccaccaaagc tacaaaccta    2751
aaatgctgct gccccaaagc acaagaggga agagcaccgc cggggccaca ggacgtctgt    2811
cctccagtca caggccatcc ttgctgctcc ctactgactc tagcttactt cccctgtgaa    2871
gaaacaggtg ttctcggctg agcccccaac cctctgcaga accaggttga tctgccacag    2931
aaaaagcatc tttgaagaca aagagggtga ggtcttcatg agtctcctgg gcccaaagcc    2991
atcttctgat ggaaggaaga gagtagggcc agtgaaggct gcccagagag aatgtcacag    3051
atgaggctgc ccctgcccccc tccccgccag ggaggtttca tgagctcatg tctatgcagc    3111
acataagggt tcttcagtga aaagcaggag aagagcccac tgcaaggata gctcattagg    3171
cacatgaccg atgcagggaa ggccatgccg gggaagctct tcctgcaggt attttccatc    3231
tgctgtgcca aggctgagcg gcagaaactt gtctcataaa ttggcactga tggagcatca    3291
gctgtggccc acagagagcc ttgctgagaa ggggcaggt aaagcagaga ttttagcatt    3351
gccttggcat aacaagggcc catcgattcc ctactaatga gaggcaggga gagcatgggc    3411
aatggagacc caccaatgat ccccaacccc ggtgggtact ggctgcctgc cctgggccag    3471
```

```
ggaatggctc cttataccaa agatgctggc acatagcaga acccagtgca cgtcctcccc      3531
ttcccaccca cctctggctg aaggtgctca agagggaagc aattataagg tgggtggcag      3591
gagggaacag gtgccacctg ctggacaatc acacgaaagg caggcgggct gtgtactggg      3651
ccctgactgt gcgtccactg ctgtcttccc tacctcacca ggctactggc agcagcatcc      3711
cgagagcaca tcatctccac agcctggtaa attccatgtg cctctgggta caaaagtgcc      3771
tcaacgacat gctctggaaa tcccaaatgc cacagtctga ggttgatatc taaaatctat      3831
gccttcaaaa gagtctctgt tttttttttt taacctggta gacggtataa aagcagtgca      3891
aataaacacc taaccttctg c                                                3912
```

<210> SEQ ID NO 61
<211> LENGTH: 488
<212> TYPE: DNA
<213> ORGANISM: Homo sapiens

<400> SEQUENCE: 61

```
Met Pro Glu Glu Met Asp Lys Pro Leu Ile Ser Leu His Leu Val Asp
1               5                   10                  15

Ser Asp Ser Ser Leu Ala Lys Val Pro Asp Glu Ala Pro Lys Val Gly
            20                  25                  30

Ile Leu Gly Ser Gly Asp Phe Ala Arg Ser Leu Ala Thr Arg Leu Val
        35                  40                  45

Gly Ser Gly Phe Lys Val Val Val Gly Ser Arg Asn Pro Lys Arg Thr
    50                  55                  60

Ala Arg Leu Phe Pro Ser Ala Ala Gln Val Thr Phe Gln Glu Glu Ala
65                  70                  75                  80

Val Ser Ser Pro Glu Val Ile Phe Val Ala Val Phe Arg Glu His Tyr
                85                  90                  95

Ser Ser Leu Cys Ser Leu Ser Asp Gln Leu Ala Gly Lys Ile Leu Val
            100                 105                 110

Asp Val Ser Asn Pro Thr Glu Gln Glu His Leu Gln His Arg Glu Ser
        115                 120                 125

Asn Ala Glu Tyr Leu Ala Ser Leu Phe Pro Thr Cys Thr Val Val Lys
    130                 135                 140

Ala Phe Asn Val Ile Ser Ala Trp Thr Leu Gln Ala Gly Pro Arg Asp
145                 150                 155                 160

Gly Asn Arg Gln Val Pro Ile Cys Gly Asp Gln Pro Glu Ala Lys Arg
                165                 170                 175

Ala Val Ser Glu Met Ala Leu Ala Met Gly Phe Met Pro Val Asp Met
            180                 185                 190

Gly Ser Leu Ala Ser Ala Trp Glu Val Glu Ala Met Pro Leu Arg Leu
        195                 200                 205

Leu Pro Ala Trp Lys Val Pro Thr Leu Leu Ala Leu Gly Leu Phe Val
    210                 215                 220

Cys Phe Tyr Ala Tyr Asn Phe Val Arg Asp Val Leu Gln Pro Tyr Val
225                 230                 235                 240

Gln Glu Ser Gln Asn Lys Phe Phe Lys Leu Pro Val Ser Val Val Asn
                245                 250                 255

Thr Thr Leu Pro Cys Val Ala Tyr Val Leu Leu Ser Leu Val Tyr Leu
            260                 265                 270

Pro Gly Val Leu Ala Ala Ala Leu Gln Leu Arg Arg Gly Thr Lys Tyr
        275                 280                 285
```

```
Gln Arg Phe Pro Asp Trp Leu Asp His Trp Leu Gln His Arg Lys Gln
        290                 295                 300
Ile Gly Leu Leu Ser Phe Phe Cys Ala Ala Leu His Ala Leu Tyr Ser
305                 310                 315                 320
Phe Cys Leu Pro Leu Arg Arg Ala His Arg Tyr Asp Leu Val Asn Leu
                325                 330                 335
Ala Val Lys Gln Val Leu Ala Asn Lys Ser His Leu Trp Val Glu Glu
                340                 345                 350
Glu Val Trp Arg Met Glu Ile Tyr Leu Ser Leu Gly Val Leu Ala Leu
                355                 360                 365
Gly Thr Leu Ser Leu Leu Ala Val Thr Ser Leu Pro Ser Ile Ala Asn
370                 375                 380
Ser Leu Asn Trp Arg Glu Phe Ser Phe Val Gln Ser Ser Leu Gly Phe
385                 390                 395                 400
Val Ala Leu Val Leu Ser Thr Leu His Thr Leu Thr Tyr Gly Trp Thr
                405                 410                 415
Arg Ala Phe Glu Glu Ser Arg Tyr Lys Phe Tyr Leu Pro Pro Thr Phe
                420                 425                 430
Thr Leu Thr Leu Leu Val Pro Cys Val Val Ile Leu Ala Lys Ala Leu
                435                 440                 445
Phe Leu Leu Pro Cys Ile Ser Arg Arg Leu Ala Arg Ile Arg Arg Gly
450                 455                 460
Trp Glu Arg Glu Ser Thr Ile Lys Phe Thr Leu Pro Thr Asp His Ala
465                 470                 475                 480
Leu Ala Glu Lys Thr Ser His Val
                485

<210> SEQ ID NO 62
<211> LENGTH: 556
<212> TYPE: DNA
<213> ORGANISM: Homo sapiens
<220> FEATURE:
<221> NAME/KEY: CDS
<222> LOCATION: (20)..(334)

<400> SEQUENCE: 62
ccttgtctga gaccgagct atg tgg ggc gac ctc tgg ctc ctc ccg cct gcc    52
                    Met Trp Gly Asp Leu Trp Leu Leu Pro Pro Ala
                     1               5                  10 tct gcc aat ccg ggc act ggg aca gag gct gag ttt gag aaa gct gca    100
Ser Ala Asn Pro Gly Thr Gly Thr Glu Ala Glu Phe Glu Lys Ala Ala
            15                  20                  25 gag gag gtt agg cac ctt aag acc aag cca tcg gat gag gag atg ctg    148
Glu Glu Val Arg His Leu Lys Thr Lys Pro Ser Asp Glu Glu Met Leu
        30                  35                  40 ttc atc tat ggc cac tac aaa caa gca act gtg ggc gac ata aat aca    196
Phe Ile Tyr Gly His Tyr Lys Gln Ala Thr Val Gly Asp Ile Asn Thr
45                  50                  55 gaa cgg ccc ggg atg ttg gac ttc acg ggc aag gcc aag tgg gat gcc    244
Glu Arg Pro Gly Met Leu Asp Phe Thr Gly Lys Ala Lys Trp Asp Ala
60                  65                  70                  75 tgg aat gag ctg aaa ggg act tcc aag gaa gat gcc atg aaa gct tac    292
Trp Asn Glu Leu Lys Gly Thr Ser Lys Glu Asp Ala Met Lys Ala Tyr
            80                  85                  90 atc aac aaa gta gaa gag cta aag aaa aaa tac ggg ata tga              334
Ile Asn Lys Val Glu Glu Leu Lys Lys Lys Tyr Gly Ile
        95                  100 gagactggat ttggttactg tgccatgtgt ttatcctaaa ctgagacaat gccttgtttt    394
```

```
tttctaatac cgtggatggt gggaattcgg gaaaataacc agttaaacca gctactcaag    454
gctgctcacc atacggctct aacagattag gggctaaaac gattactgac tttccttgag    514
tagtttttat ctgaaatcaa ttaaaagtgt atttgttact tt                       556
```

```
<210> SEQ ID NO 63
<211> LENGTH: 104
<212> TYPE: DNA
<213> ORGANISM: Homo sapiens

<400> SEQUENCE: 63
```

Met Trp Gly Asp Leu Trp Leu Leu Pro Pro Ala Ser Ala Asn Pro Gly
1               5                   10                  15

Thr Gly Thr Glu Ala Glu Phe Glu Lys Ala Ala Glu Glu Val Arg His
            20                  25                  30

Leu Lys Thr Lys Pro Ser Asp Glu Glu Met Leu Phe Ile Tyr Gly His
        35                  40                  45

Tyr Lys Gln Ala Thr Val Gly Asp Ile Asn Thr Glu Arg Pro Gly Met
    50                  55                  60

Leu Asp Phe Thr Gly Lys Ala Lys Trp Asp Ala Trp Asn Glu Leu Lys
65                  70                  75                  80

Gly Thr Ser Lys Glu Asp Ala Met Lys Ala Tyr Ile Asn Lys Val Glu
                85                  90                  95

Glu Leu Lys Lys Lys Tyr Gly Ile
            100

```
<210> SEQ ID NO 64
<211> LENGTH: 1406
<212> TYPE: DNA
<213> ORGANISM: Homo sapiens
<220> FEATURE:
<221> NAME/KEY: CDS
<222> LOCATION: (121)..(1056)

<400> SEQUENCE: 64
ggccgccctg ccgcgcgcac atgtaggcgt tccgagcggc ggcggaggtg agcgcacgga    60
cgagcgggag ggaccttct ccggcctgat gcgacccgat tgtccgcagt gactacactc     120
``` atg gca ggt ccc ctg tgg cgg acc gca gca ttt gtg cag aga cac agg    168
Met Ala Gly Pro Leu Trp Arg Thr Ala Ala Phe Val Gln Arg His Arg
1               5                   10                  15 aca ggc ctc ttg gtg ggt tcc tgt gca ggc ctg ttt gga gtt cca gtc    216
Thr Gly Leu Leu Val Gly Ser Cys Ala Gly Leu Phe Gly Val Pro Val
            20                  25                  30 tcg tac cac ctc ttc ccg gat ccc gtg gtc caa tgg ctc tac cag tac    264
Ser Tyr His Leu Phe Pro Asp Pro Val Val Gln Trp Leu Tyr Gln Tyr
        35                  40                  45 tgg cct cag ggc cag cca gct ccg ctc cct cca cag ctg cag agc ctc    312
Trp Pro Gln Gly Gln Pro Ala Pro Leu Pro Pro Gln Leu Gln Ser Leu
    50                  55                  60 ttc caa gag gtg cta cag gac ata ggt gtt cct tca ggc cat tgc tac    360
Phe Gln Glu Val Leu Gln Asp Ile Gly Val Pro Ser Gly His Cys Tyr
65                  70                  75                  80 aag ccc ttc acc acc ttc acc ttc cag cct gtg agt gca ggc ttc cca    408
Lys Pro Phe Thr Thr Phe Thr Phe Gln Pro Val Ser Ala Gly Phe Pro
                85                  90                  95 aga ctc cct gct ggg gct gtg gtg ggc atc cct gcc agt ttc ttg gga    456
Arg Leu Pro Ala Gly Ala Val Val Gly Ile Pro Ala Ser Phe Leu Gly
            100                 105                 110

```
gac cta gtg atc aac act aac cat ccc gtg gtc ata cat ggg cat aca    504
Asp Leu Val Ile Asn Thr Asn His Pro Val Val Ile His Gly His Thr
            115                 120                 125 gtg gac tgg cgg agc cca gca ggc gcc cgg ctg aga gct tcc ctg acc    552
Val Asp Trp Arg Ser Pro Ala Gly Ala Arg Leu Arg Ala Ser Leu Thr
130                 135                 140 ttg tcc cgt gaa gcc cag aag ttc gcc ttg gcc agg gaa gtg gtg tac    600
Leu Ser Arg Glu Ala Gln Lys Phe Ala Leu Ala Arg Glu Val Val Tyr
145                 150                 155                 160 ctg gaa agc agt acc act gcc gtg cac gcc ctg ctg gcc cca gct tgc    648
Leu Glu Ser Ser Thr Thr Ala Val His Ala Leu Leu Ala Pro Ala Cys
                165                 170                 175 ctg gca ggg acc tgg gca ctg ggc gtg ggt gcc aag tac acc ctg ggg    696
Leu Ala Gly Thr Trp Ala Leu Gly Val Gly Ala Lys Tyr Thr Leu Gly
            180                 185                 190 ctc cat gca ggc ccc atg aat tta cgg gct gcc ttc agc ttg gtg gca    744
Leu His Ala Gly Pro Met Asn Leu Arg Ala Ala Phe Ser Leu Val Ala
        195                 200                 205 gca gtg gca ggc ttt gtg gcc tac gcc ttc tcc cag gat tct ctc act    792
Ala Val Ala Gly Phe Val Ala Tyr Ala Phe Ser Gln Asp Ser Leu Thr
210                 215                 220 cat gcc gtg gag tcc tgg ctg gac cgc gcc acg gcc tcc ctc tct gca    840
His Ala Val Glu Ser Trp Leu Asp Arg Ala Thr Ala Ser Leu Ser Ala
225                 230                 235                 240 gcc tat gcc tgt ggt gga gtg gag ttc tat gag aag ctt ctg tcg ggc    888
Ala Tyr Ala Cys Gly Gly Val Glu Phe Tyr Glu Lys Leu Leu Ser Gly
                245                 250                 255 aac ctg gcc ctg cgc agt ctc ttg ggc aaa gag ggg gag aag ctg tat    936
Asn Leu Ala Leu Arg Ser Leu Leu Gly Lys Glu Gly Glu Lys Leu Tyr
            260                 265                 270 aca ccc agc ggg aac atc gtc ccc aga cac ttg ttc cga atc aaa cat    984
Thr Pro Ser Gly Asn Ile Val Pro Arg His Leu Phe Arg Ile Lys His
        275                 280                 285 tta ccc tac acc acc cgc cgg gac tct gtg ctg cag atg tgg agg ggg   1032
Leu Pro Tyr Thr Thr Arg Arg Asp Ser Val Leu Gln Met Trp Arg Gly
290                 295                 300 atg ctc aat ccg ggc cgc tcc tga tgggctcatc acaaggacac ttccagcttg  1086
Met Leu Asn Pro Gly Arg Ser
305                 310 tgcagacacc accctgccat tgagtctgga gggccctgtt ggagcctttg gacctatagc  1146
tcaaggccag aaaaatcact ggctttggaa ttaaatagct tagattgtac tataaccact  1206
acttatgaac tcagggacta tgagggacta ttcaggggct atgaatctga gcctttgttt  1266
cttgaactgt aaagtggaga tgatgtaaac cgccttgcaa gattgtagag ttgggtaagg  1326
tcatgaacat aagggcctgg cacaaagggt gcactgtaaa taaacagaca tccctcctta  1386
aaaaaaaaaa aaaaaaaaa                                              1406
```

<210> SEQ ID NO 65
<211> LENGTH: 311
<212> TYPE: DNA
<213> ORGANISM: Homo sapiens

<400> SEQUENCE: 65

```
Met Ala Gly Pro Leu Trp Arg Thr Ala Ala Phe Val Gln Arg His Arg
1               5                   10                  15

Thr Gly Leu Leu Val Gly Ser Cys Ala Gly Leu Phe Gly Val Pro Val
            20                  25                  30

Ser Tyr His Leu Phe Pro Asp Pro Val Val Gln Trp Leu Tyr Gln Tyr
```

-continued

```
                    35                  40                  45
Trp Pro Gln Gly Gln Pro Ala Pro Leu Pro Pro Gln Leu Gln Ser Leu
 50                  55                  60

Phe Gln Glu Val Leu Gln Asp Ile Gly Val Pro Ser Gly His Cys Tyr
 65                  70                  75                  80

Lys Pro Phe Thr Thr Phe Thr Phe Gln Pro Val Ser Ala Gly Phe Pro
                 85                  90                  95

Arg Leu Pro Ala Gly Ala Val Gly Ile Pro Ala Ser Phe Leu Gly
                100                 105                 110

Asp Leu Val Ile Asn Thr Asn His Pro Val Val Ile His Gly His Thr
                115                 120                 125

Val Asp Trp Arg Ser Pro Ala Gly Ala Arg Leu Arg Ala Ser Leu Thr
130                 135                 140

Leu Ser Arg Glu Ala Gln Lys Phe Ala Leu Ala Arg Glu Val Val Tyr
145                 150                 155                 160

Leu Glu Ser Ser Thr Thr Ala Val His Ala Leu Leu Ala Pro Ala Cys
                165                 170                 175

Leu Ala Gly Thr Trp Ala Leu Gly Val Gly Ala Lys Tyr Thr Leu Gly
                180                 185                 190

Leu His Ala Gly Pro Met Asn Leu Arg Ala Ala Phe Ser Leu Val Ala
                195                 200                 205

Ala Val Ala Gly Phe Val Ala Tyr Ala Phe Ser Gln Asp Ser Leu Thr
210                 215                 220

His Ala Val Glu Ser Trp Leu Asp Arg Arg Thr Ala Ser Leu Ser Ala
225                 230                 235                 240

Ala Tyr Ala Cys Gly Gly Val Glu Phe Tyr Glu Lys Leu Leu Ser Gly
                245                 250                 255

Asn Leu Ala Leu Arg Ser Leu Leu Gly Lys Gly Glu Lys Leu Tyr
                260                 265                 270

Thr Pro Ser Gly Asn Ile Val Pro Arg His Leu Phe Arg Ile Lys His
                275                 280                 285

Leu Pro Tyr Thr Thr Arg Arg Asp Ser Val Leu Gln Met Trp Arg Gly
                290                 295                 300

Met Leu Asn Pro Gly Arg Ser
305                 310

<210> SEQ ID NO 66
<211> LENGTH: 6567
<212> TYPE: DNA
<213> ORGANISM: Homo sapiens
<220> FEATURE:
<221> NAME/KEY: CDS
<222> LOCATION: (127)..(2328)

<400> SEQUENCE: 66
agccggtggg ctcgttgtgg gcgccatttc tcggcgtcta ccgaggagcc gccccttttct      60 cagccttgct cggctcttcc ccgctctggt cgccggggct gcgccgtccc cagctcagtg     120 acaaaa atg ctg agt ttc ttc cgt aga aca cta ggg cgt cgg tct atg        168
       Met Leu Ser Phe Phe Arg Arg Thr Leu Gly Arg Arg Ser Met
        1               5                  10 cgt aaa cat gca gag aag gaa cga ctc cga gaa gca caa cgc gcc gcc       216
Arg Lys His Ala Glu Lys Glu Arg Leu Arg Glu Ala Gln Arg Ala Ala
 15                  20                  25                  30 aca cat att cct gca gct gga gat tct aag tcc atc atc acg tgt cgg      264
Thr His Ile Pro Ala Ala Gly Asp Ser Lys Ser Ile Ile Thr Cys Arg
                 35                  40                  45
```

```
gtg tcc ctt ctg gat ggt act gat gtt agt gtg gac ttg cca aaa aaa       312
Val Ser Leu Leu Asp Gly Thr Asp Val Ser Val Asp Leu Pro Lys Lys
             50                  55                  60 gcc aaa gga caa gag ttg ttt gat cag att atg tac cac ctg gac ctg       360
Ala Lys Gly Gln Glu Leu Phe Asp Gln Ile Met Tyr His Leu Asp Leu
         65                  70                  75 att gaa agc gac tat ttt ggt ctg aga ttt atg gat tca gca caa gta       408
Ile Glu Ser Asp Tyr Phe Gly Leu Arg Phe Met Asp Ser Ala Gln Val
     80                  85                  90 gca cat tgg ttg gat ggt aca aaa agc atc aaa aag caa gta aaa att       456
Ala His Trp Leu Asp Gly Thr Lys Ser Ile Lys Lys Gln Val Lys Ile
 95                 100                 105                 110 ggt tca ccc tat tgt ctg cat ctt cga gtt aag ttt tat tcc tca gaa       504
Gly Ser Pro Tyr Cys Leu His Leu Arg Val Lys Phe Tyr Ser Ser Glu
                115                 120                 125 cca aat aac ctt cgt gag gag cta acc cgg tat tta ttt gtt ctt cag       552
Pro Asn Asn Leu Arg Glu Glu Leu Thr Arg Tyr Leu Phe Val Leu Gln
            130                 135                 140 tta aaa caa gat att ctc agt gga aaa tta gac tgt ccc ttt gat aca       600
Leu Lys Gln Asp Ile Leu Ser Gly Lys Leu Asp Cys Pro Phe Asp Thr
        145                 150                 155 gca gtg caa ttg gca gct tat aat ctg caa gct gaa ctt ggt gac tat       648
Ala Val Gln Leu Ala Ala Tyr Asn Leu Gln Ala Glu Leu Gly Asp Tyr
    160                 165                 170 gat ctt gct gag cat agt cct gaa ctt gtc tca gag ttc aga ttc gtg       696
Asp Leu Ala Glu His Ser Pro Glu Leu Val Ser Glu Phe Arg Phe Val
175                 180                 185                 190 cct att cag act gaa gag atg gaa ctg gct att ttt gag aaa tgg aag       744
Pro Ile Gln Thr Glu Glu Met Glu Leu Ala Ile Phe Glu Lys Trp Lys
                195                 200                 205 gaa tac aga ggt caa aca cca gca cag gct gaa acc aat tat ctg aat       792
Glu Tyr Arg Gly Gln Thr Pro Ala Gln Ala Glu Thr Asn Tyr Leu Asn
            210                 215                 220 aaa gcc aaa tgg cta gaa atg tat ggg gtt gat atg cat gtg gtc aag       840
Lys Ala Lys Trp Leu Glu Met Tyr Gly Val Asp Met His Val Val Lys
        225                 230                 235 gct aga gat ggg aat gac tat agt ttg gga cta aca cca aca gga gtc       888
Ala Arg Asp Gly Asn Asp Tyr Ser Leu Gly Leu Thr Pro Thr Gly Val
    240                 245                 250 ctt gtt ttt gaa gga gat acc aaa att ggc tta ttt ttt tgg ccg aag       936
Leu Val Phe Glu Gly Asp Thr Lys Ile Gly Leu Phe Phe Trp Pro Lys
255                 260                 265                 270 ata acc aga ttg gat ttt aag aag aat aaa tta acc ttg gtg gtt gta       984
Ile Thr Arg Leu Asp Phe Lys Lys Asn Lys Leu Thr Leu Val Val Val
                275                 280                 285 gaa gat gat gat cag ggc aaa gaa cag gaa cat aca ttt gtc ttt aga      1032
Glu Asp Asp Asp Gln Gly Lys Glu Gln Glu His Thr Phe Val Phe Arg
            290                 295                 300 ctg gat cat cca aaa gca tgc aaa cat tta tgg aaa tgt gct gtg gag      1080
Leu Asp His Pro Lys Ala Cys Lys His Leu Trp Lys Cys Ala Val Glu
        305                 310                 315 cat cat gct ttc ttc cgc ctt cga ggc ccc gtc caa aag agt tct cat      1128
His His Ala Phe Phe Arg Leu Arg Gly Pro Val Gln Lys Ser Ser His
    320                 325                 330 cga tca gga ttt att cga cta gga tca cga ttt aga tat agt ggg aaa      1176
Arg Ser Gly Phe Ile Arg Leu Gly Ser Arg Phe Arg Tyr Ser Gly Lys
335                 340                 345                 350 aca gag tat cag acc aca aaa acc aat aaa gca aga aga tca aca tcc      1224
Thr Glu Tyr Gln Thr Thr Lys Thr Asn Lys Ala Arg Arg Ser Thr Ser
```

|   |   |   |
|---|---|---|
| 355 | 360 | 365 |

```
ttt gaa aga agg ccc agc aaa cga tat tct aga cga act cta caa atg    1272
Phe Glu Arg Arg Pro Ser Lys Arg Tyr Ser Arg Arg Thr Leu Gln Met
            370                 375                 380 aaa gca tgt gct aca aaa cct gaa gaa ctt agt gtt cac aat aat gtt    1320
Lys Ala Cys Ala Thr Lys Pro Glu Glu Leu Ser Val His Asn Asn Val
        385                 390                 395 tcg acc caa agt aat ggc tcc caa cag gct tgg ggg atg aga tct gct    1368
Ser Thr Gln Ser Asn Gly Ser Gln Gln Ala Trp Gly Met Arg Ser Ala
    400                 405                 410 ctg cct gtg agt cct tcc att tcc tct gct cct gtg cca gtg gag ata    1416
Leu Pro Val Ser Pro Ser Ile Ser Ser Ala Pro Val Pro Val Glu Ile
415                 420                 425                 430 gag aat ctt cca cag agt cct gga aca gac cag cat gac agg aaa tgc    1464
Glu Asn Leu Pro Gln Ser Pro Gly Thr Asp Gln His Asp Arg Lys Cys
                435                 440                 445 att cct ctg aat att gat ttg ctg aat agc cca gac tta ttg gaa gca    1512
Ile Pro Leu Asn Ile Asp Leu Leu Asn Ser Pro Asp Leu Leu Glu Ala
            450                 455                 460 acg att ggt gat gta att ggg gca tct gac act atg gaa aca tcc caa    1560
Thr Ile Gly Asp Val Ile Gly Ala Ser Asp Thr Met Glu Thr Ser Gln
        465                 470                 475 gca ctg aat gac gtt aat gta gcc acc agg ctt ccg gga tta ggg gaa    1608
Ala Leu Asn Asp Val Asn Val Ala Thr Arg Leu Pro Gly Leu Gly Glu
    480                 485                 490 cct gaa gtt gaa tat gag aca tta aaa gac acc tca gag aag ctc aaa    1656
Pro Glu Val Glu Tyr Glu Thr Leu Lys Asp Thr Ser Glu Lys Leu Lys
495                 500                 505                 510 cag ctt gag atg gag aac agt cct ttg ctg tcc cct cga tcc aac atc    1704
Gln Leu Glu Met Glu Asn Ser Pro Leu Leu Ser Pro Arg Ser Asn Ile
                515                 520                 525 gat gtt aac ata aac agc cag gag gaa gtg gtg aag ttg act gag aaa    1752
Asp Val Asn Ile Asn Ser Gln Glu Glu Val Val Lys Leu Thr Glu Lys
            530                 535                 540 tgc ctt aat aat gtc att gag agc cca gga ttg aat gtc atg aga gtt    1800
Cys Leu Asn Asn Val Ile Glu Ser Pro Gly Leu Asn Val Met Arg Val
        545                 550                 555 cct cct gac ttc aag agt aac att ttg aag gct caa gta gaa gca gtg    1848
Pro Pro Asp Phe Lys Ser Asn Ile Leu Lys Ala Gln Val Glu Ala Val
    560                 565                 570 cat aag gtt aca aaa gaa gat agc tta tta agt cat aaa aat gcc aat    1896
His Lys Val Thr Lys Glu Asp Ser Leu Leu Ser His Lys Asn Ala Asn
575                 580                 585                 590 gtt cag gat gct gcc aca aac agt gct gtg tta aat gag aat aat gtg    1944
Val Gln Asp Ala Ala Thr Asn Ser Ala Val Leu Asn Glu Asn Asn Val
                595                 600                 605 ccc ctc ccc aaa gag tct ctt gag act ctg atg ctt atc aca cct gcc    1992
Pro Leu Pro Lys Glu Ser Leu Glu Thr Leu Met Leu Ile Thr Pro Ala
            610                 615                 620 gac agt ggt tct gtt cta aag gaa gct aca gat gaa ttg gat gcc ttg    2040
Asp Ser Gly Ser Val Leu Lys Glu Ala Thr Asp Glu Leu Asp Ala Leu
        625                 630                 635 ctt gca tct cta act gag aat cta att gat cac aca gtt gca cct cag    2088
Leu Ala Ser Leu Thr Glu Asn Leu Ile Asp His Thr Val Ala Pro Gln
    640                 645                 650 gtg tct tcc aca tcc atg atc aca ccc cgg tgg att gtt ccg cag agt    2136
Val Ser Ser Thr Ser Met Ile Thr Pro Arg Trp Ile Val Pro Gln Ser
655                 660                 665                 670 ggt gcc atg tct aat gga ctt gcg gga tgt gaa atg ctt ttg aca ggg    2184
Gly Ala Met Ser Asn Gly Leu Ala Gly Cys Glu Met Leu Leu Thr Gly
```

-continued

|  |  |  |
|---|---|---|
| Gly Ala Met Ser Asn Gly Leu Ala Gly Cys Glu Met Leu Leu Thr Gly<br>675 680 685 | | |
| aag gag gga cat ggt aat aaa gat gga atc tca ctg atc tct ccc cca<br>Lys Glu Gly His Gly Asn Lys Asp Gly Ile Ser Leu Ile Ser Pro Pro<br>690 695 700 | 2232 | |
| gcg cca ttc ttg gta gat gct gtg acc agc tct ggt ccc att ttg gca<br>Ala Pro Phe Leu Val Asp Ala Val Thr Ser Ser Gly Pro Ile Leu Ala<br>705 710 715 | 2280 | |
| gaa gaa gct gtc ctg aag cag aag tgt tta ctg acc act gag ctc tga<br>Glu Glu Ala Val Leu Lys Gln Lys Cys Leu Leu Thr Thr Glu Leu<br>720 725 730 | 2328 | |
| gggcctgtag ctggaatacg catctctcca gcattccgtc ctgggatccg tttcagctag | 2388 | |
| aatatgttgg attcaggagc ttgtccatta tttgtaggta aaaaaagctg cacgtagatt | 2448 | |
| tgacttcaac tccgtaaaaa agacagctgt attttccgtc caactggaat tgttgaatca | 2508 | |
| cactgcatag ctgcccaaaa gagagtgttt ggtcttgaac tttctatact tttataaatg | 2568 | |
| ttacaaattc ccgaaagaag ggaatttctt tttctgggt tccttcaaa ctcttggctc | 2628 | |
| cacctagcgg ttctatttgt tcataacaac ttcataacaa gcctgcctct ggtagtcaac | 2688 | |
| agccttttga aagctatttc catctagtat cagggtgaga gcatccttga tctggctgcc | 2748 | |
| tgttagagaa attgcacttt tcctgactta cctagaaatc aagaatttag gaaattaatg | 2808 | |
| tggacactat aaaggcagac ttagggccaa cttttttttt tttttacaat tattacaaca | 2868 | |
| ctaaagagaa gtttagaata tagagagttt ttaaatgtct cccattcttt tgatttctta | 2928 | |
| ctgtactggc tatcttaata tttcaagttt acatcaagat aaaccctgag aagaactacg | 2988 | |
| gagaaatcaa ataaaatcct gtcatatttt tttcaccctg cctttccaca ggaagcactc | 3048 | |
| acaggcacca cacacgtatc atgtaactta tcagtggggt gggttactgt tgaagagacc | 3108 | |
| ctggggcatt tacctcaggc atctgcactc ctccgagccc ggtggagaat gcaggctgct | 3168 | |
| gtagtctcag gtaatgaagg cacagcacag cagtactcca cattgtttcc tatttggaca | 3228 | |
| tagacttcat ttcctttcag tataagctga ataaatttag agctttcaaa ctggaaaaaa | 3288 | |
| aaatgaaaca aaacaaatac accaagacca aaataggcaa taggaacagg ggtgaaggga | 3348 | |
| tgttgttttct taaataccta ccatgtatga agctatacac agcatatacc gaaagaacct | 3408 | |
| gcattgcact aggaattctg tgttagttta aaagagatct ctaaaacttc cccatccctt | 3468 | |
| tgggcctgta caagaaatt ctggatgtta aaataatata tactcatcac agaaaaataa | 3528 | |
| agtatagcaa tgtccatctg taattctaat acccagaaat aacgctattt agctttataa | 3588 | |
| ttttcgaatg aacaaggtaa acctcggttg ccatggggaa gaaggatgat gtggaaacca | 3648 | |
| tattggtaaa gttgttaatc cctcgttatg gagaactgat cttaagctat acctcctgga | 3708 | |
| atttgctttc tagttttctg tcctgcaata tgtatataat taagcactaa tttgtactgc | 3768 | |
| ttagcataaa agaacatcca gtcttagatc cttaaaactt catggattgg actttcctgg | 3828 | |
| gctccttata acataatcgt gtgtccaggc aaacgcacac tagtgtctga ctggaaagct | 3888 | |
| caggaatttt aatcttgcac tgtttcccag ggagctgtag tgattggaac ccacgtttgc | 3948 | |
| acaaaacatt tttgcagaag gaaagtcaac acttcttgct ggctgcctcc ccttagccat | 4008 | |
| tatgctaaaa acagcttctg agtttcactg gtggggctct tgccagttct taattatagg | 4068 | |
| acatattttc tcaaagctga aggtgacacc tagaaccagg ggcttgaccc aggacatgat | 4128 | |
| ggaatgagca tcaaatttc agtgtcttgg caaccgtaga tgtcctacag ggttaccgtt | 4188 | |
| gtgctgctca ccacagagca gctgaggcat tatgccttgg aagacctaaa tctcccatcc | 4248 | |

-continued

```
agttcaggag gtgacaacat ccttatttta aacttcctaa aattaggaat taggtagttg      4308
gacatagtct gtgaccttta tgtcgttgga tacctgtatt cttgacagtt agaatattgg      4368
tagggacttt gttaaaattc acttgaattt caagctcaga ggaaactttg tctcatgccc      4428
tgacatgaag tggcaaacac ggaagttcat acttgaatgc tgaattggcc ccgacagatt      4488
aaatgcgtgt tggggattgg tttcctgtca tagctgctgc tgctgccatg cgcagagctg      4548
ctgtaacagc tcttcctgtt ctgctcccct gagaacagtg tggtggggag aggcagggct      4608
gaggtggtct acgaatgtgg caggtaggga aggggagatg tctgtctctt gagaagagag      4668
aggcatgtgt gccggcatcc ttgatgggtt caaagagaaa ggttggagat gatagtgggt      4728
gagaagcagg ctggtgagac tgggctgagg ttggagaagg ggcagccggg ggcactgctg      4788
agggttttgcc gtgcacgcct cggacggagc acggtggggt ggcggggagc agatagtgct      4848
gcctccctgc gggcagacag gagaggaacc tcaactcagt ccatttcata gccctgatag      4908
gggaagtggg agttgacagg atggtttaaa ataagacgtg aaggtttcag ttacctgctc      4968
tagactttgc ctgagaactt gtaaattaat cagtgagacc taatttgtga catgtcagta      5028
gcatcatctt ttgacacaca ggaggtcatg gtcatttcat tcctactctt caggagacac      5088
tgctgaacag aggaatgatt ctgttccttg tgtgcttact tccttaacat ttatacattg      5148
ttttaagaaa aaacttttaa aaatatttct tatagtctcc taacatttgt ctctagcctt      5208
tgcctttgta caatcacaga tatcctatgg agatttaagg atgaaagccc tgagttgttc      5268
ttgggttctt ggatctggac tacttgttat cttatgcttc tcacttctgg ctaaaacttg      5328
cacctcttct tctcttagct aagccccaaa atgaagattt ccttcagaag tcttgttagc      5388
agaattattt atcagtcaca gagagaaaaa tctgctattt ttctaagtaa gagtctcgag      5448
aagcagagtt tttgtcttgt cattgagagg agtcagcagt cttgttctgt aaaggaccag      5508
agatggtaaa tactgtccca ctcagctctg ctggcgcagt acagcagcag cagccccagc      5568
acagctgtgt tcctgcggag tccccttac aaagccgctg accccctgatg tgaaactttg      5628
tagagcagca gagtggctgc gtgaaacggg aggctggcag gtcctcagat aggttctgca      5688
gtgttacctg tcacttggag gcagccaaca cttctggaca ttgcatcctt attcacacat      5748
gtggcagctg aacgaggtgc tgttgtgggt gtctcagctc tgagggtctt tgtgagctcc      5808
cactgttgtg ggtgtctcag ctctgagggt ctttgtgagc tcccactgtt gtgggtgtct      5868
cagctctgag ggtctttgtg agttcccacc aacttttaat tattcatgcc cttgaccatg      5928
tggttgcttg gagacctggg gtcttctgca gactgaagaa gacacatttc tagattattt      5988
gtccttttta tcctctcaaa aatttaaaca ctgtacctct tcagtggtca gaagaaagtt      6048
ggaaactttt cctacatatt aggcgttagt atgaggacat ttgtttgaat tatagaaatt      6108
tgccctgagc tgaactgggt tgtgttaaca cattggtaga gctatgattc cttcccagtt      6168
ctaagagata cgatctgtaa gtccctatgt caccacattg cttgagatga tcattcagtt      6228
acttgtcagg atttctcctc ttcagagaga ttttttttta tagcacagat tcctttgccc      6288
cttttatctc cttatctgga tatgataagt ggttatgagg gtctcactaa ctattttgtg      6348
tttacctttt atatgtgtaa aactttgcag tagcatttaa agtgtaattt atttttctat      6408
caagtgcact attcatttag tgtgttccag ttttatatga cttgtattag aaacactgca      6468
ctgagttgtt tgtacactga aatgagaact ctagatgtaa ctctattcaa ataaaccttc      6528
gtgagacatt caaaaaaaaa aaaaaaaaaa aaaaaaaaa                            6567
```

```
<210> SEQ ID NO 67
<211> LENGTH: 733
<212> TYPE: DNA
<213> ORGANISM: Homo sapiens

<400> SEQUENCE: 67
```

| | | | | | | | | | | | | | | |
|---|---|---|---|---|---|---|---|---|---|---|---|---|---|---|
| Met | Leu | Ser | Phe | Phe | Arg | Arg | Thr | Leu | Gly | Arg | Arg | Ser | Met | Arg | Lys |
| 1 | | | | 5 | | | | | 10 | | | | | 15 | |
| His | Ala | Glu | Lys | Glu | Arg | Leu | Arg | Glu | Ala | Gln | Arg | Ala | Ala | Thr | His |
| | | | 20 | | | | | 25 | | | | | 30 | | |
| Ile | Pro | Ala | Ala | Gly | Asp | Ser | Lys | Ser | Ile | Ile | Thr | Cys | Arg | Val | Ser |
| | | | 35 | | | | 40 | | | | | 45 | | | |
| Leu | Leu | Asp | Gly | Thr | Asp | Val | Ser | Val | Asp | Leu | Pro | Lys | Lys | Ala | Lys |
| | 50 | | | | | 55 | | | | | 60 | | | | |
| Gly | Gln | Glu | Leu | Phe | Asp | Gln | Ile | Met | Tyr | His | Leu | Asp | Leu | Ile | Glu |
| 65 | | | | | 70 | | | | | 75 | | | | | 80 |
| Ser | Asp | Tyr | Phe | Gly | Leu | Arg | Phe | Met | Asp | Ser | Ala | Gln | Val | Ala | His |
| | | | | 85 | | | | | 90 | | | | | 95 | |
| Trp | Leu | Asp | Gly | Thr | Lys | Ser | Ile | Lys | Lys | Gln | Val | Lys | Ile | Gly | Ser |
| | | | 100 | | | | | 105 | | | | | 110 | | |
| Pro | Tyr | Cys | Leu | His | Leu | Arg | Val | Lys | Phe | Tyr | Ser | Ser | Glu | Pro | Asn |
| | | 115 | | | | | 120 | | | | | 125 | | | |
| Asn | Leu | Arg | Glu | Glu | Leu | Thr | Arg | Tyr | Leu | Phe | Val | Leu | Gln | Leu | Lys |
| | 130 | | | | | 135 | | | | | 140 | | | | |
| Gln | Asp | Ile | Leu | Ser | Gly | Lys | Leu | Asp | Cys | Pro | Phe | Asp | Thr | Ala | Val |
| 145 | | | | | 150 | | | | | 155 | | | | | 160 |
| Gln | Leu | Ala | Ala | Tyr | Asn | Leu | Gln | Ala | Glu | Leu | Gly | Asp | Tyr | Asp | Leu |
| | | | | 165 | | | | | 170 | | | | | 175 | |
| Ala | Glu | His | Ser | Pro | Glu | Leu | Val | Ser | Glu | Phe | Arg | Phe | Val | Pro | Ile |
| | | | 180 | | | | | 185 | | | | | 190 | | |
| Gln | Thr | Glu | Glu | Met | Glu | Leu | Ala | Ile | Phe | Glu | Lys | Trp | Lys | Glu | Tyr |
| | | 195 | | | | | 200 | | | | | 205 | | | |
| Arg | Gly | Gln | Thr | Pro | Ala | Gln | Ala | Glu | Thr | Asn | Tyr | Leu | Asn | Lys | Ala |
| | 210 | | | | | 215 | | | | | 220 | | | | |
| Lys | Trp | Leu | Glu | Met | Tyr | Gly | Val | Asp | Met | His | Val | Val | Lys | Ala | Arg |
| 225 | | | | | 230 | | | | | 235 | | | | | 240 |
| Asp | Gly | Asn | Asp | Tyr | Ser | Leu | Gly | Leu | Thr | Pro | Thr | Gly | Val | Leu | Val |
| | | | | 245 | | | | | 250 | | | | | 255 | |
| Phe | Glu | Gly | Asp | Thr | Lys | Ile | Gly | Leu | Phe | Phe | Trp | Pro | Lys | Ile | Thr |
| | | | 260 | | | | | 265 | | | | | 270 | | |
| Arg | Leu | Asp | Phe | Lys | Lys | Asn | Lys | Leu | Thr | Leu | Val | Val | Val | Glu | Asp |
| | | 275 | | | | | 280 | | | | | 285 | | | |
| Asp | Asp | Gln | Gly | Lys | Glu | Gln | Glu | His | Thr | Phe | Val | Phe | Arg | Leu | Asp |
| | 290 | | | | | 295 | | | | | 300 | | | | |
| His | Pro | Lys | Ala | Cys | Lys | His | Leu | Trp | Lys | Cys | Ala | Val | Glu | His | His |
| 305 | | | | | 310 | | | | | 315 | | | | | 320 |
| Ala | Phe | Phe | Arg | Leu | Arg | Gly | Pro | Val | Gln | Lys | Ser | Ser | His | Arg | Ser |
| | | | | 325 | | | | | 330 | | | | | 335 | |
| Gly | Phe | Ile | Arg | Leu | Gly | Ser | Arg | Phe | Arg | Tyr | Ser | Gly | Lys | Thr | Glu |
| | | | 340 | | | | | 345 | | | | | 350 | | |
| Tyr | Gln | Thr | Thr | Lys | Thr | Asn | Lys | Ala | Arg | Arg | Ser | Thr | Ser | Phe | Glu |
| | | 355 | | | | | 360 | | | | | 365 | | | |
| Arg | Arg | Pro | Ser | Lys | Arg | Tyr | Ser | Arg | Arg | Thr | Leu | Gln | Met | Lys | Ala |
| | 370 | | | | | 375 | | | | | 380 | | | | |

```
Cys Ala Thr Lys Pro Glu Glu Leu Ser Val His Asn Asn Val Ser Thr
385                 390                 395                 400

Gln Ser Asn Gly Ser Gln Gln Ala Trp Gly Met Arg Ser Ala Leu Pro
            405                 410                 415

Val Ser Pro Ser Ile Ser Ser Ala Pro Val Pro Val Glu Ile Glu Asn
        420                 425                 430

Leu Pro Gln Ser Pro Gly Thr Asp Gln His Asp Arg Lys Cys Ile Pro
    435                 440                 445

Leu Asn Ile Asp Leu Leu Asn Ser Pro Asp Leu Leu Glu Ala Thr Ile
    450                 455                 460

Gly Asp Val Ile Gly Ala Ser Asp Thr Met Glu Thr Ser Gln Ala Leu
465                 470                 475                 480

Asn Asp Val Asn Val Ala Thr Arg Leu Pro Gly Leu Gly Glu Pro Glu
                485                 490                 495

Val Glu Tyr Glu Thr Leu Lys Asp Thr Ser Glu Lys Leu Lys Gln Leu
            500                 505                 510

Glu Met Glu Asn Ser Pro Leu Leu Ser Pro Arg Ser Asn Ile Asp Val
    515                 520                 525

Asn Ile Asn Ser Gln Glu Glu Val Val Lys Leu Thr Glu Lys Cys Leu
530                 535                 540

Asn Asn Val Ile Glu Ser Pro Gly Leu Asn Val Met Arg Val Pro Pro
545                 550                 555                 560

Asp Phe Lys Ser Asn Ile Leu Lys Ala Gln Val Glu Ala Val His Lys
                565                 570                 575

Val Thr Lys Glu Asp Ser Leu Leu Ser His Lys Asn Ala Asn Val Gln
            580                 585                 590

Asp Ala Ala Thr Asn Ser Ala Val Leu Asn Glu Asn Val Pro Leu
                595                 600                 605

Pro Lys Glu Ser Leu Glu Thr Leu Met Leu Ile Thr Pro Ala Asp Ser
    610                 615                 620

Gly Ser Val Leu Lys Glu Ala Thr Asp Glu Leu Asp Ala Leu Leu Ala
625                 630                 635                 640

Ser Leu Thr Glu Asn Leu Ile Asp His Thr Val Ala Pro Gln Val Ser
                645                 650                 655

Ser Thr Ser Met Ile Thr Pro Arg Trp Ile Val Pro Gln Ser Gly Ala
            660                 665                 670

Met Ser Asn Gly Leu Ala Gly Cys Glu Met Leu Leu Thr Gly Lys Glu
        675                 680                 685

Gly His Gly Asn Lys Asp Gly Ile Ser Leu Ile Ser Pro Pro Ala Pro
    690                 695                 700

Phe Leu Val Asp Ala Val Thr Ser Ser Gly Pro Ile Leu Ala Glu Glu
705                 710                 715                 720

Ala Val Leu Lys Gln Lys Cys Leu Leu Thr Thr Glu Leu
                725                 730

<210> SEQ ID NO 68
<211> LENGTH: 1787
<212> TYPE: DNA
<213> ORGANISM: Homo sapiens
<220> FEATURE:
<221> NAME/KEY: CDS
<222> LOCATION: (12)..(545)

<400> SEQUENCE: 68
acttaaacgg a atg gaa cgg aac ggg agg ccc cgg ctg gtg ggc agg tcg      50
             Met Glu Arg Asn Gly Arg Pro Arg Leu Val Gly Arg Ser
```

```
                1               5                    10
cct gct gct gat aca gga agg gac aaa ggg ctc gga cga ttc cgg tct        98
Pro Ala Ala Asp Thr Gly Arg Asp Lys Gly Leu Gly Arg Phe Arg Ser
    15                  20                  25 ttc ctt agc tgc tct cct tgc aag ctc ttt cct ccc cat ggg tct ctt       146
Phe Leu Ser Cys Ser Pro Cys Lys Leu Phe Pro Pro His Gly Ser Leu
30                  35                  40                  45 gat gag tcc aac aag acg ggc atg gag ccc gat ctc aca gat ggg gaa       194
Asp Glu Ser Asn Lys Thr Gly Met Glu Pro Asp Leu Thr Asp Gly Glu
                    50                  55                  60 gct gag gcc agc ggc agc ttc ccc cag cac aga aga gag ctc ctg gca       242
Ala Glu Ala Ser Gly Ser Phe Pro Gln His Arg Arg Glu Leu Leu Ala
                65                  70                  75 ttc cag cag ggg gtg act gga aga aaa cca ggg acc tgg tct aac cac       290
Phe Gln Gln Gly Val Thr Gly Arg Lys Pro Gly Thr Trp Ser Asn His
            80                  85                  90 ctc act ctt cag atg ggg aat agc tgg aga tac agg aaa tgg cag agt       338
Leu Thr Leu Gln Met Gly Asn Ser Trp Arg Tyr Arg Lys Trp Gln Ser
        95                  100                 105 acg att tct gca ctg gag gtt tcc cca ggt gcc cct gct ggt tgg tgg       386
Thr Ile Ser Ala Leu Glu Val Ser Pro Gly Ala Pro Ala Gly Trp Trp
110                 115                 120                 125 gga aca cag gag cca cga cca tcc cca cga gtt ggc tgt cag ttt tat       434
Gly Thr Gln Glu Pro Arg Pro Ser Pro Arg Val Gly Cys Gln Phe Tyr
                    130                 135                 140 gga ttc cca gaa tat tta aca gct gag tgg atg gca ctg gtc aag gcc       482
Gly Phe Pro Glu Tyr Leu Thr Ala Glu Trp Met Ala Leu Val Lys Ala
                145                 150                 155 ggc ctg ttc cct ccc aca tct acc cac aag gta tct tcc tgg gaa gca       530
Gly Leu Phe Pro Pro Thr Ser Thr His Lys Val Ser Ser Trp Glu Ala
            160                 165                 170 ggg aag aca gtg tag ccctgcccc gccagtgcat gagtgtctgg gagtcaggac        585
Gly Lys Thr Val
        175 tcctgtgttt gggtggccct gactccagtt tgctctgtgg ccccaggcaa gccactcacc     645 ctctctgggc catccatcaa acaagagata agatgctctc caggggctag cccttccttc     705 ggaccgtgag aaaaatctag ggagggcaca ggcatccatc catgaggaca ggatggagga     765 gggactacct aaaccctgt ccatctctga ccccaagag gcctgtgagg cagtgggggc       825 agcgcctggc ccagccacca tcctctaggc agggtgctgc cgtgggaaga gagcactgtg     885 gtgaggtggt gagaccgcgt gccccgggtc accctgaccg gtccaattgc ctgtcactca     945 ccagaggccc aatcttgggc aagtgactca gcctcttggt gtgcgaaatg gcccccatga   1005 ggcctcctca gctgggggg ctccatggca gaagggttcc aagaaggcag gagctggagc   1065 tgttcttgcc gctgctggga ggtcctgtcc accctctagc ctccctctcc ctgatccccc   1125 accactgccc attcccagta aggcacctat tctctttgcc accctgacac caagtcactg   1185 ttcagcttgt gggcaacaga gccggaagca tggaaaaatc tcatgctgct cccaaagcca   1245 agggagggct caaagaaggc tggtggaaaa aggcccagag ctgtggccgg acagagtagg   1305 ccccgaacaa ccacagagcc gccttgacag aagccagggc acggtcctga gatgagcctc   1365 atccctggag ggcagcaatg gaccatacac gtgtctaagc cccatcacc agccggggac    1425 ccagtgactc agagcctgct cttcctgaac ccactcggca ggaagaaaac tgaaggccca   1485 agagccccag ccacactgtg acctggaggt gacctggagg gagacagggt gacagcacca   1545 agctcagcct ttcctccgag gcttcgcagg actgaatgaa ggcaaacttc ccaacacccc   1605
```

```
aagccatggg attgtccttc ctggggccct gactgagctg tgacgggctg tgtggccctg    1665
ggtgagttac ttgccttccc tgaggctcat ctcagcacat ataatagaaa atggagacaa    1725
aaggatgccc tttgcatggg ttttgggaaa gattaagtca catgtttata aaagtgcctg    1785
gc                                                                   1787

<210> SEQ ID NO 69
<211> LENGTH: 177
<212> TYPE: DNA
<213> ORGANISM: Homo sapiens

<400> SEQUENCE: 69

Met Glu Arg Asn Gly Arg Pro Arg Leu Val Gly Arg Ser Pro Ala Ala
1               5                   10                  15

Asp Thr Gly Arg Asp Lys Gly Leu Gly Arg Phe Arg Ser Phe Leu Ser
            20                  25                  30

Cys Ser Pro Cys Lys Leu Phe Pro Pro His Gly Ser Leu Asp Glu Ser
        35                  40                  45

Asn Lys Thr Gly Met Glu Pro Asp Leu Thr Asp Gly Glu Ala Glu Ala
    50                  55                  60

Ser Gly Ser Phe Pro Gln His Arg Arg Glu Leu Leu Ala Phe Gln Gln
65                  70                  75                  80

Gly Val Thr Gly Arg Lys Pro Gly Thr Trp Ser Asn His Leu Thr Leu
                85                  90                  95

Gln Met Gly Asn Ser Trp Arg Tyr Arg Lys Trp Gln Ser Thr Ile Ser
            100                 105                 110

Ala Leu Glu Val Ser Pro Gly Ala Pro Ala Gly Trp Trp Gly Thr Gln
        115                 120                 125

Glu Pro Arg Pro Ser Pro Arg Val Gly Cys Gln Phe Tyr Gly Phe Pro
    130                 135                 140

Glu Tyr Leu Thr Ala Glu Trp Met Ala Leu Val Lys Ala Gly Leu Phe
145                 150                 155                 160

Pro Pro Thr Ser Thr His Lys Val Ser Ser Trp Glu Ala Gly Lys Thr
                165                 170                 175

Val

<210> SEQ ID NO 70
<211> LENGTH: 4909
<212> TYPE: DNA
<213> ORGANISM: Homo sapiens
<220> FEATURE:
<221> NAME/KEY: CDS
<222> LOCATION: (91)..(1530)

<400> SEQUENCE: 70
ttcggagcgc gaagccgccg ctgggacctc ggcgcgcccc gcgtctgcgc ttgctgccgc     60
gccccggtcg gcgcgctggg agttccagcc atg ctc ttc tgg cac acg cag ccc    114
                                 Met Leu Phe Trp His Thr Gln Pro
                                 1               5 gag cac tac aac cag cac aac tcc ggc agc tac ctg cgt gat gtg ctc    162
Glu His Tyr Asn Gln His Asn Ser Gly Ser Tyr Leu Arg Asp Val Leu
    10                  15                  20 gct ctg ccc atc ttc aag cag gag gaa ccc cag ctg tcc ccc gag aac    210
Ala Leu Pro Ile Phe Lys Gln Glu Glu Pro Gln Leu Ser Pro Glu Asn
25                  30                  35                  40 gag gcc cgc ctg cca ccc ctg caa tat gtg ttg tgt gct gcc acg tcc    258
Glu Ala Arg Leu Pro Pro Leu Gln Tyr Val Leu Cys Ala Ala Thr Ser
```

```
                45                  50                  55
cca gcc gtg aag ctg cat gaa gag acg ctg acc tac ctc aac caa ggt    306
Pro Ala Val Lys Leu His Glu Glu Thr Leu Thr Tyr Leu Asn Gln Gly
             60                  65                  70 cag tct tat gaa atc cga cta ctg gag aat cgg aag ctg gga gac ttt    354
Gln Ser Tyr Glu Ile Arg Leu Leu Glu Asn Arg Lys Leu Gly Asp Phe
         75                  80                  85 caa gat ctg aac aca aaa tat gtc aag agc atc atc cgt gtg gtc ttc    402
Gln Asp Leu Asn Thr Lys Tyr Val Lys Ser Ile Ile Arg Val Val Phe
     90                  95                 100 cat gac cgc cgg ctg cag tat acg gag cac cag cag ctg gag ggc tgg    450
His Asp Arg Arg Leu Gln Tyr Thr Glu His Gln Gln Leu Glu Gly Trp
105                 110                 115                 120 cgg tgg agt cgg cca ggg gac cgg atc ctg gac atc gat att cca ctg    498
Arg Trp Ser Arg Pro Gly Asp Arg Ile Leu Asp Ile Asp Ile Pro Leu
                125                 130                 135 tct gtt ggt atc ttg gac ccc agg gcc agc ccg acc cag ctg aat gca    546
Ser Val Gly Ile Leu Asp Pro Arg Ala Ser Pro Thr Gln Leu Asn Ala
            140                 145                 150 gtc gag ttt ttg tgg gac cct gcg aag aga gct tct gca ttc att cag    594
Val Glu Phe Leu Trp Asp Pro Ala Lys Arg Ala Ser Ala Phe Ile Gln
        155                 160                 165 gta cac tgc atc agc aca gaa ttc acc ccc agg aag cac ggg ggc gag    642
Val His Cys Ile Ser Thr Glu Phe Thr Pro Arg Lys His Gly Gly Glu
    170                 175                 180 aag gga gtg ccc ttt cga gtc cag att gac acg ttt aag cag aac gag    690
Lys Gly Val Pro Phe Arg Val Gln Ile Asp Thr Phe Lys Gln Asn Glu
185                 190                 195                 200 aat ggg gag tac acg gag cac ctg cac tca gcc agc tgc cag atc aag    738
Asn Gly Glu Tyr Thr Glu His Leu His Ser Ala Ser Cys Gln Ile Lys
                205                 210                 215 gtg ttc aag ccg aag gga gcc gat cgg aaa cag aag act gac cgg gag    786
Val Phe Lys Pro Lys Gly Ala Asp Arg Lys Gln Lys Thr Asp Arg Glu
            220                 225                 230 aag atg gag aaa aga act gcc caa gag aag gag aaa tac cag ccg tcc    834
Lys Met Glu Lys Arg Thr Ala Gln Glu Lys Glu Lys Tyr Gln Pro Ser
        235                 240                 245 tat gaa acc acc atc ctc aca gag tgc tct cca tgg ccc gac gtg gcc    882
Tyr Glu Thr Thr Ile Leu Thr Glu Cys Ser Pro Trp Pro Asp Val Ala
    250                 255                 260 tac cag gtg aac agc gcc ccg tcc cca agc tac aat ggt tct cca aac    930
Tyr Gln Val Asn Ser Ala Pro Ser Pro Ser Tyr Asn Gly Ser Pro Asn
265                 270                 275                 280 agc ttt ggc ctc ggc gaa ggc aac gcc tct ccg acc cac ccg gtg gag    978
Ser Phe Gly Leu Gly Glu Gly Asn Ala Ser Pro Thr His Pro Val Glu
                285                 290                 295 gcc ctg ccc gtg ggc agt gac cac ctg ctc cca tca gct tcg atc cag   1026
Ala Leu Pro Val Gly Ser Asp His Leu Leu Pro Ser Ala Ser Ile Gln
            300                 305                 310 gat gcc cag cag tgg ctt cac cgc aac agg ttc tcg cag ttc tgc cgg   1074
Asp Ala Gln Gln Trp Leu His Arg Asn Arg Phe Ser Gln Phe Cys Arg
        315                 320                 325 ctc ttt gcc agc ttc tca ggt gct gac ttg ctg aag atg tcc cga gat   1122
Leu Phe Ala Ser Phe Ser Gly Ala Asp Leu Leu Lys Met Ser Arg Asp
    330                 335                 340 gat ttg gtc cag atc tgt ggt ccc gca gat ggg atc cgg ctc ttc aac   1170
Asp Leu Val Gln Ile Cys Gly Pro Ala Asp Gly Ile Arg Leu Phe Asn
345                 350                 355                 360 gcc atc aaa ggc cgg aat gtg agg cca aag atg acc att tat gtc tgt   1218
```

```
Ala Ile Lys Gly Arg Asn Val Arg Pro Lys Met Thr Ile Tyr Val Cys
            365                 370                 375 cag gag ctg gag cag aat cga gtg ccc ctg cag cag aag cgg gac ggc      1266
Gln Glu Leu Glu Gln Asn Arg Val Pro Leu Gln Gln Lys Arg Asp Gly
        380                 385                 390 agt gga gac agc aac ctg tct gtg tac cac gcc atc ttc ctg gaa gag      1314
Ser Gly Asp Ser Asn Leu Ser Val Tyr His Ala Ile Phe Leu Glu Glu
            395                 400                 405 ctg acc acc ttg gag ctg att gag aag att gcc aac ctg tac agc atc      1362
Leu Thr Thr Leu Glu Leu Ile Glu Lys Ile Ala Asn Leu Tyr Ser Ile
        410                 415                 420 tcc ccc cag cac atc cac cga gtc tac cgg cag ggc ccc acg ggc atc      1410
Ser Pro Gln His Ile His Arg Val Tyr Arg Gln Gly Pro Thr Gly Ile
425                 430                 435                 440 cat gtg gtg gtg agc aac gag atg gtg cag aac ttc caa gat gaa tcc      1458
His Val Val Val Ser Asn Glu Met Val Gln Asn Phe Gln Asp Glu Ser
                445                 450                 455 tgt ttt gtc ctc agc aca att aaa gct gag agc aat gat ggc tac cac      1506
Cys Phe Val Leu Ser Thr Ile Lys Ala Glu Ser Asn Asp Gly Tyr His
            460                 465                 470 atc atc ctg aaa tgt gga ctc tga gcagcagtgg acctcatacc tgtctccagc     1560
Ile Ile Leu Lys Cys Gly Leu
            475 tcccagccct gtggatcccc gtggatgtag acattgcccc actgtaagct gtggcctcac   1620 caggcaagct gaggccagga gggaccctgc ccagtctgtg aaagctacag agcaccaacc   1680 agcagaagcc tgtggacacc aagtacggtg tacagaaagc cagtggctcc tttctccctt   1740 cctcttggcc tccagatttt gaatggttcc ttgttctttt ctattggtcc aaccctgacg   1800 ttctaaaagg gcaaacagtg gagacgtctg ctctgaaatc cctcatccct tagttggaag   1860 ctgattgggt atcttggtgc tgcctgtatt ggtcccttct gaccactctc ctgcctccag   1920 agaaagctct gcttcaccct gaaagctggt acctttacct cctcctctgg gagttggctg   1980 catggccagc actgccgact tgatgggagc agtttgccct cattctcctg tttcaggttt   2040 gcttcccttc tcagtgaccc tggtgagcat ccgcctttcc tgttcttgga tgaattgatg   2100 ggagtggggc tattctgtgc cttctacctc tttcttctct acgttgtttc taaggatctg   2160 ctgctgcgga acccaaagat gtgctcctgt ctctgcactg gcgcattggc atggtagatg   2220 ccacaatgta tgtgcacggc ctttctcaga gacattagtt ctgaggccct tgtggggag    2280 gttaggggga tggtaataga aaaagactat tttatttcct ggcaatcacg ggtaaggagg   2340 attaggaatg agtattccat tcctaggtgt catcagatga ccttgaccac cacaatacca   2400 ggccctcttg gatggactta tagaaagtta gagaagacct tgttgaaccg ctgctaaact   2460 tgccacagga gcgatgtgtt ttctctgagt gcccctcact tacatgttta tctttgtttg   2520 tagaggctat gtttaggata ttttgcctgc atcagaatgg gtgcatcatc tttcttaatg   2580 gcctatcggg aaatttgagt gtcagtaact gtggtagact cagaaattcg tctttgtctt   2640 gcctctggtt cctgggatcc agtgatctct actggcccag ggcttcagct cttggttaat   2700 ttaggttcat ggggaaccct ctgaccacct gaatgggatg tcatagcttc taaatggagc   2760 ttctgtggaa tgaagtgcta gactgaagga ctaccagaat aaaacagggt ctacaatggg   2820 gagaacttgt tttatagatg aggaaaccaa ggctcagagg ggcaaagtca cctgcatggt   2880 agcacatagt gataggggtag cgatataaat ttatcatata aaccaggaca tctcggaata   2940 aaagggggctc tgttagtcat tatgtttggg aatagccatg gcattcctac agaacagagt  3000
```

```
gaggacaggc tcctgattcc tcttccttct ttagagagaa gcggggagtg ggttaactaa    3060
cagctttatt gagatgtcat tcacatgcca ttcagtttac ccattgctag tgtccaattg    3120
tattcacaga accaccatca attcacagaa ttacagtcaa cgttggtaca ttttcatcac    3180
ccccagtaaa accccgtacc cttggtctgt cactcctgct ttcctaactc ctgcagtcca    3240
aggcagccat gaatctactt tctatgtaag attaacctac tctggacatt tcatatatct    3300
ggaatcatgt gatatctctt tgtgactgg cttcttccac tgaatgtttt ctagggccgt    3360
ccaagttgag gatgtatcag tacttcattc ttttgtattg ctgaataata cttcattgta    3420
tagatagacc acatttgttt attgattcat cagttgatgg acatttgtgt gtttttactt    3480
tttggctact ctgaatgatg ctgctatgaa catatttcta caagattttg tgtggacata    3540
tgttttcatt tcttttagca atatacatag gagtggaatt gctaggtctt acagtaactc    3600
cgtgttttaa cttttgaga aactgccaga ctgttttcta tagcagctgt accatttac     3660
attcccacca gcaatgtatc caggtttcaa tttgtctaca tcctcatcaa cacttgctat    3720
tatctgtctt tttgctttta gcatcctaat gagtatgaaa tgctatcttg tggttttgat    3780
ttgcattccc ctgatggcaa ctgatgctga gtgtcttttc ctgtgcttac gggccatgcg    3840
tatttctttg gagaaaggtc tatccaggtc ctttgcctat ttttaattga gttgtctttt    3900
tttttaagt tttctgtttt cctaaccact agactaccag ggatgagcct tcttttatt     3960
attgagttgg gtgagctatt tgtatattct agacgccagt cttttatcag gtatatgact    4020
ggtaaaaatg ttctcccctt ctgtggattg ttttcagttt cttgttggtg tcctttgaga    4080
cacaaaactt tttaactttg atgatttcca agatacgtat ttttttctta ttgtcacttg    4140
tgcttttggt gccatatcta gaaaaccatt gcctaatcca aggtcaagaa gattaatgcc    4200
tgtgttttct tctaagaact tgtatagttt tagttctcac aatggtcttt gatccatttc    4260
gagtatattt ttatatatga tgtgatgtag gggtccagct tcattctttt gcttgtggat    4320
ctccacttgt cccactgctg attattgaga aaaatatcct ttctccacgg aattgtcttg    4380
gcatccttgc taaaggcctc tgcttcttac tggatcttct ttcctgggac atggtgtcgt    4440
tgggaagctt accttttttt ttttttactt agtctgtgtt tggttccacc agttttatgc    4500
tgcctttcta ctctgttctt gctgtctccc tctttacctg agtcaacggt actgagtcct    4560
atctctctct gatgttcccc agtcttcctt ggtgcatgtt ctagctccac acactagtcc    4620
ttggaggaag gttgagacca atgatttcct gttatgagtc atgaggaaac tgaatcacct    4680
agaagtggaa taatgtgctc agggtcacca tagcccatta gtggaaggac caggactaga    4740
cctttagtct tctgaggtcc agccccttag gctgtctgtc atcactgtac ccaagtgatg    4800
tcactaccaa ggccaaatga tggtgggcta aattttaatt ctcaaaagtg taggaggcta    4860
atattgtctt ctaagttcca aaagaagatg taataaaagt ctgttacct                4909
```

<210> SEQ ID NO 71
<211> LENGTH: 479
<212> TYPE: DNA
<213> ORGANISM: Homo sapiens

<400> SEQUENCE: 71

```
Met Leu Phe Trp His Thr Gln Pro Glu His Tyr Asn Gln His Asn Ser
1               5                   10                  15

Gly Ser Tyr Leu Arg Asp Val Leu Ala Leu Pro Ile Phe Lys Gln Glu
            20                  25                  30

Glu Pro Gln Leu Ser Pro Glu Asn Glu Ala Arg Leu Pro Pro Leu Gln
```

```
                35                  40                  45
Tyr Val Leu Cys Ala Ala Thr Ser Pro Ala Val Lys Leu His Glu Glu
 50                  55                  60

Thr Leu Thr Tyr Leu Asn Gln Gly Gln Ser Tyr Glu Ile Arg Leu Leu
65                  70                  75                  80

Glu Asn Arg Lys Leu Gly Asp Phe Gln Asp Leu Asn Thr Lys Tyr Val
                85                  90                  95

Lys Ser Ile Ile Arg Val Val Phe His Asp Arg Arg Leu Gln Tyr Thr
            100                 105                 110

Glu His Gln Gln Leu Glu Gly Trp Arg Trp Ser Arg Pro Gly Asp Arg
        115                 120                 125

Ile Leu Asp Ile Asp Ile Pro Leu Ser Val Gly Ile Leu Asp Pro Arg
    130                 135                 140

Ala Ser Pro Thr Gln Leu Asn Ala Val Glu Phe Leu Trp Asp Pro Ala
145                 150                 155                 160

Lys Arg Ala Ser Ala Phe Ile Gln Val His Cys Ile Ser Thr Glu Phe
                165                 170                 175

Thr Pro Arg Lys His Gly Gly Glu Lys Gly Val Pro Phe Arg Val Gln
            180                 185                 190

Ile Asp Thr Phe Lys Gln Asn Glu Asn Gly Glu Tyr Thr Glu His Leu
        195                 200                 205

His Ser Ala Ser Cys Gln Ile Lys Val Phe Lys Pro Lys Gly Ala Asp
    210                 215                 220

Arg Lys Gln Lys Thr Asp Arg Glu Lys Met Glu Lys Arg Thr Ala Gln
225                 230                 235                 240

Glu Lys Glu Lys Tyr Gln Pro Ser Tyr Glu Thr Thr Ile Leu Thr Glu
                245                 250                 255

Cys Ser Pro Trp Pro Asp Val Ala Tyr Gln Val Asn Ser Ala Pro Ser
            260                 265                 270

Pro Ser Tyr Asn Gly Ser Pro Asn Ser Phe Gly Leu Gly Glu Gly Asn
        275                 280                 285

Ala Ser Pro Thr His Pro Val Glu Ala Leu Pro Val Gly Ser Asp His
    290                 295                 300

Leu Leu Pro Ser Ala Ser Ile Gln Asp Ala Gln Gln Trp Leu His Arg
305                 310                 315                 320

Asn Arg Phe Ser Gln Phe Cys Arg Leu Phe Ala Ser Phe Ser Gly Ala
                325                 330                 335

Asp Leu Leu Lys Met Ser Arg Asp Asp Leu Val Gln Ile Cys Gly Pro
            340                 345                 350

Ala Asp Gly Ile Arg Leu Phe Asn Ala Ile Lys Gly Arg Asn Val Arg
        355                 360                 365

Pro Lys Met Thr Ile Tyr Val Cys Gln Glu Leu Glu Gln Asn Arg Val
    370                 375                 380

Pro Leu Gln Gln Lys Arg Asp Gly Ser Gly Asp Ser Asn Leu Ser Val
385                 390                 395                 400

Tyr His Ala Ile Phe Leu Glu Glu Leu Thr Thr Leu Glu Leu Ile Glu
                405                 410                 415

Lys Ile Ala Asn Leu Tyr Ser Ile Ser Pro Gln His Ile His Arg Val
            420                 425                 430

Tyr Arg Gln Gly Pro Thr Gly Ile His Val Val Ser Asn Glu Met
        435                 440                 445

Val Gln Asn Phe Gln Asp Glu Ser Cys Phe Val Leu Ser Thr Ile Lys
    450                 455                 460
```

Ala Glu Ser Asn Asp Gly Tyr His Ile Ile Leu Lys Cys Gly Leu
465                 470                 475

<210> SEQ ID NO 72
<211> LENGTH: 19
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 72
ttttaggtat tgttgggt                                                   19

<210> SEQ ID NO 73
<211> LENGTH: 19
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 73
ctacaaaaaa aactacctc                                                  19

<210> SEQ ID NO 74
<211> LENGTH: 20
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 74
gttgggtaga atgttatatt                                                 20

<210> SEQ ID NO 75
<211> LENGTH: 20
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 75
tcacacaaaa caactaaacc                                                 20

<210> SEQ ID NO 76
<211> LENGTH: 21
<212> TYPE: DNA
<213> ORGANISM: artificial sequence
<220> FEATURE:
<223> OTHER INFORMATION: Oligonucleotide for amplifying CpG island CpG49
      from Homo sapiens

<400> SEQUENCE: 76
gttgtttggt tagtaaataa t                                               21

<210> SEQ ID NO 77
<211> LENGTH: 21
<212> TYPE: DNA
<213> ORGANISM: artificial sequence
<220> FEATURE:
<223> OTHER INFORMATION: Oligonucleotide for amplifying CpG island CpG49
      from Homo sapiens

<400> SEQUENCE: 77
aaactacaaa aacacaaata a                                               21

<210> SEQ ID NO 78
<211> LENGTH: 20
<212> TYPE: DNA
<213> ORGANISM: artificial sequence
<220> FEATURE:
<223> OTHER INFORMATION: Oligonucleotide for amplifying CpG island CpG49
      from Homo sapiens

<400> SEQUENCE: 78
ttagtaaata atagtagatt                                                 20

<210> SEQ ID NO 79
<211> LENGTH: 19
<212> TYPE: DNA
<213> ORGANISM: artificial sequence
<220> FEATURE:
<223> OTHER INFORMATION: Oligonucleotide for amplifying CpG island CpG49
      from Homo sapiens

<400> SEQUENCE: 79
taattcttct tcccaaaaa                                                  19

<210> SEQ ID NO 80
<211> LENGTH: 20
<212> TYPE: DNA
<213> ORGANISM: artificial sequence
<220> FEATURE:
<223> OTHER INFORMATION: Oligonucleotide for amplifying CpG island
      CpG41.2 from Homo sapiens

<400> SEQUENCE: 80
agttgtagtg ttgaggattt                                                 20

<210> SEQ ID NO 81
<211> LENGTH: 20
<212> TYPE: DNA
<213> ORGANISM: artificial sequence
<220> FEATURE:
<223> OTHER INFORMATION: Oligonucleotide for amplifying CpG island
      CpG41.2 from Homo sapiens

<400> SEQUENCE: 81
taaatcctta acaaaataaa                                                 20

<210> SEQ ID NO 82
<211> LENGTH: 19
<212> TYPE: DNA
<213> ORGANISM: artificial sequence
<220> FEATURE:
<223> OTHER INFORMATION: Oligonucleotide for amplifying CpG island
      CpG41.2 from Homo sapiens

<400> SEQUENCE: 82
tgtaaggtag aaatattaa                                                  19

<210> SEQ ID NO 83
<211> LENGTH: 20
<212> TYPE: DNA
<213> ORGANISM: artificial sequence
<220> FEATURE:
<223> OTHER INFORMATION: Oligonucleotide for amplifying CpG island
      CpG41.2 from Homo sapiens

<400> SEQUENCE: 83
aaatctccaa actatcccaa                                           20

<210> SEQ ID NO 84
<211> LENGTH: 20
<212> TYPE: DNA
<213> ORGANISM: artificial sequence
<220> FEATURE:
<223> OTHER INFORMATION: Oligonucleotide for amplifying CpG island
      CpG61 from Homo sapiens

<400> SEQUENCE: 84
gaaagtagat ttagtttttg                                           20

<210> SEQ ID NO 85
<211> LENGTH: 21
<212> TYPE: DNA
<213> ORGANISM: artificial sequence
<220> FEATURE:
<223> OTHER INFORMATION: Oligonucleotide for amplifying CpG island CpG61
      from Homo sapiens

<400> SEQUENCE: 85
cccattaaaa actatttatt a                                         21

<210> SEQ ID NO 86
<211> LENGTH: 20
<212> TYPE: DNA
<213> ORGANISM: artificial sequence
<220> FEATURE:
<223> OTHER INFORMATION: Oligonucleotide for amplifying CpG island CpG61
      from Homo sapiens

<400> SEQUENCE: 86
ttgttaattt ttgggtaatt                                           20

<210> SEQ ID NO 87
<211> LENGTH: 20
<212> TYPE: DNA
<213> ORGANISM: artificial sequence
<220> FEATURE:
<223> OTHER INFORMATION: Oligonucleotide for amplifying CpG island CpG61
      from Homo sapiens

<400> SEQUENCE: 87
acaaaataaa accaacctat                                           20

<210> SEQ ID NO 88
<211> LENGTH: 20
<212> TYPE: DNA
<213> ORGANISM: artificial sequence
<220> FEATURE:
<223> OTHER INFORMATION: Oligonucleotide for amplifying CpG island CpG29
      from Homo sapiens

<400> SEQUENCE: 88
attgttttgg tgtaaagtat                                           20

<210> SEQ ID NO 89
<211> LENGTH: 20
<212> TYPE: DNA
<213> ORGANISM: artificial sequence
<220> FEATURE:
<223> OTHER INFORMATION: Oligonucleotide for amplifying CpG island CpG29
      from Homo sapiens

<400> SEQUENCE: 89
cctctactta tattaactaa                                           20

<210> SEQ ID NO 90
<211> LENGTH: 20
<212> TYPE: DNA
<213> ORGANISM: artificial sequence
<220> FEATURE:
<223> OTHER INFORMATION: Oligonucleotide for amplifying CpG island CpG29
      from Homo sapiens

<400> SEQUENCE: 90
tgaatttata gtttttagtt                                               20

<210> SEQ ID NO 91
<211> LENGTH: 20
<212> TYPE: DNA
<213> ORGANISM: artificial sequence
<220> FEATURE:
<223> OTHER INFORMATION: Oligonucleotide for amplifying CpG island CpG29
      from Homo sapiens

<400> SEQUENCE: 91
atttcattat aaattccatt                                               20

<210> SEQ ID NO 92
<211> LENGTH: 20
<212> TYPE: DNA
<213> ORGANISM: artificial sequence
<220> FEATURE:
<223> OTHER INFORMATION: Oligonucleotide for amplifying CpG island 20Kb
      from Homo sapiens

<400> SEQUENCE: 92
tttagtttgg atttagattt                                               20

<210> SEQ ID NO 93
<211> LENGTH: 20
<212> TYPE: DNA
<213> ORGANISM: artificial sequence
<220> FEATURE:
<223> OTHER INFORMATION: Oligonucleotide for amplifying CpG island 20Kb
      from Homo sapiens

<400> SEQUENCE: 93
cctcaatcct aatatattta                                               20

<210> SEQ ID NO 94
<211> LENGTH: 20
<212> TYPE: DNA
<213> ORGANISM: artificial sequence
<220> FEATURE:
<223> OTHER INFORMATION: Oligonucleotide for amplifying CpG island 20Kb
      from Homo sapiens

<400> SEQUENCE: 94
atttagggtt gagggttttt                                               20

<210> SEQ ID NO 95
<211> LENGTH: 20
<212> TYPE: DNA
<213> ORGANISM: artificial sequence
<220> FEATURE:
<223> OTHER INFORMATION: Oligonucleotide for amplifying CpG island 20Kb
      from Homo sapiens

<400> SEQUENCE: 95
cttcacccaa aatctaaaaa                                               20

<210> SEQ ID NO 96
<211> LENGTH: 22
<212> TYPE: DNA
<213> ORGANISM: artificial sequence
<220> FEATURE:
<223> OTHER INFORMATION: Oligonucleotide for amplifying Z fragment from
      Homo sapiens

<400> SEQUENCE: 96
aaaaattatt taaaaactcc cc                                              22

<210> SEQ ID NO 97
<211> LENGTH: 20
<212> TYPE: DNA
<213> ORGANISM: artificial sequence
<220> FEATURE:
<223> OTHER INFORMATION: Oligonucleotide for amplifying Z fragment from
      Homo sapiens

<400> SEQUENCE: 97
ataagtatag aattttaggg                                                 20

<210> SEQ ID NO 98
<211> LENGTH: 20
<212> TYPE: DNA
<213> ORGANISM: artificial sequence
<220> FEATURE:
<223> OTHER INFORMATION: Oligonucleotide for amplifying Z fragment from
      Homo sapiens

<400> SEQUENCE: 98
tagtgtttta gttttttagg                                                 20

<210> SEQ ID NO 99
<211> LENGTH: 22
<212> TYPE: DNA
<213> ORGANISM: artificial sequence
<220> FEATURE:
<223> OTHER INFORMATION: Oligonucleotide for amplifying Z fragment from
      Homo sapiens

<400> SEQUENCE: 99
aaaatttaac ccaccaatcc ta                                              22

<210> SEQ ID NO 100
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 100
tttagttttt attggagaga                                                 20

<210> SEQ ID NO 101
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 101
taaaaaacta ttatccctcc                                                 20

-continued

```
<210> SEQ ID NO 102
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 102
tttagttttt attggagaga                                                    20

<210> SEQ ID NO 103
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 103
taaaaataac ctcaacacct                                                    20

<210> SEQ ID NO 104
<211> LENGTH: 21
<212> TYPE: DNA
<213> ORGANISM: artificial sequence
<220> FEATURE:
<223> OTHER INFORMATION: Oligonucleotide for amplifying CpG island
      CpG103 from Homo sapiens

<400> SEQUENCE: 104
aattagattt tgatttggga t                                                  21

<210> SEQ ID NO 105
<211> LENGTH: 21
<212> TYPE: DNA
<213> ORGANISM: artificial sequence
<220> FEATURE:
<223> OTHER INFORMATION: Oligonucleotide for amplifying CpG island
      CpG103 from Homo sapiens

<400> SEQUENCE: 105
ataatctaat aaaaaacact t                                                  21

<210> SEQ ID NO 106
<211> LENGTH: 21
<212> TYPE: DNA
<213> ORGANISM: artificial sequence
<220> FEATURE:
<223> OTHER INFORMATION: Oligonucleotide for amplifying CpG island
      CpG103 from Homo sapiens

<400> SEQUENCE: 106
ttgagttttt gggttagggt t                                                  21

<210> SEQ ID NO 107
<211> LENGTH: 21
<212> TYPE: DNA
<213> ORGANISM: artificial sequence
<220> FEATURE:
<223> OTHER INFORMATION: Oligonucleotide for amplifying CpG island
      CpG103 from Homo sapiens

<400> SEQUENCE: 107
ccaaaaattc aacaaaacct c                                                  21

<210> SEQ ID NO 108
```

```
<211> LENGTH: 21
<212> TYPE: DNA
<213> ORGANISM: artificial sequence
<220> FEATURE:
<223> OTHER INFORMATION: Oligonucleotide for amplifying CpG island
      CpG128 from Homo sapiens

<400> SEQUENCE: 108
agaataataa agataagaga t                                        21

<210> SEQ ID NO 109
<211> LENGTH: 20
<212> TYPE: DNA
<213> ORGANISM: artificial sequence
<220> FEATURE:
<223> OTHER INFORMATION: Oligonucleotide for amplifying CpG island
      CpG128 from Homo sapiens

<400> SEQUENCE: 109
actatcctac ttataaactc                                          20

<210> SEQ ID NO 110
<211> LENGTH: 20
<212> TYPE: DNA
<213> ORGANISM: artificial sequence
<220> FEATURE:
<223> OTHER INFORMATION: Oligonucleotide for amplifying CpG island
      CpG128 from Homo sapiens

<400> SEQUENCE: 110
gttttaggga tttagagttt                                          20

<210> SEQ ID NO 111
<211> LENGTH: 20
<212> TYPE: DNA
<213> ORGANISM: artificial sequence
<220> FEATURE:
<223> OTHER INFORMATION: Oligonucleotide for amplifying CpG island
      CpG128 from Homo sapiens

<400> SEQUENCE: 111
ctacttataa actcaaccaa                                          20

<210> SEQ ID NO 112
<211> LENGTH: 21
<212> TYPE: DNA
<213> ORGANISM: artificial sequence
<220> FEATURE:
<223> OTHER INFORMATION: Oligonucleotide for amplifying CpG island
      CpG41 from Homo sapiens

<400> SEQUENCE: 112
gaagataatt tataggtttt a                                        21

<210> SEQ ID NO 113
<211> LENGTH: 20
<212> TYPE: DNA
<213> ORGANISM: artificial sequence
<220> FEATURE:
<223> OTHER INFORMATION: Oligonucleotide for amplifying CpG island
      CpG41 from Homo sapiens

<400> SEQUENCE: 113
atcccattac tataacaaat                                          20

<210> SEQ ID NO 114
<211> LENGTH: 20
```

```
<212> TYPE: DNA
<213> ORGANISM: artificial sequence
<220> FEATURE:
<223> OTHER INFORMATION: Oligonucleotide for amplifying CpG island
      CpG41 from Homo sapiens

<400> SEQUENCE: 114
ataggtttgt gaataaaatt                                             20

<210> SEQ ID NO 115
<211> LENGTH: 19
<212> TYPE: DNA
<213> ORGANISM: artificial sequence
<220> FEATURE:
<223> OTHER INFORMATION: Oligonucleotide for amplifying CpG island
      CpG41 from Homo sapiens

<400> SEQUENCE: 115
aactccacta cataaaaaa                                              19

<210> SEQ ID NO 116
<211> LENGTH: 20
<212> TYPE: DNA
<213> ORGANISM: artificial sequence
<220> FEATURE:
<223> OTHER INFORMATION: Oligonucleotide for amplifying CpG island
      CpG173 from Homo sapiens

<400> SEQUENCE: 116
agggattgga ggttttatta                                             20

<210> SEQ ID NO 117
<211> LENGTH: 20
<212> TYPE: DNA
<213> ORGANISM: artificial sequence
<220> FEATURE:
<223> OTHER INFORMATION: Oligonucleotide for amplifying CpG island
      CpG173 from Homo sapiens

<400> SEQUENCE: 117
caaataacaa ctaaccccaa                                             20

<210> SEQ ID NO 118
<211> LENGTH: 21
<212> TYPE: DNA
<213> ORGANISM: artificial sequence
<220> FEATURE:
<223> OTHER INFORMATION: Oligonucleotide for amplifying CpG island
      CpG173 from Homo sapiens

<400> SEQUENCE: 118
tgagtagttt tttgaatatt a                                           21

<210> SEQ ID NO 119
<211> LENGTH: 19
<212> TYPE: DNA
<213> ORGANISM: artificial sequence
<220> FEATURE:
<223> OTHER INFORMATION: Oligonucleotide for amplifying CpG island
      CpG173 from Homo sapiens

<400> SEQUENCE: 119
cctcacaaaa tccaaaatt                                              19

<210> SEQ ID NO 120
<211> LENGTH: 20
<212> TYPE: DNA
```

```
<213> ORGANISM: artificial sequence
<220> FEATURE:
<223> OTHER INFORMATION: Oligonucleotide for amplifying CpG island
      CpG48 from Homo sapiens

<400> SEQUENCE: 120
tagatttgtt tatggttatt                                              20

<210> SEQ ID NO 121
<211> LENGTH: 20
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 121
attccaaaac ttaaaacaaa                                              20

<210> SEQ ID NO 122
<211> LENGTH: 20
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 122
ggataaggtt tagttttttt                                              20

<210> SEQ ID NO 123
<211> LENGTH: 20
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 123
ataacaaaaa aaccaacaaa                                              20

<210> SEQ ID NO 124
<211> LENGTH: 20
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 124
gggattagtg gaattatgtt                                              20

<210> SEQ ID NO 125
<211> LENGTH: 20
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 125
aaaaacaaaa cccaaccttc                                              20

<210> SEQ ID NO 126
<211> LENGTH: 21
<212> TYPE: DNA
<213> ORGANISM: artificial sequence
```

```
<220> FEATURE:
<223> OTHER INFORMATION: Oligonucleotide for amplifying CpG island CpG48
      from Homo sapiens

<400> SEQUENCE: 126
atgttggttt ttagttattt t                                             21

<210> SEQ ID NO 127
<211> LENGTH: 21
<212> TYPE: DNA
<213> ORGANISM: artificial sequence
<220> FEATURE:
<223> OTHER INFORMATION: Oligonucleotide for amplifying CpG island CpG48
      from Homo sapiens

<400> SEQUENCE: 127
tcaactatca aaatacaaat a                                             21

<210> SEQ ID NO 128
<211> LENGTH: 20
<212> TYPE: DNA
<213> ORGANISM: artificial sequence
<220> FEATURE:
<223> OTHER INFORMATION: Oligonucleotide for amplifying CpG island MARCO
      from Homo sapiens

<400> SEQUENCE: 128
tgagaaataa gaaaattttt                                               20

<210> SEQ ID NO 129
<211> LENGTH: 20
<212> TYPE: DNA
<213> ORGANISM: artificial sequence
<220> FEATURE:
<223> OTHER INFORMATION: Oligonucleotide for amplifying CpG island MARCO
      from Homo sapiens

<400> SEQUENCE: 129
aaaaattcca aattaaaaca                                               20

<210> SEQ ID NO 130
<211> LENGTH: 20
<212> TYPE: DNA
<213> ORGANISM: artificial sequence
<220> FEATURE:
<223> OTHER INFORMATION: Oligonucleotide for amplifying CpG island MARCO
      from Homo sapiens

<400> SEQUENCE: 130
gtttttgagt gagatttaat                                               20

<210> SEQ ID NO 131
<211> LENGTH: 20
<212> TYPE: DNA
<213> ORGANISM: artificial sequence
<220> FEATURE:
<223> OTHER INFORMATION: Oligonucleotide for amplifying CpG island MARCO
      from Homo sapiens

<400> SEQUENCE: 131
aacactccaa acaatattaa                                               20

<210> SEQ ID NO 132
<211> LENGTH: 19
<212> TYPE: DNA
<213> ORGANISM: artificial sequence
<220> FEATURE:
```

<223> OTHER INFORMATION: Oligonucleotide for amplifying CpG island
      CpG229 from Homo sapiens

<400> SEQUENCE: 132
agagaaagga ggttggttt                                                   19

<210> SEQ ID NO 133
<211> LENGTH: 20
<212> TYPE: DNA
<213> ORGANISM: artificial sequence
<220> FEATURE:
<223> OTHER INFORMATION: Oligonucleotide for amplifying CpG island
      CpG229 from Homo sapiens

<400> SEQUENCE: 133
ataaatctca aaaccccca                                                   20

<210> SEQ ID NO 134
<211> LENGTH: 19
<212> TYPE: DNA
<213> ORGANISM: artificial sequence
<220> FEATURE:
<223> OTHER INFORMATION: Oligonucleotide for amplifying CpG island
      CpG229 from Homo sapiens

<400> SEQUENCE: 134
gagtgtaggg gttattgat                                                   19

<210> SEQ ID NO 135
<211> LENGTH: 19
<212> TYPE: DNA
<213> ORGANISM: artificial sequence
<220> FEATURE:
<223> OTHER INFORMATION: Oligonucleotide for amplifying CpG island
      CpG229 from Homo sapiens

<400> SEQUENCE: 135
acaatcacta taaccccac                                                   19

<210> SEQ ID NO 136
<211> LENGTH: 20
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 136
gtttagaggt tattttggtt                                                  20

<210> SEQ ID NO 137
<211> LENGTH: 20
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 137
aaaaaataca ctcacctcta                                                  20

<210> SEQ ID NO 138
<211> LENGTH: 19
<212> TYPE: DNA
<213> ORGANISM: artificial sequence
<220> FEATURE:
<223> OTHER INFORMATION: Oligonucleotide for amplifying CpG island CpG85 from Homo sapiens

<400> SEQUENCE: 138
gagttttgtt tattttagt                                               19

<210> SEQ ID NO 139
<211> LENGTH: 19
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 139
aacctacaaa aaaaataac                                               19

<210> SEQ ID NO 140
<211> LENGTH: 19
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 140
ttgtttatgg ggtggattt                                               19

<210> SEQ ID NO 141
<211> LENGTH: 20
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 141
ctcaaacaaa aatctacact                                              20

<210> SEQ ID NO 142
<211> LENGTH: 20
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 142
aggagattta gttttattt                                               20

<210> SEQ ID NO 143
<211> LENGTH: 19
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 143
aaaaaaaacc cctaaatca                                               19

<210> SEQ ID NO 144
<211> LENGTH: 20
<212> TYPE: DNA
<213> ORGANISM: artificial sequence
<220> FEATURE:
<223> OTHER INFORMATION: Oligonucleotide for amplifying CpG island CpG85
      from Homo sapiens

```
<400> SEQUENCE: 144
aaatagggtt ttatattttt                                              20

<210> SEQ ID NO 145
<211> LENGTH: 18
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 145
aaaaaacccc taaaaaac                                                18

<210> SEQ ID NO 146
<211> LENGTH: 20
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 146
gtaggattgt tttaaaaagt                                              20

<210> SEQ ID NO 147
<211> LENGTH: 20
<212> TYPE: DNA
<213> ORGANISM: artificial sequence
<220> FEATURE:
<223> OTHER INFORMATION: Oligonucleotide for amplifying CpG island CpG85
      from Homo sapiens

<400> SEQUENCE: 147
cacttaaaaa aaaaaatccc                                              20

<210> SEQ ID NO 148
<211> LENGTH: 19
<212> TYPE: DNA
<213> ORGANISM: artificial sequence
<220> FEATURE:
<223> OTHER INFORMATION: Oligonucleotide for amplifying CpG island CpG67
      from Homo sapiens

<400> SEQUENCE: 148
gtagtagtag ttgttgtag                                               19

<210> SEQ ID NO 149
<211> LENGTH: 20
<212> TYPE: DNA
<213> ORGANISM: artificial sequence
<220> FEATURE:
<223> OTHER INFORMATION: Oligonucleotide for amplifying CpG island CpG67
      from Homo sapiens

<400> SEQUENCE: 149
tccaaaaaca atactctttc                                              20

<210> SEQ ID NO 150
<211> LENGTH: 19
<212> TYPE: DNA
<213> ORGANISM: artificial sequence
<220> FEATURE:
<223> OTHER INFORMATION: Oligonucleotide for amplifying CpG island CpG67
      from Homo sapiens
```

```
<400> SEQUENCE: 150
gtagtagtag ttgttgtag                                              19

<210> SEQ ID NO 151
<211> LENGTH: 20
<212> TYPE: DNA
<213> ORGANISM: artificial sequence
<220> FEATURE:
<223> OTHER INFORMATION: Oligonucleotide for amplifying CpG island CpG67
      from Homo sapiens

<400> SEQUENCE: 151
ctaacctcct ccaacttaaa                                             20

<210> SEQ ID NO 152
<211> LENGTH: 19
<212> TYPE: DNA
<213> ORGANISM: artificial sequence
<220> FEATURE:
<223> OTHER INFORMATION: Oligonucleotide for amplifying CpG island CpG86
      from Homo sapiens

<400> SEQUENCE: 152
tttgtaggga ggtaggaga                                              19

<210> SEQ ID NO 153
<211> LENGTH: 19
<212> TYPE: DNA
<213> ORGANISM: artificial sequence
<220> FEATURE:
<223> OTHER INFORMATION: Oligonucleotide for amplifying CpG island CpG86
      from Homo sapiens

<400> SEQUENCE: 153 acttaccccca cctaactca                                             19

<210> SEQ ID NO 154
<211> LENGTH: 20
<212> TYPE: DNA
<213> ORGANISM: artificial sequence
<220> FEATURE:
<223> OTHER INFORMATION: Oligonucleotide for amplifying CpG island CpG86
      from Homo sapiens

<400> SEQUENCE: 154
ttagtagtat gaggtggtgt                                             20

<210> SEQ ID NO 155
<211> LENGTH: 20
<212> TYPE: DNA
<213> ORGANISM: artificial sequence
<220> FEATURE:
<223> OTHER INFORMATION: Oligonucleotide for amplifying CpG island CpG86
      from Homo sapiens

<400> SEQUENCE: 155
cccaaaaacc acacatacaa                                             20

<210> SEQ ID NO 156
<211> LENGTH: 24
<212> TYPE: DNA
<213> ORGANISM: artificial sequence
<220> FEATURE:
<223> OTHER INFORMATION: Oligonucleotide for amplifying CpG island
      CpG102 from Homo sapiens

<400> SEQUENCE: 156
```
ggatgaatga atttagtagt tagt                                          24

<210> SEQ ID NO 157
<211> LENGTH: 20
<212> TYPE: DNA
<213> ORGANISM: artificial sequence
<220> FEATURE:
<223> OTHER INFORMATION: Oligonucleotide for amplifying CpG island
      CpG102 from Homo sapiens

<400> SEQUENCE: 157 tccrccccett aaaactccct                                              20

<210> SEQ ID NO 158
<211> LENGTH: 21
<212> TYPE: DNA
<213> ORGANISM: artificial sequence
<220> FEATURE:
<223> OTHER INFORMATION: Oligonucleotide for amplifying CpG island
      CpG102 from Homo sapiens

<400> SEQUENCE: 158
gataggatta attggggttt g                                             21

<210> SEQ ID NO 159
<211> LENGTH: 20
<212> TYPE: DNA
<213> ORGANISM: artificial sequence
<220> FEATURE:
<223> OTHER INFORMATION: Oligonucleotide for amplifying CpG island
      CpG102 from Homo sapiens

<400> SEQUENCE: 159
ttaaaactcc ctcccaactc                                               20

<210> SEQ ID NO 160
<211> LENGTH: 20
<212> TYPE: DNA
<213> ORGANISM: artificial sequence
<220> FEATURE:
<223> OTHER INFORMATION: Oligonucleotide for amplifying CpG island
      CpG115 from Homo sapiens

<400> SEQUENCE: 160
aggatttttt gggggagttt                                               20

<210> SEQ ID NO 161
<211> LENGTH: 20
<212> TYPE: DNA
<213> ORGANISM: artificial sequence
<220> FEATURE:
<223> OTHER INFORMATION: Oligonucleotide for amplifying CpG island
      CpG115 from Homo sapiens

<400> SEQUENCE: 161
cttcccctta aaacccctt                                                20

<210> SEQ ID NO 162
<211> LENGTH: 20
<212> TYPE: DNA
<213> ORGANISM: artificial sequence
<220> FEATURE:
<223> OTHER INFORMATION: Oligonucleotide for amplifying CpG island
      CpG115 from Homo sapiens

<400> SEQUENCE: 162

```
tttttttgggt tgtttggggt                                              20
```

<210> SEQ ID NO 163
<211> LENGTH: 21
<212> TYPE: DNA
<213> ORGANISM: artificial sequence
<220> FEATURE:
<223> OTHER INFORMATION: Oligonucleotide for amplifying CpG island
      CpG115 from Homo sapiens

<400> SEQUENCE: 163

```
accaaaacaa aaccaacaaa c                                             21
```

<210> SEQ ID NO 164
<211> LENGTH: 23
<212> TYPE: DNA
<213> ORGANISM: artificial sequence
<220> FEATURE:
<223> OTHER INFORMATION: Oligonucleotide for amplifying CpG island
      CpG285 from Homo sapiens

<400> SEQUENCE: 164

```
aagttttgag gtttagtggt ttt                                           23
```

<210> SEQ ID NO 165
<211> LENGTH: 20
<212> TYPE: DNA
<213> ORGANISM: artificial sequence
<220> FEATURE:
<223> OTHER INFORMATION: Oligonucleotide for amplifying CpG island
      CpG285 from Homo sapiens

<400> SEQUENCE: 165

```
aaaccctacc tctatcccaa                                               20
```

<210> SEQ ID NO 166
<211> LENGTH: 22
<212> TYPE: DNA
<213> ORGANISM: artificial sequence
<220> FEATURE:
<223> OTHER INFORMATION: Oligonucleotide for amplifying CpG island
      CpG285 from Homo sapiens

<400> SEQUENCE: 166

```
ggttaggttt ttagtggtta tt                                            22
```

<210> SEQ ID NO 167
<211> LENGTH: 19
<212> TYPE: DNA
<213> ORGANISM: artificial sequence
<220> FEATURE:
<223> OTHER INFORMATION: Oligonucleotide for amplifying CpG island
      CpG285 from Homo sapiens

<400> SEQUENCE: 167

```
cctccccaac caacaaaaa                                                19
```

<210> SEQ ID NO 168
<211> LENGTH: 20
<212> TYPE: DNA
<213> ORGANISM: artificial sequence
<220> FEATURE:
<223> OTHER INFORMATION: Oligonucleotide for amplifying CpG island
      CpG26 from Homo sapiens

<400> SEQUENCE: 168

```
aggtttttga aagtttttta                                               20
```

<210> SEQ ID NO 169
<211> LENGTH: 20
<212> TYPE: DNA
<213> ORGANISM: artificial sequence
<220> FEATURE:
<223> OTHER INFORMATION: Oligonucleotide for amplifying CpG island CpG26
     from Homo sapiens

<400> SEQUENCE: 169
aaatatcact atcaatcaaa                                              20

<210> SEQ ID NO 170
<211> LENGTH: 20
<212> TYPE: DNA
<213> ORGANISM: artificial sequence
<220> FEATURE:
<223> OTHER INFORMATION: Oligonucleotide for amplifying CpG island CpG26
     from Homo sapiens

<400> SEQUENCE: 170 gattttttt gattgaaggg                                               20

<210> SEQ ID NO 171
<211> LENGTH: 20
<212> TYPE: DNA
<213> ORGANISM: artificial sequence
<220> FEATURE:
<223> OTHER INFORMATION: Oligonucleotide for amplifying CpG island CpG26
     from Homo sapiens

<400> SEQUENCE: 171
cctaatccca aaacaaata                                               20

<210> SEQ ID NO 172
<211> LENGTH: 20
<212> TYPE: DNA
<213> ORGANISM: artificial sequence
<220> FEATURE:
<223> OTHER INFORMATION: Oligonucleotide for amplifying CpG island
     CpG206 from Homo sapiens

<400> SEQUENCE: 172
gtaagttata tgtattaaat                                              20

<210> SEQ ID NO 173
<211> LENGTH: 19
<212> TYPE: DNA
<213> ORGANISM: artificial sequence
<220> FEATURE:
<223> OTHER INFORMATION: Oligonucleotide for amplifying CpG island
     CpG206 from Homo sapiens

<400> SEQUENCE: 173 aaaacaaaa actactcta                                                19

<210> SEQ ID NO 174
<211> LENGTH: 20
<212> TYPE: DNA
<213> ORGANISM: artificial sequence
<220> FEATURE:
<223> OTHER INFORMATION: Oligonucleotide for amplifying CpG island
     CpG206 from Homo sapiens

<400> SEQUENCE: 174
tattaaattt agaaggttgt                                              20

```
<210> SEQ ID NO 175
<211> LENGTH: 20
<212> TYPE: DNA
<213> ORGANISM: artificial sequence
<220> FEATURE:
<223> OTHER INFORMATION: Oligonucleotide for amplifying CpG island
      CpG206 from Homo sapiens

<400> SEQUENCE: 175
tctattttca atctctaaaa                                              20

<210> SEQ ID NO 176
<211> LENGTH: 20
<212> TYPE: DNA
<213> ORGANISM: artificial sequence
<220> FEATURE:
<223> OTHER INFORMATION: Oligonucleotide for amplifying CpG island CpG22
      from Homo sapiens

<400> SEQUENCE: 176
gaggatgatt tggtgttttt                                              20

<210> SEQ ID NO 177
<211> LENGTH: 19
<212> TYPE: DNA
<213> ORGANISM: artificial sequence
<220> FEATURE:
<223> OTHER INFORMATION: Oligonucleotide for amplifying CpG island CpG22
      from Homo sapiens

<400> SEQUENCE: 177
cccccaaaac taacctata                                               19

<210> SEQ ID NO 178
<211> LENGTH: 18
<212> TYPE: DNA
<213> ORGANISM: artificial sequence
<220> FEATURE:
<223> OTHER INFORMATION: Oligonucleotide for amplifying CpG island CpG22
      from Homo sapiens

<400> SEQUENCE: 178
tggtgtagta tattaagg                                                18

<210> SEQ ID NO 179
<211> LENGTH: 18
<212> TYPE: DNA
<213> ORGANISM: artificial sequence
<220> FEATURE:
<223> OTHER INFORMATION: Oligonucleotide for amplifying CpG island CpG22
      from Homo sapiens

<400> SEQUENCE: 179
aacaaacttc tactacac                                                18

<210> SEQ ID NO 180
<211> LENGTH: 20
<212> TYPE: DNA
<213> ORGANISM: artificial sequence
<220> FEATURE:
<223> OTHER INFORMATION: Oligonucleotide for amplifying CpG island
      CpG112 from Homo sapiens

<400> SEQUENCE: 180
tgtgttagaa gagtatggtt                                              20
```

```
<210> SEQ ID NO 181
<211> LENGTH: 21
<212> TYPE: DNA
<213> ORGANISM: artificial sequence
<220> FEATURE:
<223> OTHER INFORMATION: Oligonucleotide for amplifying CpG island
      CpG112 from Homo sapiens

<400> SEQUENCE: 181
taaaccccac atcaaaattt a                                              21

<210> SEQ ID NO 182
<211> LENGTH: 20
<212> TYPE: DNA
<213> ORGANISM: artificial sequence
<220> FEATURE:
<223> OTHER INFORMATION: Oligonucleotide for amplifying CpG island
      CpG112 from Homo sapiens

<400> SEQUENCE: 182
agagtatggt tggaattttt                                                20

<210> SEQ ID NO 183
<211> LENGTH: 21
<212> TYPE: DNA
<213> ORGANISM: artificial sequence
<220> FEATURE:
<223> OTHER INFORMATION: Oligonucleotide for amplifying CpG island
      CpG112 from Homo sapiens

<400> SEQUENCE: 183
taaaccccac atcaaaattt a                                              21

<210> SEQ ID NO 184
<211> LENGTH: 19
<212> TYPE: DNA
<213> ORGANISM: artificial sequence
<220> FEATURE:
<223> OTHER INFORMATION: Oligonucleotide for amplifying CpG island CpG51
      from Homo sapiens

<400> SEQUENCE: 184
gataggatgt ttatgttta                                                 19

<210> SEQ ID NO 185
<211> LENGTH: 20
<212> TYPE: DNA
<213> ORGANISM: artificial sequence
<220> FEATURE:
<223> OTHER INFORMATION: Oligonucleotide for amplifying CpG island CpG51
      from Homo sapiens

<400> SEQUENCE: 185
tataaaaaat catccttctt                                                20

<210> SEQ ID NO 186
<211> LENGTH: 20
<212> TYPE: DNA
<213> ORGANISM: artificial sequence
<220> FEATURE:
<223> OTHER INFORMATION: Oligonucleotide for amplifying CpG island CpG51
      from Homo sapiens

<400> SEQUENCE: 186
ggatgtttat gtttagtaga                                                20

<210> SEQ ID NO 187
```

```
<211> LENGTH: 20
<212> TYPE: DNA
<213> ORGANISM: artificial sequence
<220> FEATURE:
<223> OTHER INFORMATION: Oligonucleotide for amplifying CpG island CpG51
      from Homo sapiens

<400> SEQUENCE: 187
tactaatctc tttaatcctc                                               20

<210> SEQ ID NO 188
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 188
tattggttgg ataaataatt                                               20

<210> SEQ ID NO 189
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 189
tttttttttt ttttaatccc                                               20

<210> SEQ ID NO 190
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 190
tttaaagtgt atttaagagt                                               20

<210> SEQ ID NO 191
<211> LENGTH: 20
<212> TYPE: DNA
<213> ORGANISM: artificial sequence
<220> FEATURE:
<223> OTHER INFORMATION: Oligonucleotide for amplifying CpG island
      CpG104 from Homo sapiens

<400> SEQUENCE: 191
cttaacctca ttaaaataaa                                               20

<210> SEQ ID NO 192
<211> LENGTH: 21
<212> TYPE: DNA
<213> ORGANISM: artificial sequence
<220> FEATURE:
<223> OTHER INFORMATION: Oligonucleotide for amplifying CpG island CpG37
      from Homo sapiens

<400> SEQUENCE: 192
agtttgggtt agggtgtttg t                                             21

<210> SEQ ID NO 193
<211> LENGTH: 20
```

```
<212> TYPE: DNA
<213> ORGANISM: artificial sequence
<220> FEATURE:
<223> OTHER INFORMATION: Oligonucleotide for amplifying CpG island CpG37
      from Homo sapiens

<400> SEQUENCE: 193
aacaactcct actccaaccc                                                   20

<210> SEQ ID NO 194
<211> LENGTH: 23
<212> TYPE: DNA
<213> ORGANISM: artificial sequence
<220> FEATURE:
<223> OTHER INFORMATION: Oligonucleotide for amplifying CpG island CpG37
      from Homo sapiens

<400> SEQUENCE: 194
ggtgtttgtt tatttgggtt atg                                               23

<210> SEQ ID NO 195
<211> LENGTH: 20
<212> TYPE: DNA
<213> ORGANISM: artificial sequence
<220> FEATURE:
<223> OTHER INFORMATION: Oligonucleotide for amplifying CpG island CpG37
      from Homo sapiens

<400> SEQUENCE: 195
ccctatccta cctctacttc                                                   20

<210> SEQ ID NO 196
<211> LENGTH: 20
<212> TYPE: DNA
<213> ORGANISM: artificial sequence
<220> FEATURE:
<223> OTHER INFORMATION: Oligonucleotide for amplifying CpG island CpG59
      from Homo sapiens

<400> SEQUENCE: 196 tttttttgt tttttatgt                                                     20

<210> SEQ ID NO 197
<211> LENGTH: 20
<212> TYPE: DNA
<213> ORGANISM: artificial sequence
<220> FEATURE:
<223> OTHER INFORMATION: Oligonucleotide for amplifying CpG island CpG59
      from Homo sapiens

<400> SEQUENCE: 197
aaacaaataa tactaaaaaa                                                   20

<210> SEQ ID NO 198
<211> LENGTH: 20
<212> TYPE: DNA
<213> ORGANISM: artificial sequence
<220> FEATURE:
<223> OTHER INFORMATION: Oligonucleotide for amplifying CpG island CpG59
      from Homo sapiens

<400> SEQUENCE: 198
tttatgttta gttgggttat                                                   20

<210> SEQ ID NO 199
<211> LENGTH: 21
<212> TYPE: DNA
```

```
<213> ORGANISM: artificial sequence
<220> FEATURE:
<223> OTHER INFORMATION: Oligonucleotide for amplifying CpG island CpG59
      from Homo sapiens

<400> SEQUENCE: 199
aaatcaaaac aaaacaacaa a                                                    21

<210> SEQ ID NO 200
<211> LENGTH: 24
<212> TYPE: DNA
<213> ORGANISM: artificial sequence
<220> FEATURE:
<223> OTHER INFORMATION: Oligonucleotide for amplifying DDX18 transcript

<400> SEQUENCE: 200
gggtttgaag aggaattaaa gcaa                                                 24

<210> SEQ ID NO 201
<211> LENGTH: 24
<212> TYPE: DNA
<213> ORGANISM: artificial sequence
<220> FEATURE:
<223> OTHER INFORMATION: Oligonucleotide for amplifying DDX18 transcript

<400> SEQUENCE: 201
tggcagaaaa gagcatagtc tgtc                                                 24

<210> SEQ ID NO 202
<211> LENGTH: 24
<212> TYPE: DNA
<213> ORGANISM: artificial sequence
<220> FEATURE:
<223> OTHER INFORMATION: Oligonucleotide for amplifying INSIG2
      transcript

<400> SEQUENCE: 202
gttggtataa atcatgccag tgct                                                 24

<210> SEQ ID NO 203
<211> LENGTH: 22
<212> TYPE: DNA
<213> ORGANISM: artificial sequence
<220> FEATURE:
<223> OTHER INFORMATION: Oligonucleotide for amplifying INSIG2
      transcript

<400> SEQUENCE: 203
gcagccagtg tgagagacaa ct                                                   22

<210> SEQ ID NO 204
<211> LENGTH: 23
<212> TYPE: DNA
<213> ORGANISM: artificial sequence
<220> FEATURE:
<223> OTHER INFORMATION: Oligonucleotide for amplifying EN1 transcript

<400> SEQUENCE: 204
tgggtgtact gcacacgtta ttc                                                  23

<210> SEQ ID NO 205
<211> LENGTH: 24
<212> TYPE: DNA
<213> ORGANISM: artificial sequence
<220> FEATURE:
<223> OTHER INFORMATION: Oligonucleotide for amplifying EN1 transcript
```

```
<400> SEQUENCE: 205
cttgtcctcc ttctcgttct tctt                                              24

<210> SEQ ID NO 206
<211> LENGTH: 20
<212> TYPE: DNA
<213> ORGANISM: artificial sequence
<220> FEATURE:
<223> OTHER INFORMATION: Oligonucleotide for amplifying MARCO transcript

<400> SEQUENCE: 206
gctgcagcgg gtagacaact                                                   20

<210> SEQ ID NO 207
<211> LENGTH: 23
<212> TYPE: DNA
<213> ORGANISM: artificial sequence
<220> FEATURE:
<223> OTHER INFORMATION: Oligonucleotide for amplifying MARCO transcript

<400> SEQUENCE: 207
gccttgttca cctttgattc tga                                               23

<210> SEQ ID NO 208
<211> LENGTH: 24
<212> TYPE: DNA
<213> ORGANISM: artificial sequence
<220> FEATURE:
<223> OTHER INFORMATION: Oligonucleotide for amplifying SCTR transcript

<400> SEQUENCE: 208
ctctgaaaga aagtacctcc aggg                                              24

<210> SEQ ID NO 209
<211> LENGTH: 21
<212> TYPE: DNA
<213> ORGANISM: artificial sequence
<220> FEATURE:
<223> OTHER INFORMATION: Oligonucleotide for amplifying SCTR transcript

<400> SEQUENCE: 209
gcaacaaaaa tggctggaga a                                                 21

<210> SEQ ID NO 210
<211> LENGTH: 20
<212> TYPE: DNA
<213> ORGANISM: artificial sequence
<220> FEATURE:
<223> OTHER INFORMATION: Oligonucleotide for amplifying PTPN4 transcript

<400> SEQUENCE: 210
gatctccacc gggaactcct                                                   20

<210> SEQ ID NO 211
<211> LENGTH: 18
<212> TYPE: DNA
<213> ORGANISM: artificial sequence
<220> FEATURE:
<223> OTHER INFORMATION: Oligonucleotide for amplifying PTPN4 transcript

<400> SEQUENCE: 211
aaccgggttc cttcctgc                                                     18

<210> SEQ ID NO 212
<211> LENGTH: 25
```

```
<212> TYPE: DNA
<213> ORGANISM: artificial sequence
<220> FEATURE:
<223> OTHER INFORMATION: Oligonucleotide for amplifying RALB transcript

<400> SEQUENCE: 212
gaacatgaat cctttacagc aactg                                           25

<210> SEQ ID NO 213
<211> LENGTH: 23
<212> TYPE: DNA
<213> ORGANISM: artificial sequence
<220> FEATURE:
<223> OTHER INFORMATION: Oligonucleotide for amplifying RALB transcript

<400> SEQUENCE: 213
cgacgagcag tggaatttta tct                                             23

<210> SEQ ID NO 214
<211> LENGTH: 19
<212> TYPE: DNA
<213> ORGANISM: artificial sequence
<220> FEATURE:
<223> OTHER INFORMATION: Oligonucleotide for amplifying INHBB transcript

<400> SEQUENCE: 214
cgcgtttccg aaatcatca                                                  19

<210> SEQ ID NO 215
<211> LENGTH: 22
<212> TYPE: DNA
<213> ORGANISM: artificial sequence
<220> FEATURE:
<223> OTHER INFORMATION: Oligonucleotide for amplifying INHBB transcript

<400> SEQUENCE: 215
ggaccacaaa caggttctgg tt                                              22

<210> SEQ ID NO 216
<211> LENGTH: 19
<212> TYPE: DNA
<213> ORGANISM: artificial sequence
<220> FEATURE:
<223> OTHER INFORMATION: Oligonucleotide for amplifying GLI2 transcript

<400> SEQUENCE: 216
caccagaatc gcacccact                                                  19

<210> SEQ ID NO 217
<211> LENGTH: 20
<212> TYPE: DNA
<213> ORGANISM: artificial sequence
<220> FEATURE:
<223> OTHER INFORMATION: Oligonucleotide for amplifying GLI2 transcript

<400> SEQUENCE: 217
gcctgggatc ttgcagatgt                                                 20

<210> SEQ ID NO 218
<211> LENGTH: 23
<212> TYPE: DNA
<213> ORGANISM: artificial sequence
<220> FEATURE:
<223> OTHER INFORMATION: Oligonucleotide for amplifying TSN transcript

<400> SEQUENCE: 218
```
agaccaaatt tcctgctgaa cag                                             23

<210> SEQ ID NO 219
<211> LENGTH: 20
<212> TYPE: DNA
<213> ORGANISM: artificial sequence
<220> FEATURE:
<223> OTHER INFORMATION: Oligonucleotide for amplifying TSN transcript

<400> SEQUENCE: 219
aagcgctgca acacaaacct                                                 20

<210> SEQ ID NO 220
<211> LENGTH: 136
<212> TYPE: PRT
<213> ORGANISM: Homo sapiens

<400> SEQUENCE: 220

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Thr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 221
<211> LENGTH: 103
<212> TYPE: PRT
<213> ORGANISM: Homo sapiens

<400> SEQUENCE: 221

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

```
<210> SEQ ID NO 222
<211> LENGTH: 130
<212> TYPE: PRT
<213> ORGANISM: Homo sapiens

<400> SEQUENCE: 222

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 223
<211> LENGTH: 126
<212> TYPE: PRT
<213> ORGANISM: Homo sapiens

<400> SEQUENCE: 223

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 224
<211> LENGTH: 15
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 224
tggcaaacac agccc                                              15
```

<210> SEQ ID NO 225
<211> LENGTH: 17
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 225
gcttcattta ttcccgc                                              17

<210> SEQ ID NO 226
<211> LENGTH: 19
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 226
ccgatgcttc atttattcc                                            19

<210> SEQ ID NO 227
<211> LENGTH: 23
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 227
aaagctcttt tatggagatt acc                                       23

<210> SEQ ID NO 228
<211> LENGTH: 24
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 228
caacttagtt tcagagaatg aagc                                      24

<210> SEQ ID NO 229
<211> LENGTH: 24
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 229
ttaaaagtct cttttctcct ttcc                                      24

<210> SEQ ID NO 230
<211> LENGTH: 15
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 230
cccgggctgt gtttg                                                15

-continued

```
<210> SEQ ID NO 231
<211> LENGTH: 17
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 231
gctgtgtttg ccattcg                                                   17

<210> SEQ ID NO 232
<211> LENGTH: 18
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 232
tcgcgggaat aaatgaag                                                  18

<210> SEQ ID NO 233
<211> LENGTH: 22
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 233
atcggtaatc tccataaaag ag                                             22

<210> SEQ ID NO 234
<211> LENGTH: 21
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 234
ctccataaaa gagctttcac g                                              21

<210> SEQ ID NO 235
<211> LENGTH: 23
<212> TYPE: DNA
<213> ORGANISM: artificial sequence
<220> FEATURE:
<223> OTHER INFORMATION: Oligonucleotide for pyrosequencing the Z
      fragment

<400> SEQUENCE: 235
cattctctga aactaagttg agg                                            23

<210> SEQ ID NO 236
<211> LENGTH: 17
<212> TYPE: DNA
<213> ORGANISM: artificial sequence
<220> FEATURE:
<223> OTHER INFORMATION: Oligonucleotide for amplifying DDX18 fragment
      for ChIP analysis

<400> SEQUENCE: 236
aattgcggca gcggaac                                                   17

<210> SEQ ID NO 237
```

```
<211> LENGTH: 17
<212> TYPE: DNA
<213> ORGANISM: artificial sequence
<220> FEATURE:
<223> OTHER INFORMATION: Oligonucleotide for amplifying DDX18 fragment
      for ChIP analysis

<400> SEQUENCE: 237
ccgcgagtca acgcatc                                                  17

<210> SEQ ID NO 238
<211> LENGTH: 21
<212> TYPE: DNA
<213> ORGANISM: artificial sequence
<220> FEATURE:
<223> OTHER INFORMATION: Oligonucleotide for amplifying INSIG2 fragment
      for ChIP analysis

<400> SEQUENCE: 238
agcaaacaac agcagatccg a                                             21

<210> SEQ ID NO 239
<211> LENGTH: 16
<212> TYPE: DNA
<213> ORGANISM: artificial sequence
<220> FEATURE:
<223> OTHER INFORMATION: Oligonucleotide for amplifying INSIG2 fragment
      for ChIP analysis

<400> SEQUENCE: 239
ggtgggcgtg gaccgt                                                   16

<210> SEQ ID NO 240
<211> LENGTH: 18
<212> TYPE: DNA
<213> ORGANISM: artificial sequence
<220> FEATURE:
<223> OTHER INFORMATION: Oligonucleotide for amplifying EN1 fragment for
      ChIP analysis

<400> SEQUENCE: 240
cagaggccag gatcgcat                                                 18

<210> SEQ ID NO 241
<211> LENGTH: 20
<212> TYPE: DNA
<213> ORGANISM: artificial sequence
<220> FEATURE:
<223> OTHER INFORMATION: Oligonucleotide for amplifying EN1 fragment for
      ChIP analysis

<400> SEQUENCE: 241
tcaccccagt tccagtcaca                                               20

<210> SEQ ID NO 242
<211> LENGTH: 23
<212> TYPE: DNA
<213> ORGANISM: artificial sequence
<220> FEATURE:
<223> OTHER INFORMATION: Oligonucleotide for amplifying MARCO fragment
      for ChIP analysis

<400> SEQUENCE: 242
gaaaattctc aaggaggacg agc                                           23

<210> SEQ ID NO 243
<211> LENGTH: 21
```

```
<212> TYPE: DNA
<213> ORGANISM: artificial sequence
<220> FEATURE:
<223> OTHER INFORMATION: Oligonucleotide for amplifying MARCO fragment
      for ChIP analysis

<400> SEQUENCE: 243
tgcaatttgg tgaaaagcag c                                              21

<210> SEQ ID NO 244
<211> LENGTH: 21
<212> TYPE: DNA
<213> ORGANISM: artificial sequence
<220> FEATURE:
<223> OTHER INFORMATION: Oligonucleotide for amplifying SCTR fragment
      for ChIP analysis

<400> SEQUENCE: 244
actgtctctg gagtccacgg a                                              21

<210> SEQ ID NO 245
<211> LENGTH: 19
<212> TYPE: DNA
<213> ORGANISM: artificial sequence
<220> FEATURE:
<223> OTHER INFORMATION: Oligonucleotide for amplifying SCTR fragment
      for ChIP analysis

<400> SEQUENCE: 245
tgacctaagt tgcccaccg                                                 19

<210> SEQ ID NO 246
<211> LENGTH: 20
<212> TYPE: DNA
<213> ORGANISM: artificial sequence
<220> FEATURE:
<223> OTHER INFORMATION: Oligonucleotide for amplifying PTPN4 fragment
      for ChIP analysis

<400> SEQUENCE: 246
ttttctccag ccgagaggac                                                20

<210> SEQ ID NO 247
<211> LENGTH: 21
<212> TYPE: DNA
<213> ORGANISM: artificial sequence
<220> FEATURE:
<223> OTHER INFORMATION: Oligonucleotide for amplifying PTPN4 fragment
      for ChIP analysis

<400> SEQUENCE: 247
gggaccggag aacctcttac c                                              21

<210> SEQ ID NO 248
<211> LENGTH: 18
<212> TYPE: DNA
<213> ORGANISM: artificial sequence
<220> FEATURE:
<223> OTHER INFORMATION: Oligonucleotide for amplifying RALB fragment
      for ChIP analysis

<400> SEQUENCE: 248
tgccctcgga acttgcac                                                  18

<210> SEQ ID NO 249
<211> LENGTH: 22
<212> TYPE: DNA
```

```
<213> ORGANISM: artificial sequence
<220> FEATURE:
<223> OTHER INFORMATION: Oligonucleotide for amplifying RALB fragment
      for ChIP analysis

<400> SEQUENCE: 249
aaaccgaagc cctttaggaa ca                                              22

<210> SEQ ID NO 250
<211> LENGTH: 18
<212> TYPE: DNA
<213> ORGANISM: artificial sequence
<220> FEATURE:
<223> OTHER INFORMATION: Oligonucleotide for amplifying INHBB fragment
      for ChIP analysis

<400> SEQUENCE: 250
cagtggctga gcccgagt                                                   18

<210> SEQ ID NO 251
<211> LENGTH: 21
<212> TYPE: DNA
<213> ORGANISM: artificial sequence
<220> FEATURE:
<223> OTHER INFORMATION: Oligonucleotide for amplifying INHBB fragment
      for ChIP analysis

<400> SEQUENCE: 251
ctttcgccag cagacaaact t                                               21

<210> SEQ ID NO 252
<211> LENGTH: 24
<212> TYPE: DNA
<213> ORGANISM: artificial sequence
<220> FEATURE:
<223> OTHER INFORMATION: Oligonucleotide for amplifying GLI2 fragment
      for ChIP analysis

<400> SEQUENCE: 252
gatgcgatgt ctaaaacgtt caag                                            24

<210> SEQ ID NO 253
<211> LENGTH: 24
<212> TYPE: DNA
<213> ORGANISM: artificial sequence
<220> FEATURE:
<223> OTHER INFORMATION: Oligonucleotide for amplifying GLI2 fragment
      for ChIP analysis

<400> SEQUENCE: 253
tcggtaaagc agcacatgta ttct                                            24

<210> SEQ ID NO 254
<211> LENGTH: 22
<212> TYPE: DNA
<213> ORGANISM: artificial sequence
<220> FEATURE:
<223> OTHER INFORMATION: Oligonucleotide for amplifying TSN fragment
      for ChIP analysis

<400> SEQUENCE: 254
atgtctgtga gcgagatctt cg                                              22

<210> SEQ ID NO 255
<211> LENGTH: 18
<212> TYPE: DNA
<213> ORGANISM: artificial sequence
```

```
<220> FEATURE:
<223> OTHER INFORMATION: Oligonucleotide for amplifying TSN fragment
      for ChIP analysis

<400> SEQUENCE: 255
ggatgtcctg ctcggcag                                              18

<210> SEQ ID NO 256
<211> LENGTH: 24
<212> TYPE: DNA
<213> ORGANISM: artificial sequence
<220> FEATURE:
<223> OTHER INFORMATION: Oligonucleotide for amplifying p21 fragment
      for ChIP analysis

<400> SEQUENCE: 256
cttctgggag aggtgaccta gtga                                       24

<210> SEQ ID NO 257
<211> LENGTH: 21
<212> TYPE: DNA
<213> ORGANISM: artificial sequence
<220> FEATURE:
<223> OTHER INFORMATION: Oligonucleotide for amplifying p21 fragment
      for ChIP analysis

<400> SEQUENCE: 257
aatttccaga aaagccccac a                                          21

<210> SEQ ID NO 258
<211> LENGTH: 21
<212> TYPE: DNA
<213> ORGANISM: artificial sequence
<220> FEATURE:
<223> OTHER INFORMATION: Oligonucleotide for amplifying p21 from Homo
      sapiens in RT-PCR

<400> SEQUENCE: 258
ctggagactc tcagggtcga a                                          21

<210> SEQ ID NO 259
<211> LENGTH: 23
<212> TYPE: DNA
<213> ORGANISM: artificial sequence
<220> FEATURE:
<223> OTHER INFORMATION: Oligonucleotide for amplifying p21 from Homo
      sapiens in RT-PCR

<400> SEQUENCE: 259
ggcttcctct tggagaagat cag                                        23

<210> SEQ ID NO 260
<211> LENGTH: 21
<212> TYPE: DNA
<213> ORGANISM: artificial sequence
<220> FEATURE:
<223> OTHER INFORMATION: oligonucleotide for amplifiying  CpG island
      associated with EN1 from Homo sapiens

<400> SEQUENCE: 260
agaataataa agataagaga t                                          21

<210> SEQ ID NO 261
<211> LENGTH: 20
<212> TYPE: DNA
<213> ORGANISM: artificial sequence
<220> FEATURE:
```

```
<223> OTHER INFORMATION: oligonucleotide for amplifiying  CpG island
      associated with EN1 from Homo sapiens

<400> SEQUENCE: 261
actatcctac ttataaactc                                                 20

<210> SEQ ID NO 262
<211> LENGTH: 20
<212> TYPE: DNA
<213> ORGANISM: artificial sequence
<220> FEATURE:
<223> OTHER INFORMATION: oligonucleotide for amplifiying  CpG island
      associated with EN1 from Homo sapiens

<400> SEQUENCE: 262
gttttaggga tttagagttt                                                 20

<210> SEQ ID NO 263
<211> LENGTH: 20
<212> TYPE: DNA
<213> ORGANISM: artificial sequence
<220> FEATURE:
<223> OTHER INFORMATION: oligonucleotide for amplifiying  CpG island
      associated with EN1 from Homo sapiens

<400> SEQUENCE: 263
ctacttataa actcaaccaa                                                 20

<210> SEQ ID NO 264
<211> LENGTH: 23
<212> TYPE: DNA
<213> ORGANISM: artificial sequence
<220> FEATURE:
<223> OTHER INFORMATION: oligonucleotide for amplifiying  CpG island
      associated with INHBB from Homo sapiens

<400> SEQUENCE: 264
aagttttgag gtttagtggt ttt                                             23

<210> SEQ ID NO 265
<211> LENGTH: 20
<212> TYPE: DNA
<213> ORGANISM: artificial sequence
<220> FEATURE:
<223> OTHER INFORMATION: oligonucleotide for amplifiying  CpG island
      associated with INHBB from Homo sapiens

<400> SEQUENCE: 265
aaaccctacc tctatcccaa                                                 20

<210> SEQ ID NO 266
<211> LENGTH: 22
<212> TYPE: DNA
<213> ORGANISM: artificial sequence
<220> FEATURE:
<223> OTHER INFORMATION: oligonucleotide for amplifiying  CpG island
      associated with INHBB from Homo sapiens

<400> SEQUENCE: 266
ggttaggttt ttagtggtta tt                                              22

<210> SEQ ID NO 267
<211> LENGTH: 19
<212> TYPE: DNA
<213> ORGANISM: artificial sequence
<220> FEATURE:
<223> OTHER INFORMATION: oligonucleotide for amplifiying  CpG island
``` associated with INHBB from Homo sapiens

<400> SEQUENCE: 267
cctccccaac caacaaaaa                                                    19

<210> SEQ ID NO 268
<211> LENGTH: 19
<212> TYPE: DNA
<213> ORGANISM: artificial sequence
<220> FEATURE:
<223> OTHER INFORMATION: oligonucleotide for amplifiying  CpG island
      associated with INHBB from Homo sapiens

<400> SEQUENCE: 268
gtagtagtag ttgttgtag                                                    19

<210> SEQ ID NO 269
<211> LENGTH: 20
<212> TYPE: DNA
<213> ORGANISM: artificial sequence
<220> FEATURE:
<223> OTHER INFORMATION: oligonucleotide for amplifiying  CpG island
      associated with INHBB from Homo sapiens

<400> SEQUENCE: 269
tccaaaaaca atactctttc                                                   20

<210> SEQ ID NO 270
<211> LENGTH: 19
<212> TYPE: DNA
<213> ORGANISM: artificial sequence
<220> FEATURE:
<223> OTHER INFORMATION: oligonucleotide for amplifiying  CpG island
      associated with INHBB from Homo sapiens

<400> SEQUENCE: 270
gtagtagtag ttgttgtag                                                    19

<210> SEQ ID NO 271
<211> LENGTH: 20
<212> TYPE: DNA
<213> ORGANISM: artificial sequence
<220> FEATURE:
<223> OTHER INFORMATION: oligonucleotide for amplifiying  CpG island
      associated with INHBB from Homo sapiens

<400> SEQUENCE: 271
ctaacctcct ccaacttaaa                                                   20

<210> SEQ ID NO 272
<211> LENGTH: 46
<212> TYPE: DNA
<213> ORGANISM: artificial sequence
<220> FEATURE:
<223> OTHER INFORMATION: oligonnucleotide for amplifying CpG island
      associated with EN1 by headloop PCR

<400> SEQUENCE: 272
aacacaaaaa accccaaaac acacgtgttt cgggtatttg gtgttt                      46

<210> SEQ ID NO 273
<211> LENGTH: 36
<212> TYPE: DNA
<213> ORGANISM: artificial sequence
<220> FEATURE:
<223> OTHER INFORMATION: oligonucleotide fdor amplifying CpG island
      associated with EN1 by headloop PCR

```
<400> SEQUENCE: 273
tgtttgggtg aataaaaacc ctatccaccc gttaaa                          36

<210> SEQ ID NO 274
<211> LENGTH: 39
<212> TYPE: DNA
<213> ORGANISM: artificial sequence
<220> FEATURE:
<223> OTHER INFORMATION: Oligonucleotide for amplifying CpG island
      associated with SCTR by headloop PCR

<400> SEQUENCE: 274
acaccaaccc cacagttttt tttattcggt agggattgg                       39

<210> SEQ ID NO 275
<211> LENGTH: 43
<212> TYPE: DNA
<213> ORGANISM: artificial sequence
<220> FEATURE:
<223> OTHER INFORMATION: Oligonucleotide for amplifying CpG island
      associated with SCTR by headloop PCR

<400> SEQUENCE: 275
tgtggtaatt ttgtttaaaa caatactctt tccgaacccg aaa                  43
```